United States Patent
Aznarez et al.

(10) Patent No.: US 11,814,622 B2
(45) Date of Patent: Nov. 14, 2023

(54) OPA1 ANTISENSE OLIGOMERS FOR TREATMENT OF CONDITIONS AND DISEASES

(71) Applicant: Stoke Therapeutics, Inc., Bedford, MA (US)

(72) Inventors: Isabel Aznarez, Boston, MA (US); Aditya Venkatesh, Natick, MA (US); Gene Liau, Wayland, MA (US)

(73) Assignee: STOKE THERAPEUTICS, INC., Bedford, MA (US)

(*) Notice: Subject to any disclaimer, the term of this patent is extended or adjusted under 35 U.S.C. 154(b) by 0 days.

(21) Appl. No.: 18/304,878

(22) Filed: Apr. 21, 2023

(65) Prior Publication Data

US 2023/0250429 A1   Aug. 10, 2023

Related U.S. Application Data

(63) Continuation of application No. 17/924,966, filed as application No. PCT/US2021/030254 on Apr. 30, 2021.

(60) Provisional application No. 63/112,458, filed on Nov. 11, 2020, provisional application No. 63/023,013, filed on May 11, 2020.

(51) Int. Cl.
| | | |
|---|---|---|
| *C12N 15/113* | (2010.01) | |
| *A61P 27/02* | (2006.01) | |
| *A61K 9/00* | (2006.01) | |
| *C12N 15/86* | (2006.01) | |

(52) U.S. Cl.
CPC .......... *C12N 15/113* (2013.01); *A61K 9/0048* (2013.01); *A61P 27/02* (2018.01); *C12N 15/86* (2013.01); *C12N 2310/11* (2013.01); *C12N 2310/20* (2017.05); *C12N 2310/314* (2013.01); *C12N 2310/315* (2013.01); *C12N 2310/321* (2013.01); *C12N 2750/14143* (2013.01)

(58) Field of Classification Search
CPC .............. C12N 15/113; C12N 2310/14; C12N 2310/321
See application file for complete search history.

(56) References Cited

U.S. PATENT DOCUMENTS

| | | |
|---|---|---|
| 4,866,042 A | 9/1989 | Neuwelt |
| 5,151,510 A | 9/1992 | Stec et al. |
| 5,656,612 A | 8/1997 | Monia |
| 5,665,593 A | 9/1997 | Kole et al. |
| 5,914,396 A | 6/1999 | Cook et al. |
| 5,916,808 A | 6/1999 | Kole et al. |
| 5,976,879 A | 11/1999 | Kole et al. |
| 6,083,482 A | 7/2000 | Wang |
| 6,166,197 A | 12/2000 | Cook et al. |
| 6,210,892 B1 | 4/2001 | Bennett et al. |
| 6,294,520 B1 | 9/2001 | Naito |
| 6,383,752 B1 | 5/2002 | Agrawal et al. |
| 6,436,657 B1 | 8/2002 | Famodu et al. |
| 6,451,991 B1 | 9/2002 | Martin et al. |
| 6,485,960 B1 | 11/2002 | Harris et al. |
| 6,531,591 B1 | 3/2003 | Fensholdt |
| 6,573,073 B2 | 6/2003 | Harris |
| 6,605,611 B2 | 8/2003 | Simmonds et al. |
| 6,632,427 B1 | 10/2003 | Finiels et al. |
| 6,639,059 B1 | 10/2003 | Kochkine et al. |
| 6,670,461 B1 | 12/2003 | Wengel et al. |
| 6,677,445 B1 | 1/2004 | Innis et al. |
| 6,734,291 B2 | 5/2004 | Kochkine et al. |
| 6,756,523 B1 | 6/2004 | Kahn et al. |
| 6,770,748 B2 | 8/2004 | Imanishi et al. |
| 6,794,499 B2 | 9/2004 | Wengel et al. |
| 6,846,921 B2 | 1/2005 | Innis et al. |
| 6,936,589 B2 | 8/2005 | Naito |
| 6,963,589 B1 | 11/2005 | Sugata et al. |
| 6,998,484 B2 | 2/2006 | Koch et al. |
| 7,015,315 B1 | 3/2006 | Cook et al. |
| 7,034,133 B2 | 4/2006 | Wengel et al. |
| 7,053,199 B2 | 5/2006 | Imanishi et al. |
| 7,053,207 B2 | 5/2006 | Wengel |
| 7,060,809 B2 | 6/2006 | Wengel et al. |
| 7,071,324 B2 | 7/2006 | Preparata et al. |
| 7,084,125 B2 | 8/2006 | Wengel |
| 7,101,993 B1 | 9/2006 | Cook et al. |
| 7,169,594 B2 | 1/2007 | Guan |
| 7,214,783 B2 | 5/2007 | Jeon et al. |

(Continued)

FOREIGN PATENT DOCUMENTS

| | | |
|---|---|---|
| AU | 2018355237 A1 | 5/2020 |
| CN | 103667438 A | 3/2014 |

(Continued)

OTHER PUBLICATIONS

Aartsma-Rus et al.: Antisense-mediated exon skipping: a versatile tool with therapeutic and research applications. RNA 13(10):1609-24 (2007). Epub Aug. 7, 2007.

Aceti et al.: Syngap1 haploinsufficiency damages a postnatal critical period of pyramidal cell structural maturation linked to cortical circuit assembly, Biol Psychiatry 77(9):805-815 (2015).

Aizer et al.: Lack of reduction in racial disparities in cancer-specific mortality over a 20-year period. Cancer 120:1532-9 (2014).

Altschul et al.: Basic local alignment search tool. J. Mol. Biol. 215(3)403-410 (1990).

(Continued)

*Primary Examiner* — Brian Whiteman
(74) *Attorney, Agent, or Firm* — Wilson Sonsini Goodrich Rosati

(57) ABSTRACT

Alternative splicing events in genes can lead to non-productive mRNA transcripts which in turn can lead to aberrant protein expression, and therapeutic agents which can target the alternative splicing events in genes can modulate the expression level of functional proteins in patients and/or inhibit aberrant protein expression. Such therapeutic agents can be used to treat a condition or disease caused by protein deficiency and/or mitochondrial function deficit.

21 Claims, 67 Drawing Sheets
Specification includes a Sequence Listing.

(56) References Cited

U.S. PATENT DOCUMENTS

| | | | |
|---|---|---|---|
| 7,217,805 B2 | 5/2007 | Imanishi et al. |
| 7,314,923 B2 | 1/2008 | Kaneko et al. |
| 7,335,765 B2 | 2/2008 | Kaneko et al. |
| 7,368,549 B2 | 5/2008 | Dempcy et al. |
| 7,399,845 B2 | 7/2008 | Seth et al. |
| 7,432,249 B2 | 10/2008 | Crooke |
| 7,432,250 B2 | 10/2008 | Crooke |
| 7,547,684 B2 | 6/2009 | Seth et al. |
| 7,553,644 B2 | 6/2009 | Germino et al. |
| 7,569,575 B2 | 8/2009 | Soerensen et al. |
| 7,569,686 B1 | 8/2009 | Bhat et al. |
| 7,572,582 B2 | 8/2009 | Wengel et al. |
| 7,595,304 B2 | 9/2009 | Zhao et al. |
| 7,615,619 B2 | 11/2009 | Imanishi et al. |
| 7,662,946 B2 | 2/2010 | Ginsburg et al. |
| 7,662,948 B2 | 2/2010 | Kurreck et al. |
| 7,666,854 B2 | 2/2010 | Seth et al. |
| 7,687,617 B2 | 3/2010 | Thrue et al. |
| 7,696,345 B2 | 4/2010 | Allerson et al. |
| 7,741,457 B2 | 6/2010 | Seth et al. |
| 7,750,131 B2 | 7/2010 | Seth et al. |
| 7,816,333 B2 | 10/2010 | Kaneko et al. |
| 7,846,686 B2 | 12/2010 | Kramer |
| 7,951,934 B2 | 5/2011 | Freier |
| 7,994,145 B2 | 8/2011 | Imanishi et al. |
| 8,022,193 B2 | 9/2011 | Seth et al. |
| 8,030,467 B2 | 10/2011 | Seth et al. |
| 8,048,998 B2 | 11/2011 | Rasmussen et al. |
| 8,067,569 B2 | 11/2011 | Iversen et al. |
| 8,084,458 B2 | 12/2011 | Soerensen et al. |
| 8,088,746 B2 | 1/2012 | Seth et al. |
| 8,090,542 B2 | 1/2012 | Khvorova et al. |
| 8,110,674 B2 | 2/2012 | Manoharan et al. |
| 8,124,745 B2 | 2/2012 | Allerson et al. |
| 8,129,515 B2 | 3/2012 | Esau et al. |
| 8,168,605 B2 | 5/2012 | Zhao et al. |
| 8,258,109 B2 | 9/2012 | Bennett et al. |
| 8,268,980 B2 | 9/2012 | Seth et al. |
| 8,278,036 B2 | 10/2012 | Kariko et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,293,684 B2 | 10/2012 | Mouritzen et al. |
| 8,361,979 B2 | 1/2013 | Aartsma-Rus et al. |
| 8,383,792 B2 | 2/2013 | Okamoto et al. |
| 8,394,947 B2 | 3/2013 | Bhat et al. |
| 8,415,465 B2 | 4/2013 | Freier |
| 8,436,163 B2 | 5/2013 | Iversen et al. |
| 8,450,467 B2 | 5/2013 | Manoharan et al. |
| 8,461,124 B2 | 6/2013 | Chattopadhyaya |
| 8,492,390 B2 | 7/2013 | Detlef et al. |
| 8,501,703 B2 | 8/2013 | Bennett et al. |
| 8,501,805 B2 | 8/2013 | Seth et al. |
| 8,518,908 B2 | 8/2013 | Hrdlicka et al. |
| 8,530,640 B2 | 9/2013 | Seth et al. |
| 8,541,562 B2 | 9/2013 | Obika et al. |
| 8,546,556 B2 | 10/2013 | Seth et al. |
| 8,592,156 B2 | 11/2013 | Liu et al. |
| 8,637,478 B2 | 1/2014 | Bennett |
| RE44,779 E | 2/2014 | Imanishi et al. |
| 8,653,252 B2 | 2/2014 | Elmen et al. |
| 8,673,560 B2 | 3/2014 | Leamon et al. |
| 8,680,254 B2 | 3/2014 | Lutz et al. |
| 8,691,783 B2 | 4/2014 | Thum et al. |
| 8,703,728 B2 | 4/2014 | Swayze et al. |
| 8,710,021 B2 | 4/2014 | Anro et al. |
| 8,735,366 B2 | 5/2014 | Bauer et al. |
| 8,748,089 B2 | 6/2014 | Kariko et al. |
| 8,779,118 B2 | 7/2014 | Allerson et al. |
| 8,796,437 B2 | 8/2014 | Swayze et al. |
| 8,809,516 B2 | 8/2014 | Manoharan et al. |
| 8,846,386 B2 | 9/2014 | Ambati et al. |
| 8,846,637 B2 | 9/2014 | Seth et al. |
| 8,846,639 B2 | 9/2014 | Swayze et al. |
| 8,846,885 B2 | 9/2014 | Hirai et al. |
| 8,895,722 B2 | 11/2014 | Iversen et al. |
| 8,957,040 B2 | 2/2015 | Bennett et al. |
| 8,957,200 B2 | 2/2015 | Seth et al. |
| 8,957,201 B2 | 2/2015 | Kaneko et al. |
| 9,005,906 B2 | 4/2015 | Swayze et al. |
| 9,006,194 B2 | 4/2015 | Katsikis et al. |
| 9,006,415 B2 | 4/2015 | Ren et al. |
| 9,012,139 B2 | 4/2015 | Collard et al. |
| 9,029,335 B2 | 5/2015 | Prakash et al. |
| 9,045,518 B2 | 6/2015 | Christensen et al. |
| 9,045,754 B2 | 6/2015 | Bhanot et al. |
| 9,057,066 B2 | 6/2015 | Hung et al. |
| 9,109,001 B2 | 8/2015 | Parsy et al. |
| 9,127,272 B2 | 9/2015 | Esau et al. |
| 9,127,276 B2 | 9/2015 | Prakash et al. |
| 9,156,873 B2 | 10/2015 | Prakash et al. |
| 9,157,081 B2 | 10/2015 | Bennett et al. |
| 9,181,549 B2 | 11/2015 | Prakash et al. |
| 9,187,515 B2 | 11/2015 | Mayes et al. |
| 9,192,621 B2 | 11/2015 | Mayes et al. |
| 9,193,752 B2 | 11/2015 | Migawa et al. |
| 9,193,969 B2 | 11/2015 | Montefeltro et al. |
| 9,211,300 B2 | 12/2015 | Mayes et al. |
| 9,217,147 B2 | 12/2015 | Singh et al. |
| 9,221,864 B2 | 12/2015 | Seth et al. |
| 9,243,245 B2 | 1/2016 | De Kimpe et al. |
| 9,290,534 B2 | 3/2016 | Seth et al. |
| 9,296,778 B2 | 3/2016 | Parsy et al. |
| 9,309,275 B2 | 4/2016 | Stewart et al. |
| 9,315,535 B2 | 4/2016 | Mitsuoka et al. |
| 9,334,495 B2 | 5/2016 | Khvorova et al. |
| 9,339,541 B2 | 5/2016 | Dousson et al. |
| 9,347,068 B2 | 5/2016 | Dhugga et al. |
| 9,359,445 B2 | 6/2016 | Finkbeiner et al. |
| 9,359,603 B2 | 6/2016 | Lutz et al. |
| 9,359,609 B2 | 6/2016 | Duffield et al. |
| 9,410,155 B2 | 8/2016 | Collard et al. |
| 9,428,534 B2 | 8/2016 | Christensen et al. |
| 9,447,166 B2 | 9/2016 | Ambati et al. |
| 9,453,261 B2 | 9/2016 | Lee et al. |
| 9,464,292 B2 | 10/2016 | Okumura et al. |
| 9,499,818 B2 | 11/2016 | Van |
| 9,518,259 B2 | 12/2016 | Rigo et al. |
| 9,534,222 B2 | 1/2017 | Ambati et al. |
| 9,550,988 B2 | 1/2017 | Swayze |
| 9,714,422 B2 | 7/2017 | Vorechovsky et al. |
| 9,745,577 B2 | 8/2017 | Vorechovsky et al. |
| 9,771,579 B2 | 9/2017 | Collard et al. |
| 9,976,143 B2 | 5/2018 | Krainer et al. |
| 10,119,168 B2 | 11/2018 | Vaidya et al. |
| 10,196,639 B2 | 2/2019 | Vorechovsky et al. |
| 10,517,853 B2 | 12/2019 | Welch et al. |
| 10,583,128 B2 | 3/2020 | Collard et al. |
| 10,683,503 B2 | 6/2020 | Aznarez et al. |
| 10,941,405 B2 | 3/2021 | Vorechovsky et al. |
| 11,702,660 B2 | 7/2023 | Vorechovsky et al. |
| 2003/0148974 A1 | 8/2003 | Monia et al. |
| 2004/0063129 A1 | 4/2004 | Gaarde et al. |
| 2004/0219515 A1 | 11/2004 | Bentwich |
| 2005/0221354 A1 | 10/2005 | Mounts |
| 2005/0233327 A1 | 10/2005 | Welch et al. |
| 2006/0062790 A1 | 3/2006 | Reinhard et al. |
| 2006/0134670 A1 | 6/2006 | Piu |
| 2007/0009899 A1 | 1/2007 | Mounts |
| 2007/0087376 A1 | 4/2007 | Potashkin |
| 2007/0249538 A1 | 10/2007 | Sazani et al. |
| 2008/0269123 A1 | 10/2008 | Li et al. |
| 2009/0186846 A1 | 7/2009 | Chabot et al. |
| 2009/0186946 A1 | 7/2009 | Taketomi et al. |
| 2009/0264353 A1 | 10/2009 | Orum et al. |
| 2009/0270332 A1 | 10/2009 | Bare et al. |
| 2010/0111935 A1 | 5/2010 | Bhagat et al. |
| 2010/0150839 A1 | 6/2010 | Kelleher |
| 2010/0166784 A1 | 7/2010 | Murphy et al. |
| 2011/0124591 A1 | 5/2011 | Bennett |
| 2011/0229891 A1 | 9/2011 | Michaud et al. |
| 2012/0157512 A1 | 6/2012 | Ben-Chanoch et al. |
| 2012/0190728 A1 | 7/2012 | Bennett et al. |
| 2012/0252877 A1 | 10/2012 | Lo |

(56) References Cited

U.S. PATENT DOCUMENTS

| | | |
|---|---|---|
| 2013/0072671 A1 | 3/2013 | Van Deutekom |
| 2013/0096183 A1 | 4/2013 | Collard et al. |
| 2013/0109850 A1 | 5/2013 | Prakash et al. |
| 2013/0136732 A1 | 5/2013 | Wagner et al. |
| 2013/0184223 A1 | 7/2013 | Land et al. |
| 2013/0253036 A1 | 9/2013 | Collard et al. |
| 2013/0266560 A1 | 10/2013 | Demopulos et al. |
| 2013/0289092 A1 | 10/2013 | Rigo et al. |
| 2014/0011761 A1 | 1/2014 | Hotamisligil et al. |
| 2014/0128449 A1 | 5/2014 | Liu et al. |
| 2014/0154783 A1 | 6/2014 | Rossomando et al. |
| 2014/0186839 A1 | 7/2014 | Margulies et al. |
| 2014/0194610 A1 | 7/2014 | Verdine et al. |
| 2014/0235605 A1 | 8/2014 | Shiffman et al. |
| 2014/0309181 A1 | 10/2014 | Collard et al. |
| 2014/0336238 A1 | 11/2014 | Collin et al. |
| 2014/0343127 A1 | 11/2014 | Kammler |
| 2014/0349290 A1 | 11/2014 | Watnick et al. |
| 2014/0378526 A1 | 12/2014 | Rossi et al. |
| 2014/0378527 A1 | 12/2014 | Van |
| 2014/0378533 A1 | 12/2014 | Freier |
| 2015/0004217 A1 | 1/2015 | Guild et al. |
| 2015/0018540 A1 | 1/2015 | Prakash et al. |
| 2015/0184153 A1 | 7/2015 | Freier et al. |
| 2015/0211006 A1 | 7/2015 | Butler et al. |
| 2015/0211010 A1 | 7/2015 | Kerem et al. |
| 2015/0232845 A1 | 8/2015 | Ozsolak |
| 2015/0232858 A1 | 8/2015 | Ozsolak |
| 2015/0238516 A1 | 8/2015 | Dowdy et al. |
| 2015/0267192 A1 | 9/2015 | Heartlein et al. |
| 2015/0291957 A1 | 10/2015 | Smith |
| 2015/0329918 A1 | 11/2015 | Kang et al. |
| 2015/0337310 A1 | 11/2015 | Walker et al. |
| 2015/0361497 A1 | 12/2015 | Rose |
| 2016/0017322 A1 | 1/2016 | Vorechovsky et al. |
| 2016/0024500 A1 | 1/2016 | Popplewell et al. |
| 2016/0046935 A1 | 2/2016 | Bentwich et al. |
| 2016/0122767 A1 | 5/2016 | Gouya et al. |
| 2016/0201063 A1 | 7/2016 | Ozsolak |
| 2016/0201064 A1 | 7/2016 | Ozsolak |
| 2016/0208264 A1 | 7/2016 | Wilton et al. |
| 2016/0215291 A1 | 7/2016 | Garcia et al. |
| 2016/0244762 A1 | 8/2016 | Vorechovsky et al. |
| 2016/0244767 A1 | 8/2016 | Hastings |
| 2016/0298121 A1 | 10/2016 | Krainer et al. |
| 2017/0159049 A9 | 6/2017 | Krainer et al. |
| 2017/0240904 A1 | 8/2017 | Tallent et al. |
| 2018/0002694 A1 | 1/2018 | Vorechovsky et al. |
| 2018/0296501 A1 | 10/2018 | During |
| 2018/0362987 A1 | 12/2018 | Krainer et al. |
| 2018/0369275 A1 | 12/2018 | Arnarez et al. |
| 2019/0024118 A1 | 1/2019 | Tagliatela et al. |
| 2019/0024119 A1 | 1/2019 | Tagliatela et al. |
| 2019/0024120 A1 | 1/2019 | Tagliatela et al. |
| 2019/0024121 A1 | 1/2019 | Tagliatela et al. |
| 2019/0070213 A1 | 3/2019 | Aznarez et al. |
| 2019/0192691 A1 | 6/2019 | Barrett et al. |
| 2019/0218255 A1 | 7/2019 | Chung et al. |
| 2019/0225939 A1 | 7/2019 | Chambers et al. |
| 2019/0264211 A1 | 8/2019 | Vorechovsky et al. |
| 2020/0085838 A1 | 3/2020 | Martinez Botella et al. |
| 2020/0101174 A1 | 4/2020 | Coller et al. |
| 2020/0399640 A1 | 12/2020 | Gottesman et al. |
| 2021/0268667 A1 | 9/2021 | Aznarez et al. |
| 2023/0116704 A1 | 4/2023 | Aznarez et al. |
| 2023/0287410 A1 | 9/2023 | Aznarez et al. |

FOREIGN PATENT DOCUMENTS

| | | |
|---|---|---|
| EP | 0549615 A1 | 7/1993 |
| EP | 1281758 A2 | 2/2003 |
| EP | 1201678 B1 | 9/2004 |
| EP | 1409497 B1 | 1/2005 |
| EP | 1007714 B1 | 12/2005 |
| EP | 1334109 B1 | 5/2006 |
| EP | 1178999 B1 | 3/2007 |
| EP | 1203827 B1 | 5/2007 |
| EP | 1501848 B1 | 8/2007 |
| EP | 1569661 B1 | 9/2009 |
| EP | 1161439 B1 | 4/2010 |
| EP | 1984381 B1 | 9/2010 |
| EP | 1013661 B1 | 1/2012 |
| EP | 2092065 B1 | 1/2012 |
| EP | 2099461 B1 | 3/2012 |
| EP | 2170917 B1 | 6/2012 |
| EP | 2066684 B1 | 7/2012 |
| EP | 2284269 A3 | 8/2012 |
| EP | 2356129 B1 | 4/2013 |
| EP | 2376516 B1 | 4/2013 |
| EP | 2114981 B1 | 5/2013 |
| EP | 2149605 B1 | 7/2013 |
| EP | 2285819 B1 | 10/2013 |
| EP | 2161038 B1 | 12/2013 |
| EP | 1562971 B1 | 2/2014 |
| EP | 2295441 B1 | 5/2014 |
| EP | 2314594 B1 | 7/2014 |
| EP | 2410053 B1 | 10/2014 |
| EP | 2176280 B2 | 6/2015 |
| EP | 2361921 B1 | 6/2015 |
| EP | 2462153 B1 | 7/2015 |
| EP | 1015469 B2 | 11/2015 |
| EP | 2173760 B2 | 11/2015 |
| EP | 1937312 B1 | 6/2016 |
| EP | 2141233 B1 | 10/2016 |
| EP | 2410054 B1 | 1/2017 |
| EP | 3329909 A1 | 6/2018 |
| EP | 2753317 B1 | 2/2020 |
| GB | 2546719 A | 8/2017 |
| WO | WO-9402501 A1 | 2/1994 |
| WO | WO-9426887 A1 | 11/1994 |
| WO | WO-2005049651 A2 | 6/2005 |
| WO | WO-2006107846 A2 | 10/2006 |
| WO | WO-2007002390 A2 | 1/2007 |
| WO | WO-2007048628 A2 | 5/2007 |
| WO | WO-2007048629 A2 | 5/2007 |
| WO | WO-2009003694 A2 | 1/2009 |
| WO | WO-2009084472 A1 | 7/2009 |
| WO | WO-2010148249 A1 | 12/2010 |
| WO | WO-2011057350 A1 | 5/2011 |
| WO | WO-2012168435 A1 | 12/2012 |
| WO | WO-2012178146 A1 | 12/2012 |
| WO | WO-2013036105 A1 | 3/2013 |
| WO | WO-2013081755 A1 | 6/2013 |
| WO | WO-2013106770 A1 | 7/2013 |
| WO | WO-2013119916 A2 | 8/2013 |
| WO | WO-2014012081 A2 | 1/2014 |
| WO | WO-201428459 A1 | 2/2014 |
| WO | WO-2014028459 A1 | 2/2014 |
| WO | WO-2014031575 A1 | 2/2014 |
| WO | WO-2014049536 A2 | 4/2014 |
| WO | WO-2014121287 A2 | 8/2014 |
| WO | WO-2014172698 A1 | 10/2014 |
| WO | WO-2014201413 A1 | 12/2014 |
| WO | WO-2014209841 A2 | 12/2014 |
| WO | WO-2015024876 A2 | 2/2015 |
| WO | WO-2015035091 A1 | 3/2015 |
| WO | WO-2015190922 A1 | 12/2015 |
| WO | WO-2015193651 A1 | 12/2015 |
| WO | WO-2015198054 A1 | 12/2015 |
| WO | WO-2016022914 A1 | 2/2016 |
| WO | WO-2016027168 A2 | 2/2016 |
| WO | WO-2016054615 A2 | 4/2016 |
| WO | WO-2016061509 A1 | 4/2016 |
| WO | WO-2016077837 A1 | 5/2016 |
| WO | WO-2016087842 A1 | 6/2016 |
| WO | WO-2016118697 A1 | 7/2016 |
| WO | WO-2016128343 A1 | 8/2016 |
| WO | WO-2016138534 A2 | 9/2016 |
| WO | WO-2016161429 A1 | 10/2016 |
| WO | WO-2016196386 A1 | 12/2016 |
| WO | WO-2017053982 A1 | 3/2017 |
| WO | WO-2017060731 A1 | 4/2017 |
| WO | WO-2017106210 A1 | 6/2017 |
| WO | WO-2017106211 A1 | 6/2017 |

(56) References Cited

FOREIGN PATENT DOCUMENTS

| | | |
|---|---|---|
| WO | WO-2017106283 A1 | 6/2017 |
| WO | WO-2017106292 A1 | 6/2017 |
| WO | WO-2017106364 A2 | 6/2017 |
| WO | WO-2017106370 A1 | 6/2017 |
| WO | WO-2017106375 A1 | 6/2017 |
| WO | WO-2017106377 A1 | 6/2017 |
| WO | WO-2017106382 A1 | 6/2017 |
| WO | WO-2018187363 A1 | 10/2018 |
| WO | WO-2018191482 A2 | 10/2018 |
| WO | WO-2018206924 A1 | 11/2018 |
| WO | WO-2019040923 A1 | 2/2019 |
| WO | WO-2019084050 A1 | 5/2019 |
| WO | WO-2019109051 A1 | 6/2019 |
| WO | WO-2019191341 A1 | 10/2019 |
| WO | WO-2019199867 A1 | 10/2019 |
| WO | WO-2019227096 A1 | 11/2019 |
| WO | WO-2019236750 A2 | 12/2019 |
| WO | WO-2019243430 A1 | 12/2019 |
| WO | WO-2020041348 A1 | 2/2020 |

OTHER PUBLICATIONS

Altschul et al.: Iterated profile searches with PSI-BLAST—a tool for discovery in protein databases. J. Mol. Biol. 215:403-410 (1990).
Aly et al.: Extreme genetic risk for type 1A diabetes. Proc Natl Acad Sci U.S.A. 103(38):14074-9 (2006). Epub Sep. 11, 2006.
Amarnath et al.: The PDL1-PD1 Axis Converts Human TH1 Cells into Regulatory T Cells. Science Translational Medicine 3(111):1-13 (2011).
Anders et al.: Detecting differential usage of exons from RNA-seq data. Genome Res. 22(10):2008-17 (2012). Epub Jun. 23, 2012. doi: gr.133744.111 [pii] 10.1101/gr.133744.111. PubMed PMID: 22722343.
Au et al.: Molecular Genetic Basis of Tuberous Sclerosis Complex: From Bench to Bedside. Journal of Child Neurology 19:9 (2004).
Audentes Therapeutics Announces Expansion of AAV Technology Platform and Pipeline with New Development Programs for Duchenne Muscular Dystrophy and Myotonic Dystrophy. PRNewswire Apr. 8, 2019 (7 pgs).
Aznarez et al.: TANGO-Targeted augmentation of nuclear gene output—for the treatment of genetic diseases [abstract]. In: 2018 Annual Meeting Abstract of the American Society of Gene and Cell Therapy, May 16-19, 2018, Chicago, IL (2018), Abstract No. 304.
Bakkenist et al.: DNA damage activates ATM through intermolecular autophosphorylation and dimer dissociation. Nature 421(6922):499-506 (2003). doi: 10.1038/nature01368. PubMed PMID: 12556884.
Balagurumoorthy et al.: Hairpin and parallel quartet structures for telomeric sequences. Nucleic Acids Res. 20(15):4061-7 (1992).
Balkwill et al.: Repression of translation of human estrogen receptor alpha by G-quadruplex formation. Biochemistry 48(48):11487-95 (2009). doi: 10.1021/bi901420k.
Barratt et al.: Remapping the insulin gene/IDDM2 locus in type 1 diabetes. Diabetes 53(7):1884-9 (2004).
Bassi et al.: A novel mutation in the ATP1A2 gene causes alternating hemiplegia of childhood. J. Med. Genet. 41:621-628 (2004).
Battistini et al.: A new CACNA1A gene mutation in acetazolamide-responsive familial hemiplegic migraine and ataxia. Neurology 53(1):38-43 (1999).
Baughan et al.: Delivery of bifunctional RNAs that target an intronic repressor and increase SMN levels in an animal model of spinal muscular atrophy. Hum Mol Genet. 18(9):1600-11 (2009). doi: 10.1093/hmg/ddp076. Epub Feb. 19, 2009.
Bauman et al.: Therapeutic potential of splice-switching oligonucleotides. Oligonucleotides 19.1:1-13 (2009).
Beaudoin et al.: 5'-UTR G-quadruplex structures acting as translational repressors. Nucleic Acids Res. 38(20):7022-36 (2010). doi: 10.1093/nar/gkq557. Epub Jun. 22, 2010.
Beli et al.: Proteomic investigations reveal a role for RNA processing factor THRAP3 in the DNA damage response. Mol Cell.
46(2):212-25 (2012). doi: 10.1016/j.molcel.2012.01.026. PubMed PMID: 22424773; PubMed Central PMCID: PMC3565437.
Berge et al.: Pharmaceutical Salts. J. Pharmaceutical Sciences 66(1):1-19 (1977).
Berger et al.: The molecular basis of human retinal and vitreoretinal diseases. Progress in Retinal and Eye Research 29:335-375 (2010).
Bethke et al.: Comprehensive analysis of the role of DNA repair gene polymorphisms on risk of glioma. Hum Mol Genet. 17(6):800-5 (2008). Epub Dec. 1, 2007.doi: ddm351 [pii] 10.1093/hmg/ddm351. PubMed PMID: 18048407.
Bicknell et al.: Introns in UTRs: why we should stop ignoring them. Bioessays 34(12):1025-34 (2012). doi: 10.1002/bies.201200073. Epub Oct. 26, 2012.
Blencowe, Benjamin: Reflections for the 20th anniversary issue of RNA journal. RNA Journal 21(4):573-575 (2015).
Blencowe BJ: Splicing regulation: the cell cycle connection. Curr. Biol. 13(4):R149-51 (2003). PubMed PMID: 12593819.
Bolognini et al.: Characterization of two novel intronic OPA1 mutations resulting in aberrant pre-mRNA splicing. BMC Medical Genetics 18:22 (2017).
Bonifert et al.: Antisense Oligonucleotide Mediated Splice Correction of a Deep Intronic Mutation in OPA1. Molecular Therapy—Nucleic Acids, vol. 5 (2016).
Bonifert et al.: Pure and syndromic optic atrophy explained by deep intronic OPA1 mutations and an intralocus modifier. Brain 137(8):2164-2177 (2014).
Bonnen et al.: Haplotypes at ATM identify coding-sequence variation and indicate a region of extensive linkage disequilibrium. Am J Hum Genet. 67(6):1437-51 (2000). Epub Nov. 15, 2000.doi: S0002-9297(07)63213-3 [pii] 10.1086/316908. PubMed PMID: 11078475.
Boothby et al.: Removal of Retained Introns Regulates Translation in the Rapidly Developing Gametophyte of Marsilea vestita. Developmental Cell 24:517-529 (2013).
Booy et al.: The RNA helicase Rhau (DHX36) unwinds a G4-quadruplex in human telomerase RNA and promotes the formation of the P1 helix template boundary. Nucleic Acids Res. (9):4110-24 (2012). doi: 10.1093/nar/gkr1306. Epub Jan. 11, 2012.
Boutz et al.: Detained introns are a novel, widespread class of post-transcriptionally spliced introns. Genes Dev. 29(1):63-80 (2015). doi: 10.1101/gad.247361.114.
Braunschweig et al.: Widespread intron retention in mammals functionally tunes transcriptomes. Widespread intron retention in mammals functionally tunes transcriptomes. Genome Res. 24(11):1774-86 (2014). doi: 10.1101/gr.177790.114. Epub Sep. 25, 2014.
Bravo-Gil et al.: Improving the management of Inherited Retinal Dystrophies by targeted sequencing of a population-specific gene panel. Scientific Reports 6:23910, 10 pages (2015).
Brooks et al.: A pan-cancer analysis of transcriptome changes associated with somatic mutations in U2AF1 reveals commonly altered splicing events. PLoS One. 9(1):e87361 (2014). Epub Feb. 6, 2014.doi: 10.1371/journal.pone.0087361 PONE-D-13-26905 [pii]. PubMed PMID: 24498085.
Buchman et al.: Comparison of intron-dependent and intron-independent gene expression. Mol Cell Biol. 8(10):4395-405 (1988).
Buckley et al.: Cytoplasmic intron retention, function, splicing, and the sentinel RNA hypothesis.WIREs RNA 5:223-2330 (2014).
Bugaut et al.: 5'-UTR RNA G-quadruplexes: translation regulation and targeting. Nucleic Acids Res. 40(11):4727-41 (2012). doi: 10.1093/nar/gks068. Epub Feb. 20, 2012.
Bugaut et al.: An RNA hairpin to G-quadruplex conformational transition. J Am Chem Soc. 134(49):19953-6 (2012). doi: 10.1021/ja308665g. Epub Nov. 29, 2012.
Buratti et al.: DBASS3 and DBASS5: databases of aberrant 3'- and 5'-splice sites. Nucleic Acids Res. 39(Database issue):D86-91 (2011). doi: 10.1093/nar/gkq887. Epub Oct. 6, 2010.
Buratti et al.: RNA folding affects the recruitment of SR proteins by mouse and human polypurinic enhancer elements in the fibronectin EDA exon. Mol Cell Biol. 24(3):1387-400 (2004).
Burnette et al.: Subdivision of large introns in *Drosophila* by recursive splicing at non-exonic elements. Genetics (2005).

(56) References Cited

OTHER PUBLICATIONS

Burns et al.: Connections between pre-mRNA processing and regulation of the eukaryotic cell cycle. Front Horm Res. 25:59-82 (1999).
Buschmann et al.: Chitosans for delivery of nucleic acids. Advanced drug delivery reviews 65.9:1234-1270 (2013).
Busslinger et al.: β Thalassemia: Aberrant splicing results from a single point mutation in an intron. Cell 27.2:289-298 (1981).
Callis et al. Introns increase gene expression in cultured maize cells. Genes Dev. 1(10):1183-200 (1987).
Catterall et al.: Nav1.1 channels and epilepsy. J Physiol. 1;588(Pt 11):1849-59 (2010).
Cavaloc et al.: The splicing factors 9G8 and SRp20 transactivate splicing through different and specific enhancers. RNA 5(3):468-83 (1999).
Cazzola et al.: Translational pathophysiology: a novel molecular mechanism of human disease. Blood 95(11):3280-8 (2000).
Chambers et al.: The INO80 chromatin remodeling complex prevents polyploidy and maintains normal chromatin structure at centromeres. Genes Dev. 26(23):2590-603 (2012). Epub Dec. 5, 2012.doi: 26/23/2590 [pii] 10.1101/gad.199976.112. PubMed PMID: 23207916.
Chen et al.: A functional single nucleotide polymorphism in promoter of ATM is associated with longevity. Mech Ageing Dev. 131:636-40 (2010).
Chen et al.: Chk1 kinase negatively regulates mitotic function of Cdc25A phosphatase through 14-3-3 binding. Mol Cell Biol. 23(21):7488-97 (2003). PubMed PMID: 14559997; PubMed Central PMCID: PMC207598.
"Schimpf, S. et al., "Activation of cryptic splice sites is a frequent splicing defect mechanism caused by mutations in exon and intron sequences of the OPA1 gene," Human Genetics, 2006, vol. 118, No. 6, pp. 767-771".
Choi et al.: CHK2 kinase promotes pre-mRNA splicing via phosphorylating CDK11p110. Oncogene 33:108-15 (2014).
Colla et al.: Telomere dysfunction drives aberrant hematopoietic differentiation and myelodysplastic syndrome. Cancer Cell. 27(5):644-57 (2015). doi: 10.1016/j.ccell.2015.04.007. PubMed PMID: 25965571.
Collie et al.: The application of DNA and RNA G-quadruplexes to therapeutic medicines. Chem Soc Rev. 40(12):5867-92 (2011). doi: 10.1039/c1cs15067g. Epub Jul. 25, 2011.
Collin et al.: Antisense Oligonucleotide (AON)-based Therapy for Leber Congenital Amaurosis caused by a Frequent Mutation in CEP290. Molecular Therapy—Nucleic Acids, pp. 1-7 (2012).
Consortium. TGP. An integrated map of genetic variation from 1,092 human genomes. Nature (London). 491:56-65 (2012).
Corallini et al.: Transcriptional and Posttranscriptional Regulation of the CTNS Gene. Pediatric Research 70(2):130-135 (2011).
Corey et al.: A non-classical translocation involving 17q12 (retinoic acid receptor alpha) in acute promyelocytic leukemia (APML) with atypical features. Leukemia 8(8):1350-3 (1994). PubMed PMID: 8057672.
Cornille et al.: Reversible optic neuropathy with OPA1 exon 5b mutation. Annals of Neurology 63(5):667-671 (2008).
Corvelo et al.: Genome-wide association between branch point properties and alternative splicing. PLoS Comput Biol. 6(11):e1001016 (2010). Epub Dec. 3, 2010.doi: 10.1371/journal.pcbi.1001016. PubMed PMID: 21124863.
Coulombe-Huntington et al.: Fine-Scale Variation and Genetic Determinants of Alternative Splicing across Individuals. PLoS Genet. 5(12):e1000766 (2009). Epub Dec. 17, 2009.doi: 10.1371/journal.pgen.1000766. PubMed PMID: 20011102.
Coutinho et al.: Functional significance of a deep intronic mutation in the ATM gene and evidence for an alternative exon 28a. Hum Mutat. 25(2):118-24 (2005). Epub Jan. 12, 2005.doi: 10.1002/humu.20170. PubMed PMID: 15643608.
Creacy, et al. G4 resolvase 1 binds both DNA and RNA tetramolecular quadruplex with high affinity and is the major source of tetramolecular quadruplex G4-DNA and G4-RNA resolving activity in HeLa cell lysates. J Biol Chem. 283(50):34626-34 (2008). doi: 10.1074/jbc.M806277200. Epub Oct. 7, 2008.
Creson et al.: Re-expression of SynGAP Protein in Adulthood Improves Translatable Measures of Brain Function and Behavior in a Model of Neurodevelopmental Disorders. Departments of Neuroscience and Molecular medicine, The Scripps Research Institute (2018).
Culler et al.: Functional selection and systematic analysis of intronic splicing elements identify active sequence motifs and associated splicing factors. Nucleic Acids Res. 38(15):5152-65 (2010). doi: 10.1093/nar/gkq248. Epub Apr. 12, 2010.
Database Geneseq [Online],Nov. 13, 2008 (Nov. 13, 2008), Dual label detection probe, QF probe 1, 5. 3.11, XP055572852, retrieved from EBI Accession No. GSN:ARK21623.
Davies et al.: A genome-wide search for human type 1 diabetes susceptibility genes. Nature 8;371(6493):130-6 (1994).
Decorsiere et al.: Essential role for the interaction between hnRNP H/F and a G quadruplex in maintaining p53 pre-mRNA 3'-end processing and function during DNA damage. Genes Dev. 25(3):220-5 (2011). doi: 10.1101/gad.607011.
Dedic et al.: Alagille Syndrome Mimicking Biliary Atresia in Early Infancy, PLOS OOne, 10(11):e0143939: pp. 1-7 (2015).
Deere et al.: AntisensePhosphorodiamidate Morpholino OligomerLengthand TargetPositionEffects on Gene-SpecificInhibitionin *Escherichia coli*. Antimicrobial Agents Andchemotherapy 49(1):249-255 (2005).
Del Dotto et al.: OPA1 Isoforms in the Hierarchical Organization of Mitochondrial Functions. Cell Reports 19(12):2557-2571 (2017).
Derecka et al.: Occurrence of a quadruplex motif in a unique insert within exon C of the bovine estrogen receptor alpha gene (ESR1). Biochemistry 49(35):7625-33 (2010). doi: 10.1021/bi100804f.
Dias et al.: Antisense oligonucleotides: basic concepts and mechanisms Mol. Cancer Ther. 1:347-355 (2002).
Didiot et al.: The G-quartet containing FMRP binding site in FMR1 mRNA is a potent exonic splicing enhancer. Nucleic Acids Res. Sep. 2008;36(15):4902-12. doi: 10.1093/nar/gkn472. Epub Jul. 24, 2008.
Ding, H. et al. DeliveringPD-1 inhibitory signal concomitant with blocking ICOS co-stimulation suppresses lupus-like syndrome in autoimmune BXSB mice.Clinical Immunology, vol. 118, pp. 258-267, (2006).
Divina, P. et al. Ab initio prediction of cryptic splice-site activation and exon skipping. Eur J Hum Genet. 2009; 17:759-65.
Dominski, et al. Restoration of correct splicing in thalassemic pre-mRNA by antisense oligonucleotides. Proc Natl Acad Sci U S A. Sep. 15, 1993;90(18):8673-7.
Dredge, et al. NeuN/Rbfox3 Nuclear and Cytoplasmic Isoforms Differentially Regulate Alternative Splicing and Nonsense-Mediated Decay of Rbfox2. PLoS One. 2011; 6(6): e21585.
Du, et al. "Correction of prototypic ATM splicing utations and aberrant ATM function with antisense morpholino oligonucleotides" (2007) PNAS, vol. 104, No. 14, pp. 6007-6012.
Ducros et al.Recurrence of the T666M calcium channel CACNA1A gene mutation in familial hemiplegic migraine with progressive cerebellar ataxia.Am J Hum Genet. vol. 64, No. 1, pp. 89-98 (Jan. 1999).
Duikers, et al. "Antisense Oligonucleotide-Based Splicing Correction in Individuals with Leber Congenital Amaurosis due to Compound Heterozygosity for the c.2991+1655AG Mutation in CEP290" (2018) International Journal of Molecular Sciences, 19, 753, pp. 1-12.
Dulla, et al., "Splice-Modulating Oligonucleotide QR-110 Restores CEP290 mRNA and Function in Human c.2991+1655AG LCA10 Models" (2018) Molecular Therapy: Nucleic Acids, vol., pp. 730-740.
Duryagina R, et al. Overexpression of Jagged-1 and its intracellular domain in human mesenchymal stromal cells differentially affect the interaction with hematopoietic stem and progenitor cells. Stem Cells Dev. vol. 22, No. 20, pp. 2736-2750 (2013).
Dutertre, M., et al. et al. DNA damage: RNA-binding proteins protect from near and far. Trends Biochem Sci. 2014; 39(3):141-9. Epub Feb. 19, 2014.doi: S0968-0004(14)00015-2 [pii] 10.1016/j.tibs.2014.01.003. PubMed PMID: 24534650.

(56) References Cited

OTHER PUBLICATIONS

Eddy, et al. G4 motifs correlate with promoter-proximal transcriptional pausing in human genes. Nucleic Acids Res. Jul. 2011;39(12):4975-83. doi: 10.1093/nar/gkr079. Epub Mar. 3, 2011.
El Bougrini et al.: PML positively regulates interferon gamma signaling. Biochimie. 2011; 93(3):389-98. doi: 10.1016/j.biochi. 2010.11.005. PubMed PMID: 21115099.
Emerick, et al. Multivariate analysis and visualization of splicing correlations in single-gene transcriptomes. BMC Bioinformatics. Jan. 18, 2007;8:16.
EP 15846242.4 Partial Supplementary Search Report and Search Opinion dated May 2, 2018.
EP 16876621.0 Extended European Search Report and Search Opinion dated Mar. 7, 2019.
EP15729929.8 Office Action dated Dec. 22, 2017.
EP15729929.8 Office Action dated Oct. 30, 2018.
EP15846242.4 Extended European Search Report dated Aug. 21, 2018.
EP16781187.6 Office Action dated May 20, 2019.
EP16876499.1 Extended Search Report dated Jun. 14, 2019.
EP168766061.1 Extended Search Report dated May 24, 2019.
Fairbrother, W.G., et al. Predictive identification of exonic splicing enhancers in human genes. Science. 2002; 297(5583):1007-13. PubMed PMID: 12114529.
Fededa, et al. A polar mechanism coordinates different regions of alternative splicing within a single gene. Mol Cell. Aug. 5, 2005;19(3):393-404.
Ferreira, P.G., et al.: Transcriptome characterization by RNA sequencing identifies a major molecular and clinical subdivision in chronic lymphocytic leukemia. Genome Res. 2014; 24:212-26.
Fletcher, Sue et al. Antisense suppression of donor splice site mutations in the dystrophin gene transcript.Molecular Genetics & Genomic Medicine, vol. 1, No. 3, pp. 162-173, Jun. 13, 2013.
Fred et al.: The human insulin mRNA is partly translated via a cap- and eIF4A-independent mechanism. Biochem Biophys Res Commun. Sep. 9, 2011;412(4):693-8. doi: 10.1016/j.bbrc.2011.08.030. Epub Aug. 16, 2011.
Friedman, et al., "Correction of Aberrant Splicing of the Cystic Fibrosis Transmembrane conductance Regulator (CFTR) Gene by Antisense Oligonucleotides" (1999) The Journal of Biological Chemistry, vol. 274, No. 51, pp. 36193-36199.
Friend, KL et al. Detection of a novel missense mutation and second recurrent mutation in the CACNA1A gene in individuals with EA-2 and FHM. Hum Genet. vol. 105(3):261-5 (Sep. 1999).
Furukawa & Kish 2008, GeneReviews Pagon Ra et al. eds. Univ. of WA Seattle, NCBI Bookshelf ID NBK1437.
Galante, et al.: Detection and evaluation of intron retention events in the human transcriptome. RNA. May 2004;10(5):757-65.
"Gallus, G. N. et al., "Alu-element insertion in an OPA1 intron sequence associated with autosomal dominant optic atrophy," Molecular vision, 2010, vol. 16, pp. 178-183".
Garanto, et al., "In vitro and in vivo rescue of aberrant splicing in CEP290-associted LCA by antisense oligonucleotide delivery" (2016) Human Molecular Genetics, vol. 25, No. 12, pp. 2552-2563.
Garner, et al. Selectivity of small molecule ligands for parallel and anti-parallel DNA G-quadruplex structures. Org Biomol Chem. Oct. 21, 2009;7(20):4194-200. doi: 10.1039/b910505k. Epub Aug. 14, 2009.
Geary et al.: Absolute Bioavailability of 29-O-(2-Methoxyethyl)-Modified Antisense Oligonucleotides following Intraduodenal Instillation in Rats. J Pharmacal Exp Ther. vol. 296, No. 3, pp. 898-904 (Mar. 2001).
Geary, et al., "Pharmacokinetics, biodistribution and cell uptake of antisense oligonucleotides", (2015) Advance Drug Delivery Reviews.
Geary, RS, et al., Pharmacokinetic properties of 2'-O-(2-methoxyethyl)-modified oligonucleotide analogs in ratsJ Pharmacal Exp Ther. vol. 296, No. 3, pp. 890-897 (Mar. 2001).

Gerard, et al., "AON-mediated Exon Skipping Restores ciliation in Fibroblasts Harboring the Common Leber Congenital Amaurosis CEP290 Mutation" (2012) Molecular Therapy—Nucleic Acids, pp. 1-9.
Gianchecchi et al. Recent insights into the role of the PD-1/PD-L1 pathway in immunological tolerance and autoimmunity. Autoimmunity Reviews 12:1091-1100 (2013).
Gibson, G.: Hints of hidden heritability in GWAS. Nat Genet. 2010; 42(7):558-60. Epub Jun. 29, 2010.doi: ng0710-558 [pii] 10.1038/ng0710-558. PubMed PMID: 20581876.
Gohring, J. et al. Imaging of Endogenous MessengerRNA Splice Variants in Living Cells Reveals Nuclear Retention of Transcripts Inaccessible to Nonsense-Mediated Decay in *Arabidopsis*. The Plant Cell.vol. 26, pp. 754-764.(Feb. 2014).
Gomes et al. Translating chitosan to clinical delivery of nucleic acid-based drugs. MRS bulletin 39.1 (2014): 60-70.
Gomez, et al. Telomerase downregulation induced by the G-quadruplex ligand 12459 in A549 cells is mediated by hTERT RNA alternative splicing. Nucleic Acids Res. Jan. 16, 2004;32(1):371-9. Print 2004.
Goncharova et al. Tuberin regulates p70 S6 kinase activation and ribosomal protein S6 phosphorylation. A role for the TSC2 tumor suppressor gene in pulmonary lymphangioleiomyomatosis (LAM). J. Biol. Chem. (Aug. 23, 2002) 277(34);30958-67. EPub Jun. 3, 2002.
Gonzalez-Santos, et al., Mutation in the splicing factor Hprp3p linked to retinitis pigmentosa impairs interactions within the U4/U6 snRNP pigmentosa impairs interactions within the U4/U6 snRNP complex, PubMed Central Canada , Author Manuscript, 29 pages.
Goto, et al., "Targeted skipping of a Single Exon Harboring a Premature termination Codon Mutation: Implications and Potential for Gene Correction Therapy for Selective Dystrophic Epidermolysis Bullosa Patients" (2006) Journal of Investigative Dermatology, vol. 126, pp. 2614-262.
Goyenvalie et al.: Therapeutic approaches to muscular dystrophy. Hum Mol Genet. Apr. 15, 2011;20(R1):R69-78. doi: 10.1093/hmg/ddr105. Epub Mar. 24, 2011.
Gozani, O., et al.: A potential role for U2AF-SAP 155 interactions in recruiting U2 snRNP to the branch site. Mol Cell Biol. 1998; 18(8):4752-60. PubMed PMID: 9671485.
Graveley, B.R. The haplo-spliceo-transcriptome: common variations in alternative splicing in the human population. Trends Genet. 2008; 24(1):5-7. Epub Dec. 7, 2007.doi: S0168-9525(07)00349-6 [pii] 10.1016/j.tig.2007.10.004. PubMed PMID: 18054116.
Gutell, R.R., et al. A story: unpaired adenosine bases in ribosomal RNAs. J Mol Biol. 2000; 304(3):335-54. Epub Nov. 25, 2000.doi: 10.1006/jmbi.2000.4172 S0022-2836(00)94172-X [pii]. PubMed PMID: 11090278.
Guth, S., et al. Dual function for U2AF(35) in AG-dependent pre-mRNA splicing. Mol Cell Biol. 2001;21(22):7673-81. PubMed PMID: 11604503.
Guy et al. A mouse Mecp2-null mutation causes neurological symptoms that mimic Rett syndrome. Nat Genet 27:322-326 (2001).
Hai, et al.: A G-tract element in apoptotic agents-induced alternative splicing. Nucleic Acids Res. Jun. 2008;36(10):3320-31. doi: 10.1093/nar/gkn207. Epub Apr. 24, 2008.
"Hamdan, et al., "Mutations in SYNGAP1 in autosomal nonsyndromic mental retardation," New England Journal of Medicine, 2009, vol. 360, No. 6, pp. 599-605".
Hamdan, F. F. et al. De Novo SYNGAP1 Mutations in Nonsyndromic Intellectual Disability and Autism, Biol. Psychiatry, 69:898-901 (2011).
Hammond, et al."Genetic therapies for RNA mis-splicing diseases" (2011) Cell Press 10 pages.
Han, et al., "Antisense oligonucleotides increase Scn1 a expression and reduce seizures and SUDEP incidence in a mouse model of Dravet syndrome" (2020) Science Translational Medicine, 12, pp. 1-14.
Han, et al. TANGO-Targeted augmentation of nuclear gene output for the treatment of genetic diseases. Poster session presented at the American Society of Gene and Cell Therapy, Chicago, IL. (May 2018).

(56) References Cited

OTHER PUBLICATIONS

Hargous, et al. Molecular basis of RNA recognition and TAP binding by the SR proteins SRp20 and 9G8. EMBO J. Nov. 1, 2006;25(21):5126-37. Epub Oct. 12, 2006.
Harkin, et al. The spectrum of SCN1A-related infantile epileptic encephalopathies. Brain. Mar. 2007; 130(Pt 3):843-52.
Hastings, M.L., et al. Control of pre-mRNA splicing by the general splicing factors PUF60 and U2AF. PLoS One. 2007;2:e538. PubMed PMID: 17579712.
Havens, et al., "Targeting RNA Splicing fo rDisease Therapy" (2013) Wiley Interdiscip Rev RNA , 4(3): 247-266.
He, Y.H., et al. Association of the insulin-like growth factor binding protein 3 (IGFBP-3) polymorphism with longevity in Chinese nonagenarians and centenarians. Aging (Milano). 2014;6:944-56.
Hegele et al.: Dynamic protein-protein interaction wiring of the human spliceosome. Mol Cell. Feb. 24, 2012;45(4):567-80. doi: 10.1016/j.molcel.2011.12.034.
Hernan, I. et al. : Cellular Expression and siRNA-Mediated Interference of Rhodopsin cis-Acting Splicing Mutants Associated with Autosomal Dominant Retinitis Pigmentosa, Invest Ophthalmol. Vis. Sci. (2011) 52:3723-3729.
Heyn, P. et al.: Introns and gene expression: Cellular constraints, transcriptional regulation, and evolutionary consequences. Bioessays vol. 37, pp. 148-154 (2014).
Hiller et al. Pre-mRNA secondary structures influence exon recognition. PLoS genetics 3.11 (2007): e204.
Hirata et al.Prevention of Experimental Autoimmune Encephalomyelitis by Transfer of Embryonic Stem Cell-Derived Dendritic Cells Expressing Myelin Oligodendrocyte Glycoprotein Peptide along with TRAIL or Programmed Death-1 Ligand.J. Immunology vol. 174 pp. 1888-1897 (2005).
Hishida, A. et al.: Polymorphisms in PPAR Genes (PPARD, PPARG, and PPARGC1A) and the Risk of Chronic Kidney Disease in Japanese: Cross-Sectional Data from the J-MICC Study. PPAR 2013; 980471 pp. 1-8.
*Homo sapiens* pre-mRNA processing factor 3 (PRPF3), mRNA, NCBI Reference Sequence: NM_004698.2 Accessed Apr. 6, 2017.
Hua, et al.: Antisense correction of SMN2 splicing in the CNS rescues necrosis in a type III SMA mouse model. Genes Dev. Aug. 1, 2010;24(15):1634-44. doi: 10.1101/gad.1941310. Epub Jul. 12, 2010.
Hua et al.: Antisense masking of an hnRNP A1/A2 intronic splicing silencer corrects SMN2 splicing in transgenic mice. Am. J. Hum. Genet. 82:834-848 (Mar. 27, 2008).
Hua, Y., et al. Enhancement of SMN2 exon 7 inclusion by antisense oligonucleotides targeting the exon. PLOS Biol. 2007;5(4):e73. Epub Mar. 16, 2007.doi: 06-PLBI-RA-1492R3 [pii] 10.1371/journal.pbio.0050073. PubMed PMID: 17355180.
Hunt, et al. Negligible impact of rare autoimmune-locus coding-region variants on missing heritability. Nature. Jun. 13, 2013;498(7453):232-5. doi: 10.1038/nature12170. Epub May 22, 2013.
Huynh, K.D., et al. BCoR, a novel corepressor involved in BCL-6 repression. Genes Dev. 2000;14(14):1810-23. PubMed PMID: 10898795; PubMed Central PMCID: PMC316791.
International Application No. PCT/GB2015/051756 International Preliminary Report on Patentability, dated Dec. 26, 2016.
International Application No. PCT/GB2015/051756 International Search Report and Written Opinion dated Nov. 30, 2015.
International Application No. PCT/GB2016/053136 International Search Report and Written Opinion dated Mar. 6, 2017.
International Application No. PCT/GB2016/053136 Partial International Search Report dated Jan. 19, 2017.
International Application No. PCT/US16/66576 International Search Report and Written Opinion dated May 4, 2017.
International Application No. PCT/US16/66691 International Search Report and Written Opinion dated May 10, 2017.
International Application No. PCT/US16/66708 International Search Report and Written Opinion dated May 8, 2017.
International Application No. PCT/US16/66721 International Search Report and Written Opinion dated May 1, 2017.
International Application No. PCT/US2015/053896 International Preliminary Report on Patentability dated Apr. 4, 2017.
International Application No. PCT/US2015/53896 International Search Report and Written Opinion dated Mar. 3, 2016.
International Application No. PCT/US2016/066414 International Search Report and Written Opinion dated Apr. 19, 2017.
International Application No. PCT/US2016/066417 International Search Report and Written Opinion dated Apr. 19, 2017.
International Application No. PCT/US2016/066564 International Search Report and Written Opinion dated May 4, 2017.
International Application No. PCT/US2016/066705 International Search Report and Written Opinion dated Apr. 24, 2017.
International Application No. PCT/US2018/048031 International Search Report and Written Opinion dated Jan. 22, 2019.
International Preliminary Report on Patentability issued in PCT/US2021/030254, dated Nov. 15, 2022.
International search report and written opinion dated Jun. 5, 2017 for PCT Application No. PCT/US2016/066684.
International Search Report and Written Opinion issued in PCT/US2021/030254, dated Jul. 28, 2021.
International Search Report and Written Opinion dated Mar. 28, 2019 for PCT/US2018/057165.
Itoh et al.: Methyl CpG-binding Protein Isoform MeCP2_e2 is Dispensable for Rett Syndrome Phenotypes but Essential for Embryo Viability and Placenta Development. J Biol Chem 287:13859-13867 (2012).
Iwamoto, et al.: Transcription-dependent nucleolar cap localization and possible nuclear function of DExH RNA helicase RHAU. Exp Cell Res. Apr. 1, 2008;314(6):1378-91. doi: 10.1016/j.yexcr.2008.01.006. Epub Jan. 16, 2008.
Jacob et al.: Intron retention as a component of regulated gene expression programs. Hum Genet 136:1043-1057 (2017).
Jarver, P. et al., "A Chemical View of Oligonucleotides for Exon Skipping and Related Drug Applications," Nucleic Acid Therapeutics, 2014, vol. 24, No. 1, pp. 37-47.
Jearawiriyapaisarn et al. Sustained Dystrophin Expression Induced by Peptide-conjugated Morpholino Oligomers in the Muscles of mdx Mice. Mol Ther. 16(9): 1624-1629 (2008).
Jurka et al. Identification of new medium reiteration frequency repeats in the genomes of Primates, Rodentia and Lagomorpha. Genetica98.3 (1996): 235-247.
Jurkiewicz, D. et al.: Spectrum of JAG1 gene mutations in Polish patients with Alagille syndrome J. Appl. Genetics vol. 55, pp. 329-336, (2014).
Kach et al. A novel antisense oligonucleotide approach to treat eye diseases by increasing target gene expression. No. 3423-A0194 ARVO Poster Apr. 19, 2019 (1 pg.).
"Kamakari, S. et al., "First report of OPA1 screening in Greek patients with autosomal dominant optic atrophy and identification of a previously undescribed OPA1 mutation," Molecular Vision, 2014, vol. 20, pp. 691-703".
Kaminker, P.G., et al. A novel form of the telomere-associated protein TIN2 localizes to the nuclear matrix. Cell Cycle. 2009;8(6):931-9. PubMed PMID: 19229133; PubMed Central PMCID: PMC2751576.
Kang et al. Up-regulation of luciferase gene expression with antisense oligonucleotides: implications and applications in functional assay development. Biochemistry 37.18 (1998): 6235-6239.
Kaplan et al. Medium reiteration frequency repetitive sequences in the human genome. Nucleic acids research 19.17 (1991): 4731-4738.
Katsani, K.R. et al.: Functional Genomics Evidence Unearths New Moonlighting Roles of Outer Ring Coat Nucleoporins Scientific Reports vol. 4, No. 4655 (Apr. 11, 2014).
Kawamata, N., et al. Genetic differences between Asian and Caucasian chronic lymphocytic leukemia. Int J Oncol. 2013;43(2):561-5. doi: 10.3892/ijo.2013.1966. PubMed PMID: 23708256; PubMed Central PMCID: PMC3775563.
Ke, et al.: Quantitative evaluation of all hexamers as exonic splicing elements. Genome Res. Aug. 2011;21(8):1360-74. doi: 10.1101/gr.119628.110. Epub Jun. 9, 2011.

(56) References Cited

OTHER PUBLICATIONS

Keir, M.E. et al.: PD-1 and Its Ligands in Tolerance and Immunity. Annu. Rev. Immunol. vol. 26, pp. 677-704 (2008).

Kervestin et al. NMD: a multifaceted response to premature translational termination. Nature reviews Molecular cell biology13.11 (2012): 700.

Kikin, et al.: QGRS Mapper: a web-based server for predicting G-quadruplexes in nucleotide sequences. Nucleic Acids Res. Jul. 1, 2006;34(Web Server issue):W676-82.

Kim, E., et al. SRSF2 Mutations Contribute to Myelodysplasia by Mutant-Specific Effects on Exon Recognition. Cancer Cell. 2015;27(5):617-30. doi: 10.1016/j.ccell.2015.04.006. PubMed PMID: 25965569; PubMed Central PMCID: PMC4429920.

Kim et al.: ChimerDB 2.0—a knowledgebase for fusion genes updated. Nucleic Acids Res. 2009;38(Database issue):D81-5. Epub Nov. 13, 2009.doi: gkp982 [pii] 10.1093/nar/gkp982. PubMed PMID: 19906715.

Kim et al. The role of synaptic GTPase-activating protein in neuronal development and synaptic plasticity. J. Neurosci. 23(4):1119-1124 (Feb. 15, 2003).

Kim et al.: The splicing factor U2AF65 stabilizes TRF1 protein by inhibiting its ubiquitin-dependent proteolysis. Biochem Biophys Res Commun. 2014;443(3):1124-30. doi: 10.1016/j.bbrc.2013.12. 118. PubMed PMID: 24389012.

Knudsen et al. Increased skewing of X chromosome inactivation in Rett syndrome patients and their mothers. Eur J Hum Genet 14:1189-1194 (2006).

Kole, et al. RNA therapeutics: beyond RNA interference and antisense oligonucleotides. Nat Rev Drug Discov. Jan. 20, 2012;11(2):125-40. doi: 10.1038/nrd3625.

Kralovicova, et al.: Allele-specific recognition of the 3' splice site of INS intron 1. Hum Genet. Oct. 2010;128(4):383-400. doi: 10.1007/s00439-010-0860-1. Epub Jul. 14, 2010.

Kralovicova, et al.: Compensatory signals associated with the activation of human GC 5' splice sites. Nucleic Acids Res. Sep. 1, 2011;39(16):7077-91. doi: 10.1093/nar/gkr306. Epub May 23, 2011.

Kralovicova et al.: Exon-centric regulation of ATM expression is population-dependent and amenable to antisense modification by pseudoexon targeting, Scientific Reports, 6:18741, doi:10.1038/srep18741, Jan. 6, 2016, 13 pages.

Kralovicova, et al. Global control of aberrant splice-site activation by auxiliary splicing sequences: evidence for a gradient in exon and intron definition. Nucleic Acids Res. Oct. 2007; 35(19): 6399-6413.

Kralovicova, et al. Identification of U2AF(35)-dependent exons by RNA-Seq reveals a link between 3' splice-site organization and activity of U2AF-related proteins. Nucleic Acids Res. Apr. 20, 2015;43(7):3747-63. doi: 10.1093/nar/gkv194. Epub Mar. 16, 2015.

Kralovicova, et al. Optimal antisense target reducing INS intron 1 retention is adjacent to a parallel G quadruplex. Nucleic Acids Res. Jul. 2014;42(12):8161-73. doi: 10.1093/nar/gku507. Epub Jun. 17, 2014.

Kralovicova, et al. Phenotypic consequences of branch point substitutions. Hum Mutat. Aug. 2006;27(8):803-13.

Kralovicova, et al. Position-dependent repression and promotion of DQB1 intron 3 splicing by GGGG motifs. J Immunol. Feb. 15, 2006;176(4):2381-8.

Kralovicova, et al.: Variants in the human insulin gene that affect pre-mRNA splicing: is—23Hphl a functional single nucleotide polymorphism at IDDM2? Diabetes. Jan. 2006;55(1):260-4.

Kralovicova, et al.Antisense Oligonucleotides Modulating Activation of a Nonsense-Mediated RNA Decay Switch Exon in theATMGene. Nucleic Acid Ther. Dec. 1, 2016; 26(6): 392-400.

Kralovicova, J. et al. Branch sites haplotypes that control alternative splicing. Hum Mol Genet. 2004;13:3189-202.

Kralovicova, J. et al. The role of short RNA loops in recognition of a single-hairpin exon derived from a mammalian-wide interspersed repeat. RNA Biol. 2015;12(1):54-69. doi: 10.1080/15476286.2015. 1017207. PubMed PMID: 25826413.

Kriaucionis et al.: The major form of MeCP2 has a novel N-terminus generated by alternative splicing. Nucleic Acids Res 32:1818-1823 (2004).

Krishnaraj et al. RettBASE: Rett syndrome database update. Hum Mutat 38:922-931 (2017).

Laceerra, et al., "Restoration of hemoglobin A synthesis in erythroid cells from peripheral blood of thalassemic patients" (2000) PNAS, vol. 97, No. 17, pp. 9591-9596.

Lander, et al. Initial sequencing and analysis of the human genome. Nature 409:860-921 (Feb. 15, 2001).

Laplanche, L.A. et al., "Phosphorothioate-modified oligodeoxyribonucleotides. III. NMR and UV spectroscoptc studies of the Rp-Rp, Sp-Sp, and Rp—Sp duplexes, [d(GGsAATTCC)]2, derived from diastereomeric O-ethyl phosphorothioates," Nucleic Acids Res., 1986, vol. 14, No. 22, pp. 9081-9083.

Le Hir, et al. How introns influence and enhance eukaryotic gene expression. Trends Biochem Sci. Apr. 2003;28(4):215-20.

Lee et al.: The Consensus 5' Splice Site Motif Inhibits mRNA Nuclear Export.PLoS One vol. 10, No. 3, p. e0122743 (Mar. 31, 2015).

Lee, J., et al.: Metastasis of neuroendocrine tumors are characterized by increased cell proliferation and reduced expression of the ATM gene. PLoS One. 2012;7:e34456.

LeFave, et al., "Splicing factor hnRNPH drives an oncogenic splicing switch in gliomas",(2011) The EMBO Journal, vol. 30, No. 19, pp. 4084-4097.

LeHir, H. et al.: 5'-End RET Splicing: Absence of Variants in Normal Tissues and Intron Retention in Pheochromocytomas, Oncology 63:84-91 (2002).

Lei et al. Exonization of Alu Ya5 in the human ACE gene requires mutations in both 3' and 5' splice sites and is facilitated by a conserved splicing enhancer. Nucleic acids research 33.12 (2005): 3897-3906.

Lei, et al.: Identification of splicing silencers and enhancers in sense Alus: a role for pseudoacceptors in splice site repression. Mol Cell Biol. Aug. 2005;25(16):6912-20.

Lemaire, M., et al. CDC25B phosphorylation by p38 and MK-2. Cell Cycle. 2006;5(15):1649-53. PubMed PMID: 16861915.

Lenaers, G. et al., "Dominant optic atrophy," Orphanet J Rare Diseases, 2012, vol. 7, No. 46, pp. 1-12.

Levin, et al., "Treating Disease at the RNA Level with Oligonucleotides" (2019) The New England Journal of Medicine 380:57-70.

Lev-Maor et al. Intronic Alus influence alternative splicing. PLoS genetics 4.9 (2008): e1000204.

Lev-Maor et al. The birth of an alternatively spliced exon: 3'splice-site selection in Alu exons. Science 300.5623 (2003): 1288-1291.

Levy et al.TranspoGene and microTranspoGene: transposed elements influence on the transcriptome of seven vertebrates and invertebrates. Nucleic acids research 36.suppl_1 (2007): D47-D52.

Li et al. JAG1 Mutation Spectrum and Origin in Chinese Children with Clinical Features of Alagille Syndrome. PLoS One 10(6):e0130355 (2015).

Li et al. PD-L1-Driven Tolerance Protects Neurogenin3-Induced Islet Neogenesis to Reverse Established Type 1 Diabetes in NOD Mice.Diabetes vol. 64, pp. 529-540 (Feb. 2015; epub Oct. 20, 2014).

Liang et al. Short intronic repeat sequences facilitate circular RNA production. Genes & development (2014): gad-251926.

Lianoglou, S., et al. Ubiquitously transcribed genes use alternative polyadenylation to achieve tissue-specific expression. Genes Dev. 2013;27(21):2380-96. Epub Oct. 23, 2013.doi: gad.229328.113 [pii] 10.1101/gad.229328.113. PubMed PMID: 24145798.

Lim et al. A computational analysis of sequence features involved in recognition of short introns. Proceedings of the National Academy of Sciences98.20 (2001): 11193-11198.

Lim, et al., "Antisense oligonucleotide modulation of non-productive alternative splicing upregulates gene expression" (2020) Nature Communication.

Litchfield, D.W., et al. Pin1: Intimate involvement with the regulatory protein kinase networks in the global phosphorylation landscape. Biochem Biophys Acta. 2015. doi: 10.1016/j.bbagen.2015. 02.018. PubMed PMID: 25766872.

Liu et al. Alternative splicing and retinal degeneration. Clinical Genetics 84(2):142-149 (2013).

(56) References Cited

OTHER PUBLICATIONS

Llorian et al. Position-dependent alternative splicing activity revealed by global profiling of alternative splicing events regulated by PTB. Nature structural & molecular biology 17.9 (2010): 1114.

Lo, YL et al. ATM Polymorphisms and risk of lung cancer among never smokers, Lung Cancer 69(2):148-154 (2010).

Long et al.: Correction of diverse muscular dystrophy mutations in human engineered heart muscle by single-site genome editing. Sci Adv 4:eaap9004 (2018).

Lorenz, et al. 2D meets 4G: G-Quadruplexes in RNA Secondary Structure Prediction. IEEE/ACM Trans Comput Biol Bioinform. Jul.-Aug. 2013;10(4):832-44. doi: 10.1109/TCBB.2013.7.

Lu, F.: Conditional JAG1 MutationShows the Developing Heart is More Sensitive Than Developing Liver to JAG1 Dosage.Am. J. Hum. Genet. vol. 72, pp. 1065-1070 (2003).

Ludecke et al.Recessively inherited L-DOPA-responsive parkinsonism in infancy caused by a point mutation (L205P) in the tyrosine hydroxylase gene Hum. Mol. Genet. vol 5, pp. 1023-1028, (1996).

Luo et al.: Palmitic Acid Suppresses Apolipoprotein M Gene Expression via the Pathway of PPARb/d in HepG2 Cells. Biochemical and Biophysical Research Communications, 445(1):203-207 (Feb. 2014).

Magi-Galuzzi, C et al. TMPRSS2-ERG gene fusion prevalence and class are significantly difference in prostate cancer of Caucasian, African-American and Japanese patients. The Prostate. 2011;71:489-97.

Makishima, et al. Mutations in the spliceosome machinery, a novel and ubiquitous pathway in leukemogenesis. Blood. Apr. 5, 2012;119(14):3203-10. doi: 10.1182/blood-2011-12-399774. Epub Feb. 9, 2012.

Maniatis et al. An extensive network of coupling among gene expression machines. Nature 416.6880 (2002): 499.

Mansouri, S. et al.: Epstein-Barr Virus EBNA1 Protein Regulates Viral Latency through Effects on let-7 MicroRNA and Dicer.Journal of Virology, vol. 88, No. 19, pp. 11166-11177, (Oct. 2014).

Marcel, et al. G-quadruplex structures in TP53 intron 3: role in alternative splicing and in production of p53 mRNA isoforms. Carcinogenesis. Mar. 2011;32(3):271-8. doi: 10.1093/carcin/bgq253. Epub Nov. 26, 2010.

Marquez, Y. et al. Unmasking alternative splicing inside protein-coding exons defines exitrons and their role inproteome plasticity. Genome vol. 25, pp. 995-1007 (2015).

Matsuoka et al. ATM and ATR substrate analysis reveals extensive protein networks responsive to DNA damage. Science 316(5828):1160-1166 (2007).

Matsuoka, S., et al. Ataxia telangiectasia-mutated phosphorylates Chk2 in vivo and in vitro. Proc Natl Acad Sci USA. 2000;97:10389-94.

Mayeda, et al. Surveying cis-acting sequences of pre-mRNA by adding antisense 2'-O-methyl oligoribonucleotides to a splicing reaction. J Biochem. Sep. 1990;108(3):399-405.

McKie et al. Mutations in the pre-mRNA splicing factor gene PRPC8 in autosomal dominant retinitis pigmentosa (RP13). Human Molecular Genetics 10(15):1555-1562 (2001).

Melhuish, et al. The Tgif2 gene contains a retained intron within the coding sequence, BMC Molecular Biology 7(2);1-10 (2006).

Melko, et al. Functional characterization of the AFF (AF4/FMR2) family of RNA-binding proteins: insights into the molecular pathology of FRAXE intellectual disability. Hum Mol Genet. May 15, 2011;20(10):1873-85. doi: 10.1093/hmg/ddr069. Epub Feb. 17, 2011.

Mendell, J.T., ap Rhys CM, Dietz HC. Separable roles for rent1/hUpf1 in altered splicing and decay of nonsense transcripts. Science. 2002;298(5592):419-22. Epub Sep. 14, 2002.doi: 10.1126/science.1074428 1074428 [pii]. PubMed PMID: 12228722.

Merendino, L., et al. Inhibition of msl-2 splicing by Sex-lethal reveals interaction between U2AF35 and the 3' splice site AG. Nature. 1999;402(6763):838-41. PubMed PMID: 10617208.

Michael, et al. Mfold web server for nucleic acid folding and hybridization prediction. Nucleic Acids Research. 31 (2003): 3406-3415.

Miller at al. 1993-2015 GeneReviews Eds. Pagon RA et al. Seattle (WA); University of WA, Seattle Bookshelf ID NBK1318.

Millevoi, et al. G-quadruplexes in RNA biology. Wiley Interdiscip Rev RNA. Jul.-Aug. 2012;3(4):495-507. doi: 10.1002/wrna.1113. Epub Apr. 4, 2012.

Min et al. Optimization of a novel series of ataxia-telangiectasia mutated kinase inhibitors as potential radiosensitizing agents. Journal of medicinal chemistry 59.2 (2016): 559-577.

Mirey, G., et al. CDC25B phosphorylated by pEg3 localizes to the centrosome and the spindle poles at mitosis. Cell Cycle. 2005;4(6):806-11. PubMed PMID: 15908796.

Mitelman, F., et al. The impact of translocations and gene fusions on cancer causation. Nat Rev Cancer. 2007;7(4):233-45. Epub Mar. 16, 2007.

Mnatzakanian et al. A previously unidentified MECP2 open reading frame defines a new protein isoform relevant to Rett syndrome. Nat Genet 36:339-341 (2004).

Mochizuki, T. et al. PKD2, a gene for polycystic kidney disease that encodes an integral membrane protein. Science vol. 272, pp. 1339-1342 (1996).

Montecucco, A., et al. Pre-mRNA processing factors meet the DNA damage response. Front Genet. 2013;4:102. doi: 10.3389/fgene.2013.00102. PubMed PMID: 23761808; PubMed Central PMCID: PMC3674313.

Moreno et al. Delivery of splice switching oligonucleotides by amphiphilic chitosan-based nanoparticles. Molecular pharmaceutics13.2 (2016): 344-356.

Morris, et al. An RNA G-quadruplex is essential for cap-independent translation initiation in human VEGF IRES. J Am Chem Soc. Dec. 22, 2010;132(50):17831-9. doi: 10.1021/ja106287x. Epub Nov. 24, 2010.

Morrison, A.J., et al. Mec1/Tel1 phosphorylation of the INO80 chromatin remodeling complex influences DNA damage checkpoint responses. Cell. 2007;130(3):499-511. doi: 10.1016/j.cell.2007.06.010. PubMed PMID: 17693258.

Moskowitz, et al., Mutation in Scheie syndrome (MPS IS): a G—>A transition creates new splice site in intron 5 of one IDUA allele, Hum. Mutat. 2(2):141-144 (1993).

Mulley et al. A new molecular mechanism for severe myoclonic epilepsy of infancy: Exonic deletions in SCN1A.Neurol. vol. 67, pp. 1094-1095 (2006).

Mulley et al. SCN1A mutations and epilepsy.Hum. Muta. vol. 25, pp. 535-542 (2005).

Murray, S.F. et al. Allele-Specific Inhibition of Rhodopsin with an Antisense Oligonucleotide Slows Photoreceptor Cell Degeneration, Invest Ophthalmol. Vis. Sci. 56:6362-6375 (Oct. 2015).

Neidle, S. and Balasubramanian, S. (2006) Quadruplex Nucleic Acids. RSC Biomolecular Sciences, Cambridge, UK.

Nemeroff et al. Identification of cis-acting intron and exon regions in influenza virus NS1 mRNA that inhibit splicing and cause the formation of aberrantly sedimenting presplicing complexes. Molecular and cellular biology 12.3 (1992): 962-970.

Nguyen, L.A., et al. Physical and functional link of the leukemia-associated factors AML1 and PML. Blood. 2005;105(1):292-300. doi: 10.1182/blood-2004-03-1185. PubMed PMID: 15331439.

Nishi, M. et al. Insulin gene mutations and diabetes. Journal of Diabetes Investigation vol. 2 Issue 2 (Apr. 2011).

Nishida, A. et al. Tissue- and Case-specific retention of intron 40 in mature dystrophin mRNA, Journal of Human Genetic 60;327-333 (2015).

Nisole, S., et al. Differential Roles of PML Isoforms. Front Oncol. 2013;3:125. doi: 10.3389/fonc.2013.00125. PubMed PMID: 23734343; PubMed Central PMCID: PMC3660695.

Nomakuchi et al. Antisense-oligonucleotide-directed inhibition of nonsense-mediated mRNA decay. Nat. Biotechnol. 34(2):164-166 (Feb. 2016).

Nozu et al. Alport syndrome caused by a COL4A5 deletion and exonization of an adjacent AluY. Molecular genetics & genomic medicine 2.5 (2014): 451-453.

(56) References Cited

OTHER PUBLICATIONS

Nussinov. Conserved quartets near 5' intron junctions in primate nuclear pre-mRNA. J Theor Biol. Jul. 8, 1988;133(1):73-84.
Oda, T. et al. Identification and cloning of the human homolog (JAG) of the rat Jagged1 gene from the Alagille syndrome critical region at 20p12.Genomics vol. 43, No. 3, pp. 376-379 (1997).
Okazaki, T. et al. PD-1 and PD-1 ligands: from discovery to clinical application. International Immunology(The Japanese Society for Immunology), vol. 19, No. 7, pp. 813-824, (2007).
Oustric, V. et al. Antisense oligonucleotide-based therapy in human erythropoietic protoporphyria. Am J Hum Genet. 2014;94(4):611-7. doi: 10.1016/j.ajhg.2014.02.010. PubMed PMID: 24680888; PubMed Central PMCID: PMC3980518.
Pacheco, et al. Diversity of vertebrate splicing factor U2AF35: identification of alternatively spliced U2AF1 mRNAS. J Biol Chem. Jun. 25, 2004;279(26):27039-49. Epub Apr. 19, 2004.
Pacheco, et al. RNA interference knockdown of hU2AF35 impairs cell cycle progression and modulates alternative splicing of Cdc25 transcripts. Mol Biol Cell. Oct. 2006;17(10):4187-99. Epub Jul. 19, 2006.
Page-McCaw, P.S., et al. PUF60: a novel U2AF65-related splicing activity. RNA. 1999;5(12):1548-60. PubMed PMID: 10606266.
Palazzo et al. Non-coding RNA: what is functional and what is junk ?. Frontiers in genetics 6 (2015): 2.
Pandit et al. Genome-wide analysis reveals SR protein cooperation and competition in regulated splicing. Molecular cell 50.2 (2013): 223-235.
Papaemmanuil, et al. Clinical and biological implications of driver mutations in myelodysplastic syndromes. Blood. Nov. 21, 2013;122(22):3616-27; quiz 3699. doi: 10.1182/blood-2013-08-518886. Epub Sep. 12, 2013.
Passamonti, C. et al. A novel inherited SCN1A mutation associated with different neuropsychological phenotypes: Is there a common core deficit? Epilepsy & Behavior 43:89-92 (2015).
Pastor, et al. Interaction of hnRNPA1/A2 and DAZAP1 with an Alu-derived intronic splicing enhancer regulates ATM aberrant splicing. PLoS One. 2011;6(8):e23349. doi: 10.1371/journal.pone.0023349. Epub Aug. 8, 2011.
Pastor, F., et al. Induction of tumour immunity by targeted inhibition of nonsense-mediated mRNA decay. Nature. 2010;465(7295):227-30. doi: 10.1038/nature08999. PubMed PMID: 20463739; PubMed Central PMCID: PMC3107067.
Paz, A., et al. SPIKE: a database of highly curated human signaling pathways. Nucleic Acids Res. 2011;39(Database issue):D793-9. doi: 10.1093/nar/gkq1167. PubMed PMID: 21097778; PubMed Central PMCID: PMC3014840.
PCT/US2021/030254 International Search Report and Written Opinion dated Jul. 28, 2023.
Pear, Warren S.: New roles for Notch in tuberous sclerosis, Journal of Clinical Investigation, 120(1):84-87 (Jan. 4, 2010).
Pecarelli et al. Regulation of natural mRNAs by the nonsense-mediated mRNA decay pathway. Eukaryotic cell(2014): EC-00090.
Pellagatti, A., et al. Deregulated gene expression pathways in myelodysplastic syndrome hematopoietic stem cells. Leukemia. 2010;24(4):756-64. doi: 10.1038/leu.2010.31. PubMed PMID: 20220779.
Peng, et al. Functional importance of different patterns of correlation between adjacent cassette exons in human and mouse. BMC Genomics. Apr. 26, 2008;9:191. doi: 10.1186/1471-2164-9-191.
Penton, A.L.Notch signaling in humandevelopment and disease. Seminars in Cell & Developmental Biology. vol. 23, pp. 450-457 (2012).
Perdiguero, E., et al. Regulation of Cdc25C activity during the meiotic G2/M transition. Cell Cycle. 2004;3(6):733-7. PubMed PMID: 15136768.
Piaceri, I., et al. Ataxia-telangiectasia mutated (ATM) genetic variant in Italian centenarians. Neurophysiology. 2013;34:573-5.
Pilia et al. Jagged-1 mutation analysis in Italian Alagille syndrome patients. Hum Mut 14(5):394-400 (1999).

Pomentel et al. A dynamic intron retention program enriched in RNA processing genes regulates gene expression during terminal erythropoiesis. Nucleic acids research 44.2 (2015): 838-851.
Precursor mRNA-Processing Factor 3, *S. cerevisiae*, Homolog OF; PRPF3m, 3 pages.
Przychodzen, B., et al. Patterns of missplicing due to somatic U2AF1 mutations in myeloid neoplasms. Blood. 2013;122:999-1006. Epub Jun. 19, 2013.doi: blood-2013-01-480970 [pii] 10.1182/blood-2013-01-480970. PubMed PMID: 23775717.
Pugliese, et al. The insulin gene is transcribed in the human thymus and transcription levels correlated with allelic variation at the INS VNTR-IDDM2 susceptibility locus for type 1 diabetes. Nat Genet. Mar. 1997; 15(3):293-7.
Rainey et al. Transient inhibition of ATM kinase is sufficient to enhance cellular sensitivity to ionizing radiation. Cancer research68. 18 (2008): 7466-7474.
Ramocki et al. The MECP2 duplication syndrome. Am J Med Genet A 152A:1079-1088 (2010).
Rangasamy et al.: Reduced neuronal size and mTOR pathway activity in the Mecp2 A140V Rett syndrome mouse model. F1000research 5:2269 (2016).
Ray, D. et al. A compendium of RNA-binding motifs for decoding gene regulation. Nature. vol. 499, No. 7457, pp. 172-177 (Jul. 11, 2013).
Reineke, E.L., et al. Degradation of the tumor suppressor PML by Pin1 contributes to the cancer phenotype of breast cancer MDA-MB-231 cells. Mol Cell Biol. 2008;28(3):997-1006. doi: 10.1128/MCB.01848-07. PubMed PMID: 18039859; PubMed Central PMCID: PMC2223389.
Rendu, J. et al. Hum Gene Ther. Exon skipping as a therapeutic strategy applied to an RYR1 mutation with pseudo-exon inclusion causing a severe core myopathy. Jul. 2013;24(7):702-13. doi: 10.1089/hum.2013.052.
Reynolds, DM et al.Aberrant Splicing in the PKD2 Gene as a Cause of Polycystic Kidney Disease.Am. Soc. Nephrol. vol. 10, pp. 2342-2351 (1999).
Ritprajak et al. Keratinocyte-Associated B7—H1 Directly Regulates Cutaneous Effector CD8+ T Cell Responses.J Immunology vol. 184, pp. 4918-4925 (2010).
RNA 2-14 The Nineteenth Annual Meeting of the RNA Society. Quebec City, Canada. (Jun. 3-8, 2014).
Roberts, Jennifer et al. Efficient and Persistent Splice Switching by Systemically Delivered LNA Oligonucleotides in Mice. Molecular Therapy, Nature Publishing, vol. 14, No. 4, pp. 471-475, Oct. 1, 2006.
Romero, P.R., et al. Alternative splicing in concert with protein intrinsic disorder enables increased functional diversity in multicellular organisms. Proc Natl Acad Sci USA. 2006;103(22):8390-5. Epub May 24, 2006.doi: 0507916103 [pii] 10.1073/pnas.0507916103. PubMed PMID: 16717195.
Rosenbloom et al. The UCSC Genome Browser database: 2015 Update. Nucleic Acids Research 43, Database Issue doi:101093/nar/gku1177.
Ruchlemer, R. et al.: Geography, ethnicity and "roots" in chronic lymphocytic leukemia. Leuk Lymphoma. 2013;54(6):1142-50. doi: 10.3109/10428194.2012.740670. PubMed PMID: 23121522.
Rudd, M.F., et al. Variants in the ATM-BRCA2-CHEK2 axis predispose to chronic lymphocytic leukemia. Blood. 2006;108(2):638-44. Epub Apr. 1, 2006.doi: 2005-12-5022 [pii] 10.1182/blood-2005-12-5022. PubMed PMID: 16574953.
Ruskin, et al. A factor, U2AF, is required for U2 snRNP binding and splicing complex assembly. Cell. Jan. 29, 1988;52(2):207-19.
Sadleir, et al. Not all SCN1A epileptic encephalopathies are Dravet syndrome. Neurology. Sep. 5, 2017; 89(10): 1-8.
Sahashi et al. Pathological impact of SMN2 mis-splicing in adult SMA mice. EMBO Mol. Med. 5(10):1586-601 (Oct. 2013).
Sahashi et al. TSUNAMI: an antisense method to phenocopy splicing-associated diseases in animals. Genes Dev. 26(16):1874-1884 (Aug. 15, 2012).
Sakabe, et al. Sequence features responsible for intron retention in human. BMC Genomics. Feb. 26, 2007;8:59.

(56) References Cited

OTHER PUBLICATIONS

Samatanga, et al. The high kinetic stability of a G-quadruplex limits hnRNP F qRRM3 binding to G-tract RNA. Nucleic Acids Res. Feb. 1, 2013;41(4):2505-16. doi: 10.1093/nar/gks1289. Epub Dec. 28, 2012.
Sazani, et al., "Therapeutic potential of antisense oligonucleotides as modulators of alternative splicing" (2003) The Journal of clinical Investigation, 112(4):481-486.
Schanen et al.: A Severely Affected Male Born into a Rett Syndrome Kindred Supports X-Linked Inheritance and Allows Extension of the Exclusion Map. Am J Hum Genetics 63:267-269 (1998).
Schwarze, et al. Redefinition of exon 7 in the COL1A1 gene of type I collagen by an intron 8 splice-donor-site mutation in a form of osteogenesis imperfecta: influence of intron splice order on outcome of splice-site mutation. Am J Hum Genet. Aug. 1999;65(2):336-44.
Scott, S.P., et al. Missense mutations but not allelic variants alter the function of ATM by dominant interference in patients with breast cancer. Proc Natl Acad Sci USA. 2002;99:925-30.
SG 11201702682P Search Report and Written Opinion dated Apr. 9, 2018.
Shao, C., et al. Mechanisms for U2AF to define 3' splice sites and regulate alternative splicing in the human genome. Nat Struct Mol Biol. 2014;doi: 10.1038/nsmb.2906.
Shcherbakova, I., et al. Alternative spliceosome assembly pathways revealed by single-molecule fluorescence microscopy. Cell Rep. 2013;5(1):151-65. Epub Oct. 1, 2013.doi: S2211-1247(13)00467-1 [pii] 10.1016/j.celrep.2013.08.026. PubMed PMID: 24075986.
Shen, M., et al. Characterization and cell cycle regulation of the related human telomeric proteins Pin2 and TRF1 suggest a role in mitosis. Proc Natl Acad Sci USA. 1997;94(25):13618-23. PubMed PMID: 9391075; PubMed Central PMCID: PMC28355.
Shiloh, Y., et al The ATM protein kinase: regulating the cellular response to genotoxic stress, and more. Nat Rev Mol Cell Biol. 2013;14(4):197-210. doi: 10.1038/nrm3546. PubMed PMID: 23486281.
Shiria, C.L. et al. Mutant U2AF1 Expression Alters Hematopoiesis and Pre-mRNA Splicing In Vivo. Cancer Cell. 2015;27(5):631-43. doi: 10.1016/j.ccell.2015.04.008. PubMed PMID: 25965570; PubMed Central PMCID: PMC4430854.
Shirley, M.H., et al Incidence of haematological malignancies by ethnic group in England, Jul. 2001. Br J Haematol. 2013;163(4):465-77. doi: 10.1111/bjh.12562. PubMed PMID: 24033296.
Sierakowska, H et al. Repair of thalassemic human beta-globin mRNA in mammalian cells by antisense oligonucleotides. Proc Natl Acad Sci U S A. Nov. 12, 1996;93(23):12840-4.
Singh, et al. An antisense microwalk reveals critical role of an intronic position linked to a unique long-distance interaction in pre-mRNA splicing. RNA. Jun. 2010; 16(6):1167-81. doi: 10.1261/rna.2154310. Epub Apr. 22, 2010.
Sirand-Pugnet, et al.: An intronic (A/U)GGG repeat enhances the splicing of an alternative intron of the chicken beta-tropomyosin pre-mRNA. Nucleic Acids Res. Sep. 11, 1995;23(17):3501-7.
Skjevik et al. The N-Terminal Sequence of Tyrosine Hydroxylase is a Conformationally Versatile Motif That Binds 14-3-3 Proteins and Membranes.J. Mol. Bio. vol. 426, pp. 150-168 (2014).
Smith, C.W., et al. Scanning and competition between AGs are involved in 3' splice site selection in mammalian introns. Mol Cell Biol. 1993;13(8):4939-52. PubMed PMID: 8336728.
Smith, et al.: Alternative pre-mRNA splicing: the logic of combinatorial control. Trends Biochem Sci. 25(8):381-8 (2000).
Smith, et al.,: Nonsense-mediated RNA decay—a switch and dial for regulating gene expression. Bioessays 37(6): 612-623 (2015).
Smith, P.J., et al. An increased specificity score matrix for the prediction of SF2/ASF-specific exonic splicing enhancers. Hum Mol Genet. 2006;15(16):2490-508. PubMed PMID: 16825284.
Soo, R.A., et al.: Ethnic differences in survival outcome in patients with advanced stage non-small cell lung cancer. J Thorac Oncol. 2011;6:1030-8.
Sorek et al. Minimal conditions for exonization of intronic sequences: 5' splice site formation in alu exons. Molecular cell 14.2 (2004): 221-231.

Soutar et al. Mechanisms of disease: genetic causes of familial hpercholesterolemia. Nat. Clin. Pract. Cardiovasc. Med. 4:214-255 (Apr. 1, 2007).
Spellman et al. Regulation of alternative splicing by PTB and associated factors. (2005): 457-460.
Spinner et al. Jagged1 mutations in alagille syndrome. Hum Mutat 17(1):18-33 (2001).
Stamm, S.: Regulation of alternative splicing by reversible protein phosphorylation. J Biol Chem. 2008;283(3):1223-7. PubMed PMID: 18024427.
Stankovic, T., et al.: Inactivation of ataxia telangiectasia mutated gene in B-cell chronic lymphocytic leukaemia. Lancet. 1999;353(9146):26-9. doi: 10.1016/S0140-6736(98)10117-4. PubMed PMID: 10023947.
Staropoli et al. Rescue of gene-expression changes in an induced mouse model of spinal muscular atrophy by an antisense oligonucleotide that promotes inclusion of SMN2 exon 7. Genomics 105:220-228 (2015).
Stead, et al. Global haplotype diversity in the human insulin gene region. Genome Res. Sep. 2003;13(9):2101-11.
Stec, W.J. et al., "Automated solid-phase synthesis, separation, and stereochemistry of phosphorothioate analogs of oligodeoxyribonucleotides," J. Am. Chem. Soc., 1984, vol. 106, No. 20, pp. 6077-6079.
Stein, C.A. et al., "Physicochemical properties of phosphorothioate oligodeoxynucleotides," Nucleic Acids Res., 1988, vol. 16, No. 8, pp. 3209-3221.
Stein et al.: FDA-Approved Oligonucleotide Therapies in 2017. Mol Ther 25:1069-1075 (2017).
Story, M.D. et al. ATM has a major role in the double-stand break repair pathway dysregulation in sporadic breast carcinomas and is an independent prognostic marker at both mRNA and protein levels, Breast Diseases: A Yearbook Quarterly, 26(4);297-299 (Mar. 17, 2015).
Strausfeld, U., et al. Activation of p34cdc2 protein kinase by microinjection of human cdc25C into mammalian cells. Requirement for prior phosphorylation of cdc25C by p34cdc2 on sites phosphorylated at mitosis. J Biol Chem. 1994;269(8):5989-6000. PubMed PMID: 8119945.
Suarez, F. et al. Incidence, presentation, and prognosis of malignancies in ataxia-telangiectasia: a report from the French national registry of primary immune deficiencies. J Clin Oncol. 2015;33(2):202-8. doi: 10.1200/JCO.2014.56.5101. PubMed PMID: 25488969.
Summerton, James. Morpholino Antisense Oligos: Applications in Biopharmaceutical ResearchMorpholinos constitute a radical redesign of DNA, providing decisive advantages over the moreconventional oligo types used for modulating gene expression. Innovations in Pharmaceutical Technology Issue No. 17 (2005).
Sun, H., et al.: Multiple splicing defects in an intronic false exon. Mol Cell Biol. 2000;20(17):6414-25. PubMed PMID: 10938119.
Supplementary European Search Report dated Apr. 18, 2019 for EP16876615.2.
Svasti, et al. RNA repair restores hemoglobin expression in IVS2-654 thalassemic mice. Proc Natl Acad Sci U S A. Jan. 27, 2009; 106(4): 1205-1210.
Swaans, RJM et al.Four novel mutations in the Tyrosine Hydroxylase gene in patients with infantile parkinsonism Annals of Human Genetic, vol. 64, No. 1, pp. 25-31, (Jan. 2000).
Tabrez, S. et al.: A Synopsis of the Role of Tyrosine Hydroxylase in Parkinson's Disease.CNS & Neurological Disorders—Drug Targets vol. 11, No. 4 (2012).
Takahashi et al. Skewed X chromosome inactivation failed to explain the normal phenotype of a carrier female with MECP2 mutation resulting in Rett syndrome. Clin Genet 73:257-261 (2008).
Tavanez, J.P., et al. hnRNP A1 proofreads 3' splice site recognition by U2AF. Mol Cell. 2012;45(3):314-29. Epub Feb. 14, 2012. doi: S1097-2765(12)00032-9 [pii] 10.1016/j.molcel.2011.11.033. PubMed PMID: 22325350.
Taylor, A.M., et al. Ataxia telangiectasia: more variation at clinical and cellular levels. Clin Genet. 2015;87(3):199-208. doi: 10.1111/cge.12453. PubMed PMID: 25040471.
Taylor, A.M., et al.: Leukemia and lymphoma in ataxia telangiectasia. Blood. 1996;87(2):423-38. PubMed PMID: 8555463.

(56) References Cited

OTHER PUBLICATIONS

Thisted, et al. Optimized RNA targets of two closely related triple KH domain proteins, heterogeneous nuclear ribonucleoprotein K and alphaCP-2KL, suggest Distinct modes of RNA recognition. J Biol Chem. May 18, 2001;276(20):17484-96. Epub Feb. 2, 2001.
Tilgner, H. et al., "Deep sequencing of subcellular RNA fractions shows splicing to be predominantly co-transcriptional in the human genome but inefficient for lncRNAs," Genome Research, 2012, vol. 22, No. 9, pp. 1616-1625.
Tillotson et al. Radically truncated MeCP2 rescues Rett syndrome-like neurological defects. Nature 550:398 (2017).
Torres, V.E. et al. Autosomal dominant polycystic kidney disease: the last 3 years.Kidney International vol. 76, pp. 149-168 (May 20, 2009).
Trabattoni et al.: Costimulatory Pathways in Multiple Disease Sclerosis: Distinctive Expression of PD-1 and PD-L1 in Patients with Different Patterns of Disease.J. Immunol. vol. 183, pp. 4984-4993 (2009).
Trapnell, C. et al. Differential gene and transcript expression analysis of RNA-seq experiments with Top Hat and Cufflinks. Nat Protoc. 2012;7(3):562-78. Epub Mar. 3, 2012.doi: nprot.2012.016 [pii] 10.1038/nprot.2012.016. PubMed PMID: 22383036.
Turnpenny, P.D. et al. Alagille syndrome: pathogenesis, diagnosis and management.European Journal of Human Genetics vol. 20, pp. 251-257 (2012.
Uhlmann, E. et al., "Antisense oligonucleotides: a new therapeutic principle," Chemical Reviews, 1990, vol. 90, No. 4, pp. 543-584.
U.S. Appl. No. 14/741,071 Non-Final Office Action dated Dec. 1, 2016.
U.S. Appl. No. 14/874,420 Non-Final Office Action dated Mar. 21, 2017.
U.S. Appl. No. 14/874,420 Office Action dated Oct. 24, 2017.
U.S. Appl. No. 15/619,984 Office Action dated Dec. 17, 2018.
U.S. Appl. No. 15/949,902 Office Action dated Mar. 1, 2019.
U.S. Appl. No. 15/288,415 Office Action dated Jun. 26, 2018.
Vafiadis, et al. Insulin expression in human thymus is modulated by INS VNTR alleles at the IDDM2 locus. Nat Genet. Mar. 1997; 15(3):289-92.
Van Nostrand et al. Robust transcriptome-wide discovery of RNA-binding protein binding sites with enhanced CLIP (eCLIP). Nature methods 13.6 (2016): 508.
Venkatesh, A. et al., "Antisense oligonucleotide mediated increase of OPA1 expression using TANGO technology for the treatment of autosomal dominant optic atrophy," Molecular Therapy, 2020, vol. 28, No. 4S1.
Venkatesh, A. et al., "Antisense oligonucleotide mediated increase of OPA1 expression using TANGO technology for the treatment of autosomal dominant optic atrophy," ARVO Annual Meeting (Abrstract), 2020, vol. 61, No. 2755.
Verhaart, I.E.C. AON-Mediated Exon Skipping for Duchenne Muscular Dystrophy. Chapter 3. pp. 1-26 (Aug. 1, 2012).
Verret et al., Inhibitory Interneuron Deficit Links Altered Network Activity and Cognitive Dysfunction in Alzheimer Model, Cell, 149(3): 708-721 (2012).
Vieira, N. et al. Jagged 1Rescues the Duchenne Muscular Dystrophy Phenotype. Cell vol. 163, pp. 1204-1213 (Nov. 19, 2015).
Voelker, et al. A comprehensive computational characterization of conserved mammalian intronic sequences reveals conserved motifs associated with constitutive and alternative splicing. Genome Res. Jul. 2007; 17(7):1023-33. Epub May 24, 2007.
Vorechovsky Correspondence Pediatric Research 2010.
Vorechovsky, I. Letter to the Editor: MER91B-assisted cryptic exon activation in Gitelman syndrome. Pediatric research 67.4 (2010): 444-445.
Vorechovsky Transposable elements in disease-associated cryptic exons. Human genetics 127.2 (2010): 135-154.
Wahl, et al. The spliceosome: design principles of a dynamic RNP machine. Cell. Feb. 20, 2009;136(4):701-18. doi: 10.1016/j.cell. 2009.02.009.
Wan, W.B. et al., "Synthesis, biophysical properties and biological activity of second generation antisense oligonucleotides containing chiral phosphorothioate linkages," Nucleic Acids Research, 2014, vol. 42, No. 22, pp. 13456-13468.
Wang, et al. A complex network of factors with overlapping affinities represses splicing through intronic elements. Nat Struct Mol Biol. Jan. 2013;20(1):36-45. doi: 10.1038/nsmb.2459. Epub Dec. 16, 2012.
Wang et al. Alternative isoform regulation in human tissue transcriptomes. Nature. 2008;456(November):470-476.
Wang et al. Human Adenovirus Type 36 Enhances Glucose Uptake in Diabetic and Nondiabetic Human Skeletal Muscle Cells Independent of Insulin Signaling.Diabetes vol. 57, pp. 1861-1869 (2008).
Wang, et al.: Intronic splicing enhancers, cognate splicing factors and context-dependent regulation rules. Nat Struct Mol Biol. Oct. 2012; 19(10):1044-52. doi: 10.1038/nsmb.2377. Epub Sep. 16, 2012.
Wang, et al.: Regulation of insulin preRNA splicing by glucose. Proc Natl Acad Sci U S A. Apr. 29, 1997;94(9):4360-5.
Wang, Z. et al.: Systematic identification and analysis of exonic splicing silencers. Cell. 2004;119(6):831-45. PubMed PMID: 15607979.
Warf, M.B., et al.: Role of RNA structure in regulating pre-mRNA splicing. Trends Biochem Sci. 2010;35(3):169-78. Epub Dec. 5, 2009.doi: S0968-0004(09)00196-0 [pii].
Wieland, et al.: RNA quadruplex-based modulation of gene expression. Chem Biol. Jul. 2007;14(7):757-63.
Wilton, et al. Splice modification to restore functional dystrophin synthesis in Duchenne muscular dystrophy. Current pharmaceutical design 16.8 (2010): 988-1001.
Wong et al. Orchestrated intron retention regulates normal granulocyte differentiation. Cell 154.3 (2013): 583-595.
Wu et al. AT—AC Pre-mRNA Splicing Mechanisms and Conservation of Minor Introns in Voltage-Gated Ion Channel Genes. Molecular and Cellular Biology 19(5): 3225-3236 (May 1999).
Wu et al.: Functional recognition of the 3' splice site AG by the splicing factor U2AF35.Nature. 1999;402(6763):832-5. PubMed PMID: 10617206.
Wu et al.: MRE11-RAD50-NBS1 and ATM function as co-mediators of TRF1 in telomere length control. Nat Struct Mol Biol. 2007;14(9):832-40. doi: 10.1038/nsmb1286. PubMed PMID: 17694070.
Wu, J.Y., et al.: Specific interactions between proteins implicated in splice site selection and regulated alternative splicing. Cell. 1993;75(6):1061-70. Epub Dec. 17, 1993.doi: 0092-8674(93)90316-I [pii]. PubMed PMID: 8261509.
Xia, Y. et al.: Frequencies of SF3B1, NOTCH1, MYD88, BIRC3 and IGHV mutations and TP53 disruptions in Chinese with chronic lymphocytic leukemia: disparities with Europeans. Oncotarget. 2015;6(7):5426-34. PubMed PMID: 25605254.
Xing, et al.: The multiassembly problem: reconstructing multiple transcript isoforms from EST fragment mixtures. Genome Res. Mar. 2004;14(3):426-41. Epub Feb. 12, 2004.
Yamamoto et al. Mib-Jag1-Notch signalling regulates patterning and structural roles of the notochord by controlling cell-fate decisions. Development 137(15):2527-2537 (2010).
Yamamoto, Y., et al. BCOR as a novel fusion partner of retinoic acid receptor alpha in a t(X;17)(p11;q12) variant of acute promyelocytic leukemia. Blood. 2010;116(20):4274-83. doi: 10.1182/blood-2010-01-264432. PubMed PMID: 20807888.
Yan, et al. Systematic discovery of regulated and conserved alternative exons in the mammalian brain reveals NMD modulating chromatin regulators. Proc Natl Acad Sci U S A. Mar. 17, 2015; 112(11): 3445-3450.
Yang et al.: Biophysical analysis and small-angle X-ray scattering-derived structures of MeCP2-nucleosome complexes. Nucleic Acids Res 39:4122-4135 (2011).
Yang, S. et al. PML-dependent apoptosis after DNA damage is regulated by the checkpoint kinase hCds1/Chk2. Nat Cell Biol. 2002;4(11):865-70. doi: 10.1038/ncb869. PubMed PMID: 12402044.
Yang, S., et al. Promyelocytic leukemia activates Chk2 by mediating Chk2 autophosphorylation. J Biol Chem. 2006;281(36):26645-54. doi: 10.1074/jbc.M604391200. PubMed PMID: 16835227.

(56) References Cited

OTHER PUBLICATIONS

Yang, Y. et al. Oligomerization of the polycystin-2 C-terminal tail and effects on its Ca2+binding properties. J. Bio. Chem. vol. 290, No. 16, pp. 10544-10554 (2015).

Yeo, et al.: Discovery and analysis of evolutionarily conserved intronic splicing regulatory elements. PLoS Genet. May 25, 2007;3(5):e85. Epub Apr. 13, 2007.

Yoshida, et al. Frequent pathway mutations of splicing machinery in myelodysplasia. Nature. Sep. 11, 2011;478(7367):64-9. doi: 10.1038/nature10496.

Yoshida, K., et al. Splicing factor mutations and cancer. Wiley Interdiscip Rev RNA. 2014;5(4):445-59. doi: 10.1002/wrna.1222. PubMed PMID: 24523246.

Young et al. 915—a GABA-Selective AAV Vector-Based Approach to Up-Regulate Endogenous Scn1a Expression reverses key Phenotypes in a Mouse Model of Dravet Syndrome. 22nd Annual Meeting American Society of Gene & Cell Therapy. Washington, D.C. Apr. 29-May 2, 2019 (Abstract).

Yu, E.Y., et al. Regulation of telomere structure and functions by subunits of the INO80 chromatin remodeling complex. Mol Cell Biol. 2007;27(16):5639-49. doi: 10.1128/MCB.00418-07. PubMed PMID: 17562861; PubMed Central PMCID: PMC1952117.

Yuan et al. Brain localization and neurotoxicity evaluation of polysorbate 80-modified chitosan nanoparticles in rats. PloS one 10.8 (2015): e0134722.

Yuan X., et al. Nuclear protein profiling of Jurkat cells during heat stress-induced apoptosis by 2-DE and MS/MS. Electrophoresis. 2007;28(12):2018-26. doi: 10.1002/elps.200600821. PubMed PMID: 17523140.

Zammarchi, et al. "Antitumorigenic potential of STAT3 alternative splicing modulation", (2011) PNAS, vol. 108, No. 43, pp. 17779-17784.

Zamore, P.D., et al. Identification, purification, and biochemical characterization of U2 small nuclear ribonucleoprotein auxiliary factor. Proc Natl Acad Sci USA. 1989;86(23):9243-7. PubMed PMID: 2531895.

Zarnack K., et al. Direct competition between hnRNP C and U2AF65 protects the transcriptome from the exonization of Alu elements. Cell. 2013;152(3):453-66. Epub Feb. 5, 2013.doi: S0092-8674(12)01545-0 [pii] 10.1016/j.cell.2012.12.023. PubMed PMID: 23374342.

Zhang C., et al. RNA landscape of evolution for optimal exon and intron discrimination. Proc Natl Acad Sci USA. 2008;105(15):5797-802. Epub Apr. 9, 2008.doi: 0801692105 [pii] 10.1073/pnas.0801692105. PubMed PMID: 18391195.

Zhang et al.: Computational definition of sequence motifs governing constitutive exon splicing. Genes Dev. 2004;18:1241-50. PubMed PMID: 15145827.

Zhang, et al. Insulin as an autoantigen in NOD/human diabetes. Curr Opin Immunol. Feb. 2008;20(1):111-8. doi: 10.1016/j.coi.2007.11.005.

Zhang, et al.: The kinetics and folding pathways of intramolecular G-quadruplex nucleic acids. J Am Chem Soc. Nov. 21, 2012;134(46):19297-308. doi: 10.1021/ja309851t. Epub Nov. 12, 2012.

Zhang, J. et al., "PowerBlast: A network application for automated analysis of large genomic sequences," Genome Methods, 1997, vol. 7, pp. 649-656.

Zimrin et al. An Antisense Oligonucleotide to the Notch Ligand Jagged Enhances Firbroblast Growth Factor-induced Angiogenesis in Vitro. J. Biol. Chem. 271(51):32499-502 (Dec. 20, 1996).

Zon et al. Phosphorothioate oligonucleotides: chemistry, purification, analysis, scale-up and future directions. Anti Cancer Drug Design vol. 6, No. 6, pp. 539-568 (1991).

Zon G. and Stec,W.J. (1991) In Eckstein,F. (ed.), Oligonucleotides and Analogues: A Practical Approach. Oxford University Press, Oxford, UK, pp. 87-108.

Zorio, D.A., et al. Both subunits of U2AF recognize the 3' splice site in Caenorhabditis elegans. Nature. 1999;402(6763):835-8. PubMed PMID: 10617207.

Zuker, M. Mfold web server for nucleic acid folding and hybridization prediction. Nucleic Acids Res. 31, 3406-3415 (2003).

Office Action issued in European Patent Application No. 18871437.2 dated Sep. 12, 2023.

OPA1

Intron: GRCh38/hg38: chr3 193626204 193631611
Event: GRCh38/hg38: chr3 193628509 193628616 (7X)

FIG. 5

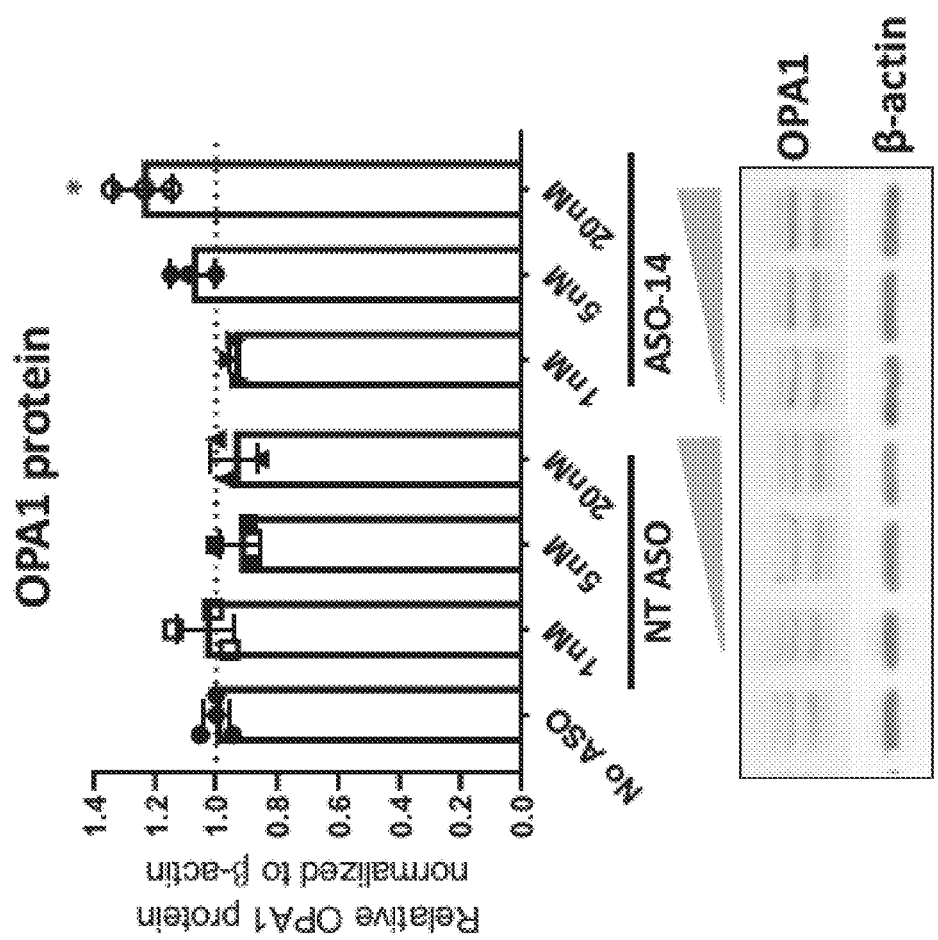

| Compound ID No.: | Sequence (5'-3') | Chemistry (All MOE unless otherwise noted; G-LNA, C-5MeC-MOE) |
|---|---|---|
| 1 | AGGCCATTCTGAAATTCT | AGGCCATTCTGAAATTCT |
| 2 | CATTGAGGCCATTCTGAA | CATTGAGGCCATTCTGAA |
| 3 | TAAGGCATTGAGGCCATT | TAAGGCATTGAGGCCATT |
| 4 | CCTATTAAGGCATTGAGG | CCTATTAAGGCATTGAGG |
| 5 | TTCTTCCTATTAAGGCAT | TTCTTCCTATTAAGGCAT |
| 6 | AGTATTTCTTCCTATTAA | AGTATTTCTTCCTATTAA |
| 7 | TTTCAAGTATTTCTTCCT | TTTCAAGTATTTCTTCCT |
| 8 | AAAAATTTCAAGTATTTC | AAAAATTTCAAGTATTTC |
| 9 | AATTTAAAAATTTCAAGT | AATTTAAAAATTTCAAGT |
| 10 | GCCCTAATTTAAAAATTT | GCCCTAATTTAAAAATTT |
| 11 | ACCAAGCCCTAATTTAAA | ACCAAGCCCTAATTTAAA |
| 12 | ACAAAACCAAGCCCTAAT | ACAAAACCAAGCCCTAAT |
| 13 | TCCTCACAAAACCAAGCC | TCCTCACAAAACCAAGCC |
| 14 | CTAGCTCCTCACAAAACC | CTAGCTCCTCACAAAACC |
| 15 | CTTTACTAGCTCCTCACA | CTTTACTAGCTCCTCACA |
| 16 | AAAACCTTTACTAGCTCC | AAAACCTTTACTAGCTCC |
| 17 | AGAGAAAAACCTTTACTA | AGAGAAAAACCTTTACTA |
| 18 | CTGAAAGAGAAAAACCTT | CTGAAAGAGAAAAACCTT |
| 19 | AAGCTGAAAGAGAAAAAC | AAGCTGAAAGAGAAAAAC |
| 20 | CTAAAGCTGAAAGAGAAA | CTAAAGCTGAAAGAGAAA |

FIG. 15

| Compound ID No.: | Sequence (5'-3') | Chemistry |
|---|---|---|
| | | (All MOE unless otherwise noted; G-LNA, C-5MeC-MOE) |
| 21 | AAGCTAAAGCTGAAAGAG | AAGCTAAAGCTGAAAGAG |
| 22 | AACAAGCTAAAGCTGAAA | AACAAGCTAAAGCTGAAA |
| 23 | AGAAACAAGCTAAAGCTG | AGAAACAAGCTAAAGCTG |
| 24 | CGCAGAAACAAGCTAAAG | CGCAGAAACAAGCTAAAG |
| 25 | TCCTCCGCAGAAACAAGC | TCCTCCGCAGAAACAAGC |
| 26 | CGGAATCCTCCGCAGAAA | CGGAATCCTCCGCAGAAA |
| 27 | AAGAGCGGAATCCTCCGC | AAGAGCGGAATCCTCCGC |
| 28 | GGAGAAAGAGCGGAATCC | GGAGAAAGAGCGGAATCC |
| 29 | CTGATGGAGAAAGAGCGG | CTGATGGAGAAAGAGCGG |
| 30 | TGAAACTGATGGAGAAAG | TGAAACTGATGGAGAAAG |
| 31 | GGCTATGAAACTGATGGA | GGCTATGAAACTGATGGA |
| 32 | TCCAGGGCTATGAAACTG | TCCAGGGCTATGAAACTG |
| 33 | ACAATTCCAGGGCTATGA | ACAATTCCAGGGCTATGA |
| 34 | TTTCTACAATTCCAGGGC | TTTCTACAATTCCAGGGC |
| 35 | GAGCTTTTCTACAATTCC | GAGCTTTTCTACAATTCC |
| 36 | AACCAGAGCTTTTCTACA | AACCAGAGCTTTTCTACA |
| 37 | CTTGAAACCAGAGCTTTT | CTTGAAACCAGAGCTTTT |
| 38 | ATGGTCTTGAAACCAGAG | ATGGTCTTGAAACCAGAG |
| 39 | TATCAATGGTCTTGAAAC | TATCAATGGTCTTGAAAC |
| 40 | ATGGATATCAATGGTCTT | ATGGATATCAATGGTCTT |

FIG. 15 cont.

| Compound ID No.: | Sequence (5'-3') | Chemistry (All MOE unless otherwise noted; G-LNA, C-5MeC-MOE) |
|---|---|---|
| 41 | CAGAAATGGATATCAATG | CAGAAATGGATATCAATG |
| 42 | CCTGACAGAAATGGATAT | CCTGACAGAAATGGATAT |
| 43 | CACCCTGACAGAAATGGA | CACCCTGACAGAAATGGA |
| 44 | ACTCACCCTGACAGAAAT | ACTCACCCTGACAGAAAT |
| 45 | AAAACTCACCCTGACAGA | AAAACTCACCCTGACAGA |
| 46 | TTTAAAACTCACCCTGAC | TTTAAAACTCACCCTGAC |
| 47 | AAATTTAAAACTCACCCT | AAATTTAAAACTCACCCT |
| 48 | AATAAATTTAAAACTCAC | AATAAATTTAAAACTCAC |
| 49 | CATGAAATAAATTTAAAA | CATGAAATAAATTTAAAA |
| 50 | TGCATCATGAAATAAATT | TGCATCATGAAATAAATT |
| 51 | TTGTTTGCATCATGAAAT | TTGTTTGCATCATGAAAT |
| 52 | ATATATTGTTTGCATCAT | ATATATTGTTTGCATCAT |
| 53 | GTTCAATATATTGTTTGC | GTTCAATATATTGTTTGC |
| 54 | CTGTTGTTCAATATATTG | CTGTTGTTCAATATATTG |
| 55 | ATGTCCTGTTGTTCAATA | ATGTCCTGTTGTTCAATA |
| 56 | AGTTCATGTCCTGTTGTT | AGTTCATGTCCTGTTGTT |
| 57 | GAACAAGTTCATGTCCTG | GAACAAGTTCATGTCCTG |
| 58 | AACAAGAACAAGTTCATG | AACAAGAACAAGTTCATG |
| 59 | CTTACAACAAGAACAAGT | CTTACAACAAGAACAAGT |
| 60 | AGCCACTTACAACAAGAA | AGCCACTTACAACAAGAA |

FIG. 15 cont.

| Compound ID No.: | Sequence (5'-3') | Chemistry (All MOE unless otherwise noted; G-LNA, C-5MeC-MOE) |
|---|---|---|
| 61 | AATTCAGCCACTTACAAC | AATTCAGCCACTTACAAC |
| 62 | GATAAATTCAGCCACTT | GATAAATTCAGCCACTT |
| 63 | TTACTGATAAATTCAGC | TTACTGATAAATTCAGC |
| 64 | GTGCTTTACTGATAAAAT | GTGCTTTACTGATAAAAT |
| 65 | TTGATGTGCTTTACTGAT | TTGATGTGCTTTACTGAT |
| 66 | TGGAGAAAGAGCGGAATC | TGGAGAAAGAGCGGAATC |
| 67 | ATGGAGAAAGAGCGGAAT | ATGGAGAAAGAGCGGAAT |
| 68 | GATGGAGAAAGAGCGGAA | GATGGAGAAAGAGCGGAA |
| 69 | TGATGGAGAAAGAGCGGA | TGATGGAGAAAGAGCGGA |
| 70 | ACTGATGGAGAAAGAGCG | ACTGATGGAGAAAGAGCG |
| 71 | AACTGATGGAGAAAGAGC | AACTGATGGAGAAAGAGC |
| 72 | AAACTGATGGAGAAAGAG | AAACTGATGGAGAAAGAG |
| 73 | GAAACTGATGGAGAAAGA | GAAACTGATGGAGAAAGA |
| 74 | ATGAAACTGATGGAGAAA | ATGAAACTGATGGAGAAA |
| 75 | TATGAAACTGATGGAGAA | TATGAAACTGATGGAGAA |
| 76 | CTATGAAACTGATGGAGA | CTATGAAACTGATGGAGA |
| 77 | GCTATGAAACTGATGGAG | GCTATGAAACTGATGATGGAG |
| 78 | GGGCTATGAAACTGATGG | GGGCTATGAAACTGATGG |
| 79 | AGGGCTATGAAACTGATG | AGGGCTATGAAACTGATG |
| 80 | CAGGGCTATGAAACTGAT | CAGGGCTATGAAACTGAT |

FIG. 15 cont.

| Compound ID No.: | Sequence (5'-3') | Chemistry (All MOE unless otherwise noted; G-LNA, C-5MeC-MOE) |
|---|---|---|
| 81 | CCAGGGCTATGAAACTGA | CCAGGGCTATGAAACTGA |
| 82 | CTGATGGAGAAAGAGCGGAATC | CTGATGGAGAAAGAGCGGAATC |
| 83 | CTGATGGAGAAAGAGCGGAA | CTGATGGAGAAAGAGCGGAA |
| 84 | AACTGATGGAGAAAGAGCGGAA | AACTGATGGAGAAAGAGCGGAA |
| 85 | AACTGATGGAGAAAGAGCGG | AACTGATGGAGAAAGAGCGG |
| 86 | GAAACTGATGGAGAAAGAGCGG | GAAACTGATGGAGAAAGAGCGG |
| 87 | GGCTATGAAACTGATGGAGAAA | GGCTATGAAACTGATGGAGAAA |
| 88 | GGCTATGAAACTGATGGAGA | GGCTATGAAACTGATGGAGA |
| 89 | AGGGCTATGAAACTGATGGAGA | AGGGCTATGAAACTGATGGAGA |
| 90 | AGGGCTATGAAACTGATGGA | AGGGCTATGAAACTGATGGA |
| 91 | CCAGGGCTATGAAACTGATGGA | CCAGGGCTATGAAACTGATGGA |
| 92 | TTCTTACCCATTTAATTA | TTCTTACCCATTTAATTA |
| 93 | TGCTTCTTACCCATTTAA | TGCTTCTTACCCATTAA |
| 94 | TAATGCTTCTTACCCATT | TAATGCTTCTTACCATT |
| 95 | AGATAATGCTTCTTACCC | AGATAATGCTTCTTACCC |
| 96 | CAGATAATGCTTCTTTACC | CAGATAATGCTTCTTTACC |
| 97 | CCCTTCAGATAATGCTTC | CCCTTCAGATAATGCTTC |
| 98 | CTACTCCCTTCAGATAAT | CTACTCCCTTCAGATAAT |
| 99 | AGTCCTACTCCCTTCAG | AGTCCTACTCCCTTCAG |
| 100 | TTCACAGCTCCTACTCCC | TTCACAGCTCCTACTCCC |

FIG. 15 cont.

| Compound ID No.: | Sequence (5'-3') | Chemistry (All MOE unless otherwise noted; G-LNA, C-5MeC-MOE) |
|---|---|---|
| 101 | TAAAATTCACAGCTCCTA | TAAAATTCACAGCTCCTA |
| 102 | AAATCTAAAATTCACAGC | AAATCTAAAATTCACAGC |
| 103 | GAATAAAATCTAAAATTC | GAATAAAATCTAAAATTC |
| 104 | GATGGGAATAAAATCTAA | GATGGGAATAAAATCTAA |
| 105 | GCTGTGATGGGAATAAAA | GCTGTGATGGGAATAAAA |
| 106 | TAGAGGCTGTGATGGGAA | TAGAGGCTGTGATGGGAA |
| 107 | AAAGATAGAGGCTGTGAT | AAAGATAGAGGCTGTGAT |
| 108 | AAAAGAAAGATAGAGGCT | AAAAGAAAGATAGAGGCT |
| 109 | GACCTAAAAGAAAGATAG | GACCTAAAAGAAAGATAG |
| 110 | ATAAAGACCTAAAAGAAA | ATAAAGACCTAAAAGAAA |
| 111 | GAGATATAAAGACCTAAA | GAGATATAAAGACCTAAA |
| 112 | GGCTGTGATGGGAATAAA | GCTGTGATGGGAATAAA |
| 113 | AGGCTGTGATGGGAATA | AGGCTGTGATGGGAATA |
| 114 | GAGGCTGTGATGGGAAT | GAGGCTGTGATGGGAAT |
| 115 | AGAGGCTGTGATGGGAAT | AGAGGCTGTGATGGGAAT |
| 116 | ATAGAGGCTGTGATGGGA | ATAGAGGCTGTGATGGGA |
| 117 | GATAGAGGCTGTGATGGG | GATAGAGGCTGTGATGG |
| 118 | AGATAGAGGCTGTGATGG | AGATAGAGGCTGTGATGG |
| 119 | AAGATAGAGGCTGTGATG | AAGATAGAGGCTGTGATG |
| 120 | TAGAGGCTGTGATGGGAATAAA | TAGAGGCTGTGATGGGAATAAA |

FIG. 15 cont.

| Compound ID No.: | Sequence (5'-3') | Chemistry |
|---|---|---|
| | | (All MOE unless otherwise noted; G-LNA, C-5MeC-MOE) |
| 121 | ATAGAGGCTGTGATGGGAATAA | ATAGAGGCTGTGATGGGAATAA |
| 122 | GATAGAGGCTGTGATGGGAATA | GATAGAGGCTGTGATGGGAATA |
| 123 | AGATAGAGGCTGTGATGGGAAT | AGATAGAGGCTGTGATGGGAAT |
| 124 | AAGATAGAGGCTGTGATGGGAA | AAGATAGAGGCTGTGATGGGAA |
| 125 | GAGGCTGTGATGGGAATAAA | GAGGCTGTGATGGGAATAAA |
| 126 | AGAGGCTGTGATGGGAATAA | AGAGGCTGTGATGGGAATAA |
| 127 | TAGAGGCTGTGATGGGAATA | TAGAGGCTGTGATGGGAATA |
| 128 | ATAGAGGCTGTGATGGGAAT | ATAGAGGCTGTGATGGGAAT |
| 129 | GATAGAGGCTGTGATGGGAA | GATAGAGGCTGTGATGGGAA |
| 130 | AGATAGAGGCTGTGATGGGA | AGATAGAGGCTGTGATGGGA |
| 131 | AAGATAGAGGCTGTGATGGG | AAGATAGAGGCTGTGATGGG |
| 132 | CTGTGATGGGAATAAA | CTGTGATGGGAATAAA |
| 133 | GCTGTGATGGGAATAA | GCTGTGATGGGAATAA |
| 134 | GGCTGTGATGGGAATA | GGCTGTGATGGGAATA |
| 135 | AGGCTGTGATGGGAAT | AGGCTGTGATGGGAAT |
| 136 | GAGGCTGTGATGGGAA | GAGGCTGTGATGGGAA |
| 137 | AGAGGCTGTGATGGGA | AGAGGCTGTGATGGGA |
| 138 | TAGAGGCTGTGATGGG | TAGAGGCTGTGATGGG |
| 139 | ATAGAGGCTGTGATGG | ATAGAGGCTGTGATGG |
| 140 | GATAGAGGCTGTGATG | GATAGAGGCTGTGATG |

FIG. 15 cont.

| Compound ID No.: | Sequence (5'-3') | Chemistry (All MOE unless otherwise noted; G-LNA, C-5MeC-MOE) |
|---|---|---|
| 141 | AGATAGAGGCTGTGAT | AGATAGAGGCTGTGAT |
| 142 | AAGATAGAGGCTGTGA | AAGATAGAGGCTGTGA |
| 143 | AGGCTGTGATGTGAATAA | AGGCTGTGATGTGAATAA |
| 144 | AGGCTGTGATGTGAATAA | AGGCTGTGATGTGAATAA |
| 145 | AGGCTGTGATGTGAATAA | AGGCTGTGATGTGAATAA |
| 146 | AGAGGCTGTGATGTGAAT | AGAGGCTGTGATGTGAAT |
| 147 | AGAGGCTGTGATGTGAAT | AGAGGCTGTGATGTGAAT |
| 148 | AGAGGCTGTGATGTGAAT | AGAGGCTGTGATGTGAAT |
| 149 | TAGAGGCTGTGATGTGAA | TAGAGGCTGTGATGTGAA |
| 150 | TAGAGGCTGTGATGTGAA | TAGAGGCTGTGATGTGAA |
| 151 | TAGAGGCTGTGATGTGAA | TAGAGGCTGTGATGTGAA |
| 152 | GATAGAGGCTGTGATTGG | GATAGAGGCTGTGATTGG |
| 153 | GATAGAGGCTGTGATTGG | GATAGAGGCTGTGATTGG |
| 154 | GATAGAGGCTGTGATTGG | GATAGAGGCTGTGATTGG |
| 155 | AGATAGAGGCTGTGATGG | AGATAGAGGCTGTGATGG |
| 156 | GGCTGTGATGTGAATA | GGCTGTGATGTGAATA |
| 157 | GGCTGTGATGTGAATA | GGCTGTGATGTGAATA |
| 158 | GGCTGTGATGTGAATA | GGCTGTGATGTGAATA |
| 159 | GAGGCTGTGATGTGAA | GAGGCTGTGATGTGAA |
| 160 | GAGGCTGTGATGTGAA | GAGGCTGTGATGTGAA |

FIG. 15 cont.

| Compound ID No.: | Sequence (5'-3') | Chemistry (All MOE unless otherwise noted; G-LNA, C-5MeC-MOE) |
|---|---|---|
| 161 | GAGGCTGTGATGTGAA | gAggCTgTgATgTGAA |
| 162 | TAGAGGCTGTGATTGG | TAGAGgCTgTGATTGG |
| 163 | TAGAGGCTGTGATTGG | TAgAGGCTgTGATTGg |
| 164 | TAGAGGCTGTGATTGG | TAgAGGCTgTGATTGg |
| 165 | ATAGAGGCTGTGATGG | ATAgAGGCTgTGATGg |
| 166 | GATAGAGGCTGTGATG | gATAgAGgCTgTGATg |
| 167 | AGATAGAGGCTGTGAT | AGATAGAGgCTgTgAT |
| 168 | GGCTATGAAACTGATGGAGA | GGCTATgAAACTgATGGAGA |
| 169 | CTATGAAACTGATGATGGAGA | CTATgAaACTGATGgAGA |
| 170 | GCTATGAAACTGATGATGGAG | gCTATGAAACTgATGGAg |
| 171 | GGCTATGAAACTGATGATGGA | GGCTATgAAACTgATGGA |
| 172 | ATGAAACTGATGATGGAGA | ATgAAACTgATGgAGA |
| 173 | ATGAAACTGATGATGGAGA | ATgAAACTgATGGAGA |
| 174 | CTATGAAACTGATGGA | CTATgAAACTgATGGA |
| 175 | CTATGAAACTGATG | CTATgAAACTgATGGA |
| 176 | GGCTATGAAACTGATG | GGCTATgAAACTgATg |
| 177 | GGCTATGAAACTGATG | GGCTATgAAACTgATg |
| 178 | GAAACTGATGGAGA | gAAACTgATGgAGA |
| 179 | ATGAAACTGATGGA | ATgAAACTgATGgA |
| 180 | CTATGAAACTGATG | CTATGAAACTgATG |

FIG. 15 cont.

| Compound ID No.: | Sequence (5'-3') | (All MOE unless otherwise noted; G-LNA, C-5MeC-MOE) | Chemistry |
|---|---|---|---|
| 181 | GGCTATGAAACTGA | GGCTATGAAACTGA | |
| 182 | TAGAGGCTGTGATGGGAATAAA | TAGAGGCTGTGATGGGAATAAA | PMO |
| 183 | TAGAGGCTGTGATGGGAATAAAT | TAGAGGCTGTGATGGGAATAAAT | PMO |
| 184 | ATAGAGGCTGTGATGGGAATAA | ATAGAGGCTGTGATGGGAATAA | PMO |
| 185 | ATAGAGGCTGTGATGGGAATAAAA | ATAGAGGCTGTGATGGGAATAAAA | PMO |
| 186 | ATAGAGGCTGTGATGGGAATAAAAT | ATAGAGGCTGTGATGGGAATAAAAT | PMO |
| 187 | AAAGATAGAGGCTGTGATGGGAATA | AAAGATAGAGGCTGTGATGGGAATA | PMO |
| 188 | GGCTATGAAACTGATGGAGAA | GGCTATGAAACTGATGGAGAA | PMO |
| 189 | GGCTATGAAACTGATGGAGAAA | GGCTATGAAACTGATGGAGAAA | PMO |
| 190 | GGCTATGAAACTGATGGAGAAAGA | GGCTATGAAACTGATGGAGAAAGA | PMO |
| 191 | AGGGCTATGAAACTGATGGAGAAAG | AGGGCTATGAAACTGATGGAGAAAG | PMO |
| 192 | CATTTAATTAAATTATAT | CATTTAATTAAATTATAT | |
| 193 | CCATTTAATTAAATTATA | CCATTTAATTAAATTATA | |
| 194 | CCCATTTAATTAAATTAT | CCCATTTAATTAAATTAT | |
| 195 | ACCATTTAATTAAATTA | ACCATTTAATTAAATTA | |
| 196 | TACCCATTTAATTAAATT | TACCCATTTAATTAAATT | |
| 197 | TTACCCATTTAATTAAAT | TTACCCATTTAATTAAAT | |
| 198 | CTTACCCATTTAATTAAA | CTTACCCATTTAATTAAA | |
| 199 | TCTTACCCATTTAATTAA | TCTTACCCATTTAATTAA | |
| 200 | GATAGAGGCTGTGATGG | GATAGAGGCTGTGATGG | |

FIG. 15 cont.

| Compound ID No.: | Sequence (5'-3') | (All MOE unless otherwise noted; G-LNA, C-5MeC-MOE) | Chemistry |
|---|---|---|---|
| 201 | GGCTGTGAAACTGATGGA | GGCTGTGAAACTGATGGA | |
| 202 | GGCTGTGAAACTGATGGAGA | GGCTGTGAAACTGATGGAGA | |
| 203 | CTATGAAACTGATGGA | CTATGAAACTGATGGA | |
| 204 | GCTATGAAACTGATGG | GCTATGAAACTGATGG | |
| 205 | GGCTATGAAACTGATG | GGCTATGAAACTGATG | |
| 206 | ATGAAACTGATGGA | ATGAAACTGATGGA | |
| 207 | TATGAAACTGATGG | TATGAAACTGATGG | |
| 208 | CTATGAAACTGATG | CTATGAAACTGATG | |
| 209 | GCTATGAAACTGAT | GCTATGAAACTGA | |
| 210 | GGCTATGAAACTGA | GGCTATGAAACTGA | |
| 211 | GCTGTGAAACTGATGGAGAA | GCTGTGAAACTGATGGAGAA | |
| 212 | GGGCTGTGAAACTGATGGAG | GGGCTGTGAAACTGATGGAG | |
| 213 | TGTGAAACTGATGGAGAA | TGTGAAACTGATGGAGAA | |
| 214 | CTGTGAAACTGATGGAGA | CTGTGAAACTGATGGAGA | |
| 215 | GCTGTGAAACTGATGGAG | GCTGTGAAACTGATGGAG | |
| 216 | GGGCTGTGAAACTGATGG | GGCTGTGAAACTGATGG | |
| 217 | TGAAACTGATGGAGAA | TGAAACTGATGGAGAA | |
| 218 | GTGAAACTGATGGAGA | GTGAAACTGATGGAGA | |
| 219 | TGTGAAACTGATGGAG | TGTGAAACTGATGGAG | |
| 220 | CTGTGAAACTGATGGA | CTGTGAAACTGATGGA | |

FIG. 15 cont.

| Compound ID No.: | Sequence (5'-3') | Chemistry (All MOE unless otherwise noted: G-LNA, C-5MeC-MOE) |
|---|---|---|
| 221 | GCTGTGAAACTGATGG | GCTGTGAAACTGATGG |
| 222 | GGCTGTGAAACTGATG | GGCTGTGAAACTGATG |
| 223 | GGGCTGTGAAACTGAT | GGGCTGTGAAACTGAT |
| 224 | CGGTCCAGGAATGAC | CGGTCCAGGAATGAC |
| 225 | CCGGTCCAGGAATGA | CCGGTCCAGGAATGA |
| 226 | CCCGGTCCAGGAATG | CCCGGTCCAGGAATG |
| 227 | TCCCGGTCCAGGAAT | TCCCGGTCCAGGAAT |
| 228 | CTCCCGGTCCAGGAA | CTCCCGGTCCAGGAA |
| 229 | GCTCCCGGTCCAGGA | GCTCCCGGTCCAGGA |
| 230 | GGCTCCCGGTCCAGG | GGCTCCCGGTCCAGG |
| 231 | CGGGAGCCCCCGTGT | CGGGAGCCCCCGTGT |
| 232 | GCGGGAGCCCCCGTG | GCGGGAGCCCCCGTG |
| 233 | CGCGGGAGCCCCCGT | CGCGGGAGCCCCCGT |
| 234 | ACGCGGGAGCCCCCG | ACGCGGGAGCCCCCG |
| 235 | CACGCGGGAGCCCCC | CACGCGGGAGCCCCC |
| 236 | CCACGCGGGAGCCCC | CCACGCGGGAGCCCC |
| 237 | GCCACGCGGGAGCCC | GCCACGCGGGAGCCC |
| 238 | GGCCACGCGGGAGCC | GGCCACGCGGGAGCC |
| 239 | CGGCCACGCGGGAGC | CGGCCACGCGGGAGC |
| 240 | ACGGCCACGCGGGAG | ACGGCCACGCGGGAG |

FIG. 15 cont.

| Compound ID No.: | Sequence (5'-3") | Chemistry (All MOE unless otherwise noted; G-LNA, C-5MeC-MOE) |
|---|---|---|
| 241 | GACGGCCACGCGGGA | GACGGCCACGCGGGA |
| 242 | AGACGGCCACGCGGG | AGACGGCCACGCGGG |
| 243 | GCTAGGGAGGGATGGTTA | GCTAGGGAGGGATGGTTA |
| 244 | TGTAAGCTAGGAGGAT | TGTAAGCTAGGAGGAT |
| 245 | ACAGATGTAAGCTAGGA | ACAGATGTAAGCTAGGA |
| 246 | AAGGAACAGATGTAAGCT | AAGGAACAGATGTAAGCT |
| 247 | CAACAAAGGAACAGATGT | CAACAAAGGAACAGATGT |
| 248 | GGGTGCAACAAAGGAACA | GGGTGCAACAAAGGAACA |
| 249 | ACCAAGGGTGCAACAAAG | ACCAAGGGTGCAACAAAG |
| 250 | GTTAAACCAAGGGTGCAA | GTTAAACCAAGGGTGCAA |
| 251 | ATAATGTTAAACCAAGGG | ATAATGTTAAACCAAGGG |
| 252 | GGAGAATAATGTTAAACC | GGAGAATAATGTTAAACC |
| 253 | GGGGAGGAGAATAATGTT | GGGGAGGAGAATAATGTT |
| 254 | AAATTGGGAGGAGAATA | AAATTGGGAGGAGAATA |
| 255 | AGAGGAAATTGGGAGGA | AGAGGAAATTGGGAGGA |
| 256 | GGAGAAGAGGAAATTGGG | GGAGAAGAGGAAATTGGG |
| 257 | AATGAGGAGAAGAGGAAA | AATGAGGAGAAGAGGAAA |
| 258 | TTCACAATGAGGAGAAGA | TTCACAATGAGGAGAAGA |
| 259 | ACGAGTTCACAATGAGGA | ACGAGTTCACAATGAGGA |
| 260 | CTGCCACGAGTTCACAAT | CTGCCACGAGTTCACAAT |

FIG. 15 cont.

| Compound ID No.: | Sequence (5'-3') | Chemistry |
|---|---|---|
| | | (All MOE unless otherwise noted; G-LNA, C-5MeC-MOE) |
| 261 | AGACCCTGCCACGAGTTC | AGACCCTGCCACGAGTTC |
| 262 | CAAGCAGACCCTGCCACG | CAAGCAGACCCTGCCACG |
| 263 | CTCACCAAGCAGACCCTG | CTCACCAAGCAGACCCTG |
| 264 | GAGCTCACCAAGCAGACC | GAGCTCACCAAGCAGACC |
| 265 | AGAATGAGCTCACCAAGC | AGAATGAGCTCACCAAGC |
| 266 | GTAAGAGAATGAGCTCAC | GTAAGAGAATGAGCTCAC |
| 267 | TTGTTGTAAGAGAATGAG | TTGTTGTAAGAGAATGAG |
| 268 | ATTTGTTGTGTAAGAGA | ATTTGTTGTGTAAGAGA |
| 269 | CTTGAATTTGTTGTTGTA | CTTGAATTTGTTGTTGTA |
| 270 | ATGCTCTTGAATTTGTTG | ATGCTCTTGAATTTGTTG |
| 271 | TCTTCATGCTCTTGAATT | TCTTCATGCTCTTGAATT |
| 272 | CTTCCTCTTCATGCTCTT | CTTCCTCTTCATGCTCTT |
| 273 | GCGGCTTCCTCTTCATG | GCGGCTTCCTCTTCATG |
| 274 | GCTCTGCGCGCTTCCTCT | GCTCTGCGCGCTTCCTCT |
| 275 | GGCCAGCGGCTCTGCGCG | GGCCAGCGGCTCTGCGCG |
| 276 | ATATTGGCCAGCGGCTCT | ATATTGGCCAGCGGCTCT |
| 277 | GTGCTATATTGGCCAGCG | GTGCTATATTGGCCAGCG |
| 278 | AGCTCGTGCTATATTGGC | AGCTCGTGCTATATTGGC |
| 279 | GGCATAGCTCGTGCTATA | GGCATAGCTCGTGCTATA |
| 280 | TGTTGGGCATAGCTCGTG | TGTTGGGCATAGCTCGTG |

FIG. 15 cont.

| Compound ID No.: | Sequence (5'-3') | Chemistry (All MOE unless otherwise noted; G-LNA, C-5MeC-MOE) |
|---|---|---|
| 281 | GCTTCTGTGTTGGGCATAGC | |
| 282 | CTTGCGCTTCTGTTGGGC | |
| 283 | CACCTTGCGCTTCTGTTG | |
| 284 | TCCATCACCTTGCGCTTC | |
| 285 | AACCATCCATCACCTTGC | |
| 286 | CCTTAAACCATCCATCAC | |
| 287 | AGCCCCTTAAACCATCC | |
| 288 | TCGGTAGCCCCTTAAAC | |
| 289 | ATGTATCGGTAGCCCCT | |
| 290 | TGTGAATGTATCGGTAGC | |
| 291 | ATTAGTGTGAATGTATCG | |
| 292 | GGCTGATTAGTGTGAATG | |
| 293 | GAAATGGCTGATTAGTGT | |
| 294 | TGGCAGAAATGGCTGATT | |
| 295 | GATCTTGGCAGAAATGGC | |
| 296 | GACATGATCTTGGCAGAA | |
| 297 | GAGGTGACATGATCTTGG | |
| 298 | AGATTGAGGTGACATGAT | |
| 299 | TGAACAGATTGAGGTGAC | |
| 300 | GTCCATGAACAGATTGAG | |

FIG. 15 cont.

| Compound ID No.: | Sequence (5'-3') | Chemistry (All MOE unless otherwise noted; G-LNA, C-5MeC-MOE) |
|---|---|---|
| 301 | TTGGAGTCCATGAACAGA | TTGGAGTCCATGAACAGA |
| 302 | TGTATTTGGAGTCCATGA | TGTATTTGGAGTCCATGA |
| 303 | TTTCTTGTATTTGGAGTC | TTTCTTGTATTTGGAGTC |

FIG. 15 cont.

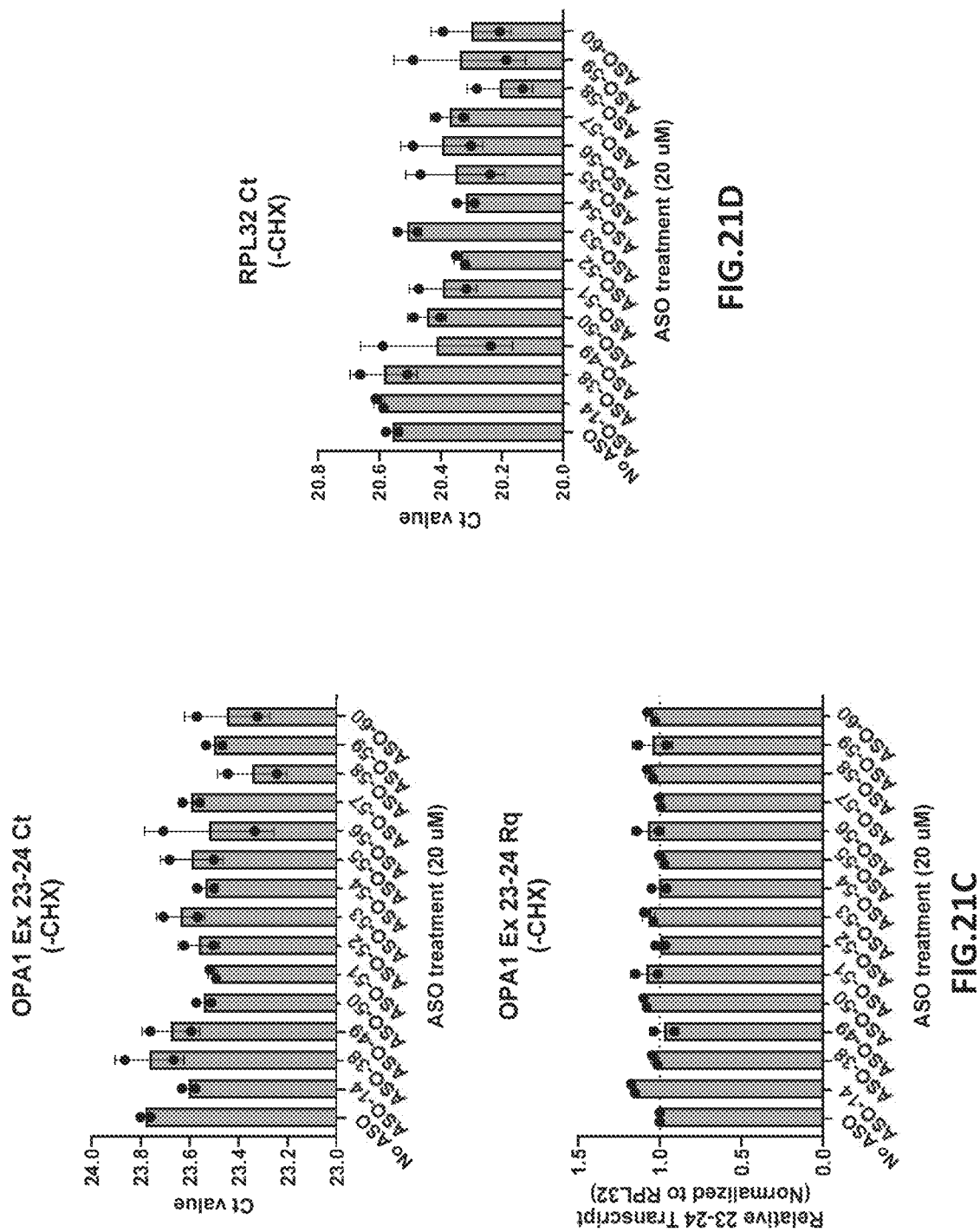

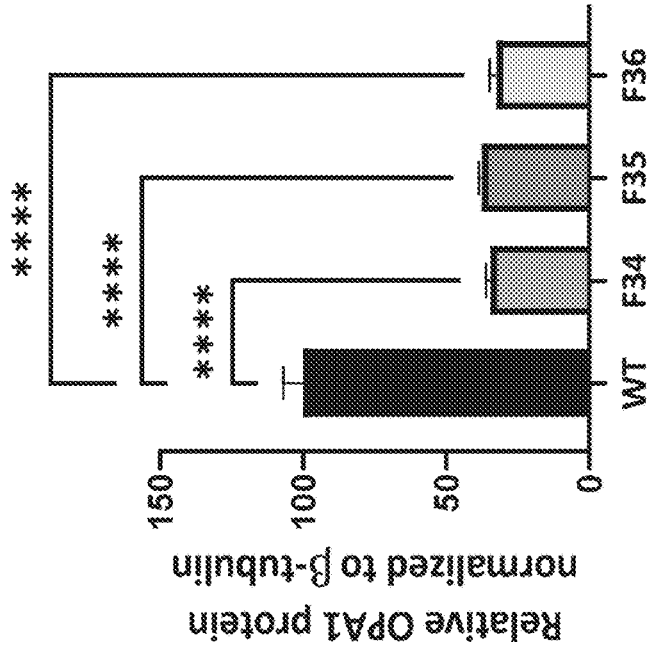
FIG. 25A
FIG. 25B
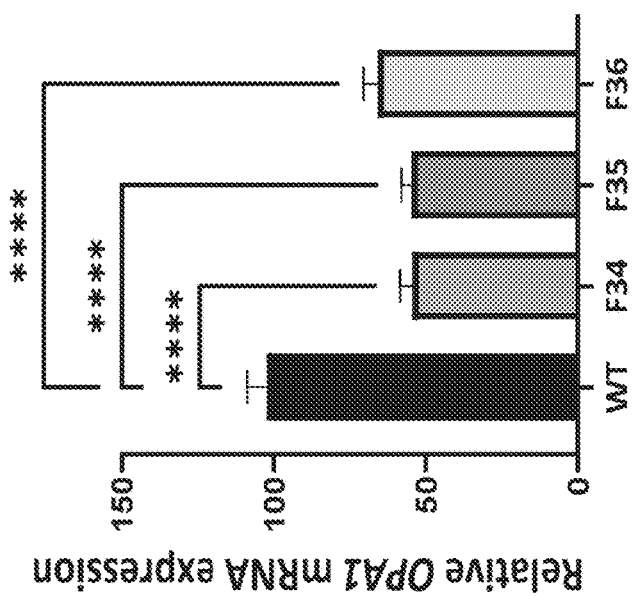
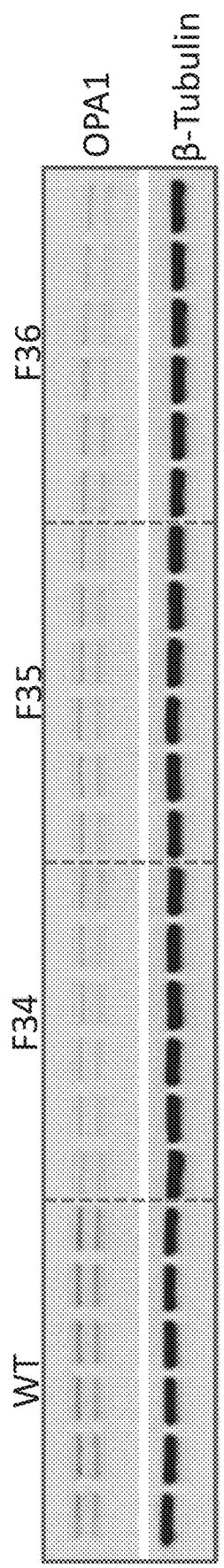
FIG. 25C

OPA1 ANTISENSE OLIGOMERS FOR TREATMENT OF CONDITIONS AND DISEASES

CROSS-REFERENCE

This application is a continuation of U.S. patent application Ser. No. 17/924,966 filed Nov. 11, 2022, which is US. National Stage entry of International Patent Application No. PCT/US2021/030254, filed Apr. 30, 2021, which claims the benefit of U.S. Provisional Application No. 63/023,013, filed May 11, 2020, and U.S. Provisional Application No. 63/112,458, filed Nov. 11, 2020, each of which is incorporated herein by reference in its entirety.

SEQUENCE LISTING

The instant application contains a Sequence Listing which has been submitted electronically in XML format and is hereby incorporated by reference in its entirety. Said XML copy, created on Apr. 14, 2023, is named 47991-731_301.xml and is 971,903 bytes in size.

BACKGROUND

Alternative splicing events in genes can lead to non-productive mRNA transcripts which in turn can lead to aberrant or reduced protein expression, and therapeutic agents which can target the alternative splicing events in genes can modulate the expression level of functional proteins in patients and/or inhibit aberrant protein expression. Such therapeutic agents can be used to treat a condition or disease caused by the protein deficiency.

Autosomal dominant optic atrophy (ADOA) is one of the most commonly diagnosed optic neuropathies. This optic nerve disease is associated with structural and functional mitochondrial deficits that lead to degeneration of the retinal ganglion cells and progressive, irreversible loss of vision. A majority of ADOA patients carry mutations in OPA1 and most mutations lead to haploinsufficiency (Lenaers G. et al. Orphanet J Rare Dis 2012). OPA1 encodes a mitochondrial GTPase with a critical role in mitochondrial fusion, ATP synthesis and apoptosis. Currently, there is no approved disease-modifying treatment for ADOA patients and there is a need for such treatments.

SUMMARY

Described herein, in some aspects, is a method of modulating expression of an OPA1 protein in a cell having a pre-mRNA that is transcribed from an OPA1 gene and that comprises a non-sense mediated RNA decay-inducing exon (NMD exon), the method comprising contacting an agent or a vector encoding the agent to the cell, whereby the agent modulates splicing of the NMD exon from the pre-mRNA, thereby modulating a level of processed mRNA that is processed from the pre-mRNA, and modulating the expression of the OPA1 protein in the cell, wherein the agent comprises an antisense oligomer with at least 80% sequence identity to a sequence selected from the group consisting of SEQ ID NOs: 6-275 and 280-299.

In some embodiments, the agent: (a) binds to a targeted portion of the pre-mRNA; (b) modulates binding of a factor involved in splicing of the NMD exon; or (c) a combination of (a) and (b). In some embodiments, the agent interferes with binding of the factor involved in splicing of the NMD exon to a region of the targeted portion. In some embodiments, the targeted portion of the pre-mRNA is proximal to the NMD exon. In some embodiments, the targeted portion of the pre-mRNA is at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream of 5' end of the NMD exon. In some embodiments, the targeted portion of the pre-mRNA is at least about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides, about 40 nucleotides, about 30 nucleotides, about 20 nucleotides, about 10 nucleotides, about 5 nucleotides, about 4 nucleotides, about 2 nucleotides, about 1 nucleotides upstream of 5' end of the NMD exon. In some embodiments, the targeted portion of the pre-mRNA is at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream of 3' end of the NMD exon. In some embodiments, the targeted portion of the pre-mRNA is at least about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides, about 40 nucleotides, about 30 nucleotides, about 20 nucleotides, about 10 nucleotides, about 5 nucleotides, about 4 nucleotides, about 2 nucleotides, about 1 nucleotides downstream of 3' end of the NMD exon. In some embodiments, the targeted portion of the pre-mRNA is at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream of genomic site GRCh38/hg38: chr3 193628509. In some embodiments, the targeted portion of the pre-mRNA is about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream of genomic site GRCh38/hg38: chr3 193628509. In some embodiments, the targeted portion of the pre-mRNA is at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream of genomic site GRCh38/hg38: chr3 193628616. In some embodiments, the targeted portion of the pre-mRNA is about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream of genomic site GRCh38/hg38: chr3 193628616. In some embodiments, the targeted portion of the pre-mRNA is located in an intronic region between two canonical exonic regions of the pre-mRNA, and wherein the intronic region contains the NMD exon. In some embodiments, the targeted portion of the pre-mRNA at least partially overlaps with the NMD exon. In some embodiments, the targeted portion of the pre-mRNA at least partially overlaps with an intron upstream or downstream of the NMD exon. In some embodiments, the targeted portion of the pre-mRNA comprises 5' NMD exon-intron junction or 3' NMD exon-intron junction. In some embodiments, the targeted portion of the pre-mRNA is within the NMD exon. In some embodiments, the targeted portion of the pre-mRNA comprises about 5, 6, 7, 8, 9, 10, 11, 12, 13, 14, 15, 16, 17, 18, 19, 20, 21, 22, 23, 24, 25, 26, 27, 28, 29, 30, or more consecutive nucleotides of the NMD exon.

In some embodiments, the NMD exon comprises a sequence with at least 80%, at least 90%, or 100% sequence identity to SEQ ID NO: 279. In some embodiments, the NMD exon comprises a sequence of SEQ ID NO: 279. In some embodiments, the targeted portion of the pre-mRNA is within the non-sense mediated RNA decay-inducing exon GRCh38/hg38: chr3 193628509 to 193628616. In some embodiments, the targeted portion of the pre-mRNA is upstream or downstream of the non-sense mediated RNA decay-inducing exon GRCh38/hg38: chr3 193628509 to 193628616. In some embodiments, the targeted portion of the pre-mRNA comprises an exon-intron junction of exon GRCh38/hg38: chr3 193628509 to 193628616. In some embodiments, the OPA1 protein expressed from the processed mRNA is a full-length OPA1 protein or a wild-type OPA1 protein. In some embodiments, the OPA1 protein expressed from the processed mRNA is a functional OPA1 protein. In some embodiments, the OPA1 protein expressed from the processed mRNA is at least partially functional as compared to a wild-type OPA1 protein. In some embodiments, the OPA1 protein expressed from the processed mRNA is at least partially functional as compared to a full-length wild-type OPA1 protein. In some embodiments, the OPA1 protein expressed from the processed mRNA is an OPA1 protein that lacks an amino acid sequence encoded by a nucleic acid sequence with at least 80% sequence identity to SEQ ID NO: 277.

In some embodiments, the method promotes exclusion of the NMD exon from the pre-mRNA. In some embodiments, the exclusion of the NMD exon from the pre-mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent. In some embodiments, the method results in an increase in the level of the processed mRNA in the cell. In some embodiments, the level of the processed mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent. In some embodiments, the method results in an increase in the expression of the OPA1 protein in the cell. In some embodiments, a level of the OPA1 protein expressed from the processed mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent.

In some embodiments, the agent comprises an antisense oligomer with at least 80%, at least 90%, or 100% sequence identity to a sequence selected from the group consisting of SEQ ID NOs: 36, 236, 242, 250, 280-283, 288, and 290-292. In some embodiments, the agent further comprises a gene editing molecule. In some embodiments, the gene editing molecule comprises CRISPR-Cas9.

Described herein, in some aspects, is a method of modulating expression of an OPA1 protein in a cell having a pre-mRNA that is transcribed from an OPA1 gene, wherein the pre-mRNA comprises a coding exon, the method comprising contacting an agent or a vector encoding the agent to the cell, whereby the agent promotes exclusion of the coding exon from the pre-mRNA, thereby increasing a level of a processed mRNA that is processed from the pre-mRNA and that lacks the coding exon in the cell. In some embodiments, the agent: (a) binds to a targeted portion of the pre-mRNA; (b) modulates binding of a factor involved in splicing of the coding exon; or (c) a combination of (a) and (b). In some embodiments, the agent interferes with binding of the factor involved in splicing of the coding exon to a region of the targeted portion. In some embodiments, the targeted portion of the pre-mRNA is proximal to the coding exon. In some embodiments, the targeted portion of the pre-mRNA is located in an intronic region immediately upstream of the coding exon. In some embodiments, the targeted portion of the pre-mRNA is within a region spanning from 100 to 50, from 90 to 50, from 80 to 50, from 70 to 50, from 60 to 50, from 60 to 40, from 60 to 30, from 60 to 20, from 60 to 10, from 49 to 1, from 39 to 1, from 29 to 1, or from 19 to 1 nucleotides upstream of 5' end of the coding exon. In some embodiments, the targeted portion of the pre-mRNA is within a region spanning from 49 to 1, from 39 to 1, from 29 to 1, or from 19 to 1 nucleotides upstream of 5' end of the coding exon. In some embodiments, the targeted portion of the pre-mRNA is located in an intronic region immediately downstream of the coding exon. In some embodiments, the targeted portion of the pre-mRNA is within a region spanning from 1 to 49, from 1 to 39, from 1 to 29, from 1 to 19, from 10 to 60, from 20 to 60, from 30 to 60, from 40 to 60, from 50 to 60, from 50 to 70, from 50 to 80, from 50 to 90, or from 50 to 100 nucleotides downstream of 3' end of the coding exon. In some embodiments, the targeted portion of the pre-mRNA is within a region spanning from 1 to 49, from 1 to 39, from 1 to 29, or from 1 to 19 nucleotides downstream of 3' end of the coding exon. In some embodiments, the targeted portion of the pre-mRNA at least partially overlaps with the coding exon. In some embodiments, the targeted portion of the pre-mRNA at least partially overlaps with an intron immediately upstream or immediately downstream of the coding exon. In some embodiments, the targeted portion of the pre-mRNA comprises 5' coding exon-intron junction or 3' coding exon-intron junction. In some embodiments, the targeted portion is within the coding exon of the pre-mRNA. In some embodiments, the coding exon is an alternatively spliced exon.

In some embodiments, the coding exon comprises a sequence with at least 80%, at least 90%, or 100% sequence identity to SEQ ID NO: 277. In some embodiments, the coding exon comprises SEQ ID NO: 277. In some embodiments, the targeted portion of the pre-mRNA is immediately upstream of the coding exon GRCh38/hg38: chr3 193626092 to 193626202. In some embodiments, the targeted portion of the pre-mRNA is within a region spanning from 49 to 1, from 39 to 1, from 29 to 1, or from 19 to 1 nucleotides upstream of genomic site GRCh38/hg38: chr3 193626092. In some embodiments, the targeted portion of the pre-mRNA is immediately downstream of the coding exon GRCh38/hg38: chr3 193626092 to 193626202. In some embodiments, the targeted portion of the pre-mRNA is within a region spanning from 1 to 49, from 1 to 39, from 1 to 29, or from 1 to 19 nucleotides downstream of genomic site GRCh38/hg38: chr3 193626202. In some embodiments, the targeted portion of the pre-mRNA is within the coding exon GRCh38/hg38: chr3 193626092 to 193626202. In some embodiments, the targeted portion of the pre-mRNA comprises an exon-intron junction of exon GRCh38/hg38: chr3 193626092 to 193626202. In some embodiments, the targeted portion comprises about 5, 6, 7, 8, 9, 10, 11, 12, 13, 14, 15, 16, 17, 18, 19, 20, 21, 22, 23, 24, 25, 26, 27, 28, 29, 30, or more consecutive nucleotides of the coding exon. In some embodiments, the targeted portion of the pre-mRNA comprises a sequence with at least 80%, 85%, 90%, 95%, 97%, or 100% sequence identity to a region comprising at least 8 contiguous nucleic acids of SEQ ID NO: 277.

In some embodiments, the exclusion of the coding exon from the pre-mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent. In some embodiments, the method results in an increase in expression of the OPA1 protein in the cell. In some embodiments, a level of the OPA1 protein expressed from the processed mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent. In some embodiments, a level of the OPA1 protein expressed from the processed mRNA in the cell contacted with the agent is increased by at least about 1.5-fold compared to in the absence of the agent.

In some embodiments, the OPA1 protein expressed from the processed mRNA is a functional OPA1 protein. In some embodiments, the OPA1 protein expressed from the processed mRNA is at least partially functional as compared to a wild-type OPA1 protein. In some embodiments, the OPA1 protein expressed from the processed mRNA is at least partially functional as compared to a full-length wild-type OPA1 protein. In some embodiments, the agent promotes exclusion of a non-sense mediated RNA decay-inducing exon (NMD exon) from the pre-mRNA. In some embodiments, the NMD exon comprises a sequence with at least 80%, at least 90%, or 100% sequence identity to SEQ ID NO: 279. In some embodiments, the NMD exon comprises a sequence of SEQ ID NO: 279. In some embodiments, the OPA1 protein expressed from the processed mRNA comprises fewer proteolytic cleavage sites than an OPA1 protein encoded by a corresponding mRNA containing the coding exon.

In some embodiments, the agent comprises an antisense oligomer with at least 80%, at least 90%, or 100% sequence identity to a sequence selected from the group consisting of SEQ ID NOs: 227-242, 250, 280-283, 288, and 290-292. In some embodiments, the agent comprises a gene editing molecule. In some embodiments, the gene editing molecule comprises CRISPR-Cas9.

Described herein, in some aspects, is a method of modulating expression of an OPA1 protein in a cell having a pre-mRNA that is transcribed from an OPA1 gene, wherein the pre-mRNA comprises a coding exon, the method comprising contacting an agent or a vector encoding the agent to the cell, wherein the agent comprises an antisense oligomer that binds to: (a) a targeted portion of the pre-mRNA within an intronic region immediately upstream of a 5' end of the coding exon of the pre-mRNA; or (b) a targeted portion of the pre-mRNA within an intronic region immediately downstream of a 3' end of the coding exon of the pre-mRNA; whereby the agent increases a level of a processed mRNA that is processed from the pre-mRNA and that contains the coding exon in the cell.

In some embodiments, the coding exon is an alternatively spliced exon. In some embodiments, the method promotes inclusion of the coding exon in the processed mRNA during splicing of the pre-mRNA in the cell. In some embodiments, the target portion of the pre-mRNA is within a region spanning from 100 to 50, from 100 to 60, from 100 to 70, from 100 to 80, or from 100 to 90 nucleotides upstream of a 5' end of the coding exon. In some embodiments, the target portion of the pre-mRNA is within a region spanning from 40 to 100, from 50 to 100, from 60 to 100, from 70 to 100, from 80 to 100, or from 90 to 100 nucleotides downstream of a 3' end of the coding exon. In some embodiments, the coding exon comprises a sequence with at least 80%, at least 90%, or 100% sequence identity to SEQ ID NO: 277. In some embodiments, the coding exon comprises SEQ ID NO: 277. In some embodiments, the targeted portion of the pre-mRNA is within a region spanning from 100 to 50, from 100 to 60, from 100 to 70, from 100 to 80, or from 100 to 90 nucleotides upstream of genomic site GRCh38/hg38: chr3 193626092. In some embodiments, the targeted portion of the pre-mRNA is within a region spanning from 40 to 100, from 50 to 100, from 60 to 100, from 70 to 100, from 80 to 100, or from 90 to 100 nucleotides downstream of genomic site GRCh38/hg38: chr3 193626202. In some embodiments, the inclusion of the coding exon in the processed mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent. In some embodiments, the agent comprises an antisense oligomer with at least 80%, at least 90%, or 100% sequence identity to SEQ ID NO: 267.

Described herein, in some aspects, is a method of modulating expression of a target protein in a cell having a pre-mRNA transcribed from a gene that encodes the target protein, wherein the pre-mRNA comprises a coding exon and a non-sense mediated RNA decay-inducing exon (NMD exon), the method comprising contacting an agent or a vector encoding the agent to the cell, wherein the agent promotes exclusion of both the coding exon and the NMD exon from the pre-mRNA, thereby increasing a level of a processed mRNA that is processed from the pre-mRNA and that lacks both the NMD exon and the coding exon in the cell.

In some embodiments, the agent: (a) binds to a targeted portion of the pre-mRNA; (b) modulates binding of a factor involved in splicing of the coding exon, the NMD exon, or both; or (c) a combination of (a) and (b). In some embodiments, the agent interferes with binding of the factor involved in splicing of the coding exon, the NMD exon, or both, to a region of the targeted portion. In some embodiments, the NMD exon is within an intronic region adjacent to the coding exon. In some embodiments, the NMD exon is within an intronic region immediately upstream of the coding exon. In some embodiments, the NMD exon is within an intronic region immediately downstream of the coding exon. In some embodiments, the targeted portion of the pre-mRNA is proximal to the coding exon. In some embodiments, the targeted portion of the pre-mRNA is located in an intronic region immediately upstream of the coding exon. In some embodiments, the targeted portion of the pre-mRNA is located in an intronic region immediately downstream of the coding exon. In some embodiments, the targeted portion of the pre-mRNA is located within the coding exon. In some embodiments, the targeted portion of the pre-mRNA is within a region spanning from 49 to 1, from 39 to 1, from 29 to 1, or from 19 to 1 nucleotides upstream of 5' end of the coding exon. In some embodiments, the targeted portion of the pre-mRNA is within a region spanning from 100 nucleotides upstream of the coding exon to 100 nucleotides downstream of the coding exon. In some embodiments, the coding exon is an alternatively spliced exon. In some embodiments, the coding exon comprises a sequence with at least 80%, at least 90%, or 100% sequence identity to SEQ ID NO: 277.

In some embodiments, the coding exon comprises SEQ ID NO: 277. In some embodiments, the targeted portion of the pre-mRNA is immediately upstream of the coding exon GRCh38/hg38: chr3 193626092 to 193626202. In some embodiments, the targeted portion of the pre-mRNA is immediately downstream of the coding exon GRCh38/hg38: chr3 193626092 to 193626202. In some embodiments, the targeted portion of the pre-mRNA is within a region spanning from 49 to 1, from 39 to 1, from 29 to 1, or from 19 to 1 nucleotides upstream of GRCh38/hg38: chr3 193626092. In some embodiments, the targeted portion of the pre-mRNA is within a region spanning from 100 nucleotides upstream of genomic site GRCh38/hg38: chr3 193626092. to 100 nucleotides downstream of genomic site GRCh38/hg38: chr3 193626202. In some embodiments, the targeted portion of the pre-mRNA is within the coding exon GRCh38/hg38: chr3 193626092 to 193626202. In some embodiments, the targeted portion of the pre-mRNA comprises an exon-intron junction of the coding exon GRCh38/hg38: chr3 193626092 to 193626202. In some embodiments, the targeted portion comprises about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more consecutive nucleotides of the coding exon. In some embodiments, the targeted portion of the pre-mRNA is proximal to the NMD exon. In some embodiments, the targeted portion of the pre-mRNA is located in an intronic region immediately upstream of the NMD exon. In some embodiments, the targeted portion of the pre-mRNA is located in an intronic region immediately downstream of the NMD exon. In some embodiments, the targeted portion of the pre-mRNA is located within the NMD exon. In some embodiments, the targeted portion of the pre-mRNA is within a region spanning from 100 nucleotides upstream of the NMD exon to 100 nucleotides downstream of the NMD exon. In some embodiments, the NMD exon comprises a sequence with at least 80%, at least 90%, or 100% sequence identity to SEQ ID NO: 279. In some embodiments, the NMD exon comprises SEQ ID NO: 279. In some embodiments, the targeted portion of the pre-mRNA is immediately upstream of the NMD exon GRCh38/hg38: chr3 193628509 to 193628616. In some embodiments, the targeted portion of the pre-mRNA is immediately downstream of the NMD exon GRCh38/hg38: chr3 193628509 to 193628616. In some embodiments, the targeted portion of the pre-mRNA is within a region spanning from 100 nucleotides upstream of genomic site GRCh38/hg38: chr3 193628509 to 100 nucleotides downstream of genomic site GRCh38/hg38: chr3 193628616. In some embodiments, the targeted portion of the pre-mRNA is within the NMD exon GRCh38/hg38: chr3 193628509 to 193628616. In some embodiments, the targeted portion of the pre-mRNA comprises an exon-intron junction of the NMD exon GRCh38/hg38: chr3 193628509 to 193628616. In some embodiments, the targeted portion comprises about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more consecutive nucleotides of the NMD exon.

In some embodiments, the exclusion of the coding exon from the pre-mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent. In some embodiments, the exclusion of the NMD exon from the pre-mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent. In some embodiments, the agent results in an increase in the level of the processed mRNA in the cell. In some embodiments, the level of the processed mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent. In some embodiments, the method results in an increase in expression of the target protein in the cell. In some embodiments, a level of the target protein expressed from the processed mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent. In some embodiments, the target protein is an OPA1 protein. In some embodiments, a level of the OPA1 protein expressed from the processed mRNA in the cell contacted with the agent is increased by at least about 1.5-fold compared to in the absence of the agent. In some embodiments, the OPA1 protein expressed from the processed mRNA is a functional OPA1 protein.

In some embodiments, the OPA1 protein expressed from the processed mRNA is at least partially functional as compared to a wild-type OPA1 protein. In some embodiments, the OPA1 protein expressed from the processed mRNA is at least partially functional as compared to a full-length wild-type OPA1 protein.

In some embodiments, the agent comprises an antisense oligomer with at least 80%, at least 90%, or 100% sequence identity to a sequence selected from the group consisting of SEQ ID NOs: 236, 242, 250, 280-283, 288, and 290-292. In some embodiments, the agent comprises a gene editing molecule. In some embodiments, the gene editing molecule comprises CRISPR-Cas9.

In some embodiments, the agent is an antisense oligomer (ASO) and wherein the antisense oligomer comprises a backbone modification comprising a phosphorothioate linkage or a phosphorodiamidate linkage. In some embodiments, the agent is an antisense oligomer (ASO) and wherein the antisense oligomer comprises a phosphorodiamidate morpholino, a locked nucleic acid, a peptide nucleic acid, a 2'-O-methyl moiety, a 2'-Fluoro moiety, or a 2'-O-methoxyethyl moiety. In some embodiments, the therapeutic agent is an antisense oligomer (ASO) and wherein the antisense oligomer comprises at least one modified sugar moiety. In some embodiments, each sugar moiety is a modified sugar moiety. In some embodiments, the agent is an antisense oligomer (ASO) and wherein the antisense oligomer consists of from 8 to 50 nucleobases, 8 to 40 nucleobases, 8 to 35 nucleobases, 8 to 30 nucleobases, 8 to 25 nucleobases, 8 to 20 nucleobases, 8 to 15 nucleobases, 9 to 50 nucleobases, 9 to 40 nucleobases, 9 to 35 nucleobases, 9 to 30 nucleobases, 9 to 25 nucleobases, 9 to 20 nucleobases, 9 to 15 nucleobases, 10 to 50 nucleobases, 10 to 40 nucleobases, 10 to 35 nucleobases, 10 to 30 nucleobases, 10 to 25 nucleobases, 10 to 20 nucleobases, 10 to 15 nucleobases, 11 to 50 nucleobases, 11 to 40 nucleobases, 11 to 35 nucleobases, 11 to 30 nucleobases, 11 to 25 nucleobases, 11 to 20 nucleobases, 11 to 15 nucleobases, 12 to 50 nucleobases, 12 to 40 nucleobases, 12 to 35 nucleobases, 12 to 30 nucleobases, 12 to 25 nucleobases, 12 to 20 nucleobases, or 12 to 15 nucleobases. In some embodiments, the vector comprises a viral vector encoding the agent. In some embodiments, the viral vector comprises an adenoviral vector, adeno-associated viral (AAV) vector, lentiviral vector, Herpes Simplex Virus (HSV) viral vector, or retroviral vector.

In some embodiments, the method further comprises assessing mRNA level or expression level of the OPA1 protein. In some embodiments, the agent is a therapeutic agent.

Described herein, in some aspects, is a pharmaceutical composition comprising the therapeutic agent as disclosed herein or a vector encoding the therapeutic agent as disclosed herein, and a pharmaceutically acceptable excipient.

Described herein, in some aspects, is a pharmaceutical composition, comprising a therapeutic agent or a vector encoding a therapeutic agent, and a pharmaceutically acceptable excipient, wherein the therapeutic agent comprises an antisense oligomer with at least 80% sequence identity to a sequence selected from the group consisting of SEQ ID NOs: 6-275 and 280-299. In some embodiments, the therapeutic agent comprises an antisense oligomer with at least 80%, at least 90%, or 100% sequence identity to a sequence selected from the group consisting of SEQ ID NOs: 36, 236, 242, 250, 280-283, 288, and 290-292. In some embodiments, the therapeutic agent comprises an antisense oligomer with at least 80%, at least 90%, or 100% sequence identity to a sequence selected from the group consisting of SEQ ID NOs: 227-242, 250, 280-283, 288, and 290-292. In some embodiments, the therapeutic agent comprises an antisense oligomer with at least 80%, at least 90%, or 100% sequence identity to SEQ ID NO: 267. In some embodiments, the therapeutic agent comprises an antisense oligomer with at least 80%, at least 90%, or 100% sequence identity to a sequence selected from the group consisting of SEQ ID NOs: 236, 242, 250, 280-283, 288, and 290-292.

Described herein, in some aspects, is a composition, comprising an antisense oligomer with at least 80% sequence identity to a sequence selected from the group consisting of SEQ ID NOs: 6-275 and 280-299, wherein the antisense oligomer comprises a backbone modification, a sugar moiety modification, or a combination thereof. In some embodiments, the antisense oligomer has at least 80%, at least 90%, or 100% sequence identity to a sequence selected from the group consisting of SEQ ID NOs: 36, 236, 242, 250, 280-283, 288, and 290-292. In some embodiments, the antisense oligomer has at least 80%, at least 90%, or 100% sequence identity to a sequence selected from the group consisting of SEQ ID NOs: 227-242, 250, 280-283, 288, and 290-292. In some embodiments, the antisense oligomer has at least 80%, at least 90%, or 100% sequence identity to SEQ ID NO: 267. In some embodiments, the antisense oligomer has at least 80%, at least 90%, or 100% sequence identity to a sequence selected from the group consisting of SEQ ID NOs: 236, 242, 250, 280-283, 288, and 290-292.

Described herein, in some aspects, is a pharmaceutical composition, comprising a therapeutic agent or a vector encoding the therapeutic agent, and a pharmaceutically acceptable excipient, wherein the therapeutic agent promotes exclusion of a coding exon from a pre-mRNA, thereby increasing a level of a processed mRNA that is processed from the pre-mRNA and that lacks the coding exon in a cell, wherein the pre-mRNA is transcribed from an OPA1 gene and that comprises the coding exon.

Described herein, in some aspects, is a pharmaceutical composition, comprising a therapeutic agent or a vector encoding the therapeutic agent, and a pharmaceutically acceptable excipient, wherein the therapeutic agent comprises an antisense oligomer that binds to a pre-mRNA that is transcribed from an OPA1 gene in a cell, wherein the antisense oligomer binds to: (a) a targeted portion of the pre-mRNA within an intronic region immediately upstream of a 5' end of the coding exon of the pre-mRNA; or (b) a targeted portion of the pre-mRNA within an intronic region immediately downstream of a 3' end of the coding exon of the pre-mRNA; whereby the therapeutic agent increases a level of a processed mRNA that is processed from the pre-mRNA and that contains the coding exon in the cell.

Described herein, in some aspects, is a pharmaceutical composition, comprising a therapeutic agent or a vector encoding the therapeutic agent, and a pharmaceutically acceptable excipient, wherein the therapeutic agent promotes exclusion of both a coding exon and a non-sense mediated RNA decay-inducing exon (NMD exon) from a pre-mRNA, thereby increasing a level of a processed mRNA that is processed from the pre-mRNA and that lacks the coding exon and the NMD exon in a cell, wherein the pre-mRNA is transcribed from an OPA1 gene in the cell and comprises the coding exon and the NMD exon.

In some embodiments, the pharmaceutical composition is formulated for intracerebroventricular injection, intraperitoneal injection, intramuscular injection, intrathecal injection, subcutaneous injection, oral administration, synovial injection, intravitreal administration, subretinal injection, topical application, implantation, or intravenous injection. In some embodiments, the pharmaceutical composition is formulated for intravitreal injection. In some embodiments, the pharmaceutical composition further comprises a second therapeutic agent. In some embodiments, the second therapeutic agent comprises a small molecule. In some embodiments, the second therapeutic agent comprises an antisense oligomer. In some embodiments, the second therapeutic agent corrects intron retention. In some embodiments, the antisense oligomer is selected from the group consisting of Compound ID NOs: 1-303.

Described herein, in some aspects, is a method of treating or reducing the likelihood of developing a disease or condition in a subject in need thereof by modulating expression of an OPA1 protein in a cell of the subject, comprising contacting to cells of the subject the therapeutic agent as disclosed herein. In some embodiments, the disease or condition is associated with a loss-of-function mutation in an OPA1 gene. In some embodiments, the disease or condition is associated with haploinsufficiency of the OPA1 gene, and wherein the subject has a first allele encoding a functional OPA1 protein, and a second allele from which the OPA1 protein is not produced or produced at a reduced level, or a second allele encoding a nonfunctional OPA1 protein or a partially functional OPA1 protein. In some embodiments, the disease or condition comprises an eye disease or condition. In some embodiments, the disease or condition comprises ADOA-plus syndrome; a mitochondrial disorder; glaucoma; normal tension glaucoma; Charcot-Marie-Tooth disease; mitochondria dysfunction; diabetic retinopathy; age-related macular degeneration; retinal ganglion cell death; mitochondrial fission-mediated mitochondrial dysfunction; progressive external ophthalmoplegia; deafness; ataxia; motor neuropathy; sensory neuropathy; myopathy; Behr syndrome; brain dysfunction; encephalopathy; peripheral neuropathy; fatal infantile mitochondrial encephalomyopathy; hypertrophic cardiomyopathy; spastic ataxic syndrome; sensory motor peripheral neuropathy; hypotonia; gastrointestinal dysmotility and dysphagia; optic atrophy; optic atrophy plus syndrome; Mitochondrial DNA depletion syndrome 14; late-onset cardiomyopathy; diabetic cardiomyopathy; Alzheimer's Disease; focal segmental glomerulosclerosis; kidney disease; Huntington's Disease; cognitive function decline in healthy aging; Prion diseases; late onset dementia and parkinsonism; mitochondrial myopathy; Leigh syndrome; Friedreich's ataxia; Parkinson's disease; MELAS (Mitochondrial encephalomyopathy, lactic acidosis, and stroke-like episodes); pyruvate dehydrogenase complex deficiency; chronic kidney disease; Leber's hereditary optic neuropathy; obesity; age-related systemic neurodegeneration; skeletal muscle atrophy; heart and brain ischemic damage; or massive liver apoptosis. In some embodiments, the disease or condition comprises Optic atrophy type 1. In some embodiments, the disease or condition comprises autosomal dominant optic atrophy (ADOA). In some embodiments, the disease or condition is associated with an autosomal recessive mutation of OPA1 gene, wherein the subject has a first allele encoding from which: (i) OPA1 protein is not produced or produced at a reduced level compared to a wild-type allele; or (ii) the OPA1 protein produced is nonfunctional or partially functional compared to a wild-type allele, and a second allele from which: (iii) the OPA1 protein is produced at a reduced level compared to a wild-type allele and the OPA1 protein produced is at least partially functional compared to a wild-type allele; or (iv) the OPA1 protein produced is partially functional compared to a wild-type allele.

In some embodiments, the subject is a human. In some embodiments, the subject is a non-human animal. In some embodiments, the subject is a fetus, an embryo, or a child. In some embodiments, the cells that the methods and compositions described herein are applicable to are ex vivo. In some embodiments, the therapeutic agent is administered by intracerebroventricular injection, intraperitoneal injection, intramuscular injection, intrathecal injection, subcutaneous injection, oral administration, synovial injection, intravitreal administration, subretinal injection, topical application, implantation, or intravenous injection. In some embodiments, the therapeutic agent is administered by intravitreal injection. In some embodiments, the method disclosed herein treats the disease or condition.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1A shows a cell divided into nuclear and cytoplasmic compartments. In the nucleus, a pre-mRNA transcript of a target gene undergoes splicing to generate mRNA, and this mRNA is exported to the cytoplasm and translated into target protein. For this target gene, some fraction of the mRNA contains a nonsense-mediated mRNA decay-inducing exon (NMD exon mRNA) that is degraded in the cytoplasm, thus leading to no target protein production. FIG. 1B shows an example of the same cell divided into nuclear and cytoplasmic compartments. Treatment with a therapeutic agent, such as an antisense oligomer (ASO), promotes the exclusion of the nonsense-mediated mRNA decay-inducing exon and results in an increase in mRNA, which is in turn translated into higher levels of target protein. FIG. 1C shows an example schematic of a Novel NMD exon inclusion event (Exon X) identified in the OPA1 gene which leads to the introduction of a premature termination codon (PTC) resulting in a non-productive mRNA transcript degraded by non-sense mediated decay (NMD).

FIG. 2 discloses SEQ ID NO: 300.

FIG. 3 discloses SEQ ID NO: 301.

FIG. 5 depicts an exemplary ASO walk around OPA1 exon 7x (GRCh38/hg38: chr3 193628509 193628616) region. A graphic representation of an ASO walk performed for around OPA1 exon 7x (GRCh38/hg38: chr3 193628509 193628616) region targeting sequences upstream of the 3' splice site, across the 3'splice site, exon 7x, across the 5' splice site, and downstream of the 5' splice site is shown. ASOs were designed to cover these regions by shifting 5 nucleotides at a time or 3 nucleotides across the splice site regions. FIG. 5 discloses SEQ ID NOS 302-304, respectively, in order of appearance.

FIG. 9A confirms expression of OPA1 transcripts containing the NMD exon in these cells.

FIG. 12C illustrates protein expression of OPA1 in HEK293 cells after treatment with ASO-14 in the absence of cycloheximide.

FIG. 15 illustrates exemplary OPA1 ASOs of this disclosure. The right two columns in the chart illustrate the chemical modifications of the exemplary ASOs. Each nucleotide of all the ASOs has 2'-O-methoxyethyl (2'MOE) modification ("MOE") unless otherwise noted, for instance, letters of larger font size (e.g., G) are locked nucleic acids ("LNA"), underlined letters (e.g., C) are 5' methyl-cytosines that have 2'-MOE moiety ("SMeC-MOE"), and some ASOs are noted as phosphorodiamidate morpholino oligomers ("PMO"). FIG. 15 discloses SEQ ID NOS 6-148, 148, 148, 149, 149, 149, 150, 150, 150-151, 151, 151, 123, 152, 152, 152-153, 153, 153-154, 154, 154, 144-146, 93, 81-82, 36, 155, 155-156, 156-157, 157-161, 125, 162, 126, 163-166, 92, 167-179, 156, 180, 157, 159, 181, 160, 182, 161, 183-275, and 305-607 respectively, in order of column.

FIG. 18D summarizes the Ct values for the qPCR reactions, and FIG. 18E summarizes the relative amounts.

FIGS. 21A-21D illustrate RT-PCR results for OPA1 mRNAs using probes spanning exon 6 and exon 8 ("Exon 6-8"), or probes spanning exon 7x and exon 8 ("Exon 7-8"), in HEK293 cells after treatment with various exemplary OPA1 ASO 16-mers and treatment with or without cycloheximide.

FIG. 24B shows the immunoblot gel images of OPA1 and β-actin proteins, and FIG. 24C is a histogram that summarizes quantification of the immunoblot results.

FIGS. 25A-25B show histograms that demonstrate mRNA (FIG. 25A) and protein expression (FIG. 25B) of OPA1 gene were reduced in fibroblast cells from diagnosed patients that have haploinsufficient mutation in OPA1 gene as compared to wildtype (WT) fibroblast cells. FIG. 25C shows a representative immunoblot image of OPA protein expression level in diseased fibroblast cells.

in wildtype (WT) fibroblast cells and fibroblast cells from diagnosed patients that have haploinsufficient mutation in OPA1 gene.

Figure 26B:
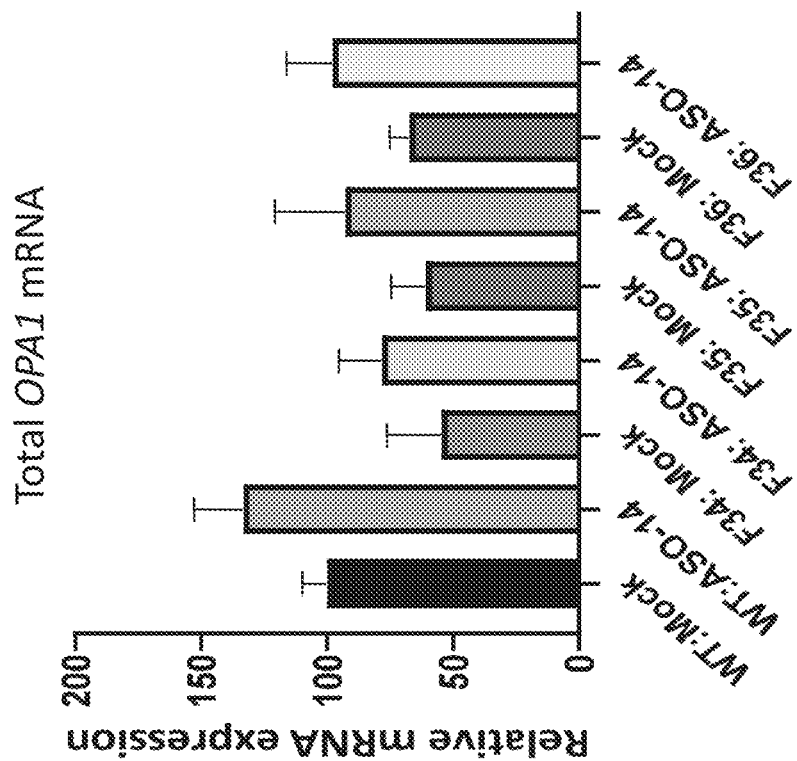
FIGS. 26A, 26B, and 26D show histograms that demonstrate exemplary antisense oligomer, ASO-14, decreased OPA1 NMD exon inclusion (FIG. 26A), increased OPA1 total mRNA level (FIG. 26B), and protein level (FIG. 26D)
Figure 26A:
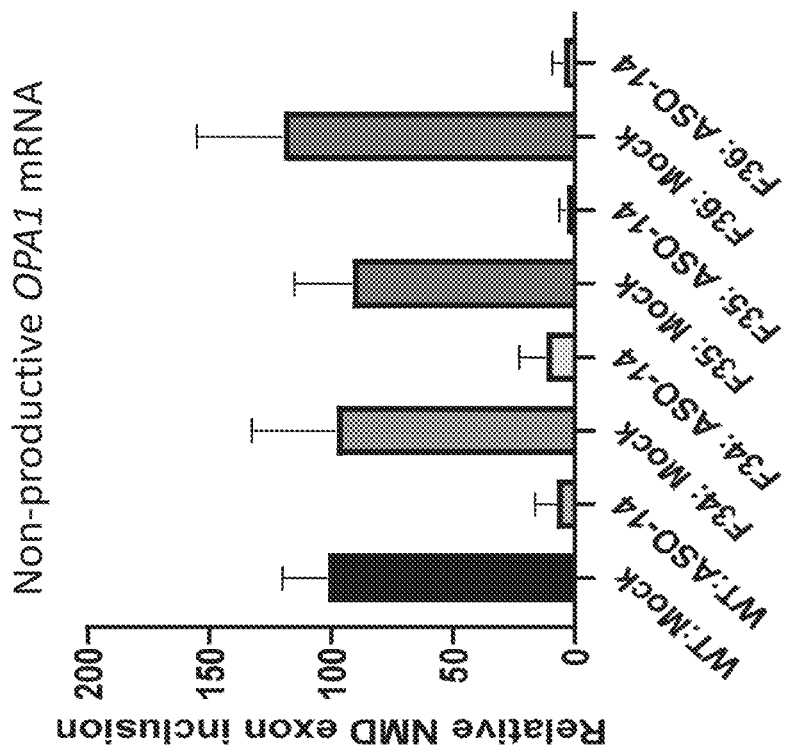
Figure 26C:

FIG. 26C shows representative immunoblot images of OPA1 protein and loading control 13-Tubulin under all types of conditions.

Figure 27C:
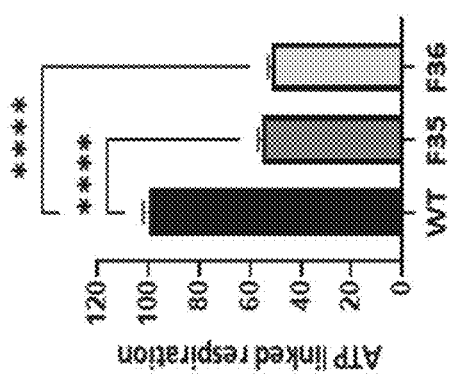
Figure 27E:
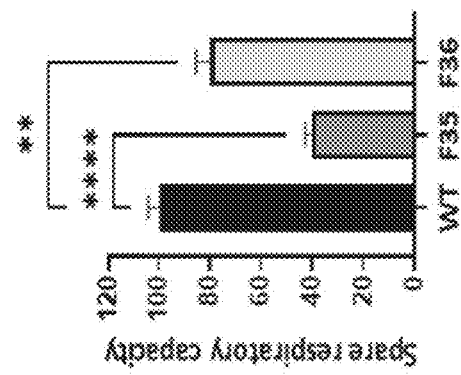
Figure 27B:
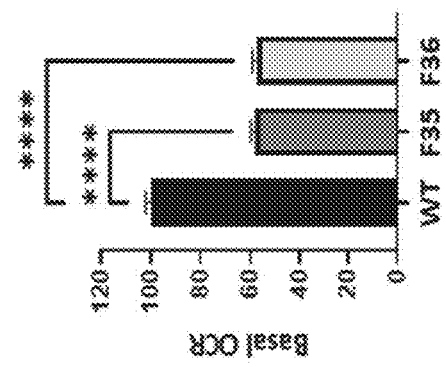
Figure 27D:
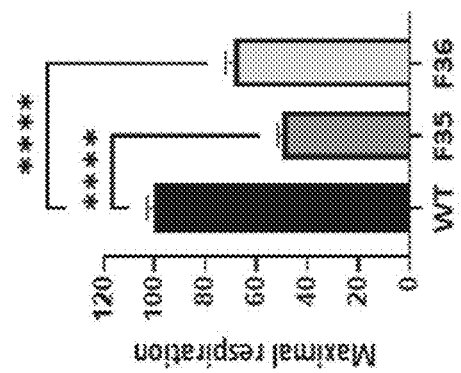
Figure 27A:
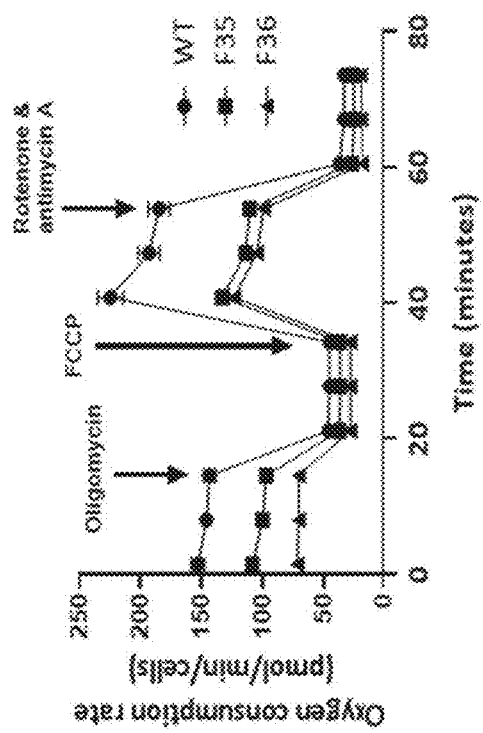

FIGS. 27A-27E demonstrate that patient fibroblast cells (cell lines F35 and F36) show deficiencies in mitochondrial bioenergetics. FIG. 27A shows representative time courses of the oxygen consumption rate of WT cells, F35 cells, and F36 cells at baseline level and when challenged sequentially with oligomycin, FCCP, rotenone and antimycin A. FIGS. 27B-27E show histograms demonstrating that patient fibroblast cells, F35 and F36 cells had reduced basal oxygen consumption rate (FIG. 27B), ATP linked respiration (FIG. 27C), maximal respiration (FIG. 27D), and spare respiratory capacity (FIG. 27E), as compared to WT fibroblast cells.

FIGS. 28A-28D show histograms demonstrating that treatment of ASO-14 at 20 nM, 40 nM, and 60 nM increased basal oxygen consumption rate (FIG. 28A), ATP linked respiration (FIG. 28B), maximal respiration (FIG. 28C), and spare respiratory capacity (FIG. 28D) of F35 patient cells in a dose-dependent manner.

FIGS. 29A-29D show histograms demonstrating that treatment of ASO-14 at 20 nM, 40 nM, and 60 nM increased basal oxygen consumption rate (FIG. 29A), ATP linked respiration (FIG. 29B), maximal respiration (FIG. 29C), and spare respiratory capacity (FIG. 29D) of F36 patient cells in a dose-dependent manner.

DETAILED DESCRIPTION

Alternative splicing events in the OPA1 gene can lead to non-productive mRNA transcripts which in turn can lead to aberrant protein expression, and therapeutic agents which can target the alternative splicing events in the OPA1 gene can modulate the expression level of functional proteins in DS patients and/or inhibit aberrant protein expression. Such therapeutic agents can be used to treat a condition caused by OPA1 protein deficiency.

One of the alternative splicing events that can lead to non-productive mRNA transcripts is the inclusion of an extra exon in the mRNA transcript that can induce non-sense mediated mRNA decay. The present disclosure provides compositions and methods for modulating alternative splicing of OPA1 to increase the production of protein-coding mature mRNA, and thus, translated functional OPA1 protein. These compositions and methods include antisense oligomers (ASOs) that can cause exon skipping, e.g., pseudoexon skipping, and promote constitutive splicing of OPA1 pre-mRNA. In various embodiments, functional OPA1 protein can be increased using the methods of the disclosure to treat a condition caused by OPA1 protein deficiency.

mRNA Splicing

Intervening sequences in RNA sequences or introns are removed by a large and highly dynamic RNA-protein complex termed the spliceosome, which orchestrates complex interactions between primary transcripts, small nuclear RNAs (snRNAs) and a large number of proteins. Spliceosomes assemble ad hoc on each intron in an ordered manner, starting with recognition of the 5' splice site (5'ss) by U1 snRNA or the 3'splice site (3'ss) by the U2 pathway, which involves binding of the U2 auxiliary factor (U2AF) to the 3'ss region to facilitate U2 binding to the branch point sequence (BPS). U2AF is a stable heterodimer composed of a U2AF2-encoded 65-kD subunit (U2AF65), which binds the polypyrimidine tract (PPT), and a U2AF1-encoded 35-kD subunit (U2AF35), which interacts with highly conserved AG dinucleotides at 3'ss and stabilizes U2AF65 binding. In addition to the BPS/PPT unit and 3'ss/5'ss, accurate splicing requires auxiliary sequences or structures that activate or repress splice site recognition, known as intronic or exonic splicing enhancers or silencers. These elements allow genuine splice sites to be recognized among a vast excess of cryptic or pseudo-sites in the genome of higher eukaryotes, which have the same sequences but outnumber authentic sites by an order of magnitude. Although they often have a regulatory function, the exact mechanisms of their activation or repression are poorly understood.

The decision of whether to splice or not to splice can be typically modeled as a stochastic rather than deterministic process, such that even the most defined splicing signals can sometimes splice incorrectly. However, under normal conditions, pre-mRNA splicing proceeds at surprisingly high fidelity. This is attributed in part to the activity of adjacent cis-acting auxiliary exonic and intronic splicing regulatory elements (ESRs or ISRs). Typically, these functional elements are classified as either exonic or intronic splicing enhancers (ESEs or ISEs) or silencers (ESSs or ISSs) based on their ability to stimulate or inhibit splicing, respectively. Although there is now evidence that some auxiliary cis-acting elements may act by influencing the kinetics of spliceosome assembly, such as the arrangement of the complex between U1 snRNP and the 5'ss, it seems very likely that many elements function in concert with trans-acting RNA-binding proteins (RBPs). For example, the serine- and arginine-rich family of RBPs (SR proteins) is a conserved family of proteins that have a key role in defining exons. SR proteins promote exon recognition by recruiting components of the pre-spliceosome to adjacent splice sites or by antagonizing the effects of ESSs in the vicinity. The repressive effects of ESSs can be mediated by members of the heterogeneous nuclear ribonucleoprotein (hnRNP) family and can alter recruitment of core splicing factors to adjacent splice sites. In addition to their roles in splicing regulation, silencer elements are suggested to have a role in repression of pseudo-exons, sets of decoy intronic splice sites with the typical spacing of an exon but without a functional open reading frame. ESEs and ESSs, in cooperation with their cognate trans-acting RBPs, represent important components in a set of splicing controls that specify how, where and when mRNAs are assembled from their precursors.

Alternative splicing is a regulated process during gene expression that can result in multiple isoforms of mature mRNA transcripts that are processed from a single primary mRNA transcript that is transcribed from a single gene, and the resultant multiple proteins that are translated from at least some of the multiple mature mRNA isoforms. In this process, particular exons of a gene may be included within or excluded from the final, processed mRNA produced from that gene. Consequently, the proteins translated from alternatively splices mRNAs will contain differences in their amino acid sequence and, in some cases, in their biological functions.

As described herein, an "alternatively spliced exon" can refer to an exon of a gene that can be either included or excluded naturally from a mature mRNA transcript, thus resulting in different protein products that are translated from the different mature mRNA transcripts. The inclusion or skipping of an alternatively spliced exon can take place naturally in a cell, either randomly, or in a regulated manner, e.g., subject to regulation by external physiological or pathological stimuli, or intracellular signaling. In some cases, the production of alternatively spliced mRNAs, e.g., the splicing of the alternatively spliced exon, is regulated by a system of trans-acting proteins that bind to cis-acting sites on the primary transcript itself. In some cases, an alternatively spliced exon is a coding exon, e.g., an exon that, when included in the mature mRNA transcript, is translated into an amino acid sequence as part of the protein product translated from the mature mRNA transcript. In some cases, the inclusion of an alternatively spliced exon in the mature mRNA transcript would maintain the canonical open reading frame as compared to a mature mRNA transcript without the alternatively spliced exon, e.g., the number of nucleotides in the alternatively spliced exon is divisible by 3.

The sequences marking the exon-intron boundaries are degenerate signals of varying strengths that can occur at high frequency within human genes. In multi-exon genes, different pairs of splice sites can be linked together in many different combinations, creating a diverse array of transcripts from a single gene. This is commonly referred to as alternative pre-mRNA splicing. Although most mRNA isoforms produced by alternative splicing can be exported from the nucleus and translated into functional polypeptides, different mRNA isoforms from a single gene can vary greatly in their translation efficiency. Those mRNA isoforms with premature termination codons (PTCs) at least 50 bp upstream of an exon junction complex are likely to be targeted for degradation by the nonsense-mediated mRNA decay (NMD) pathway. Mutations in traditional (BPS/PPT/3'ss/5'ss) and auxiliary splicing motifs can cause aberrant splicing, such as exon skipping or cryptic (or pseudo-) exon inclusion or splice-site activation, and contribute significantly to human morbidity and mortality. Both aberrant and alternative splicing patterns can be influenced by natural DNA variants in exons and introns.

Given that exon-intron boundaries can occur at any of the three positions of a codon, it is clear that only a subset of alternative splicing events can maintain the canonical open reading frame. For example, only exons that are evenly divisible by 3 can be skipped or included in the mRNA without any alteration of reading frame. Splicing events that do not have compatible phases will induce a frame-shift. Unless reversed by downstream events, frame-shifts can certainly lead to one or more PTCs, probably resulting in subsequent degradation by NMD. NMD is a translation-coupled mechanism that eliminates mRNAs containing PTCs. NMD can function as a surveillance pathway that exists in all eukaryotes. NMD can reduce errors in gene expression by eliminating mRNA transcripts that contain premature stop codons. Translation of these aberrant mRNAs could, in some cases, lead to deleterious gain-of-function or dominant-negative activity of the resulting proteins. NMD targets not only transcripts with PTCs but also a broad array of mRNA isoforms expressed from many endogenous genes, suggesting that NMD is a master regulator that drives both fine and coarse adjustments in steady-state RNA levels in the cell.

A NMD-inducing exon ("NIE" or "NMD exon") is an exon or a pseudo-exon that is a region within an intron and can activate the NMD pathway if included in a mature RNA transcript. In constitutive splicing events, the intron containing an NMD exon is usually spliced out, but the intron or a portion thereof (e.g. NMD exon) may be retained during alternative or aberrant splicing events. Mature mRNA transcripts containing such an NMD exon may be non-productive due to frame shifts which induce the NMD pathway. Inclusion of a NMD exon in mature RNA transcripts may downregulate gene expression. mRNA transcripts containing an NMD exon may be referred to as "NIE-containing mRNA" or "NMD exon mRNA" in the current disclosure.

Cryptic (or pseudo-splice sites) have the same splicing recognition sequences as genuine splice sites but are not used in splicing reactions. They outnumber genuine splice sites in the human genome by an order of a magnitude and are normally repressed by thus far poorly understood molecular mechanisms. Cryptic 5' splice sites have the consensus NNN/GUNNNN or NNN/GCNNNN where N is any nucleotide and/is the exon-intron boundary. Cryptic 3' splice sites have the consensus NAG/N. Their activation is positively influenced by surrounding nucleotides that make them more similar to the optimal consensus of authentic splice sites, namely MAG/GURAGU and YAG/G, respectively, where M is C or A, R is G or A, and Y is C or U.

Splice sites and their regulatory sequences can be readily identified by a skilled person using suitable algorithms publicly available, listed for example in Kralovicova, J. and Vorechovsky, I. (2007) Global control of aberrant splice site activation by auxiliary splicing sequences: evidence for a gradient in exon and intron definition. *Nucleic Acids Res.*, 35, 6399-6413 (www.ncbi.nlm.nih.gov/pmc/articles/PMC2095810/pdf/gkm680.pdf).

The cryptic splice sites or splicing regulatory sequences may compete for RNA-binding proteins, such as U2AF, with a splice site of the NMD exon. In some embodiments, an agent may bind to a cryptic splice site or splicing regulatory sequence to prevent binding of RNA-binding proteins and thereby favor binding of RNA-binding proteins to the NMD exon splice sites.

In some embodiments, the cryptic splice site may not comprise the 5' or 3' splice site of the NMD exon. In some embodiments, the cryptic splice site may be at least 10 nucleotides, at least 20 nucleotides, at least 50 nucleotides, at least 100 nucleotides or at least 200 nucleotides upstream of the NMD exon 5' splice site. In some embodiments, the cryptic splice site may be at least 10 nucleotides, at least 20 nucleotides, at least 50 nucleotides, at least 100 nucleotides, at least 200 nucleotides downstream of the NMD exon 3' splice site.

Target Transcripts

In some embodiments, the methods and compositions of the present disclosure exploit the presence of NMD exon in the pre-mRNA transcribed from the OPA1 gene. Splicing of the identified OPA1 NMD exon pre-mRNA species to produce functional mature OPA1 mRNA may be induced using an agent such as an ASO that stimulates exon skipping of an NMD exon. Induction of exon skipping may result in inhibition of an NMD pathway. The resulting mature OPA1 mRNA can be translated normally without activating NMD pathway, thereby increasing the amount of OPA1 protein in the patient's cells and alleviating symptoms of a condition or disease associated with OPA1 deficiency, such as an eye disease or condition, Optic atrophy type 1, autosomal dominant optic atrophy (ADOA), ADOA-plus syndrome; a mitochondrial disorder; glaucoma; normal tension glaucoma; Charcot-Marie-Tooth disease; mitochondria dysfunction; diabetic retinopathy; age-related macular degeneration; retinal ganglion cell death; mitochondrial fission-mediated mitochondrial dysfunction; progressive external ophthalmoplegia; deafness; ataxia; motor neuropathy; sensory neuropathy; myopathy; Behr syndrome; brain dysfunction; encephalopathy; peripheral neuropathy; fatal infantile mitochondrial encephalomyopathy; hypertrophic cardiomyopathy; spastic ataxic syndrome; sensory motor peripheral neuropathy; hypotonia; gastrointestinal dysmotility and dysphagia; optic atrophy; optic atrophy plus syndrome; Mitochondrial DNA depletion syndrome 14; late-onset cardiomyopathy; diabetic cardiomyopathy; Alzheimer's Disease; focal segmental glomerulosclerosis; kidney disease; Huntington's Disease; cognitive function decline in healthy aging; Prion diseases; late onset dementia and parkinsonism; mitochondrial myopathy; Leigh syndrome; Friedreich's ataxia; Parkinson's disease; MELAS (Mitochondrial encephalomyopathy, lactic acidosis, and stroke-like episodes); pyruvate dehydrogenase complex deficiency; chronic kidney disease; Leber's hereditary optic neuropathy; obesity; age-related systemic neurodegeneration; skeletal muscle atrophy; heart and brain ischemic damage; or massive liver apoptosis.

In some embodiments, the methods and compositions of the present disclosure exploit the alternative splicing of the pre-mRNA transcribed from the OPA1 gene. In some cases, splicing of a coding exon, e.g., an alternatively spliced exon, e.g., OPA1 exon 7 (or an exon encoded by genomic region spanning from GRCh38/hg38: chr3 193626092 to 193626202), can modulate the level of OPA1 protein expressed from the OPA1 gene. As described herein, the term "OPA1 exon 7" or grammatically equivalents thereof, is used interchangeably with the term "exon (GRCh38/hg38: chr3 193626092 to 193626202)" or "an exon encoded by genomic region spanning from GRCh38/hg38: chr3 193626092 to 193626202." Without wishing to be bound by a certain theory, the presence or absence of an amino acid sequence encoded by exon 7 or exon (GRCh38/hg38: chr3 193626092 to 193626202) can modulate the stability of the OPA1 protein. For instance, in some cases, the OPA1 protein encoded by a mature mRNA transcript that lacks exon 7 can have fewer proteolytic cleavage sites as compared to an OPA1 protein encoded by a corresponding mature mRNA transcript that has contains exon 7. In some cases, the OPA1 protein an OPA1 protein encoded by a corresponding mature mRNA transcript that has contains encoded by a mature mRNA transcript that lacks exon 7 is a functional protein. The OPA1 protein encoded by a mature mRNA transcript that lacks exon 7 can be at least partially functional as compared to an OPA1 protein encoded by a corresponding mature mRNA transcript that has contains exon 7. In some cases, the OPA1 protein encoded by a mature mRNA transcript that lacks exon 7 is at least partially functional as compared to a full-length wild-type OPA1 protein. In some cases, increase of OPA1 protein encoded by a mature mRNA transcript that lacks exon 7 in a cell can result in more functional OPA1 protein in the cell, due to the higher stability of the OPA1 protein lacking exon 7 and its at least partial functional equivalence.

In other embodiments, a coding exon of OPA1 pre-mRNA other than exon 7 is targeted by an agent disclosed herein, which promotes exclusion of the coding exon other than exon 7. In these other embodiments, the agent that promotes exclusion of the coding exon other than exon 7 increases expression of OPA1 protein encoded by a mature mRNA transcript that lacks the excluded exon.

Alternative splicing of the OPA1 pre-mRNA species, e.g., skipping of a coding exon, e.g., an alternatively spliced exon, e.g., exon 7, to produce functional mature OPA1 protein may be induced using an agent such as an ASO that stimulates the exon skipping. Induction of exon skipping may result in modulation of levels of different alternatively spliced mRNA transcripts. The resulting mature OPA1 mRNA can be translated into different OPA1 proteins, thereby modulating the amount of OPA1 protein in the patient's cells and alleviating symptoms of a condition or disease associated with OPA1 deficiency, such as an eye disease or condition, Optic atrophy type 1, autosomal dominant optic atrophy (ADOA), ADOA-plus syndrome; a mitochondrial disorder; glaucoma; normal tension glaucoma; charcot-Marie-tooth disease; mitochondria dysfunction; diabetic retinopathy; age-related macular degeneration; retinal ganglion cell death; mitochondrial fission-mediated mitochondrial dysfunction; progressive external ophthalmoplegia; deafness; ataxia; motor neuropathy; sensory neuropathy; myopathy; Behr syndrome; brain dysfunction; encephalopathy; peripheral neuropathy; fatal infantile mitochondrial encephalomyopathy; hypertrophic cardiomyopathy; spastic ataxic syndrome; sensory motor peripheral neuropathy; hypotonia; gastrointestinal dysmotility and dysphagia; optic atrophy; optic atrophy plus syndrome; Mitochondrial DNA depletion syndrome 14; late-onset cardiomyopathy; diabetic cardiomyopathy; Alzheimer's Disease; focal segmental glomerulosclerosis; kidney disease; Huntington's Disease; cognitive function decline in healthy aging; Prion diseases; late onset dementia and parkinsonism; mitochondrial myopathy; Leigh syndrome; Friedreich's ataxia; Parkinson's disease; MELAS (Mitochondrial encephalomyopathy, lactic acidosis, and stroke-like episodes); pyruvate dehydrogenase complex deficiency; chronic kidney disease; Leber's hereditary optic neuropathy; obesity; age-related systemic neurodegeneration; skeletal muscle atrophy; heart and brain ischemic damage; or massive liver apoptosis.

In some embodiments, the diseases or conditions that can be treated or ameliorated using the method or composition disclosed herein are not directly associated with the target protein (gene) that the therapeutic agent targets. In some embodiments, a therapeutic agent provided herein can target a protein (gene) that is not directly associated with a disease or condition, but the modulation of expression of the target protein (gene) can treat or ameliorate the disease or condition.

In various embodiments, the present disclosure provides a therapeutic agent which can target OPA1 mRNA transcripts to modulate splicing or protein expression level. The therapeutic agent can be a small molecule, polynucleotide, or polypeptide. In some embodiments, the therapeutic agent is an ASO. Various regions or sequences on the OPA1 pre-mRNA can be targeted by a therapeutic agent, such as an ASO. In some embodiments, the ASO targets an OPA1 pre-mRNA transcript containing an NMD exon. In some embodiments, the ASO targets a sequence within an NMD exon of an OPA1 pre-mRNA transcript. In some embodiments, the ASO targets a sequence upstream (or 5') from the 5' end of an NMD exon (3'ss) of an OPA1 pre-mRNA transcript. In some embodiments, the ASO targets a sequence downstream (or 3') from the 3' end of an NMD exon (5'ss) of an OPA1 pre-mRNA transcript. In some embodiments, the ASO targets a sequence that is within an intron flanking on the 5' end of the NMD exon of an OPA1 pre-mRNA transcript. In some embodiments, the ASO targets a sequence that is within an intron flanking the 3' end of the NMD exon of an OPA1 pre-mRNA transcript. In some embodiments, the ASO targets a sequence comprising an NMD exon-intron boundary of an OPA1 pre-mRNA transcript. An NMD exon-intron boundary can refer to the junction of an intron sequence and an NMD exon region. The intron sequence can flank the 5' end of the NMD exon, or the 3' end of the NMD exon. In some embodiments, the ASO targets a sequence within an exon of an OPA1 pre-mRNA transcript. In some embodiments, the ASO targets a sequence within an intron of an OPA1 pre-mRNA transcript.

In some embodiments, the ASO targets a sequence comprising both a portion of an intron and a portion of an exon of an OPA1 pre-mRNA transcript.

In some embodiments, the ASO targets a sequence about 4 to about 300 nucleotides upstream (or 5') from the 5' end of the NMD exon. In some embodiments, the ASO targets a sequence about 1 to about 20 nucleotides, about 20 to about 50 nucleotides, about 50 to about 100 nucleotides, about 100 to about 150 nucleotides, about 150 to about 200 nucleotides, about 200 to about 250 nucleotides, or about 250 to about 300 nucleotides upstream (or 5') from the 5' end of the NMD exon region. In some embodiments, the ASO may target a sequence more than 300 nucleotides upstream from the 5' end of the NMD exon. In some embodiments, the ASO targets a sequence about 4 to about 300 nucleotides downstream (or 3') from the 3' end of the NMD exon. In some embodiments, the ASO targets a sequence about 1 to about 20 nucleotides, about 20 to about 50 nucleotides, about 50 to about 100 nucleotides, about 100 to about 150 nucleotides, about 150 to about 200 nucleotides, about 200 to about 250 nucleotides, or about 250 to about 300 nucleotides downstream from the 3' end of the NMD exon. In some embodiments, the ASO targets a sequence more than 300 nucleotides downstream from the 3' end of the NMD exon.

In some embodiments, the OPA1 NMD exon-containing pre-mRNA transcript is encoded by a genetic sequence with at least about 80%, 85%, 90%, 95%, 96%, 97%, 98%, 99% or 100% sequence identity to SEQ ID NO. 1. In some embodiments, the OPA1 NMD exon pre-mRNA transcript comprises a sequence with at least about 80%, 85%, 90%, 95%, 96%, 97%, 98%, 99% or 100% sequence identity to any one of SEQ ID NOs: 2-5.

In some embodiments, the OPA1 NMD exon-containing pre-mRNA transcript (or NMD exon mRNA) comprises a sequence with at least about 80%, 85%, 90%, 95%, 97%, or 100% sequence identity to any one of SEQ ID NOs: 2-5. In some embodiments, OPA1 NMD exon-containing pre-mRNA transcript (or NMD exon mRNA) is encoded by a sequence with at least about 80%, 85%, 90%, 95%, 97%, or 100% sequence identity to any one of SEQ ID NOs: 2-5. In some embodiments, the targeted portion of the NMD exon mRNA comprises a sequence with at least about 80%, 85%, 90%, 95%, 97%, or 100% sequence identity to a region comprising at least 8 contiguous nucleic acids of any one of SEQ ID NOs: 2-5.

In some embodiments, the ASO targets exon 6x of an OPA1 NMD exon-containing pre-mRNA comprising NIE exon 6, exon 7x of an OPA1 NMD exon-containing pre-mRNA comprising NIE exon 7, or exon 28x of an OPA1 NMD exon-containing pre-mRNA comprising NIE exon 28. In some embodiments, the ASO targets exon (GRCh38/hg38: chr3 193628509 193628616) of OPA1 pre-mRNA; or exon (GRCh38/hg38: chr3 193603500 193603557) of OPA1. In some embodiments, the ASO targets an NMD exon of OPA1 pre-mRNA other than NMD exon (GRCh38/hg38: chr3 193628509 193628616).

In some embodiments, the ASO targets a sequence about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream (or 5') from the 5' end of exon 6x of OPA1, exon 7x of OPA1, or exon 28x of OPA1. In some embodiments, the ASO targets a sequence about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream (or 5') from GRCh38/hg38: chr3 193628509 of OPA1; or GRCh38/hg38: chr3 193603500 of OPA1.

In some embodiments, the ASO targets a sequence at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream (or 5') from the 5' end of exon 6x of OPA1, exon 7x of OPA1, or exon 28x of OPA1. In some embodiments, the ASO targets a sequence at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream (or 5') from GRCh38/hg38: chr3 193628509 of OPA1; or GRCh38/hg38: chr3 193603500 of OPA1.

In some embodiments, the ASO targets a sequence about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream (or 3') from the 3' end of exon 6x of OPA1, exon 7x of OPA1, or exon 28x of OPA1. In some embodiments, the ASO targets a sequence about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream (or 3') from GRCh38/hg38: chr3 193628616 of OPA1; or GRCh38/hg38: chr3 193603557 of OPA1.

In some embodiments, the ASO targets a sequence at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream (or 3') from the 3' end of exon 6x of OPA1, exon 7x of OPA1, or exon 28x of OPA1. In some embodiments, the ASO targets a sequence at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream (or 3') from GRCh38/hg38: chr3 193628616 of OPA1; or GRCh38/hg38: chr3 193603557 of OPA1.

In some embodiments, the ASO has a sequence complementary to the targeted portion of the NMD exon mRNA according to any one of SEQ ID NOs: 2-5, or 279.

In some embodiments, the ASO targets a sequence upstream from the 5' end of an NMD exon. For example, ASOs targeting a sequence upstream from the 5' end of an NMD exon (exon 6x of OPA1, exon 7x of OPA1, or exon 28x of OPA1) comprises a sequence that is at least about 80%, 85%, 90%, 95%, 97%, or 100% complimentary to at least 8 contiguous nucleic acids of SEQ ID NO: 2 or 3. For example, ASOs targeting a sequence upstream from the 5' end of an NMD exon (e.g., exon (GRCh38/hg38: chr3 193628509 to 193628616) of OPA1; or exon (GRCh38/hg38: chr3 193603500 193603557) of OPA1) can comprise a sequence with at least 80%, 85%, 90%, 95%, 97%, or 100% sequence identity to SEQ ID NO: 4 or 5.

In some embodiments, the ASOs target a sequence containing an exon-intron boundary (or junction). For example, ASOs targeting a sequence containing an exon-intron boundary can comprise a sequence that is at least about 80%, 85%, 90%, 95%, 97%, or 100% complimentary to at least 8 contiguous nucleic acids of any one of SEQ ID NOs: 2-5. In some embodiments, the ASOs target a sequence downstream from the 3' end of an NMD exon. For example, ASOs targeting a sequence downstream from the 3' end of an NMD exon (e.g., exon 6x of OPA1, exon 7x of OPA1, or exon 28x of OPA1) can comprise a sequence with at least 80%, 85%, 90%, 95%, 97%, or 100% sequence identity to SEQ ID NO: 2 or 3, or at least 8 contiguous nucleic acids of SEQ ID NO: 2 or 3. For example, ASOs targeting a sequence downstream from the 3' end of an NMD exon (e.g., exon (GRCh38/hg38: chr3 193628509 to 193628616) of OPA1; or exon (GRCh38/hg38: chr3 193603500 to 193603557) of OPA1) can comprise a sequence with at least 80%, 85%, 90%, 95%, 97%, or 100% sequence identity to SEQ ID NO: 4 or 5, or at least 8 contiguous nucleic acids of SEQ ID NO: 4 or 5. In some embodiments, ASOs target a sequence within an NMD exon.

In some embodiments, the ASO targets exon 6x of an OPA1 NMD exon-containing pre-mRNA comprising NIE exon 6, exon 7x of an OPA1 NMD exon-containing pre-mRNA comprising NIE exon 7, or exon 28x of an OPA1 NMD exon-containing pre-mRNA comprising NIE exon 28. In some embodiments, the ASO targets a sequence downstream (or 3') from the 5' end of exon 6x, exon 7x, or exon 28x of an OPA1 pre-mRNA. In some embodiments, the ASO targets a sequence upstream (or 5') from the 3' end of exon 6x, exon 7x, or exon 28x of an OPA1 pre-mRNA.

In some embodiments, the targeted portion of the OPA1 NMD exon-containing pre-mRNA is in intron 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In some embodiments, hybridization of an ASO to the targeted portion of the NMD exon pre-mRNA results in exon skipping of at least one of NMD exon within intron 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, and subsequently increases OPA1 protein production. In some embodiments, the targeted portion of the OPA1 NMD exon-containing pre-mRNA is in intron 6 of OPA1, or intron 28 of OPA1. In some embodiments, the targeted portion of the OPA1 NMD exon-containing pre-mRNA is intron (GRCh38/hg38: chr3 193626203 to 193631611) of OPA1; or intron (GRCh38/hg38: chr3 193593374 to 193614710) of OPA1.

In some embodiments, the methods and compositions of the present disclosure are used to increase the expression of OPA1 by inducing exon skipping of a pseudo-exon of an OPA1 NMD exon-containing pre-mRNA. In some embodiments, the pseudo-exon is a sequence within any of introns 1-50. In some embodiments, the pseudo-exon is a sequence within any of introns 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In some embodiments, the pseudo-exon can be an OPA1 intron or a portion thereof. In some embodiments, the pseudo-exon is within intron 6 of OPA1, or intron 28 of OPA1. In some embodiments, the pseudo-exon is within intron (GRCh38/hg38: chr3 193626203 to 193631611) of OPA1; or intron (GRCh38/hg38: chr3 193593374 to 193614710) of OPA1.

In some embodiments, the ASO targets an OPA1 pre-mRNA transcript to induce exon skipping of a coding exon, e.g., an alternatively spliced exon. In some embodiments, the ASO targets a sequence within a coding exon, e.g., an alternatively spliced exon, of an OPA1 pre-mRNA transcript. In some embodiments, the ASO targets a sequence upstream (or 5') from the 5' end of a coding exon (3'ss) of an OPA1 pre-mRNA transcript. In some embodiments, the ASO targets a sequence downstream (or 3') from the 3' end of a coding exon (5'ss) of an OPA1 pre-mRNA transcript. In some embodiments, the ASO targets a sequence that is within an intron flanking on the 5' end of the coding exon of an OPA1 pre-mRNA transcript. In some embodiments, the ASO targets a sequence that is within an intron flanking the 3' end of the coding exon of an OPA1 pre-mRNA transcript. In some embodiments, the ASO targets a sequence comprising an exon-intron boundary of an OPA1 pre-mRNA transcript. An exon-intron boundary can refer to the junction of an intron sequence and an exon sequence. The intron sequence can flank the 5' end of the coding exon, or the 3' end of the coding exon. In some embodiments, the ASO targets a sequence within an exon of an OPA1 pre-mRNA transcript. In some embodiments, the ASO targets a sequence within an intron of an OPA1 pre-mRNA transcript. In some embodiments, the ASO targets a sequence comprising both a portion of an intron and a portion of an exon of an OPA1 pre-mRNA transcript.

In some embodiments, the ASO targets a sequence about 4 to about 300 nucleotides upstream (or 5') from the 5' end of the coding exon, e.g., alternatively spliced exon. In some embodiments, the ASO targets a sequence about 1 to about 20 nucleotides, about 20 to about 50 nucleotides, about 50 to about 100 nucleotides, about 100 to about 150 nucleotides, about 150 to about 200 nucleotides, about 200 to about 250 nucleotides, or about 250 to about 300 nucleotides upstream (or 5') from the 5' end of the coding exon region. In some embodiments, the ASO may target a sequence more than 300 nucleotides upstream from the 5' end of the coding exon. In some embodiments, the ASO targets a sequence about 4 to about 300 nucleotides downstream (or 3') from the 3' end of the coding exon. In some embodiments, the ASO targets a sequence about 1 to about 20 nucleotides, about 20 to about 50 nucleotides, about 50 to about 100 nucleotides, about 100 to about 150 nucleotides, about 150 to about 200 nucleotides, about 200 to about 250 nucleotides, or about 250 to about 300 nucleotides downstream from the 3' end of the coding exon. In some embodiments, the ASO targets a sequence more than 300 nucleotides downstream from the 3' end of the coding exon.

In some embodiments, the OPA1 pre-mRNA transcript is encoded by a genetic sequence with at least about 80%, 85%, 90%, 95%, 96%, 97%, 98%, 99% or 100% sequence identity to SEQ ID NO. 1. In some embodiments, the OPA1 pre-mRNA transcript comprises a sequence with at least about 80%, 85%, 90%, 95%, 96%, 97%, 98%, 99% or 100% sequence identity to any one of SEQ ID NOs: 2-5.

In some embodiments, the OPA1 pre-mRNA transcript (or NMD exon mRNA) comprises a sequence with at least about 80%, 85%, 90%, 95%, 97%, or 100% sequence identity to any one of SEQ ID NOs: 2-5. In some embodiments, OPA1 pre-mRNA transcript (or NMD exon mRNA) is encoded by a sequence with at least about 80%, 85%, 90%, 95%, 97%, or 100% sequence identity to any one of SEQ ID NOs: 2-5. In some embodiments, the targeted portion of the OPA1 pre-mRNA comprises a sequence with at least 80%, 85%, 90%, 95%, 97%, or 100% sequence identity to a region comprising at least 8 contiguous nucleic acids of any one of SEQ ID NOs: 2-5.

In some embodiments, the ASO targets exon 7 of an OPA1 pre-mRNA, i.e., the ASO targets exon (GRCh38/hg38: chr3 193626092 to 193626202) of OPA1 pre-mRNA.

In some embodiments, the ASO targets a coding exon of an OPA1 pre-mRNA other than exon 7, i.e., the ASO targets an exon of OPA1 pre-mRNA other than exon defined by (GRCh38/hg38: chr3 193626092 to 193626202).

In some embodiments, the ASO targets a sequence about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream (or 5') from the 5' end of exon 7 of OPA1. In some embodiments, the ASO targets a sequence about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream (or 5') from GRCh38/hg38: chr3 193626092 of OPA1.

In some embodiments, the ASO targets a sequence at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream (or 5') from the 5' end of exon 7 of OPA1. In some embodiments, the ASO targets a sequence at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream (or 5') from GRCh38/hg38: 193626092 of OPA1.

In some embodiments, the ASO targets a sequence about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream (or 3') from the 3' end of exon 7 of OPA1. In some embodiments, the ASO targets a sequence about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream (or 3') from GRCh38/hg38: chr3 193626202 of OPA1.

In some embodiments, the ASO targets a sequence at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream (or 3') from the 3' end of exon 7 of OPA1. In some embodiments, the ASO targets a sequence at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream (or 3') from GRCh38/hg38: chr3 193626202 of OPA1.

In some embodiments, the ASO has a sequence complementary to the targeted portion of the NMD exon mRNA according to any one of SEQ ID NOs: 2-5, or 277.

In some embodiments, the ASO targets a sequence upstream from the 5' end of a coding exon, e.g., an alternatively spliced exon. For example, ASOs targeting a sequence upstream from the 5' end of a coding exon (e.g., exon 7 of OPA1) comprises a sequence that is at least about 80%, 85%, 90%, 95%, 97%, or 100% complimentary to at least 8 contiguous nucleic acids of SEQ ID NO: 2 or 3. For example, ASOs targeting a sequence upstream from the 5' end of a coding exon (e.g., exon (GRCh38/hg38: 193626092 to 193626202) of OPA1) can comprise a sequence with at least 80%, 85%, 90%, 95%, 97%, or 100% sequence identity to SEQ ID NO: 4 or 5.

In some embodiments, the ASOs target a sequence containing an exon-intron boundary (or junction). For example, ASOs targeting a sequence containing an exon-intron boundary can comprise a sequence that is at least about 80%, 85%, 90%, 95%, 97%, or 100% complimentary to at least 8 contiguous nucleic acids of any one of SEQ ID NOs: 2-5. In some embodiments, the ASOs target a sequence downstream from the 3' end of a coding exon, e.g., an alternatively spliced exon. For example, ASOs targeting a sequence downstream from the 3' end of a coding exon (e.g., exon 7 of OPA1) can comprise a sequence with at least 80%, 85%, 90%, 95%, 97%, or 100% sequence identity to SEQ ID NO: 2 or 3, or at least 8 contiguous nucleic acids of SEQ ID NO: 2 or 3. For example, ASOs targeting a sequence downstream from the 3' end of a coding exon (e.g., exon 7 of OPA1) can comprise a sequence with at least 80%, 85%, 90%, 95%, 97%, or 100% sequence identity to SEQ ID NO: 4 or 5, or at least 8 contiguous nucleic acids of SEQ ID NO: 4 or 5. In some embodiments, ASOs target a sequence within a coding exon, e.g., an alternatively spliced exon.

Protein Expression

In some embodiments, the methods described herein are used to increase the production of a functional OPA1 protein or RNA. As used herein, the term "functional" refers to the amount of activity or function of an OPA1 protein or RNA that is necessary to eliminate any one or more symptoms of a treated condition or disease, e.g., Optic atrophy type 1. In some embodiments, the methods are used to increase the production of a partially functional OPA1 protein or RNA. As used herein, the term "partially functional" refers to any amount of activity or function of the OPA1 protein or RNA that is less than the amount of activity or function that is necessary to eliminate or prevent any one or more symptoms of a disease or condition. In some embodiments, a partially functional protein or RNA will have at least 10%, at least 20%, at least 30%, at least 40%, at least 50%, at least 60%, at least 70%, at least 75%, at least 80%, at least 85%, at least 90%, or at least 95% less activity relative to the fully functional protein or RNA.

In some embodiments, the method is a method of increasing the expression of the OPA1, protein by cells of a subject having an OPA1 pre-mRNA, wherein the subject has a disease or condition, e.g., Optic atrophy type 1, caused by a deficient amount of activity of OPA1 protein, and wherein the deficient amount of the OPA1 protein is caused by haploinsufficiency of the OPA1 protein. In such an embodiment, the subject has a first allele encoding a functional OPA1 protein, and a second allele from which the OPA1 protein is not produced. In another such embodiment, the subject has a first allele encoding a functional OPA1 protein, and a second allele encoding a nonfunctional OPA1 protein. In another such embodiment, the subject has a first allele encoding a functional OPA1 protein, and a second allele encoding a partially functional OPA1 protein. In any of these embodiments, the antisense oligomer binds to a targeted portion of the OPA1 pre-mRNA transcribed from the second allele, thereby inducing exon skipping of the pseudo-exon from the pre-mRNA, and causing an increase in the level of mature mRNA encoding functional OPA1 protein, and an increase in the expression of the OPA1 protein in the cells of the subject.

In some embodiments, the method is a method of increasing the expression of the OPA1 protein by cells of a subject having an OPA1 pre-mRNA, wherein the subject has a disease or condition caused by a deficient amount of activity of OPA1 protein, and wherein the deficient amount of the OPA1 protein is caused by autosomal recessive inheritance.

In some embodiments, the method is a method of increasing the expression of the OPA1 protein by cells of a subject having an OPA1 pre-mRNA, wherein the subject has a disease or condition, e.g., Optic atrophy type 1, caused by a deficient amount of activity of OPA1, protein, and wherein the deficient amount of the OPA1 protein is caused by autosomal dominant inheritance.

In related embodiments, the method is a method of using an ASO to increase the expression of a protein or functional RNA. In some embodiments, an ASO may be used to increase the expression of OPA1 protein in cells of a subject having an OPA1 pre-mRNA, wherein the subject has a deficiency, e.g., Optic atrophy type 1; in the amount or function of an OPA1 protein.

In some embodiments, the pre-mRNA transcript that encodes the protein that is causative of the disease or condition is targeted by the agent, e.g., the oligonucleotides, described herein. In some cases, it is the NMD exon-containing pre-mRNA transcript targeted by the agent, e.g., the oligonucleotides, described herein. In some cases, the agent, e.g., the oligonucleotides, described herein, are designed to target a coding exon of the pre-mRNA. In some cases, the agent, e.g., the oligonucleotides, described herein can induce skipping of the NMD exon, a coding exon, or both. In some embodiments, a NMD exon-containing pre-mRNA transcript that encodes a protein that is not causative of the disease is targeted by the ASOs. For example, a disease that is the result of a mutation or deficiency of a first protein in a particular pathway may be ameliorated by targeting a pre-mRNA that encodes a second protein, thereby increasing production of the second protein. In some embodiments, the function of the second protein is able to compensate for the mutation or deficiency of the first protein (which is causative of the disease or condition).

In some embodiments, the subject has:
(a) a first mutant allele from which
 (i) the OPA1 protein is produced at a reduced level compared to production from a wild-type allele,
 (ii) the OPA1 protein is produced in a form having reduced function compared to an equivalent wild-type protein, or
 (iii) the OPA1 protein or functional RNA is not produced; and
(b) a second mutant allele from which
 (i) the OPA1 protein is produced at a reduced level compared to production from a wild-type allele,
 (ii) the OPA1 protein is produced in a form having reduced function compared to an equivalent wild-type protein, or
 (iii) the OPA1 protein is not produced, and
wherein the NMD exon-containing pre-mRNA is transcribed from the first allele and/or the second allele. In these embodiments, the ASO binds to a targeted portion of the NMD exon-containing pre-mRNA transcribed from the first allele or the second allele, thereby inducing exon skipping of the pseudo-exon from the NMD exon-containing pre-mRNA, and causing an increase in the level of mRNA encoding OPA1 protein and an increase in the expression of the target protein or functional RNA in the cells of the subject. In these embodiments, the target protein or functional RNA having an increase in expression level resulting from the exon skipping of the pseudo-exon from the NMD exon-containing pre-mRNA may be either in a form having reduced function compared to the equivalent wild-type protein (partially-functional), or having full function compared to the equivalent wild-type protein (fully-functional).

In some embodiments, the subject has:
(a) a first mutant allele from which
 (i) the OPA1 protein is produced at a reduced level compared to production from a wild-type allele,
 (ii) the OPA1 protein is produced in a form having reduced function compared to an equivalent wild-type protein, or
 (iii) the OPA1 protein or functional RNA is not produced; and
(b) a second mutant allele from which
 (i) the OPA1 protein is produced at a reduced level compared to production from a wild-type allele,
 (ii) the OPA1 protein is produced in a form having reduced function compared to an equivalent wild-type protein, or
 (iii) the OPA1 protein is not produced, and
wherein the OPA1 pre-mRNA is transcribed from the first allele and/or the second allele. In these embodiments, the ASO binds to a targeted portion of the OPA1 pre-mRNA transcribed from the first allele or the second allele, thereby inducing exon skipping of a coding exon from the OPA1 pre-mRNA, and causing an increase in the expression of the target OPA1 protein in the cells of the subject. In these embodiments, the target OPA1 protein having an increase in expression level resulting from the exon skipping of the coding exon from the OPA1 pre-mRNA may be either in a form having reduced function compared to the equivalent full-length wild-type protein (partially-functional), or having full function compared to the equivalent full-length wild-type protein (fully-functional).

In some embodiments, the level of mRNA encoding OPA1 protein is increased 1.1 to 10-fold, when compared to the amount of mRNA encoding OPA1 protein that is produced in a control cell, e.g., one that is not treated with the antisense oligomer or one that is treated with an antisense oligomer that does not bind to the targeted portion of the OPA1 pre-mRNA.

In some embodiments, a subject treated using the methods of the present disclosure expresses a partially functional OPA1 protein from one allele, wherein the partially functional OPA1 protein may be caused by a frameshift mutation, a nonsense mutation, a missense mutation, or a partial gene deletion. In some embodiments, a subject treated using the methods of the disclosure expresses a nonfunctional OPA1 protein from one allele, wherein the nonfunctional OPA1 protein may be caused by a frameshift mutation, a nonsense mutation, a missense mutation, a partial gene deletion, in one allele. In some embodiments, a subject treated using the methods of the disclosure has an OPA1 whole gene deletion, in one allele.

Exon Inclusion

As used herein, a "NMD exon-containing pre-mRNA" is a pre-mRNA transcript that contains at least one pseudo-exon. Alternative or aberrant splicing can result in inclusion of the at least one pseudo-exon in the mature mRNA transcripts. The terms "mature mRNA," and "fully-spliced mRNA," are used interchangeably herein to describe a fully processed mRNA. Inclusion of the at least one pseudo-exon can be non-productive mRNA and lead to NMD of the mature mRNA. NMD exon-containing mature mRNA may sometimes lead to aberrant protein expression.

In some embodiments, the included pseudo-exon is the most abundant pseudo-exon in a population of NMD exon-containing pre-mRNAs transcribed from the gene encoding the target protein in a cell. In some embodiments, the included pseudo-exon is the most abundant pseudo-exon in a population of NMD exon-containing pre-mRNAs transcribed from the gene encoding the target protein in a cell, wherein the population of NMD exon-containing pre-mRNAs comprises two or more included pseudo-exons. In some embodiments, an antisense oligomer targeted to the most abundant pseudo-exon in the population of NMD exon-containing pre-mRNAs encoding the target protein induces exon skipping of one or two or more pseudo-exons in the population, including the pseudo-exon to which the antisense oligomer is targeted or binds. In some embodiments, the targeted region is in a pseudo-exon that is the most abundant pseudo-exon in a NMD exon-containing pre-mRNA encoding the OPA1 protein.

The degree of exon inclusion can be expressed as percent exon inclusion, e.g., the percentage of transcripts in which a given pseudo-exon is included. In brief, percent exon inclusion can be calculated as the percentage of the amount of RNA transcripts with the exon inclusion, over the sum of the average of the amount of RNA transcripts with exon inclusion plus the average of the amount of RNA transcripts with exon exclusion.

In some embodiments, an included pseudo-exon is an exon that is identified as an included pseudo-exon based on a determination of at least about 5%, at least about 10%, at least about 15%, at least about 20%, at least about 25%, at least about 30%, at least about 35%, at least about 40%, at least about 45%, or at least about 50%, inclusion. In embodiments, a included pseudo-exon is an exon that is identified as a included pseudo-exon based on a determination of about 5% to about 100%, about 5% to about 95%, about 5% to about 90%, about 5% to about 85%, about 5% to about 80%, about 5% to about 75%, about 5% to about 70%, about 5% to about 65%, about 5% to about 60%, about 5% to about 55%, about 5% to about 50%, about 5% to about 45%, about 5% to about 40%, about 5% to about 35%, about 5% to about 30%, about 5% to about 25%, about 5% to about 20%, about 5% to about 15%, about 10% to about 100%, about 10% to about 95%, about 10% to about 90%, about 10% to about 85%, about 10% to about 80%, about 10% to about 75%, about 10% to about 70%, about 10% to about 65%, about 10% to about 60%, about 10% to about 55%, about 10% to about 50%, about 10% to about 45%, about 10% to about 40%, about 10% to about 35%, about 10% to about 30%, about 10% to about 25%, about 10% to about 20%, about 15% to about 100%, about 15% to about 95%, about 15% to about 90%, about 15% to about 85%, about 15% to about 80%, about 15% to about 75%, about 15% to about 70%, about 15% to about 65%, about 15% to about 60%, about 15% to about 55%, about 15% to about 50%, about 15% to about 45%, about 15% to about 40%, about 15% to about 35%, about 15% to about 30%, about 15% to about 25%, about 20% to about 100%, about 20% to about 95%, about 20% to about 90%, about 20% to about 85%, about 20% to about 80%, about 20% to about 75%, about 20% to about 70%, about 20% to about 65%, about 20% to about 60%, about 20% to about 55%, about 20% to about 50%, about 20% to about 45%, about 20% to about 40%, about 20% to about 35%, about 20% to about 30%, about 25% to about 100%, about 25% to about 95%, about 25% to about 90%, about 25% to about 85%, about 25% to about 80%, about 25% to about 75%, about 25% to about 70%, about 25% to about 65%, about 25% to about 60%, about 25% to about 55%, about 25% to about 50%, about 25% to about 45%, about 25% to about 40%, or about 25% to about 35%, inclusion. ENCODE data (described by, e.g., Tilgner, et al., 2012, "Deep sequencing of subcellular RNA fractions shows splicing to be predominantly co-transcriptional in the human genome but inefficient for lncRNAs," Genome Research 22(9):1616-25) can be used to aid in identifying exon inclusion.

In some embodiments, contacting cells with an ASO that is complementary to a targeted portion of an OPA1 pre-mRNA transcript results in an increase in the amount of OPA1 protein produced by at least 10, 20, 30, 40, 50, 60, 80, 100, 150, 200, 250, 300, 350, 400, 450, 500, or 1000%, compared to the amount of the protein produced by a cell in the absence of the ASO/absence of treatment. In some embodiments, the total amount of OPA1 protein produced by the cell to which the antisense oligomer is contacted is increased about 20% to about 300%, about 50% to about 300%, about 100% to about 300%, about 150% to about 300%, about 20% to about 50%, about 20% to about 100%, about 20% to about 150%, about 20% to about 200%, about 20% to about 250%, about 50% to about 100%, about 50% to about 150%, about 50% to about 200%, about 50% to about 250%, about 100% to about 150%, about 100% to about 200%, about 100% to about 250%, about 150% to about 200%, about 150% to about 250%, about 200% to about 250%, at least about 10%, at least about 20%, at least about 50%, at least about 100%, at least about 150%, at least about 200%, at least about 250%, or at least about 300%, compared to the amount of target protein produced by a control compound. In some embodiments, the total amount of OPA1 protein produced by the cell to which the antisense oligomer is contacted is increased about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to the amount of target protein produced by a control compound. A control compound can be, for example, an oligonucleotide that is not complementary to a targeted portion of the pre-mRNA.

In some embodiments, contacting cells with an ASO that is complementary to a targeted portion of an OPA1 premRNA transcript results in an increase in the amount of mRNA encoding OPA1, including the mature mRNA encoding the target protein. In some embodiments, the amount of mRNA encoding OPA1 protein, or the mature mRNA encoding the OPA1 protein, is increased by at least 10, 20, 30, 40, 50, 60, 80, 100, 150, 200, 250, 300, 350, 400, 450, 500, or 1000%, compared to the amount of the protein produced by a cell in the absence of the ASO/absence of treatment. In some embodiments, the total amount of the mRNA encoding OPA1 protein, or the mature mRNA encoding OPA1 protein produced in the cell to which the antisense oligomer is contacted is increased about 20% to about 300%, about 50% to about 300%, about 100% to about 300%, about 150% to about 300%, about 20% to about 50%, about 20% to about 100%, about 20% to about 150%, about 20% to about 200%, about 20% to about 250%, about 50% to about 100%, about 50% to about 150%, about 50% to about 200%, about 50% to about 250%, about 100% to about 150%, about 100% to about 200%, about 100% to about 250%, about 150% to about 200%, about 150% to about 250%, about 200% to about 250%, at least about 10%, at least about 20%, at least about 50%, at least about 100%, at least about 150%, at least about 200%, at least about 250%, or at least about 300%, compared to the amount of mature RNA produced in an untreated cell, e.g., an untreated cell or a cell treated with a control compound. In some embodiments, the total amount of the mRNA encoding OPA1 protein, or the mature mRNA encoding OPA1 protein produced in the cell to which the antisense oligomer is contacted is increased about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold compared to the amount of mature RNA produced in an untreated cell, e.g., an untreated cell or a cell treated with a control compound. A control compound can be, for example, an oligonucleotide that is not complementary to a targeted portion of the OPA1 NMD exon-containing pre-mRNA.

The NMD exon can be in any length. In some embodiments, the NMD exon comprises a full sequence of an intron, in which case, it can be referred to as intron retention. In some embodiments, the NMD exon can be a portion of the intron. In some embodiments, the NMD exon can be a 5' end portion of an intron including a 5'ss sequence. In some embodiments, the NMD exon can be a 3' end portion of an intron including a 3'ss sequence. In some embodiments, the NMD exon can be a portion within an intron without inclusion of a 5'ss sequence. In some embodiments, the NMD exon can be a portion within an intron without inclusion of a 3'ss sequence. In some embodiments, the NMD exon can be a portion within an intron without inclusion of either a 5'ss or a 3'ss sequence. In some embodiments, the NMD exon can be from 5 nucleotides to 10 nucleotides in length, from 10 nucleotides to 15 nucleotides in length, from 15 nucleotides to 20 nucleotides in length, from 20 nucleotides to 25 nucleotides in length, from 25 nucleotides to 30 nucleotides in length, from 30 nucleotides to 35 nucleotides in length, from 35 nucleotides to 40 nucleotides in length, from 40 nucleotides to 45 nucleotides in length, from 45 nucleotides to 50 nucleotides in length, from 50 nucleotides to 55 nucleotides in length, from 55 nucleotides to 60 nucleotides in length, from 60 nucleotides to 65 nucleotides in length, from 65 nucleotides to 70 nucleotides in length, from 70 nucleotides to 75 nucleotides in length, from 75 nucleotides to 80 nucleotides in length, from 80 nucleotides to 85 nucleotides in length, from 85 nucleotides to 90 nucleotides in length, from 90 nucleotides to 95 nucleotides in length, or from 95 nucleotides to 100 nucleotides in length. In some embodiments, the NMD exon can be at least 10 nucleotides, at least 20 nucleotides, at least 30 nucleotides, at least 40 nucleotides, at least 50 nucleotides, at least 60 nucleoids, at least 70 nucleotides, at least 80 nucleotides in length, at least 90 nucleotides, or at least 100 nucleotides in length. In some embodiments, the NMD exon can be from 100 to 200 nucleotides in length, from 200 to 300 nucleotides in length, from 300 to 400 nucleotides in length, from 400 to 500 nucleotides in length, from 500 to 600 nucleotides in length, from 600 to 700 nucleotides in length, from 700 to 800 nucleotides in length, from 800 to 900 nucleotides in length, from 900 to 1,000 nucleotides in length. In some embodiments, the NMD exon may be longer than 1,000 nucleotides in length.

Inclusion of a pseudo-exon can lead to a frameshift and the introduction of a premature termination codon (PIC) in the mature mRNA transcript rendering the transcript a target of NMD. Mature mRNA transcript containing NMD exon can be non-productive mRNA transcript which does not lead to protein expression. The PIC can be present in any position downstream of an NMD exon. In some embodiments, the PIC can be present in any exon downstream of an NMD exon. In some embodiments, the PIC can be present within the NMD exon. For example, inclusion of exon 6x of OPA1, exon 7x of OPA1, or exon 28x of OPA1, in an mRNA transcript encoded by the OPA1 gene can induce a PIC in the mRNA transcript. For example, inclusion of exon (GRCh38/hg38: chr3 193628509 193628616) of OPA1; or exon (GRCh38/hg38: chr3 193603500 193603557) of OPA1 in an mRNA transcript encoded by the OPA1.

In some aspects, provided herein is a method of modulating expression of an OPA1 protein by promoting inclusion of a coding exon. The method can comprise contacting an agent to a cell having an OPA1 pre-mRNA, wherein the agent comprises an oligonucleotide that binds to: (a) a targeted portion of the pre-mRNA within an intronic region immediately upstream of a 5' end of the coding exon of the pre-mRNA; or (b) a targeted portion of the pre-mRNA within an intronic region immediately downstream of a 3' end of the coding exon of the pre-mRNA; whereby the agent increases a level of a processed mRNA that is processed from the pre-mRNA and that contains the coding exon in the cell. In some cases, the coding exon to be included is an alternatively spliced exon. In some cases, the method promotes inclusion of the coding exon in the processed mRNA during splicing of the pre-mRNA in the cell.

In some of these embodiments for inclusion of coding exon, the target portion of the pre-mRNA is within a region spanning from 100 to 50, from 100 to 60, from 100 to 70, from 100 to 80, or from 100 to 90 nucleotides upstream of a 5' end of the coding exon. In some cases, the target portion of the pre-mRNA is within a region spanning from 40 to 100, from 50 to 100, from 60 to 100, from 70 to 100, from 80 to 100, or from 90 to 100 nucleotides downstream of a 3' end of the coding exon. In some cases, the coding exon is exon 7 of OPA1. In some cases, the coding exon comprises a sequence with at least 80%, at least 90%, or 100% sequence identity to SEQ ID NO: 277. In some cases, the coding exon comprises SEQ ID NO: 277. The targeted portion of the pre-mRNA can be within a region spanning from 100 to 50, from 100 to 60, from 100 to 70, from 100 to 80, or from 100 to 90 nucleotides upstream of genomic site GRCh38/hg38: chr3 193626092. In some cases, the targeted portion of the pre-mRNA is within a region spanning from 40 to 100, from 50 to 100, from 60 to 100, from 70 to 100, from 80 to 100, or from 90 to 100 nucleotides downstream of genomic site GRCh38/hg38: chr3 193626202.

In some cases, the inclusion of the coding exon in the processed mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent.

Exclusion of Both NMD Exon and Coding Exon

In some embodiments, provided herein is a method of modulating expression of a target protein by targeting a pre-mRNA and modulating exclusion of both a coding exon and a non-sense mediated RNA decay-inducing exon (NMD exon) from the pre-mRNA. In some cases, the method comprises contacting an agent to the cell, and the agent promotes exclusion of both the coding exon and the NMD exon from the pre-mRNA, thereby increasing level of a processed mRNA that is processed from the pre-mRNA and lacks both the coding exon and the NMD exon. In some cases, the agent binds to a targeted portion of the pre-mRNA, or modulates binding of a factor involved in splicing of the coding exon, the NMD exon, or both. In some cases, the agent interferes with binding of the factor involved in splicing of the coding exon, the NMD exon, or both, to a region of the targeted portion. In some cases, the NMD exon is within an intronic region adjacent to the coding exon. In some cases, the NMD exon is within an intronic region immediately upstream of the coding exon. In some cases, the NMD exon is within an intronic region immediately downstream of the coding exon. In some cases, the coding exon is an alternatively spliced exon.

In some cases, the targeted portion of the pre-mRNA is proximal to the coding exon. The targeted portion of the pre-mRNA can be located in an intronic region immediately upstream of the coding exon. The targeted portion of the pre-mRNA can be located in an intronic region immediately downstream of the coding exon. In some cases, the targeted portion of the pre-mRNA can be located within the coding exon. In some cases, the targeted portion of the pre-mRNA is within a region spanning from 49 to 1, from 39 to 1, from 29 to 1, or from 19 to 1 nucleotides upstream of 5' end of the coding exon. In some cases, the targeted portion of the pre-mRNA is within a region spanning from 100 nucleotides upstream of the coding exon to 100 nucleotides downstream of the coding exon. In some cases, the targeted portion comprises about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more consecutive nucleotides of the coding exon.

In some cases, the targeted portion of the pre-mRNA is proximal to the NMD exon. In some cases, the targeted portion of the pre-mRNA is located in an intronic region immediately upstream of the NMD exon. In some cases, the targeted portion of the pre-mRNA is located in an intronic region immediately downstream of the NMD exon. In some cases, the targeted portion of the pre-mRNA is located within the NMD exon. In some cases, the targeted portion of the pre-mRNA is within a region spanning from 100 nucleotides upstream of the NMD exon to 100 nucleotides downstream of the NMD exon.

In some embodiments, the method described herein is applicable to modulation of expression of OPA1 protein by modulating exclusion of both exon 7 and an NMD exon (e.g., exon 7x) of OPA1 pre-mRNA that contains both exon 7 and exon 7x. In some cases, the coding exon comprises a sequence with at least 80%, at least 90%, or 100% sequence identity to SEQ ID NO: 277. In some cases, the coding exon comprises SEQ ID NO: 277. In some cases, the targeted portion of the pre-mRNA is immediately upstream of the coding exon GRCh38/hg38: chr3 193626092 to 193626202. In some cases, the targeted portion of the pre-mRNA is immediately downstream of the coding exon GRCh38/hg38: chr3 193626092 to 193626202. In some cases, the targeted portion of the pre-mRNA is within a region spanning from 49 to 1, from 39 to 1, from 29 to 1, or from 19 to 1 nucleotides upstream of GRCh38/hg38: chr3 193626092. In some cases, the targeted portion of the pre-mRNA is within a region spanning from 100 nucleotides upstream of genomic site GRCh38/hg38: chr3 193626092 to 100 nucleotides downstream of genomic site GRCh38/hg38: chr3 193626202. In some cases, the targeted portion of the pre-mRNA is within the coding exon GRCh38/hg38: chr3 193626092 to 193626202. In some cases, the targeted portion of the pre-mRNA comprises an exon-intron junction of the coding exon GRCh38/hg38: chr3 193626092 to 193626202. In some cases, the NMD exon comprises a sequence with at least 80%, at least 90%, or 100% sequence identity to SEQ ID NO: 279. In some cases, the NMD exon comprises SEQ ID NO: 279. In some cases, the targeted portion of the pre-mRNA is immediately upstream of the NMD exon GRCh38/hg38: chr3 193628509 to 193628616. In some cases, the targeted portion of the pre-mRNA is immediately downstream of the NMD exon GRCh38/hg38: chr3 193628509 to 193628616. In some cases, the targeted portion of the pre-mRNA is within a region spanning from 100 nucleotides upstream of genomic site GRCh38/hg38: chr3 193628509 to 100 nucleotides downstream of genomic site GRCh38/hg38: chr3 193628616.

In some cases, the targeted portion of the pre-mRNA is within the NMD exon GRCh38/hg38: chr3 193628509 to 193628616. In some cases, the targeted portion of the pre-mRNA comprises an exon-intron junction of the NMD exon GRCh38/hg38: chr3 193628509 to 193628616. In some cases, the targeted portion comprises about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more consecutive nucleotides of the NMD exon.

In some cases, the exclusion of the coding exon from the pre-mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of contacting with the agent. In some cases, the exclusion of the NMD exon from the pre-mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of contacting with the agent. In some cases, the method results in an increase in the level of the processed mRNA in the cell. The level of the processed mRNA in the cell contacted with the agent can be increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of contacting with the agent.

In some cases, the method results in an increase in expression of the OPA1 protein in the cell. A level of the OPA1 protein expressed from the processed mRNA in the cell contacted with the agent can be increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of contacting with the agent.

In some cases, a level of the OPA1 protein expressed from the processed mRNA in the cell contacted with the agent is increased by at least about 1.5-fold compared to in the absence of contacting with the agent.

In some cases, the OPA1 protein expressed from the processed mRNA that lacks exon 7 and exon 7x is a functional OPA1 protein. The OPA1 protein expressed from the processed mRNA that lacks exon 7 and exon 7x can be at least partially functional as compared to a wild-type OPA1 protein. The OPA1 protein expressed from the processed mRNA that lacks exon 7 and exon 7x can be at least partially functional as compared to a full-length wild-type OPA1 protein.

Therapeutic Agents

In various embodiments of the present disclosure, compositions and methods comprising a therapeutic agent are provided to modulate protein expression level of OPA1. In some embodiments, provided herein are compositions and methods to modulate alternative splicing of OPA1 pre-mRNA. In some embodiments, provided herein are compositions and methods to induce exon skipping in the splicing of OPA1 pre-mRNA, e.g., to induce skipping of a pseudo-exon during splicing of OPA1 pre-mRNA. In other embodiments, therapeutic agents may be used to induce the inclusion of an exon in order to decrease the protein expression level.

A therapeutic agent disclosed herein can be a NIE repressor agent. A therapeutic agent may comprise a polynucleic acid polymer.

According to one aspect of the present disclosure, provided herein is a method of treatment or prevention of a condition or disease associated with a functional OPA1 protein deficiency, comprising administering a NIE repressor agent to a subject to increase levels of functional OPA1 protein, wherein the agent binds to a region of the pre-mRNA transcript to decrease inclusion of the NMD exon in the mature transcript. For example, provided herein is a method of treatment or prevention of a condition associated with a functional OPA1 protein deficiency, comprising administering a NIE repressor agent to a subject to increase levels of functional OPA1 protein, wherein the agent binds to a region of an intron containing an NMD exon (e.g., exon 6x of OPA1, exon 7x of OPA1, or exon 28x of OPA1) of the pre-mRNA transcript or to a NMD exon-activating regulatory sequence in the same intron. For example, provided herein is a method of treatment or prevention of a condition associated with a functional OPA1 protein deficiency, comprising administering a NIE repressor agent to a subject to increase levels of functional OPA1 protein, wherein the agent binds to a region of an intron containing an NMD exon (e.g., exon (GRCh38/hg38: chr3 193628509 193628616) of OPA1; or exon (GRCh38/hg38: chr3 193603500 193603557) of OPA1) of the pre-mRNA transcript or to a NMD exon-activating regulatory sequence in the same intron. In some embodiments, the method comprises administering a NIE repressor agent to a subject to increase levels of functional OPA1 protein, wherein the agent binds to a region of an intron containing an NMD exon (e.g., exon of OPA1 other than exon 7x defined by (GRCh38/hg38: chr3 193628509 193628616) or exon defined by (GRCh38/hg38: 3 to about 8-fold, about 3 to about 9-fold, about 4 to about 7-fold, about 4 to about 8-fold, about 4 to about 9-fold, at chr3 193603500 193603557)) of the pre-mRNA transcript or to a NMD exon-activating regulatory sequence in the same intron. In some embodiments, the therapeutic agent promotes exclusion of an NMD exon of OPA1 pre-mRNA other than exon 7x defined by (GRCh38/hg38: chr3 193628509 193628616) or exon defined by (GRCh38/hg38: chr3 193603500 193603557). In some embodiments, the composition disclosed herein includes an agent that promotes exclusion of an NMD exon of OPA1 pre-mRNA other than exon 7x defined by (GRCh38/hg38: chr3 193628509 193628616) or exon defined by (GRCh38/hg38: chr3 193603500 193603557).

Where reference is made to reducing NMD exon inclusion in the mature mRNA, the reduction may be complete, e.g., 100%, or may be partial. The reduction may be clinically significant. The reduction/correction may be relative to the level of NMD exon inclusion in the subject without treatment, or relative to the amount of NMD exon inclusion in a population of similar subjects. The reduction/correction may be at least 10% less NMD exon inclusion relative to the average subject, or the subject prior to treatment. The reduction may be at least 20% less NMD exon inclusion relative to an average subject, or the subject prior to treatment. The reduction may be at least 40% less NMD exon inclusion relative to an average subject, or the subject prior to treatment. The reduction may be at least 50% less NMD exon inclusion relative to an average subject, or the subject prior to treatment. The reduction may be at least 60% less NMD exon inclusion relative to an average subject, or the subject prior to treatment. The reduction may be at least 80% less NMD exon inclusion relative to an average subject, or the subject prior to treatment. The reduction may be at least 90% less NMD exon inclusion relative to an average subject, or the subject prior to treatment.

According to one aspect of the present disclosure, provided herein is a method of treatment or prevention of a condition or disease associated with a functional OPA1 protein deficiency, comprising administering an agent to a subject to increase levels of functional OPA1 protein, wherein the agent binds to a region of the pre-mRNA transcript to decrease inclusion of a coding exon (e.g., exon 7) in the mature transcript. For example, provided herein is a method of treatment or prevention of a condition associated with a functional OPA1 protein deficiency, comprising administering an agent to a subject to increase levels of functional OPA1 protein, wherein the agent binds to a region containing a coding exon (e.g., exon 7 of OPA1) of the pre-mRNA transcript. For example, provided herein is a method of treatment or prevention of a condition associated with a functional OPA1 protein deficiency, comprising administering an agent to a subject to increase levels of functional OPA1 protein, wherein the agent binds to a region containing a coding exon (e.g., exon (GRCh38/hg38: chr3 193626092 to 193626202) of OPA1) of the pre-mRNA transcript. In some embodiments, the method comprises administering an agent to a subject to increase levels of functional OPA1 protein, wherein the agent binds to a region containing a coding exon (e.g., exon of OPA1 other than exon 7 defined by (GRCh38/hg38: chr3 193626092 to 193626202)) of the pre-mRNA transcript. In some embodiments, the therapeutic agent promotes exclusion of a coding exon of OPA1 pre-mRNA other than exon 7 defined by (GRCh38/hg38: chr3 193626092 to 193626202). In some embodiments, the composition disclosed herein includes an agent that promotes exclusion of a coding exon of OPA1 pre-mRNA other than exon 7 defined by (GRCh38/hg38: chr3 193626092 to 193626202).

Where reference is made to increasing active OPA1 protein levels, the increase may be clinically significant. The increase may be relative to the level of active OPA1 protein in the subject without treatment, or relative to the amount of active OPA1 protein in a population of similar subjects. The increase may be at least 10% more active OPA1 protein relative to the average subject, or the subject prior to treatment. The increase may be at least 20% more active OPA1 protein relative to the average subject, or the subject prior to treatment. The increase may be at least 40% more active OPA1 protein relative to the average subject, or the subject prior to treatment. The increase may be at least 50% more active OPA1 protein relative to the average subject, or the subject prior to treatment. The increase may be at least 80% more active OPA1 protein relative to the average subject, or the subject prior to treatment. The increase may be at least 100% more active OPA1 protein relative to the average subject, or the subject prior to treatment. The increase may be at least 200% more active OPA1 protein relative to the average subject, or the subject prior to treatment. The increase may be at least 500% more active OPA1 protein relative to the average subject, or the subject prior to treatment.

In embodiments wherein the NIE repressor agent comprises a polynucleic acid polymer, the polynucleic acid polymer may be about 50 nucleotides in length. The polynucleic acid polymer may be about 45 nucleotides in length. The polynucleic acid polymer may be about 40 nucleotides in length. The polynucleic acid polymer may be about 35 nucleotides in length. The polynucleic acid polymer may be about 30 nucleotides in length. The polynucleic acid polymer may be about 24 nucleotides in length. The polynucleic acid polymer may be about 25 nucleotides in length. The polynucleic acid polymer may be about 20 nucleotides in length. The polynucleic acid polymer may be about 19 nucleotides in length. The polynucleic acid polymer may be about 18 nucleotides in length. The polynucleic acid polymer may be about 17 nucleotides in length. The polynucleic acid polymer may be about 16 nucleotides in length. The polynucleic acid polymer may be about 15 nucleotides in length. The polynucleic acid polymer may be about 14 nucleotides in length. The polynucleic acid polymer may be about 13 nucleotides in length. The polynucleic acid polymer may be about 12 nucleotides in length. The polynucleic acid polymer may be about 11 nucleotides in length. The polynucleic acid polymer may be about 10 nucleotides in length. The polynucleic acid polymer may be between about 10 and about 50 nucleotides in length. The polynucleic acid polymer may be between about 10 and about 45 nucleotides in length. The polynucleic acid polymer may be between about 10 and about 40 nucleotides in length. The polynucleic acid polymer may be between about 10 and about 35 nucleotides in length. The polynucleic acid polymer may be between about 10 and about 30 nucleotides in length. The polynucleic acid polymer may be between about 10 and about 25 nucleotides in length. The polynucleic acid polymer may be between about 10 and about 20 nucleotides in length. The polynucleic acid polymer may be between about 15 and about 25 nucleotides in length. The polynucleic acid polymer may be between about 15 and about 30 nucleotides in length. The polynucleic acid polymer may be between about 12 and about 30 nucleotides in length.

The sequence of the polynucleic acid polymer may be at least 50%, 55%, 60%, 65%, 70%, 75%, 80%, 85%, 90%, 91%, 92%, 93%, 94%, 95%, 96%, 97%, 98%, 99%, or 99.5% complementary to a target sequence of an mRNA transcript, e.g., a partially processed mRNA transcript. The sequence of the polynucleic acid polymer may be 100% complementary to a target sequence of a pre-mRNA transcript.

The sequence of the polynucleic acid polymer may have 4 or fewer mismatches to a target sequence of the pre-mRNA transcript. The sequence of the polynucleic acid polymer may have 3 or fewer mismatches to a target sequence of the pre-mRNA transcript. The sequence of the polynucleic acid polymer may have 2 or fewer mismatches to a target sequence of the pre-mRNA transcript. The sequence of the polynucleic acid polymer may have 1 or fewer mismatches to a target sequence of the pre-mRNA transcript. The sequence of the polynucleic acid polymer may have no mismatches to a target sequence of the pre-mRNA transcript.

The polynucleic acid polymer may specifically hybridize to a target sequence of the pre-mRNA transcript. For example, the polynucleic acid polymer may have 91%, 92%, 93%, 94%, 95%, 96%, 97%, 98%, 99%, 99.5% or 100% sequence complementarity to a target sequence of the pre-mRNA transcript. The hybridization may be under high stringent hybridization conditions.

The polynucleic acid polymer comprising a sequence with at least 50%, 55%, 60%, 65%, 70%, 75%, 80%, 85%, 90%, 91%, 92%, 93%, 94%, 95%, 96%, 97%, 98%, 99%, or 99.5% sequence identity to a sequence selected from the group consisting of SEQ ID NOs: 2-5. The polynucleic acid polymer may comprise a sequence with 100% sequence identity to a sequence selected from the group consisting of SEQ ID NOs: 2-5.

Where reference is made to a polynucleic acid polymer sequence, the skilled person will understand that one or more substitutions may be tolerated, optionally two substitutions may be tolerated in the sequence, such that it maintains the ability to hybridize to the target sequence; or where the substitution is in a target sequence, the ability to be recognized as the target sequence. References to sequence identity may be determined by BLAST sequence alignment using standard/default parameters. For example, the sequence may have 99% identity and still function according to the present disclosure. In other embodiments, the sequence may have 98% identity and still function according to the present disclosure. In another embodiment, the sequence may have 95% identity and still function according to the present disclosure. In another embodiment, the sequence may have 90% identity and still function according to the present disclosure.

Antisense Oligomers

Provided herein is a composition comprising an antisense oligomer that induces exon skipping by binding to a targeted portion of an OPA1 pre-mRNA, e.g., an OPA1 NMD exon-containing pre-mRNA. As used herein, the terms "ASO" and "antisense oligomer" are used interchangeably and refer to an oligomer such as a polynucleotide, comprising nucleobases that hybridizes to a target nucleic acid (e.g., an OPA1 pre-mRNA, e.g., an OPA1 NMD exon-containing pre-mRNA) sequence by Watson-Crick base pairing or wobble base pairing (G-U). The ASO may have exact sequence complementarity to the target sequence or near complementarity (e.g., sufficient complementarity to bind the target sequence and enhancing splicing at a splice site). ASOs are designed so that they bind (hybridize) to a target nucleic acid (e.g., a targeted portion of a pre-mRNA transcript) and remain hybridized under physiological conditions. Typically, if they hybridize to a site other than the intended (targeted) nucleic acid sequence, they hybridize to a limited number of sequences that are not a target nucleic acid (to a few sites other than a target nucleic acid). Design of an ASO can take into consideration the occurrence of the nucleic acid sequence of the targeted portion of the pre-mRNA transcript or a sufficiently similar nucleic acid sequence in other locations in the genome or cellular pre-mRNA or transcriptome, such that the likelihood the ASO will bind other sites and cause "off-target" effects is limited. Any antisense oligomers known in the art (for example, in PCT Application No. PCT/US2014/054151, published as WO 2015/035091, titled "Reducing Nonsense-Mediated mRNA Decay," incorporated by reference herein), can be used to practice the methods described herein.

In some embodiments, ASOs "specifically hybridize" to or are "specific" to a target nucleic acid or a targeted portion of an OPA1 pre-mRNA, e.g., a NMD exon-containing pre-mRNA. Typically such hybridization occurs with a $T_m$ substantially greater than 37° C., preferably at least 50° C., and typically between 60° C. to approximately 90° C. Such hybridization preferably corresponds to stringent hybridization conditions. At a given ionic strength and pH, the $T_m$ is the temperature at which 50% of a target sequence hybridizes to a complementary oligonucleotide.

Oligomers, such as oligonucleotides, are "complementary" to one another when hybridization occurs in an antiparallel configuration between two single-stranded polynucleotides. A double-stranded polynucleotide can be "complementary" to another polynucleotide, if hybridization can occur between one of the strands of the first polynucleotide and the second. Complementarity (the degree to which one polynucleotide is complementary with another) is quantifiable in terms of the proportion (e.g., the percentage) of bases in opposing strands that are expected to form hydrogen bonds with each other, according to generally accepted base-pairing rules. The sequence of an antisense oligomer (ASO) need not be 100% complementary to that of its target nucleic acid to hybridize. In certain embodiments, ASOs can comprise at least 70%, at least 75%, at least 80%, at least 85%, at least 90%, at least 95%, at least 96%, at least 97%, at least 98%, or at least 99% sequence complementarity to a target region within the target nucleic acid sequence to which they are targeted. For example, an ASO in which 18 of 20 nucleobases of the oligomeric compound are complementary to a target region, and would therefore specifically hybridize, would represent 90 percent complementarity. In this example, the remaining non-complementary nucleobases may be clustered together or interspersed with complementary nucleobases and need not be contiguous to each other or to complementary nucleobases. Percent complementarity of an ASO with a region of a target nucleic acid can be determined routinely using BLAST programs (basic local alignment search tools) and PowerBLAST programs known in the art (Altschul, et al., J. Mol. Biol., 1990, 215, 403-410; Zhang and Madden, Genome Res., 1997, 7, 649-656).

An ASO need not hybridize to all nucleobases in a target sequence and the nucleobases to which it does hybridize may be contiguous or noncontiguous. ASOs may hybridize over one or more segments of a pre-mRNA transcript, such that intervening or adjacent segments are not involved in the hybridization event (e.g., a loop structure or hairpin structure may be formed). In certain embodiments, an ASO hybridizes to noncontiguous nucleobases in a target pre-mRNA transcript. For example, an ASO can hybridize to nucleobases in a pre-mRNA transcript that are separated by one or more nucleobase(s) to which the ASO does not hybridize.

The ASOs described herein comprise nucleobases that are complementary to nucleobases present in a target portion of an OPA1 pre-mRNA, e.g., a NMD exon-containing pre-mRNA. The term ASO embodies oligonucleotides and any other oligomeric molecule that comprises nucleobases capable of hybridizing to a complementary nucleobase on a target mRNA but does not comprise a sugar moiety, such as a peptide nucleic acid (PNA). The ASOs may comprise naturally-occurring nucleotides, nucleotide analogs, modified nucleotides, or any combination of two or three of the preceding. The term "naturally occurring nucleotides" includes deoxyribonucleotides and ribonucleotides. The term "modified nucleotides" includes nucleotides with modified or substituted sugar groups and/or having a modified backbone. In some embodiments, all of the nucleotides of the ASO are modified nucleotides. Chemical modifications of ASOs or components of ASOs that are compatible with the methods and compositions described herein will be evident to one of skill in the art and can be found, for example, in U.S. Pat. No. 8,258,109 B2, U.S. Pat. No. 5,656,612, U.S. Patent Publication No. 2012/0190728, and Dias and Stein, Mol. Cancer Ther. 2002, 347-355, herein incorporated by reference in their entirety.

One or more nucleobases of an ASO may be any naturally occurring, unmodified nucleobase such as adenine, guanine, cytosine, thymine and uracil, or any synthetic or modified nucleobase that is sufficiently similar to an unmodified nucleobase such that it is capable of hydrogen bonding with a nucleobase present on a target pre-mRNA. Examples of modified nucleobases include, without limitation, hypoxanthine, xanthine, 7-methylguanine, 5, 6-dihydrouracil, 5-methylcytosine, and 5-hydroxymethoylcytosine.

The ASOs described herein also comprise a backbone structure that connects the components of an oligomer. The term "backbone structure" and "oligomer linkages" may be used interchangeably and refer to the connection between monomers of the ASO. In naturally occurring oligonucleotides, the backbone comprises a 3'-5' phosphodiester linkage connecting sugar moieties of the oligomer. The backbone structure or oligomer linkages of the ASOs described herein may include (but are not limited to) phosphorothioate, phosphorodithioate, phosphoroselenoate, phosphorodiselenoate, phosphoroanilothioate, phosphoranilidate, phosphoramidate, and the like. See, e.g., LaPlanche, et al., Nucleic Acids Res. 14:9081 (1986); Stec, et al., J. Am. Chem. Soc. 106:6077 (1984), Stein, et al., Nucleic Acids Res. 16:3209 (1988), Zon, et al., Anti-Cancer Drug Design 6:539 (1991); Zon, et al., Oligonucleotides and Analogues: A Practical Approach, pp. 87-108 (F. Eckstein, Ed., Oxford University Press, Oxford England (1991)); Stec, et al., U.S. Pat. No. 5,151,510; Uhlmann and Peyman, Chemical Reviews 90:543 (1990). In some embodiments, the backbone structure of the ASO does not contain phosphorous but rather contains peptide bonds, for example in a peptide nucleic acid (PNA), or linking groups including carbamate, amides, and linear and cyclic hydrocarbon groups. In some embodiments, the backbone modification is a phosphorothioate linkage. In some embodiments, the backbone modification is a phosphoramidate linkage.

In some embodiments, the stereochemistry at each of the phosphorus internucleotide linkages of the ASO backbone is random. In some embodiments, the stereochemistry at each of the phosphorus internucleotide linkages of the ASO backbone is controlled and is not random. For example, U.S. Pat. App. Pub. No. 2014/0194610, "Methods for the Synthesis of Functionalized Nucleic Acids," incorporated herein by reference, describes methods for independently selecting the handedness of chirality at each phosphorous atom in a nucleic acid oligomer. In some embodiments, an ASO used in the methods of the disclosure, including, but not limited to, any of the ASOs set forth herein in Tables 5 and 6, comprises an ASO having phosphorus internucleotide linkages that are not random. In some embodiments, a composition used in the methods of the disclosure comprises a pure diastereomeric ASO. In some embodiments, a composition used in the methods of the disclosure comprises an ASO that has diastereomeric purity of at least about 90%, at least about 91%, at least about 92%, at least about 93%, at least about 94%, at least about 95%, at least about 96%, at least about 97%, at least about 98%, at least about 99%, about 100%, about 90% to about 100%, about 91% to about 100%, about 92% to about 100%, about 93% to about 100%, about 94% to about 100%, about 95% to about 100%, about 96% to about 100%, about 97% to about 100%, about 98% to about 100%, or about 99% to about 100%.

In some embodiments, the ASO has a nonrandom mixture of Rp and Sp configurations at its phosphorus internucleotide linkages. For example, it has been suggested that a mix of Rp and Sp is required in antisense oligonucleotides to achieve a balance between good activity and nuclease stability (Wan, et al., 2014, "Synthesis, biophysical properties and biological activity of second generation antisense oligonucleotides containing chiral phosphorothioate linkages," Nucleic Acids Research 42(22): 13456-13468, incorporated herein by reference). In some embodiments, an ASO used in the methods of the disclosure, including, but not limited to, any of the ASOs set forth herein in SEQ ID NOs: 2-5, comprises about 5-100% Rp, at least about 5% Rp, at least about 10% Rp, at least about 15% Rp, at least about 20% Rp, at least about 25% Rp, at least about 30% Rp, at least about 35% Rp, at least about 40% Rp, at least about 45% Rp, at least about 50% Rp, at least about 55% Rp, at least about 60% Rp, at least about 65% Rp, at least about 70% Rp, at least about 75% Rp, at least about 80% Rp, at least about 85% Rp, at least about 90% Rp, or at least about 95% Rp, with the remainder Sp, or about 100% Rp. In some embodiments, an ASO used in the methods of the disclosure, including, but not limited to, any of the ASOs set forth herein comprise a sequence with at least about 80%, 85%, 90%, 95%, 97%, or 100% sequence identity to a region comprising at least 8 contiguous nucleic acids of any one of SEQ ID NOs: 2-5, comprises about 10% to about 100% Rp, about 15% to about 100% Rp, about 20% to about 100% Rp, about 25% to about 100% Rp, about 30% to about 100% Rp, about 35% to about 100% Rp, about 40% to about 100% Rp, about 45% to about 100% Rp, about 50% to about 100% Rp, about 55% to about 100% Rp, about 60% to about 100% Rp, about 65% to about 100% Rp, about 70% to about 100% Rp, about 75% to about 100% Rp, about 80% to about 100% Rp, about 85% to about 100% Rp, about 90% to about 100% Rp, or about 95% to about 100% Rp, about 20% to about 80% Rp, about 25% to about 75% Rp, about 30% to about 70% Rp, about 40% to about 60% Rp, or about 45% to about 55% Rp, with the remainder Sp.

In some embodiments, an ASO used in the methods of the disclosure, including, but not limited to, any of the ASOs set forth herein comprise a sequence with at least about 80%, 85%, 90%, 95%, 97%, or 100% sequence identity to a region comprising at least 8 contiguous nucleic acids of any one of SEQ ID NOs: 2-5, comprises about 5-100% Sp, at least about 5% Sp, at least about 10% Sp, at least about 15% Sp, at least about 20% Sp, at least about 25% Sp, at least about 30% Sp, at least about 35% Sp, at least about 40% Sp, at least about 45% Sp, at least about 50% Sp, at least about 55% Sp, at least about 60% Sp, at least about 65% Sp, at least about 70% Sp, at least about 75% Sp, at least about 80% Sp, at least about 85% Sp, at least about 90% Sp, or at least about 95% Sp, with the remainder Rp, or about 100% Sp. In embodiments, an ASO used in the methods of the disclosure, including, but not limited to, any of the ASOs set forth herein comprise a sequence with at least about 80%, 85%, 90%, 95%, 97%, or 100% sequence identity to a region comprising at least 8 contiguous nucleic acids of any one of SEQ ID NOs: 2-5, comprises about 10% to about 100% Sp, about 15% to about 100% Sp, about 20% to about 100% Sp, about 25% to about 100% Sp, about 30% to about 100% Sp, about 35% to about 100% Sp, about 40% to about 100% Sp, about 45% to about 100% Sp, about 50% to about 100% Sp, about 55% to about 100% Sp, about 60% to about 100% Sp, about 65% to about 100% Sp, about 70% to about 100% Sp, about 75% to about 100% Sp, about 80% to about 100% Sp, about 85% to about 100% Sp, about 90% to about 100% Sp, or about 95% to about 100% Sp, about 20% to about 80% Sp, about 25% to about 75% Sp, about 30% to about 70% Sp, about 40% to about 60% Sp, or about 45% to about 55% Sp, with the remainder Rp.

Any of the ASOs described herein may contain a sugar moiety that comprises ribose or deoxyribose, as present in naturally occurring nucleotides, or a modified sugar moiety or sugar analog, including a morpholine ring. Non-limiting examples of modified sugar moieties include 2' substitutions such as 2'-O-methyl (2'-O-Me), 2'-O-methoxyethyl (2'MOE), 2'-O-aminoethyl, 2'F; N3'→P5' phosphoramidate, 2'dimethylaminooxyethoxy, 2'dimethylaminoethoxyethoxy, 2'-guanidinidium, 2'-O-guanidinium ethyl, carbamate modified sugars, and bicyclic modified sugars. In some embodiments, the sugar moiety modification is selected from 2'-O-Me, 2'F, and 2'MOE. In some embodiments, the sugar moiety modification is an extra bridge bond, such as in a locked nucleic acid (LNA). In some embodiments the sugar analog contains a morpholine ring, such as phosphorodiamidate morpholino (PMO). In some embodiments, the sugar moiety comprises a ribofuransyl or 2'deoxyribofuransyl modification. In some embodiments, the sugar moiety comprises 2'4'-constrained 2'O-methyloxyethyl (cMOE) modifications. In some embodiments, the sugar moiety comprises cEt 2', 4' constrained 2'-O ethyl BNA modifications. In some embodiments, the sugar moiety comprises tricycloDNA (tcDNA) modifications. In some embodiments, the sugar moiety comprises ethylene nucleic acid (ENA) modifications. In some embodiments, the sugar moiety comprises MCE modifications. Modifications are known in the art and described in the literature, e.g., by Jarver, et al., 2014, "A Chemical View of Oligonucleotides for Exon Skipping and Related Drug Applications," Nucleic Acid Therapeutics 24(1): 37-47, incorporated by reference for this purpose herein.

In some embodiments, each monomer of the ASO is modified in the same way, for example each linkage of the backbone of the ASO comprises a phosphorothioate linkage or each ribose sugar moiety comprises a 2'O-methyl modification. Such modifications that are present on each of the monomer components of an ASO are referred to as "uniform modifications." In some examples, a combination of different modifications may be desired, for example, an ASO may comprise a combination of phosphorodiamidate linkages and sugar moieties comprising morpholine rings (morpholinos). Combinations of different modifications to an ASO are referred to as "mixed modifications" or "mixed chemistries."

In some embodiments, the ASO comprises one or more backbone modifications. In some embodiments, the ASO comprises one or more sugar moiety modification. In some embodiments, the ASO comprises one or more backbone modifications and one or more sugar moiety modifications. In some embodiments, the ASO comprises a 2'MOE modification and a phosphorothioate backbone. In some embodiments, the ASO comprises a phosphorodiamidate morpholino (PMO). In some embodiments, the ASO comprises a peptide nucleic acid (PNA). Any of the ASOs or any component of an ASO (e.g., a nucleobase, sugar moiety, backbone) described herein may be modified in order to achieve desired properties or activities of the ASO or reduce undesired properties or activities of the ASO. For example, an ASO or one or more components of any ASO may be modified to enhance binding affinity to a target sequence on a pre-mRNA transcript; reduce binding to any non-target sequence; reduce degradation by cellular nucleases (i.e., RNase H); improve uptake of the ASO into a cell and/or into the nucleus of a cell; alter the pharmacokinetics or pharmacodynamics of the ASO; and/or modulate the half-life of the ASO.

In some embodiments, the ASOs are comprised of 2'-O-(2-methoxyethyl) (MOE) phosphorothioate-modified nucleotides. ASOs comprised of such nucleotides are especially well-suited to the methods disclosed herein; oligomers having such modifications have been shown to have significantly enhanced resistance to nuclease degradation and increased bioavailability, making them suitable, for example, for oral delivery in some embodiments described herein. See e.g., Geary, et al., J Pharmacol Exp Ther. 2001; 296(3):890-7; Geary, et al., J Pharmacol Exp Ther. 2001; 296(3):898-904.

Methods of synthesizing ASOs will be known to one of skill in the art. Alternatively or in addition, ASOs may be obtained from a commercial source.

Unless specified otherwise, the left-hand end of single-stranded nucleic acid (e.g., pre-mRNA transcript, oligonucleotide, ASO, etc.) sequences is the 5' end and the left-hand direction of single or double-stranded nucleic acid sequences is referred to as the 5' direction. Similarly, the right-hand end or direction of a nucleic acid sequence (single or double stranded) is the 3' end or direction. Generally, a region or sequence that is 5' to a reference point in a nucleic acid is referred to as "upstream," and a region or sequence that is 3' to a reference point in a nucleic acid is referred to as "downstream." Generally, the 5' direction or end of an mRNA is where the initiation or start codon is located, while the 3' end or direction is where the termination codon is located. In some aspects, nucleotides that are upstream of a reference point in a nucleic acid may be designated by a negative number, while nucleotides that are downstream of a reference point may be designated by a positive number. For example, a reference point (e.g., an exon-exon junction in mRNA) may be designated as the "zero" site, and a nucleotide that is directly adjacent and upstream of the reference point is designated "minus one," e.g., "−1," while a nucleotide that is directly adjacent and downstream of the reference point is designated "plus one," e.g., "+1."

In some embodiments, the ASOs are complementary to (and bind to) a targeted portion of an OPA1 pre-mRNA, e.g., an OPA1 NMD exon-containing pre-mRNA, that is downstream (in the 3' direction) of the 5' splice site (or 3' end of the NMD exon) of the included exon in an OPA1 pre-mRNA (e.g., the direction designated by positive numbers relative to the 5' splice site). In some embodiments, the ASOs are complementary to a targeted portion of the OPA1 pre-mRNA, e.g., the OPA1 NMD exon-containing pre-mRNA that is within the region about +1 to about +500 relative to the 5' splice site (or 3' end) of the included exon. In some embodiments, the ASOs may be complementary to a targeted portion of an OPA1 pre-mRNA, e.g., an OPA1 NMD exon-containing pre-mRNA, that is within the region between nucleotides +6 and +40,000 relative to the 5' splice site (or 3' end) of the included exon. In some aspects, the ASOs are complementary to a targeted portion that is within the region about +1 to about +40,000, about +1 to about +30,000, about +1 to about +20,000, about +1 to about +15,000, about +1 to about +10,000, about +1 to about +5,000, about +1 to about +4,000, about +1 to about +3,000, about +1 to about +2,000, about +1 to about +1,000, about +1 to about +500, about +1 to about +490, about +1 to about +480, about +1 to about +470, about +1 to about +460, about +1 to about +450, about +1 to about +440, about +1 to about +430, about +1 to about +420, about +1 to about +410, about +1 to about +400, about +1 to about +390, about +1 to about +380, about +1 to about +370, about +1 to about +360, about +1 to about +350, about +1 to about +340, about +1 to about +330, about +1 to about +320, about +1 to about +310, about +1 to about +300, about +1 to about +290, about +1 to about +280, about +1 to about +270, about +1 to about +260, about +1 to about +250, about +1 to about +240, about +1 to about +230, about +1 to about +220, about +1 to about +210, about +1 to about +200, about +1 to about +190, about +1 to about +180, about +1 to about +170, about +1 to about +160, about +1 to about +150, about +1 to about +140, about +1 to about +130, about +1 to about +120, about +1 to about +110, about +1 to about +100, about +1 to about +90, about +1 to about +80, about +1 to about +70, about +1 to about +60, about +1 to about +50, about +1 to about +40, about +1 to about +30, or about +1 to about +20 relative to 5' splice site (or 3' end) of the included exon. In some aspects, the ASOs are complementary to a targeted portion that is within the region from about +1 to about +100, from about +100 to about +200, from about +200 to about +300, from about +300 to about +400, or from about +400 to about +500 relative to 5' splice site (or 3' end) of the included exon.

In some embodiments, the ASOs are complementary to (and bind to) a targeted portion of an OPA1 pre-mRNA, e.g., an OPA1 NMD exon-containing pre-mRNA, that is upstream (in the 5' direction) of the 5' splice site (or 3' end) of the included exon in an OPA1 pre-mRNA, e.g., an OPA1 NMD exon-containing pre-mRNA (e.g., the direction designated by negative numbers relative to the 5' splice site). In some embodiments, the ASOs are complementary to a targeted portion of the OPA1 pre-mRNA, e.g., the OPA1 NMD exon-containing pre-mRNA, that is within the region about −4 to about −270 relative to the 5' splice site (or 3'end) of the included exon. In some embodiments, the ASOs may be complementary to a targeted portion of an OPA1 pre-mRNA, e.g., an OPA1 NMD exon-containing pre-mRNA, that is within the region between nucleotides −1 and −40,000 relative to the 5' splice site (or 3' end) of the included exon. In some aspects, the ASOs are complementary to a targeted portion that is within the region about −1 to about −40,000, about −1 to about −30,000, about −1 to about −20,000, about −1 to about −15,000, about −1 to about −10,000, about −1 to about −5,000, about −1 to about −4,000, about −1 to about −3,000, about −1 to about −2,000, about −1 to about −1,000, about −1 to about −500, about −1 to about −490, about −1 to about −480, about −1 to about −470, about −1 to about −460, about −1 to about −450, about −1 to about −440, about −1 to about −430, about −1 to about −420, about −1 to about −410, about −1 to about −400, about −1 to about −390, about −1 to about −380, about −1 to about −370, about −1 to about −360, about −1 to about −350, about −1 to about −340, about −1 to about −330, about −1 to about −320, about −1 to about −310, about −1 to about −300, about −1 to about −290, about −1 to about −280, about −1 to about −270, about −1 to about −260, about −1 to about −250, about −1 to about −240, about −1 to about −230, about −1 to about −220, about −1 to about −210, about −1 to about −200, about −1 to about −190, about −1 to about −180, about −1 to about −170, about −1 to about −160, about −1 to about −150, about −1 to about −140, about −1 to about −130, about −1 to about −120, about −1 to about −110, about −1 to about −100, about −1 to about −90, about −1 to about −80, about −1 to about −70, about −1 to about −60, about −1 to about −50, about −1 to about −40, about −1 to about −30, or about −1 to about −20 relative to 5' splice site (or 3' end) of the included exon.

In some embodiments, the ASOs are complementary to a targeted region of an OPA1 pre-mRNA, e.g., an OPA1 NMD exon-containing pre-mRNA, that is upstream (in the 5' direction) of the 3' splice site (or 5' end) of the included exon in an OPA1 pre-mRNA (e.g., in the direction designated by negative numbers). In some embodiments, the ASOs are complementary to a targeted portion of the OPA1 pre-mRNA, e.g., the OPA1 NMD exon-containing pre-mRNA, that is within the region about −1 to about −500 relative to the 3' splice site (or 5' end) of the included exon. In some embodiments, the ASOs are complementary to a targeted portion of the OPA1 pre-mRNA that is within the region −1 to −40,000 relative to the 3' splice site of the included exon. In some aspects, the ASOs are complementary to a targeted portion that is within the region about −1 to about −40,000, about −1 to about −30,000, −1 to about −20,000, about −1 to about −15,000, about −1 to about −10,000, about −1 to about −5,000, about −1 to about −4,000, about −1 to about −3,000, about −1 to about −2,000, about −1 to about −1,000, about −1 to about −500, about −1 to about −490, about −1 to about −480, about −1 to about −470, about −1 to about −460, about −1 to about −450, about −1 to about −440, about −1 to about −430, about −1 to about −420, about −1 to about −410, about −1 to about −400, about −1 to about −390, about −1 to about −380, about −1 to about −370, about −1 to about −360, about −1 to about −350, about −1 to about −340, about −1 to about −330, about −1 to about −320, about −1 to about −310, about −1 to about −300, about −1 to about −290, about −1 to about −280, about −1 to about −270, about −1 to about −260, about −1 to about −250, about −1 to about −240, about −1 to about −230, about −1 to about −220, about −1 to about −210, about −1 to about −200, about −1 to about −190, about −1 to about −180, about −1 to about −170, about −1 to about −160, about −1 to about −150, about −1 to about −140, about −1 to about −130, about −1 to about −120, about −1 to about −110, about −1 to about −100, about −1 to about −90, about −1 to about −80, about −1 to about −70, about −1 to about −60, about −1 to about −50, about −1 to about −40, about −1 to about −30, or about −1 to about −20 relative to 3' splice site of the included exon. In some aspects, the ASOs are complementary to a targeted portion that is within the region from about −1 to about −100, from about −100 to about −200, from about −200 to about −300, from about −300 to about −400, or from about −400 to about −500 relative to 3' splice site of the included exon.

In some embodiments, the ASOs are complementary to a targeted region of an OPA1 pre-mRNA, e.g., an OPA1 NMD exon-containing pre-mRNA, that is downstream (in the 3' direction) of the 3' splice site (5' end) of the included exon in an OPA1 pre-mRNA, e.g., an OPA1 NMD exon-containing pre-mRNA (e.g., in the direction designated by positive numbers). In some embodiments, the ASOs are complementary to a targeted portion of the OPA1 pre-mRNA that is within the region of about +1 to about +40,000 relative to the 3' splice site of the included exon. In some aspects, the ASOs are complementary to a targeted portion that is within the region about +1 to about +40,000, about +1 to about +30,000, about +1 to about +20,000, about +1 to about +15,000, about +1 to about +10,000, about +1 to about +5,000, about +1 to about +4,000, about +1 to about +3,000, about +1 to about +2,000, about +1 to about +1,000, about +1 to about +500, about +1 to about +490, about +1 to about +480, about +1 to about +470, about +1 to about +460, about +1 to about +450, about +1 to about +440, about +1 to about +430, about +1 to about +420, about +1 to about +410, about +1 to about +400, about +1 to about +390, about +1 to about +380, about +1 to about +370, about +1 to about +360, about +1 to about +350, about +1 to about +340, about +1 to about +330, about +1 to about +320, about +1 to about +310, about +1 to about +300, about +1 to about +290, about +1 to about +280, about +1 to about +270, about +1 to about +260, about +1 to about +250, about +1 to about +240, about +1 to about +230, about +1 to about +220, about +1 to about +210, about +1 to about +200, about +1 to about +190, about +1 to about +180, about +1 to about +170, about +1 to about +160, about +1 to about +150, about +1 to about +140, about +1 to about +130, about +1 to about +120, about +1 to about +110, about +1 to about +100, about +1 to about +90, about +1 to about +80, about +1 to about +70, about +1 to about +60, about +1 to about +50, about +1 to about +40, about +1 to about +30, or about +1 to about +20, or about +1 to about +10 relative to 3' splice site of the included exon.

In some embodiments, the targeted portion of the OPA1 pre-mRNA, e.g., the OPA1 NMD exon-containing pre-mRNA, is within the region +100 relative to the 5' splice site (3' end) of the included exon to −100 relative to the 3' splice site (5' end) of the included exon. In some embodiments, the targeted portion of the OPA1 NMD exon-containing pre-mRNA is within the NMD exon. In some embodiments, the target portion of the OPA1 NMD exon-containing pre-mRNA comprises a pseudo-exon and intron boundary.

The ASOs may be of any length suitable for specific binding and effective enhancement of splicing. In some embodiments, the ASOs consist of 8 to 50 nucleobases. For example, the ASO may be 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, or 50 nucleobases in length. In some embodiments, the ASOs consist of more than 50 nucleobases. In some embodiments, the ASO is from 8 to 50 nucleobases, 8 to 40 nucleobases, 8 to 35 nucleobases, 8 to 30 nucleobases, 8 to 25 nucleobases, 8 to 20 nucleobases, 8 to 15 nucleobases, 9 to 50 nucleobases, 9 to 40 nucleobases, 9 to 35 nucleobases, 9 to 30 nucleobases, 9 to 25 nucleobases, 9 to 20 nucleobases, 9 to 15 nucleobases, 10 to 50 nucleobases, 10 to 40 nucleobases, 10 to 35 nucleobases, 10 to 30 nucleobases, 10 to 25 nucleobases, 10 to 20 nucleobases, 10 to 15 nucleobases, 11 to 50 nucleobases, 11 to 40 nucleobases, 11 to 35 nucleobases, 11 to 30 nucleobases, 11 to 25 nucleobases, 11 to 20 nucleobases, 11 to 15 nucleobases, 12 to 50 nucleobases, 12 to 40 nucleobases, 12 to 35 nucleobases, 12 to 30 nucleobases, 12 to 25 nucleobases, 12 to 20 nucleobases, 12 to 15 nucleobases, 13 to 50 nucleobases, 13 to 40 nucleobases, 13 to 35 nucleobases, 13 to 30 nucleobases, 13 to 25 nucleobases, 13 to 20 nucleobases, 14 to 50 nucleobases, 14 to 40 nucleobases, 14 to 35 nucleobases, 14 to 30 nucleobases, 14 to 25 nucleobases, 14 to 20 nucleobases, 15 to 50 nucleobases, 15 to 40 nucleobases, 15 to 35 nucleobases, 15 to 30 nucleobases, 15 to 25 nucleobases, 15 to 20 nucleobases, 20 to 50 nucleobases, 20 to 40 nucleobases, 20 to 35 nucleobases, 20 to 30 nucleobases, 20 to 25 nucleobases, 25 to 50 nucleobases, 25 to 40 nucleobases, 25 to 35 nucleobases, or 25 to 30 nucleobases in length. In some embodiments, the ASOs are 18 nucleotides in length. In some embodiments, the ASOs are 15 nucleotides in length. In some embodiments, the ASOs are 25 nucleotides in length.

In some embodiments, two or more ASOs with different chemistries but complementary to the same targeted portion of the pre-mRNA, e.g., NMD exon-containing pre-mRNA, are used. In some embodiments, two or more ASOs that are complementary to different targeted portions of the pre-mRNA, e.g., the NMD exon-containing pre-mRNA, are used.

In some embodiments, the antisense oligonucleotides of the disclosure are chemically linked to one or more moieties or conjugates, e.g., a targeting moiety or other conjugate that enhances the activity or cellular uptake of the oligonucleotide. Such moieties include, but are not limited to, a lipid moiety, e.g., as a cholesterol moiety, a cholesteryl moiety, an aliphatic chain, e.g., dodecandiol or undecyl residues, a polyamine or a polyethylene glycol chain, or adamantane acetic acid. Oligonucleotides comprising lipophilic moieties and preparation methods have been described in the published literature. In embodiments, the antisense oligonucleotide is conjugated with a moiety including, but not limited to, an abasic nucleotide, a polyether, a polyamine, a polyamide, a peptides, a carbohydrate, e.g., N-acetylgalactosamine (GalNAc), N-Ac-Glucosamine (GluNAc), or mannose (e.g., mannose-6-phosphate), a lipid, or a polyhydrocarbon compound. Conjugates can be linked to one or more of any nucleotides comprising the antisense oligonucleotide at any of several positions on the sugar, base or phosphate group, as understood in the art and described in the literature, e.g., using a linker. Linkers can include a bivalent or trivalent branched linker. In embodiments, the conjugate is attached to the 3' end of the antisense oligonucleotide. Methods of preparing oligonucleotide conjugates are described, e.g., in U.S. Pat. No. 8,450,467, "Carbohydrate conjugates as delivery agents for oligonucleotides," incorporated by reference herein.

In some embodiments, the nucleic acid to be targeted by an ASO is an OPA1 pre-mRNA, e.g., NMD exon-containing pre-mRNA expressed in a cell, such as a eukaryotic cell. In some embodiments, the term "cell" may refer to a population of cells. In some embodiments, the cell is in a subject. In some embodiments, the cell is isolated from a subject. In some embodiments, the cell is ex vivo. In some embodiments, the cell is a condition or disease-relevant cell or a cell line. In some embodiments, the cell is in vitro (e.g., in cell culture).

Pharmaceutical Compositions

Pharmaceutical compositions or formulations comprising the agent, e.g., antisense oligonucleotide, of the described compositions and for use in any of the described methods can be prepared according to conventional techniques well known in the pharmaceutical industry and described in the published literature. In embodiments, a pharmaceutical composition or formulation for treating a subject comprises an effective amount of any antisense oligomer as described herein, or a pharmaceutically acceptable salt, solvate, hydrate or ester thereof. The pharmaceutical formulation comprising an antisense oligomer may further comprise a pharmaceutically acceptable excipient, diluent or carrier.

Pharmaceutically acceptable salts are suitable for use in contact with the tissues of humans and lower animals without undue toxicity, irritation, allergic response, etc., and are commensurate with a reasonable benefit/risk ratio. (See, e.g., S. M. Berge, et al., J. Pharmaceutical Sciences, 66: 1-19 (1977), incorporated herein by reference for this purpose. The salts can be prepared in situ during the final isolation and purification of the compounds, or separately by reacting the free base form with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other documented methodologies such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

In some embodiments, the compositions are formulated into any of many possible dosage forms such as, but not limited to, tablets, capsules, gel capsules, liquid syrups, soft gels, suppositories, and enemas. In embodiments, the compositions are formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers. In embodiments, a pharmaceutical formulation or composition of the present disclosure includes, but is not limited to, a solution, emulsion, microemulsion, foam or liposome-containing formulation (e.g., cationic or noncationic liposomes).

The pharmaceutical composition or formulation described herein may comprise one or more penetration enhancers, carriers, excipients or other active or inactive ingredients as appropriate and well known to those of skill in the art or described in the published literature. In embodiments, liposomes also include sterically stabilized liposomes, e.g., liposomes comprising one or more specialized lipids. These specialized lipids result in liposomes with enhanced circulation lifetimes. In embodiments, a sterically stabilized liposome comprises one or more glycolipids or is derivatized with one or more hydrophilic polymers, such as a polyethylene glycol (PEG) moiety. In some embodiments, a surfactant is included in the pharmaceutical formulation or compositions. The use of surfactants in drug products, formulations and emulsions is well known in the art. In embodiments, the present disclosure employs a penetration enhancer to effect the efficient delivery of the antisense oligonucleotide, e.g., to aid diffusion across cell membranes and/or enhance the permeability of a lipophilic drug. In some embodiments, the penetration enhancers are a surfactant, fatty acid, bile salt, chelating agent, or non-chelating nonsurfactant.

In some embodiments, the pharmaceutical formulation comprises multiple antisense oligonucleotides. In embodiments, the antisense oligonucleotide is administered in combination with another drug or therapeutic agent.

Combination Therapies

In some embodiments, the ASOs disclosed in the present disclosure can be used in combination with one or more additional therapeutic agents. In some embodiments, the one or more additional therapeutic agents can comprise a small molecule. For example, the one or more additional therapeutic agents can comprise a small molecule described in WO2016128343A1, WO2017053982A1, WO2016196386A1, WO201428459A1, WO201524876A2, WO2013119916A2, and WO2014209841A2, which are incorporated by reference herein in their entirety. In some embodiments, the one or more additional therapeutic agents comprise an ASO that can be used to correct intron retention.

Treatment of Subjects

Any of the compositions provided herein may be administered to an individual. "Individual" may be used interchangeably with "subject" or "patient." An individual may be a mammal, for example a human or animal such as a non-human primate, a rodent, a rabbit, a rat, a mouse, a horse, a donkey, a goat, a cat, a dog, a cow, a pig, or a sheep. In embodiments, the individual is a human. In embodiments, the individual is a fetus, an embryo, or a child. In other embodiments, the individual may be another eukaryotic organism, such as a plant. In some embodiments, the compositions provided herein are administered to a cell ex vivo.

In some embodiments, the compositions provided herein are administered to an individual as a method of treating a disease or disorder. In some embodiments, the individual has a genetic disease, such as any of the diseases described herein. In some embodiments, the individual is at risk of having a disease, such as any of the diseases described herein. In some embodiments, the individual is at increased risk of having a disease or disorder caused by insufficient amount of a protein or insufficient activity of a protein. If an individual is "at an increased risk" of having a disease or disorder caused insufficient amount of a protein or insufficient activity of a protein, the method involves preventative or prophylactic treatment. For example, an individual may be at an increased risk of having such a disease or disorder because of family history of the disease. Typically, individuals at an increased risk of having such a disease or disorder benefit from prophylactic treatment (e.g., by preventing or delaying the onset or progression of the disease or disorder). In embodiments, a fetus is treated in utero, e.g., by administering the ASO composition to the fetus directly or indirectly (e.g., via the mother).

In some cases, the subject pharmaceutical composition and method are applicable for treatment of a condition or disease associated with OPA1 deficiency. In some cases, the subject pharmaceutical composition and method are applicable for treatment of an eye disease or condition. In some cases, the subject pharmaceutical composition and method are applicable for treatment of Optic atrophy type 1, autosomal dominant optic atrophy (ADOA), ADOA-plus syndrome; a mitochondrial disorder; glaucoma; normal tension glaucoma; Charcot-Marie-Tooth disease; mitochondria dysfunction; diabetic retinopathy; age-related macular degeneration; retinal ganglion cell death; mitochondrial fission-mediated mitochondrial dysfunction; progressive external ophthalmoplegia; deafness; ataxia; motor neuropathy; sensory neuropathy; myopathy; Behr syndrome; brain dysfunction; encephalopathy; peripheral neuropathy; fatal infantile mitochondrial encephalomyopathy; hypertrophic cardiomyopathy; spastic ataxic syndrome; sensory motor peripheral neuropathy; hypotonia; gastrointestinal dysmotility and dysphagia; optic atrophy; optic atrophy plus syndrome; Mitochondrial DNA depletion syndrome 14; late-onset cardiomyopathy; diabetic cardiomyopathy; Alzheimer's Disease; focal segmental glomerulosclerosis; kidney disease; Huntington's Disease; cognitive function decline in healthy aging; Prion diseases; late onset dementia and parkinsonism; mitochondrial myopathy; Leigh syndrome; Friedreich's ataxia; Parkinson's disease; MELAS (Mitochondrial encephalomyopathy, lactic acidosis, and stroke-like episodes); pyruvate dehydrogenase complex deficiency; chronic kidney disease; Leber's hereditary optic neuropathy;

obesity; age-related systemic neurodegeneration; skeletal muscle atrophy; heart and brain ischemic damage; or massive liver apoptosis.

Autosomal dominant optic atrophy (ADOA) is the most common inherited optic nerve disorder and is characterized by retinal ganglion cell loss. In some cases, 65-90% of ADOA cases are caused by mutations in one allele of the OPA1 gene. OPA1 gene encodes an OPA1 protein that is a mitochondrial GTPase, which can have a critical maintenance role in mitochondria structure and function. Most OPA1 mutations can lead to a haploinsufficiency, resulting in about a 50% decrease of normal OPA1 protein levels. Approximately 1 out of 30,000 people are affected globally with a higher incidence of ~1 out of 10,000 in Denmark due to a founder effect. ADOA can present within the first decade of life. 80% of ADOA patients are symptomatic before 10 years of age. The disease can cause progressive and irreversible vision loss and up to 46% of patients are registered as legally blind.

In some cases, a therapeutic agent comprises an oligonucleotide. In some cases, a therapeutic agent comprises a vector, e.g., a viral vector, expressing a oligonucleotide that binds to the targeted region of a pre-mRNA the encodes the target peptide sequence. The methods provided herein can be adapted to contacting a vector that encodes an agent, e.g., an oligonucleotide, to a cell, so that the agent binds to a pre-mRNA in the cell and modulates the processing of the pre-mRNA. In some cases, the viral vector comprises an adenoviral vector, adeno-associated viral (AAV) vector, lentiviral vector, Herpes Simplex Virus (HSV) viral vector, retroviral vector, or any applicable viral vector. In some cases, a therapeutic agent comprises a gene editing tool that is configured to modify a gene encoding the target peptide sequence such that a gene region that encodes the inefficient translation region is deleted. In some cases, a gene editing tool comprises vector, e.g., viral vector, for gene editing based on CRISPR-Cas9, TALEN, Zinc Finger, or other applicable technologies.

Suitable routes for administration of ASOs of the present disclosure may vary depending on cell type to which delivery of the ASOs is desired. Multiple tissues and organs are affected by ADOA, with the eye being the most significantly affected tissue. The ASOs of the present disclosure may be administered to patients parenterally, for example, by intravitreal injection, intrathecal injection, intracerebroventricular injection, intraperitoneal injection, intramuscular injection, subcutaneous injection, or intravenous injection.

In embodiments, the antisense oligonucleotide is administered with one or more agents capable of promoting penetration of the subject antisense oligonucleotide across the blood-brain barrier by any method known in the art. For example, delivery of agents by administration of an adenovirus vector to motor neurons in muscle tissue is described in U.S. Pat. No. 6,632,427, "Adenoviral-vector-mediated gene transfer into medullary motor neurons," incorporated herein by reference. Delivery of vectors directly to the brain, e.g., the striatum, the thalamus, the hippocampus, or the substantia nigra, is described, e.g., in U.S. Pat. No. 6,756, 523, "Adenovirus vectors for the transfer of foreign genes into cells of the central nervous system particularly in brain," incorporated herein by reference.

In some embodiments, the antisense oligonucleotides are linked or conjugated with agents that provide desirable pharmaceutical or pharmacodynamic properties. In embodiments, the antisense oligonucleotide is coupled to a substance, known in the art to promote penetration or transport across the blood-brain barrier, e.g., an antibody to the transferrin receptor. In embodiments, the antisense oligonucleotide is linked with a viral vector, e.g., to render the antisense compound more effective or increase transport across the blood-brain barrier. In embodiments, osmotic blood brain barrier disruption is assisted by infusion of sugars, e.g., meso erythritol, xylitol, D(+) galactose, D(+) lactose, D(+) xylose, dulcitol, myo-inositol, L(-) fructose, D(-) mannitol, D(+) glucose, D(+) arabinose, D(-) arabinose, cellobiose, D(+) maltose, D(+) raffinose, L(+) rhamnose, D(+) melibiose, D(-) ribose, adonitol, D(+) arabitol, L(-) arabitol, D(+) fucose, L(-) fucose, D(-) lyxose, L(+) lyxose, and L(-) lyxose, or amino acids, e.g., glutamine, lysine, arginine, asparagine, aspartic acid, cysteine, glutamic acid, glycine, histidine, leucine, methionine, phenylalanine, proline, serine, threonine, tyrosine, valine, and taurine. Methods and materials for enhancing blood brain barrier penetration are described, e.g., in U.S. Pat. No. 9,193,969, "Compositions and methods for selective delivery of oligonucleotide molecules to specific neuron types," U.S. Pat. No. 4,866,042, "Method for the delivery of genetic material across the blood brain barrier," U.S. Pat. No. 6,294,520, "Material for passage through the blood-brain barrier," and U.S. Pat. No. 6,936,589, "Parenteral delivery systems," each incorporated herein by reference.

In some embodiments, subjects treated using the methods and compositions are evaluated for improvement in condition using any methods known and described in the art.

Methods of Identifying Additional ASOs that Induce Exon Skipping

Also within the scope of the present disclosure are methods for identifying or determining ASOs that induce exon skipping of an OPA1 NMD exon-containing pre-mRNA. For example, a method can comprise identifying or determining ASOs that induce pseudo-exon skipping of an OPA1 NMD exon-containing pre-mRNA. ASOs that specifically hybridize to different nucleotides within the target region of the pre-mRNA may be screened to identify or determine ASOs that improve the rate and/or extent of splicing of the target intron. In some embodiments, the ASO may block or interfere with the binding site(s) of a splicing repressor(s)/ silencer. Any method known in the art may be used to identify (determine) an ASO that when hybridized to the target region of the exon results in the desired effect (e.g., pseudo-exon skipping, protein or functional RNA production). These methods also can be used for identifying ASOs that induce exon skipping of the included exon by binding to a targeted region in an intron flanking the included exon, or in a non-included exon. An example of a method that may be used is provided below.

A round of screening, referred to as an ASO "walk" may be performed using ASOs that have been designed to hybridize to a target region of a pre-mRNA. For example, the ASOs used in the ASO walk can be tiled every 5 nucleotides from approximately 100 nucleotides upstream of the 3' splice site of the included exon (e.g., a portion of sequence of the exon located upstream of the target/included exon) to approximately 100 nucleotides downstream of the 3' splice site of the target/included exon and/or from approximately 100 nucleotides upstream of the 5' splice site of the included exon to approximately 100 nucleotides downstream of the 5' splice site of the target/included exon (e.g., a portion of sequence of the exon located downstream of the target/included exon). For example, a first ASO of 15 nucleotides in length may be designed to specifically hybridize to nucleotides +6 to +20 relative to the 3' splice site of the target/included exon. A second ASO may be designed to specifically hybridize to nucleotides +11 to +25 relative to the 3' splice site of the target/included exon. ASOs are designed as such spanning the target region of the pre-mRNA. In embodiments, the ASOs can be tiled more closely, e.g., every 1, 2, 3, or 4 nucleotides. Further, the ASOs can be tiled from 100 nucleotides downstream of the 5' splice site, to 100 nucleotides upstream of the 3' splice site. In some embodiments, the ASOs can be tiled from about 1,160 nucleotides upstream of the 3' splice site, to about 500 nucleotides downstream of the 5' splice site. In some embodiments, the ASOs can be tiled from about 500 nucleotides upstream of the 3' splice site, to about 1,920 nucleotides downstream of the 3' splice site.

One or more ASOs, or a control ASO (an ASO with a scrambled sequence, sequence that is not expected to hybridize to the target region) are delivered, for example by transfection, into a disease-relevant cell line that expresses the target pre-mRNA (e.g., a NMD exon-containing pre-mRNA described herein). The exon skipping effects of each of the ASOs may be assessed by any method known in the art, for example by reverse transcriptase (RT)-PCR using primers that span the splice junction, as described in Example 4. A reduction or absence of a longer RT-PCR product produced using the primers spanning the region containing the included exon (e.g. including the flanking exons of the NMD exon) in ASO-treated cells as compared to in control ASO-treated cells indicates that splicing of the target NMD exon has been enhanced. In some embodiments, the exon skipping efficiency (or the splicing efficiency to splice the intron containing the NMD exon), the ratio of spliced to unspliced pre-mRNA, the rate of splicing, or the extent of splicing may be improved using the ASOs described herein. The amount of protein or functional RNA that is encoded by the target pre-mRNA can also be assessed to determine whether each ASO achieved the desired effect (e.g., enhanced functional protein production). Any method known in the art for assessing and/or quantifying protein production, such as Western blotting, flow cytometry, immunofluorescence microscopy, and ELISA, can be used.

A second round of screening, referred to as an ASO "micro-walk" may be performed using ASOs that have been designed to hybridize to a target region of a pre-mRNA. The ASOs used in the ASO micro-walk are tiled every 1 nucleotide to further refine the nucleotide acid sequence of the pre-mRNA that when hybridized with an ASO results in exon skipping (or enhanced splicing of NMD exon).

Regions defined by ASOs that promote splicing of the target intron are explored in greater detail by means of an ASO "micro-walk", involving ASOs spaced in 1-nt steps, as well as longer ASOs, typically 18-25 nt.

As described for the ASO walk above, the ASO micro-walk is performed by delivering one or more ASOs, or a control ASO (an ASO with a scrambled sequence, sequence that is not expected to hybridize to the target region), for example by transfection, into a disease-relevant cell line that expresses the target pre-mRNA. The splicing-inducing effects of each of the ASOs may be assessed by any method known in the art, for example by reverse transcriptase (RT)-PCR using primers that span the NMD exon, as described herein (see, e.g., Example 4). A reduction or absence of a longer RT-PCR product produced using the primers spanning the NMD exon in ASO-treated cells as compared to in control ASO-treated cells indicates that exon skipping (or splicing of the target intron containing an NMD exon) has been enhanced. In some embodiments, the exon skipping efficiency (or the splicing efficiency to splice the intron containing the NMD exon), the ratio of spliced to unspliced pre-mRNA, the rate of splicing, or the extent of splicing may be improved using the ASOs described herein. The amount of protein or functional RNA that is encoded by the target pre-mRNA can also be assessed to determine whether each ASO achieved the desired effect (e.g., enhanced functional protein production). Any method known in the art for assessing and/or quantifying protein production, such as Western blotting, flow cytometry, immunofluorescence microscopy, and ELISA, can be used.

ASOs that when hybridized to a region of a pre-mRNA result in exon skipping (or enhanced splicing of the intron containing a NMD exon) and increased protein production may be tested in vivo using animal models, for example transgenic mouse models in which the full-length human gene has been knocked-in or in humanized mouse models of disease. Suitable routes for administration of ASOs may vary depending on the disease and/or the cell types to which delivery of the ASOs is desired. ASOs may be administered, for example, by intravitreal injection, intrathecal injection, intracerebroventricular injection, intraperitoneal injection, intramuscular injection, subcutaneous injection, or intravenous injection. Following administration, the cells, tissues, and/or organs of the model animals may be assessed to determine the effect of the ASO treatment by for example evaluating splicing (e.g., efficiency, rate, extent) and protein production by methods known in the art and described herein. The animal models may also be any phenotypic or behavioral indication of the disease or disease severity.

Also within the scope of the present disclosure is a method to identify or validate an NMD-inducing exon in the presence of an NMD inhibitor, for example, cycloheximide. An exemplary method is provided in Example 2.

SPECIFIC EMBODIMENTS (A)

Embodiment A1. A method of treating Optic atrophy type 1 in a subject in need thereof, by increasing the expression of a target protein or functional RNA by a cell of the subject, wherein the cell has an mRNA that contains a non-sense mediated RNA decay-inducing exon (NMD exon mRNA), and wherein the NMD exon mRNA encodes the target protein or functional RNA, the method comprising contacting the cell of the subject with a therapeutic agent that binds to a targeted portion of the NMD exon mRNA encoding the target protein or functional RNA, whereby the non-sense mediated RNA decay-inducing exon is excluded from the NMD exon mRNA encoding the target protein or functional RNA, thereby increasing the level of mRNA encoding the target protein or functional RNA, and increasing the expression of the target protein or functional RNA in the cell of the subject.

Embodiment A2. The method of embodiment A1, wherein the target protein is OPA1.

Embodiment A3. A method of increasing expression of OPA1 protein by a cell having an mRNA that contains a non-sense mediated RNA decay-inducing exon (NMD exon mRNA) and encodes OPA1 protein, the method comprising contacting the cell with an agent that binds to a targeted portion of the NMD exon mRNA encoding OPA1 protein, whereby the non-sense mediated RNA decay-inducing exon is excluded from the NMD exon mRNA encoding OPA1 protein, thereby increasing the level of mRNA encoding OPA1 protein, and increasing the expression of OPA1 protein in the cell.

Embodiment A4. The method of any one of embodiments A1 to A3, wherein the non-sense mediated RNA decay-inducing exon is spliced out from the NMD exon mRNA encoding the target protein or functional RNA.

Embodiment A5. The method of any one of embodiments A1 to A4, wherein the target protein does not comprise an amino acid sequence encoded by the non-sense mediated RNA decay-inducing exon.

Embodiment A6. The method of any one of embodiments A1 to A5, wherein the target protein is a full-length target protein.

Embodiment A7. The method of any one of embodiments A1 to A6, wherein the agent is an antisense oligomer (ASO) complementary to the targeted portion of the NMD exon mRNA.

Embodiment A8. The method of any one of embodiments A1 to A7, wherein the mRNA is pre-mRNA.

Embodiment A9. The method of any one of embodiments A1 to A8, wherein the contacting comprises contacting the therapeutic agent to the mRNA, wherein the mRNA is in a nucleus of the cell.

Embodiment A10. The method of any one of embodiments A1 to A9, wherein the target protein or the functional RNA corrects a deficiency in the target protein or functional RNA in the subject.

Embodiment A11. The method of any one of embodiments A1 to A10, wherein the cells are in or from a subject with a condition caused by a deficient amount or activity of an OPA1 protein.

Embodiment A12. The method of any one of embodiments A1 to A11, wherein the deficient amount of the target protein is caused by haploinsufficiency of the target protein, wherein the subject has a first allele encoding a functional target protein, and a second allele from which the target protein is not produced, or a second allele encoding a nonfunctional target protein, and wherein the antisense oligomer binds to a targeted portion of a NMD exon mRNA transcribed from the first allele.

Embodiment A13. The method of any one of embodiments A1 to A11, wherein the subject has a condition caused by a disorder resulting from a deficiency in the amount or function of the target protein, wherein the subject has
(a) a first mutant allele from which
  (i) the target protein is produced at a reduced level compared to production from a wild-type allele,
  (ii) the target protein is produced in a form having reduced function compared to an equivalent wild-type protein, or
  (iii) the target protein is not produced, and
(b) a second mutant allele from which
  (i) the target protein is produced at a reduced level compared to production from a wild-type allele,
  (ii) the target protein is produced in a form having reduced function compared to an equivalent wild-type protein, or
  (iii) the target protein is not produced, and
wherein when the subject has a first mutant allele (a)(iii)., the second mutant allele is (b)(i) or (b)(ii) and wherein when the subject has a second mutant allele (b)(iii), the first mutant allele is (a)(i) or (a)(ii), and wherein the NMD exon mRNA is transcribed from either the first mutant allele that is (a)(i) or (a)(ii), and/or the second allele that is (b)(i) or (b)(ii).

Embodiment A14. The method of embodiment A13, wherein the target protein is produced in a form having reduced function compared to the equivalent wild-type protein.

Embodiment A15. The method of embodiment A13, wherein the target protein is produced in a form that is fully-functional compared to the equivalent wild-type protein.

Embodiment A16. The method of any one of embodiments A1 to A15, wherein the targeted portion of the NMD exon mRNA is within the non-sense mediated RNA decay-inducing exon.

Embodiment A17. The method of any one of embodiments A1 to A15, wherein the targeted portion of the NMD exon mRNA is either upstream or downstream of the non-sense mediated RNA decay-inducing exon.

Embodiment A18. The method of any one of embodiments A1 to A17, wherein the NMD exon mRNA comprises a sequence with at least about 80%, 85%, 90%, 95%, 97%, or 100% sequence identity to SEQ ID NO: 2 or 3.

Embodiment A19. The method of any one of embodiments A1 to A17, wherein the NMD exon mRNA is encoded by a genetic sequence with at least about 80%, 85%, 90%, 95%, 97%, or 100% sequence identity to SEQ ID NO: 1.

Embodiment A20. The method of any one of embodiments A1 to A17, wherein the targeted portion of the NMD exon mRNA comprises a sequence with at least 80%, 85%, 90%, 95%, 97%, or 100% sequence identity to a region comprising at least 8 contiguous nucleic acids of SEQ ID NO: 2 or 3.

Embodiment A21. The method of any one of embodiments A1 to A20, wherein the agent is an antisense oligomer (ASO) and wherein the ASO comprises a sequence that is at least about 80%, 85%, 90%, 95%, 97%, or 100% complementary to at least 8 contiguous nucleic acids of SEQ ID NO: 2 or 3.

Embodiment A22. The method of any one of embodiments A1 to A15, wherein the targeted portion of the NMD exon mRNA is within the non-sense mediated RNA decay-inducing exon 6x of OPA1, exon 7x of OPA1, or exon 28x of OPA1.

Embodiment A23. The method of any one of embodiments A1 to A15, wherein the targeted portion of the NMD exon mRNA is upstream or downstream of the non-sense mediated RNA decay-inducing exon 6x of OPA1, exon 7x of OPA1, or exon 28x of OPA1.

Embodiment A24. The method of any one of embodiments A1 to A15, wherein the targeted portion of the NMD exon mRNA comprises an exon-intron junction exon 6x of OPA1, exon 7x of OPA1, or exon 28x of OPA1.

Embodiment A25. The method of any one of embodiments A1 to A24, wherein the target protein produced is full-length protein, or wild-type protein.

Embodiment A26. The method of any one of embodiments A1 to A25, wherein the total amount of the mRNA encoding the target protein or functional RNA produced in the cell contacted with the antisense oligomer is increased about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to the total amount of the mRNA encoding the target protein or functional RNA produced in a control cell.

Embodiment A27. The method of any one of embodiments A1 to A25, wherein the total amount of the mRNA encoding the target protein or functional RNA produced in the cell contacted with the antisense oligomer is increased about 20% to about 300%, about 50% to about 300%, about 100% to about 300%, about 150% to about 300%, about 20% to about 50%, about 20% to about 100%, about 20% to about 150%, about 20% to about 200%, about 20% to about 250%, about 50% to about 100%, about 50% to about 150%, about 50% to about 200%, about 50% to about 250%, about 100% to about 150%, about 100% to about 200%, about 100% to about 250%, about 150% to about 200%, about 150% to about 250%, about 200% to about 250%, at least about 10%, at least about 20%, at least about 50%, at least about 100%, at least about 150%, at least about 200%, at least about 250%, or at least about 300%, compared to the total amount of the mRNA encoding the target protein or functional RNA produced in a control cell.

Embodiment A28. The method of one any of embodiments A1 to A25, wherein the total amount of target protein produced by the cell contacted with the antisense oligomer is increased about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to the total amount of target protein produced by a control cell.

Embodiment A29. The method of one any of embodiments A1 to A25, wherein the total amount of target protein produced by the cell contacted with the antisense oligomer is increased about 20% to about 300%, about 50% to about 300%, about 100% to about 300%, about 150% to about 300%, about 20% to about 50%, about 20% to about 100%, about 20% to about 150%, about 20% to about 200%, about 20% to about 250%, about 50% to about 100%, about 50% to about 150%, about 50% to about 200%, about 50% to about 250%, about 100% to about 150%, about 100% to about 200%, about 100% to about 250%, about 150% to about 200%, about 150% to about 250%, about 200% to about 250%, at least about 10%, at least about 20%, at least about 50%, at least about 100%, at least about 150%, at least about 200%, at least about 250%, or at least about 300%, compared to the total amount of target protein produced by a control cell.

Embodiment A30. The method of any one of embodiments A1 to 29, wherein the agent is an antisense oligomer (ASO) and wherein the antisense oligomer comprises a backbone modification comprising a phosphorothioate linkage or a phosphorodiamidate linkage.

Embodiment A31. The method of any one of embodiments A1 to A30, wherein the agent is an antisense oligomer (ASO) and wherein the antisense oligomer comprises a phosphorodiamidate morpholino, a locked nucleic acid, a peptide nucleic acid, a 2'-O-methyl, a 2'-Fluoro, or a 2'-O-methoxyethyl moiety.

Embodiment A32. The method of any one of embodiments A1 to A31, wherein the agent is an antisense oligomer (ASO) and wherein the antisense oligomer comprises at least one modified sugar moiety.

Embodiment A33. The method of embodiment A32, wherein each sugar moiety is a modified sugar moiety.

Embodiment A34. The method of any one of embodiments A1 to A33, wherein the agent is an antisense oligomer (ASO) and wherein the antisense oligomer consists of from 8 to 50 nucleobases, 8 to 40 nucleobases, 8 to 35 nucleobases, 8 to 30 nucleobases, 8 to 25 nucleobases, 8 to 20 nucleobases, 8 to 15 nucleobases, 9 to 50 nucleobases, 9 to 40 nucleobases, 9 to 35 nucleobases, 9 to 30 nucleobases, 9 to 25 nucleobases, 9 to 20 nucleobases, 9 to 15 nucleobases, 10 to 50 nucleobases, 10 to 40 nucleobases, 10 to 35 nucleobases, 10 to 30 nucleobases, 10 to 25 nucleobases, 10 to 20 nucleobases, 10 to 15 nucleobases, 11 to 50 nucleobases, 11 to 40 nucleobases, 11 to 35 nucleobases, 11 to 30 nucleobases, 11 to 25 nucleobases, 11 to 20 nucleobases, 11 to 15 nucleobases, 12 to 50 nucleobases, 12 to 40 nucleobases, 12 to 35 nucleobases, 12 to 30 nucleobases, 12 to 25 nucleobases, 12 to 20 nucleobases, or 12 to 15 nucleobases.

Embodiment A35. The method of any one of embodiments A1 to A34, wherein the agent is an antisense oligomer (ASO) and wherein the antisense oligomer is at least 80%, at least 85%, at least 90%, at least 95%, at least 98%, at least 99%, or 100%, complementary to the targeted portion of the NMD exon mRNA encoding the protein.

Embodiment A36. The method of any one of embodiments A1 to A35, wherein the method further comprises assessing OPA1 mRNA or protein expression.

Embodiment A37. The method of any one of embodiments A1 to A36, wherein Optic atrophy type 1 is treated and wherein the antisense oligomer binds to a targeted portion of an OPA1 NMD exon mRNA, wherein the targeted portion is within SEQ ID NO: 2 or 3.

Embodiment A38. The method of any one of embodiments A1 to A37, wherein the subject is a human.

Embodiment A39. The method of any one of embodiments A1 to A38, wherein the subject is a non-human animal.

Embodiment A40. The method of any one of embodiments A1 to A39, wherein the subject is a fetus, an embryo, or a child.

Embodiment A41. The method of any one of embodiments A1 to A40, wherein the cells are ex vivo.

Embodiment A42. The method of any one of embodiments A1 to A41, wherein the therapeutic agent is administered by intrathecal injection, intracerebroventricular injection, intraperitoneal injection, intramuscular injection, subcutaneous injection, or intravenous injection of the subject.

Embodiment A43. The method of any of embodiments A1 to A42, wherein the method further comprises administering a second therapeutic agent to the subject.

Embodiment A44. The method of embodiment A43, wherein the second therapeutic agent is a small molecule.

Embodiment A45. The method of embodiment A43, wherein the second therapeutic agent is an ASO.

Embodiment A46. The method of any one of embodiments A43 to A45, wherein the second therapeutic agent corrects intron retention.

Embodiment A47. An antisense oligomer as used in a method of any of embodiments A1 to A46.

Embodiment A48. An antisense oligomer comprising a sequence with at least about 80%, 85%, 90%, 95%, 97%, or 100% sequence identity to a region comprising at least 8 contiguous nucleic acids of SEQ ID NO: 2 or 3.

Embodiment A49. A pharmaceutical composition comprising the antisense oligomer of embodiment A47 or A48 and an excipient.

Embodiment A50. A method of treating a subject in need thereof, comprising administering the pharmaceutical composition of embodiment A49 to the subject, wherein the administering is by intravitreal injection, intrathecal injection, intracerebroventricular injection, intraperitoneal injection, intramuscular injection, subcutaneous injection, or intravenous injection.

Embodiment A51. A composition comprising a therapeutic agent for use in a method of increasing expression of a target protein or a functional RNA by cells to treat Optic atrophy type 1 in a subject in need thereof, associated with a deficient protein or deficient functional RNA, wherein the deficient protein or deficient functional RNA is deficient in amount or activity in the subject, wherein the target protein is:
  (a) the deficient protein; or
  (b) a compensating protein which functionally augments or replaces the deficient protein or in the subject;
  and wherein the functional RNA is:
  (c) the deficient RNA; or
  (d) a compensating functional RNA which functionally augments or replaces the deficient functional RNA in the subject;
  wherein the therapeutic agent enhances exclusion of the non-sense mediated RNA decay-inducing exon from the NMD exon mRNA encoding the target protein or functional RNA, thereby increasing production or activity of the target protein or the functional RNA in the subject.

Embodiment A52. A composition comprising a therapeutic agent for use in a method of treating a condition associated with OPA1 protein in a subject in need thereof, the method comprising the step of increasing expression of OPA1 protein by cells of the subject, wherein the cells have an mRNA that contains a non-sense mediated RNA decay-inducing exon (NMD exon mRNA) and encodes OPA1 protein, the method comprising contacting the cells with the therapeutic agent, whereby the non-sense mediated RNA decay-inducing exon is excluded from the NMD exon mRNA that encodes OPA1 protein, thereby increasing the level of mRNA encoding OPA1 protein, and increasing the expression of OPA1 protein in the cells of the subject.

Embodiment A53. The composition of embodiment A52, wherein the condition is a disease or disorder.

Embodiment A54. The composition of embodiment A53, wherein the disease or disorder is Optic atrophy type 1.

Embodiment A55. The composition of any one of embodiments A52 to 54, wherein the OPA1 protein and NMD exon mRNA are encoded by the OPA1 gene.

Embodiment A56. The composition of any one of embodiments A51 to A55, wherein the non-sense mediated RNA decay-inducing exon is spliced out from the NMD exon mRNA encoding the OPA1 protein.

Embodiment A57. The composition of any one of embodiments A51 to A56, wherein the OPA1 protein does not comprise an amino acid sequence encoded by the non-sense mediated RNA decay-inducing exon.

Embodiment A58. The composition of any one of embodiments A51 to A57, wherein the OPA1 protein is a full-length OPA1 protein.

Embodiment A59. The composition of any one of embodiments A51 to A58, wherein the therapeutic agent is an antisense oligomer (ASO) complementary to the targeted portion of the NMD exon mRNA.

Embodiment A60. The composition of any of embodiments A51 to A59, wherein the therapeutic agent is an antisense oligomer (ASO) and wherein the antisense oligomer targets a portion of the NMD exon mRNA that is within the non-sense mediated RNA decay-inducing exon.

Embodiment A61. The composition of any of embodiments A51 to A59, wherein the therapeutic agent is an antisense oligomer (ASO) and wherein the antisense oligomer targets a portion of the NMD exon mRNA that is upstream or downstream of the non-sense mediated RNA decay-inducing exon.

Embodiment A62. The composition of any one of embodiments A51 to A61, wherein the target protein is OPA1.

Embodiment A63. The composition of embodiment A62, wherein the NMD exon mRNA comprises a sequence with at least about 80%, 85%, 90%, 95%, 97%, or 100% sequence identity to SEQ ID NO: 2 or 3.

Embodiment A64. The composition of embodiment A62, wherein the NMD exon mRNA is encoded by a genetic sequence with at least about 80%, 85%, 90%, 95%, 97%, or 100% sequence identity to SEQ ID NO: 1.

Embodiment A65. The composition of embodiment A62, wherein the targeted portion of the NMD exon mRNA comprises a sequence with at least 80%, 85%, 90%, 95%, 97%, or 100% sequence identity to a region comprising at least 8 contiguous nucleic acids of SEQ ID NO: 2 or 3.

Embodiment A66. The composition of any one of embodiments A62 to A65, wherein the targeted portion of the NMD exon mRNA is within the non-sense mediated RNA decay-inducing exon 6x of OPA1, exon 7x of OPA1, or exon 28x of OPA1.

Embodiment A67. The composition of any one of embodiments A62 to A65, wherein the targeted portion of the NMD exon mRNA is upstream or downstream of the non-sense mediated RNA decay-inducing exon 6x of OPA1, exon 7x of OPA1, or exon 28x of OPA1.

Embodiment A68. The composition of any one of embodiments A62 to A65, wherein the targeted portion of the NMD exon mRNA comprises an exon-intron junction of exon 6x of OPA1, exon 7x of OPA1, or exon 28x of OPA1.

Embodiment A69. The composition of any one of embodiments A62 to A68, wherein the therapeutic agent is an antisense oligomer (ASO) and wherein the ASO comprises a sequence that is at least about 80%, 85%, 90%, 95%, 97%, or 100% complementary to a region comprising at least 8 contiguous nucleic acids of SEQ ID NO: 2 or 3.

Embodiment A70. The composition of any one of embodiments A51 to A69, wherein the mRNA encoding the target protein or functional RNA is a full-length mature mRNA, or a wild-type mature mRNA.

Embodiment A71. The composition of any one of embodiments A51 to A70, wherein the target protein produced is full-length protein, or wild-type protein.

Embodiment A72. The composition of any one of embodiments A51 to A71, wherein the therapeutic agent is an antisense oligomer (ASO) and wherein the antisense oligomer comprises a backbone modification comprising a phosphorothioate linkage or a phosphorodiamidate linkage.

Embodiment A73. The composition of any of embodiments A51 to A72, wherein the therapeutic agent is an antisense oligomer (ASO) and wherein said antisense oligomer is an antisense oligonucleotide.

Embodiment A74. The composition of any of embodiments A51 to A73, wherein the therapeutic agent is an antisense oligomer (ASO) and wherein the antisense oligomer comprises a phosphorodiamidate morpholino, a locked nucleic acid, a peptide nucleic acid, a 2'-O-methyl, a 2'-Fluoro, or a 2'-O-methoxyethyl moiety.

Embodiment A75. The composition of any of embodiments A51 to A74, wherein the therapeutic agent is an antisense oligomer (ASO) and wherein the antisense oligomer comprises at least one modified sugar moiety.

Embodiment A76. The composition of embodiment A75, wherein each sugar moiety is a modified sugar moiety.

Embodiment A77. The composition of any of embodiments A51 to A76, wherein the therapeutic agent is an antisense oligomer (ASO) and wherein the antisense oligomer consists of from 8 to 50 nucleobases, 8 to 40 nucleobases, 8 to 35 nucleobases, 8 to 30 nucleobases, 8 to 25 nucleobases, 8 to 20 nucleobases, 8 to 15 nucleobases, 9 to 50 nucleobases, 9 to 40 nucleobases, 9 to 35 nucleobases, 9 to 30 nucleobases, 9 to 25 nucleobases, 9 to 20 nucleobases, 9 to 15 nucleobases, 10 to 50 nucleobases, 10 to 40 nucleobases, 10 to 35 nucleobases, 10 to 30 nucleobases, 10 to 25 nucleobases, 10 to 20 nucleobases, 10 to 15 nucleobases, 11 to 50 nucleobases, 11 to 40 nucleobases, 11 to 35 nucleobases, 11 to 30 nucleobases, 11 to 25 nucleobases, 11 to 20 nucleobases, 11 to 15 nucleobases, 12 to 50 nucleobases, 12 to 40 nucleobases, 12 to 35 nucleobases, 12 to 30 nucleobases, 12 to 25 nucleobases, 12 to 20 nucleobases, or 12 to 15 nucleobases.

Embodiment A78. A pharmaceutical composition comprising the therapeutic agent of any of the compositions of embodiments A51 to A77, and an excipient.

Embodiment A79. A method of treating a subject in need thereof, comprising administering the pharmaceutical composition of embodiment A78 to the subject, wherein the administering is by intravitreal injection, intrathecal injection, intracerebroventricular injection, intraperitoneal injection, intramuscular injection, subcutaneous injection, or intravenous injection.

Embodiment A80. The method of any of embodiments A51 to A79, wherein the method further comprises administering a second therapeutic agent to the subject.

Embodiment A81. The method of embodiment A80, wherein the second therapeutic agent is a small molecule.

Embodiment A82. The method of embodiment A80, wherein the second therapeutic agent is an ASO.

Embodiment A83. The method of any one of embodiments A80 to A82, wherein the second therapeutic agent corrects intron retention.

Embodiment A84. A pharmaceutical composition comprising: an antisense oligomer that hybridizes to a target sequence of an OPA1 mRNA transcript, wherein the OPA1 mRNA transcript comprises a non-sense mediated RNA decay-inducing exon, wherein the antisense oligomer induces exclusion of the non-sense mediated RNA decay-inducing exon from the OPA1 mRNA transcript; and a pharmaceutical acceptable excipient.

Embodiment A85. The pharmaceutical composition of embodiment A84, wherein the OPA1 mRNA transcript is an OPA1 NMD exon mRNA transcript.

Embodiment A86. The pharmaceutical composition of embodiment A84 or A85, wherein the targeted portion of the NMD exon mRNA is within the non-sense mediated RNA decay-inducing exon 6x of OPA1, exon 7x of OPA1, or exon 28x of OPA1.

Embodiment A87. The pharmaceutical composition of embodiment A84 or A85, wherein the targeted portion of the NMD exon mRNA is upstream or downstream of the non-sense mediated RNA decay-inducing exon 6x of OPA1, exon 7x of OPA1, or exon 28x of OPA1.

Embodiment A88. The pharmaceutical composition of embodiment A84 or A85, wherein the targeted portion of the NMD exon mRNA comprises an exon-intron junction exon 6x of OPA1, exon 7x of OPA1, or exon 28x of OPA1.

Embodiment A89. The pharmaceutical composition of any one of embodiments A84 to A88, wherein the OPA1 NMD exon mRNA transcript is encoded by a genetic sequence with at least about 80%, 85%, 90%, 95%, 96%, 97%, 98%, 99% or 100% sequence identity to SEQ ID NO: 1.

Embodiment A90. The pharmaceutical composition of embodiment A84 or A88, wherein the OPA1 NMD exon mRNA transcript comprises a sequence with at least about 80%, 85%, 90%, 95%, 96%, 97%, 98%, 99% or 100% sequence identity to SEQ ID NO: 2 or 3.

Embodiment A91. The pharmaceutical composition of embodiment A84, wherein the antisense oligomer comprises a backbone modification comprising a phosphorothioate linkage or a phosphorodiamidate linkage.

Embodiment A92. The pharmaceutical composition of embodiment A84, wherein the antisense oligomer is an antisense oligonucleotide.

Embodiment A93. The pharmaceutical composition of embodiment A84, wherein the antisense oligomer comprises a phosphorodiamidate morpholino, a locked nucleic acid, a peptide nucleic acid, a 2'-O-methyl, a 2'-Fluoro, or a 2'-O-methoxyethyl moiety.

Embodiment A94. The pharmaceutical composition of embodiment A84, wherein the antisense oligomer comprises at least one modified sugar moiety.

Embodiment A95. The pharmaceutical composition of embodiment A84, wherein the antisense oligomer comprises from 8 to 50 nucleobases, 8 to 40 nucleobases, 8 to 35 nucleobases, 8 to 30 nucleobases, 8 to 25 nucleobases, 8 to 20 nucleobases, 8 to 15 nucleobases, 9 to 50 nucleobases, 9 to 40 nucleobases, 9 to 35 nucleobases, 9 to 30 nucleobases, 9 to 25 nucleobases, 9 to 20 nucleobases, 9 to 15 nucleobases, 10 to 50 nucleobases, 10 to 40 nucleobases, 10 to 35 nucleobases, 10 to 30 nucleobases, 10 to 25 nucleobases, 10 to 20 nucleobases, 10 to 15 nucleobases, 11 to 50 nucleobases, 11 to 40 nucleobases, 11 to 35 nucleobases, 11 to 30 nucleobases, 11 to 25 nucleobases, 11 to 20 nucleobases, 11 to 15 nucleobases, 12 to 50 nucleobases, 12 to 40 nucleobases, 12 to 35 nucleobases, 12 to 30 nucleobases, 12 to 25 nucleobases, 12 to 20 nucleobases, or 12 to 15 nucleobases.

Embodiment A96. The pharmaceutical composition of embodiment A84 or A85, wherein the antisense oligomer is at least 80%, at least 85%, at least 90%, at least 95%, at least 98%, at least 99%, or is 100% complementary to a targeted portion of the OPA1 NMD exon mRNA transcript.

Embodiment A97. The pharmaceutical composition of embodiment A84 or A85, wherein the targeted portion of the OPA1 NMD exon mRNA transcript is within SEQ ID NO: 2 or 3.

Embodiment A98. The pharmaceutical composition of embodiment A84, wherein the antisense oligomer comprises a nucleotide sequence that is at least about 80%, 85%, 90%, 91%, 92%, 93%, 94%, 95%, 96%, 97%, 98%, or 99% sequence identity to a region comprising at least 8 contiguous nucleic acids of SEQ ID NO: 2 or 3.

Embodiment A99. The pharmaceutical composition of embodiment A84, wherein the antisense oligomer comprises a nucleotide sequence that is identical a region comprising at least 8 contiguous nucleic acids SEQ ID NO: 2 or 3.

Embodiment A100. The pharmaceutical composition of any one of the embodiments A84 to A99, wherein the pharmaceutical composition is formulated for intravitreal injection, intrathecal injection, intracerebroventricular injection, intraperitoneal injection, intramuscular injection, subcutaneous injection, or intravenous injection.

Embodiment A101. The method of any of embodiments A84 to A100, wherein the method further comprises administering a second therapeutic agent to the subject.

Embodiment A102. The method of embodiment A101, wherein the second therapeutic agent is a small molecule.

Embodiment A103. The method of embodiment A101, wherein the second therapeutic agent is an ASO.

Embodiment A104. The method of any one of embodiments A101 to A103, wherein the second therapeutic agent corrects intron retention.

Embodiment A105. A method of inducing processing of a deficient OPA1 mRNA transcript to facilitate removal of a non-sense mediated RNA decay-inducing exon to produce a fully processed OPA1 mRNA transcript that encodes a functional form of an OPA1 protein, the method comprising:

(a) contacting an antisense oligomer to a target cell of a subject;

(b) hybridizing the antisense oligomer to the deficient OPA1 mRNA transcript, wherein the deficient OPA1 mRNA transcript is capable of encoding the functional form of an OPA1 protein and comprises at least one non-sense mediated RNA decay-inducing exon;

(c) removing the at least one non-sense mediated RNA decay-inducing exon from the deficient OPA1 mRNA transcript to produce the fully processed OPA1 mRNA transcript that encodes the functional form of OPA1 protein; and (d) translating the functional form of OPA1 protein from the fully processed OPA1 mRNA transcript.

Embodiment A106. A method of treating a subject having a condition caused by a deficient amount or activity of OPA1 protein comprising administering to the subject an antisense oligomer comprising a nucleotide sequence with at least about 80%, 85%, 90%, 91%, 92%, 93%, 94%, 95%, 96%, 97%, 98%, or 99% sequence identity to a region comprising at least 8 contiguous nucleic acids of SEQ ID NO: 2 or 3.

Embodiment A107. A method of treating Optic atrophy type 1 in a subject in need thereof, by increasing the expression of a target protein or functional RNA by a cell of the subject, wherein the cell has an mRNA that contains a non-sense mediated RNA decay-inducing exon (NMD exon mRNA), and wherein the NMD exon mRNA encodes the target protein or functional RNA, the method comprising contacting the cell of the subject with a therapeutic agent that modulates splicing of the NMD exon mRNA encoding the target protein or functional RNA, whereby the non-sense mediated RNA decay-inducing exon is excluded from the NMD exon mRNA encoding the target protein or functional RNA, thereby increasing the level of mRNA encoding the target protein or functional RNA, and increasing the expression of the target protein or functional RNA in the cell of the subject.

Embodiment A108. A method of increasing expression of OPA1 protein by a cell having an mRNA that contains a non-sense mediated RNA decay-inducing exon (NMD exon mRNA) and encodes OPA1 protein, the method comprising contacting the cell with an agent that modulates splicing of the NMD exon mRNA encoding OPA1 protein, whereby the non-sense mediated RNA decay-inducing exon is excluded from the NMD exon mRNA encoding OPA1 protein, thereby increasing the level of mRNA encoding OPA1 protein, and increasing the expression of OPA1 protein in the cell.

Embodiment A109. The method of embodiment A107 or A108, wherein the agent
(a) binds to a targeted portion of the NMD exon mRNA encoding the target protein or functional RNA;
(b) binds to one or more components of a spliceosome; or
(c) a combination of (a) and (b).

Embodiment B1. A method of modulating expression of a target protein, by a cell having an mRNA that comprises a non-sense mediated RNA decay-inducing exon (NMD exon) and encodes the target protein, the method comprising contacting a therapeutic agent to the cell, whereby the therapeutic agent modulates splicing of the NMD exon from the mRNA, thereby modulating level of processed mRNA encoding the target protein, and modulating the expression of the target protein in the cell, wherein the target protein is selected from the group consisting of: OPA1 proteins.

Embodiment B2. A method of treating a disease or condition in a subject in need thereof by modulating expression of a target protein in a cell of the subject, comprising: contacting the cell of the subject with a therapeutic agent that modulates splicing of a non-sense mediated mRNA decay-inducing exon (NMD exon) from an mRNA in the cell, wherein the mRNA comprises the NMD exon and encodes the target protein, thereby modulating level of processed mRNA encoding the target protein, and modulating expression of the target protein in the cell of the subject, wherein the target protein is selected from the group consisting of: OPA1 proteins.

Embodiment B3. The method of embodiment B1 or B2, wherein the therapeutic agent
(a) binds to a targeted portion of the mRNA encoding the target protein;
(b) modulates binding of a factor involved in splicing of the NMD exon; or
(c) a combination of (a) and (b).

Embodiment B4. The method of embodiment B3, wherein the therapeutic agent interferes with binding of the factor involved in splicing of the NMD exon to a region of the targeted portion.

Embodiment B5. The method of embodiment B3 or B4, wherein the targeted portion is proximal to the NMD exon.

Embodiment B6. The method of any one of embodiments B3 to B5, wherein the targeted portion is at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream of 5' end of the NMD exon.

Embodiment B7. The method of any one of embodiments B3 to B6, wherein the targeted portion is at least about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides, about 40 nucleotides, about 30 nucleotides, about 20 nucleotides, about 10 nucleotides, about 5 nucleotides, about 4 nucleotides, about 2 nucleotides, about 1 nucleotides upstream of 5' end of the NMD exon.

Embodiment B8. The method of any one of embodiments B3 to B5, wherein the targeted portion is at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream of 3' end of the NMD exon.

Embodiment B9. The method of any one of embodiments B3 to B5 or B8, wherein the targeted portion is at least about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides, about 40 nucleotides, about 30 nucleotides, about 20 nucleotides, about 10 nucleotides, about 5 nucleotides, about 4 nucleotides, about 2 nucleotides, about 1 nucleotides downstream of 3' end of the NMD exon.

Embodiment B10. The method of any one of embodiments B3 to B5, wherein the targeted portion is at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream of genomic site selected from the group consisting of: GRCh38/hg38: chr3 193628509; and GRCh38/hg38: chr3 193603500.

Embodiment B11. The method of any one of embodiments B3 to B5 or B10, wherein the targeted portion is about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream of genomic site selected from the group consisting of: GRCh38/hg38: chr3 193628509; and GRCh38/hg38: chr3 193603500.

Embodiment B12. The method of any one of embodiments B3 to B5, wherein the targeted portion is at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream of genomic site selected from the group consisting of: GRCh38/hg38: chr3 193628616; and GRCh38/hg38: chr3 193603557.

Embodiment B13. The method of any one of embodiments B3 to B5 or B12, wherein the targeted portion is about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream of genomic site selected from the group consisting of: GRCh38/hg38: chr3 193628616; and GRCh38/hg38: chr3 193603557.

Embodiment B14. The method of any one of embodiments B3 to B13, wherein the targeted portion is located in an intronic region between two canonical exonic regions of the mRNA encoding the target protein, and wherein the intronic region contains the NMD exon.

Embodiment B15. The method of any one of embodiments B3 to B14, wherein the targeted portion at least partially overlaps with the NMD exon.

Embodiment B16. The method of any one of embodiments B3 to B15, wherein the targeted portion at least partially overlaps with an intron upstream or downstream of the NMD exon.

Embodiment B17. The method of any one of embodiments B3 to B16, wherein the targeted portion comprises 5' NMD exon-intron junction or 3' NMD exon-intron junction.

Embodiment B18. The method of any one of embodiments B3 to B16, wherein the targeted portion is within the NMD exon.

Embodiment B19. The method of any one of embodiments B1 to B18, wherein the targeted portion comprises about 5, 6, 7, 8, 9, 10, 11, 12, 13, 14, 15, 16, 17, 18, 19, 20, 21, 22, 23, 24, 25, 26, 27, 28, 29, 30, or more consecutive nucleotides of the NMD exon.

Embodiment B20. The method of any one of embodiments B1 to B19, wherein the mRNA encoding the target protein comprises a sequence with at least about 80%, 85%, 90%, 95%, 97%, or 100% sequence identity to SEQ ID NO: 4 or 5.

Embodiment B21. The method of any one of embodiments B1 to B20, wherein the mRNA encoding the target protein is encoded by a genetic sequence with at least about 80%, 85%, 90%, 95%, 97%, or 100% sequence identity to SEQ ID NO: 1.

Embodiment B22. The method of any one of embodiments B3 to B21, wherein the targeted portion of the mRNA comprises a sequence with at least 80%, 85%, 90%, 95%, 97%, or 100% sequence identity to a region comprising at least 8 contiguous nucleic acids of SEQ ID NO: 4 or 5.

Embodiment B23. The method of any one of embodiments B1 to B22, wherein the agent is an antisense oligomer (ASO) and wherein the ASO comprises a sequence that is at least about 80%, 85%, 90%, 95%, 97%, or 100% complementary to at least 8 contiguous nucleic acids of SEQ ID Ns: 4 or 5.

Embodiment B24. The method of any one of embodiments B3 to B23, wherein the targeted portion of the mRNA is within the non-sense mediated RNA decay-inducing exon selected from the group consisting of: GRCh38/hg38: chr3 193628509 193628616; and GRCh38/hg38: chr3 193603500 193603557.

Embodiment B25. The method of any one of embodiments B3 to B23, wherein the targeted portion of the mRNA is upstream or downstream of the non-sense mediated RNA decay-inducing exon selected from the group consisting of: GRCh38/hg38: chr3 193628509 193628616; and GRCh38/hg38: chr3 193603500 193603557.

Embodiment B26. The method of any one of embodiments B3 to B23, wherein the targeted portion of the mRNA comprises an exon-intron junction of exon selected from the group consisting of: GRCh38/hg38: chr3 193628509 193628616; and GRCh38/hg38: chr3 193603500 193603557.

Embodiment B27. The method of any one of embodiments B1 to B26, wherein the target protein produced is a full-length protein or a wild-type protein.

Embodiment B28. The method of any one of embodiments B1 to B27, wherein the therapeutic agent promotes exclusion of the NMD exon from the pre-mRNA encoding the target protein.

Embodiment B29. The method of embodiment B28, wherein exclusion of the NMD exon from the pre-mRNA encoding the target protein in the cell contacted with the therapeutic agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to exclusion of the NMD exon from the pre-mRNA encoding the target protein in a control cell.

Embodiment B30. The method of embodiment B28 or B29, wherein the therapeutic agent increases the level of the processed mRNA encoding the target protein in the cell.

Embodiment B31. The method of any one of embodiments B28 to B30, wherein the level of the processed mRNA encoding the target protein produced in the cell contacted with the therapeutic agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to a level of the processed mRNA encoding the target protein in a control cell.

Embodiment B32. The method of any one of embodiments B28 to B31, wherein the therapeutic agent increases the expression of the target protein in the cell.

Embodiment B33. The method of any one of embodiments B28 to B32, wherein a level of the target protein produced in the cell contacted with the therapeutic agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to a level of the target protein produced in a control cell.

Embodiment B34. The method of any one of embodiments B2 to B33, wherein the disease or condition is induced by a loss-of-function mutation in the target protein.

Embodiment B35. The method of embodiment B34, wherein the disease or condition is associated with haploinsufficiency of a gene encoding the target protein, and wherein the subject has a first allele encoding a functional target protein, and a second allele from which the target protein is not produced or produced at a reduced level, or a second allele encoding a nonfunctional target protein or a partially functional target protein.

Embodiment B36. The method of any one of embodiments B2 to B35, wherein the disease or condition is selected from the group consisting of: Optic atrophy type 1.

Embodiment B37. The method of any one of embodiments B34 to B36, wherein the therapeutic agent promotes exclusion of the NMD exon from the pre-mRNA encoding the target protein and increases the expression of the target protein in the cell.

Embodiment B38. The method of any one of embodiments B1 to B27, wherein the therapeutic agent inhibits exclusion of the NMD exon from the pre-mRNA encoding the target protein.

Embodiment B39. The method of embodiment B38, wherein exclusion of the NMD exon from the pre-mRNA encoding the target protein in the cell contacted with the therapeutic agent is decreased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to exclusion of the NMD exon from the pre-mRNA encoding the target protein in a control cell.

Embodiment B40. The method of embodiment B38 or B39, wherein the therapeutic agent decreases the level of the processed mRNA encoding the target protein in the cell.

Embodiment B41. The method of any one of embodiments B38 to B40, wherein the level of the processed mRNA encoding the target protein in the cell contacted with the therapeutic agent is decreased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to a level of the processed mRNA encoding the target protein in a control cell.

Embodiment B42. The method of any one of embodiments B38 to B41, wherein the therapeutic agent decreases the expression of the target protein in the cell.

Embodiment B43. The method of any one of embodiments B38 to B42, wherein a level of the target protein produced in the cell contacted with the therapeutic agent is decreased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to a level of the target protein produced in a control cell.

Embodiment B44. The method of any one of embodiments B2 to B27 or B38 to B43, wherein the disease or condition is induced by a gain-of-function mutation in the target protein Embodiment B45. The method of embodiment B44, wherein the subject has an allele from which the target protein is produced at an increased level, or an allele encoding a mutant target protein that exhibits increased activity in the cell.

Embodiment B46. The method of embodiment B44 or B45, wherein the therapeutic agent inhibits exclusion of the NMD exon from the pre-mRNA encoding the target protein and decreases the expression of the target protein in the cell.

Embodiment B47. The method of any one of embodiments B1 to B46, wherein the therapeutic agent is an antisense oligomer (ASO) and wherein the antisense oligomer comprises a backbone modification comprising a phosphorothioate linkage or a phosphorodiamidate linkage.

Embodiment B48. The method of any one of embodiments B1 to B47, wherein the therapeutic agent is an antisense oligomer (ASO) and wherein the antisense oligomer comprises a phosphorodiamidate morpholino, a locked nucleic acid, a peptide nucleic acid, a 2'-O-methyl, a 2'-Fluoro, or a 2'-O-methoxyethyl moiety.

Embodiment B49. The method of any one of embodiments B1 to B48, wherein the therapeutic agent is an antisense oligomer (ASO) and wherein the antisense oligomer comprises at least one modified sugar moiety.

Embodiment B50. The method of embodiment B49, wherein each sugar moiety is a modified sugar moiety.

Embodiment B51. The method of any one of embodiments B1 to B50, wherein the therapeutic agent is an antisense oligomer (ASO) and wherein the antisense oligomer consists of from 8 to 50 nucleobases, 8 to 40 nucleobases, 8 to 35 nucleobases, 8 to 30 nucleobases, 8 to 25 nucleobases, 8 to 20 nucleobases, 8 to 15 nucleobases, 9 to 50 nucleobases, 9 to 40 nucleobases, 9 to 35 nucleobases, 9 to 30 nucleobases, 9 to 25 nucleobases, 9 to 20 nucleobases, 9 to 15 nucleobases, 10 to 50 nucleobases, 10 to 40 nucleobases, 10 to 35 nucleobases, 10 to 30 nucleobases, 10 to 25 nucleobases, 10 to 20 nucleobases, 10 to 15 nucleobases, 11 to 50 nucleobases, 11 to 40 nucleobases, 11 to 35 nucleobases, 11 to 30 nucleobases, 11 to 25 nucleobases, 11 to 20 nucleobases, 11 to 15 nucleobases, 12 to 50 nucleobases, 12 to 40 nucleobases, 12 to 35 nucleobases, 12 to 30 nucleobases, 12 to 25 nucleobases, 12 to 20 nucleobases, or 12 to 15 nucleobases.

Embodiment B52. The method of any one of embodiments B3 to B51, wherein the therapeutic agent is an antisense oligomer (ASO) and wherein the antisense oligomer is at least 80%, at least 85%, at least 90%, at least 95%, at least 98%, at least 99%, or 100%, complementary to the targeted portion of the mRNA.

Embodiment B53. The method of any one of embodiments B1 to B52, wherein the method further comprises assessing mRNA level or expression level of the target protein.

Embodiment B54. The method of any one of embodiments B1 to B53, wherein the subject is a human.

Embodiment B55. The method of any one of embodiments B1 to B53, wherein the subject is a non-human animal.

Embodiment B56. The method of any one of embodiments B2 to B54, wherein the subject is a fetus, an embryo, or a child.

Embodiment B57. The method of any one of embodiments B1 to B56, wherein the cells are ex vivo.

Embodiment B58. The method of any one of embodiments B2 to B56, wherein the therapeutic agent is administered by intravitreal injection, intrathecal injection, intracerebroventricular injection, intraperitoneal injection, intramuscular injection, subcutaneous injection, intravitreal, or intravenous injection of the subject.

Embodiment B59. The method of any one of embodiments B2 to B56 or B58, wherein the method further comprises administering a second therapeutic agent to the subject.

Embodiment B60. The method of any one of embodiments B1 to B59, wherein the second therapeutic agent is a small molecule.

Embodiment B61. The method of any one of embodiments B1 to B59, wherein the second therapeutic agent is an antisense oligomer.

Embodiment B62. The method of any one of embodiments B1 to B61, wherein the second therapeutic agent corrects intron retention.

Embodiment B63. The method of any one of embodiments B2 to B62, wherein the disease or condition is Optic atrophy type 1.

FURTHER SPECIFIC EMBODIMENTS

Embodiment 1. A method of modulating expression of an OPA1 protein in a cell having a pre-mRNA that is transcribed from an OPA1 gene and that comprises a non-sense mediated RNA decay-inducing exon (NMD exon), the method comprising contacting an agent or a vector encoding the agent to the cell, whereby the agent modulates splicing of the NMD exon from the pre-mRNA, thereby modulating a level of processed mRNA that is processed from the pre-mRNA, and modulating the expression of the OPA1 protein in the cell, wherein the agent comprises an antisense oligomer with at least 80% sequence identity to a sequence selected from the group consisting of SEQ ID NOs: 6-275 and 280-299.

Embodiment 2. The method of embodiment 1, wherein the agent:
 (a) binds to a targeted portion of the pre-mRNA;
 (b) modulates binding of a factor involved in splicing of the NMD exon; or
 (c) a combination of (a) and (b).

Embodiment 3. The method of embodiment 2, wherein the agent interferes with binding of the factor involved in splicing of the NMD exon to a region of the targeted portion Embodiment 4. The method of embodiment 2, wherein the targeted portion of the pre-mRNA is proximal to the NMD exon.

Embodiment 5. The method of embodiment 2, wherein the targeted portion of the pre-mRNA is at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream of 5' end of the NMD exon.

Embodiment 6. The method of embodiment 2, wherein the targeted portion of the pre-mRNA is at least about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides, about 40 nucleotides, about 30 nucleotides, about 20 nucleotides, about 10 nucleotides, about 5 nucleotides, about 4 nucleotides, about 2 nucleotides, about 1 nucleotides upstream of 5' end of the NMD exon.

Embodiment 7. The method of embodiment 2, wherein the targeted portion of the pre-mRNA is at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream of 3' end of the NMD exon.

Embodiment 8. The method of embodiment 2, wherein the targeted portion of the pre-mRNA is at least about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides, about 40 nucleotides, about 30 nucleotides, about 20 nucleotides, about 10 nucleotides, about 5 nucleotides, about 4 nucleotides, about 2 nucleotides, about 1 nucleotides downstream of 3' end of the NMD exon.

Embodiment 9. The method of embodiment 2, wherein the targeted portion of the pre-mRNA is at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream of genomic site GRCh38/hg38: chr3 193628509.

Embodiment 10. The method of embodiment 2, wherein the targeted portion of the pre-mRNA is about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream of genomic site GRCh38/hg38: chr3 193628509.

Embodiment 11. The method of embodiment 2, wherein the targeted portion of the pre-mRNA is at most about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream of genomic site GRCh38/hg38: chr3 193628616.

Embodiment 12. The method of embodiment 2, wherein the targeted portion of the pre-mRNA is about 1500 nucleotides, about 1000 nucleotides, about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream of genomic site GRCh38/hg38: chr3 193628616.

Embodiment 13. The method of embodiment 2, wherein the targeted portion of the pre-mRNA is located in an intronic region between two canonical exonic regions of the pre-mRNA, and wherein the intronic region contains the NMD exon.

Embodiment 14. The method of embodiment 2, wherein the targeted portion of the pre-mRNA at least partially overlaps with the NMD exon.

Embodiment 15. The method of embodiment 2, wherein the targeted portion of the pre-mRNA at least partially overlaps with an intron upstream or downstream of the NMD exon.

Embodiment 16. The method of embodiment 2, wherein the targeted portion of the pre-mRNA comprises 5' NMD exon-intron junction or 3' NMD exon-intron junction.

Embodiment 17. The method of embodiment 2, wherein the targeted portion of the pre-mRNA is within the NMD exon.

Embodiment 18. The method of embodiment 2, wherein the targeted portion of the pre-mRNA comprises about 5, 6, 7, 8, 9, 10, 11, 12, 13, 14, 15, 16, 17, 18, 19, 20, 21, 22, 23, 24, 25, 26, 27, 28, 29, 30, or more consecutive nucleotides of the NMD exon.

Embodiment 19. The method of any one of embodiments 1 to 18, wherein the NMD exon comprises a sequence with at least 80%, at least 90%, or 100% sequence identity to SEQ ID NO: 279.

Embodiment 20. The method of any one of embodiments 1 to 18, wherein the NMD exon comprises a sequence of SEQ ID NO: 279.

Embodiment 21. The method of embodiment 2, wherein the targeted portion of the pre-mRNA is within the non-sense mediated RNA decay-inducing exon GRCh38/hg38: chr3 193628509 to 193628616.

Embodiment 22. The method of embodiment 2, wherein the targeted portion of the pre-mRNA is upstream or downstream of the non-sense mediated RNA decay-inducing exon GRCh38/hg38: chr3 193628509 to 193628616.

Embodiment 23. The method of embodiment 2, wherein the targeted portion of the pre-mRNA comprises an exon-intron junction of exon GRCh38/hg38: chr3 193628509 to 193628616.

Embodiment 24. The method of any one of embodiments 1 to 23, wherein the OPA1 protein expressed from the processed mRNA is a full-length OPA1 protein or a wild-type OPA1 protein.

Embodiment 25. The method of any one of embodiments 1 to 23, wherein the OPA1 protein expressed from the processed mRNA is a functional OPA1 protein.

Embodiment 26. The method of any one of embodiments 1 to 23, wherein the OPA1 protein expressed from the processed mRNA is at least partially functional as compared to a wild-type OPA1 protein.

Embodiment 27. The method of any one of embodiments 1 to 23, wherein the OPA1 protein expressed from the processed mRNA is at least partially functional as compared to a full-length wild-type OPA1 protein.

Embodiment 28. The method of any one of embodiments 1 to 23, or 25 to 27, wherein the OPA1 protein expressed from the processed mRNA is an OPA1 protein that lacks an amino acid sequence encoded by a nucleic acid sequence with at least 80% sequence identity to SEQ ID NO: 277.

Embodiment 29. The method of any one of embodiments 1 to 28, wherein the method promotes exclusion of the NMD exon from the pre-mRNA.

Embodiment 30. The method of embodiment 29, wherein the exclusion of the NMD exon from the pre-mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent.

Embodiment 31. The method of any one of embodiments 1 to 30, wherein the method results in an increase in the level of the processed mRNA in the cell.

Embodiment 32. The method of embodiment 31, wherein the level of the processed mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent.

Embodiment 33. The method of any one of embodiments 1 to 32, wherein the method results in an increase in the expression of the OPA1 protein in the cell.

Embodiment 34. The method of embodiment 33, wherein a level of the OPA1 protein expressed from the processed mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent.

Embodiment 35. The method of any one of embodiments 1 to 34, wherein the agent comprises an antisense oligomer with at least 80%, at least 90%, or 100% sequence identity to a sequence selected from the group consisting of SEQ ID NOs: 36, 236, 242, 250, 280-283, 288, and 290-292.

Embodiment 36. The method of any one of embodiments 1 to 34, wherein the agent further comprises a gene editing molecule.

Embodiment 37. The method of embodiment 36, wherein the gene editing molecule comprises CRISPR-Cas9.

Embodiment 38. A method of modulating expression of an OPA1 protein in a cell having a pre-mRNA that is transcribed from an OPA1 gene, wherein the pre-mRNA comprises a coding exon, the method comprising contacting an agent or a vector encoding the agent to the cell, whereby the agent promotes exclusion of the coding exon from the pre-mRNA, thereby increasing a level of a processed mRNA that is processed from the pre-mRNA and that lacks the coding exon in the cell.

Embodiment 39. The method of embodiment 38, wherein the agent:
  (a) binds to a targeted portion of the pre-mRNA;
  (b) modulates binding of a factor involved in splicing of the coding exon; or
  (c) a combination of (a) and (b).

Embodiment 40. The method of embodiment 39, wherein the agent interferes with binding of the factor involved in splicing of the coding exon to a region of the targeted portion.

Embodiment 41. The method of embodiment 39, wherein the targeted portion of the pre-mRNA is proximal to the coding exon.

Embodiment 42. The method of embodiment 39, wherein the targeted portion of the pre-mRNA is located in an intronic region immediately upstream of the coding exon.

Embodiment 43. The method of embodiment 39, wherein the targeted portion of the pre-mRNA is within a region spanning from 100 to 50, from 90 to 50, from 80 to 50, from 70 to 50, from 60 to 50, from 60 to 40, from 60 to 30, from 60 to 20, from 60 to 10, from 49 to 1, from 39 to 1, from 29 to 1, or from 19 to 1 nucleotides upstream of 5' end of the coding exon.

Embodiment 44. The method of embodiment 39, wherein the targeted portion of the pre-mRNA is within a region spanning from 49 to 1, from 39 to 1, from 29 to 1, or from 19 to 1 nucleotides upstream of 5' end of the coding exon.

Embodiment 45. The method of embodiment 39, wherein the targeted portion of the pre-mRNA is located in an intronic region immediately downstream of the coding exon.

Embodiment 46. The method of embodiment 39, wherein the targeted portion of the pre-mRNA is within a region spanning from 1 to 49, from 1 to 39, from 1 to 29, from 1 to 19, from 10 to 60, from 20 to 60, from 30 to 60, from 40 to 60, from 50 to 60, from 50 to 70, from 50 to 80, from 50 to 90, or from 50 to 100 nucleotides downstream of 3' end of the coding exon.

Embodiment 47. The method of embodiment 39, wherein the targeted portion of the pre-mRNA is within a region spanning from 1 to 49, from 1 to 39, from 1 to 29, or from 1 to 19 nucleotides downstream of 3' end of the coding exon.

Embodiment 48. The method of embodiment 39, wherein the targeted portion of the pre-mRNA at least partially overlaps with the coding exon.

Embodiment 49. The method of embodiment 39, wherein the targeted portion of the pre-mRNA at least partially overlaps with an intron immediately upstream or immediately downstream of the coding exon.

Embodiment 50. The method of embodiment 39, wherein the targeted portion of the pre-mRNA comprises 5' coding exon-intron junction or 3' coding exon-intron junction.

Embodiment 51. The method of embodiment 39, wherein the targeted portion is within the coding exon of the pre-mRNA.

Embodiment 52. The method of any one of embodiments 39 to 51, wherein the coding exon is an alternatively spliced exon.

Embodiment 53. The method of any one of embodiments 39 to 52, wherein the coding exon comprises a sequence with at least 80%, at least 90%, or 100% sequence identity to SEQ ID NO: 277.

Embodiment 54. The method of any one of embodiments 39 to 52, wherein the coding exon comprises SEQ ID NO: 277.

Embodiment 55. The method of embodiment 39, wherein the targeted portion of the pre-mRNA is immediately upstream of the coding exon GRCh38/hg38: chr3 193626092 to 193626202.

Embodiment 56. The method of embodiment 39, wherein the targeted portion of the pre-mRNA is within a region spanning from 49 to 1, from 39 to 1, from 29 to 1, or from 19 to 1 nucleotides upstream of genomic site GRCh38/hg38: chr3 193626092.

Embodiment 57. The method of embodiment 39, wherein the targeted portion of the pre-mRNA is immediately downstream of the coding exon GRCh38/hg38: chr3 193626092 to 193626202.

Embodiment 58. The method of embodiment 39, wherein the targeted portion of the pre-mRNA is within a region spanning from 1 to 49, from 1 to 39, from 1 to 29, or from 1 to 19 nucleotides downstream of genomic site GRCh38/hg38: chr3 193626202.

Embodiment 59. The method of embodiment 39, wherein the targeted portion of the pre-mRNA is within the coding exon GRCh38/hg38: chr3 193626092 to 193626202.

Embodiment 60. The method of embodiment 39, wherein the targeted portion of the pre-mRNA comprises an exon-intron junction of exon GRCh38/hg38: chr3 193626092 to 193626202.

Embodiment 61. The method of embodiment 39, wherein the targeted portion comprises about 5, 6, 7, 8, 9, 10, 11, 12, 13, 14, 15, 16, 17, 18, 19, 20, 21, 22, 23, 24, 25, 26, 27, 28, 29, 30, or more consecutive nucleotides of the coding exon.

Embodiment 62. The method of embodiment 39, wherein the targeted portion of the pre-mRNA comprises a sequence with at least 80%, 85%, 90%, 95%, 97%, or 100% sequence identity to a region comprising at least 8 contiguous nucleic acids of SEQ ID NO: 277.

Embodiment 63. The method of any one of embodiments 38 to 62, wherein the exclusion of the coding exon from the pre-mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent.

Embodiment 64. The method of any one of embodiments 38 to 63, wherein the method results in an increase in expression of the OPA1 protein in the cell.

Embodiment 65. The method of embodiment 64, wherein a level of the OPA1 protein expressed from the processed mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent.

Embodiment 66. The method of embodiment 64, wherein a level of the OPA1 protein expressed from the processed mRNA in the cell contacted with the agent is increased by at least about 1.5-fold compared to in the absence of the agent.

Embodiment 67. The method of any one of embodiments 64 to 66, wherein the OPA1 protein expressed from the processed mRNA is a functional OPA1 protein.

Embodiment 68. The method of any one of embodiments 64 to 66, wherein the OPA1 protein expressed from the processed mRNA is at least partially functional as compared to a wild-type OPA1 protein.

Embodiment 69. The method of any one of embodiments 64 to 66, wherein the OPA1 protein expressed from the processed mRNA is at least partially functional as compared to a full-length wild-type OPA1 protein.

Embodiment 70. The method of any one of embodiments 64 to 69, wherein the OPA1 protein expressed from the processed mRNA comprises fewer proteolytic cleavage sites than an OPA1 protein encoded by a corresponding mRNA containing the coding exon.

Embodiment 71. The method of any one of embodiments 38 to 70, wherein the agent promotes exclusion of a nonsense mediated RNA decay-inducing exon (NMD exon) from the pre-mRNA.

Embodiment 72. The method of embodiment 71, wherein the NMD exon comprises a sequence with at least 80%, at least 90%, or 100% sequence identity to SEQ ID NO: 279.

Embodiment 73. The method of embodiment 71, wherein the NMD exon comprises a sequence of SEQ ID NO: 279.

Embodiment 74. The method of any one of embodiments 64 to 73, wherein the OPA1 protein expressed from the processed mRNA comprises fewer proteolytic cleavage sites than an OPA1 protein encoded by a corresponding mRNA containing the coding exon.

Embodiment 75. The method of any one of embodiments 38 to 74, wherein the agent comprises an antisense oligomer with at least 80%, at least 90%, or 100% sequence identity to a sequence selected from the group consisting of SEQ ID NOs: 227-242, 250, 280-283, 288, and 290-292.

Embodiment 76. The method of any one of embodiments 38 to 74, wherein the agent comprises a gene editing molecule.

Embodiment 77. The method of embodiment 76, wherein the gene editing molecule comprises CRISPR-Cas9.

Embodiment 78. A method of modulating expression of an OPA1 protein in a cell having a pre-mRNA that is transcribed from an OPA1 gene, wherein the pre-mRNA comprises a coding exon, the method comprising contacting an agent or a vector encoding the agent to the cell,
wherein the agent comprises an antisense oligomer that binds to:
(a) a targeted portion of the pre-mRNA within an intronic region immediately upstream of a 5' end of the coding exon of the pre-mRNA; or
(b) a targeted portion of the pre-mRNA within an intronic region immediately downstream of a 3' end of the coding exon of the pre-mRNA;
whereby the agent increases a level of a processed mRNA that is processed from the pre-mRNA and that contains the coding exon in the cell.

Embodiment 79. The method of embodiments 78, wherein the coding exon is an alternatively spliced exon.

Embodiment 80. The method of embodiments 78 or 79, wherein the method promotes inclusion of the coding exon in the processed mRNA during splicing of the pre-mRNA in the cell.

Embodiment 81. The method of any one of embodiments 78 to 80, wherein the target portion of the pre-mRNA is within a region spanning from 100 to 50, from 100 to 60, from 100 to 70, from 100 to 80, or from 100 to 90 nucleotides upstream of a 5' end of the coding exon.

Embodiment 82. The method of any one of embodiments 78 to 80, wherein the target portion of the pre-mRNA is within a region spanning from 40 to 100, from 50 to 100, from 60 to 100, from 70 to 100, from 80 to 100, or from 90 to 100 nucleotides downstream of a 3' end of the coding exon.

Embodiment 83. The method of any one of embodiments 78 to 80, wherein the coding exon comprises a sequence with at least 80%, at least 90%, or 100% sequence identity to SEQ ID NO: 277.

Embodiment 84. The method of any one of embodiments 78 to 80, wherein the coding exon comprises SEQ ID NO: 277.

Embodiment 85. The method of any one of embodiments 78 to 80, wherein the targeted portion of the pre-mRNA is within a region spanning from 100 to 50, from 100 to 60, from 100 to 70, from 100 to 80, or from 100 to 90 nucleotides upstream of genomic site GRCh38/hg38: chr3 193626092.

Embodiment 86. The method of any one of embodiments 78 to 80, wherein the targeted portion of the pre-mRNA is within a region spanning from 40 to 100, from 50 to 100, from 60 to 100, from 70 to 100, from 80 to 100, or from 90 to 100 nucleotides downstream of genomic site GRCh38/hg38: chr3 193626202.

Embodiment 87. The method of any one of embodiments 78 to 86, wherein the inclusion of the coding exon in the processed mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent.

Embodiment 88. The method of any one of embodiments 78 to 87, wherein the agent comprises an antisense oligomer with at least 80%, at least 90%, or 100% sequence identity to SEQ ID NO: 267.

Embodiment 89. A method of modulating expression of a target protein in a cell having a pre-mRNA transcribed from a gene that encodes the target protein, wherein the pre-mRNA comprises a coding exon and a non-sense mediated RNA decay-inducing exon (NMD exon), the method comprising contacting an agent or a vector encoding the agent to the cell,
  wherein the agent promotes exclusion of both the coding exon and the NMD exon from the pre-mRNA, thereby increasing a level of a processed mRNA that is processed from the pre-mRNA and that lacks both the NMD exon and the coding exon in the cell.

Embodiment 90. The method of embodiment 89, wherein the agent:
  (a) binds to a targeted portion of the pre-mRNA;
  (b) modulates binding of a factor involved in splicing of the coding exon, the NMD exon, or both; or
  (c) a combination of (a) and (b).

Embodiment 91. The method of embodiment 90, wherein the agent interferes with binding of the factor involved in splicing of the coding exon, the NMD exon, or both, to a region of the targeted portion.

Embodiment 92. The method of any one of embodiments 89 to 91, wherein the NMD exon is within an intronic region adjacent to the coding exon.

Embodiment 93. The method of embodiment 92, wherein the NMD exon is within an intronic region immediately upstream of the coding exon.

Embodiment 94. The method of embodiment 92, wherein the NMD exon is within an intronic region immediately downstream of the coding exon.

Embodiment 95. The method of any one of embodiments 90 to 94, wherein the targeted portion of the pre-mRNA is proximal to the coding exon.

Embodiment 96. The method of any one of embodiments 90 to 94, wherein the targeted portion of the pre-mRNA is located in an intronic region immediately upstream of the coding exon.

Embodiment 97. The method of any one of embodiments 90 to 94, wherein the targeted portion of the pre-mRNA is located in an intronic region immediately downstream of the coding exon.

Embodiment 98. The method of any one of embodiments 90 to 94, wherein the targeted portion of the pre-mRNA is located within the coding exon.

Embodiment 99. The method of any one of embodiments 90 to 94, wherein the targeted portion of the pre-mRNA is within a region spanning from 49 to 1, from 39 to 1, from 29 to 1, or from 19 to 1 nucleotides upstream of 5' end of the coding exon.

Embodiment 100. The method of any one of embodiments 90 to 94, wherein the targeted portion of the pre-mRNA is within a region spanning from 100 nucleotides upstream of the coding exon to 100 nucleotides downstream of the coding exon.

Embodiment 101. The method of any one of embodiments 89 to 100, wherein the coding exon is an alternatively spliced exon.

Embodiment 102. The method of any one of embodiments 89 to 101, wherein the coding exon comprises a sequence with at least 80%, at least 90%, or 100% sequence identity to SEQ ID NO: 277.

Embodiment 103. The method of any one of embodiments 89 to 101, wherein the coding exon comprises SEQ ID NO: 277.

Embodiment 104. The method of embodiment 90, wherein the targeted portion of the pre-mRNA is immediately upstream of the coding exon GRCh38/hg38: chr3 193626092 to 193626202.

Embodiment 105. The method of embodiment 90, wherein the targeted portion of the pre-mRNA is immediately downstream of the coding exon GRCh38/hg38: chr3 193626092 to 193626202.

Embodiment 106. The method of any one of embodiments 90 to 94, wherein the targeted portion of the pre-mRNA is within a region spanning from 49 to 1, from 39 to 1, from 29 to 1, or from 19 to 1 nucleotides upstream of GRCh38/hg38: chr3 193626092.

Embodiment 107. The method of embodiment 90, wherein the targeted portion of the pre-mRNA is within a region spanning from 100 nucleotides upstream of genomic site GRCh38/hg38: chr3 193626092. to 100 nucleotides downstream of genomic site GRCh38/hg38: chr3 193626202.

Embodiment 108. The method of embodiment 90, wherein the targeted portion of the pre-mRNA is within the coding exon GRCh38/hg38: chr3 193626092 to 193626202.

Embodiment 109. The method of embodiment 90, wherein the targeted portion of the pre-mRNA comprises an exon-intron junction of the coding exon GRCh38/hg38: chr3 193626092 to 193626202.

Embodiment 110. The method of embodiment 90, wherein the targeted portion comprises about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more consecutive nucleotides of the coding exon.

Embodiment 111. The method of embodiment 90, wherein the targeted portion of the pre-mRNA is proximal to the NMD exon.

Embodiment 112. The method of embodiment 90, wherein the targeted portion of the pre-mRNA is located in an intronic region immediately upstream of the NMD exon.

Embodiment 113. The method of embodiment 90, wherein the targeted portion of the pre-mRNA is located in an intronic region immediately downstream of the NMD exon.

Embodiment 114. The method of embodiment 90, wherein the targeted portion of the pre-mRNA is located within the NMD exon.

Embodiment 115. The method of embodiment 90, wherein the targeted portion of the pre-mRNA is within a region spanning from 100 nucleotides upstream of the NMD exon to 100 nucleotides downstream of the NMD exon.

Embodiment 116. The method of any one of embodiments 89 to 115, wherein the NMD exon comprises a sequence with at least 80%, at least 90%, or 100% sequence identity to SEQ ID NO: 279.

Embodiment 117. The method of embodiment 89, wherein the NMD exon comprises SEQ ID NO: 279.

Embodiment 118. The method of embodiment 90, wherein the targeted portion of the pre-mRNA is immediately upstream of the NMD exon GRCh38/hg38: chr3 193628509 to 193628616.

Embodiment 119. The method of embodiment 90, wherein the targeted portion of the pre-mRNA is immediately downstream of the NMD exon GRCh38/hg38: chr3 193628509 to 193628616.

Embodiment 120. The method of embodiment 90, wherein the targeted portion of the pre-mRNA is within a region spanning from 100 nucleotides upstream of genomic site GRCh38/hg38: chr3 193628509 to 100 nucleotides downstream of genomic site GRCh38/hg38: chr3 193628616.

Embodiment 121. The method of embodiment 90, wherein the targeted portion of the pre-mRNA is within the NMD exon GRCh38/hg38: chr3 193628509 to 193628616.

Embodiment 122. The method of embodiment 90, wherein the targeted portion of the pre-mRNA comprises an exon-intron junction of the NMD exon GRCh38/hg38: chr3 193628509 to 193628616.

Embodiment 123. The method of embodiment 90, wherein the targeted portion comprises about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more consecutive nucleotides of the NMD exon.

Embodiment 124. The method of any one of embodiments 89 to 123, wherein the exclusion of the coding exon from the pre-mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent.

Embodiment 125. The method of any one of embodiments 89 to 124, wherein the exclusion of the NMD exon from the pre-mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent.

Embodiment 126. The method of any one of embodiments 89 to 125, wherein the agent results in an increase in the level of the processed mRNA in the cell.

Embodiment 127. The method of embodiment 126, wherein the level of the processed mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent.

Embodiment 128. The method of any one of embodiments 89 to 127, wherein the method results in an increase in expression of the target protein in the cell.

Embodiment 129. The method of embodiment 128, wherein a level of the target protein expressed from the processed mRNA in the cell contacted with the agent is increased by about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to in the absence of the agent.

Embodiment 130. The method of any one of embodiments 89 to 128, wherein the target protein is an OPA1 protein.

Embodiment 131. The method of embodiment 130, wherein a level of the OPA1 protein expressed from the processed mRNA in the cell contacted with the agent is increased by at least about 1.5-fold compared to in the absence of the agent.

Embodiment 132. The method of embodiment 130, wherein the OPA1 protein expressed from the processed mRNA is a functional OPA1 protein.

Embodiment 133. The method of embodiment 130, wherein the OPA1 protein expressed from the processed mRNA is at least partially functional as compared to a wild-type OPA1 protein.

Embodiment 134. The method of embodiment 130, wherein the OPA1 protein expressed from the processed mRNA is at least partially functional as compared to a full-length wild-type OPA1 protein.

Embodiment 135. The method of any one of embodiments 89 to 127, wherein the agent comprises an antisense oligomer with at least 80%, at least 90%, or 100% sequence identity to a sequence selected from the group consisting of SEQ ID NOs: 236, 242, 250, 280-283, 288, and 290-292.

Embodiment 136. The method of any one of embodiments 78 to 135, wherein the agent comprises a gene editing molecule.

Embodiment 137. The method of embodiment 136, wherein the gene editing molecule comprises CRISPR-Cas9.

Embodiment 138. The method of any one of embodiments 1 to 75 or 78 to 135, wherein the agent is an antisense oligomer (ASO) and wherein the antisense oligomer comprises a backbone modification comprising a phosphorothioate linkage or a phosphorodiamidate linkage.

Embodiment 139. The method of any one of embodiments 1 to 75 or 78 to 138, wherein the agent is an antisense oligomer (ASO) and wherein the antisense oligomer comprises a phosphorodiamidate morpholino, a locked nucleic acid, a peptide nucleic acid, a 2'-O-methyl moiety, a 2'-Fluoro moiety, or a 2'-O-methoxyethyl moiety.

Embodiment 140. The method of any one of embodiments 1 to 75 or 78 to 139, wherein the therapeutic agent is an antisense oligomer (ASO) and wherein the antisense oligomer comprises at least one modified sugar moiety.

Embodiment 141. The method of embodiment 140, wherein each sugar moiety is a modified sugar moiety.

Embodiment 142. The method of any one of embodiments 1 to 75 or 78 to 141, wherein the agent is an antisense oligomer (ASO) and wherein the antisense oligomer consists of from 8 to 50 nucleobases, 8 to 40 nucleobases, 8 to 35 nucleobases, 8 to 30 nucleobases, 8 to 25 nucleobases, 8 to 20 nucleobases, 8 to 15 nucleobases, 9 to 50 nucleobases, 9 to 40 nucleobases, 9 to 35 nucleobases, 9 to 30 nucleobases, 9 to 25 nucleobases, 9 to 20 nucleobases, 9 to 15 nucleobases, 10 to 50 nucleobases, 10 to 40 nucleobases, 10 to 35 nucleobases, 10 to 30 nucleobases, 10 to 25 nucleobases, 10 to 20 nucleobases, 10 to 15 nucleobases, 11 to 50 nucleobases, 11 to 40 nucleobases, 11 to 35 nucleobases, 11 to 30 nucleobases, 11 to 25 nucleobases, 11 to 20 nucleobases, 11 to 15 nucleobases, 12 to 50 nucleobases, 12 to 40 nucleobases, 12 to 35 nucleobases, 12 to 30 nucleobases, 12 to 25 nucleobases, 12 to 20 nucleobases, or 12 to 15 nucleobases.

Embodiment 143. The method of any one of embodiments 1 to 142, wherein the vector comprises a viral vector encoding the agent.

Embodiment 144. The method of embodiment 143, wherein the viral vector comprises an adenoviral vector, adeno-associated viral (AAV) vector, lentiviral vector, Herpes Simplex Virus (HSV) viral vector, or retroviral vector.

Embodiment 145. The method of any one of embodiments 1 to 144, wherein the method further comprises assessing mRNA level or expression level of the OPA1 protein.

Embodiment 146. The method of any one of embodiments 1 to 145, wherein the agent is a therapeutic agent.

Embodiment 147. A pharmaceutical composition comprising the therapeutic agent of embodiment 146 or a vector encoding the therapeutic agent of embodiment 146, and a pharmaceutically acceptable excipient.

Embodiment 148. A pharmaceutical composition, comprising a therapeutic agent or a vector encoding a therapeutic agent, and a pharmaceutically acceptable excipient, wherein the therapeutic agent comprises an antisense oligomer with at least 80% sequence identity to a sequence selected from the group consisting of SEQ ID NOs: 6-275 and 280-299.

Embodiment 149. The pharmaceutical composition of embodiment 148, wherein the therapeutic agent comprises an antisense oligomer with at least 80%, at least 90%, or 100% sequence identity to a sequence selected from the group consisting of SEQ ID NOs: 227-242 and 250.

Embodiment 150. The pharmaceutical composition of embodiment 148, wherein the therapeutic agent comprises an antisense oligomer with at least 80%, at least 90%, or 100% sequence identity to SEQ ID NO: 267.

Embodiment 151. The pharmaceutical composition of embodiment 148, wherein the therapeutic agent comprises an antisense oligomer with at least 80%, at least 90%, or 100% sequence identity to a sequence selected from the group consisting of SEQ ID NOs: 36, 236, 242, 250, and 280-299.

Embodiment 152. A composition, comprising an antisense oligomer with at least 80% sequence identity to a sequence selected from the group consisting of SEQ ID NOs: 6-275 and 280-299, wherein the antisense oligomer comprises a backbone modification, a sugar moiety modification, or a combination thereof.

Embodiment 153. The composition of embodiment 152, wherein the antisense oligomer has at least 80%, at least 90%, or 100% sequence identity to a sequence selected from the group consisting of SEQ ID NOs: 227-242 and 250.

Embodiment 154. The composition of embodiment 152, wherein the antisense oligomer has at least 80%, at least 90%, or 100% sequence identity to SEQ ID NO: 267.

Embodiment 155. The composition of embodiment 152, wherein the antisense oligomer has at least 80%, at least 90%, or 100% sequence identity to a sequence selected from the group consisting of SEQ ID NOs: 36, 236, 242, 250, and 280-299.

Embodiment 156. A pharmaceutical composition, comprising a therapeutic agent or a vector encoding the therapeutic agent, and a pharmaceutically acceptable excipient, wherein the therapeutic agent promotes exclusion of a coding exon from a pre-mRNA, thereby increasing a level of a processed mRNA that is processed from the pre-mRNA and that lacks the coding exon in a cell, wherein the pre-mRNA is transcribed from an OPA1 gene and that comprises the coding exon.

Embodiment 157. A pharmaceutical composition, comprising a therapeutic agent or a vector encoding the therapeutic agent, and a pharmaceutically acceptable excipient, wherein the therapeutic agent comprises an antisense oligomer that binds to a pre-mRNA that is transcribed from an OPA1 gene in a cell, wherein the antisense oligomer binds to:

(a) a targeted portion of the pre-mRNA within an intronic region immediately upstream of a 5' end of the coding exon of the pre-mRNA; or (b) a targeted portion of the pre-mRNA within an intronic region immediately downstream of a 3' end of the coding exon of the pre-mRNA;

whereby the therapeutic agent increases a level of a processed mRNA that is processed from the pre-mRNA and that contains the coding exon in the cell.

Embodiment 158. A pharmaceutical composition, comprising a therapeutic agent or a vector encoding the therapeutic agent, and a pharmaceutically acceptable excipient, wherein the therapeutic agent promotes exclusion of both a coding exon and a non-sense mediated RNA decay-inducing exon (NMD exon) from a pre-mRNA, thereby increasing a level of a processed mRNA that is processed from the pre-mRNA and that lacks the coding exon and the NMD exon in a cell, wherein the pre-mRNA is transcribed from an OPA1 gene in the cell and comprises the coding exon and the NMD exon.

Embodiment 159. The pharmaceutical composition of any one of embodiments 147 to 158, wherein the pharmaceutical composition is formulated for intracerebroventricular injection, intraperitoneal injection, intramuscular injection, intrathecal injection, subcutaneous injection, oral administration, synovial injection, intravitreal administration, subretinal injection, topical application, implantation, or intravenous injection.

Embodiment 160. The pharmaceutical composition of any one of embodiments 147 to 158, wherein the pharmaceutical composition is formulated for intravitreal injection.

Embodiment 161. The pharmaceutical composition of any one of embodiments 147 to 160, wherein the pharmaceutical composition further comprises a second therapeutic agent.

Embodiment 162. The pharmaceutical composition of embodiment 161, wherein the second therapeutic agent comprises a small molecule.

Embodiment 163. The pharmaceutical composition of embodiment 161, wherein the second therapeutic agent comprises an antisense oligomer.

Embodiment 164. The pharmaceutical composition of embodiment 161, wherein the second therapeutic agent corrects intron retention.

Embodiment 165. The pharmaceutical composition or composition of any one of embodiments 147 to 160, wherein the antisense oligomer is selected from the group consisting of Compound ID NOs: 1-303.

Embodiment 166. A method of treating or reducing the likelihood of developing a disease or condition in a subject in need thereof by modulating expression of an OPA1 protein in a cell of the subject, comprising contacting to cells of the subject the therapeutic agent of any one of embodiments 147 to 165.

Embodiment 167. The method of embodiment 166, wherein the disease or condition is associated with a loss-of-function mutation in an OPA1 gene.

Embodiment 168. The method of embodiment 166 or 167, wherein the disease or condition is associated with haploinsufficiency of the OPA1 gene, and wherein the subject has a first allele encoding a functional OPA1 protein, and a second allele from which the OPA1 protein is not produced or produced at a reduced level, or a second allele encoding a nonfunctional OPA1 protein or a partially functional OPA1 protein.

Embodiment 169. The method of any one of embodiments 166 to 168, wherein the disease or condition comprises an eye disease or condition.

Embodiment 170. The method of any one of embodiments 166 to 168, wherein the disease or condition comprises ADOA-plus syndrome; a mitochondrial disorder; glaucoma; normal tension glaucoma; Charcot-Marie-Tooth disease; mitochondria dysfunction; diabetic retinopathy; age-related macular degeneration; retinal ganglion cell death; mitochondrial fission-mediated mitochondrial dysfunction; progressive external ophthalmoplegia; deafness; ataxia; motor neuropathy; sensory neuropathy; myopathy; Behr syndrome; brain dysfunction; encephalopathy; peripheral neuropathy; fatal infantile mitochondrial encephalomyopathy; hypertrophic cardiomyopathy; spastic ataxic syndrome; sensory motor peripheral neuropathy; hypotonia; gastrointestinal dysmotility and dysphagia; optic atrophy; optic atrophy plus syndrome; Mitochondrial DNA depletion syndrome 14; late-onset cardiomyopathy; diabetic cardiomyopathy; Alzheimer's Disease; focal segmental glomerulosclerosis; kidney disease; Huntington's Disease; cognitive function decline in healthy aging; Prion diseases; late onset dementia and parkinsonism; mitochondrial myopathy; Leigh syndrome; Friedreich's ataxia; Parkinson's disease; MELAS (Mitochondrial encephalomyopathy, lactic acidosis, and stroke-like episodes); pyruvate dehydrogenase complex deficiency; chronic kidney disease; Leber's hereditary optic neuropathy; obesity; age-related systemic neurodegeneration; skeletal muscle atrophy; heart and brain ischemic damage; or massive liver apoptosis.

Embodiment 171. The method of any one of embodiments 166 to 168, wherein the disease or condition comprises Optic atrophy type 1.

Embodiment 172. The method of any one of embodiments 166 to 168, wherein the disease or condition comprises autosomal dominant optic atrophy (ADOA).

Embodiment 173. The method of embodiment 166 or 167, wherein the disease or condition is associated with an autosomal recessive mutation of OPA1 gene, wherein the subject has a first allele encoding from which:

(i) OPA1 protein is not produced or produced at a reduced level compared to a wild-type allele; or (ii) the OPA1 protein produced is nonfunctional or partially functional compared to a wild-type allele, and a second allele from which:

(iii) the OPA1 protein is produced at a reduced level compared to a wild-type allele and the OPA1 protein produced is at least partially functional compared to a wild-type allele; or (iv) the OPA1 protein produced is partially functional compared to a wild-type allele.

Embodiment 174. The method of any one of embodiments 166 to 173, wherein the subject is a human.

Embodiment 175. The method of any one of embodiments 166 to 173, wherein the subject is a non-human animal.

Embodiment 176. The method of any one of embodiments 166 to 173, wherein the subject is a fetus, an embryo, or a child.

Embodiment 177. The method of any one of embodiments 166 to 173, wherein the cells are ex vivo.

Embodiment 178. The method of any one of embodiments 166 to 173, wherein the therapeutic agent is administered by intracerebroventricular injection, intraperitoneal injection, intramuscular injection, intrathecal injection, subcutaneous injection, oral administration, synovial injection, intravitreal administration, subretinal injection, topical application, implantation, or intravenous injection.

Embodiment 179. The method of any one of embodiments 166 to 173, wherein the therapeutic agent is administered by intravitreal injection.

Embodiment 180. The method of any one of embodiments 166 to 179, wherein the method treats the disease or condition.

EXAMPLES

The present disclosure will be more specifically illustrated by the following Examples. However, it should be understood that the present disclosure is not limited by these examples in any manner.

Figure 2:
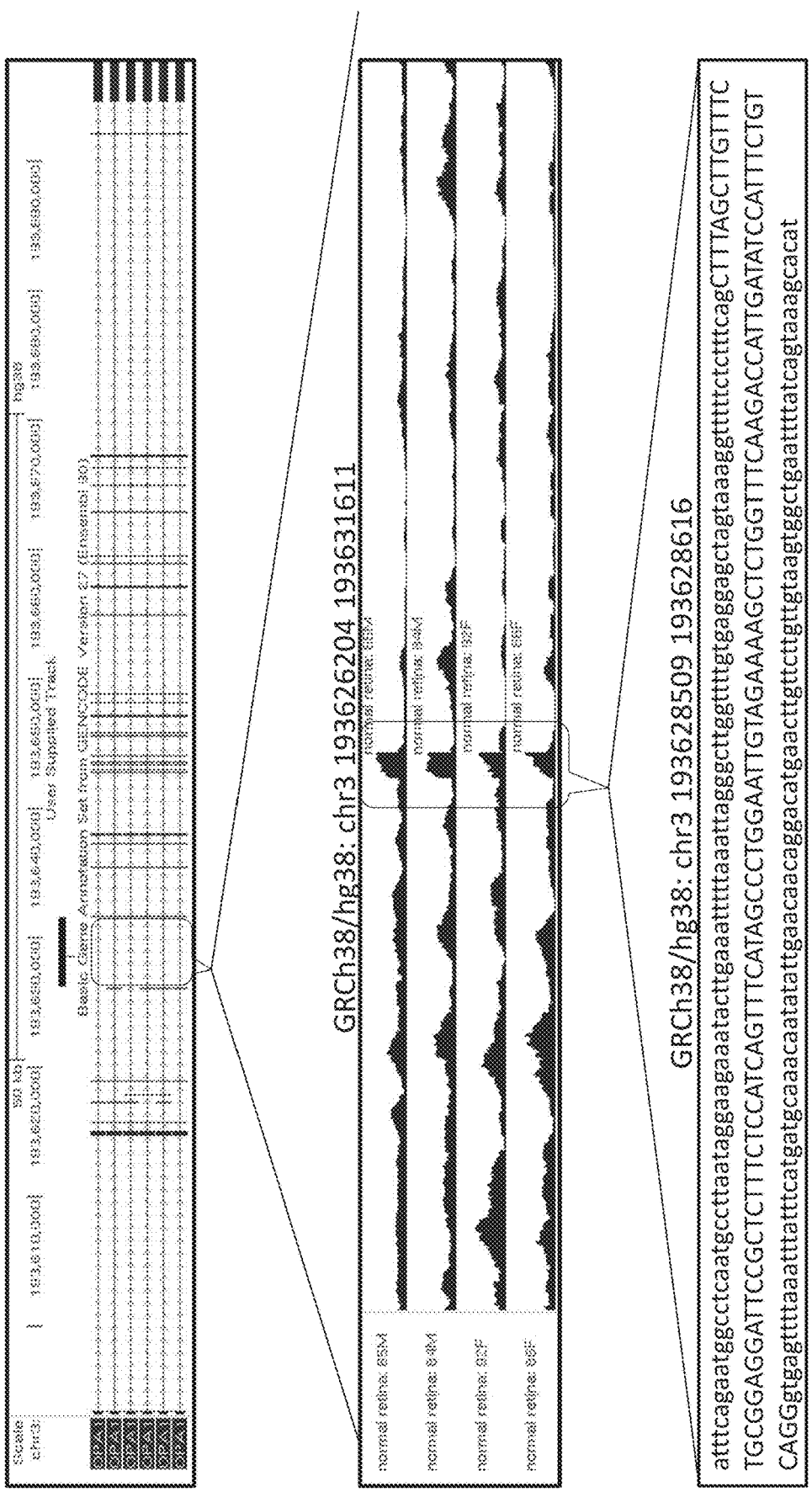
FIG. 2 depicts identification of an exemplary nonsense-mediated mRNA decay (NMD)-inducing exon in the OPA1 gene. The identification of the NMD-inducing exon in the OPA1 gene using RNA sequencing is shown, visualized in the UCSC genome browser. The upper panel shows a graphic representation of the OPA1 gene to scale. Peaks corresponding to RNA sequencing reads were identified in intron GRCh38/hg38: chr3 193626204 to 193631611, shown in the middle panel. Bioinformatic analysis identified an exon-like sequence (bottom panel, sequence highlighted in uppercase; GRCh38/hg38: chr3 193628509 to 193628616) flanked by 3' and 5' splice sites. Inclusion of this exon leads to the introduction of a premature termination codon rendering the transcript a target of NMD.
Figure 3:
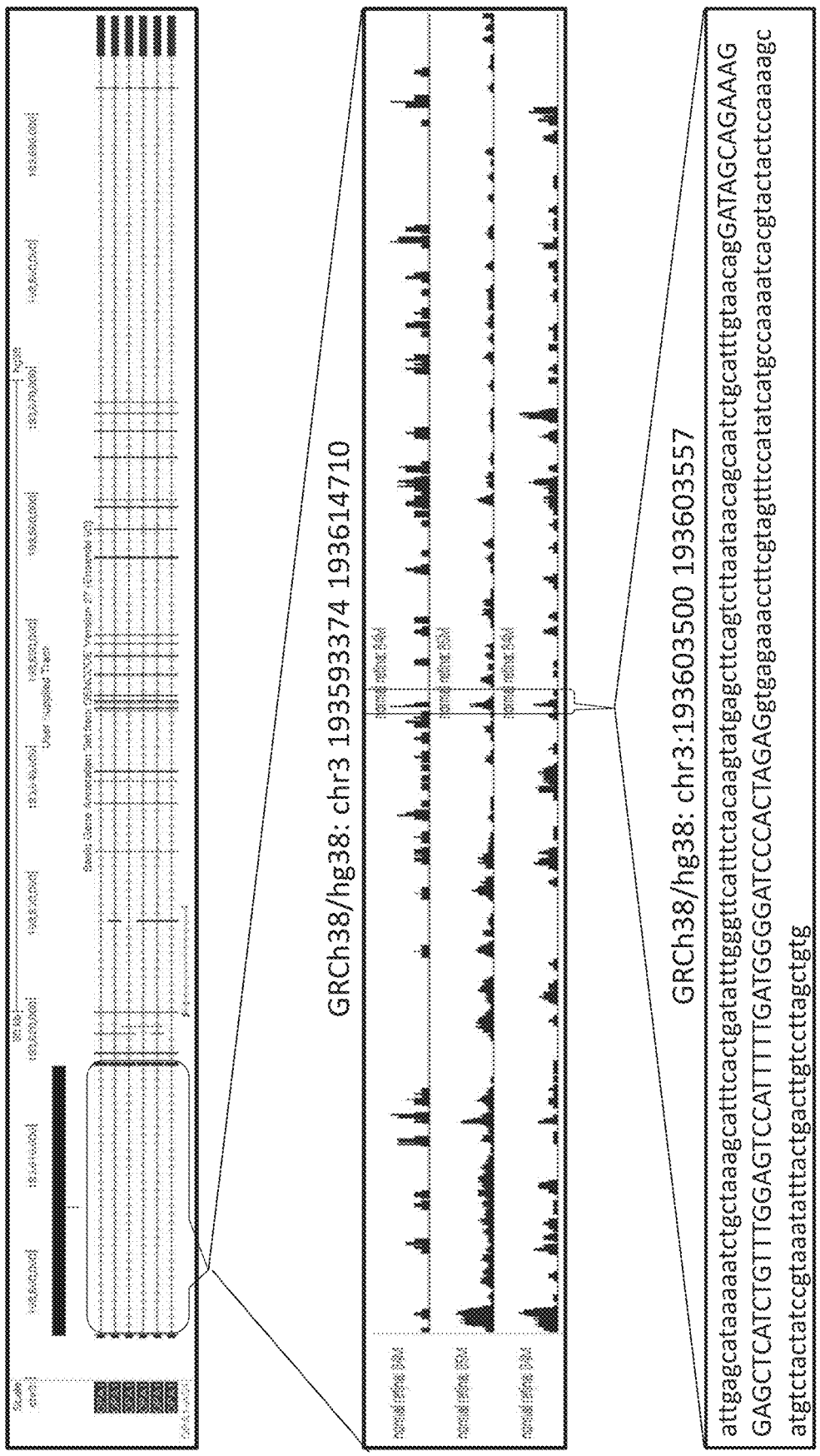
FIG. 3 depicts identification of an exemplary nonsense-mediated mRNA decay (NMD)-inducing exon in the OPA1 gene. The identification of the NMD-inducing exon in the OPA1 gene using RNA sequencing is shown, visualized in the UCSC genome browser. The upper panel shows a graphic representation of the OPA1 gene to scale. Peaks corresponding to RNA sequencing reads were identified in intron GRCh38/hg38: chr3 193593374 to 193614710, shown in the middle panel. Bioinformatic analysis identified an exon-like sequence (bottom panel, sequence highlighted in uppercase; GRCh38/hg38: chr3 193603500 to 193603557) flanked by 3' and 5' splice sites. Inclusion of this exon leads to the introduction of a premature termination codon rendering the transcript a target of NMD.

Example 1: Identification of NMD-Inducing Exon Inclusion Events in Transcripts by RNAseq Using Next Generation Sequencing Whole transcriptome shotgun sequencing is carried out using next generation sequencing to reveal a snapshot of transcripts produced by the genes described herein to identify NMD exon inclusion events. For this purpose, polyA+ RNA from nuclear and cytoplasmic fractions of human cells is isolated and cDNA libraries are constructed using Illumina's TruSeq Stranded mRNA library Prep Kit. The libraries are pair-end sequenced resulting in 100-nucleotide reads that are mapped to the human genome (February 2009, GRCh37/hg19 assembly). FIGS. 2 and 3 depict identification of different exemplary nonsense-mediated mRNA decay (NMD)-inducing exons in various genes.

Exemplary genes and intron sequences are summarized in Table 1 and Table 2 (SEQ ID NOs indicate the corresponding nucleotide sequences represented by the Gene ID Nos). The sequence for each intron is summarized in Table 3 and Table 4. Table 5 lists sequences of OPA1 antisense oligomers of this disclosure.

TABLE 1

List of exemplary target gene sequences.

| Gene Symbol | Gene ID No. | SEQ ID No. | Disease | OMIM | Genetics | Introns |
|---|---|---|---|---|---|---|
| OPA1 | 4976 | 1 | Optic atrophy type 1; Autosomal dominant optic atrophy (ADOA) | 165500 | Haploinsufficient | ENST00000361908.7:6 ENST00000361908.7:28 |

TABLE 2

List of exemplary target gene sequences.

| Gene Symbol | Gene ID No. | SEQ ID No. | Disease | OMIM | Genetics | Introns |
|---|---|---|---|---|---|---|
| OPA1 | 4976 | 1 | Optic atrophy type 1; Autosomal dominant optic atrophy (ADOA) | 165500 | Haploinsufficient | GRCh38/hg38: chr3 193626203 193631611 GRCh38/hg38: chr3 193593374 193614710 |

TABLE 3

Sequences of exemplary target introns in pre-mRNA transcripts.

| Gene | SEQ ID NO. | Intron |
|---|---|---|
| OPA1 | 2 | Intron 6: gtgatggatggtttaagggggctaccgata cattcacactaatcagccatttctgccaag atcatgtcacctcaatctgttcatggactc caaatacaagaaattaatttgacaaagtga aaatataaaagatgcatcatataaatatgt aactttctggagtgggtagtataggtaaa gccaaaagaaacaaattcaagcagaggaat tttggtttctgaaaattaggttgtctgtag ggtccctgtatttatacttagaacaaaatt aggaatttctgtttatgtggtccagttatt gagtcaccctaagtttgtaggcatcttacc tacctacttgctccccaagttttttatttct aaaatgaaaagcattgctgtagatgaccag tttacactaaagaataacatttatttattt gttttagctaaagtatatggacagggaaca ttcatattcttgtagaagaaaattattttg acttttgggcaaaagcatgtagttcttata cactttgacaaactcattgcgtacatttt cacattaatcaaagtcagcacaaataaatt ttcaccttggaccacggagggtttgaacac tggaaatttgatataattctggttgctaaa gaacaagttctaataaaagcttaagtgtat accaatatgtggctgttggtgcaatcagca ggtccgtaaaaatatgattttaatggttag gtaatcccacaacggagatcccaaagttca tgtttggaagagactttgggtcaaagtga aatcagtgtaatgaattaaaattatactc tgagatcttgaaatcagctaattatgttac atcttattgctcagaaaagttttgaagtt atatacaaatgctagtcaggaaaaagatt cagtcatgtaattcttgtacattctactat ttaaatcaaccaatattatagattatgatt tagtgcagtaattctgctggctaaccttat |

TABLE 3-continued

Sequences of exemplary target introns in pre-mRNA transcripts.

| Gene | SEQ ID NO. | Intron |
|---|---|---|
| | | ctcatttggtggtggttagtacttcagagt actccaccatagtttcatttatgttttcagc atcacttcctggtttttctcaattccatgg ctgtggaatcaattcatatgtatatttagc ttcggtgagcaaaaacatagctagaaaaag aaaagaagtgagtttcctacctggttaaat taaagtcgatgtgttaagccaaggaggact tcttttgaatggtactttaacaatccctgt tctgtatactgtgaatatatcattttaaata gcctaataaattggatgcttaggctgagcc acctatactttagttttgttatggaaagaa gggagaggagcaagtatgttcttatatgtt acttagaaataagaatgtagctgtagttac acattgttcttaagtttttttcgtaagaca acttgaaatgagtcccataggcctgctatt taacattctaagatatgacttaaggttaat gatgagcttttgaatctgacaattcaagag atatccataatgaatactgattcatttttct acattgctgaaagctaatgttcattttaag cctactttagtagcctttatttgggcttag agatgttattcctctttctgatatttattg ggttatctgtttaacccttttatatctccc tttcccgatttgtaaattagagactggcaa gacttttaccctgagtagagcaccaaaca tggcttgtttctgcccacactgtagttacc ttgaggggaagtaaatgggactttaaaagc aatttatgctctttttatagtgaaattatcc ctcttactatcccgaaagactgttaccta caatatcctccactcctttcccctgtagt tactatagagatgacttttcggttcttcac tgccataatgatcaaatcctaattcatga gattttatcattccaggcatgtgaggttt acttgatgcataaaaccgcaagtactttt gttgttttttaattgttttttctctcttat cttcttgaaagtctaagtagatcatcattt ttgatgtcttattagtagcaactaataaat tttccctgtatcttctcagcaaaagaactc aagcagagacagaagattagaactaccatt ggtagttttgcttcctatggatatgttcac atacatagaaattttttacaatgaccttttt atatatgtatttcagaatttcagaatggcc tcaatgccttaataggaagaaatacttgaa attttttaaattagggcttggttttgtgagg agctagtaaaggttttctctttcagcttt agcttgtttctgcggaggattccgctctt ctccatcagtttcatagccctggaattgta gaaaagctctgtttcaagaccattgatat ccatttctgtcagggtgagttttaaattta tttcatgatgcaaacaatatattgaacaac aggacatgaacttgttcttgttgtaagtgg ctgaattttatcagtaaagcacatcaaaat aaaatatacccccaattgctagttaagacct agagtgacagattgaaaatagcttgtgtta ttctcttaagaaaatatataaaaattatca tctcatcaatctttaatgtttgttttataa atctaaatgttttttatattgtttcctagga aatattaggtctaattttttacttaccac cagctgtctttttatttttactctttttttga gacggagtttcgctcttgttgcttaggcta gagtgcagtggcactatctcagctcactgc gacctctgcctcccggttcaagcgattct cctgcctcagtctcccgagtagctgggatt acaggcacatgccactacaccaggctaatt ttgtatttttagtagagacggggtttcttc atgttggtcaggctggtctcgaactcccga cctcaggtgatccgcctgcctcggcctccc agagtgctgggattacaggcatgagccacc gcacctggccagctgtcttttaatataaca ttatgattaattgtgatgttccattaaact aagcggagaggaaacatgctggtaaaccat gtgtgagttattcattgtaccagaaaggca aatgatacatttttatcctaaaattcaaatt tataaacatcttaacacttgtgatcattaa atactactaatctagcatataaaattatatt tgtaggcggggcacggtggctcacgcctgt aatcccagcactttgggaggctgaggtggg cagatcacgaggtcaggagatcgagaccat cctggctaacatggtgaaaccccatctcta ctaaaaatacaaaaaaaattagctgggtgt gctggcgggcacctgtagtcccagctactt gggaggctgaggcaggagaatggcgtgacc ccaggaggcagagcttccagcctgggcgac tccgtctcaaaaaaaaagaaaaagaaatt atatttgtaatattctactaaccttatatc attttaacttttttatataacttttttattt taccaaattaagttaacctttatagccct tggcttatactaaacatcctaactttttg tttaattgtattagttttaagttattgcc ccagatgtcaagtaatgttggattttctat aataatttaggatatattgcatgaagtcag ttagtatttacatttaaaactaaaacaatt tatactaatacagtttatacatttcatact aatttagctacagttggataaatatttaat ggaacaaagtaaatcaaagtacctttcaa atgaattggaaattaaatccacataacaat tttttatgaccacactattacagtgtgatg gcatgccaaatgatcataatgtggaattat gtatttcttcattggcttttcaagattctgt tctttagtttgtgggctcctctccaacttg cttgtctcctcacagtttaggcgactgttt ataattcttgtccatcctgcataaacacac acagtcaaaatgaaaaaaagcttctatcag cagatctgtgcttgctgtacagaaatggga aaacaattgaagtttgcattatcttttttc taattaccagatcgttttttggagctattta ggcatacgcttttaaggaaaaaagaaaaaa agagtgtacctttttgtttctaacaaaggtt gttatctatattattgaaataaaaaattgg ggatagttatgacaaagtatttagaaatag gaattaaaatcttaaaataacttttcatag catggacaagacttattaatgtctacctca ataagcaaatcatttaaaaattttttcatgt atatttgctgccatgatgtgttgtgattgc ttaaataaccaatgaatgaagatcaacaag gatttaaatgaagaagaatatggatttaac tattttctcctgtgaaataagttcatatttt acaagttttgattttcagaaattagacaat tatttttaaaggctgggatgacaacttctg cctcttaccaagaagtcaaagcacagttat gtgaattcatcataaatcacatcattttta ttatatttttgtatttataattgtattgtga ctacttttaaaacctgttataaaataaaatt gttttttaatattttattttagaattatta gcattaataacaatttgaagtagtttacac aatacctgtgagttttattttttgttttata ttgaaattaattttagttgctttacttggc ttcattgctatggatgcattctctgtgtta cgagttagcagatctttccttggaactgaa tttaaaagcaagcatttggctccacttaaa tctctgaaaatgcaacttgttctttgcatt tattacataattcgctacttatggtacaga aatggatacaatacaaaaatatttccttat aagatacactgtgaccaatgagcttttaa atagctgtaatcagtaacatgtatttgact tttcaaaacacatttctggagggatatcac tctttgttttctaactagtctttcataaga aatgactagaatagcaacagggaaatgatt gcctttaaggttttttgtttctcaatataa aattttggtgaaccattttttattgataaat acaggtattttttactttcttaaatcacttg atttaaaattactttgattaaatatgcata taaagtcagttgttttttaactctcaatact tatcaaaaaattttaacttgctgtacattc tgtataaacctaattctattcaactaaaat tatttttaaacatttag |

TABLE 3-continued

Sequences of exemplary target introns in pre-mRNA transcripts.

| Gene | SEQ ID NO. | Intron |
|---|---|---|
| 3 | | Intron 28:<br>gtgagtagttcttactgccctctaccttac<br>tacctttccacctttcccatttccatttgt<br>ttgttgatccatttaatctcaaacttacag<br>aaaagttacaaggaactgggctgagcacgg<br>tggctcacgcttgtaatcccagcactttgg<br>gaggccaagatgggtggaaaacaaggtcag<br>aagatcaagaccatcctggctaacacagtg<br>aaaccccgtctctactaaaaatacaaaaaa<br>cttagccaggtgtggtggtgggtgcctata<br>gtcccagctacttgggaggctgaggcagga<br>gaatggtgtgaacccgggaggcggagcttg<br>cggtgagccaagatcctgccactgcactcc<br>agcctgagcgacagggcgagattctgtctc<br>aaaaaaaaaaaaaaaaaaaagttacaagg<br>aatttttttcttctctgaagtatttgagag<br>taagttgctgaccttaagtcctatcacttc<br>caagtaggttcatgtatagttcttagaaac<br>agattttctcatagcaaccgaacattgata<br>aattacaatatctaattctcagacccctt<br>caagtttcacccgttgtcccagtattatcc<br>ctccatataacaagatgttccaggctcaat<br>acctgacccagcttccttttttttgaagaat<br>ggtgtttagaaatggagacctagaaattat<br>atatgctgttattggaatatcactgttccc<br>tggtttctcagtggaaagagctaggaacta<br>agtgttgtgaatgtttgtcgtgtgcaggt<br>gaatatacacacactgacatctgtattcct<br>aaatcatgtgtatatttatttattaaaaac<br>tgtgagttgatgctgatacttcccatttta<br>atccagcattacaaggtttgttctagtgtt<br>ctccctttcgatatttgtcacttgctttcc<br>tgatagaaaacgggcttctagtatccttaa<br>tatattttcatattttggtcagtcctccta<br>tacgtaacccaacttgaatgaagatatgtc<br>cttttccattgcagaaatgttcttttttccc<br>cagctcggactcaacactacacaccaggcc<br>accacatggcgccgcacccagcattgacac<br>ttcttttaccttgtctggctctgacatcc<br>gtgccaggttgctcttcgtcatggagtccc<br>ttttactgagctctgctctgacgctttgtg<br>ccaggtgcctcttgtggagataccctcttt<br>accctgcctgtgctcgccagcctgcacca<br>ggccacccctcctgcacagatactctcctca<br>gtactggaccaggctaccaacagcccatg<br>tgaacccattgtaacccaggtcaggcatta<br>acacctgcagtaggctaccatggcttcccc<br>ttcccaccccccctagcttggccctactaat<br>aatcactttgtcactgtttgggttgatat<br>ttggttgtttcttgtaggttcctagctta<br>agataggattgcatactaaaatttacttag<br>atctttgagaactcaaagcaatcagtgaaa<br>cattattgttattaaataaaaataaaatac<br>ctgtagttggtacctctgtttgagcctgcc<br>ttgttacaagtttcactgacttcagcttcg<br>tgtaacaaagtatctttttcttcaacgtg<br>tacttaaatttcctgtcttattagttttct<br>gatatctaaaaggaaaaaaagcagatatcg<br>ttaataaattagaaagaagttctgcaaatt<br>taaaagtgccttctaagctgagttgtagga<br>ttacagtacaatccatagggttatcctgaa<br>gaagccaggcagggctcttctgtgttacac<br>cctgtgcctgcgcagcatgctcaccccttg<br>ccatcagcgcttgcggccccattctctccc<br>tctagtaataatctaagttctgcattgctt<br>tctccttctcttttcttcttcctttaaat<br>attcttcttcgagacatatctcatttaa<br>cttttattttcattttctgtcacttttggt<br>tttttctcatgccaccttggcaatgtagtta<br>agtttgtgctaacgtagaagattagtgctc<br>aaatctgaattgccatttactactagctgt<br>gtcatcttcggcagggaatctcccagagcc<br>ttagcttctttatttgtaaaatgactatta<br>tagtggttatttctcaggattgttagaatt<br>acttccgcaaacatttgcaagtccctggtt<br>cataatttcatgctaaattagtaccgttac<br>aggaagtggtatatcattgtcacagtgtat<br>acaaatatatttctttttatatccctcgtga<br>tataattatcaagacagtgaaacaattcaa<br>tgaattttaccagcataacacatttttaag<br>tgattggaaaatcataagtatcttttctta<br>tgttttagtagaggctttgcaaccccatt<br>actctccgctcccaatttgattatttaaag<br>gaagtggattactaactcagatatgtacac<br>tgtcaagccaagttctatgttctactgctg<br>gttttcctgagaaagcagtcatataactcc<br>cttgaaatgatttactacttttgtacatat<br>aaaattataatggtgttaatgtaccaaata<br>atgtccttggaagcaagggttttgccagta<br>actcagctgcatcagtcaccctcaaggaga<br>tgagccatgactttgttcattagttggaaa<br>agagtctgagagtgccttctgttactgt<br>ttatcttggtctgacacttgggaataggg<br>tcatggatacttcagccagaaaacttcca<br>aatttaagttattaatgtattataaggatc<br>aaagtttctagtatagcctgttcaattaga<br>acatagtgtgttggttgattggatttggag<br>aaagggaggcaatcaaatttttactacagt<br>ttcagcctgttacagaatattgtatagagt<br>gttaaaatgttgatgcattcatatttttgc<br>cagttttaagcttgtacgattttaaatcat<br>ttccttaccttggagacttcccccccacct<br>tttttttttttttttgagatggagtctcgct<br>gtgtcgcccaggctagagtgcagtggcacg<br>atctcggctcactgcaaggtggttctccca<br>cctctgcctcccgagtagctggggctacag<br>gcgcccgccaccatgcctggcttatttttt<br>gtatttttagtagagacggggttcccccat<br>gttagccaggatggtctcgatctcctgacc<br>tcatgatccgcccgcctcggcctcccaaag<br>tgctggaattataggcatgagccaccatgc<br>ccagccctgactgcccttaagatgagtac<br>ataagtagtagtagtacattttttcttttcac<br>atcctggagaagatatactgtgttcactat<br>tgaaatgaaaccataaagctagagttagga<br>agattgaagaaatgaaaaaggagctcacat<br>gattttgtctcaggagaggctcttccagga<br>ttcttttggagatatggtagattccatagct<br>ggagcagggaaaggacaggatgagcctgtg<br>ggtgtagaaaggaagggagtgcttgaaaga<br>tgatgaggagatgtcagcaggtcacagaaa<br>ccctctgaaggaggctccaactggccaggc<br>tggggacaatttgggccccaaaataatgac<br>agtaacaaattgtaactcattgaatgaaat<br>aggaatccatacattggtaattatataaat<br>aagggaataaaaccatgatgcaaaaaggga<br>tgtttatgtcatcacgcaaaatatgttcac<br>agaaaatatgtactaattaaaagagggaaa<br>agagtaactttacagtggatgaagcctggc<br>aatcatcacttaagcaagtggtcagagtt<br>aatattatcagtaatggtcaaatcaaaacc<br>atatgcaagaagactctaaaatgcaagaag<br>actcctgaagtacttcttaccaaagatgta<br>gaacttaaattcagtcataacaatacatga<br>gacaaacccaagttagagcacagtctgcaa<br>aataactggcctgtaatcttcaaatgcatc<br>aagatcatgaaagacaaggaaagagtgaag<br>agctgctccagttggaagagacttaaaact<br>aaatgcaatgtatgatcctagattggatct<br>ttttgctctaaggacattaatgggccagtt<br>agtgatatttgaagggatccgagggttcc<br>attgtagtaatatcagtgttaattttta<br>aattttttattaggtgggattattttggaa<br>aataccattattcatagcgaatacaaagta<br>gaatatttggggatgataatgcatgattac<br>aacaaatgtttcaggagaaatatgatcttt<br>gtagtggtcttgcaacttttctgtaagtct |

TABLE 3-continued

Sequences of exemplary target introns in pre-mRNA transcripts.

| Gene | SEQ ID NO. | Intron |
|------|-----------|--------|
| | | gaaattgtttatgcataaaaggttaaaaaa
aggttaaattttgtttttataactaataat
ggattagggtcatgtgaaagtactttagag
gaaatgagacttttgagaacatcatccctg
aagacgttgaaacactgagttacctcatgg
ataatttaataggatatgcagctgattttt
ctaccttaatttcttgtttgcagtatctac
ccatacttagaattgtctggtgttaaaata
tgcccactgggactttcatgaaattctttt
gattttctagaaaattcagtttcaaaggat
tttttaaatagatattttaagtttggtgtc
aacttagataaaatctgtttggagtcccag
tgtaagttttagtaatgtgtccaatctgtt
tattgaaatagtataactttagaatacttt
ctttggagagatgaagattggtgtatgttata
gttcaattcaaagttgttctttctattatg
atctattttataattcataaaatctatctt
atgattgtcatcataagtgcaatttgtttt
ttgccccattctacctcagaaactaagtat
ctgggcatcaataacaattggtagtagtgt
ttgctgctaagccaagtttcaccagtacag
tgtggaattattttattgtttttctgtga
acattgtatctgctgttactaggttattgt
gaggtattgggccttcatagaaattgcctg
gaaccccttgttcactaaagcctgttacact
ttttattctctgtgcgtgtaatcagagact
tattgatactgacacattcaagggcatta
ttgatcatttagattgctctaagacctaag
gagtcttggccggatgcggtgcctcacgcc
tgtaatcccagcactatgggaggccgaggc
gggtggatcacctgaggtcaggagttcgag
atcagcctggccaacatggtgaaaccccgt
ctctactaaaaatgcgaaaattagctgggc
atggtggcaggcgcctgtaattccagctac
tcgggaggctgagacaggagaatcgcctga
acccgggaggcagaggttgcagtgagccaa
gactgtgccattgcattccagcctgggtaa
cagagcgagactccatctcaaaaaaaaaaa
aaaaacgaaaaacaaaaacctaaggagtct
tttctccttattttacaataaaattccttt
gattttgtgtaaaaacttgaaactgtttat
gaatgtaaaataacatttgaatactttct
tgtgccagatattaggttaaatgctttatg
tgaattttcatttgattctcacaacttttg
agttaggtagttattttctcattttacag
atgaaatggagggttaggaactcgtaggta
gtagatgctgaagctgagatttgggcctgg
gtcttttcactactgtgccagaatcatttg
ggagggagtaaaaactcaagcctttggaaa
atatgatgacataaaattgtccttatatt
gagaagcttccatagttaccagtgtccttc
acagggttgatcggaaagacatacatgtta
gtgatgatgataaatgatgaagataatcatt
attaccacaggtacttcctataatataagc
atctttcaaattgtatgagaactttcatag
aacatctgagtaaatgaacagtacagtgtg
catgaaaccactaagcaaaccaagggaagt
taattttctttatatgaattgtaaacatgt
ctctagatatcctttatcagattccaccat
gcgtaagtagtgtctaagttgccccatatt
tagagttttttcaatgaggttgtgttcctac
ttagaatcctaaagttcagctataacagat
atattaataaaatctgtggaatctttaatt
gagcataatggtggctgttatttaacttg
aggcttttttgttgagctggattggaagtgc
aacttattagaaattacagtgtatttattc
ctatttcttgttctttatgtgagagaagat
atactttagtagactgaatacttcagagct
gtatctcatttaccaataaaatgtgaaaac
agtggtaaattccttcacttgggctaccat
tgtacaggcctatttaatggtatagtttg
atatccttaatgttaaaagcaatatagctt
aaagaggctggtaaattagaattttccaat
atcctcagcttttttttcctctcacagttaa |

TABLE 3-continued

Sequences of exemplary target introns in pre-mRNA transcripts.

| Gene | SEQ ID NO. | Intron |
|------|-----------|--------|
| | | tttgctctgctgactccctacgcgaggtgg
caacagctggcccttttactggagcttgtg
gggattagagagtcgggctcgcagcagcgt
gctcggcctcttgcctctgttgactgttct
ttattgtttgatgcctgagcatctcccaga
cagcgagcaattgtttctggaaacttaaag
tttgtttctcttgggagtagacaatgcttt
tggggcttgtctttgtgtttcttcacttca
tgagattctaaaacttagaagtataggcta
tagatgaaagtttcttttttcagtaagcca
cctcagtaacaaatcatgtgttttaaatgaaa
actttgttcttcataatatcatttagtgag
agaaaacaaatgcatgagtgcattttgaa
attatggtactaaaagggagcagcagcaag
gtgacctaatactgccattttaaaagctag
gattagaaatgtatcataactgcttaaatc
taaaaagattcttctcactgaatccaaaata
tagttctaatttataggatagttataagaa
atctctatgccatgtggaaacatgaataaa
aagtagtcagaacatagctaaatagaaccc
tgaggtaggcagaatgatttattcttcac
atttagaaaagaaaacatcaaggtaccctg
gaacttaatttctacagtgacttcacattc
cgacacttctcccatacctgccatacccctt
gagtgttgttacggatgagaatatcgtctg
tgaagtagtatgagatggaaattttcctag
aaagattattgtactcggaatttggaactg
aaaagtgtagaaagggaagtgatgtgttt
aaaactgtttgcggaggtggggctctgcca
tgtgtattttgacaaagctacacaggtgat
tcttgccatccccgattaccgtgtacccgc
ctgccccctgagctggcactccaaagagttc
tttcagtgcatagcaagacaatttttcatg
ctattaatgggataaaattgacatacatt
catttgtagagtctgagacacaacgtcact
ttggaaaatttggtgagcaatttgaactgc
atctgcactggtgtgttcttttttgtttctg
tagacttaaccaaagaaaatgaactttaaa
gggactttaaaggcatctgcactggtgtgt
tcttttttgtttctgtagacttaaccaaaga
aaatgaatttttaaaggaagagagggtgata
ccaagttgtagaattctaggtatgtaggtt
cagaggagattttttttttttaagaaaaaa
aaaaaaaaaaaaaaaacacccaatcaaga
agaatagagcagggtgtcccgaagagaacg
tgtgagctcgaagcatcccggcagcatctt
tcatatctcagtactgttgctctgtttctt
gggctcacaacaccatttcctctctcctgg
cttttaacacatctcgaggcaaccttttcc
cttttctttttatgcacttctctcactgcgt
ctcttctatatcatcatcacttcaacctaa
cccagtatttttatcccacctgcttattta
ccttccttcagtgactaaaaaccttactca
gatactgccagtgttgtttaattgagcaga
atagaggcttctcactataggcaactgtaa
atcaatgaaaataaccatttaaagaagaaa
aacattttcatgtctatcacggtcgatccc
ttctgccaaagtgatttggttcattcataa
attcccatacctcgtgtgttacatattgt
actgtacacatttactgaatgttcgattgt
gatcttgtaatacagactgttcattagccc
ccttctcttgacttaaaaagttggggggaa
ctaactcttttcatcccaaggaaactttct
tctactctgtcttgccagaaagttactgct
catttctcttgtagagcagcttgcctgtgt
ggcattcactcctgttctgcccactcccctt
cctaatatcgtgcagtctggctttcatcta
tatcaaaaccacttattgatagatcaccaa
tgatttcctaatgccagtctacccagttca
ccaggaaactttaataactttttatgttta
ttaggaattttttaagttcattggaatacat
tcaagtactttttggaatgattatatgatg
tagaaatgtgtatgtttgagagacagaaa
attgattttttttttcctcttcactacagaa |

TABLE 3-continued

Sequences of exemplary target introns in pre-mRNA transcripts.

| Gene | SEQ ID NO. | Intron |
|---|---|---|
| | | taaataatgtatttgttttatggtagcaat acttgaactctttaaggcatcttttcatgg taaatctggcaattttaaaaatctgggctt tgtaaaataattttttttatagtaaggcag ttaacacattaaagcaactaggaaagatag tgaagaattattttttaccttgagtctgtat agatgaagtaggctctgcttttgtgttggaa cagaacaaacaaacaaaaaaacctgagttg atacaaagataaagtaatcctcaaggaaag tcctctctgttagagaagtggttatttaca cacagaattccacatgacaacgcctgagtg gtgtggtttccaggttattgatgagaaaat cgagactcaaaatgggtcttttagaatgaa gtacattttcatggcctaagtctgtctttt aaaagtcaccgttgtggccgggtgtggtgg ctcacgcctgtaatcccagcactttaggag gccaaggtgggcggatcacaaggtcaggag atccagaccatcctggctaacacagtgaaa cccgtctctactaaaaatacaaaaaattt agccaggcgtggtggcgggcgcctgtagtc ccagctgctggggaggctgaggcaggagaa tggcgtgaacctgggaggcggagcttgcgg tgagccgagatcgcgccactgcactccagc ctgggtgacagagcaagactcgtctcaaaa aaaaaaaaaaaaaaaaaaaagtcactgtt gaagaatatcaataaattagtacaagcgta aaagaacattttcttttctataatattata catgctgctggtaatcaacacttactagc aagtatattcttttgctttaaactcaagtt ttaactgattaagaataaagacaagaatgt tctctacaataatgtatggattgaatttgc catttatcattttaatgtaggttttactta tatactattgtgaaaatactcttaatgtat tcaaaaggccagtgcacaattttttttct tttacttcttttttttttcttagaaagag tgtcacttgc tgcccaggctagagtgcagtggtgtgatca tggctcactgcagccttgaactcctgggct caagtgatcaatacctttaaagttgggaa taaactttatcttaagcgttttattttta aattatgttttgcatatttgatagaaaaa gtagaatgtagtaattgaaaacctaatcac aaaacaattcattggactctgcaacagtat ataaaaaataaaattaaacgagataggaaa tcttaagggattggtggattgatgcacatg aaactggtaaccctctgttaagtacagttct ccaggtagttggagaaattagttaaatgtg aagagaattttaattttgcactattttgta catttctaaactgtgtctcccacagccctt ctcccccagtgagcacgattcagaattact ttgaaatgttgtagtcttaattatcctatt catggaaatgacgaagctaatacacgatgt gctctatcttaaaagtaacagatattttcc caagtaacctactgctggttgtgatgctga gggacatttcatgggactgcatggtcgttg ctcatcgtgataccatcctcagtggttggg ggattcacagtgaattctcatatcctgtaa ctatgcatcatggatctatcatctgaaaat aaatcaaaatcttgttgaactcacagttt ccacacttgtatcacccatttaagattgtt tcattgttacctcctgtgtacagaatattt catttcaatttctcttagaacagctcattc atctattctctagtttcaatattctgagca gtagaagtttgctgttttgattaacttcag ttagatctcttttctgggccaagaattaaa gccattttatctttagtctctccttttgtt ggcactgcttcatagactgtgtcatatata cagatctgtctttagactgatctttaccaa agtacactactggaatttgagggttttttt ttttaacatccttttcattatgagagagct agtgtatatgcattgtgggaaattagaaac tatagatggcaaaatttttaaaaaataattg ccaccacccagagattgcactgtagtttaa gacacttttgaatgtggtcctagggacata |
| | | atttctggaacacatttttcgtgaagaggt ctcaggttggcttcttatacccacagctcg ttgtcattgccccctagttttaatttcccat cgctcagtgggctagatttttttttcatttt cttcatataaacttatttcagaaatgttca ttaagaggaataagcagcattagtaaaaat gaaacctatggtacccattacttttatatag ttcaagtattctggaagccatattgtagca tagcatgtactgaaaatcactctcctttga acagtaatcccatacctgtatttgggacct ggccttcctttgtgtgcttgtgtattcatt atatccccttctctcttcaaagatgctca agtcattctcatcttaaaactaatgggttg aaccttccatgcagtctagtagctactgtg aactctaatctctattacaaaggttagctc tttgagtctcacttctactgaagttgtttt ttttttcccaagattactgaaaatttaagag aaaataatggcccaggcatgcattcaggac tagaaaatacttccatgtacagaaaaccaa acaccacatgttctcactcataagtgggaa ttgaacattgagaacacatggacacaggga ggggaacagcatacgccagggcctgttggg gcgtgggggcgaggggagggaacttagag gacttaagtgcagcagaccaccatggcaca cgtatacctgtgtagcctgcacattctgca catagagcccgcttttgttttgttttgt ttttaagaagaaataacggggaaaaaaag gtttcaaaactcataaagaaagagaaagag agggagggagggagggaagaaaatgcttcc atgtaactgcatcatttggtactttggagt ccatatcctacttgaaactctaggatctgg ccctcacatttatgtagtgcttttattttac agtttacaaaacttctgcttgtccatgtgt gtctgtaaagtcatatgaggcattatgccc attgttcagatagagaaattaacgttcatt gacataaatggttaagccatta tgtaaatatttatggcaaagctggggctaa tcatatgtgttacagataggacttttttta aagaattgtttaggtattctgttcatcatt agtctctgggtttgtgtttgtggtaaccat agcaaccaagttcatataatttggcttct ttttttatgtgattttttgatacgtgttaagg atctataacaatgaatttgcctcctaaaga ggtacataatgttttcattcctccaaaaag ataattctaggtttataaatctatgtatgc tcagtgccagttgaattttgtgattgttca atagaaaagaaattgtgacttaaaggtgat ttttccagtttaatggaataaatgaaattag tttagaagttattttattttttctgagcct gattctcactcagttgtgataaacagcacc tctgtaagataaactcggtgataaaccgag aacttctgaaatcagcctaacatgaataccc tgttcttcttgtgctaagtttcataatgct ttatcctaatacaccattttttttaagaaat ggaacttgtatttcattttttgctttcatct cacctaattcataattttattaaaacctac gatttttaattctttttttatgaatttt agtttggtgtataaatcagaattacattct ctgatcttttacttttaaaattacagtgat gaactgactgtttaagaatcattctcatga ttcattcgtctgttatgcctcctttttaaa gcttcagcactgaaggtcttttgacaaacc aatatttataacagtttgacagcaggatga ggaacagctttgtctttgtaacagcttga agaaagaccctttccaggaccagtcatgc agttacaatcttgacctcttttcttatgctg ggaacatgcatacagcagcacctcccatgt gttttcttgtcccattgactgtccattcac ttccatctgtttttgcagtcttaaaggaac agaaggggccttcttataaatctgtctttg caggtgataaatgatgcctacctcttttaag agctgcctgggtggttttccttttcttaga acatttctgctttcctcctaactaaatcag ggaaaaatacaattttaggaataagagaaa |

TABLE 3-continued

Sequences of exemplary target introns in pre-mRNA transcripts.

| Gene | SEQ ID NO. | Intron |
|---|---|---|
| | | aagaagaaaagatgaatttttaaagcattt |
| | | aattgactaagaatattttactgatctttt |
| | | ttaatcttcccaattaattgcctaaatcat |
| | | atttttttaaaatgtattatcgatatttaga |
| | | tttttgtcagggagtaaaatgaatgtattc |
| | | attttgaaataatgtaactctttttttgaga |
| | | aaacaaagccatgtatcattaatgagttaa |
| | | catataaaataacttttttaagtttttttgtg |
| | | ataatttaagtgtggagcatcttatgtatt |
| | | ggatacaaaagtaaaatatttcagagtaaa |
| | | tcattgtaatcttatggtaaaatctattca |
| | | tttttttacatttaaaaagatgatcataaat |
| | | cccataaacatttatgcttttacttctgtt |
| | | gctgaaaataagtattgtaggaatagatat |
| | | tgatatcattgggttttctaagaattcagc |
| | | agaaataaaaataatttactttttctccca |
| | | tgcagaaattatttatgcaaggttttatgt |
| | | aacaaatattgtccctctatggccctgcag |
| | | aatattcttaaattactgatttaaaaacta |
| | | ttaccagtataaaatgaccacttttagaat |
| | | attgtggtgtattatgtgaatcagctggct |
| | | aataatatatcttctgtggactagcttgtt |
| | | agtttgtttattaattccctggcatattcc |
| | | aaaaggaatttgaggcagcttacatatatc |
| | | ctacgcaaaagataaaaactacttaagtgaa |
| | | aaatttgggttgaaagaaaaggaaaatcca |
| | | ggcaagtgaaataaagtaaactttcagata |
| | | aaattggtgccctcaaagtgcatgctcaa |
| | | gggttctacgtacaggcagacctcattgta |
| | | ttgcatgtcactttattgcacttcacagtt |
| | | attgcattttaacaatagaagttttgtgg |
| | | caaccctgcattgaacaagcctgttggcac |
| | | tattttcccaacagccatgtgctcacctca |
| | | tgtcactgtcacattttggtaattcttgca |
| | | atatttcaaattttttccattattattctgt |
| | | ctgtcatggtgatctttgatgtttgtattg |
| | | tagctattttgggtaccactaactgtgccc |
| | | atattagtcagtgacccttaatcagtaaacg |
| | | tgtgtattctggctgttccaccaactagac |
| | | attccctgtctctctcctcctcttcaggcc |
| | | tccctattccataggacacaacaatattga |
| | | aatttggccagctaataaccctacaatggc |
| | | ctctacatgttcaagtgaaagaaagagtgc |
| | | catatttcactttaaatcaacaactagaaa |
| | | tgattaagcttagtaaaggaggtttgttga |
| | | aagccaaaatgggctattagccaaattgtg |
| | | aatgcaaaagaaaagttcttgaaggaaatt |
| | | aaaagtgttattccagtgaacacacgaatg |
| | | ataaagcagaacagccttattgcctgagac |
| | | gcaggaagtttcactggtctggatagaaga |
| | | tcaaaccagccataacattcccttaagcta |
| | | aaacctaatccagagcaagttcctaactct |
| | | attcaattctccgaaagctgagaggtgagg |
| | | aagctgcagaataaaatttgaagctagcaa |
| | | agtttggttcataaggtttaagaggaaaaa |
| | | agccattctgcaacatgaaagtgcaaggtg |
| | | ctgatgtagcagctgcagcaagttatcaag |
| | | aatatctaactaagtaaattgatgaaggtg |
| | | attatactaaacaacagattcttgatgcag |
| | | atgaagtagctgtctattggaagacgatgc |
| | | catctagtaatttaatagctagagagaagt |
| | | caatgcccagcttcgaggcttcgaaagaga |
| | | ggctatcccctcattttgggtgccaatgca |
| | | gcaggtgcctttaagttgaagccaacctaa |
| | | agaatttaccattctgaaaatcctagggcc |
| | | cttaaggattatgctaagtctatcctgctt |
| | | gttttctaaaagtggaacaaaaagcctgga |
| | | tgacagcacatctgtttacagcatggttta |
| | | ctgaatattataactctcgagacctgctca |
| | | gaaaagttttctttcaaaatattactgctc |
| | | attgacaatgcatctggtcaagcaagagtt |
| | | ctgagggagatgtacaaggagattttatgtt |
| | | gttttgtgcctgctagcacaacatccatt |
| | | ctgcagcccatggatcaaggaatactttca |
| | | accttgaagtcttattattttaaaaatacg |
| | | tgtcttaaggccctagctgccatagatagt |
| | | gattcctctgatggatttaggagaaaaaaa |
| | | aaggaaaagcttctggaaaggactcaccat |
| | | tttagatgctgttaagaccattcaggattc |
| | | atgggaggaggtcagaatgtcaccattaac |
| | | agtttggaagaagttgattccaaccctcat |
| | | ggatgactttgaagagtttgggacttaaga |
| | | ggaggaagtaactgcagatatggtagagac |
| | | agcaatagaactagaattagttctgttgta |
| | | atatgataaaacttgaacagatgaaacatt |
| | | gcttttatggacaagcaaagaaagtgtt |
| | | tcttttttttttttttttttttggcagtct |
| | | cagtttgaagaaagtggtttcttgagatgg |
| | | aatctgttcctggtgaagatgctgtgaaca |
| | | ttgttgaaatggcagtaaaggatttagaat |
| | | attacataaacttagtagataaagcagctg |
| | | cagggtttgagaagatagtgtcccaattttt |
| | | taaagaagaaaaatttgagtaaatttgggt |
| | | aaaatttacccaaaattacctattgtgggt |
| | | aaaatgctatcagacagcatcacatcctac |
| | | tgtgaaatctttcatgaaaggaagaatcaa |
| | | tcagtgcagcaaactacaattgttgtctta |
| | | ttttaagaaattgccatagccaccgtaacc |
| | | tgcaacagccaccaccctgatcagtcagca |
| | | gccatcaacgtcagggccagaccctccacc |
| | | agcaaaaagattatgacttgctgaaggctc |
| | | aggtgatccttagcatttgtttagcaataaa |
| | | gtacttttaaataagttatgtacattgtct |
| | | ttttagacataatgctattacacacttaat |
| | | atattacagtatactgtaaacgtaacttaa |
| | | acgcaccggaaaaccaaaaaaccttatgtg |
| | | actcactttattgtgatatacgctttattg |
| | | tggcagtctagaaccaaacttgcatatctc |
| | | ccaagtatgctgggactttgctagaggtaa |
| | | gctgcaaatttagccctcagttttcctgtg |
| | | gctggcagttacaaaatggaaagcagaggt |
| | | cattccatcattcatggtggccatcagaca |
| | | acaacacagcagttgcttaggagaagcatg |
| | | ggtcttcttcgtacgcacaactgagagaaa |
| | | tttcccttaaagtggacactgagttagatg |
| | | atacaatgaatctaatggctacacataatc |
| | | atgaaaatcatggggccctttattgtaatg |
| | | tttctcatgcgggctaacatgcgtagttct |
| | | agggaaaatatgatgctgtccaaacataca |
| | | gctatttggtttggcttatctaaagataaa |
| | | atacatagtatccagagaaatagatgaact |
| | | gtatgtcctccatacagtctcccataaata |
| | | ttatttcttttttgcagctgatccttttagt |
| | | aaatatcaggtagccagaagttcaagattt |
| | | tacactcattgacattgacaagcacctgga |
| | | atggtactaccttttttttttttttttttt |
| | | tttgagacagagtcttgctctgtcacccag |
| | | gctggagtgcagtggcatgatcttggctca |
| | | ctacaacctccgcctcctggattcaagtga |
| | | ttctcctgcctcagcctcccaggtagctgg |
| | | gattacaggcgcccgccactacgcccggct |
| | | aatttttgtatttttagtagagatgggttt |
| | | tcgccatgttggccagggtgatcttgaact |
| | | cctgacctcatgtgatccaccgcctcggc |
| | | ctcccaaagtgctgggattacaggcgtgag |
| | | ccactcgcccagccaagtactattttat |
| | | tagttaagtcagagcataatcattataac |
| | | tgagctgaaattagaattgccatccactta |
| | | agaaagttgagtggtctaacaagtataaaa |
| | | gcctaaatataaggctaattcatgttcata |
| | | ctgaagccttttggggaataggccttaaaa |
| | | tatgtagaaagtatttgaagcggttttaat |
| | | tgtactagccaaaaggagcctagtagaaat |
| | | gcttgtgttataagagtttttattttttaaa |
| | | agctgaatttatctgaccaggcgcggtggt |
| | | tcacgcctgtaatcccagcactttgggagg |
| | | ccaaggcaggtggatcacgaggtcaggagt |
| | | ttgagaccagcctagccaatatggtgaaac |

TABLE 3-continued

Sequences of exemplary target introns in pre-mRNA transcripts.

| Gene | SEQ ID NO. | Intron |
|---|---|---|
| | | cccatcactactaaaaatacaaaaaaattg gccaggcatggtgatgcctgcctgtagtcc cagctactccggaggctgaggcagaagaat catttgaaaccgggaggcggaggttgcagt gagccgagattgcgccactgcactccagcc tggacgacagagcgagactccatctcaaaa aaaaaaaaagctgaatttatcaacaaattg ctgtggagttttttatatattcagcaggca tcagttgtaatttacctcacagactttctt aaggttgctttctttctaaattatacttta tgggggtcacaaaatagcaattttaaata atcacctttaatgattaagtattgtttaag tcagatcactcaactatgaatgcatgaata ttcatggacatctattacatagcaagcagt gctatgctgggccgagtgattttaaatgac agactttttggtaagtagagaatttaccca agcagtccttgctgttctccacattaatgc tcagaaaaatacattataaaaatgatctt tccaaaatgaattatgaagccccatgagaa tgatatggcaatttgtggttacatatttta ctagaggattaatatccaataaataaaag atactaaggaataaacaaaaaaaatttaaa agatgaagtatataatgaattagaacaata cattttaatcataagttttaaattagtgtg gactttgaattctcctggacagattccttc atttatagataaagctaggactgtgactt atccagttatgaggttaacggcgaatacaa cattgtcatatattttaaatgacacacatt acaacatgttctctgctttataaaaatcat atcaaataattgccccatagattattaaag gtgttagactagggattcttaaaaaaaatt ttcatcaaatgtttctttcattattaatcc catgaagtccatgttacagaagattttgtc tacaacagtgcagttacattcttctcgtta gaaatacaaccaccagttagagttcctaat cagtataaggaagtagttgttaggagaggg gatgggtttcttgtccaaatgaagttttcc atttgagttttgaagtagtgaaactaacc cagcgtttacaggccccagaaatctgggaa cctcagcttttcaaagtactgtaccagtctt taacagttttcctggacgtgtgaattgatg cctccttctgtaacatgcaggagtgttctg tctgtcttcattgagtgttaaaaaataatc atgcctatttcaaggaaaaaatctacagaa ctaagatgcagaagataagtgctagattta atcatattccttcatctatctgtttggttc aacctttcatcaactaaagatgcacctttt tttcttgtgctaactctaagattttagcta cagtttttgagaatcttgagtgtagtctctt gtttacctttttcctttttttgtttcccc cacaccctagattcatttaaatactgaact tctaaagggcaagtatatagtgtagtttaa taaaaagcaaacctttcatgaacaatata tattacataataagaagcgttcctttactt ttcagtactctagtgaatagctttctacag tagaatctcacttagagggtgtcttaaagc ttaacaccaagtgctcaggcagcatgttat acaacagttccattaaggtacatttggatc tttggatgtgtggtttgcttaaagtacact gcattagtaagttggcagcttgctttcttt aaaaacatcaaaagttttaaaaggttatt tcagggcatgtgttagtgttttgtgtgtgg ttcttttgttcctgttctaaactgttattaa ccactgaagtgaaccttctcccggggtttgg cctttggtattcacagtgtattcaaaacc taattacagattagtctatatttgagactt ttagagcaagtatcagaagacccaaaaga aaatgagagtagcagtatcatttcatgtag agataaagagaccaaaacatgaatgggtg tcaagtcagctgaagaaagaaaaaagaga aggaacttcattcactgagacggtttatga gttggggattatgggaatattcatgactca atcaagaagcacagtgaattgatgtttgaa atagctcatcttttaagtaaacattggata aatggaaagtagactcagtattcactacac gtagaaatagctatttctgtatagcagaaa tagcagtttgttaatcccttcctgagttgg tttaatttaccaagtaaatcacaaatttta ttctttatttgtgaatatttaattcaaata tttaatggaaatatgagtttgctttataat tagtcatgctgatccatacacgtatttctg agagaaagcaatttctaatggtgaaatagt tacaataatattttgaaatttgaaagcac cgtgatactgaagcattaatctgaaggatc ggaaagtagggagttttgttgccaacatt taacttcattgtttatggataacttggttt tctgggcagcagatggcacagttagtata cagacattcttggaaacttgtatcaaaatt taaaatgaatgaatttatgagaaataattc tgcttattatttgtaatgtagctttcttga aaagcaagaaatcggaatgtagtttctaaa gctgcaagtgaatatgtatacatagccagc tcttttcagccttgataataaggtgcaacca ttaagatgaagggattttttttcccactt gtgttttgggcccgagtatcctgatctgt gttgcttgtctggttcaggtgtgagccacc agctttctttgactttcattatctatgtgt atcttgcctcctgttcccaggcttgctcta gctcttctgatcctgtcttcctccctcttg atcactagtgtagtattcatgaagccagct aagttagttttttcccttgaaaaccacagc ccttatcttctgtgccatattttgggcaac ttcgttttatcattgattgaccgtacgcagt gatcaggccttgttctagacactgaagact ctgagcatttttgggcccattttgtactcc tgtattgtctccaggggcttctccaagtg tgcgtcaatttagtcttctcaagagggcat catttttcatcagaatatgatagcatattat ggagtgtccggtcatccttaggcatagact acttaggagggtgtaactgttttgttccctg atttttactgaaatgggtcttttcttttt tttttttttgagacagagtctcgctat gtcaccaggctggagtgcagtggcatgatc tcagctcactgcaacctccgcctcccgatt ctcccctgaaatgcgtcttattttaagtcaa aggtaatacttaaaaaagaccaaagagact taaaataacagcatttgcttcgtcactatg agctttgttattatgagttaacatacagta gcagactgggtgtagtagctcacgccctgt aattccagcagtttgtgaagccgagtgggg aggattgcttgaggccaagacttcgagacc agcctgggcaacatagtgagaccccccatct tgacaaaaaaaattgtttttaaattagcag gtgtggtgctgcatgcctgtggtcccagct acttggaaggctaaggtaggagaatcgctt gagcctgggaggtcgaggctgtagtgagcc gtgtttgcatcactgcactcctgggtgaca gtgcaagactctgcgtcagacaaacaaaca tcgtagcagatgtgttcttaatcagagaa gtgtagacaaggctaactccaggctttaat gtcctcatattagcaatgatacctgcaag gttgtatgagaaccaaatgaaacgccaaat ttggaaatacatagtagatacatcatagca gagtaagccaggaatgcttctcaaaggtag gatatcatctgtgtcctcatatcacttttat gaagtacattgtgaaagtgaaagaacaaag aaataaatgttttttagttaatgtttaaag gatacatttatcataattgctcttttaaca ctcacctccagtctccctccgttcacacg tcctacccccattacttcctggtaacttag ttaagtgtcctttgtcattcctgaggtttc aaggcatggtagtactgtgtcctgatattc taatcgtaaatatttaagggaaattcggca ttttttcattttgtggttttcatattaaag tacattaaatagtcttttgcttttattta ggaaaaaaactgcttacctgttaatttag aaaaatctgattttcatttagaccttacag ggtgagacacctgcatcagggtggctcttg |

TABLE 3-continued

Sequences of exemplary target introns in pre-mRNA transcripts.

| Gene | SEQ ID NO. | Intron |
|------|------------|--------|
| | | gtatctttcaattcaattggatcttctctg |
| | | aatagtctcttgtagggagtgaggctgctg |
| | | taccacctccctgcagtagtccatccagct |
| | | taagatgggggtcaccagtaggccaaaaga |
| | | atgggtagacctggccatgcactgccctat |
| | | tgtactcaaatcgtgtatcaaatggagttg |
| | | gatttcttctctcttcatacagtacagcattt |
| | | ccaagtagaaatatttctcaatgaaatgtg |
| | | gagagaagcacccgtttgagattcccgtgt |
| | | gttgtgtgatttaagttagatggttttttta |
| | | agaccacattcatttccagcattctaggta |
| | | acaatttagaaaatgtcttctcctaacct |
| | | ccccacttttaaaaatcctccaactgatg |
| | | aactgatgtgaaactttcttacattcactg |
| | | aaaaaaaaaaaaaataggttaagctgtttc |
| | | taagcaactagatgaattaattttttaaact |
| | | aagaatgtggccttatttgggaaaacaag |
| | | aatatttacttgtttgtctgctgtttaaaa |
| | | aatggaagtcagcctaccaaaaaattgaga |
| | | ctcaacttctaggagatgggttaggatttt |
| | | ttttttttaagtttctctcagtttaattttat |
| | | atataagggttaatgctaccttcataata |
| | | actattatcatattttctcaatacatagct |
| | | tgattaaaacaactggactccccccccacc |
| | | ccaccccacacacacacagatttatatca |
| | | gtctgaatctaatgcctagaataagaagtg |
| | | cttcagccaggcatagtggcactcacctgt |
| | | agtctcagctactcaggaggctgaggcagc |
| | | aggatcaattgagcccaggagtctgagtct |
| | | agcctgggcaacatagtgagacctagaagt |
| | | tttaaattactggaaaaataatatgaaaag |
| | | aataaattactggaaaaagaattgaaaat |
| | | gttacgttctttatatccaaccgtggtagg |
| | | cttttttgagttcctgcaatgctaataaga |
| | | attcataaaaaggacaattcttcattttct |
| | | tgggtactcatcactaatagctgcctcgct |
| | | ggtaaaaaggaatacatgtatcttcaattg |
| | | cagattatttacttttaaatataaaagata |
| | | taaatgtcaaatattaaatgcatcttacat |
| | | ggttttcctacatagtgaaagtagaatgct |
| | | tgccagttttgcctctaggtcactcacttt |
| | | gaaccagccaacccaccttaattgatcatt |
| | | tccactaatatgttaaattaccttaaaaga |
| | | acaaaaatatttatcatgcttactataacc |
| | | tgtgttttaaaataggaggccaggcacagt |
| | | ggctcacacctgtaatcccaggactttggg |
| | | aggccaaggcaggaggatcacttgagccca |
| | | ggtgttcaggaccagcctgggcaacaaagt |
| | | gagatcctatctccacaaaaaaattaaaaa |
| | | taaaaacttagccaggcgtggtggcacgtg |
| | | cctgtggtcttagctacgtgggaggccaag |
| | | gcggggaggatcacctgagctcaggaggttg |
| | | aggctgcagtaagccctgccaacaccactg |
| | | cacgccaacctgggcgacagagtaggaccc |
| | | ccatctcagaatataaaataaagtaggagg |
| | | tgcatgtgaagtagtatagatcatgacttt |
| | | tccaattttaagagggggattggcatgtact |
| | | atgagcagttcacatttgtggaggaaatct |
| | | acatttcagagagtatatatttcatttgga |
| | | agtctataaacatgaaaacctaaaataaat |
| | | aatgtaaatctacctctagtggctctggta |
| | | ttttttaaacttatttatagctggcaaagta |
| | | cttttttgtatgtattttatagcaccatt |
| | | gcacttctcatgtttgttgcaagcatctcc |
| | | cacagcttcctttgtcttttaattttatga |
| | | catataaataaaagtatacatttcaatatg |
| | | gccatattgattgatcttttcctttgtaac |
| | | tcttactactttatatttaaaaagtcattt |
| | | cccagtctaaggccacctctattttcttt |
| | | agtttttttaaaatggtttcattgttttata |
| | | tttgcctatgatccagacattagtaactgt |
| | | gggttcttaattgggcttcagagaatctga |
| | | gaattccttaaaattctctacataattgta |
| | | catgtacttaatacatgcttttttccatgt |
| | | taagagtccagagttttttgttagatcctca |
| | | aaggggtcagtcagtctctcctcccacttc |
| | | caaaaaatgtctgagacctactactataat |
| | | ccatctggactttatttgggtaaaaggtgg |
| | | tatggtgagactcatatttttctttttccc |
| | | gcaaatagttaagtataccaaccatttagt |
| | | aaataattacctcctgatttgtgataccttt |
| | | tgaaaaataaatgttttctttatttttat |
| | | ctccacag |

TABLE 4

Exemplary target gene intron sequences

SEQ ID NO: 4
Gene: OPA1
Intron: GRCh38/hg38: chr3 193626203 to 193631611
Intron Sequence:
gtgatggatggtttaaggggggctaccgatacattcacactaatcagccatttctgccaagatcatgtcacctcaatctgttcatggactcca
aatacaagaaattaatttgacaaagtgaaaatataaaagatgcatcatataaatatgtaactttctggagtgggtagtataggtaaagcca
aaagaaacaaattcaagcagaggaattttggtttctgaaaattaggttgtctgtagggtccctgtatttatacttagaacaaaattaggaattt
ctgtttatgtggtccagttattgagtcaccctaagttgtaggcatcttacctacctacttgctcccaagttttttatttctaaaatgaaaagcat
tgctgtagatgaccagtttacactaaagaataacatttatttatttgttttagctaaagtatatggacagggaacattcatattcttgtagaaga
aaattattttgacttttgggcaaaagcatgtagttcttatcacttgacaaactcattgcgtacattttcacattaatcaaagtcagcacaaat
aaattttcaccttggaccacggagggttgaacactggaaatttgataatttctggttgctaaagaacaagttctaataaaagcttaagtgt
ataccaatatgtggctgttggtgcaatcagcaggtccgtaaaaatgattttaatggttaggtaatcccacaacggagatcccaaagttc
atgtttggaagagacttttgggtcaaagtgaaatcagtgtaatgaatttaaaattatactctgagatcttgaaatcagctaattatgttacatct
tattagctcagaaaagttttgaagttatatacaaatgctagtcaggaaaaaagattcagtcatgtaattcttgtacattctactatttaaatcaa
ccaatattatagattatgattttagtgcagtaattctgctggctaaccttatctcatttggtggtggttagtacttcagagtactccaccatagttc
atttatgttttcagcatcacttcctggttttttctcaattccatggctgtggaatcaattcatatgtatatttagcttcggtgagcaaaaacatagct
agaaaaagaaaagaagtgagtttcctacctggtaaattaaagtcgatgtgttaagccaaggaggacttcttttgaatggtactttaacaat
ccctgttctgtatactgtgaatatatcatttaaatagcctaataaattggatgcttaggctgagccacctatactttagttttgttatggaaaga
agggagaggagcaagtatgttcttatatgttacttagaaataagaatgtagctgtagttacacattgttcttaagttttttttcgtaagacaactt
gaaatgagtcccataggcctgctatttaacattcctaagatatgacttaaggttaatgatgagcttttgaatctgacaattcaagagatatccat
aatgaatactgattcattttctacattgctgaaagctaatgttcattttaagcctactttagtagcctttattttgggcttagagatgttattcctcttt
ctgatatttattgggttatctgtttaacccttttatatctcccttttcccgatttgtaaattagagactggcaagactttttaccctgagtagagcac
caaacatggcttgtttctgcccacactgtagttacctgaggggaagtaaatgggactttaaaagcaatttatgctcttttatagtgaaattat
ccctcttactatcccgaaagactgttacctttacaatatcctccactcctttcccccctgtagttactatagagatgacttttcggttcttcactgc
cataatgatcaaaatcctaattcatgagattttatcattccaggcatgtgagggtttacttgatgcataaaaccgcaagtacttttttgttgttttt TABLE 4-continued Exemplary target gene intron sequences aattgttttttctctcttatcttcttgaaagtctaagtagatcatcattttttgatgtcttattagtagcaactaataaattttccctgtatcttctcagc
aaaagaactcaagcagagacagaagattagaactaccattggtagttttgcttcctatggatatgttcacatacatagaaattttttacaatga
ccttttttatatatgtatttcagaatttcagaatggcctcaatgccttaataggaagaaatacttgaaatttttaaattagggcttggttttgtgag
gagctagtaaaggttttttctctttcagctttagcttgtttctgcggaggattccgctcttttctccatcagtttcatagccctggaattgtagaaa
agctctggtttcaagaccattgatatccatttctgtcagggtgagttttaaatttatttcatgatgcaaacaatatattgaacaacaggacatg
aacttgttcttgttgtaagtggctgaattttatcagtaaagcacatcaaaataaaatataccccaattgctagttaagacctagagtgacaga
ttgaaaatagcttgtgttattctcttaagaaaatatataaaaattatcatctcatcaatcttttaatgtttgtttttataaatctaaatgttttttatattgttt
cctaggaaatattaggtctaatttttttactttaccaccagctgtcttttatttttactctttttttgagacggagtttcgctcttgttgcttaggctaga
gtgcagtggcactatctcagctcactgcgacctctgcctcccgggttcaagcgattctcctgcctcagtctcccgagtagctgggattac
aggcacatgccactacaccaggctaattttgtatttttagtagagacggggtttcttcatgttggtcaggctggtctcgaactcccgacctc
aggtgatccgcctgcctcggcctcccagagtgctgggattacaggcgtgagccaccgcacctggccagctgtctttttaatataacattat
gattaattgtgatgttccattaaactaagcggagaggaaacatgctggtaaaccatgtgtgagttattcattgtaccagaaaggcaaatga
tacattttatcctaaaattcaaatttataaacatcttaacacttgtgatcattaaatactactaatctagcatataaatttatatttgtaggcggggc
acggtggctcacgcctgtaatcccagcactttgggaggctgaggtgggcagatcacgaggtcaggagatcgagaccatcctggctaa
catggtgaaaccccatctctactaaaaatacaaaaaaaattagctgggtgtgctggcgggcacctgtagtcccagctacttgggaggct
gaggcaggagaatggcgtgaccccaggaggcagagcttccagcctgggcgactccgtctcaaaaaaaaagaaaaaagaaattatat
ttgtaatattctactaaccttatatcattttaacttttttatataactttttttattttaccaaatttaagttaaccttttatagcccttggcttatactaaaca
tcctaacttttttgtttaattgtattagttttttaagttattgcccccagatgtcaagtaatgttggattttctataataatttaggatatattgcatgaag
tcagttagtatttacattttaaaactaaaacaatttatactaatacagttttatacatttcatactaatttagctacagttggataaatatttaatggaa
caaagtaaatcaaagtacctttttcaaatgaatttggaaatttaaatccacataacaattttttatgaccacactattacagtgtgatggcatgcc
aaatgatcataatgtggaattatgtatttcttcattggctttcaagattctgttctttagtttgtgggctcctctccaacttgcttgtctcctcacag
tttaggcgactgtttataattcttgtccatcctgcataaacacacacagtcaaaatgaaaaaaagcttctatcagcagatctgtgcttgctgt
acagaaatgggaaaacaattgaagttttgcattatcttttttctaattaccagatcgttttttggagctatttaggcatacgcttttaaggaaaaaa
gaaaaaaagagtgtacctttttgttttctaacaaaggttgtttatctatattattgaaataaaaaattgggggatagttgatgacaaagtatttagaaat
aggaattaaaatcttaaaataactttttcatagcatggacaagacttattaatgtctacctcaataagcaaatcatttaaaaattttttcatgtatat
ttgctgccatgatgtgttgtgattgcttaaataaccaatgaatgaagatcaacaaggattttaaatgaagaagaatatggatttaactattttct
cctgtgaaataagttcatatttacaagttttgattttcagaaattagacaattatttttaaaggctgggatgacaacttctgcctcttaccaaga
agtcaaagcacagttatgtgaattcatcataaatcacatcattttttattatattttgtatttataatttgtattgtgactactttaaaacctgttataaa
ataaaattgttttttaatattttattttagaattattagcattaataacaattttgaagtagtttacacaatacctgtgagttttattttttgtttttatattga
aattaattttagttgctttacttggcttcattgctatggatgcattctctgtgttacgagttagcagatctttccttggaactgaatttaaaagcaa
gcatttggctccacttaaatctctgaaaatgcaacttgttctttgcatttattacataattcgctacttatggtacagaaatggatacaatacaa
aaatatttccttataagatacactgtgaccaatgagcttttttaaatagctgtaatcagtaacatgtatttgactttttcaaaacacatttctggag
ggatatcagtgcttttattttccccaaatatctgaatccctatgcttagtacaaaacaactctgaagaatttagtaaccatatgtgttgatctctt
gttttttctaactagtctttcataagaaatgactagaatagcaacagggaaatgattgcctttaaggttttttgtttctcaatataaaattttggtga
accattttttattgataaatacaggtattttttactttcttaaatcacttgattttaaaattactttgattaaatatgcatataaagtcagttgttttttaactc
tcaatacttatcaaaaaatttaacttgctgtacattctgtataaacctaattctattcaactaaaattattttaaacatttag SEQ ID NO: 5
Gene: OPA1
Intron: GRCh38/hg38: chr3 193593374 to 193614710
Intron Sequence:
gtaagtgcaggctctaatctgccccgttaattctgggcctcttgagagtggggctgtcttatctctatctccaaaaatgtgcaggtgact
ctcaggccaggccgacggcagttggagaattcccagatgttcttgaggacccagaatgacaggagccctggctgggcttacgttcgg
agccggcttcaatactggcccttttctctggccctacccaaaccgaaaatttctggacgcctctcaatcttggcccgtctctattgtccttttgt
ctctgccctttacaccctttgtgtcttcagtgttctgtctgtctctggttgcctcttttgccttttttctgtcctctccctgccaggtttggctctgtcc
atgagtcacctctctccacatttctcctaactctcggtgtcttctttttcttccatttccacgccatgtgtacattgcatcttcaggtacctgggct
cttctatcggggaaaggggcgtccgtctctttccctagcccgctgatagaagtcagaactagagcaatgacgcacacggtgtcagaga
cggtgattcgagatgcccttcaatagcagctttttttctgtgtttcgggagggagacttacttttttgatgcaaggtcgtgaacgtggcacca
ccttttctaatctcaatcattgttgccctggggtggtttaattctaaatagaaaatcatagaaatcttttcatttctgtgcgttactatatgcattgta
atgagattaaattggatttatagggaatttttgttctagtatcattagatacctttcaagcttagctcattgttgcaggcatttgataggaagtaa
gatgcatcaagcaaaattggaaaaacgtggttttcctgaattaacttctaagcagttgttttgaattttttccagaccttttaagtggtatagat
aatttatcgtgtttataaggaatggaatgcattcgttagtttgtttttgtttttgagacgggagtcttgctctgtcgtccaggctggagtgca
gtagcgcatatctcggctcactgcaacctccgcctcccaggttcaagcaattctcctgtctccgcctcccggagtagctgggattacaggca
cgcgccagcacgcctagctaatttttgtattttagtagagaggggtttcaccattttggccaggctggtctcgaactcctgacctcatgt
gatccaccctcctcgacttcccaaagtgctgggattacaaccgtgagccaccgcgcccgggcccaatttgttttatataggttaactggagt
ccaaaatacagaactagatgagataacaatagttaacagtgttagtcagttagaattattgcataggtattttttaatctcatggaattttagtct
ttgagtaagttcacagcccttggtatttaaagtaagttatttacaaccccttgcatttctacttctccaatattttagtgaggaaacatatctgattttct
ttaaataaaaagagaaaagactgcagaagatagcattctctgtgttggagcaattaagatgtataagaagaactacaaaagacggagttttaa
aacaaactgatttataagtggtatttatttaattggctgtcattgggctaaattatttctaaagttaccatggatgccattgagtcatggcttaaa
aatgtctcctggtgatggcacagtttagctacctaaagaagtagagatgtgggaagccagaagcccaagctctgcagttttttcttttgct
atagttcctttgcatgttgtgaaagaataacagttaaattcctgctccctaacagatggagacataagcattcttttgggcatacatatgtaaat
acatgctcatggacatgtgaaaagatcaatactaacatttgggtgcaataaaattgtgtaaaattattttaaaagaattacatattaggaa
atgatatattgattaaaagtgatagtcaatgaacaagagagtagatttctgggggaaacctattttgcatcatacttgatttttagttttgactg
aatattgaagtctatatcaaaattcttttccttagaactgtaaaggcattgctgcatttttcttctaatgtaatgttttattgctgctgagaattctt
atgacaatctgattttttcatcttcatgattatcttgttttttcccttcatggaatctgttaggtgtttgactttatcctttatcctcaaattttctcaaggc
ttggaccaggtgtgggttttggttttttgtttttctttttgctactcatttgacttggcacactcagtggccttttccctttatctttctttcatttctgagac
gtttttctctcttatttttttattatcttccttttcattttttcctgtccttttttcttttctagacatctcttaggaggaagtagtggtcctcttagattgatatgttat
gtccgtgatttccaaagtaagatttgtactcgtcgtctgttaaaaggaaaagcatacatataccctatgtatatgtgcacacttttttatttttaa
attatatatgtatctgtactaatttatttacattgtaaagcttaaggtgatttaaagatacaaaacatactgcatctagaagctt
cagtactttcttcctgaatcccagtagatccttttgttcatcccacgggatgcattccgcccccaatcctcccactccctttggataccacatta
ccacagctctgcatcacttaacttttctcttatgttttttcacctttttttttttttttttgcatttttatgtcctggggaatttccttaattcatttcatgg
ttttactgttgattttttaatattggccatcgcaacttttctttttctttttcctttcctttcctttcctttcctttcctttcttttcttttcttttcttttct
taatttttcttttctttttcttttctttttctttttctttttctttttcttcacacaggatcttggcgtgttgtccaggctggcctcgaactcct
gggctcaggtaatcctctcacccttggcctcccaaaatgccaggattacaggcgtgcgccactgcatttggcggcaacttaatttttctattttt
tccttttagaggacacctagcactgagcattgcaactttttcatttccatgaactttttaagaaaactcttaaagacatgtttaattctgtacactt
ctattgttctttgattgctgttttgaataacaacaaggagtacgccttagcatttttgatggtatcctcttaatagtcgcaataatagtcccctg
gcgctctgtatactctcaagtcttaaatgttttgtatgcagctgtacgttgacagttgaatggtctcgctccaagtggatcagcaagaacata
aagaatcatttaactggtacaggctgcggcttgtgaattcccctattaacaccaaagaagacgtgtgagactccgtactgaaactaaagac TABLE 4-continued Exemplary target gene intron sequences

```
gacttgtgagttccacactgagatcaaataagtctttatgatggtgacagagagtggtgtcaacgcctaaagttttggttaatctctctaaat
tgaggggctgaccaaaggggggaacttaactgtattagacataattttgagaaacatgggtatgtggatggtaatggaggaaatgggtg
tagatgagattgcctagggagagtgagaagtaggttaggtctaagccttgatgagttcccaacatttccaagggtagttgaggatactga
aaatgagtggccagtgagatagaggtaaagctagagactgcccagggggaggaattttcaacaatgagggggtgtcaacattgtca
ggtattgctgagaggtcagataaaaccagaattgagcaaaatggccattggaagcctatggtgccctccgtaagagctgtttcgctgaa
gtgatagaaacggaaatcaggctgggcacagtggctcactcctgtaatcccagcactttgggaggccgaggtgggcggatcacctga
ggttaggagttcgagaccagcctggccaacatggtgaaaccctgtctctactaaaaatacaaaaagtagccaggtgtggtggcaggtc
cctgtaatcccagctactcaggaggctgaggcaggagaatcgcttgagcccagaggcggaggttgcagtgagcagagatcgagcc
actgcactccaacctgggtgacagagcaagactccgtttcaaaaaaaaaaaaaaaaagaaatggaaatcaggatggtttggcttta
ttttaataaaatagctagagcagggaaatggggtacttttttttccccttttaagatgagacatagccaggtgcagtggcttacacctgtaat
cccaacactttgaaagggagggtcgcttgagctcaggagtttgagaccagcctaggcaacagtagcaagaccttgtctctactaaaattc
aaaaaaaattaactgggcatgctggcacacacctctagtcccagctatttatgaagctgaggcaggaggatcacacttgagcccagata
cgtggggctgcagtgagccctgataatgccattgcactccacgttgggcaacagagcaagacttcgtctcaaaaataaataaatacccct
gtctcaaaaataaaaaataaatatgggaggagagatttgacttagattcctcaaagggcaggaggaaagagaattccaaacagtgattc
accttttaatggggaaaagatcgcttaattttacatgaggaagagggattggtggagatacagtaggtgaacagtttttgtatgaggaa
gttgaacatgtgtcattctaatagcttccattctctgtgaagtagagggcaaggtcatctactgagagttggggaggtcaagagagataa
ggggagattagaagagctcttctagcagagagtggaagaatgaattgctaagagagatgaagtaggattgttaagtagttttgagggcc
ctgttgagatgtgcttccagttgggtgtgattttctccagtagtgctttatttccctgggtacaggcagagagaaaaacaataaggctcatgt
aggtttgtattttgttggacaagtcaaacagaaaagtcaggagacgagggagtttagaatgtttgcaaaagagttattgaaacgatgaa
ccgcataatctaaggtggtaagtgggtgaatagataaggaggatgtgaataggtaaggagaagaaagaaatatcagattattgattattg
atggcgactctctaatacagctattatgccattttaaccgattaagaaactaaggctttagaaaattcataatttgccctaactgcacagcta
gtaagcagtggaaatgtgattggaaccagagttcttctgactcaatagactaaatggatgtaaggatgtagttgaaagaagggtgagcta
aacgttgtggaaccatgagctcttctctcggttgatatccctctctgtaagtgataacatgggtcacgctggataaaaccttgtggtgattgg
tgactttccttttgtccttcctcctgtgcctagtctggcgagtatctgcctttccctttcctttctcattgctgccacctaacttttaggctcttccct
tacatctgggtaactgaaataagtcacctttttgttcccttctgatttactttgacctaacattatctttactattttctttaaattaatgtttcatta
gtcttattctactcaggaactctgtagttccccattgcctacgaaaaaagttaagcctcagccttatattcagtgactcttcaattggatattc
agtccagttttactcctcctatgagccttctatgccagctccttgggtcttgccctttcattgtctcagctctgcaccctttcttttctctttttttatt
ctttttttttttttgtacttttttgtgttttctttttggtttctttttttgttttatttattaaacctccatcacacttcatcctatggagttttgaaccacacgaa
ggtgcagtatcatcctgggcgtctggaggaagtggcagggagtccaaaatgtcaccttagcttcttatctggggccacatgtatttctgc
atctgctgcttcccacactcttgcccacaagtgtcgcttgtggaaataatttgagatttactgtctggctgaccctagtttcaatctcttttcca
ccatttgctaatcattctaccttgggcaaaacatagaattaaaagaaaacttcagacaagttaaatttgatggagtttaattgagcaaagaa
aaaaaatgatccacaaattgggcagtctccagaatcaccgcagattcagagagactccaggggtgcctcgtggtcagaacaaatttata
gacagaaaaggtaaagtgacctacaggaatcagaattgagacatagaaacagtgagattggttacagctcggcgtttgccttatttgaa
cgcagtttgaacactcagcagtctatgagtggttgaagtatggccgctgggattggccaacactcagctgttattacagatgcatactact
aagtaggttttcgattttgtctgcctatttgagctaggttacagttcgtccacaaggactcaaatataaagtacggagtcctcttcgggcc
atatttagttcgcttttaacaattccccctttttggtcagccctcaattttagagagattgaccaaaaactttaggcgttgacaccactctctgtca
ccatcataaagacttatttggtctcagtgtggaactcacaagtcgtctttagtttcagtatggagtctcacacatcttctttggtgttaatagg
aattcacaagttgcaactttgtaccagctaaatgattcttttatgttcttgctgatccagttggagtaagaccattcaactgtcaatgtacagct
gcatacaaaacatttaagacttgagagtatacagtgcaccaaggggactattattatgactgttaagaggacaccgtcaaatgctaagg
tgtactccttaataaaagttcttatgaaatgaactgaaccaaatcagccaagttcagggttcagacaataaagcagttcagcagtattgggg
tctgattggtcagagtcttcagttggagtatgatagtgattaaggatcatagttcgctgtaaagtagcttgacttaaagaggtgctcgttttca
ttgttaccttgttaatacaagtcataataacttgaaaacctgctagaagagataaaagattagaaaccctttggaaaacccaagcttgccat
tcaccacttaggatgcctgcaaaccaactgttagttgctcctataaacatatcgtgggttcctttctcttgagagatttcttattgtacttggtg
gcagtgctcaaggaaacagcagtatcagccaccttttaaattaagtctttttgtagtaacagattgaccaaaacttttaggcgttgacaccactctctgtca
tttttgtttaacaccaaacataggcctccagcttgagcaaaaagaagatctaagactgcatgatctttccattaagtgttttcgttgaatatgtat
gttgtcatgtgcctttctgagagtagcttctaccatctgaaaccctggggagtctgattggctaccaaatccaagaatttttcccaatatata
aattagttttaaattccgtacaaatggtacttcactaccaccaagagtgagccccaggaacccagtgaaatctttcccggtagaaact
agcttatcctcgtctatttcgaggctagtgctaatttcagttattgatcatttttggcctccaagtataaggggctatcatgagaattttcagggga
agcaattcgaaaggcaggagcaggccaggccagataacaagaaccaaaccaaccaaggaggcagaacagaatatgcagattctcc
acagacccaatagagaccctcaggggttggaaaaggggggccacctagttgtatttgagcagggatcattcaggtttgttcgaccatgaa
tctgtagctcctgaataacatccagtgggaaatttacttttctatggccccttttgtagtgtgttgtaagggtgtataaccacatctagtaaaaa
gagaccctactggatatacaagcaatcacttgtactaacataagtaattcccaaatcttgagtatgtgatgcctgcaagcaatatacgtt
ttgtaggcatcatttggatttgtttttttatatttggtgtgatcgacttttatcagttgaaaagagtgttgttttttagtggtgtaggaaaagcaagta
ctagtgatgtttagagtatcaagaatagctttccattcttcccttgggtttcagggtgactcattgggaaacgtggagggcactggcac
ccttggaatcatttcctgatttttttggcattagcccacaaacccaacagttaccctggttttgtgctagagcataagcttgagctgaagccat
ccactgattatggtcccatggattttcatgtaaggaaaaggaaaggattagggaaaaaaataaggaaaaacagaaaaacacataaggctt
tcatggtggtagagaagtcttgatctggtgatctagggaaagctgtcgtaaccaggatgctgtcgcttctgggaagagattttccctggtc
agctttaccttaaagtctccaacgggtatatagtaccaggagtctgaggggggccttttgaattgtgagatggacccatggttcaaagc
cctgaagcttctctgcactgtgggtggtaagaaggacttggtatggtcccatccaacgaggttcaagagtgatcttcttctgatgtcatttc
cggaaggcccagtctccaaattccagaccatggagggtttgattgtcctcagttggtggatcttgaaatgcttccttttacctggtggaagt
atactttggcgtaatacattaaagccttgcagtatttagtcatatcagagtttaaggagcaggagaagcatgagatgctattattagggac
atgggcctcccagtgactatttcataaggggtcaatttatgttttccaacaggattgaatctgattgccattaaaaccaaaaggtagtacctt
tggccaaggcaactcaattgattcagttaacttggacagtttcagttttcaaatgccatttgttctttcaagcttttcctgaagactgagggtaa
taaggacaatggtaatgcaactgtgtcagtaacacccttatttaactgctttataacttgctcagtaaaatgagttcctctatcactggagactt
ttagaggggatcccccataaaggaaaaacatttttctaataattttcttagctatggtcacagcatcagctttcctacatgggaaggcctttatcc
aaccagaaaacatgcaaactattacaagaacatactgataccccattgaggggtggtaactgaatgaagtccatctgtaaatgttcaaatg
gtccatcaggtggtggaaatatactgcctctagttttctgggattatgagtttgacaagtcaaacattgattataagccattttagtaatgtca
gaatagtcaccccaccagtatttttcataatttggatcactttgtctgttccatgatgagctgtggagagctttcaataatggaagcttcaaa
gattcaggaaggaccaggccggcccgtccgggccctttgtgagtctttgcttcacgttaaatttacatcctttagatacccagttttgttttgca
aatcagatgcgttgcactgttttattaaataggtcatcgtaaggaaattggcttggattaatcttatggagttcattcagattgcgtatcttgatg
gttccagcactagctgattgagcataaaaatctgctaaagcatttcactgatattggttcatttctacaagtatgagcttcagtcttaataa
cagcaatctgcatttgtaacaggatagcagaaggagctcatctgtttggagtccatttttgatggggatcccactagaggtgagaaacc
ttcgtagtttccatatcatgccaaaatcacgtactactccaaaagcatgtctactatccgtaaatattttactgacttgtcctttagctgtgtgaca
tgttcaggtaagggcagaaagttctgcaggttgggctgacttgacttggaagagttcgcttctctattaactcattttgggtggtaacagcat
atcctgactgatatttttttttctgagttttttggcataggacccatcaacaaaaagttttaattcaggattatccagtggagtatcttgatagca
acacgaggggccactatttctgatactacactcacaccgttgtggtcttccatcatcaggcagagataacagagtagcagcattaagt
agattacagccttttagatgaagataagaaggagataggagaagtaattcataagatgttagtctactcactgaaaaatgctgggtttgatt
ggaatttaatagactttccacagcgtgtgggacttgcaaattaagttcatttcctaaaaccagatctgatgaagcttctaccagcttggctgc
```

TABLE 4-continued

Exemplary target gene intron sequences

```
tgctactgcttttaaacaattaggatatgccttagagactgggcctaattgcaggctatagtatgcagtggtcctatgtttagcaccgtgttc
ctgattattacattcatgaacaaacaaagtgaaaggtttagtgtaattggaagtcctaaagctgggggctgttgtaaggccaacttcatttg
gctaaaagcctgctcatgactgtcttcccaaggtaaaggctctggtacagcattttagtgagctcatacagtggtgaagctattaaggaa
aaatttggaacccaggatctgcaatatcctgcaagcctaagaaagcctttgtcttttggttgcaggtcgaggaaaactttaaataggtttta
tcctctcaggtaagagggaaatcccttcagcagccaagtcatgtcccaaatagtggacttttctcttttgaaaattgaagttttggccaggca
tggtggctaacgcctgtaatcccagcacttttgggaggctgaggcaggcggatcacctgaggtcgggagttcaaggacagcctgacca
acatggagaaaccctgtctctactaaaaatacaaaattagccaggcgtggtggtgcatgcctgtaatcccagctactcgggaggctgag
gcaggagaatcgcttgaacccaggaggcagaggttgtggtgagccagtatcacaccattgcactccagcctgggcaacaagagtga
aactccatctcaaaaaaaaaaaaaagaaaaaagaaaagaaaaaattgaagtttttccattgaagccctgtgacctttatatgcaagttgc
tgtaaaaggtaaactgagtcaatttccgggcactccttaataggagagcataacaataagttatctacatactgaatgagagtagaattttg
aggaaactgtagtgtcattaactcctgatgcagtgcctggggaaaatatgaagggcttcagtaaaccctttgtggcattacactccaggt
gtattgctgattttttccaagtaaaggcaaacaagtattgactttctttatggaatgctagagaaggctgagccaagatctattactgtggaca
acttggaatcagtgggtacattaggttataaagtattaggatttgggactacaggaaatcttggtattacaatttattaattgcctgtaaatct
ggaacaaatctccagtctcatccatttgtttttaactggtaggattggagtgttacaggggctggtgcatggaattatgagtccttgtttaat
taaatcttctacaattggtgagagcccttaaattgcttcaggttttagtggtatttgtggtaattaggcaaaggtttagaatgatctgttagtac
ttttataggttctacacttttaattcttcctatatcagttgggaagaggcccataaacattaggtgttttcgaaagatcaggggtattacaggct
tgagtttcgatcttatcaatttctgcctgtagacagcataacaattctagttcaggagaatcaggaaaactcttaagattatttctgtttctgag
gaaaattttaggtgcccttttagctttgaaagtaaatcttgccctaccaagtttactggaacagtatcacgtagtaaaaaactgtgttttttctga
aaggggctcagagttaattggatgggttcagatatgggaacctctggaacttctgattttgaaaccctgtcacagaaatgaccttttttactct
aagggatttgttggcttattaaggtggggtttatggtagatagagtagccctggtatccataaggactatacacaactccctatttatttttaac
ctctgtttccccatgttcctttaaaggtattacggggagcaatccactggagaatcccttagagcctccttttaagttgaatattgtcaggagg
actaaggtctcttgggctccctctagtggtgaaacagtttggcctagagggaggtttatcagccgacaatccccttttccagtgccctggtt
gtttgcaatacaggcagacatcttggggtaaagaaattcttgttctgggacctcttgatttgattttttttaatatataattttaaaaatattttcca
aagtgtgacttaaaaaaattttttttttattatactttaagttttaggtgcatgtgcacaacgtgcaggtttgttacatatgtatacatgtgccatg
ttggtgtgctgcacccattaactcatcatttacattaggtatatctcctaatgctatccctccccctccccaacccacaacaggcccca
gtgtgtgatgttcccctcctgtgtccaagtgttctcactgttcagttcccacctacgagtgagaacatgcggtgtttggtttttttgtccttgtg
atagtttgctgagaatgatggtttcagcttcatccatgtccctacaaaggacattaactcatcattttttatggctccatagtattccatggtg
tatatatgccacattttcttaatccagtctatcattgttggacatttgtgttggttccaagtctttgctattgtgaatagtgctgcaataaacatac
gtgtgcatgtgtctttatagcagcatgatttataatccttttgggtatatacccagtaatgggattggctgggtcaaacggtatttctagttctag
atccctgaggaattgccacactgacttccacaatggttgaactagtttacagtcccaccaacagtgtaaagtgttcctatttctccacatc
ctctccagcacctgttgtttcctgacttttttaatgattgccattctaactggtgtgagttggtatctcattgtgtttgatttgcatttctctgatg
gccagtgatgatgagcattttttcatgtgtctttttggctgcataaatgtcttctttttgaaagtgtctgttcatatccttcacccacttgttgatgg
ggttgtttgttttttctcttgtaagttttgttgagttctttgtagattctggatattagccctttgtcagatgagaagttcagaaattttctcccattct
gtaggttgcctgttcactctgatggtagtttcttttgctgtgcagaagctctttactttaatgagatcccatttgtcaatttttggcttttgttgccat
tgcttttggtgttttagacatgaagtccttggccatgcctatgtcctgaatggtattgcctaggttttcttctaggattttttatggttttaggtctaa
attaagtcttttaatctatctttgaattaatttttctgtataaggtgtaaggaagggatccagtttcagctttctacatatggctagccagttttcccag
caccatttattaaataggaatcgtttccccgttttcttgtttttgtcaggtttgtcaaagatcagatagttgtagatatgcggcgttatttctgag
ggctctgttctgttccattggcctatatctctgttttggtaccagtaccatgctgttttggtgactgtagccttgtatagtttgaagtcaggtagc
gtgatgcctccagctttgttctttggcttaggattgacttggcaatgcaggctctttttttggttccatatgaactttaaagtagtttttttccaattct
gtgaagaaagtctttggtagcttgatggggatggcattgaatctgtaatcttaaattaccctgggcagtatggccattttcacgatattgattcttccta
cccatgagcatgaatgttcttccatttgtttgtatcctcttttattcttgagcagtgtttgtagttctccttgaaggaggtcttcacatcccttt
gtatgttggattcctaggtattttattctctttgaagcaattgtgaatgagagttcactcatgatttggctctctgtttgtctgttattggtatataa
gaatgctctcttttgttctttgttagtcttgctagcggtctatcaattttgttgatctttcgaaaaaccagttactggattcattgatttttgaagg
gttttttgtgtctctatctccttcagttctgtctgttctttatttttctttgccttctgcctttgaatgtttgattcttctagttctctttta
attgtgacgttaggtgtcaatttatgatctcttcctactttctccttgtgggcatttagtgctataaatttccctctacacactgctttgaatgtgcc
cagagattctggtatgtgtgtcttttgttctcattggttttcaaagaacatctttacttctgcctcattctcgttatgtacccagtagtcattcagga
gcaggttgttcagtttccatgtagttgagcagttttgagtgagtttcttaatcctgagttctagtttgattccactgtggtctgagagacagttt
gttataatttgtattctttacattttctgaggagttgtccaactatgtggtggttttggagaagtgtattaggtccgcttggtgcagagctgagttgaatcctgatatccttgttaa
cttctgtctcgttggtctgtctaatgttgacagtggggtgttaaagtctcccattattgttgtgtgggagtctgagtctctttgtaggtcactca
gggcttgctttatgaatctgggtgctcctgtattggttgcatatatatttaggatagttagctcttcttgttgaattgatccctttaccattatgtaa
tggcctttctttgtctcttttgatctttggttaaagtctgttttaccagaagactaggattgaaaccgcctttttttgtttttccatttgcttggt
agatcttcctccatcccttttttgagcctatgtgtgactctgcacgtgagatgggtttcctgaatacagcacactgatgggtcttgactcttt
atccaatttgccagtccgtgtctttaattggagcatttagcccatttacatttaaggttaatattgttatgtgaatttgatcctgtcattctctc
aacatttgcttgtctgtaaaggattttatttctccttcacttatgaagcttagtttggctggatatgaaattctgggttgaaaattcttttctcttaag
aatgttgaatattggcctccactctcttctggcgtgtagagtttctgccgagagatcagctgttggtctgatgggcttccctttgtgggtaac
ctgaccttctctctagctgccattaacattttttccttcaactttggtgaatctgacaattatgtcttgaggttgctcttttgcaggagt
atctttgtggcattctctgtgtttcctgaatttgaatgttggcctgccttgctcagattggggaagttctcctggtaataatcctgcagagtgttt
ccaacttggtccattcttcccgtcactttcaggtacaccaatcagacgtagatttggtcttttcacatagtcccatatttcttggaggctttgtt
cgtttctttttattcttttttctctaaactctcttcccgcttcatttcattgatttgatcttccatcactgatacccttttcttccagttgatcgaatcgg
ctactgaggcttgtgcatccgtcacgtagttctcgtgccttggtttttcagctccacaggtcctctgcattagttattctagtt
agccgttcgtcgaatttttttcaaggttttaactctcttgccatgggtcgaacttcctccttagcttggatagttttgattgtctgaagtcttcttc
tctcagctcgtcaaagtcattctctgtccagctttgttccgttgctggtgaggagctgcattccttggaggaggagaggtgctctgattttta
gaattttcagtattttttgctctgtttcttcccatctttgtggttttgtctacctttggtctttgatgatggtgatgtacagatgggttttggtgtgg
atgtccttttcgttttgtttagtgggacccctcagctgcggctattgattggagttgcttcttgcttgaaggaggccactccagcatgttt
gcctgggtatcagcagcggaggctgcagaacaacgaatattggtgaacagcagatgttgctgcctgatcgttcctctgtgaagttttgtct
cagagggtacccggccatgtgaggtgtcagtctgcccctactgggggtgcctcccagttaggctattcggggtcagggacccac
ttgaggaggcagtctgtctgttctcagatctcaagctgtgtgctgggagaaccactgctctcttccaagctgtcagacagggacatttaag
tctgcagaggtttctgctgcctttttgttcggctatgccctgcctgcagaggtggagtctacagaggaaggcaggcctccttgagctgcag
tgggctccaccccagttcgagcttcccagctgcttttttacctgctcaagcctccgcaatggggggcacccctccccagcctcgctgcc
accttgcagtttgatcctcagactgctgtgctagcaatgagcgaggctccatgggcataggacccgctgagccaggcgcgggatagt
ctcctggtgtgctgtttgctaagaccatcggaaaagcgcagtattagggtgggagtgacccaattttccaggtgctgtctgtcacccctt
ccttgctaggaaagggaattccctgaccccttgtgctcctgggtgaggcgtgcctgccctgctttggctcatgctcggtcgctgc
acccactgtcctgcacactgtctgacaatcccagtgagatgaaccagtaccttcagttggaaatgcagaaatcacccgttttctgcg
tcgctcaagctgggagctgtagactgagctgttcctatttggccatcttggaaccgcccgattgtgattttaaaatgagaacgagatggtc
cctttggttcctggtccctgtaactgttgcaattgaaggggcataagcttattagccttttgagttttttttgctctagagtcttctcaaaatgc
ttagctaggttgggcacgatggctcacgcctgtaatcccagcacttggaaggccaaggtggggaggatcacgaggtcaggagatcaa
gaccatcctggctaagatggtgaaatcccatctctactaaaaatacacagattagctgggcatggtggcacacgcctgtagtcgcagct
```

TABLE 4-continued

Exemplary target gene intron sequences

```
actcgggaggctgaggcaagagaattgcttgaacctgggaggcagaggttgcagtgagccgagattgcgccactacactctagcctg
ggtgacagagcaagactccacctcaaaaaaaaaaaaaaaaaaaaaaaaagttcagctaaggccaccaattcagtcacatctctaactt
cccattgcaacttatgttttttagttaaactgctaagttcaggatggagtccatttataagtaaagcagttaatgctgtttcagccctgcagg
gaatactccttgctgtactttgagcccaggatgtttcacaaatatttctaagcgacttctgtaatctgaaactggttcatcttttctttttcttttttttt
tgcttacaagattgtatgatggaccaatttttgtggaaaaattttaggaactgaatgttaaaaggttttcagcgatttttctagctattttggtc
cttcttgtgaggagctcttagagggcccttaaaatgtcctcctcaggtttgtcccattctgctgctgccatccatttctgagcttcaccagcc
cccagtatcatatgaataaattggtaaattcatgaagtcctggatcgtaagctcctattaggattctaaattcctcagtaaattttttgagacttt
cccttggaccagggaagtccttcacaatgggctaagctcagttttagaccatggagtgaaagtagttacagcaggcaggcctggctg
atataaggtctcactttgtaagacatctgtctaactttctttttttttttttttttttaaatcatcttcagggtgaaagtgtaatttaacaaaaagtt
tagtggactcagagtatgtaggtagagatggacaaagaaggaacagtccgagttagatcagtcaaagtacagtcctctttcttcatgtcct
tggtctgttgcttaagcttttcattttggttttttgcaaagaatcttttaaggaggcacttttttgattcacttagtcttttggaggcctttgcgtatcca
tgagacaatacatcccactgtatttgtgggggctttgatcccctttttctaatatgccttgcaaacaattttttatccaaattaaaacttctccattg
tggccatttaattctaagtttttcttttagtgaggttaacccatttttactgaaaatgcacatgttctgggcccataatttttatacgtaaaattagct
ggagtccctgaagatggagtcccagactccttggattgagatgatcccattattaaataaggtacttatcagagggtctgaggcctctaact
gaatccaatccaggttaattatcaaatccaatttgatcttggatccagtccaggctaagtattgcttgagtaaactcggagagctcaaaacac
aagttagtggagctcggaatctgagagaaaactcacccatgacctccagttacaatcaagagaccagtgagagcaacggcctcagtg
ggtacctcaccaggtcacctggtgttccaggggggttgccagagttttttcttcaaatcccacttctgacaccagatctgttaaaagaaaactt
cagacaagttaaatttgatggagttttaattaagcaaggaaaataaacactttgcaaatcaggcagcctccagaattgaatgcagtttgaac
acttagcagtctattagtgcttgaagtatggccactgggattggccaacactcagctattattacagatgcagtactactcaggtttttccatttt
gtctgcctattgtgctaggttatggttttgtccacaagaacacaaatatagaagtatggagtccttctcaggccatatttagtttgctttaacaa
tacttaaaaaaaaaaatttgtaaaataaggatacttaaccttactcggtgtttctgagagttaacatttatatagttatgctgtagtgaaaacagc
tagcgtaatgtctggtatgtataggaacacaagagataccgcttttcccatatccccataccattcttcacagcattgctcctgtcttccttga
ttcctcctcctccttctttgttttttttttttgtttggttttgtttttttttgggaggtggagtctcactctgttgcccaggctggagtgcagtggtgtga
tctcagcttactgcaacctctgcctcctgggttcaagtgattctcctgcctcagcctcctgaatagctgggattacaggcacacaccaaca
cactcagctaattttttgtatttttagtagggatgggggtttcaccatgttggccaggctggtcttgaactcctgacctcaggtgattcacccac
ctcagcctcccaaagtgctgggattacaggtgtgagccaccacaccctgcctccttcttaagaagtttccagtccctttgtaattaaaggaa
ttaatatttttttaactacttagaatcagactggccctgattattagtaagcaactaatagtaagcaagcaactatgtatgcaactatgagtgtat
gttaagatatggttgttggtaacctttcattctcttcaggaagaagaagaggggtggagctctacagtcaatgtgtacattttaaattctgttccc
tttcgagcttttttgctactttcattcttctgggatccaggtgcttgagttgggattgattaacttccttaatttccaccctgtgctgtcaggat
cgggagacatagatgaaggtgttctaaactgctagaaattttgttttttgaaagcaaaagtttgcatgcatttttgttttcaacttttacttacagt
gaatagtagttaataaaataagtccctgccttttctctcttggtttcaattcctgagaccaggatcatagcccacatattagagtggagtccc
actgctttggtttgaatcatgcctttgttttcttatgtcagtgtgactttggcaagttattttaagtctttgccaccatttttcctcatctgtaaaatg
aggataatactagtacttttctacatgggattgttagcaggattaaatgagatagcacatactgtaaccatgtctgcgcacatagtcaatgatt
agtaaatgtgaactattgtgtgacattgtggttagtcacgtatgggctgtgtttcctttagtatattgctcttttaatgtcatttcctttgtactgtt
accctctctgatctttcttccatattca SEQ ID NO: 276
Gene: OPA1
Intron: GRCh38/hg38: chr3 193618937 to 193626091
Intron Sequence:
gtaagtgtaaaagagaattgttcatgtaggtagtcttgaaagattttttaaagttttttacttctttggaagattttaaaatgataacatctgagaa
gcaaatacaaaaacatccaagtagagatatcgttactaatcttagtgcaaagtacaaggtattacgtggcagttctggaaatataattgag
aagcccatttctttcacatatgtccagtgaagcattagtttcgagggttgtcccaagaaagagttgtgttgttaagtgtgtgggggagaa
aggctcgtttagacaaggcaagcggacttcttttcttcccctaggaccctctatactgtaatatactcatgcgcattgtgaatttccaaggag
tcaaagcatacagtgttttcccaaatttatttcaacagaaccctttttgctcatgtgaacgtcgtataggggactagatttcacttttggggaaact
agaaaggggaataggaattgggttattaggaaataaatcaattccctgatattgatagttaacaaagttatgtatggggtttattttatggtatgtt
attttcaacacatattcattaacaaaatccatatgaaagttataggagaattgctgaggtagaataacatactttgtttgtatttataatactcat
atattacctgacgttttctgagtcttcacttttttcattcttttggaagttggtaaaataactgattccttgaaagtttttttctaaataatacctagat
aatagatttatagaaaaaatattgtatgaatgttttaacattcatgtaatatggaacatgtaattttttatactggaggttattatagttttaatacat
caaagaaataatgtttattttggaagcagaaagaagaaataaattctatgaatagggttttcatctctcttccttgttcttcaactttgaacttttata
ttccaaattttaattatatttcaaaagatttttttctttgccttttaatttttatcttttggagaaaaatgtatgtcaaaatgtatgtacgtgtatttgtct
tttgatttgatcttttttgaccctcttttgcattgacattatttcaaccaaaggacacttcttgattgttcatgctactggggaaaaaaaaaatagt
agaaattagcctaatagttgtggcttattttgagtgaaggccttagccctttaaggcaattaaattttactgtggagagaagagctaatctaatg
gggagaaggagcctttgttacaggtgtggtagtgtggttctttgagtgacaagatttctgtttgccagattggttaggagaagtctgtgtgt
ctgctttctctcttatggcctaggatcactgtggtgaatgaaaaacctgtctcagggcctgactcagataattccctaaaacccggctaag
gtcatagatgaataatcagtaattgaacagaagctctgcaatagaaaagaagccagataattattttttggaaatttaatttatatttacagatttt
attttatacagtagacatggaattttaattttattacattatgttctaattttactcttttgcttgttttgcttgtttgacaatacatgtccttgtaaa
ctatttccttttaacttttttctcaatttatggtgcttatttttccccattaaagacttaccaattttttttttaactatttgttacacatactgaatctagag
ttgtaattaagctacttttcattactggttaagtcaaattatagcaaatgctactataaaaatttactatccaaaaatgtgtctcaagcccccaact
gatggtttcaaattctgttattaataatatgcagcattgtgtttgcaaagcttggctgttacttgtgatgcttgagaatgatgagtcactcagct
aaactgagtgattttgagacttgtgtacaaattgatggttgaatgtaacatgcaaaagagagaccttagcttagcagtaccctttttgaaatc
actctgacatcaagtttgaaaatgtgggcaataatcagaggtggtaaggtggccaggctttagctgaatacttttttaactggttcagtctg
agggctgaaagcccccagatttaaacagtatttagaatttgaagcagtcaagtattagtttaatggttgtcaggtttgtaacaaagtttctggc
tagacttctactagaaatgtaaaagtgcatgtgaatcagcttttttaaaaagtaataataattgaaaaacatttctacaactagaactaaaga
aaagatttgtcctttctaataggaaaacacatctgggagaagtgctggcaactgacagcaacctttcagaatcagaatcaaggaagtg
aaagtgacggggagctgaggggaacacagatgtttgacttcagtcagacagaataaacatgatgaaccgataacctgtgattcccag
cctggggttactactggagttttaggtgtcctggaaagttataataccggtcttcaaaaagtctacagaaagcatagatttccacataatgc
tgcacaggctaacgaattaatcaagtttctttggtttggcctggatttatatccattcagtttgtggacactactgaattatttatgtcatgttgat
caaaagttctgatatgatttgattgaacattgaaaaaaatagtaaaaccaaccattttacaactacatcatcttgaggtatgattga
catacattaaaaccacctcttaataaatgcttcttgttaatcaaaaatttgaaaacgtatgtccactggaggaaaaaagacatagccctgga
tgtgaactgaatattactgagactcggagacctttcagaacctacctgaagatgaatcgaagtgctgcctactttagagaattggactaattta
atttgggagtcagcagattgctgtatatcagtcatcatatataccggtgacaagaccacttagttcattccctttttttagattctgtaagattatt
gtgttccagtgaaattgatttttgcaaaatgagacattttattttctgtgctttttgttctatcatgttttctgattggtcataagtttctcacagaagta
agaaaatggcgattcagaaggcaacaagcacattttaatttatagaaaatattttgaaggactttttctgtgcccaaatcatgaaaagtag
tagtattgttttaagtataattattaaattataatacattaatgttcttttcttgcaacatattactctcattcttttttttttttttttgagacggagtc
tcactctgtcacccggctgagtacagtggtacgatcttggcccactgcaacctctgcctcccgggttcaagcgattctcctgcctcagc
ctcccaagtagctgggattacaggctcctgccaccacgcctagctaatttttgtatttttagtagagacaggg tttcaccaggttggccag
gatggtcttgatctcttgacctcatggtccgtccacctctgcctcccaaagtgttgggattacaggcgtgagccaccagcagtctgattc
```

TABLE 4-continued

Exemplary target gene intron sequences

```
ttaattttatagtttatgttgtacctccccagctgaagtatctcttttcttttttcccgcgtgtttagtgttcactcatctttatagcatagctcaattg
tcacttcatgaagccttccataaccttttgtagctccattaattatattcttctgagtgtttaaaacacttgccatatgaaacactatttactttggc
ttacattcttactatctaatcggccatttctgttactaaatcttttttctcagagcacctgggatagtcttgtgtcttagtaaaatcagttgattgatt
taactcggtagagtagaggctgattaaagtaaataaatctggttgatgccaacaaaattttggtcccctcaattttttgctctcattacctgca
aattctccctggccttcatatttggcaaccattgaggagaacaaggctgtaaaagtagttcatgtacttgatattctgaattggaattaagca
gagttgcttaagtaggacttgcttttctgggatttcttatgcaacaaataatgtagtaactggaaatccaagttcaagacactggcagattcg
atgtcttttgaggaccccttggcttcatagatgatgccttctccctatatccttacatagcaaaaggggccaggcagctctggccttttttttgta
aggccaataactccagaaacctcatgacctcatcacctcccaaaggccccacctctcaatactatcacattgtgaggctaggtttcaaca
tatgaattgtgggagacaaaaattcagaccatagtataatatttcaagattacttaaactcttctctaccaaactcattaacttttaggttagca
cagtattttcattgatattttggtttctggagttattactaattttcttgatctgatgttataattaaaaaaaaacaggactttgtacgtgaaatgag
actagagataaggaagctgattcagagatggagatttaaaaaaagagagatgagagattgagatctgcagtgtcaaactgacaatagcc
aggagtcaggagatattaagagactatatcatctgtgattgttaatgattatttattgttatttataaatactactgtattttatatattatatacatt
gttttaaaaattattttttgtaccatttcttgaaagaaaaatgtctaagcttgggaaaatatttattgaaaaatgtggtttgtacatctgaggagtg
tatcttgcacagtaggtgcatagatttcttcctcttcctgttccacatggccttagcttagaggctgtgtggccatcacttggtatttagggta
agactggtgcacaaaatcaaagacaggtaaccttggtataagtgtagtatcatgtaaatagcttttctatgtctaattcttgttttcttcctactt
tttcaggaggtcaatttcagttcatttcaactatctttacataatagtgcttagtaacaggcatggaaggaaagagacatgtccctagagtg
ttttcttgaaatctaatagatgattggagtatttaccatgcagttgtgtatatacataagcagtgaattcgagaggaattttttaagctgtaaaaa
aaagcattgtgtgccttatagacgcgagtgagaaatgtggaatatggctgatccaaagggaatgagttatctcaattgattaatcacagtc
agttacagattgaactctttgttctactcttttgcccccttctcactattgctctttgactagtcttaagaaagaaaatgtggaatattttctcacggc
tttgggattttataaattagaatactagtggtatgtaaatacagcaggtacactactgtataaaccaacataggaagccttctttaaagggaa
ttgtttgagaaatttgaacacttggataatttgaataaaggattgtgataaatgatcaaatgaaagaaaataaatcaggttactcttcttttctgc
ttgataaagcaataattttttttaaaggtaaaaattatgagaatgatgaggatagtagttagcattgtctttctttgataggtttgttaatgatcat
aaaactgatttatttaaagacatgtcttttttataactcattttatactgttgtatctggaaacaaatattgaattttcatttgtcatgtggaagaaatca
actagttttaacctttgatttataataaatcaaccacttttcatttattgtctaatactggcaatgaacacagcctaatgtatcaaaactaacaga
ataaaaattctccaagttatatccagactttaagacacttttctaattatataaaataaaatattttgggcagtcattttttaactctgaaactattta
aaactcctaatttagaatatcttaataaatacccattttcctcttttttattttttataacttggtaaaaattgagtccattgttttcccagaacgctgtt
cttaaacaaatggttacctccttcattagaacttttacttttttttaggattttctaattaagaaaacattaggcttgtaacattgtcaaatcttggtgg
tctttcttccacgttttttgaggtcgattatctaagaggccatcgttaataaagctagcaggaaatgacatcatgccacatgtgaatatcct
gtattaaaaattgtatcaatatactattttataattatgaagtggaatgaatttagaaatagaaaaggtgattttttgtgcataggtccaaactg
tgtttgttttcatttcagaatttcataataactatattgtctccatatcttaattgtgtttttttatagcacttttgtttagtaatttgtatatgcttggct
gtattctcagaggctgtttctatttaatgttgtcaaaacagctcataaaaagtgaaaattcggtcagactagttatttgatattatatgaaatc
aaaacaacctgaaacattctcttttaattttaaataaagaacccaaatttttaatcaaatgtatgcaaaggcacatagaatatatgacttaatgt
acaaccttttattaacttgatgatggaaacctgttcctagggaccttacttgaataaatgaaatatcaagaaaaaatactaacttaagaataa
taatttaataagtaagtaagctattatgatcttcaatcagtcctgagagaatcatggttgagaattagaaaatttagaccagtaagatcaaca
ctgttaaaaaaaaaaaaatcagtatttttttctccatatttttatatatctggatcatttttatttagcacttattattgcactttccttttcactttta
aactatgctgttttattttctgagacatctgatttactgaggaggaaaatggaaatgcggtacagagcccaagggtatgacggcttttaaat
gagtttccatttctgttttaagttaaccatccctccctagcttacatctgttcctttgttgcacccttggtttaacattattctcctccccaatttcct
cttctcctcattgtgaactcgtggcag
```

SEQ ID NO: 277
Gene: OPA1
Exon: GRCh38/hg38: chr3 193626092 to 193626202
Exon Sequence:
GGTCTGCTTGGTGAGCTCATTCTCTTACAACAACAAATTCAAGAGCATGAAGAGG
AAGCGCGCAGAGCCGCTGGCCAATATAGCACGAGCTATGCCCAACAGAAGCGCA
AG SEQ ID NO: 278
Gene: OPA1
Intron: GRCh38/hg38: chr3 193626203 to 193631611
Intron Sequence:
```
gtgatggatggtttaaggggggctaccgatacattcacactaatcagccatttctgccaagatcatgtcacctcaatctgttcatggactcca
aatacaagaaattaatttgacaaagtgaaaatataaaagatgcatcatataaatatgtaacttttctggagtgggtagtataggtaaagcca
aaagaaacaaattcaagcagaggaattttggtttctgaaaattaggttgtctgtagggtccctgtatttatacttagaacaaaattaggaattt
ctgtttatgtggtccagttattgagtcaccctaagtttgtaggcatcttacctacctacttgctccccaagttttttattctaaaatgaaaagcat
tgctgtagatgaccagtttacactaaagaataacatttatttatttgttttagctaaagtatatggacagggaacattcatattcttgtagaaga
aatttattttgacttttgggcaaaagcatgtagttcttataacacttttgacaaacttcattgcgtacatttttcacattaatcaaagtcagcacaaat
aaattttcaccttggaccacggagggtttgaacactggaaatttgatataattctggttgctaaagaacaagttctaataaaagcttaagtgt
ataccaatatggctgttggtgcaatcagcaggtccgtaaaaatatgattttaatggttaggtaatcccacaacggagatcccaaagttc
atgtttggaagagacttttgggtcaaagtgaaatcagtgtaatgaatttaaaattatactctgagatcttgaaatcagctaattatgttacatct
tattagctcagaaaagttttgaagttatatacaaatgctagtcaggaaaaaagattcagtcagttaattcttgtacattctactatttaaatcaa
ccaatattatagattatgatttagtgcagtaattctgctggctaacctttatctcatttggtggtggttagtacttcagagtactcaccatagtttc
attttatgttttcagcatcacttcctggttttttctcaattccatggctgtggaatcaattcatatgtatatttagcttcggtgagcaaaaacatagct
agaaaaagaaaagaagtgagtttcctacctggttaaattaaagtcgatgtgttaagccaaggaggacttcttttgaatggtactttaacaat
ccctgttctgtatactgtgaatatatcatttaaatagctccaatgcctaatggatgcttaggctgagccacctatactttagttttgttatggaaga
agggagaggagcaagtatgtctctatatgttacttagaaataagaatgtagctgtagttacacattgttcttaagttttttttcgtaagacaactt
gaaatgagtcccataggcctgctatttaacattctaagatatgacttaaggttaatgatgagcttttgaatctgacaattcaagagatatccat
aatgaatactgattcattttctacattgctgaaagctaatgttcattttaagcctactttagtagcctttatttgggcttagagatgttattcctcttt
ctgatatttattgggtatctgtttaacccttttatatctccctttcccgatttgtaaattagagactggcaagctttttaccctgagtagagcac
caaacatggcttgtttctgcccacactgtagttacctgaggggaagtaaatgggactttaaaagcaattttatgctcttttatagtgaaattat
ccctcttactatcccgaaagactgttacctt acaatatcctccactcctttccccctgtagttactatagagatgacttttcggttcttcactgc
cataatgatcaaaatcctaattcatgagattttttatcattccaggcatgtgaggtttacttgatgcataaaaccgcaagtacttttgttgttttttt
aattgttttttctctcttatctctcttgaaagtctaagtagatcatcattttgatgtcttattagtagcaactaaaatttccctgtatcttctcagc
aaaagaactcaagcagagacagaagattagaactaccattggtagtttgcttcctatggatatgttcacatacatagaaattttttacaatga
cctttttatatgtatttcagaatttcagaatggcctcaatgccttaataggaagaaatacttgaaattttttaaattagggcttggttttgtgag
gagctagtaaaggttttctctttcagctttagcttgtttctgcggaggattccgctcttctcccatcagtttcatagccctggaattgtagaaa
agctctggtttcaagaccattgatatccatttctgtcagggtgagttttaaatttatttcatgatgcaaacaatatattgaacaacaggacatg
aacttgttcttgttgtaagtggctgaatttatcagtaaagcacatcaaaataaaatatacccccaattgctagttaagacctagagtgacaga
```

TABLE 4-continued

Exemplary target gene intron sequences

```
ttgaaaatagcttgtgttattctcttaagaaaatatataaaaattatcatctcatcaatctttaatgtttgttttataaatctaaatgtttttatattgttt
cctaggaaatattaggtctaattttttactttaccaccagctgtcttttattttactctttttttgagacggagtttcgctcttgttgcttaggctaga
gtgcagtggcactatctcagctcactgcgacctctgcctcccggggttcaagcgattctcctgcctcagtctcccgagtagctgggattac
aggcacatgccactacaccaggctaattttgtattttagtagagacgggggtttcttcatgttggtcaggctggtctcgaactcccgacctc
aggtgatccgcctgcctcggcctcccagagtgctgggattacaggcatgagccaccgcacctggccagctgtcttttaatataacattat
gattaattgtgatgttccattaaactaagcggagaggaaacatgctggtaaaccatgtgtgagttattcattgtaccagaaaggcaaatga
tacatttttatcctaaaattcaaatttataaacatcttaacacttgtgatcattaaatactactaatctagcatataaattatatttgtaggcggggc
acggtggctcacgcctgtaatcccagcactttgggaggctgaggtgggcagatcacgaggtcaggagatcgagaccatcctggctaa
catggtgaaacccatctctactaaaaatacaaaaaaaattagctgggtgtgctggcgggcacctgtagtcccagctacttgggaggct
gaggcaggagaatggcgtgacccaggaggcagagcttccagcctgggcgactccgtctcaaaaaaaaagaaaaaagaaattatat
ttgtaatattctactaacctttatatcattttaactttttatataacttttttattttaccaaattaagttaacctttatagcccttggcttatactaaaca
tcctaacttttttgtttaattgtattagttttttaagttattgccccagatgtcaagtaatgttggattttctataataatttaggatatattgcatgaag
tcagttagtatttacatttaaaactaaaacaatttatactaatacagtttatacatttcatactaatttagctacagttggataaatatttaatggaa
caaagtaaatcaaagtaccttttcaaatgaatttggaaattaaatccacataacaattttttatgaccacactattacagtgtgatggcatgcc
aaatgatcataatgtggaattatgtatttcttcattggctttcaagattctgttctttagtttgtgggctcctctccaacttgcttgtctcctcacag
tttaggcgactgtttataattcttgtccatcctgcataaacacacacagtcaaaatgaaaaaaagcttctatcagcagatctgtgcttgctgt
acagaaatgggaaaacaattgaagtttgcattatcttttttctaattaccagatcgttttggagctatttaggcatacgctttaaggaaaaaa
gaaaaaaagagtgtaccttttgtttctaacaaaggttgttatctatattattgaaataaaaaattggggatagttatgacaaagtatttagaaat
aggaattaaaatcttaaaataacttttcatagcatggacaagacttattaatgtctacctcaataagcaaatcatttaaaaattttttcatgtatat
ttgctgccatgatgtgttgtgattgcttaaataaccaatgaatgaagatcaacaaggatttaaatgaagaagaatatggatttaactattttct
cctgtgaaataagttcatatttacaagttttgattttcagaaattagacaattattttttaaaggctgggatgacaacttctgcctcttaccaaga
agtcaaagcacagttatgtgaattcatcataaatcacatcattttttattatattttgtatttataattgtattgtgactactttaaaacctgttataaa
ataaaattgttttttaatattttattttagaattattagcattaataacaatttgaagtagtttacacaatacctgtgagtttttattttttgtttttatattga
aattaattttagttgctttacttggcttcattgctatggatgcattctctgtgttacgagttagcagatctttccttggaactgaatttaaaagcaa
gcatttggctccacttaaatctctgaaaatgcaacttgttctttgcatttattacataattcgctacttatggtacagaaatggatacaatacaa
aaatatttccttataagatacactgtgaccaatgagcttttttaaatagctgtaatcagtaacatgtatttgacttttcaaaacacatttctggag
ggatatcagtgcttttatttccccaaatatctgaatccctatgctttagtacaaaacaacttctgaagaatttagtaaccatatgtgttgatctctt
gtttttctaactagtcttcataaagaaatgactagaatagcaacagggaaatgattgccttttaaggttttttgtttctcaatataaaattttggtga
accattttttattgataaatacaggtattttttactttcttaaatcacttgatttaaaattactttgattaaatatgcatataaagtcagttgtttttaactc
tcaatacttatcaaaaaaatttaacttgctgtacattctgtataaacctaattctattcaactaaaattattttaaacatttag
```

SEQ ID NO: 279
Gene: OPA1
NMD Exon: GRCh38/hg38: chr3 193628509 to 193628616
NMD Exon Sequence:
CTTTAGCTTGTTTCTGCGGAGGATTCCGCTCTTTCTCCATCAGTTTCATAGCCCTG
GAATTGTAGAAAAGCTCTGGTTTCAAGACCATTGATATCCATTTCTGTCAGG

Example 2: Confirmation of NMD Exon Via Cycloheximide Treatment

Figure 4:
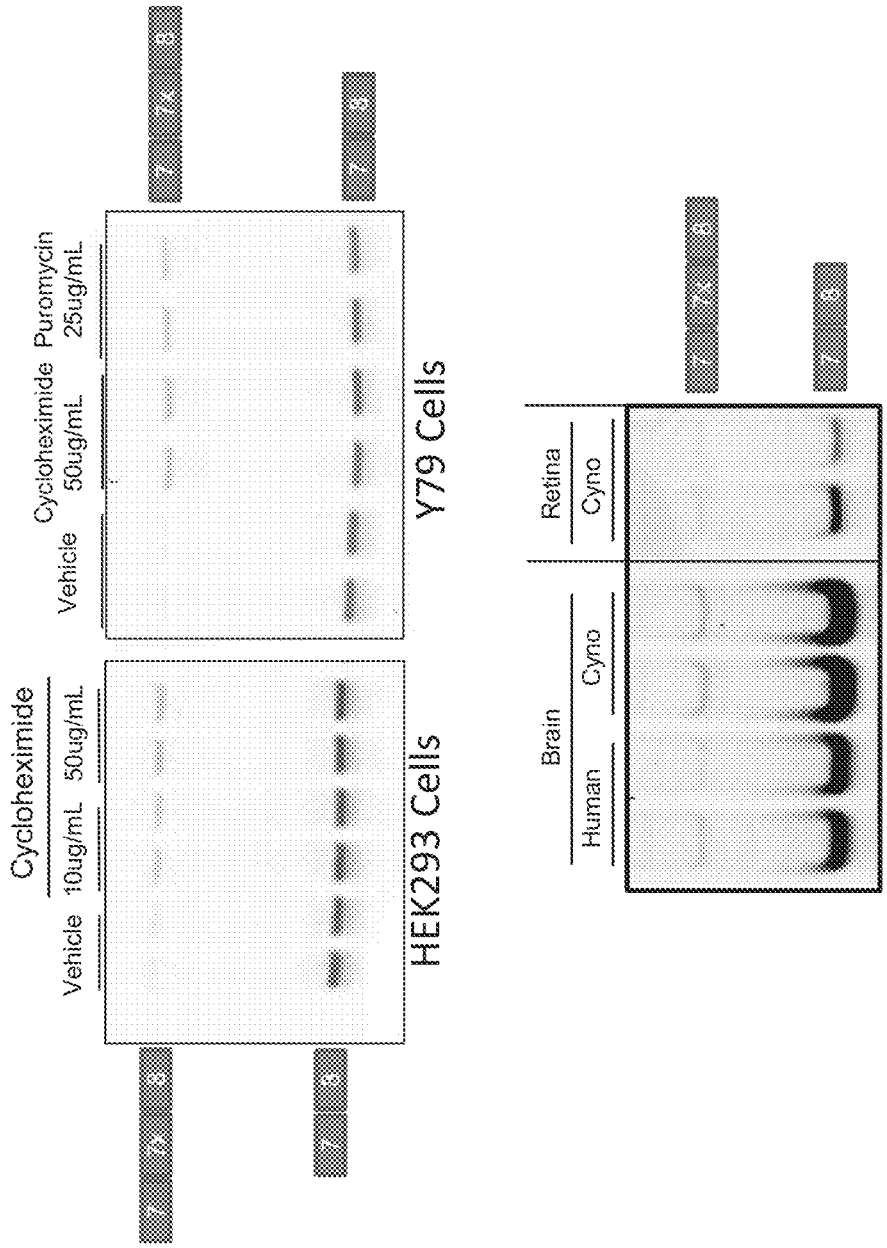
FIG. 4 depicts confirmation of NMD-inducing exon via puromycin or cycloheximide treatment in various cell lines, as well as the confirmation of NMD-inducing exon in brain and retina samples. RT-PCR analysis using total RNA from water-treated, DMSO-treated, puromycin-treated, or cycloheximide-treated cells confirmed the presence of a band corresponding to the NMD-inducing exon 7x (GRCh38/hg38: chr3 193628509 to 193628616) of OPA1 gene

RT-PCR analysis using cytoplasmic RNA from DMSO-treated or puromycin or cycloheximide-treated human cells and primers in exons was used to confirm the presence of a band corresponding to an NMD-inducing exon. The identity of the product was confirmed by sequencing. Densitometry analysis of the bands was performed to calculate percent NMD exon inclusion of total transcript. Treatment of cells with cycloheximide or puromycin to inhibit NMD can lead to an increase of the product corresponding to the NMD-inducing exon in the cytoplasmic fraction. FIG. 4 depicts confirmation of exemplary NMD exons in OPA1 gene transcripts using cycloheximide or puromycin treatment, respectively.

Example 3: NMD Exon Region ASO Walk

An ASO walk was performed for NMD exon region targeting sequences immediately upstream of the 3' splice site, across the 3'splice site, the NMD exon, across the 5' splice site, and downstream of the 5' splice site using 2'-MOE ASOs, PS backbone. ASOs were designed to cover these regions by shifting 5 nucleotides at a time. FIG. 5 depicts an ASO walk for an exemplary OPA1 NMD exon region.

Example 4: NMD Exon Region ASO Walk Evaluated by RT-PCR

Figure 6:
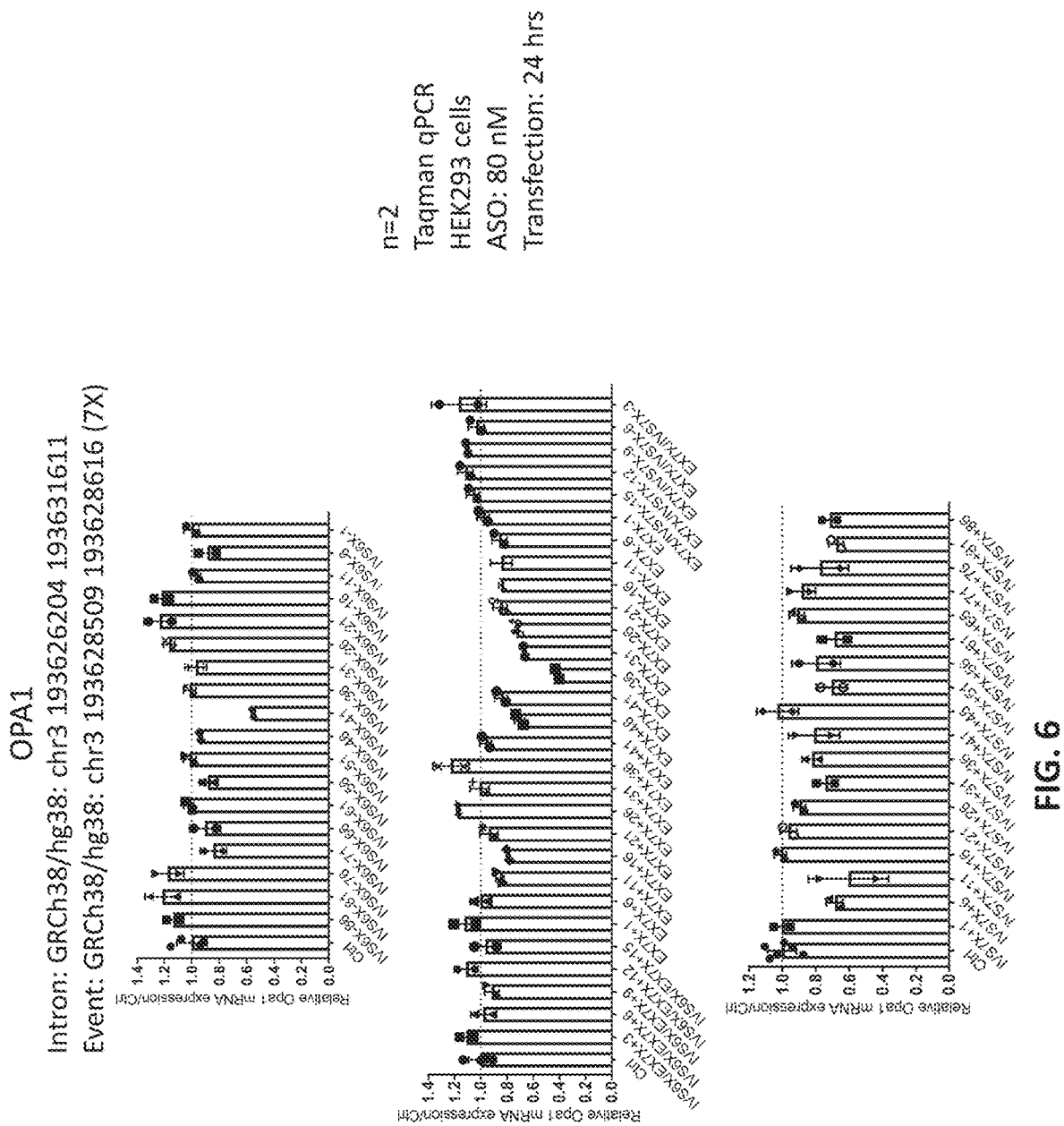
FIG. 6 depicts an OPA1 exon 7x (GRCh38/hg38: chr3 193628509 193628616) region ASO walk evaluated by Taqman RT-qPCR. Graphs of fold-change of the OPA1 productive mRNA product relative to Sham are plotted.

ASO walk sequences were evaluated by RT-PCR. HEK293 cells were transfected using Lipofectamine RNAiMax with control ASO treated (Ctrl), or with a 2'-MOE ASO targeting the OPA1 NMD exon regions as described herein. Products corresponding to OPA1 mRNA were quantified and normalized to RPL32 internal control, and fold-change relative to control was plotted. FIG. 6 depicts evaluation via TaqMan qPCR of various exemplary ASO walk along exemplary NMD exon regions. The measurement of the amount of OPA1 mRNA was carried out with HEK293 cells 24 hours after treatment with 80 nM of an exemplary ASO in the absence of cycloheximide, by Taqman qPCR using probes spanning exon 7 and exon 8.

Example 5: NMD Exon Region ASO Microwalk Evaluated by RT-qPCR

Figure 7:
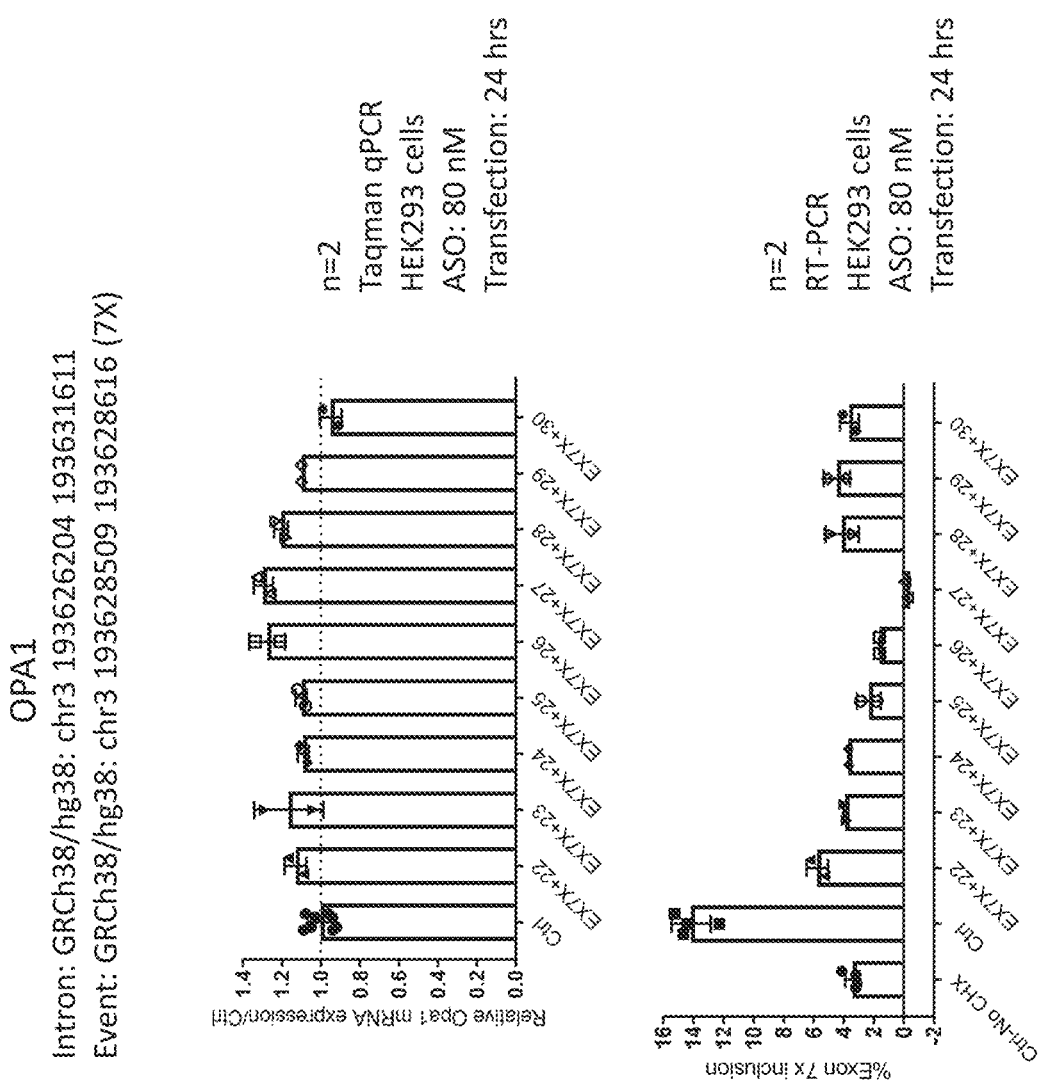
FIG. 7 depicts an OPA1 exon 7x (GRCh38/hg38: chr3 193628509 193628616) region ASO walk evaluated by Taqman RT-qPCR. Graphs of fold-change of the OPA1 productive mRNA product relative to Sham are plotted.

ASO microwalk sequences (across exon 7x) were evaluated by RT-PCR. HEK293 cells were transfected using Lipofectamine RNAiMax with control ASO treated (Ctrl), or with a 2'-MOE ASO targeting the OPA1 NMD exon regions as described herein. Products corresponding to NMD exon inclusion and full-length were quantified and percent NMD exon inclusion was plotted. FIG. 7 depicts evaluation of various exemplary ASO walk along exemplary NMD exon regions. The measurement of the amount of OPA1 mRNA was carried out with HEK293 cells 24 hours after transfection with 80 nM of an exemplary ASO in the absence of cycloheximide, by Taqman qPCR using probes spanning exon 7 and exon 8 (top panel of FIG. 7). qPCR amplification results were normalized to RPL32, and plotted as fold change relative to control. The measurement of exon 7x inclusion was carried out by quantifying exon 7x inclusion based on RT-PCR using probes spanning exon 7 and exon 8 (bottom panel of FIG. 7).

Example 6: Dose-Dependent Effect of Selected ASO in CXH-Treated Cells

PAGE can be used to show SYBR-safe-stained RT-PCR products of mock-treated (Sham, RNAiMAX alone), or treated with 2'-MOE ASOs targeting NMD exons at 30 nM, 80 nM, and 200 nM concentrations in mouse or human cells by RNAiMAX transfection. Products corresponding to NMD exon inclusion and full-length are quantified and percent NMD exon inclusion can be plotted. The full-length products can also be normalized to HPRT internal control and fold-change relative to Sham can be plotted.

Example 7: Intravitreal (IVT) Injection of Selected ASOs

PAGEs of SYBR-safe-stained RT-PCR products of mice from PBS-injected (1 µL) (−) or ASOs or Cep290 (negative control ASO; Gerard et al, Mol. Ther. Nuc. Ac., 2015) 2'-MOE ASO-injected (1 µL) (+) at 10 mM concentration. Products corresponding to NMD exon inclusion and full-length (are quantified and percent NMD exon inclusion can be plotted Full-length products can be normalized to GAPDH internal control and fold-change of ASO-injected relative to PBS-injected can plotted.

Example 8: Intracerebroventricular (ICV) Injection of Selected ASOs

PAGEs of SYBR-safe-stained RT-PCR products of mice from uninjected (−, no ASO control), or 300 µg of Cep290 (negative control ASO; Gerard et al, Mol. Ther. Nuc. Ac., 2015), 2'-MOE ASO-injected brains. Products corresponding to NMD exon inclusion and full-length can be quantified and percent NMD exon inclusion can be plotted. Taqman PCR can be performed using two different probes spanning NMD exon junctions and the products can be normalized to GAPDH internal control and fold-change of ASO-injected relative to Cep290-injected brains can be plotted.

Example 9: OPA1 Non-Productive Splicing Event Identification and Validation

Figure 1A:
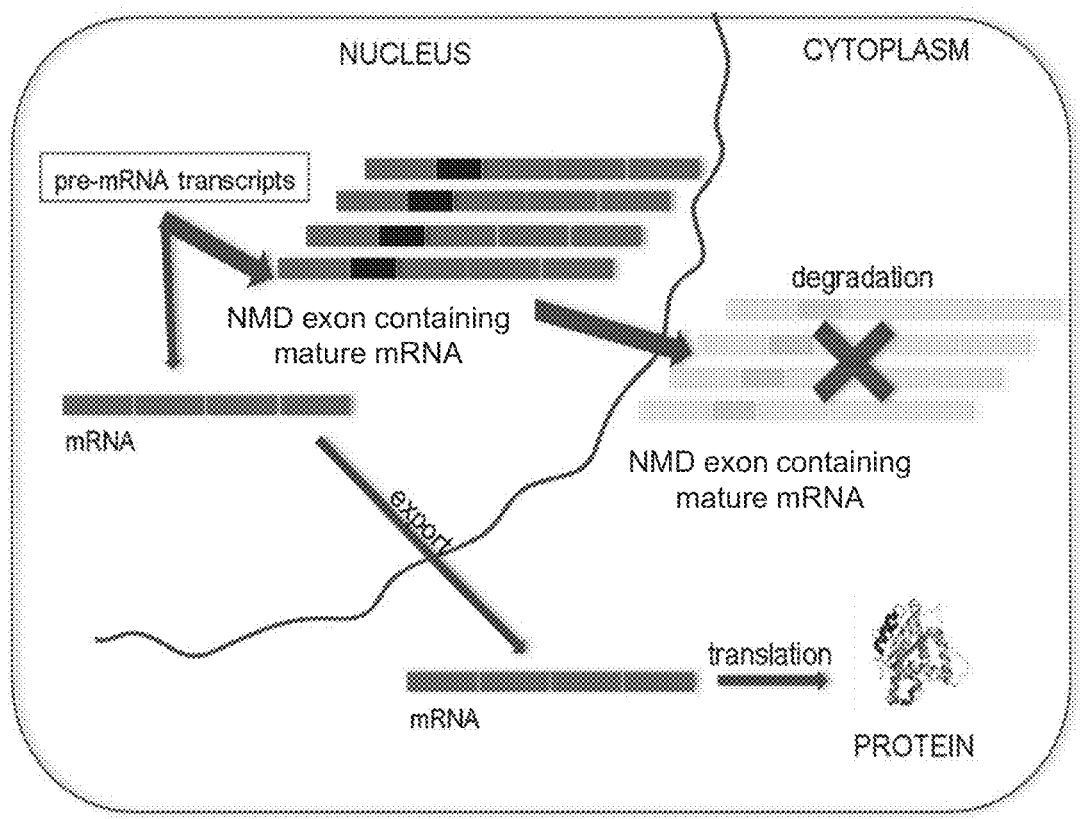
FIGS. 1A-1C depict a schematic representation of a target mRNA that contains a non-sense mediated mRNA decay-inducing exon (NMD exon mRNA) and therapeutic agent-mediated exclusion of the nonsense-mediated mRNA decay-inducing exon to increase expression of the full-length target protein or functional RNA.
Figure 1B:
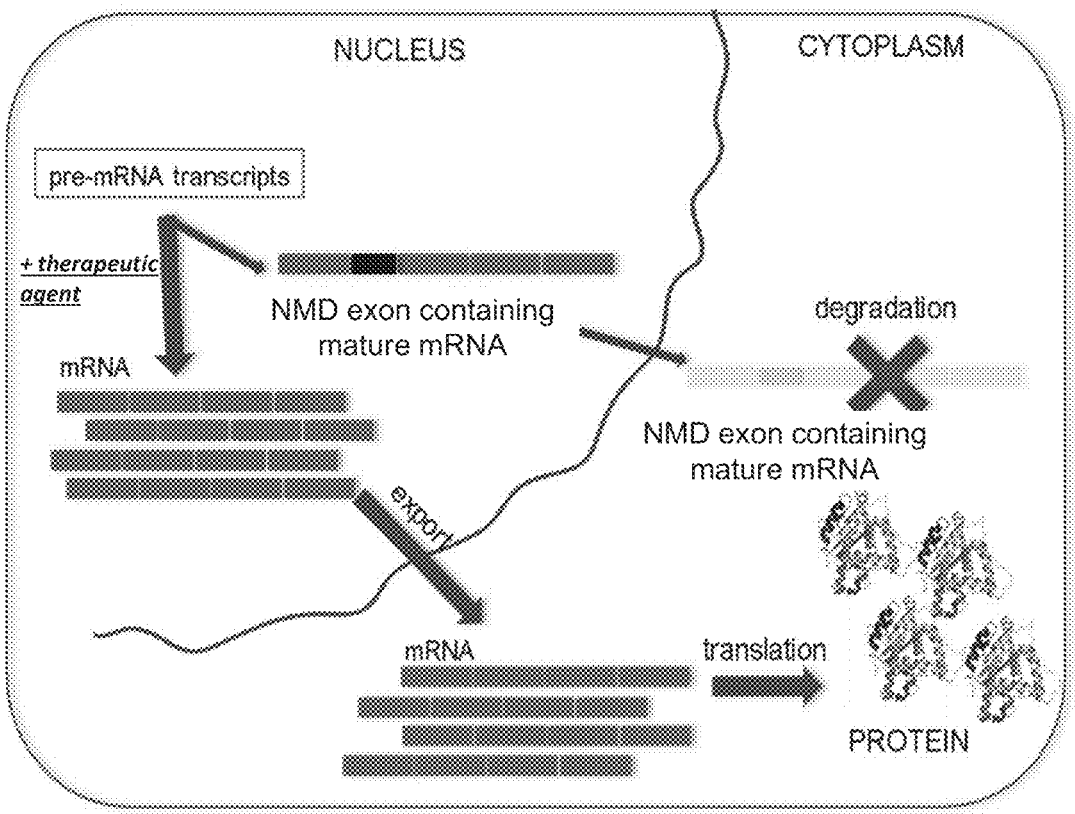
Figure 1C:
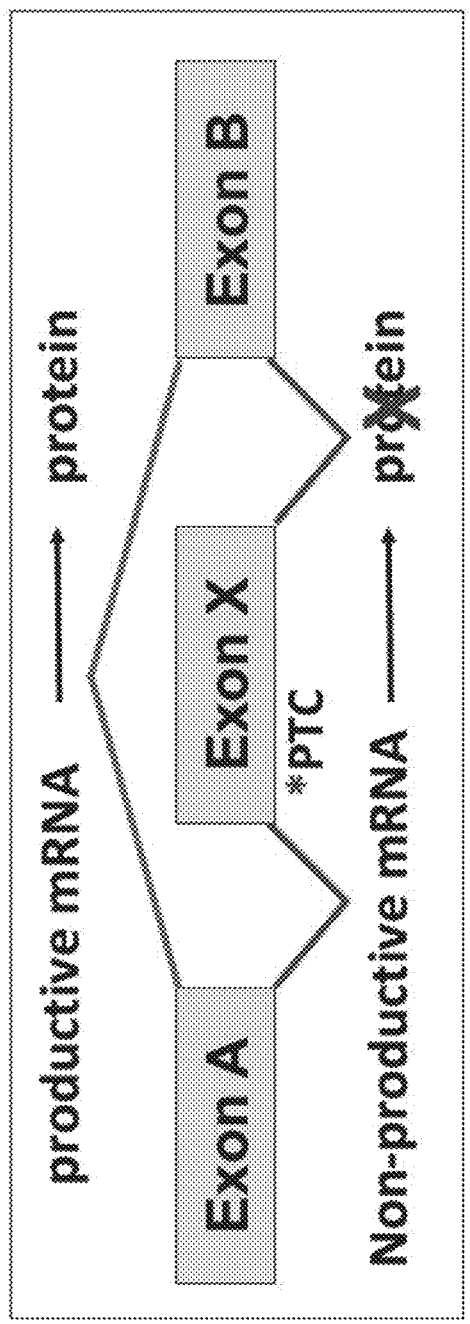
Figure 8:
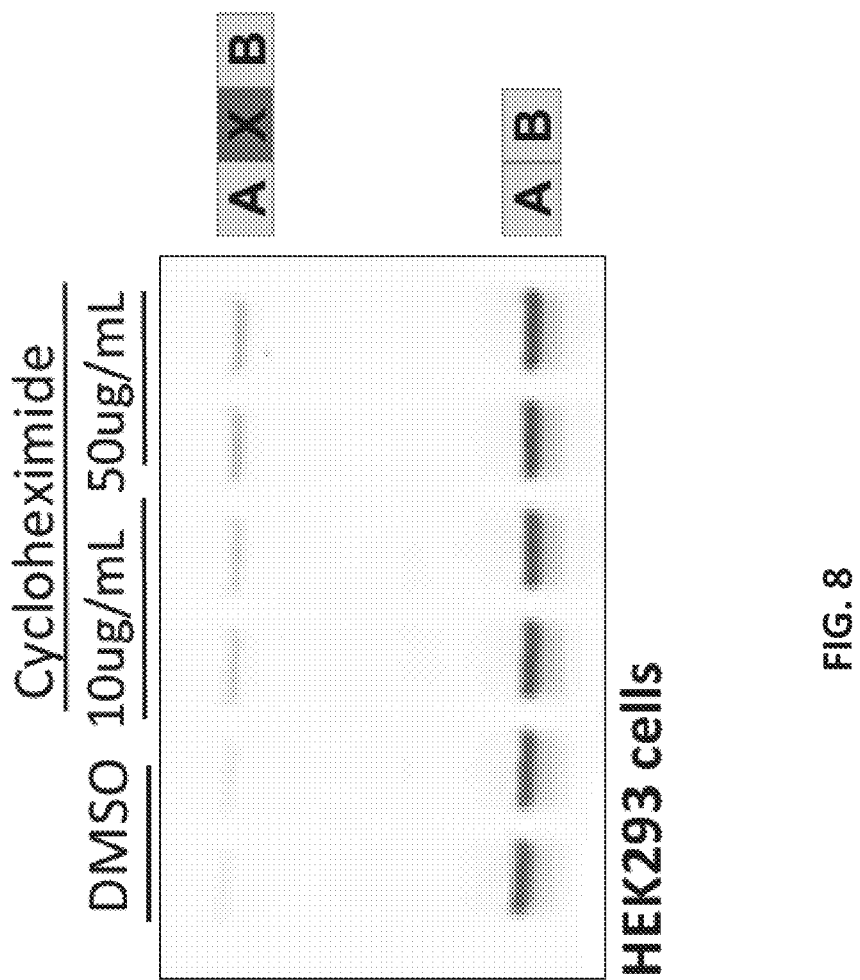
FIG. 8 illustrates expression of OPA1 transcripts containing the NMD exon in HEK293 cells treated with increasing amounts of cycloheximide.

A novel nonsense mediated decay (NMD) exon inclusion event (Exon X) was identified in the OPA1 gene which leads to the introduction of a premature termination codon (PTC) resulting in a non-productive mRNA transcript degraded by NMD, as diagramed in FIG. 1D. As NMD is a translation-dependent process, the protein synthesis inhibitor cycloheximide (CHX) was used to evaluate the true abundance of the event. FIG. 8 shows an increase in OPA1 transcripts containing the NMD exon in HEK293 cells with increasing CHX dose. Other ocular cell lines also validated for the presence of the NMD exon (ARPE-19, Y79).

Example 10: OPA1 NMD Event is Conserved in Primate Eyes

Figure 9A:
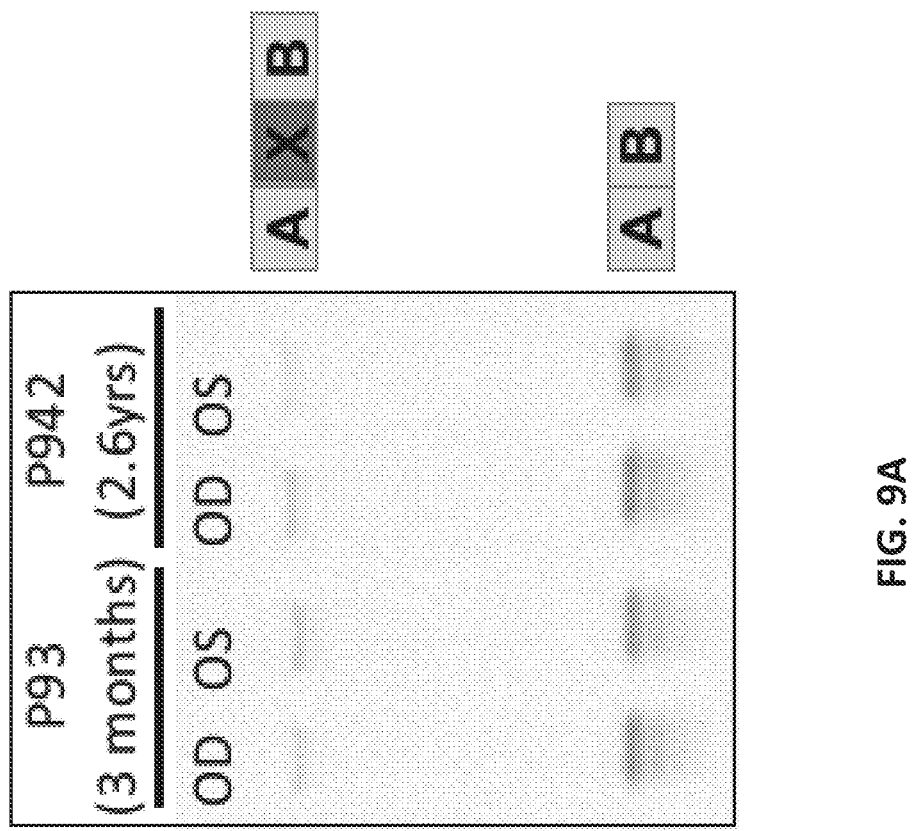
FIG. 9A illustrates RT-PCR data from the posterior segment of the eye of Chlorocebus sabaeus (green monkey) at postnatal data P93 (3 months) and postnatal day P942 (2.6 years).
Figure 9B:
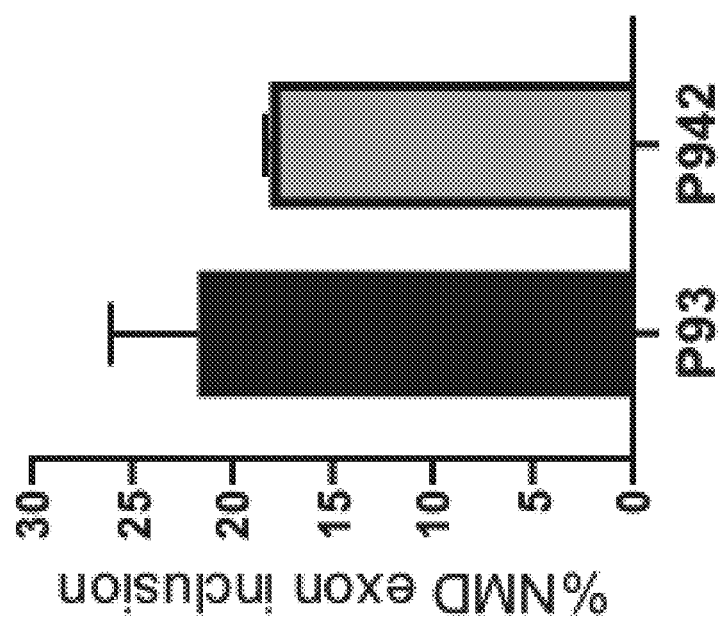
FIG. 9B illustrates quantification of the NMD exon abundance from FIG. 9A.

FIG. 9A shows reverse transcription PCR data from the posterior segment of the eye of *Chlorocebus sabaeus* (green monkey) at postnatal data P93 (3 months) and postnatal day P942 (2.6 years) for the right eye (OD) and left eye (OS). FIG. 9B shows quantification of the NMD exon abundance at 3 months and 2.6 years of age (N=1/age). Data represents average of right eye and left eye values for each animal. The abundance of the event may be higher in vivo, given that NMD is presumed active in the tissue.

Figure 10A:
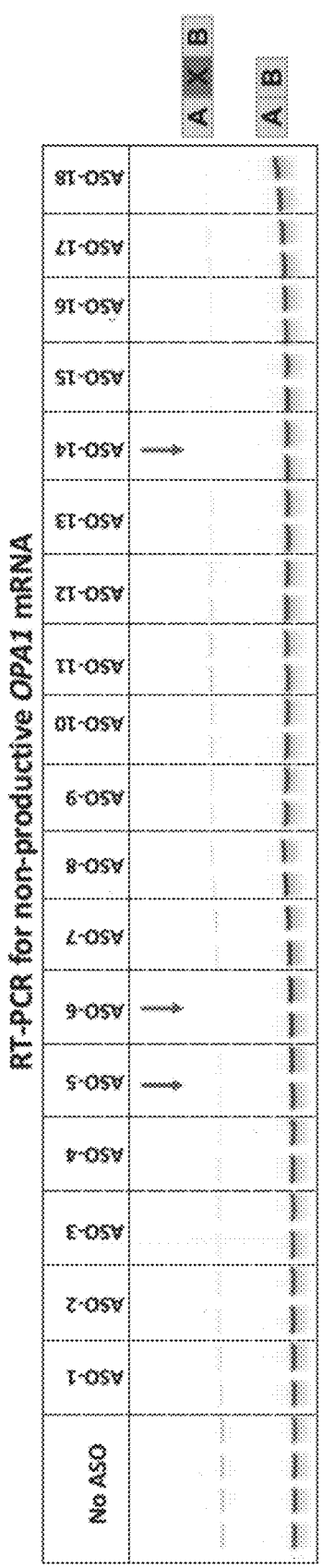
FIG. 10A illustrates RT-PCR of the productive and non-productive OPA1 mRNA after treatment of HEK293 cells with various ASOs and cycloheximide.
Figure 10B:
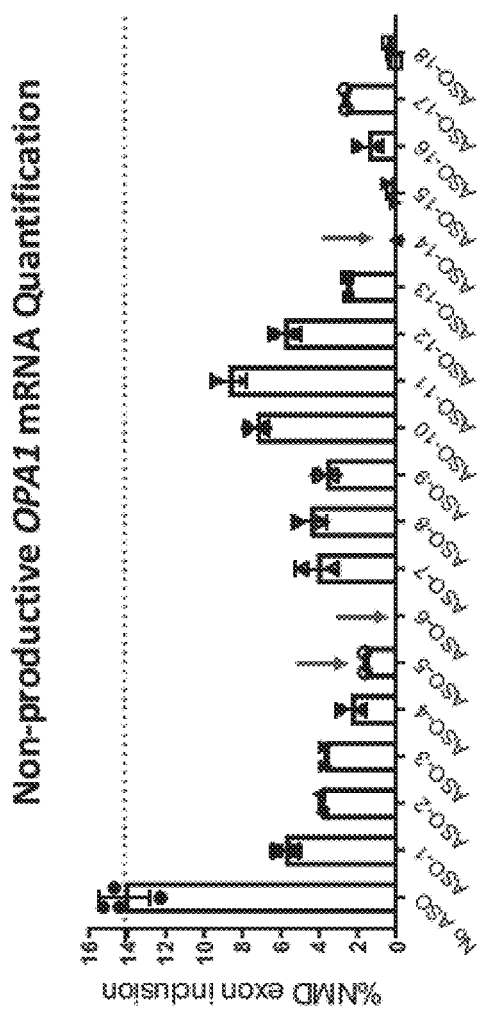
FIG. 10B illustrates quantification of the data in FIG. 10A.
Figure 11:
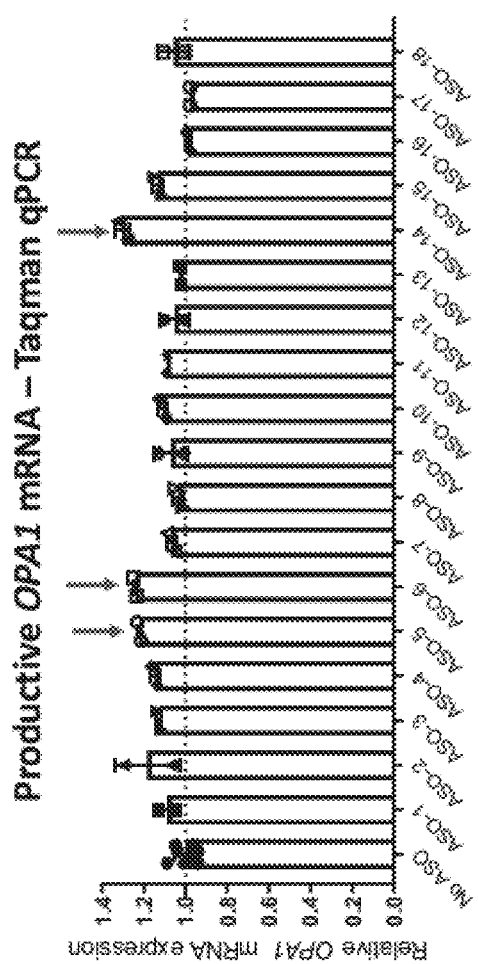
FIG. 11 illustrates expression of productive OPA1 mRNA by quantitative PCR in HEK293 cells treated with various ASOs and not treated with cycloheximide.

Example 11: OPA1 Antisense Oligonucleotides Reduce Non-Productive Splicing and Increase Productive OPA1 mRNA Levels In Vitro Exemplary antisense oligomers (ASOs) were transfected at 80 nM dose into HEK293 cells using Lipofectamine RNAiMax as a transfection agent. To assess the effect on the NMD exon, cells were treated with CHX (50 µg/ml, 3 hrs.) 21 hours after transfection. RNA was isolated for RT-PCR using probes spanning exon 7 and exon 8, as shown in FIG. 10A, and quantified in FIG. 10B. To assess levels of productive OPA1 mRNA expression, non-cycloheximide treated cells were used for Taqman qPCR using probes spanning exon 23 and exon 24, and mRNA expression of OPA1 was normalized to RPL32, as shown in FIG. 11. Arrows highlight ASOs that reduce non-productive splicing and increase OPA1 mRNA expression by at least 20%. Among these, ASO-14 produces the most increase in OPA1 mRNA (30%).

Figure 12A:
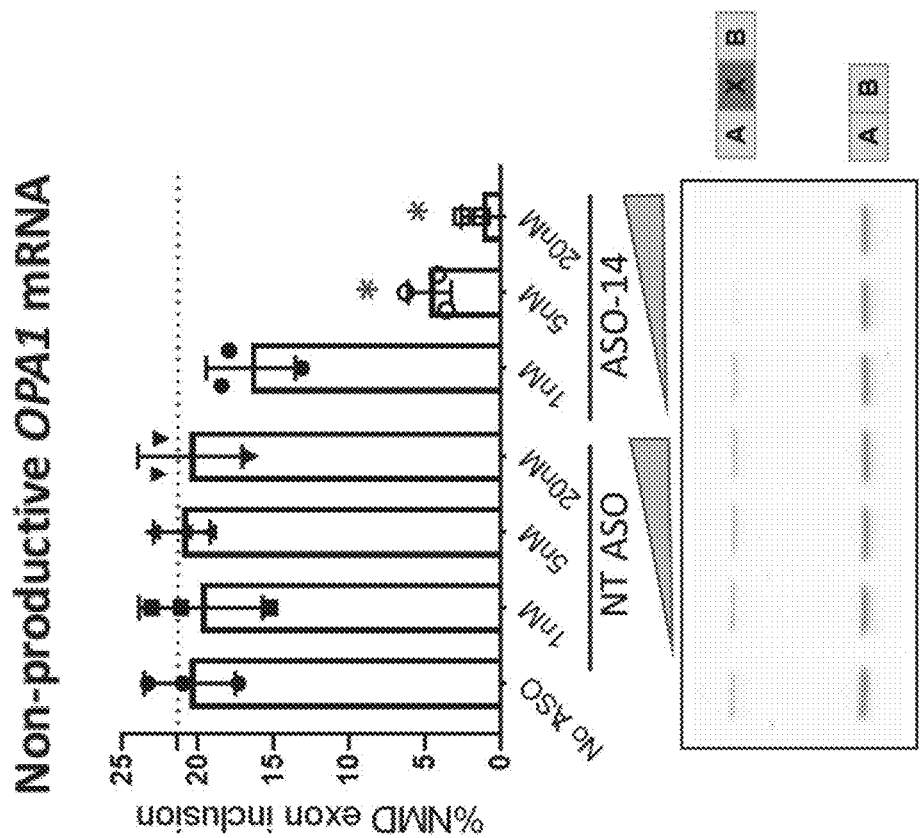
FIG. 12A illustrates RT-PCR for non-productive OPA1 mRNAs in HEK293 cells after treatment with ASO-14 and cycloheximide.
Figure 12B:
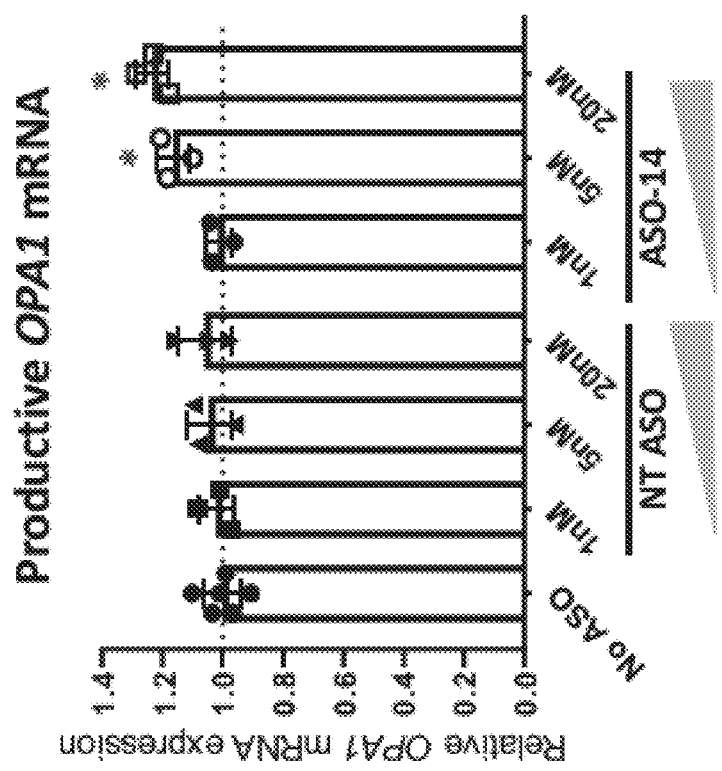
FIG. 12B illustrates quantification of productive OPA1 mRNAs in HEK293 cells after treatment with ASO-14 in the absence of cycloheximide.

Example 12: ASO-14 Decreases Non-Productive OPA1 mRNA and Increases OPA1 Expression in a Dose-Dependent Manner In Vitro HEK293 cells were transfected with different doses of ASO-14 or non-targeting (NT) ASO. RNA was isolated 24 hours after transfection and analyzed for impact on non-productive OPA1 mRNA (FIG. 12A) and OPA1 mRNA expression (FIG. 12B) similarly to in Example 11. For protein analysis, cells were lysed with RIPA buffer 48 hours after transfection and western blots were probed with antibodies targeting OPA1 and β-actin, as shown in FIG. 12C. Multiple bands correspond to different isoforms of OPA1. Data represent the average of three independent experiments (* $P<0.05$ by one-way ANOVA compared to "NO ASO" group). The Non-targeting ASO targets an unrelated gene.

Figure 13A:
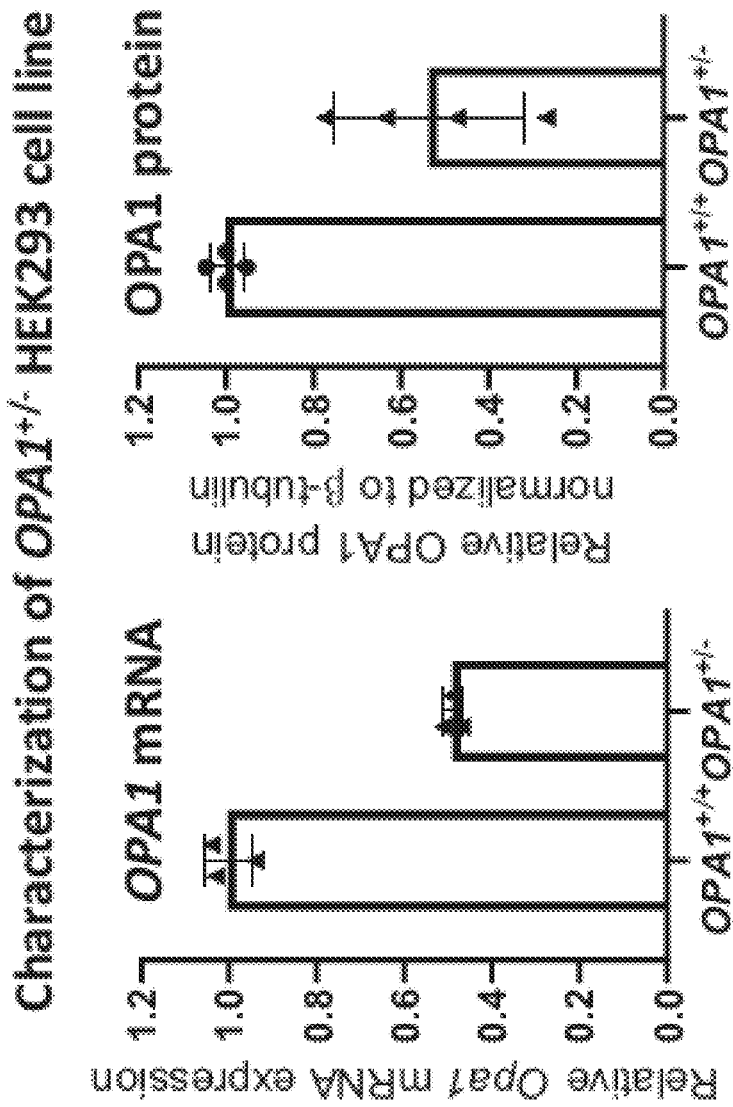
FIG. 13A illustrates mRNA and protein levels of OPA1 gene in OPA1 haploinsufficient (OPA1+/−) HEK293 cells.
Figure 13B:
FIG. 13B illustrates OPA1 protein expression in the OPA1 haploinsufficient (OPA1+/−) HEK293 cells after treatment with ASO-14.
Figure 13C:
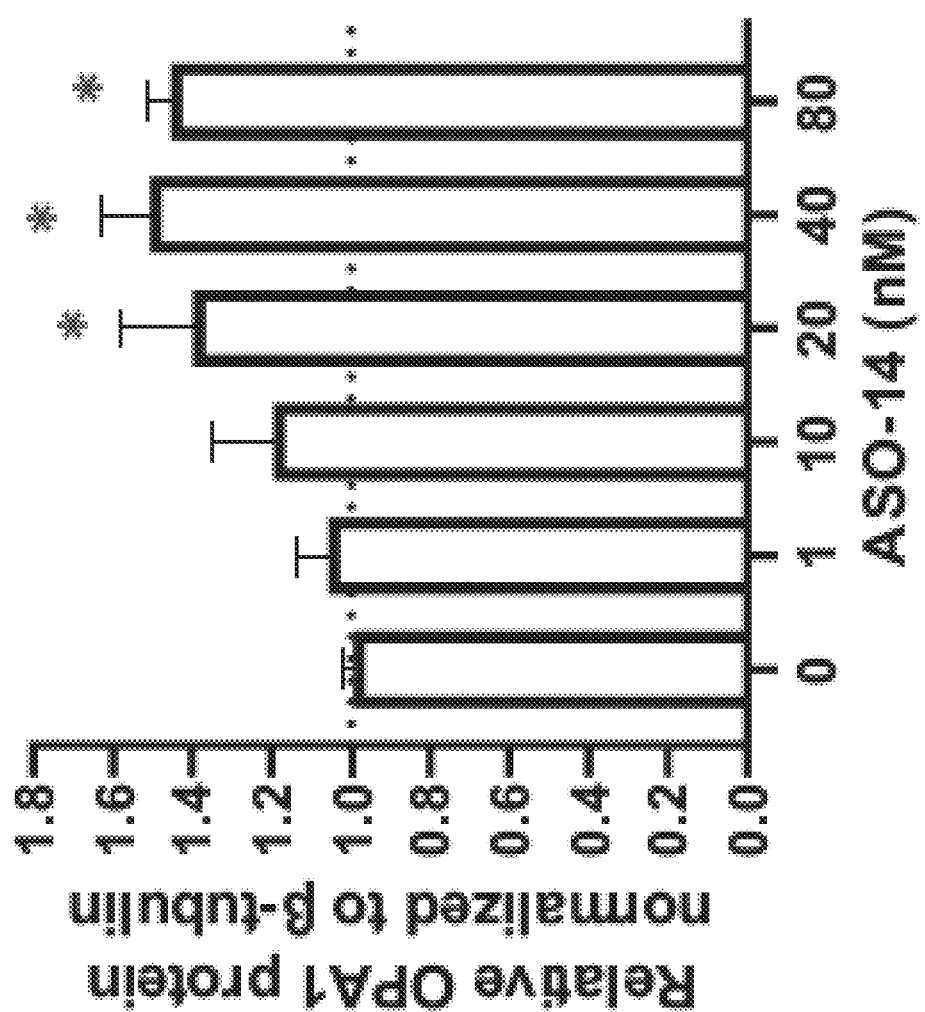
FIG. 13C illustrates quantification of OPA1 protein expression in the OPA1 haploinsufficient (OPA1+/−) HEK293 cells after treatment with ASO-14.

Example 13: ASO-14 Increases OPA1 Expression in an OPA1 Haploinsufficient (OPA1+/−) Cell Line OPA1 haploinsufficient (OPA1+/−) HEK293 cells were generated using CRISPR-Cas9 gene editing. Similar to ADOA patient cells, OPA1+/−HEK293 cells show approximately 50% mRNA and protein levels of that observed in OPA1+/+ cells (FIG. 13A). The OPA1+/−HEK293 cells were transfected with different doses of ASO-14 as indicated in FIG. 13B, and total protein was isolated 72 hours after transfection. Western blots were probed with antibodies targeting OPA1 and β-tubulin, a representative blot is shown in FIG. 13B and quantification of two independent experiments is shown in FIG. 13C (* $P<0.05$ by one-way ANOVA compared to "No ASO" group). ASO-14 increases OPA1 protein levels in OPA1+/−HEK293 cells by 50%, which translates to 75% of wild-type levels.

Figure 14A:
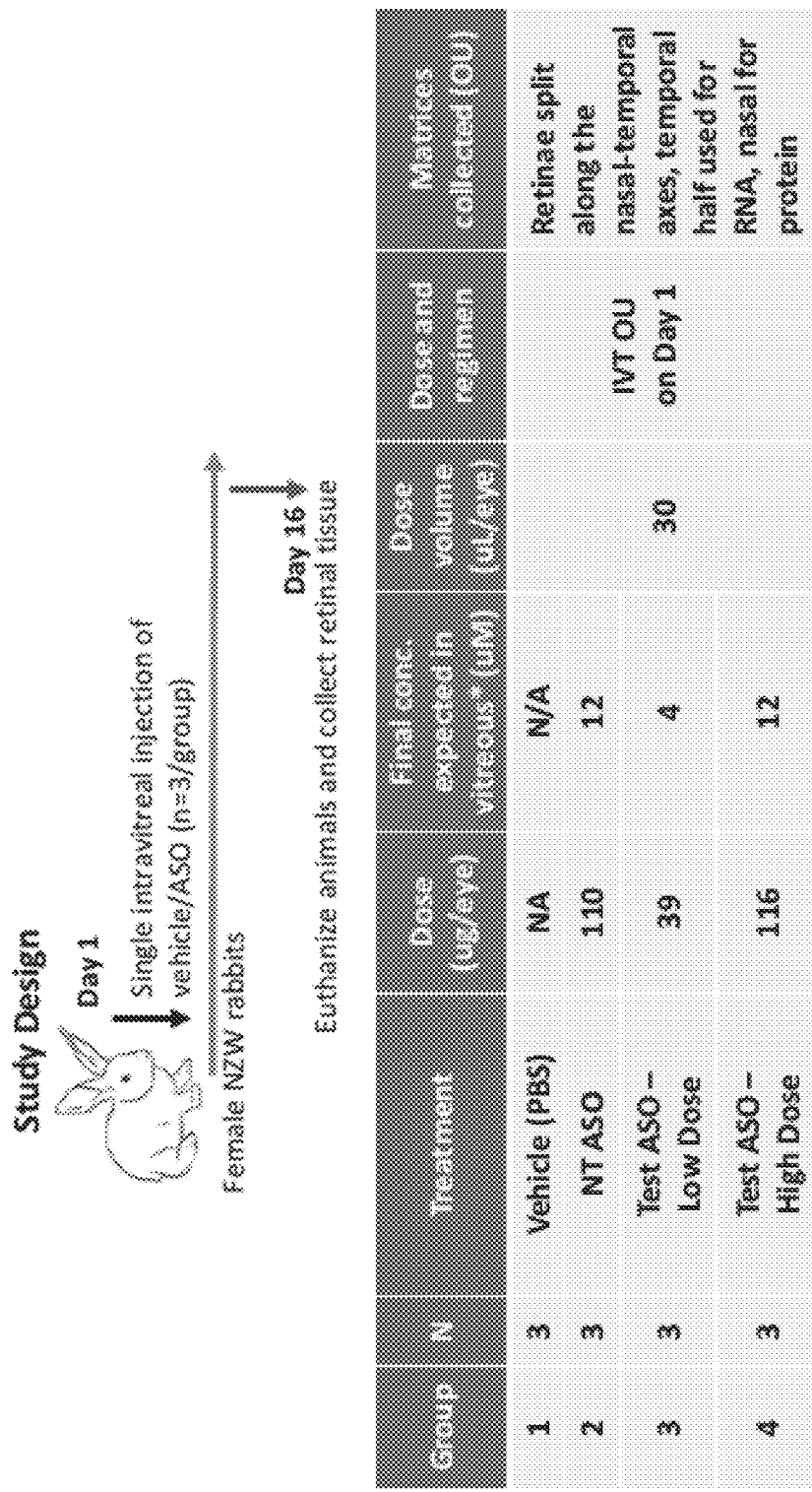
FIG. 14A illustrates study design for the in vivo rabbit experiment of Example 14.
Figure 14B:
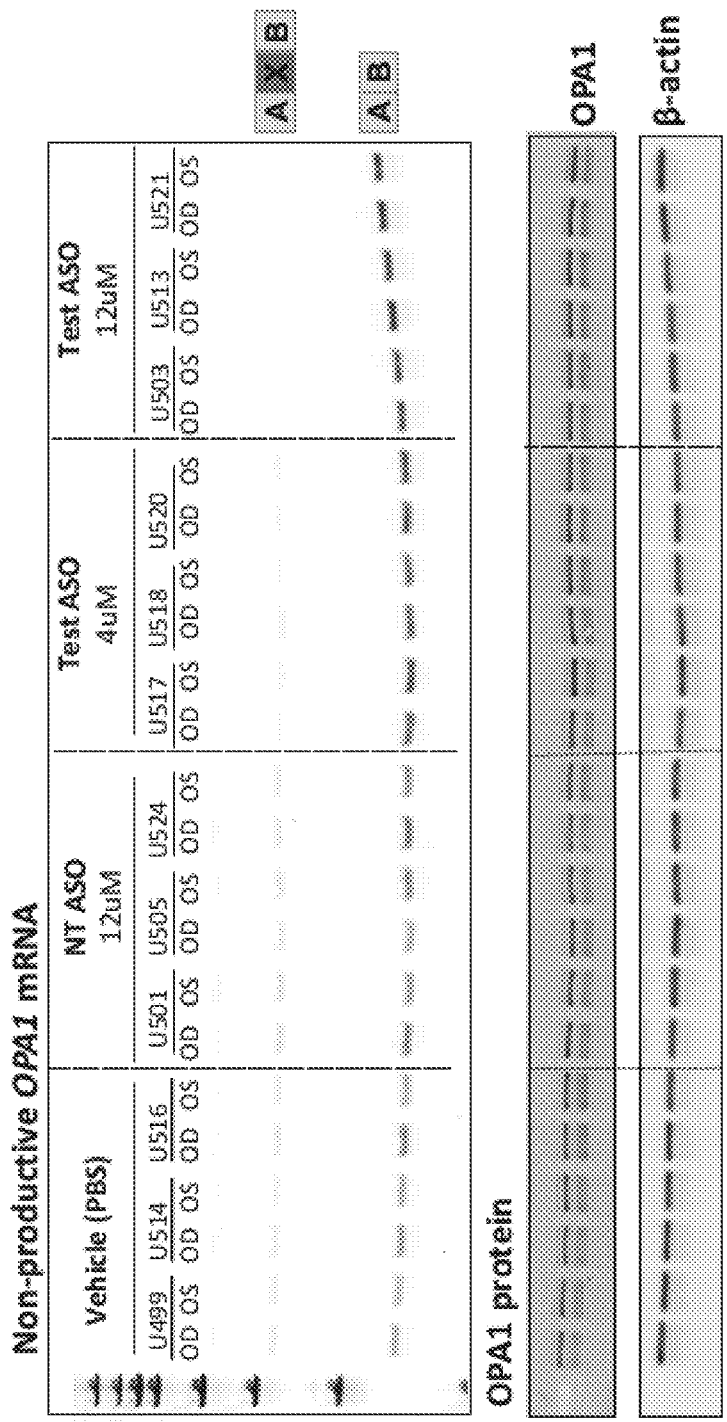
FIG. 14B illustrates levels of productive and non-productive OPA1 mRNA and protein.
Figure 14C:
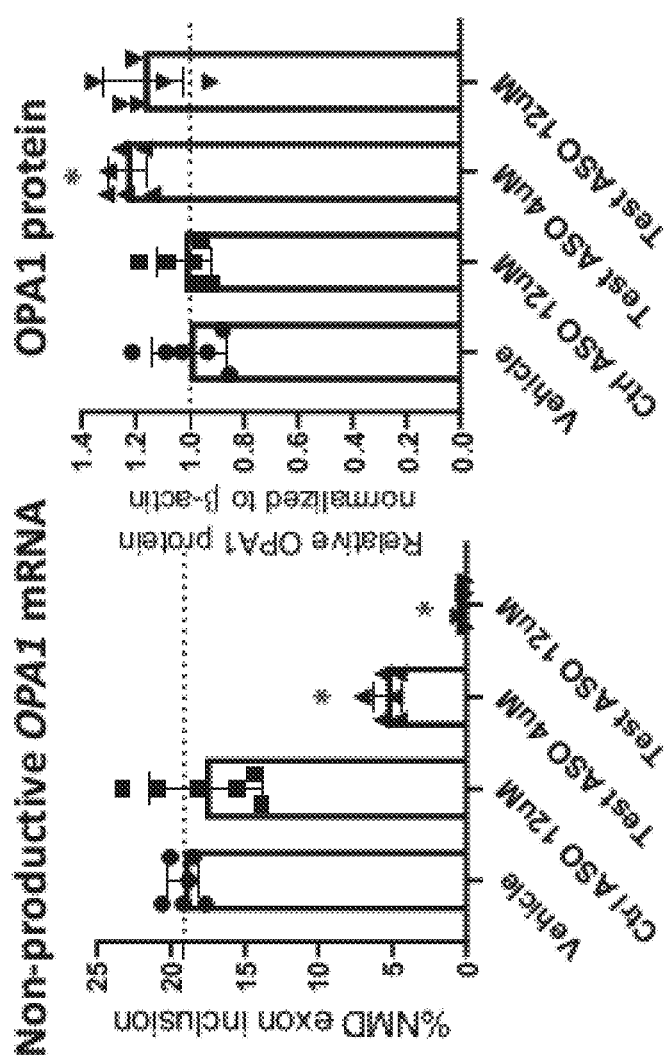
FIG. 14C illustrates quantification of the data from FIG. 14B.

Example 14: Exemplary OPA1 ASOs Decrease Non-Productive Splicing and Increase OPA1 Expression in Wild-Type Rabbit Retinae Following Intravitreal Injection Female New Zealand White (NZW) adult rabbits were injected with either vehicle, non-targeting (NT), or test, antisense oligonucleotides. Animals were euthanized after 15 days to obtain retinal tissue. FIG. 14A outlines the study design, (*Final concentration in the vitreous calculated assuming vitreal volume in the rabbit as 1.5 mL). FIG. 14B shows levels of productive and non-productive OPA1 mRNA and protein, and FIG. 14C shows quantification of this data (* P<0.05 by one-way ANOVA compared to Vehicle group). OD: oculus dextrus (right eye), OS: oculus sinister (left eye).

It was also found that the antisense oligonucleotides were well-tolerated in wild-type rabbit for up to 28 days after intravitreal injection.

Figure 16A:
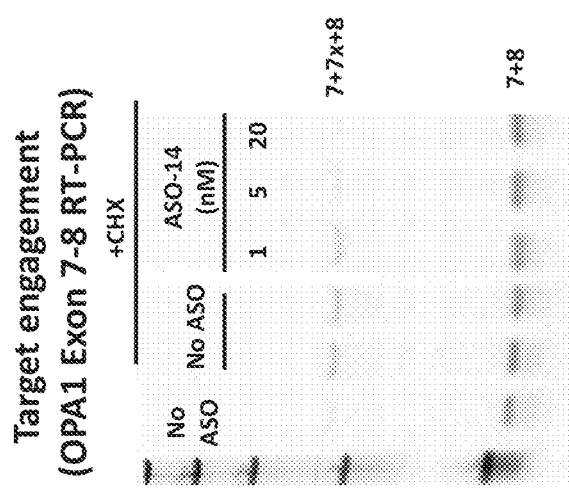
FIG. 16A illustrates RT-PCR results for OPA1 mRNAs using probes spanning exon 7 and exon 8 in HEK293 cells after treatment with ASO-14 and cycloheximide.
Figure 16B:
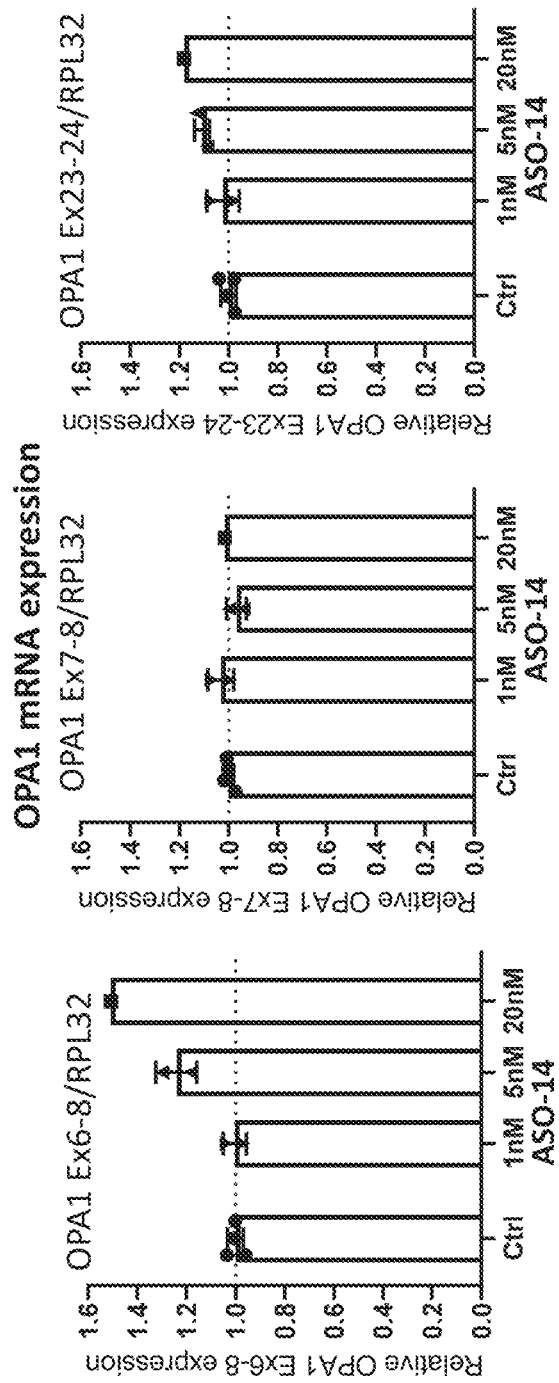
FIG. 16B illustrates quantification of OPA1 mRNAs in HEK293 cells after treatment with ASO-14 in the absence of cycloheximide based on qPCR using probes spanning exons 6 and 8, probes spanning exons 7 and 8, or probes spanning exons 23 and 24.
Figure 16C:
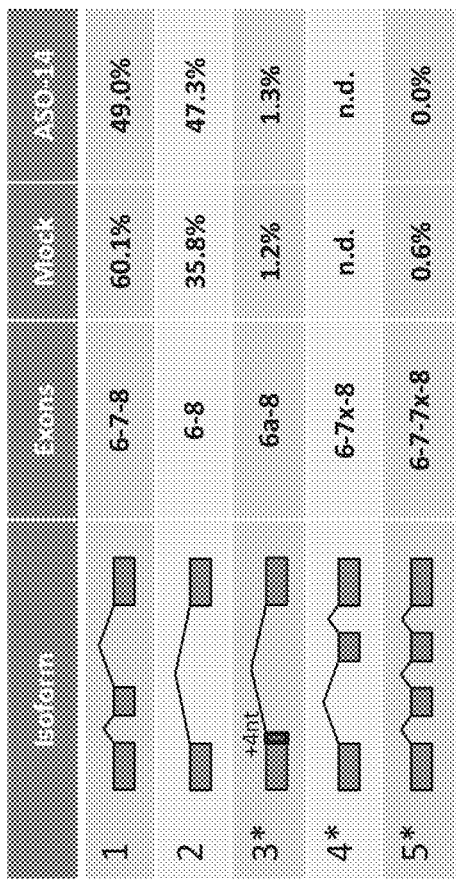
FIG. 16C illustrates sequencing data on the relative amount of various OPA1 mRNA transcripts in HEK293 cells transfected with ASO-14.

Example 15: ASO-14 Modulates Inclusion of Both Exon 7 and Exon 7x in OPA1 mRNA Transcript HEK293 cells were transfected with different doses of ASO-14 or no ASO, in the presence or absence of cycloheximide. RNA was isolated 24 hours after transfection and analyzed for impact on OPA1 mRNA splicing and OPA1 mRNA expression similarly to in Example 11. FIG. 16A shows gel image of PCR products from RT-PCR reaction using probes spanning exon 7 and 8. As shown in the figure, the dose of ASO-14 increased from 1 nM, 5 nM, to 20 nM, the amount of transcripts having exon 7x between exons 7 and 8 ("7+7x+8") gradually decreased, as compared to relatively stable amount of transcripts lacking exon 7x between exons 7 and 8 ("7+8"). FIG. 16B shows plots summarizing the relative amount of various OPA1 mRNA transcripts quantified by qPCR reactions using different pairs of probes: "Ex6-8," probes spanning exons 6 and 8; "Ex7-8," probes spanning exons 7 and 8; and "Ex23-24," probes spanning exons 23 and 24. Results were normalized to RPL32 as an internal control. FIG. 16C shows a chart summarizing the quantification of various OPA1 mRNA transcripts based on sequencing of the RNA extracts from the treated HEK293 cells in the absence of cycloheximide. As suggested by the figures, ASO-14 appeared to induce reduction in OPA1 exon 7x inclusion, increase in OPA1 Ex6-8 transcripts (transcripts having exon 6 and exon 8 in tandem, thus lacking exon 7 and exon 7x), modest decrease or no change in OPA1 Ex7-8 transcripts (transcripts having exon 7 and exon 8 in tandem, thus lacking exon 7x).

Figure 17A:
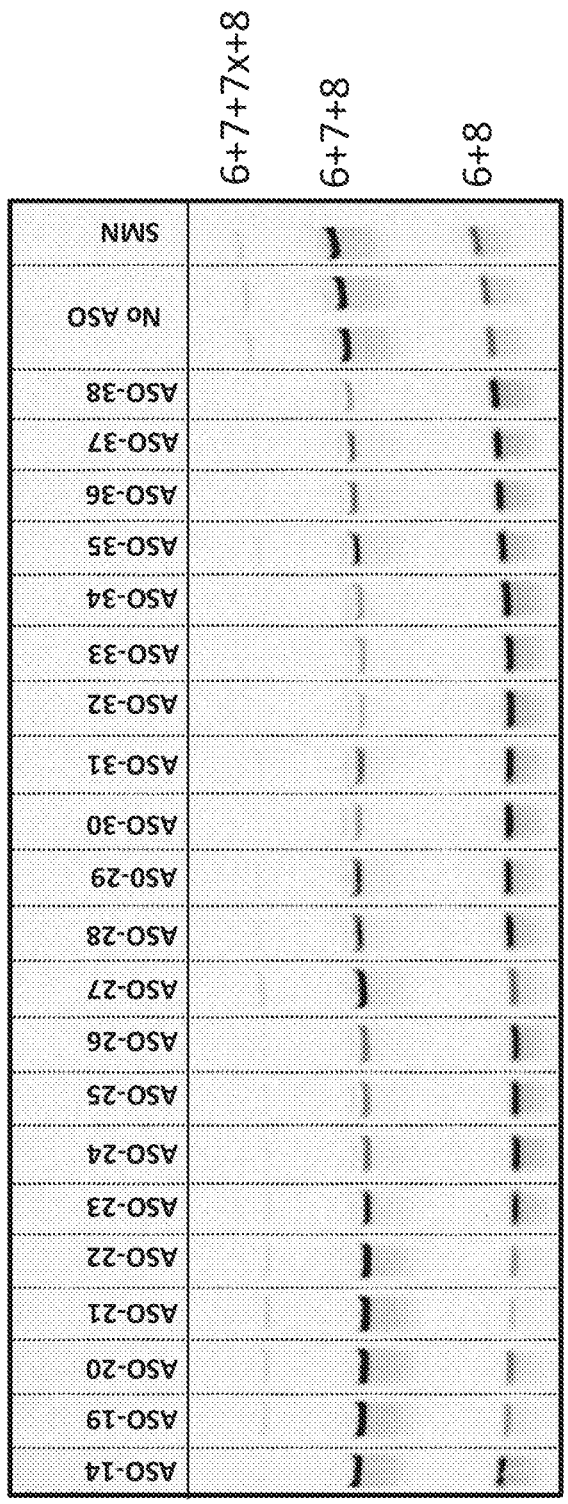
FIG. 17A illustrates RT-PCR results for OPA1 mRNAs using probes spanning exon 6 and exon 8 in HEK293 cells after treatment with various exemplary OPA1 ASOs.
Figure 17B:
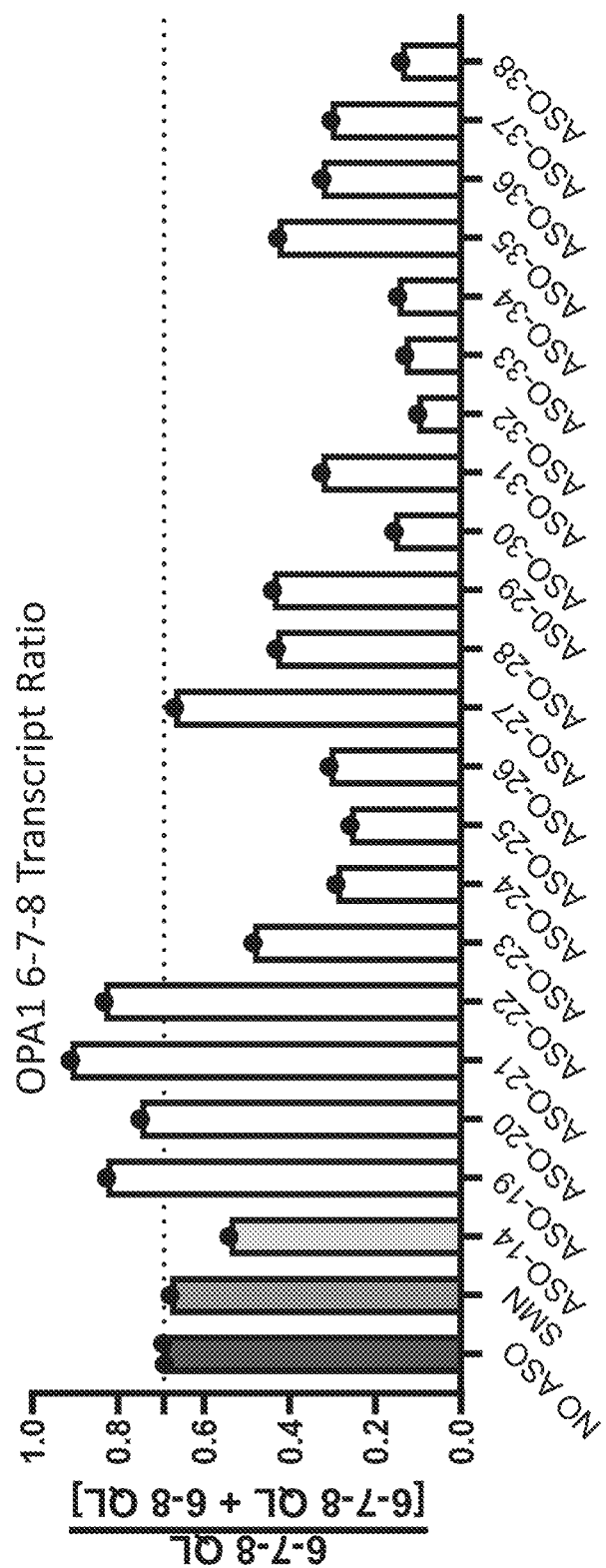
FIG. 17B illustrates relative ratio of OPA1 mRNA transcripts having exons 6, 7, and 8 in tandem ("6-7-8") over the total amount of "6-7-8" transcripts and transcripts having exons 6 and 8 in tandem ("6-8"), in HEK293 cells after treatment with various exemplary OPA1 ASOs.
Figure 17C:
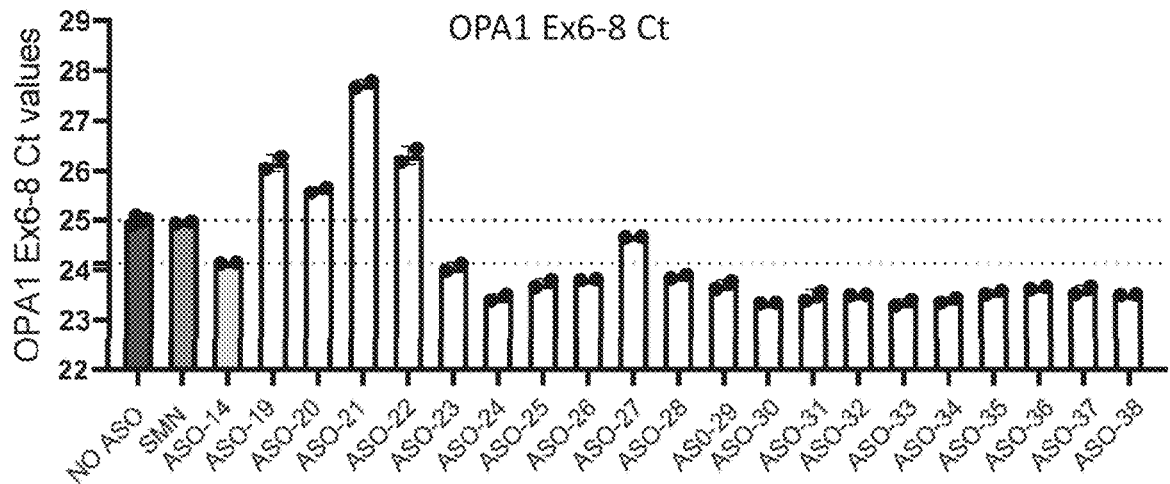
FIGS. 17C and 17D illustrate quantification of OPA1 mRNAs using probes spanning exons 6 and 8, and probes spanning exons 7 and 8, respectively, in HEK293 cells after treatment with various exemplary OPA1 ASOs.
Figure 17C:
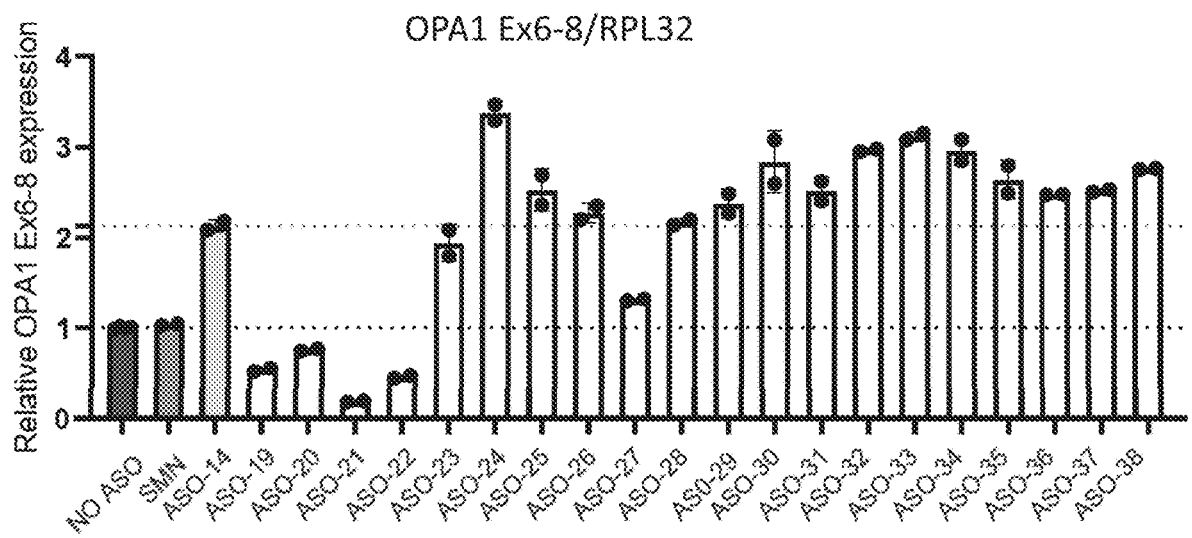
Figure 17D:
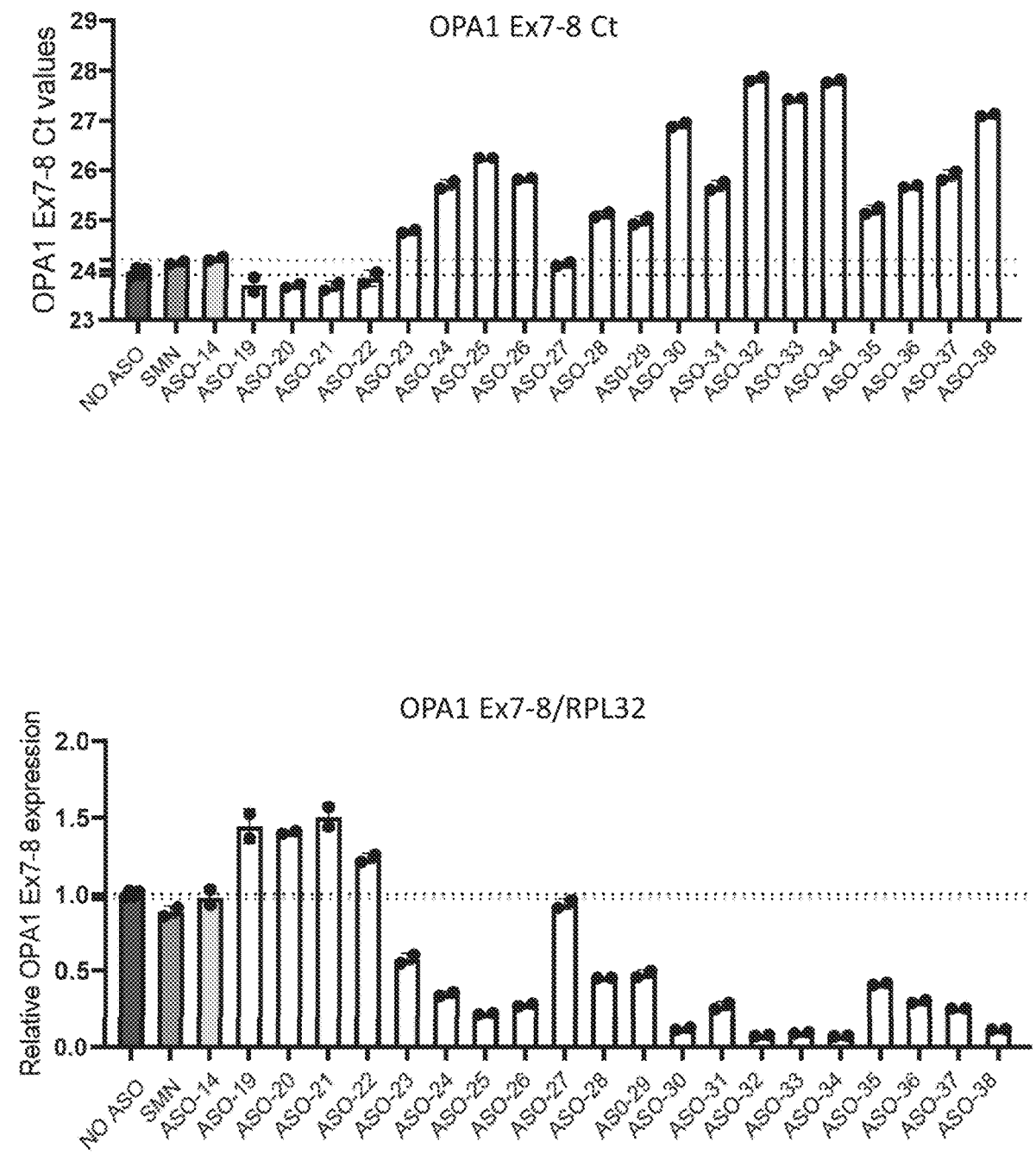

Example 16: Exemplary OPA1 Antisense Oligomers Modulate Inclusion of Exon 7, Exon 7x, or Both in OPA1 mRNA Transcript HEK293 cells were transfected with different exemplary OPA1 modified 2'MOE-PS (2' methoxyethyl and phosphorothioate) ASOs. Each well of HEK 293 cells (about 100,000 cells/well) were treated with an exemplary ASO at 80 nM final concentration in the presence of 0.9 µL of Lipofectamine® RNAiMax in the absence of cycloheximide. The cells were harvested 24 hours after transfection and RNA was isolated and analyzed for impact on OPA1 mRNA splicing and OPA1 mRNA expression similarly to in Example 11. FIG. 17A shows gel image of PCR products from RT-PCR reaction using probes spanning exon 6 and 8, and FIG. 17B is a plot summarizing the relative ratio of the amount of transcripts having exons 6, 7, and 8 in tandem ("6-7-8") over the total amount of "6-7-8" transcripts and transcripts having exons 6 and 8 in tandem ("6-8"). As shown in the figures, certain ASOs, such as ASO-19, ASO-20, ASO-21, ASO-22, induced increase in the relative amount of "6-7-8" transcripts, suggesting an increase in the inclusion of exon 7 in mature OPA1 mRNA transcripts. Some ASOs, such as ASO-23, ASO-24, ASO-25, ASO-26, ASO-28, ASO-29, ASO-30, ASO-31, ASO-32, ASO-33, ASO-34, ASO-35, ASO-36, ASO-37, and ASO-38, in contrast, induced reduction in the relative amount of "6-7-8" transcripts, suggesting a reduction in the inclusion of exon 7 in mature OPA1 mRNA transcript. FIGS. 17C and 17D show the Ct values for the qPCR reaction (upper plots) for, and quantification of the relative amount (bottom plots) of, OPA1 transcripts having exons 6 and 8 ("Ex6-8") and OPA1 transcripts having exons 7 and 8 ("Ex7-8"), respectively. Cells treated with ASO-29, ASO20, ASO-21, and ASO-22 showed reduced amount of "Ex6-8" transcripts and increased amount of "Ex7-8" transcripts, consistent with the suggestion that these ASOs promote the inclusion of exon 7 in OPA1 mature mRNA transcripts. Cells treated with ASO-23, ASO-24, ASO-25, ASO-26, ASO-28, ASO-29, ASO-30, ASO-31, ASO-32, ASO-33, ASO-34, ASO-35, ASO-36, ASO-37, and ASO-38 showed increase in the amount of "Ex6-8" transcripts and decrease in the amount of "Ex7-8" transcripts, consistent with the suggestion that these ASOs promote the exclusion of exon 7 from OPA1 mature mRNA transcripts.

Figure 18A:
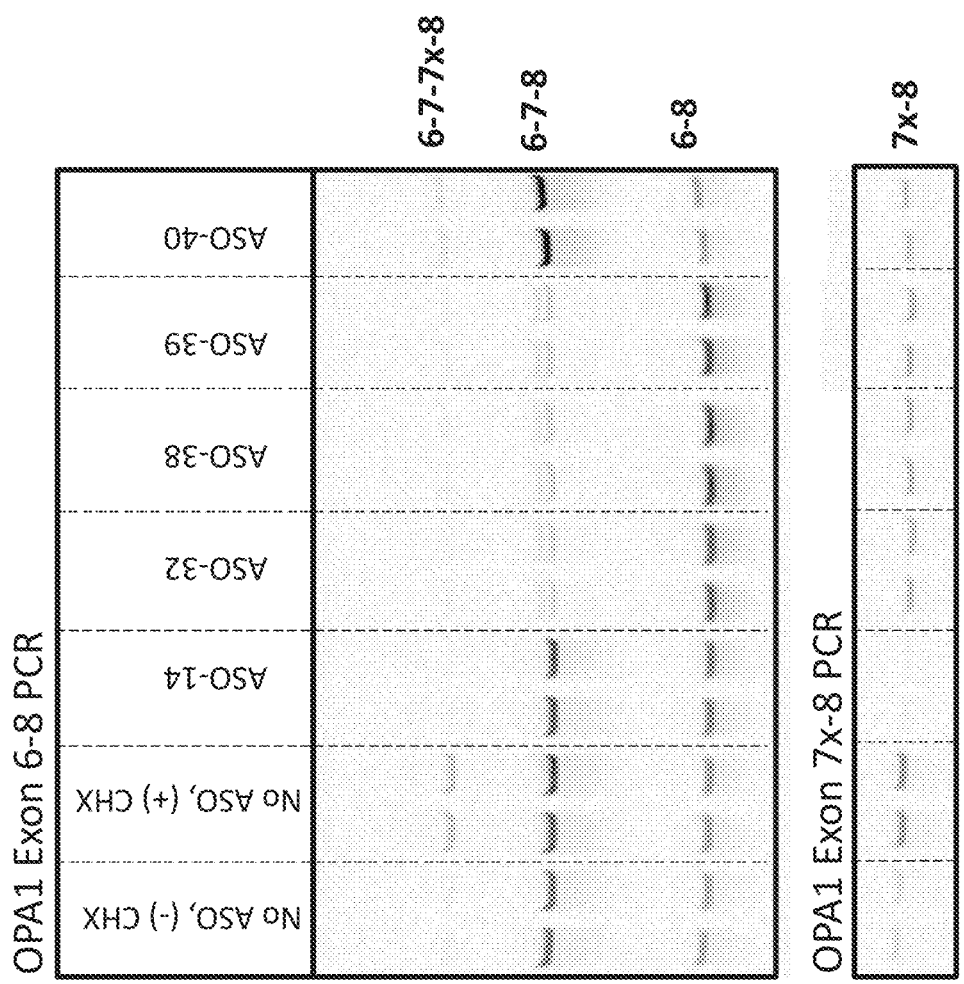
FIG. 18A illustrates RT-PCR results for OPA1 mRNAs using probes spanning exon 6 and exon 8 ("Exon 6-8 PCR"), or probes spanning exon 7x and exon 8 ("Exon 7x-8 PCR"), in HEK293 cells after treatment with various exemplary OPA1 ASOs and treatment with cycloheximide.

Example 17: Exemplary OPA1 Antisense Oligomers Modulate Inclusion of Exon 7, Exon 7x, or Both in OPA1 mRNA Transcript and Modulate Expression Level of OPA1 Protein HEK293 cells were transfected with different exemplary OPA1 modified 2'MOE-PS (2' methoxyethyl and phosphorothioate) ASOs. Each well of HEK 293 cells (about 50,000 cells/well) were treated with an exemplary ASO at 80 nM final concentration in the presence of 0.9 µL of Lipofectamine® RNAiMax. Here, the cells were harvested 72 hours after transfection to test ASO's effect on OPA1 mRNA and protein expression. The cells were treated with cycloheximide (50 µg/mL) for 3 hours prior to harvest for mRNA analysis. FIG. 18A shows gel image of PCR products from RT-PCR reaction using probes spanning exon 6 and 8. As shown in the figure, ASO-14 induced reduction in the amount of transcripts having exons 6, 7, 7x, and 8 in tandem ("6-7-7x-8"). ASO-32, ASO-38, and ASO-39 induced significant reduction in the amount of "6-7-8" transcripts, and modest reduction in the amount of "6-7-7x-8" transcripts, whereas ASO-40 induced increase in the amount of "6-7-8" transcripts. These data suggest that ASO-14 promotes exclusion of exon 7x from OPA1 mRNA transcript, ASO-32, ASO-38, and ASO-39 promote exclusion of exon 7 from OPA1 mRNA transcript, and they also promote exclusion of exon 7x from OPA1 mRNA transcript. In contrast, the data suggest that ASO-40 promotes inclusion of exon 7 in OPA1 mRNA transcript.

Figure 18B:
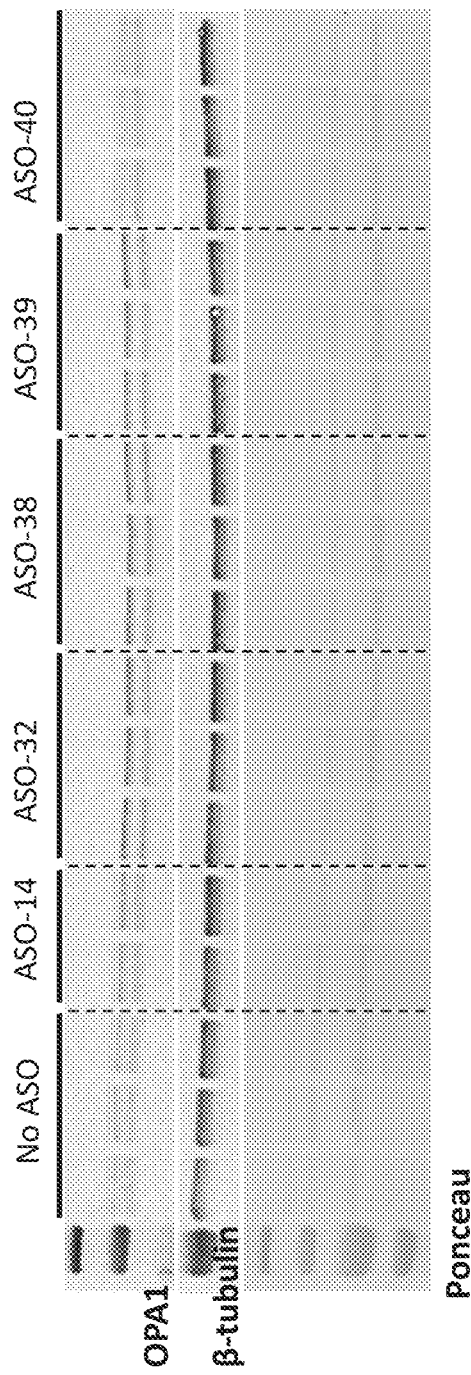
FIG. 18B illustrates expression level of OPA1 protein in HEK293 cells after treatment with various exemplary OPA1 ASOs.
Figure 18B:
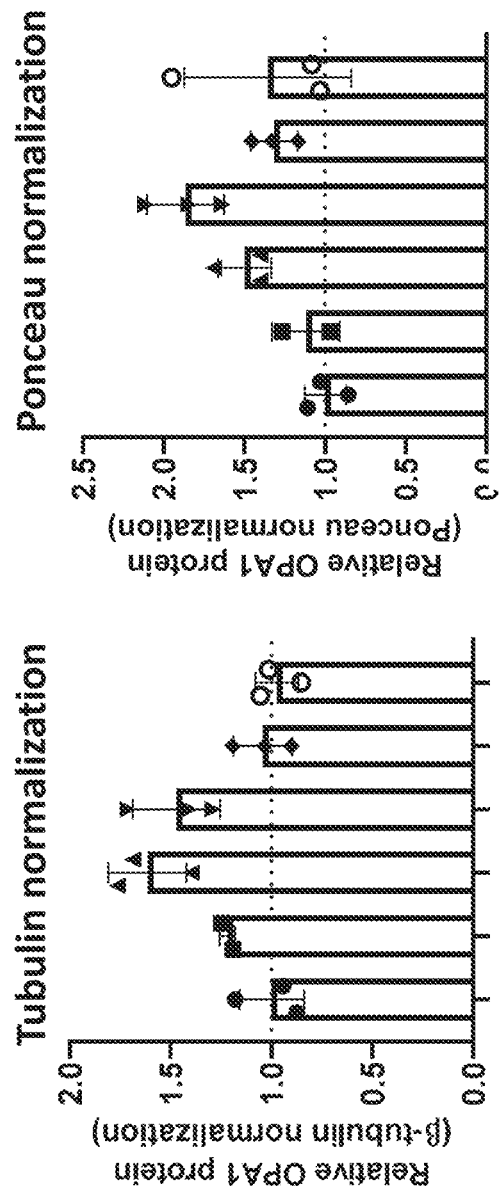

FIG. 18B shows image of Western blot using antibody against OPA1 protein and antibody against β-tubulin protein in the cells after treatment with different ASOs or no ASO (control), as well as Ponceau staining image of the same blot. FIG. 18B also shows plots summarizing the amount of OPA1 protein under different treatment conditions as normalized relative to the amount of β-tubulin or Ponceau staining intensity. The data suggest that ASO-14, ASO-32, ASO-38, and ASO-39 all may induce increase in OPA1 protein expression, whereas ASO-40 may not significantly change the expression level of OPA1 protein.

Figure 18C:
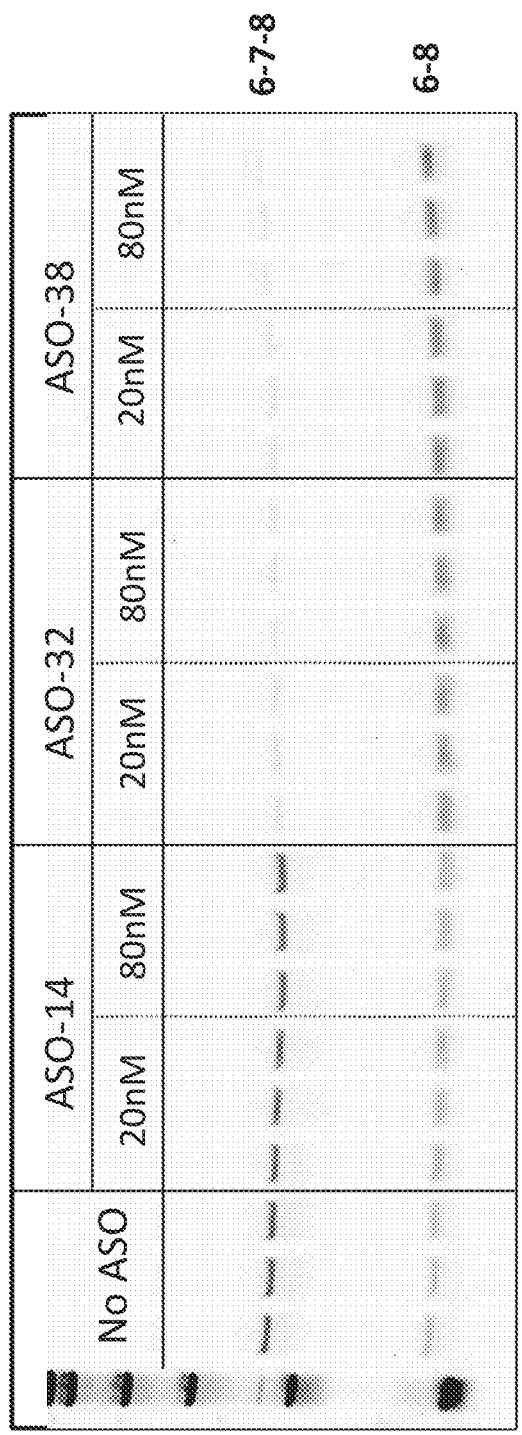
FIG. 18C illustrates dose response in OPA1 mRNAs using probes spanning exon 6 and exon 8 in HEK293 cells after treatment with various exemplary OPA1 ASOs.
Figure 18D:
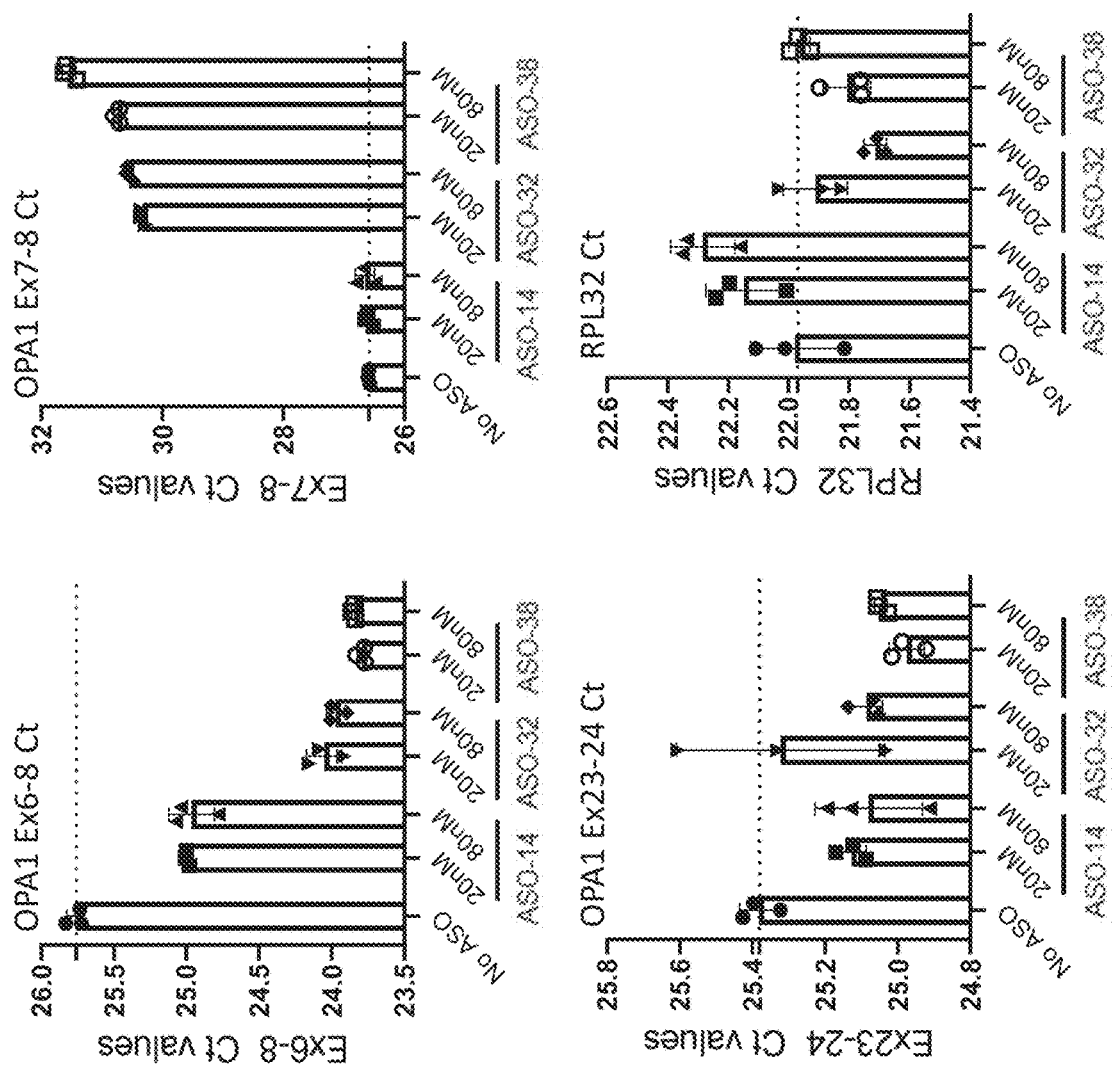
FIGS. 18D and 18E illustrate quantification of the dose response in OPA1 mRNAs using probes spanning exons 6 and 8, probes spanning exons 7 and 8, probes spanning exons 23 and 24, respectively, in HEK293 cells after treatment with various exemplary OPA1 ASOs.
Figure 18E:
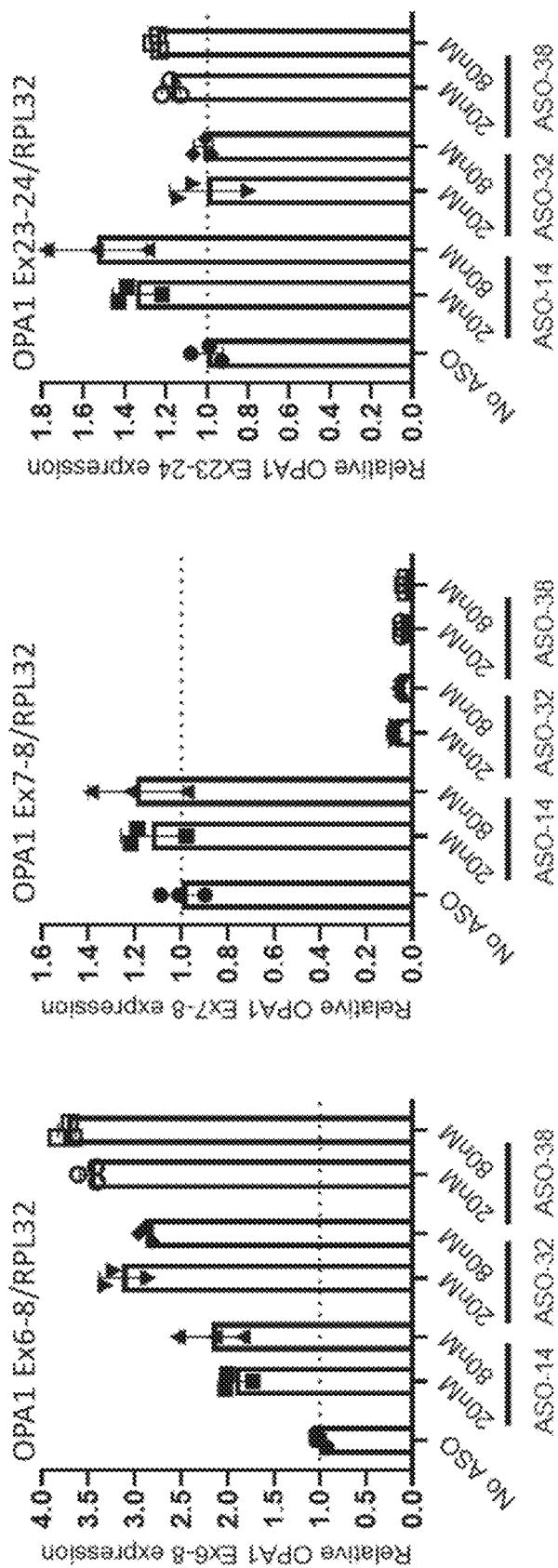
Figure 18F:
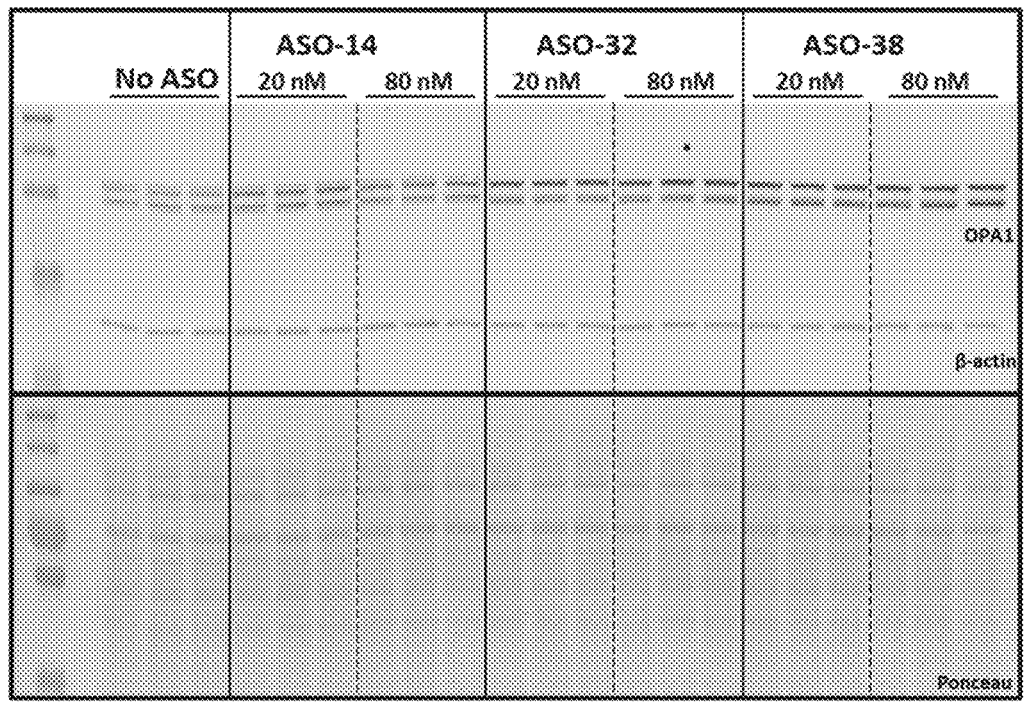
FIG. 18F illustrates dose response in expression level of OPA1 protein in HEK293 cells after treatment with various exemplary OPA1 ASOs.
Figure 18F:
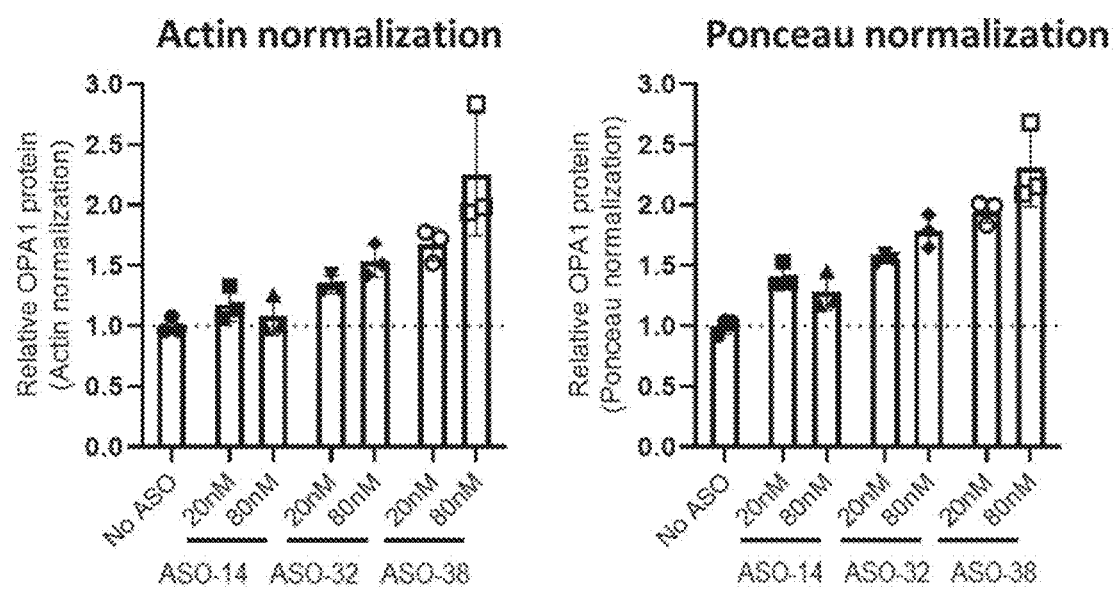

Dose response of ASO-32 and ASO-38 were also tested along with ASO-14. ASO treatment, cell harvest, and RNA isolation and analysis were conducted similarly to the experiment above in this example. Each well of HEK293 cells (about 50,000 cells/well) were treated with either 20 nM or 80 nM of ASO-14, ASO-32, ASO-38, or no ASO. FIG. 18C shows gel image of products from RT-PCR reaction using probes spanning exon 6 and 8. FIG. 18D shows quantification of qPCR Ct values for reactions under different experimental conditions using probes spanning exons and 8 ("Ex6-8"), probes spanning exons 7 and 8 ("Ex7-8"), and probes spanning exons 23 and 24 ("Ex23-24"), and FIG. 18E shows quantification of relative amount of the corresponding transcripts. The data show consistent observation that ASO-32 and ASO-38 promote exclusion of exon 7 from mature OPA1 mRNA transcripts. FIG. 18F shows the data on the OPA1 expression level after treatment of ASO-14, ASO-32, or ASO-38. Consistently, ASO-32 and ASO-38 increased OPA1 protein level.

Example 18: ASO Microwalk Evaluated by RT-qPCR

In one experiment, microwalk was conducted to test ASOs that have sequences listed in Table 7. Briefly, about 30,000 HEK293 cells per well were treated gymnotically with 20 µM one of the 20 exemplary ASOs (free uptake) listed in Table 7 for 72 hours. After the treatment, the cells were harvested for analysis. RT-PCR reactions were conducted for products corresponding to Exon 7 or Exon 7x inclusion and full-length.

Figures 19A, 19B:
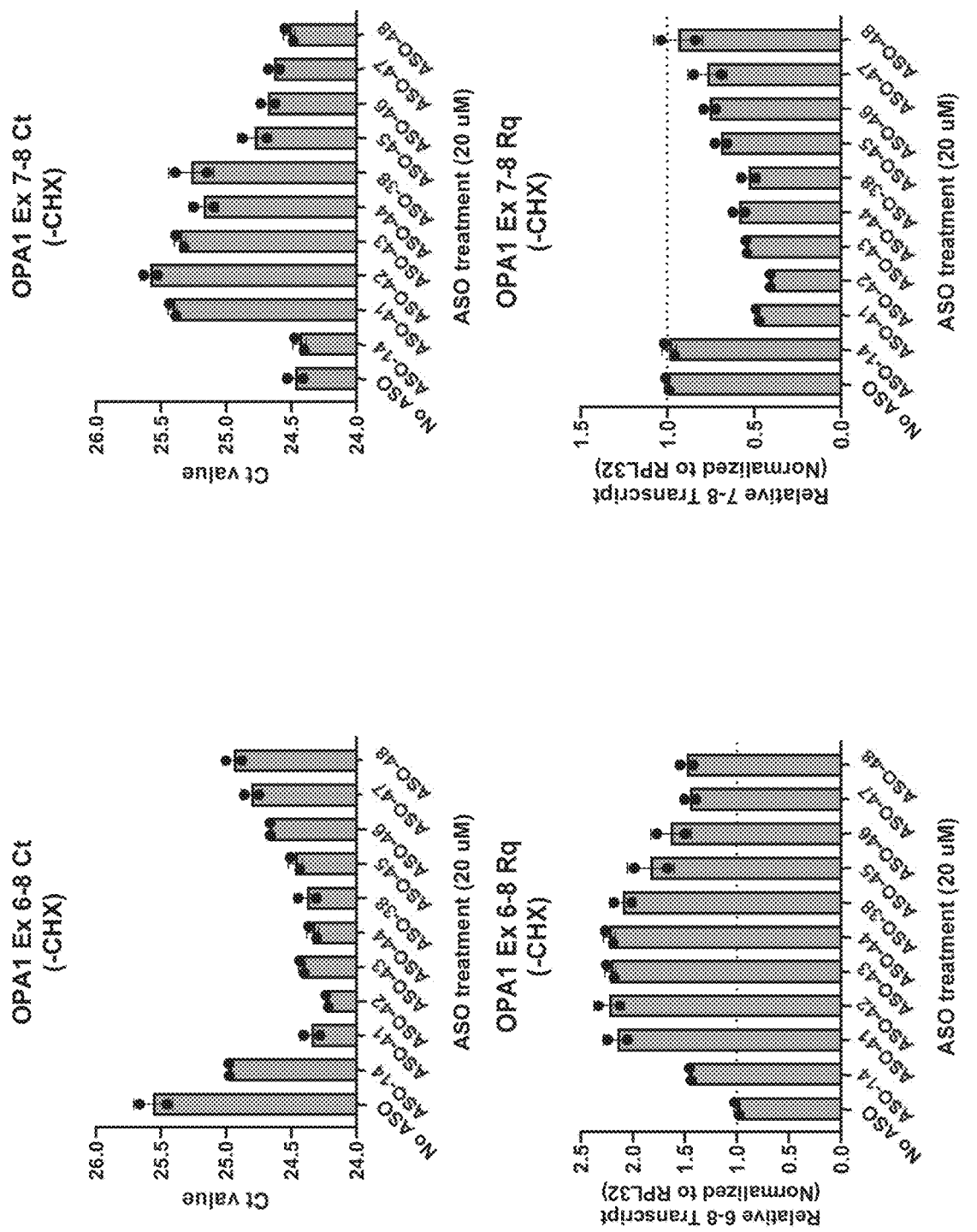
FIGS. 19A-19D illustrate RT-PCR results for OPA1 mRNAs using probes spanning exon 6 and exon 8 ("Exon 6-8"), or probes spanning exon 7x and exon 8 ("Exon 7-8"), in HEK293 cells after treatment with various exemplary OPA1 ASO 18-mers and treatment with or without cycloheximide.
Figure 19D:
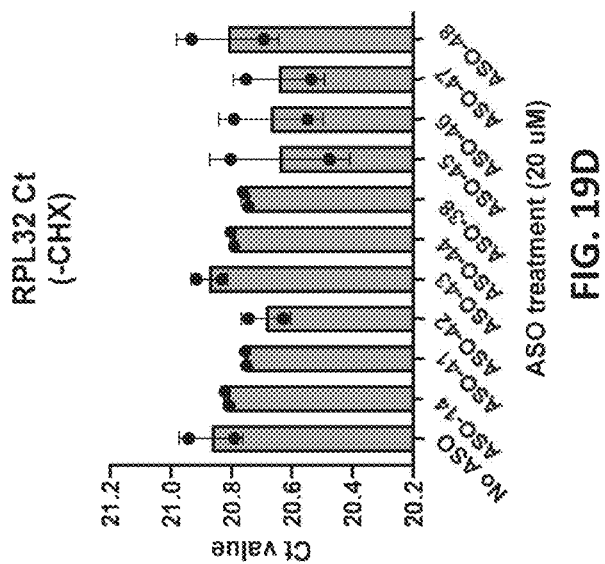
Figure 19C:
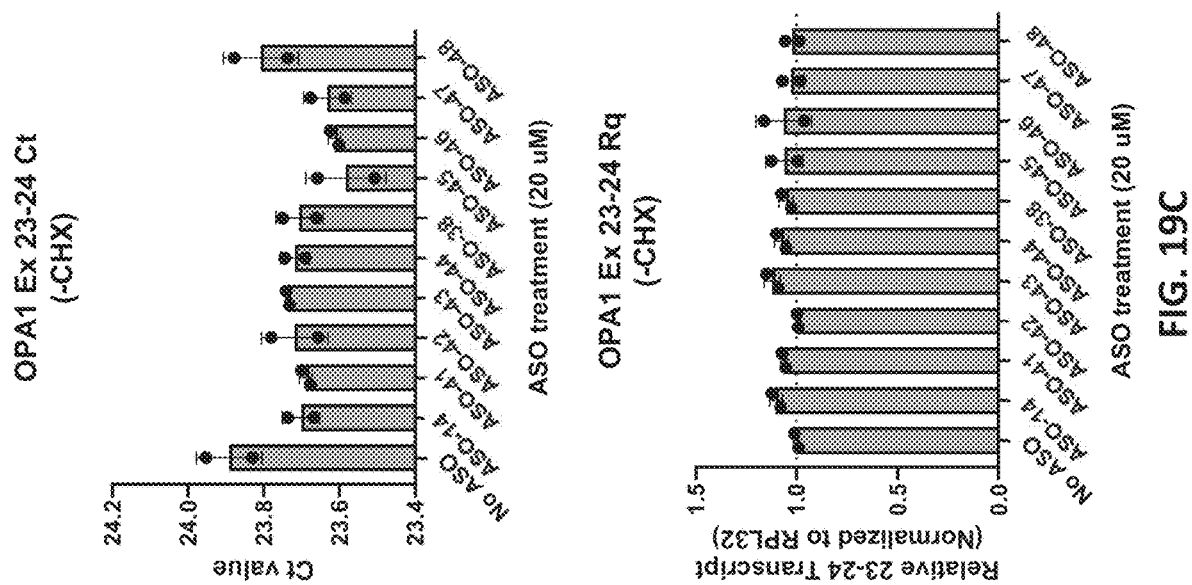
Figure 20B:
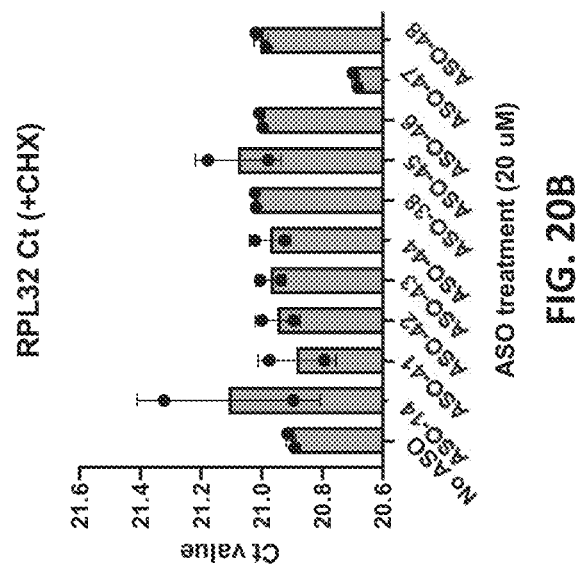
FIGS. 20A-20B illustrate RT-PCR results for OPA1 mRNAs using probes spanning exon 6 and exon 8 ("Exon 6-8"), or probes spanning exon 7x and exon 8 ("Exon 7x-8"), in HEK293 cells after treatment with various exemplary OPA1 ASO 18-mers and treatment with or without cycloheximide.
Figure 20A:
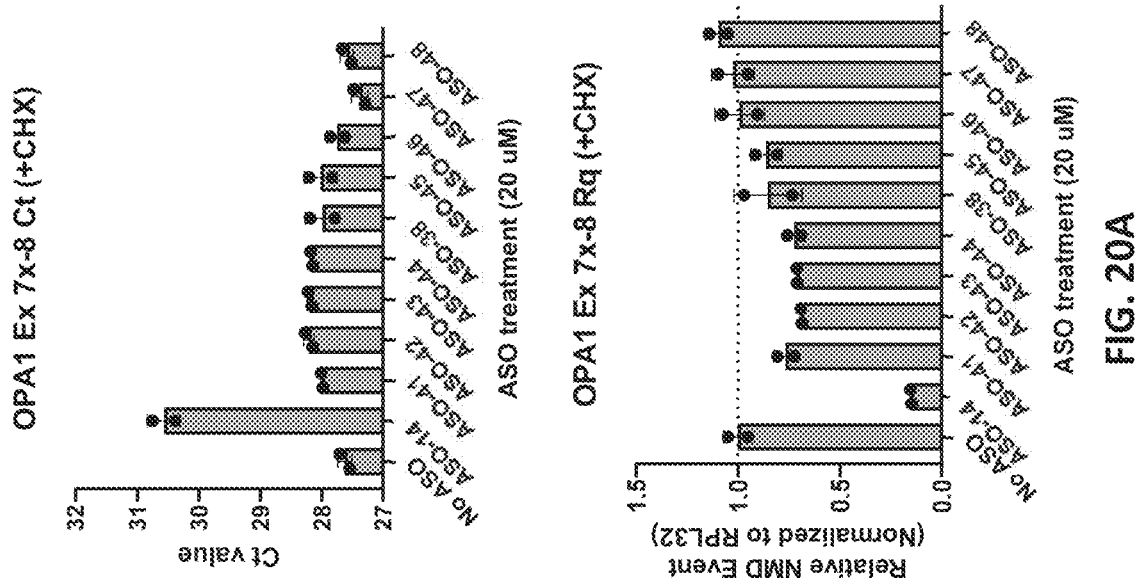

FIGS. 19A-20B demonstrate data from experiments with some of the 18-mers (named ASO-41 to ASO-48) listed in Table 7. FIGS. 19A-19B show the Ct values for the qPCR reaction (upper plots) for, and quantification of the relative amount (lower plots; normalized to Ct value of RPL32 qPCR product) of, OPA1 transcripts having exons 6 and 8 ("Ex6-8") and OPA1 transcripts having exons 7 and 8 ("Ex7-8"), respectively. FIG. 19C shows the Ct values for the qPCR reaction (upper plots) for, and quantification of the relative amount (lower plots; normalized to Ct value of RPL32 qPCR product) of, OPA1 transcripts having exons 23 and 24 ("Ex23-24"), and FIG. 19D shows the Ct values for RPL32 transcripts as a loading control. These data demonstrate that cells treated with ASO-41 to ASO-47 all showed increased amount of "Ex6-8" transcripts and decreased amount of "Ex7-8" transcripts, suggesting these ASOs promote exclusion of Exon 7 from OPA1 transcripts. No cycloheximide was applied to the cells that were subject to these analyses for Exon 7 inclusion. FIG. 20A shows the Ct values for the qPCR reaction (upper plots) for, and quantification of the relative amount (lower plots; normalized to Ct value of RPL32 qPCR product) of, OPA1 transcripts having exons 7x and 8 ("Ex7x-8"), and FIG. 20B shows the Ct values for RPL32 transcripts as a loading control. These data demonstrate that cells treated with ASO-41 to ASO-44 all showed decreased amount of "Ex7x-8" transcripts, suggesting these ASOs promote exclusion of Exon 7x from OPA1 transcripts. Cycloheximide was applied to the cells for these analyses for Exon 7x inclusion.

Figures 21A, 21B:
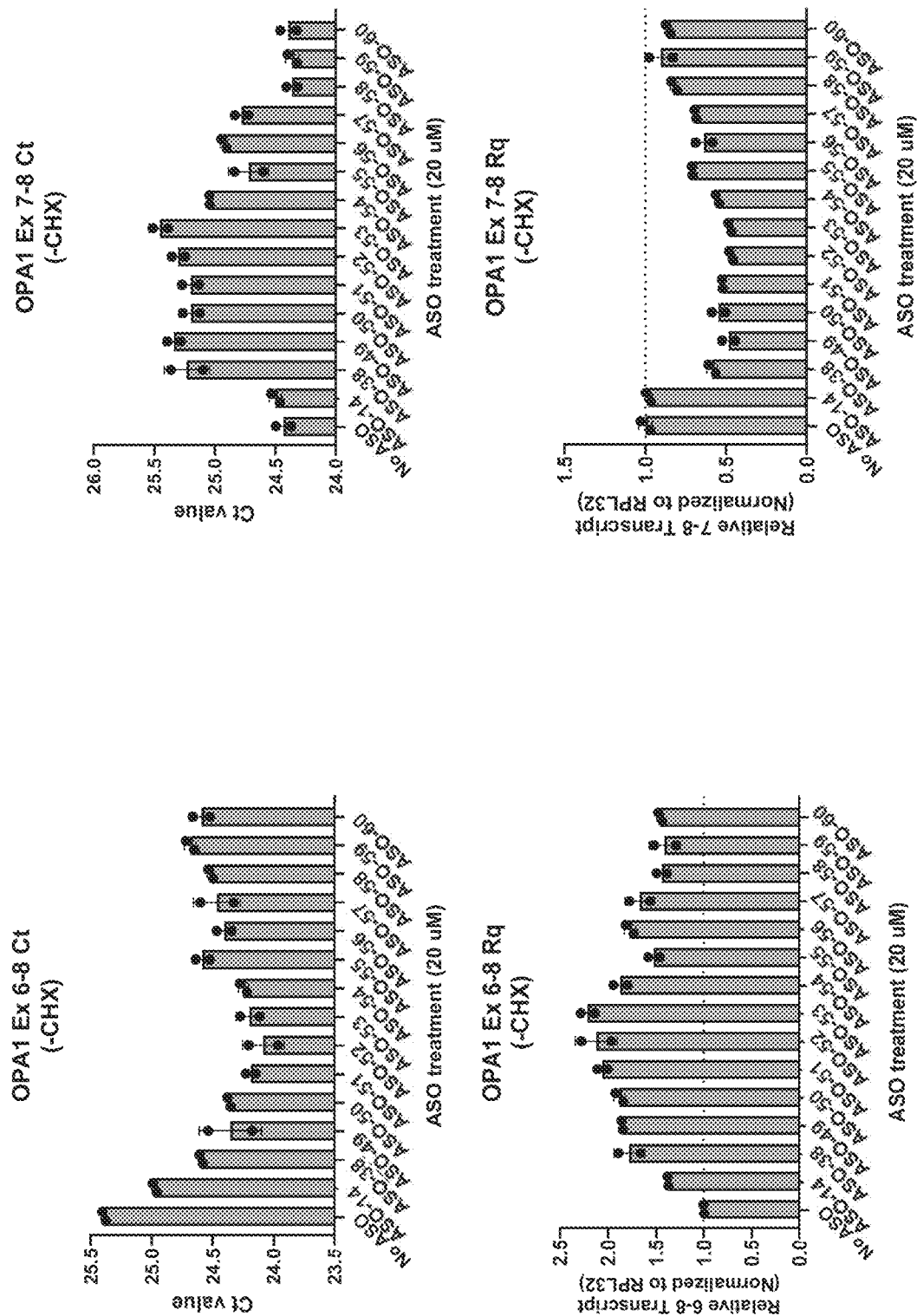
Figures 22A, 22B, 22C:
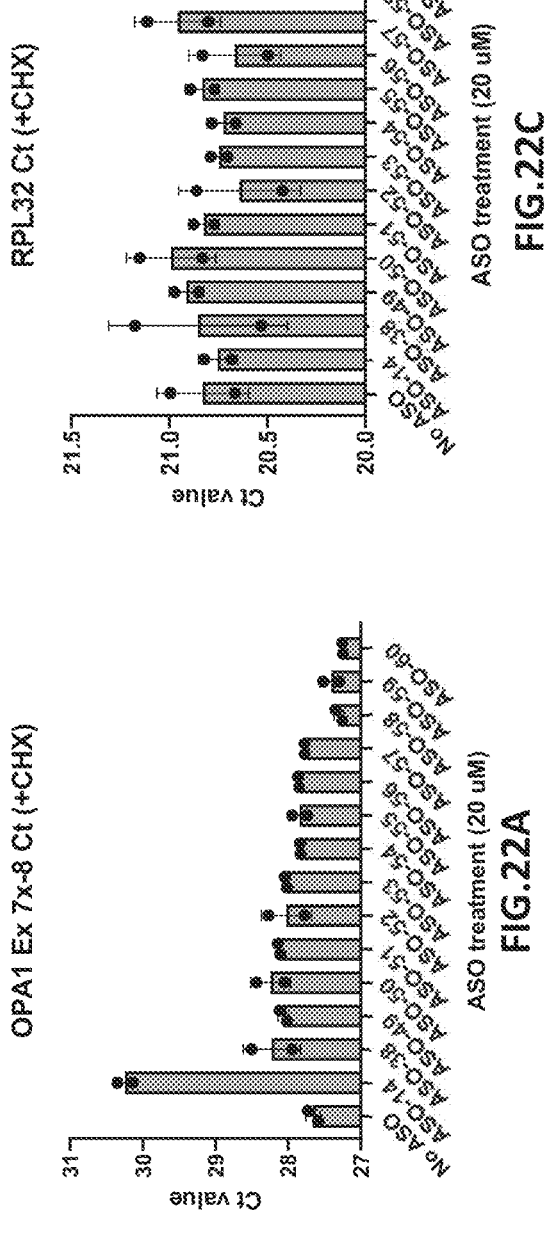
FIGS. 22A-22C illustrate RT-PCR results for OPA1 mRNAs using probes spanning exon 6 and exon 8 ("Exon 6-8"), or probes spanning exon 7x and exon 8 ("Exon 7x-8"), in HEK293 cells after treatment with various exemplary OPA1 ASO 15-mers and treatment with or without cycloheximide.

FIGS. 21A-22C demonstrate data from experiments with some of the 16-mers (named ASO-49 to ASO-60) listed in Table 7. FIGS. 21A-21B show the Ct values for the qPCR reaction (upper plots) for, and quantification of the relative amount (lower plots; normalized to Ct value of RPL32 qPCR product) of, OPA1 transcripts having exons 6 and 8 ("Ex6-8") and OPA1 transcripts having exons 7 and 8 ("Ex7-8"), respectively. FIG. 21C shows the Ct values for the qPCR reaction (upper plots) for, and quantification of the relative amount (lower plots; normalized to Ct value of RPL32 qPCR product) of, OPA1 transcripts having exons 23 and 24 ("Ex23-24"), and FIG. 21D shows the Ct values for RPL32 transcripts. These data demonstrate that cells treated with ASO-49 to ASO-60 all showed increased amount of "Ex6-8" transcripts and decreased amount of "Ex7-8" transcripts, suggesting these ASOs promote exclusion of Exon 7 from OPA1 transcripts. No cycloheximide was applied to the cells that were subject to these analyses for Exon 7 inclusion. FIG. 22A shows the Ct values for the qPCR reaction (upper plots) for, and quantification of the relative amount (lower plots; normalized to Ct value of RPL32 qPCR product) of, OPA1 transcripts having exons 7x and 8 ("Ex7x-8"), and FIG. 22C shows the Ct values for RPL32 transcripts as a loading control. These data demonstrate that cells treated with ASO-49 to ASO-56 all showed decreased amount of "Ex7x-8" transcripts, suggesting these ASOs promote exclusion of Exon 7x from OPA1 transcripts. Cycloheximide was applied to the cells for these analyses for Exon 7x inclusion.

Figure 23A:
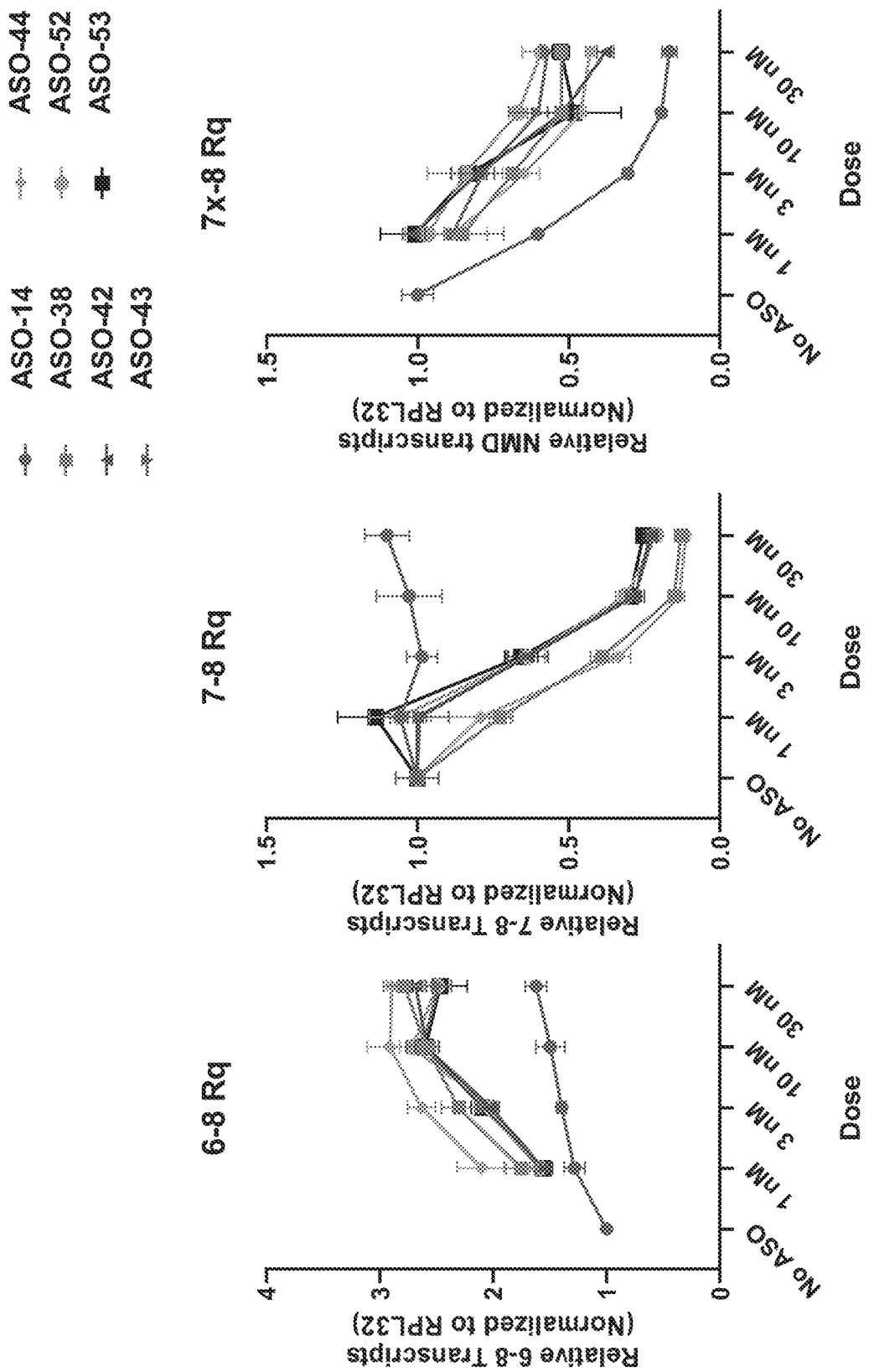
FIGS. 23A-23B illustrate dose response in OPA1 mRNAs having Exon 6 and Exon 8 ("6-8"), having Exon 7 and Exon 8 ("7-8"), or having Exon 7x and Exon 8 ("7x-8") in HEK293 cells after treatment with different concentrations of various exemplary OPA1 ASOs.
Figure 23B:
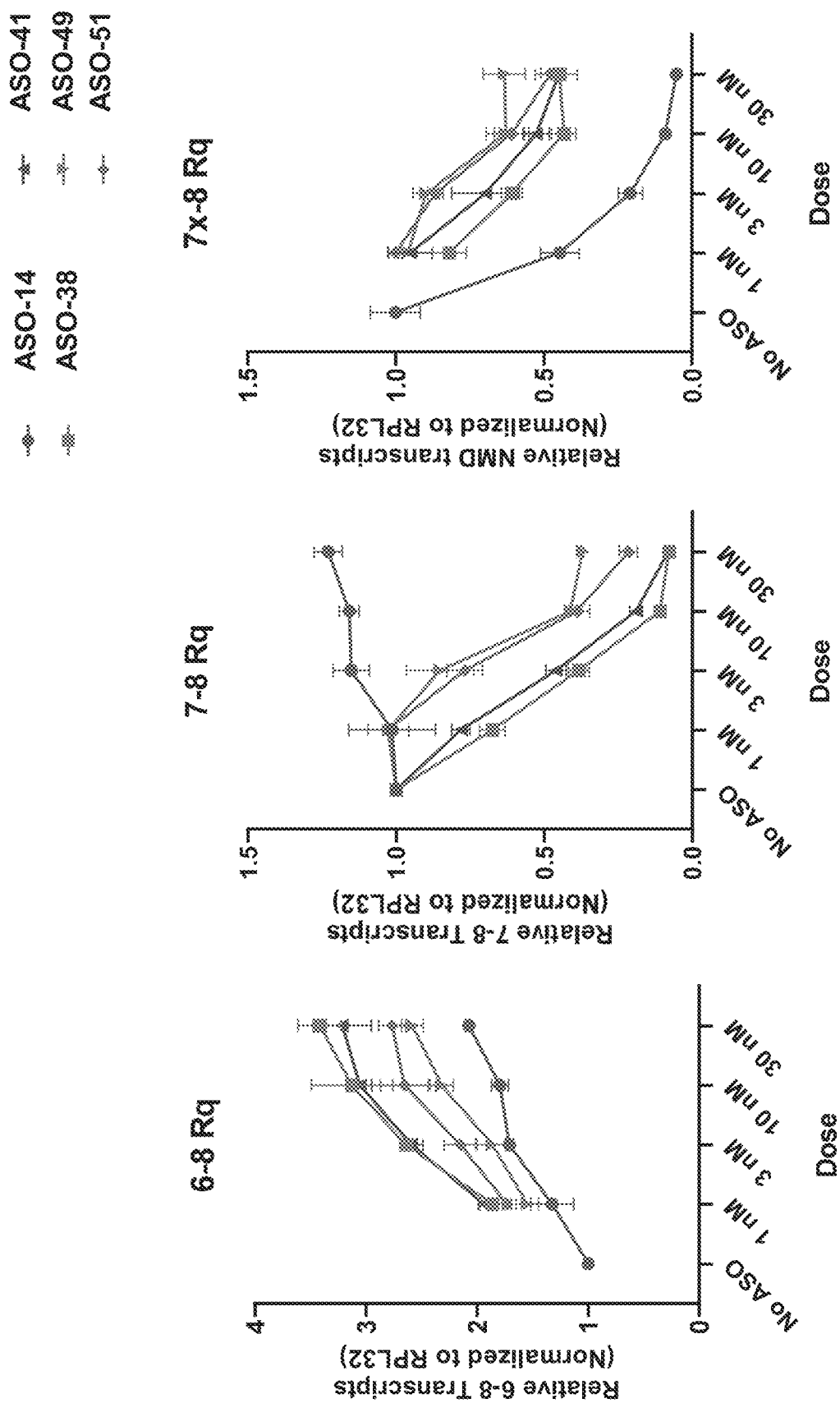

Another experiment was conducted to assess transfection dose response relationship with select ASOs among the ASOs tested above in the microwalk analyses. Briefly, 100,000 HEK293 cells per well were transfected with 1, 3, 10, or 30 nM of an exemplary ASO with 0.45 µL lipofectamine for 24 hours. Cells were later harvested for qPCR analysis as above. FIGS. 23A-23B show plots depicting the dose response curves of relative amounts of different OPA1 transcripts versus the transfection concentration of exemplary ASOs, ASO-14, 38, 41, 42, 43, 44, 49, 51, 52, and 53. The plots show that as a general trend, in cells treated with ASOs like ASO-38, 41, 42, 43, 44, 49, 51, 52, or 53, the amount of OPA1 transcripts having Exon 6 and 8 ("6-8") increased, while the amounts of OPA1 transcripts having Exon 7 and 8 ("7-8") and OPA1 transcripts having Exon 7x and 8 ("7x-8") decreased, as concentration of the exemplary ASO increased. In contrast, in cells treated with ASO-14, while "7x-8" decreased and "6-8" transcripts increased, "7-8" transcripts did not significantly change. These data suggest that ASO-38, 41, 42, 43, 44, 49, 51, 52, and 53 may all promote exclusion of both Exon 7 and Exon 7x, while ASO-14 may promote exclusion of Exon 7x

TABLE 5

Exemplary OPA1 ASO sequences

| | | Coordinates GRCh38/hg38: chr3 | |
|---|---|---|---|
| SEQ ID NO.: | Sequence (5'-3') | Oligo Start | Oligo End |
| 6 | AGGCCATTCTGAAATTCT | 193628406 | 193628423 |
| 7 | CATTGAGGCCATTCTGAA | 193628411 | 193628428 |
| 8 | TAAGGCATTGAGGCCATT | 193628416 | 193628433 |

TABLE 5-continued

Exemplary OPA1 ASO sequences

| SEQ ID NO.: | Sequence (5'-3') | Coordinates GRCh38/hg38: chr3 | |
|---|---|---|---|
| | | Oligo Start | Oligo End |
| 9 | CCTATTAAGGCATTGAGG | 193628421 | 193628438 |
| 10 | TTCTTCCTATTAAGGCAT | 193628426 | 193628443 |
| 11 | AGTATTTCTTCCTATTAA | 193628431 | 193628448 |
| 12 | TTTCAAGTATTTCTTCCT | 193628436 | 193628453 |
| 13 | AAAAATTTCAAGTATTTC | 193628441 | 193628458 |
| 14 | AATTTAAAAATTTCAAGT | 193628446 | 193628463 |
| 15 | GCCCTAATTTAAAAATTT | 193628451 | 193628468 |
| 16 | ACCAGCCCTAATTTAAA | 193628456 | 193628473 |
| 17 | ACAAAACCAAGCCCTAAT | 193628461 | 193628478 |
| 18 | TCCTCACAAAACCAAGCC | 193628466 | 193628483 |
| 19 | CTAGCTCCTCACAAAACC | 193628471 | 193628488 |
| 20 | CTTTACTAGCTCCTCACA | 193628476 | 193628493 |
| 21 | AAAACCTTTACTAGCTCC | 193628481 | 193628498 |
| 22 | AGAGAAAACCTTTACTA | 193628486 | 193628503 |
| 23 | CTGAAAGAGAAAACCTT | 193628491 | 193628508 |
| 24 | AAGCTGAAAGAGAAAAC | 193628494 | 193628511 |
| 25 | CTAAAGCTGAAAGAGAAA | 193628497 | 193628514 |
| 26 | AAGCTAAAGCTGAAAGAG | 193628500 | 193628517 |
| 27 | AACAAGCTAAAGCTGAAA | 193628503 | 193628520 |
| 28 | AGAAACAAGCTAAAGCTG | 193628506 | 193628523 |
| 29 | CGCAGAAACAAGCTAAAG | 193628509 | 193628526 |
| 30 | TCCTCCGCAGAAACAAGC | 193628514 | 193628531 |
| 31 | CGGAATCCTCCGCAGAAA | 193628519 | 193628536 |
| 32 | AAGAGCGGAATCCTCCGC | 193628524 | 193628541 |
| 33 | GGAGAAAGAGCGGAATCC | 193628529 | 193628546 |
| 34 | CTGATGGAGAAAGAGCGG | 193628534 | 193628551 |
| 35 | TGAAACTGATGGAGAAAG | 193628539 | 193628556 |
| 36 | GGCTATGAAACTGATGGA | 193628544 | 193628561 |
| 37 | TCCAGGGCTATGAAACTG | 193628549 | 193628566 |
| 38 | ACAATTCCAGGGCTATGA | 193628554 | 193628571 |
| 39 | TTTCTACAATTCCAGGGC | 193628559 | 193628576 |
| 40 | GAGCTTTTCTACAATTCC | 193628564 | 193628581 |
| 41 | AACCAGAGCTTTTCTACA | 193628569 | 193628586 |
| 42 | CTTGAAACCAGAGCTTTT | 193628574 | 193628591 |
| 43 | ATGGTCTTGAAACCAGAG | 193628579 | 193628596 |
| 44 | TATCAATGGTCTTGAAAC | 193628584 | 193628601 |
| 45 | ATGGATATCAATGGTCTT | 193628589 | 193628606 |

TABLE 5-continued

Exemplary OPA1 ASO sequences

| SEQ ID NO.: | Sequence (5'-3') | Coordinates GRCh38/hg38: chr3 | |
|---|---|---|---|
| | | Oligo Start | Oligo End |
| 46 | CAGAAATGGATATCAATG | 193628594 | 193628611 |
| 47 | CCTGACAGAAATGGATAT | 193628599 | 193628616 |
| 48 | CACCCTGACAGAAATGGA | 193628602 | 193628619 |
| 49 | ACTCACCCTGACAGAAAT | 193628605 | 193628622 |
| 50 | AAAACTCACCCTGACAGA | 193628608 | 193628625 |
| 51 | TTTAAAACTCACCCTGAC | 193628611 | 193628628 |
| 52 | AAATTTAAAACTCACCCT | 193628614 | 193628631 |
| 53 | AATAAATTTAAAACTCAC | 193628617 | 193628634 |
| 54 | CATGAAATAAATTTAAAA | 193628622 | 193628639 |
| 55 | TGCATCATGAAATAAATT | 193628627 | 193628644 |
| 56 | TTGTTTGCATCATGAAAT | 193628632 | 193628649 |
| 57 | ATATATTGTTTGCATCAT | 193628637 | 193628654 |
| 58 | GTTCAATATATTGTTTGC | 193628642 | 193628659 |
| 59 | CTGTTGTTCAATATATTG | 193628647 | 193628664 |
| 60 | ATGTCCTGTTGTTCAATA | 193628652 | 193628669 |
| 61 | AGTTCATGTCCTGTTGTT | 193628657 | 193628674 |
| 62 | GAACAAGTTCATGTCCTG | 193628662 | 193628679 |
| 63 | AACAAGAACAAGTTCATG | 193628667 | 193628684 |
| 64 | CTTACAACAAGAACAAGT | 193628672 | 193628689 |
| 65 | AGCCACTTACAACAAGAA | 193628677 | 193628694 |
| 66 | AATTCAGCCACTTACAAC | 193628682 | 193628699 |
| 67 | GATAAAATTCAGCCACTT | 193628687 | 193628704 |
| 68 | TTACTGATAAAATTCAGC | 193628692 | 193628709 |
| 69 | GTGCTTTACTGATAAAAT | 193628697 | 193628714 |
| 70 | TTGATGTGCTTTACTGAT | 193628702 | 193628719 |
| 71 | TGGAGAAAGAGCGGAATC | 193628530 | 193628547 |
| 72 | ATGGAGAAAGAGCGGAAT | 193628531 | 193628548 |
| 73 | GATGGAGAAAGAGCGGAA | 193628532 | 193628549 |
| 74 | TGATGGAGAAAGAGCGGA | 193628533 | 193628550 |
| 75 | ACTGATGGAGAAAGAGCG | 193628535 | 193628552 |
| 76 | AACTGATGGAGAAAGAGC | 193628536 | 193628553 |
| 77 | AAACTGATGGAGAAAGAG | 193628537 | 193628554 |
| 78 | GAAACTGATGGAGAAAGA | 193628538 | 193628555 |
| 79 | ATGAAACTGATGGAGAAA | 193628540 | 193628557 |
| 80 | TATGAAACTGATGGAGAA | 193628541 | 193628558 |
| 81 | CTATGAAACTGATGGAGA | 193628542 | 193628559 |

TABLE 5-continued

Exemplary OPA1 ASO sequences

| SEQ ID NO. | Sequence (5'-3') | Coordinates GRCh38/hg38: chr3 Oligo Start | Oligo End |
|---|---|---|---|
| 82 | GCTATGAAACTGATGGAG | 193628543 | 193628560 |
| 83 | GGGCTATGAAACTGATGG | 193628545 | 193628562 |
| 84 | AGGGCTATGAAACTGATG | 193628546 | 193628563 |
| 85 | CAGGGCTATGAAACTGAT | 193628547 | 193628564 |
| 86 | CCAGGGCTATGAAACTGA | 193628548 | 193628565 |
| 87 | CTGATGGAGAAAGAGCGGAATC | 193628530 | 193628551 |
| 88 | CTGATGGAGAAAGAGCGGAA | 193628532 | 193628551 |
| 89 | AACTGATGGAGAAAGAGCGGAA | 193628532 | 193628553 |
| 90 | AACTGATGGAGAAAGAGCGG | 193628534 | 193628553 |
| 91 | GAAACTGATGGAGAAAGAGCGG | 193628534 | 193628555 |
| 92 | GGCTATGAAACTGATGGAGAAA | 193628540 | 193628561 |
| 93 | GGCTATGAAACTGATGGAGA | 193628542 | 193628561 |
| 94 | AGGGCTATGAAACTGATGGAGA | 193628542 | 193628563 |
| 95 | AGGGCTATGAAACTGATGGA | 193628544 | 193628563 |
| 96 | CCAGGGCTATGAAACTGATGGA | 193628544 | 193628565 |
| 97 | TTCTTACCCATTTAATTA | 193655041 | 193655059 |
| 98 | TGCTTCTTACCCATTTAA | 193655044 | 193655062 |
| 99 | TAATGCTTCTTACCCATT | 193655047 | 193655065 |
| 100 | AGATAATGCTTCTTACCC | 193655050 | 193655068 |
| 101 | CAGATAATGCTTCTTACC | 193655051 | 193655069 |
| 102 | CCCTTCAGATAATGCTTC | 193655056 | 193655074 |
| 103 | CTACTCCCTTCAGATAAT | 193655061 | 193655079 |
| 104 | AGCTCCTACTCCCTTCAG | 193655066 | 193655084 |
| 105 | TTCACAGCTCCTACTCCC | 193655071 | 193655089 |
| 106 | TAAAATTCACAGCTCCTA | 193655076 | 193655094 |
| 107 | AAATCTAAAATTCACAGC | 193655081 | 193655099 |
| 108 | GAATAAAATCTAAAATTC | 193655086 | 193655104 |
| 109 | GATGGGAATAAAATCTAA | 193655091 | 193655109 |
| 110 | GCTGTGATGGGAATAAAA | 193655096 | 193655114 |
| 111 | TAGAGGCTGTGATGGGAA | 193655101 | 193655119 |
| 112 | AAAGATAGAGGCTGTGAT | 193655106 | 193655124 |
| 113 | AAAAGAAAGATAGAGGCT | 193655111 | 193655129 |
| 114 | GACCTAAAAGAAAGATAG | 193655116 | 193655134 |
| 115 | ATAAAGACCTAAAAGAAA | 193655121 | 193655139 |
| 116 | GAGATATAAAGACCTAAA | 193655126 | 193655144 |
| 117 | GGCTGTGATGGGAATAAA | 193655097 | 193655115 |
| 118 | AGGCTGTGATGGGAATAA | 193655098 | 193655116 |

TABLE 5-continued

Exemplary OPA1 ASO sequences

| SEQ ID NO.: | Sequence (5'-3') | Coordinates GRCh38/hg38: chr3 | |
|---|---|---|---|
| | | Oligo Start | Oligo End |
| 119 | GAGGCTGTGATGGGAATA | 193655099 | 193655117 |
| 120 | AGAGGCTGTGATGGGAAT | 193655100 | 193655118 |
| 121 | ATAGAGGCTGTGATGGGA | 193655102 | 193655120 |
| 122 | GATAGAGGCTGTGATGGG | 193655103 | 193655121 |
| 123 | AGATAGAGGCTGTGATGG | 193655104 | 193655122 |
| 124 | AAGATAGAGGCTGTGATG | 193655105 | 193655123 |
| 125 | TAGAGGCTGTGATGGGAATAAA | 193655097 | 193655119 |
| 126 | ATAGAGGCTGTGATGGGAATAA | 193655098 | 193655120 |
| 127 | GATAGAGGCTGTGATGGGAATA | 193655099 | 193655121 |
| 128 | AGATAGAGGCTGTGATGGGAAT | 193655100 | 193655122 |
| 129 | AAGATAGAGGCTGTGATGGGAA | 193655101 | 193655123 |
| 130 | GAGGCTGTGATGGGAATAAA | 193655097 | 193655117 |
| 131 | AGAGGCTGTGATGGGAATAA | 193655098 | 193655118 |
| 132 | TAGAGGCTGTGATGGGAATA | 193655099 | 193655119 |
| 133 | ATAGAGGCTGTGATGGGAAT | 193655100 | 193655120 |
| 134 | GATAGAGGCTGTGATGGGAA | 193655101 | 193655121 |
| 135 | AGATAGAGGCTGTGATGGGA | 193655102 | 193655122 |
| 136 | AAGATAGAGGCTGTGATGGG | 193655103 | 193655123 |
| 137 | CTGTGATGGGAATAAA | 193655097 | 193655113 |
| 138 | GCTGTGATGGGAATAA | 193655098 | 193655114 |
| 139 | GGCTGTGATGGGAATA | 193655099 | 193655115 |
| 140 | AGGCTGTGATGGGAAT | 193655100 | 193655116 |
| 141 | GAGGCTGTGATGGGAA | 193655101 | 193655117 |
| 142 | AGAGGCTGTGATGGGA | 193655102 | 193655118 |
| 143 | TAGAGGCTGTGATGGG | 193655103 | 193655119 |
| 144 | ATAGAGGCTGTGATGG | 193655104 | 193655120 |
| 145 | GATAGAGGCTGTGATG | 193655105 | 193655121 |
| 146 | AGATAGAGGCTGTGAT | 193655106 | 193655122 |
| 147 | AAGATAGAGGCTGTGA | 193655107 | 193655123 |
| 148 | AGGCTGTGATGTGAATAA | 193655099 | 193655116 |
| 149 | AGAGGCTGTGATGTGAAT | 193655101 | 193655118 |
| 150 | TAGAGGCTGTGATGTGAA | 193655102 | 193655119 |
| 151 | GATAGAGGCTGTGATTGG | 193655104 | 193655121 |
| 152 | GGCTGTGATGTGAATA | 193655100 | 193655115 |
| 153 | GAGGCTGTGATGTGAA | 193655102 | 193655117 |
| 154 | TAGAGGCTGTGATTGG | 193655104 | 193655119 |

TABLE 5-continued

Exemplary OPA1 ASO sequences

| SEQ ID NO. | Sequence (5'-3') | Coordinates GRCh38/hg38: chr3 | |
|---|---|---|---|
| | | Oligo Start | Oligo End |
| 155 | ATGAAACTGATGGAGA | 193628542 | 193628557 |
| 156 | CTATGAAACTGATGGA | 193628544 | 193628559 |
| 157 | GGCTATGAAACTGATG | 193628546 | 193628561 |
| 158 | GAAACTGATGGAGA | 193628542 | 193628555 |
| 159 | ATGAAACTGATGGA | 193628544 | 193628557 |
| 160 | CTATGAAACTGATG | 193628546 | 193628559 |
| 161 | GGCTATGAAACTGA | 193628548 | 193628561 |
| 162 | TAGAGGCTGTGATGGGAATAAAAT | 193655096 | 193655119 |
| 163 | ATAGAGGCTGTGATGGGAATAAAA | 193655097 | 193655120 |
| 164 | ATAGAGGCTGTGATGGGAATAAAAT | 193655096 | 193655120 |
| 165 | AAAGATAGAGGCTGTGATGGGAATA | 193655100 | 193655124 |
| 166 | GGCTATGAAACTGATGGAGAA | 193628541 | 193628561 |
| 167 | GGCTATGAAACTGATGGAGAAAGA | 193628538 | 193628561 |
| 168 | AGGGCTATGAAACTGATGGAGAAAG | 193628539 | 193628563 |
| 169 | CATTTAATTAAATTATAT | 193655033 | 193655051 |
| 170 | CCATTTAATTAAATTATA | 193655034 | 193655052 |
| 171 | CCCATTTAATTAAATTAT | 193655035 | 193655053 |
| 172 | ACCCATTTAATTAAATTA | 193655036 | 193655054 |
| 173 | TACCCATTTAATTAAATT | 193655037 | 193655055 |
| 174 | TTACCCATTTAATTAAAT | 193655038 | 193655056 |
| 175 | CTTACCCATTTAATTAAA | 193655039 | 193655057 |
| 176 | TCTTACCCATTTAATTAA | 193655040 | 193655058 |
| 177 | GATAGAGGCTGTGATGG | 193655104 | 193655122 |
| 178 | GGCTGTGAAACTGATGGA | 89481662 | 89481679 |
| 179 | GGCTGTGAAACTGATGGAGA | 89481660 | 89481679 |
| 180 | GCTATGAAACTGATGG | 193628545 | 193628560 |
| 181 | TATGAAACTGATGG | 193628545 | 193628558 |
| 182 | GCTATGAAACTGAT | 193628547 | 193628560 |
| 183 | GCTGTGAAACTGATGGAGAA | 89481659 | 89481678 |
| 184 | GGGCTGTGAAACTGATGGAG | 89481661 | 89481680 |
| 185 | TGTGAAACTGATGGAGAA | 89481659 | 89481676 |
| 186 | CTGTGAAACTGATGGAGA | 89481660 | 89481677 |
| 187 | GCTGTGAAACTGATGGAG | 89481661 | 89481678 |
| 188 | GGGCTGTGAAACTGATGG | 89481663 | 89481680 |
| 189 | TGAAACTGATGGAGAA | 89481659 | 89481674 |
| 190 | GTGAAACTGATGGAGA | 89481660 | 89481675 |
| 191 | TGTGAAACTGATGGAG | 89481661 | 89481676 |

TABLE 5-continued

Exemplary OPA1 ASO sequences

| SEQ ID NO. | Sequence (5'-3') | Coordinates GRCh38/hg38: chr3 | |
|---|---|---|---|
| | | Oligo Start | Oligo End |
| 192 | CTGTGAAACTGATGGA | 89481662 | 89481677 |
| 193 | GCTGTGAAACTGATGG | 89481663 | 89481678 |
| 194 | GGCTGTGAAACTGATG | 89481664 | 89481679 |
| 195 | GGGCTGTGAAACTGAT | 89481665 | 89481680 |
| 196 | CGGTCCAGGAATGAC | 193593285 | 193593303 |
| 197 | CCGGTCCAGGAATGA | 193593286 | 193593304 |
| 198 | CCCGGTCCAGGAATG | 193593287 | 193593305 |
| 199 | TCCCGGTCCAGGAAT | 193593288 | 193593306 |
| 200 | CTCCCGGTCCAGGAA | 193593289 | 193593307 |
| 201 | GCTCCCGGTCCAGGA | 193593290 | 193593308 |
| 202 | GGCTCCCGGTCCAGG | 193593291 | 193593309 |
| 203 | CGGGAGCCCCGTGT | 193593318 | 193593336 |
| 204 | GCGGGAGCCCCGTG | 193593319 | 193593337 |
| 205 | CGCGGGAGCCCCGT | 193593320 | 193593338 |
| 206 | ACGCGGGAGCCCCG | 193593321 | 193593339 |
| 207 | CACGCGGGAGCCCCC | 193593322 | 193593340 |
| 208 | CCACGCGGGAGCCCC | 193593323 | 193593341 |
| 209 | GCCACGCGGGAGCCC | 193593324 | 193593342 |
| 210 | GGCCACGCGGGAGCC | 193593325 | 193593343 |
| 211 | CGGCCACGCGGGAGC | 193593326 | 193593344 |
| 212 | ACGGCCACGCGGGAG | 193593327 | 193593345 |
| 213 | GACGGCCACGCGGGA | 193593328 | 193593346 |
| 214 | AGACGGCCACGCGGG | 193593329 | 193593347 |
| 215 | GCTAGGGAGGGATGGTTA | 193625988 | 193626006 |
| 216 | TGTAAGCTAGGGAGGGAT | 193625993 | 193626011 |
| 217 | ACAGATGTAAGCTAGGGA | 193625998 | 193626016 |
| 218 | AAGGAACAGATGTAAGCT | 193626003 | 193626021 |
| 219 | CAACAAAGGAACAGATGT | 193626008 | 193626026 |
| 220 | GGGTGCAACAAAGGAACA | 193626013 | 193626031 |
| 221 | ACCAAGGGTGCAACAAAG | 193626018 | 193626036 |
| 222 | GTTAAACCAAGGGTGCAA | 193626023 | 193626041 |
| 223 | ATAATGTTAAACCAAGGG | 193626028 | 193626046 |
| 224 | GGAGAATAATGTTAAACC | 193626033 | 193626051 |
| 225 | GGGGAGGAGAATAATGTT | 193626038 | 193626056 |
| 226 | AAATTGGGGAGGAGAATA | 193626043 | 193626061 |
| 227 | AGAGGAAATTGGGGAGGA | 193626048 | 193626066 |

TABLE 5-continued

Exemplary OPA1 ASO sequences

| SEQ ID NO.: | Sequence (5'-3') | Coordinates GRCh38/hg38: chr3 | |
|---|---|---|---|
| | | Oligo Start | Oligo End |
| 228 | GGAGAAGAGGAAATTGGG | 193626053 | 193626071 |
| 229 | AATGAGGAGAAGAGGAAA | 193626058 | 193626076 |
| 230 | TTCACAATGAGGAGAAGA | 193626063 | 193626081 |
| 231 | ACGAGTTCACAATGAGGA | 193626068 | 193626086 |
| 232 | CTGCCACGAGTTCACAAT | 193626073 | 193626091 |
| 233 | AGACCCTGCCACGAGTTC | 193626078 | 193626096 |
| 234 | CAAGCAGACCCTGCCACG | 193626083 | 193626101 |
| 235 | CTCACCAAGCAGACCCTG | 193626088 | 193626106 |
| 236 | GAGCTCACCAAGCAGACC | 193626091 | 193626109 |
| 237 | AGAATGAGCTCACCAAGC | 193626096 | 193626114 |
| 238 | GTAAGAGAATGAGCTCAC | 193626101 | 193626119 |
| 239 | TTGTTGTAAGAGAATGAG | 193626106 | 193626124 |
| 240 | ATTTGTTGTTGTAAGAGA | 193626111 | 193626129 |
| 241 | CTTGAATTTGTTGTTGTA | 193626116 | 193626134 |
| 242 | ATGCTCTTGAATTTGTTG | 193626121 | 193626139 |
| 243 | TCTTCATGCTCTTGAATT | 193626126 | 193626144 |
| 244 | CTTCCTCTTCATGCTCTT | 193626131 | 193626149 |
| 245 | GCGCGCTTCCTCTTCATG | 193626136 | 193626154 |
| 246 | GCTCTGCGCGCTTCCTCT | 193626141 | 193626159 |
| 247 | GGCCAGCGGCTCTGCGCG | 193626149 | 193626167 |
| 248 | ATATTGGCCAGCGGCTCT | 193626154 | 193626172 |
| 249 | GTGCTATATTGGCCAGCG | 193626159 | 193626177 |
| 250 | AGCTCGTGCTATATTGGC | 193626164 | 193626182 |
| 251 | GGCATAGCTCGTGCTATA | 193626169 | 193626187 |
| 252 | TGTTGGGCATAGCTCGTG | 193626174 | 193626192 |
| 253 | GCTTCTGTTGGGCATAGC | 193626179 | 193626197 |
| 254 | CTTGCGCTTCTGTTGGGC | 193626184 | 193626202 |
| 255 | CACCTTGCGCTTCTGTTG | 193626187 | 193626205 |
| 256 | TCCATCACCTTGCGCTTC | 193626192 | 193626210 |
| 257 | AACCATCCATCACCTTGC | 193626197 | 193626215 |
| 258 | CCTTAAACCATCCATCAC | 193626202 | 193626220 |
| 259 | AGCCCCTTAAACCATCC | 193626207 | 193626225 |
| 260 | TCGGTAGCCCCCTTAAAC | 193626212 | 193626230 |
| 261 | ATGTATCGGTAGCCCCCT | 193626217 | 193626235 |
| 262 | TGTGAATGTATCGGTAGC | 193626222 | 193626240 |
| 263 | ATTAGTGTGAATGTATCG | 193626227 | 193626245 |
| 264 | GGCTGATTAGTGTGAATG | 193626232 | 193626250 |

TABLE 5-continued

Exemplary OPA1 ASO sequences

| SEQ ID NO. | Sequence (5'-3') | Coordinates GRCh38/hg38: chr3 | |
|---|---|---|---|
| | | Oligo Start | Oligo End |
| 265 | GAAATGGCTGATTAGTGT | 193626237 | 193626255 |
| 266 | TGGCAGAAATGGCTGATT | 193626242 | 193626260 |
| 267 | GATCTTGGCAGAAATGGC | 193626247 | 193626265 |
| 268 | GACATGATCTTGGCAGAA | 193626252 | 193626270 |
| 269 | GAGGTGACATGATCTTGG | 193626257 | 193626275 |
| 270 | AGATTGAGGTGACATGAT | 193626262 | 193626280 |
| 271 | TGAACAGATTGAGGTGAC | 193626267 | 193626285 |
| 272 | GTCCATGAACAGATTGAG | 193626272 | 193626290 |
| 273 | TTGGAGTCCATGAACAGA | 193626277 | 193626295 |
| 274 | TGTATTTGGAGTCCATGA | 193626282 | 193626300 |
| 275 | TTTCTTGTATTTGGAGTC | 193626287 | 193626305 |

TABLE 6

Exemplary OPA1 ASO sequences

| SEQ ID NO | Region | Sequence (5'-3') | Coordinates: GRCh38/hg38: chr3 | |
|---|---|---|---|---|
| | | | Oligo Start | Oligo End |
| 215 | OPA1-IVS6-86 | GCTAGGGAGGGATGGTTA | 193625988 | 193626006 |
| 216 | OPA1-IVS6-81 | TGTAAGCTAGGGAGGGAT | 193625993 | 193626011 |
| 217 | OPA1-IVS6-76 | ACAGATGTAAGCTAGGGA | 193625998 | 193626016 |
| 218 | OPA1-IVS6-71 | AAGGAACAGATGTAAGCT | 193626003 | 193626021 |
| 227 | OPA1-IVS6-26 | AGAGGAAATTGGGGAGGA | 193626048 | 193626066 |
| 228 | OPA1-IVS6-21 | GGAGAAGAGGAAATTGGG | 193626053 | 193626071 |
| 229 | OPA1-IVS6-16 | AATGAGGAGAAGAGGAAA | 193626058 | 193626076 |
| 230 | OPA1-IVS6-11 | TTCACAATGAGGAGAAGA | 193626063 | 193626081 |
| 231 | OPA1-IVS6-6 | ACGAGTTCACAATGAGGA | 193626068 | 193626086 |
| 232 | OPA1-IVS6-1 | CTGCCACGAGTTCACAAT | 193626073 | 193626091 |
| 233 | OPA1-IVS6-EX7 + 5 | AGACCCTGCCACGAGTTC | 193626078 | 193626096 |
| 234 | OPA1-IVS6-EX7 + 10 | CAAGCAGACCCTGCCACG | 193626083 | 193626101 |
| 235 | OPA1-IVS6-EX7 + 15 | CTCACCAAGCAGACCCTG | 193626088 | 193626106 |
| 236 | OPA1-EX7 + 1 | GAGCTCACCAAGCAGACC | 193626091 | 193626109 |
| 237 | OPA1-EX7 + 6 | AGAATGAGCTCACCAAGC | 193626096 | 193626114 |
| 238 | OPA1-EX7 + 11 | GTAAGAGAATGAGCTCAC | 193626101 | 193626119 |
| 239 | OPA1-EX7 + 16 | TTGTTGTAAGAGAATGAG | 193626106 | 193626124 |
| 240 | OPA1-EX7 + 21 | ATTTGTTGTTGTAAGAGA | 193626111 | 193626129 |
| 241 | OPA1-EX7 + 26 | CTTGAATTTGTTGTTGTA | 193626116 | 193626134 |

TABLE 6-continued

Exemplary OPA1 ASO sequences

| SEQ ID NO | Region | Sequence (5'-3') | Coordinates: GRCh38/hg38: chr3 | |
|---|---|---|---|---|
| | | | Oligo Start | Oligo End |
| 242 | OPA1-EX7 + 31 | ATGCTCTTGAATTTGTTG | 193626121 | 193626139 |
| 250 | OPA1-EX7 − 21 | AGCTCGTGCTATATTGGC | 193626164 | 193626182 |
| 267 | OPA1-IVS7 + 46 | GATCTTGGCAGAAATGGC | 193626247 | 193626265 |

TABLE 7

Exemplary OPA1 ASO sequences

| SEQ ID NO | Region | Sequence (5'-3') | Coordinates: GRCh38/hg38: chr3 | |
|---|---|---|---|---|
| | | | Oligo Start | Oligo End |
| 280 | OPA1-EX7 + 27 | TCTTGAATTTGTTGTTGT | 193626117 | 193626135 |
| 281 | OPA1-EX7 + 28 | CTCTTGAATTTGTTGTTG | 193626118 | 193626136 |
| 282 | OPA1-EX7 + 29 | GCTCTTGAATTTGTTGTT | 193626119 | 193626137 |
| 283 | OPA1-EX7 + 30 | TGCTCTTGAATTTGTTGT | 193626120 | 193626138 |
| 284 | OPA1-EX7 + 32 | CATGCTCTTGAATTTGTT | 193626122 | 193626140 |
| 285 | OPA1-EX7 + 33 | TCATGCTCTTGAATTTGT | 193626123 | 193626141 |
| 286 | OPA1-EX7 + 34 | TTCATGCTCTTGAATTTG | 193626124 | 193626142 |
| 287 | OPA1-EX7 + 35 | CTTCATGCTCTTGAATTT | 193626125 | 193626143 |
| 288 | OPA1-EX7 + 26 | TGAATTTGTTGTTGTA | 193626116 | 193626132 |
| 289 | OPA1-EX7 + 27 | TTGAATTTGTTGTTGT | 193626117 | 193626133 |
| 290 | OPA1-EX7 + 28 | CTTGAATTTGTTGTTG | 193626118 | 193626134 |
| 291 | OPA1-EX7 + 29 | TCTTGAATTTGTTGTT | 193626119 | 193626135 |
| 292 | OPA1-EX7 + 30 | CTCTTGAATTTGTTGT | 193626120 | 193626136 |
| 293 | OPA1-EX7 + 31 | GCTCTTGAATTTGTTG | 193626121 | 193626137 |
| 294 | OPA1-EX7 + 32 | TGCTCTTGAATTTGTT | 193626122 | 193626138 |
| 295 | OPA1-EX7 + 33 | ATGCTCTTGAATTTGT | 193626123 | 193626139 |
| 296 | OPA1-EX7 + 34 | CATGCTCTTGAATTTG | 193626124 | 193626140 |
| 297 | OPA1-EX7 + 35 | TCATGCTCTTGAATTT | 193626125 | 193626141 |
| 298 | OPA1-EX7 + 36 | TTCATGCTCTTGAATT | 193626126 | 193626142 |
| 299 | OPA1-EX7 + 37 | CTTCATGCTCTTGAAT | 193626127 | 193626143 |

Example 19: ASO-14 Mediates ATP Upregulation in OPA1 Haploinsufficient HEK293 Cell Line The ATP levels generated through mitochondrial oxidative phosphorylation and glycolytic pathway were measured in HEK293 cell lysates using a commercially available kit (Cat #ab83355, Abcam; USA) according to the manufacturer's instructions. Briefly, about $3 \times 10^5$ OPA1+/+(wildtype) and OPA1+/— HEK293 cells were plated in a T-25 flask and treated with 10 µM ASO-14. For the ATP test, 96-hrs after treatment, cells were harvested, and two aliquots of cell suspension were prepared. One aliquot was processed for deproteinizing using commercially available kit (Cat #ab204708, Abcam; USA) to remove residual protein for executing ATP fluorescence assay to measure total ATP level. The second aliquot was used for BCA assay (Cat #23225, Thermo Fisher; USA) to measure total protein level. ATP level was then calculated by normalizing the measured total ATP level to the measured total protein level.

Figure 24B:
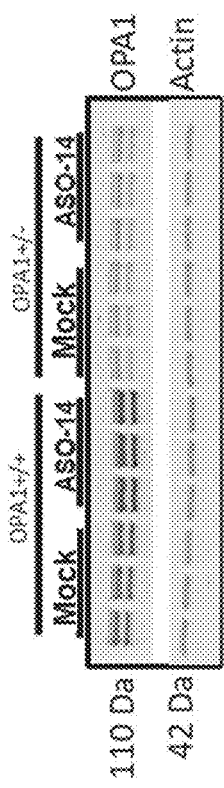
FIGS. 24B-24C demonstrate the OPA1 protein was increased by ASO-14 in OPA1+/+HEK293 cells.
Figure 24C:
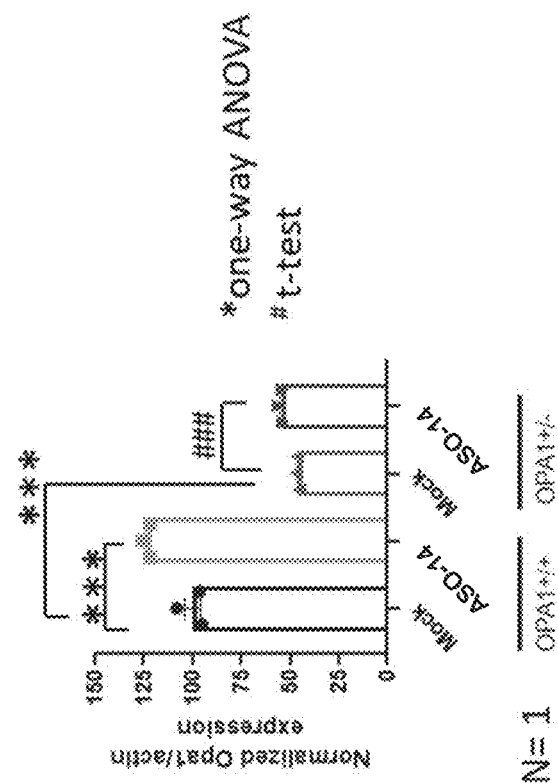
Figure 24A:
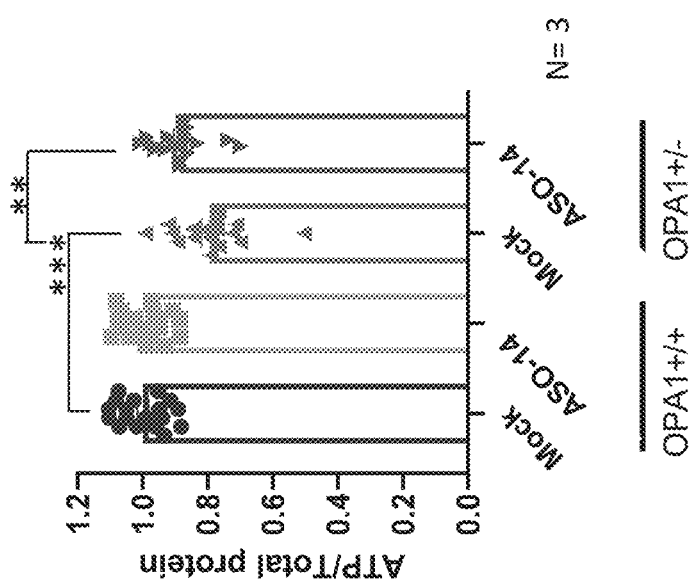
FIG. 24A is a histogram that demonstrates ATP level was reduced in mock-treated OPA1+/−HEK293 cells as compared to OPA1+/+HEK293 cells, and ASO-14 treatment of OPA1+/−HEK293 cells increased the ATP level in the cells.

FIG. 24A summarizes the ATP level measured under each condition. In the mock group, untreated OPA1+/−HEK293 cells were found to have 0.79±0.02 ATP level as compared to untreated OPA1+/+HEK293 cells. There was about 20%

ATP deficit in OPA1+/−HEK293 cells. In comparison, OPA1+/−HEK293 cells treated with ASO-14 had ATP levels 0.88±0.01, significantly higher than the mock-treated OPA1+/−HEK293 cells, suggesting that treatment of ASO-14 reduced the deficit by about 50%. Data were collected from three independent experiments. (Statistics: Ordinary one-way ANOVA; *P<0.0001; P<0.0080).

FIGS. 24B-24C demonstrate the OPA1 protein under each condition. 96 hours after treatment with ASO-14 or no treatment (mock), cells were lysed with RIPA buffer and immunoblot blot was probed with antibodies targeting OPA1 and β-actin. The data show that treatment of ASO-14 unregulated about 18% OPA1 protein in OPA1+/− cells. FIG. 24B shows the immunoblot gel images. Multiple bands on the immunoblot image represent various isoforms of OPA1 FIG. 24C summarizes quantification of the immunoblot results. Untreated (mock) OPA1+/−HEK293 cells were found to have 46±0.5% OPA1 protein level as compared to untreated (mock) OPA1+/+HEK293 cells. OPA1+/+ cells treated with ASO-14 had OPA1 levels 123.2±1.3 of untreated OPA1+/+ cells. OPA1+/− cells treated with ASO-14 had OPA1 levels 54.54±0.6% of untreated OPA1+/+ cells. Statistics performed with corresponding mock. *** P<0.0001, by Ordinary one-Way ANOVA and ####P<0.0001, by Welch's t test. Data represent average of three technical replicates.

Example 20: Exemplary Antisense Oligomers Restore OPA1 Expression in Cells with OPA1 Mutations from Diagnosed Patients This example examines OPA1 mRNA and protein levels in cells with mutations in OPA1 gene from patients diagnosed with Autosomal dominant optic atrophy (ADOA), as well as effects of exemplary antisense oligomer ASO-14 on OPA1 mRNA and protein levels, and mitochondrial bioenergetics in the patient cells.

FIGS. 25A-25C summarize mRNA and protein expression of OPA1 gene in fibroblast cells from diagnosed patients that have haploinsufficient mutation in OPA1 gene: F34 (OPA1 canonical splice mutation at c.1608+1delGT-GAGG); F35 (OPA1 frameshift mutation at c.2873_2876del); F36 (OPA1 frameshift mutation at c.635_636delAA). mRNA expression level of OPA1 gene in patient cells is about 50% to 60% of the mRNA level in wildtype (WT) cells (FIG. 25A); OPA1 protein level in patient cells is about 30% to about 40% of the protein level in WT cells (FIG. 25B). Histograms in FIGS. 25A-25B show mean±SEM of 3 independent experiments; one-way ANOVA compared to WT group (**P<0.0001). FIG. 25C** shows a representative immunoblot image of OPA protein expression level in diseased fibroblast cells.

Figure 26D:
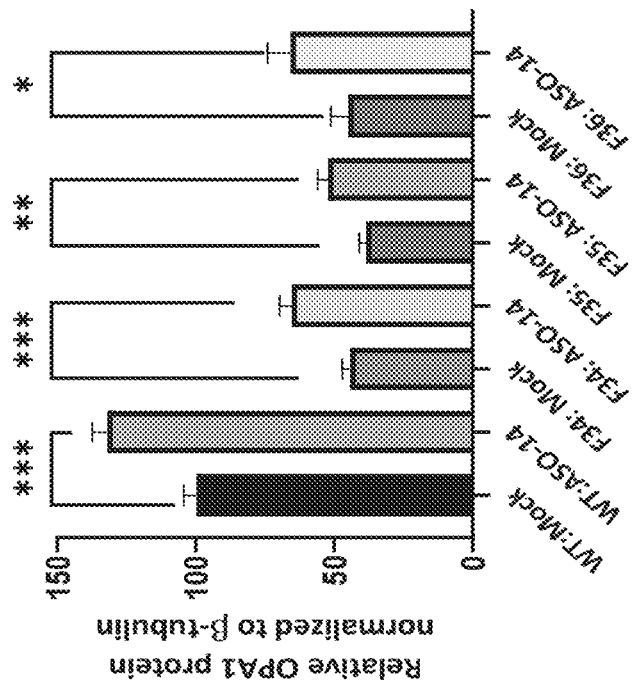

FIGS. 26A-26D demonstrate the effects of exemplary antisense oligomer, ASO-14, on OPA1 NMD exon inclusion, mRNA level, and protein level in wildtype (WT) fibroblast cells and fibroblast cells from diagnosed patients that have haploinsufficient mutation in OPA1 gene. The fibroblast cells were transfected with ASO-14 (40 nM), and RNA was isolated 24 hrs after transfection and analyzed. For non-productive OPA1 mRNA measurement, cells were treated with cycloheximide (50 μg/mL) for 3 hrs. prior to RNA isolation. Immunoblot was performed 72 hrs. post transfection with antibodies targeting OPA1 and β-tubulin. As shown in FIG. 26A, ASO-14 significantly decreased inclusion of NMD exon (exon 7x), measured by level of non-productive OPA1 mRNA, in WT cells and all diseased cells to lower than 20% level of the normalized level in WT cells. There was a trend of increase in total OPA1 mRNA level in all types of cells by the treatment of ASO-14 (FIG. 26B). Histograms in FIGS. 26A-26B show mean±SEM of 2-3 independent experiments; one-way ANOVA vs. Mock for respective cell line (*P<0.05; *P<0.001; P<0.0001). Correspondingly, OPA1 protein level was significantly increased by the treatment of ASO-14 in all types of cells (FIGS. 26C-26D). FIG. 26C shows representative immunoblot images of OPA1 protein and loading control β-Tubulin under all types of conditions; FIG. 26D** shows the statistical summary of the OPA1 protein levels, the histograms show mean±SEM of 3 independent experiments; unpaired t-test vs. Mock for respective cell line (*P<0.05,  P<0.01, *<0.001).

FIGS. 27A-27E demonstrate that patient fibroblast cells (cell lines F35 and F36) show deficiencies in mitochondrial bioenergetics. FIG. 27A shows representative time courses of the oxygen consumption rate of WT cells, F35 cells, and F36 cells at baseline level and when challenged sequentially with oligomycin, FCCP, rotenone and antimycin A. Patient fibroblast cells, F35 and F36 cells, were found to have reduced basal oxygen consumption rate (FIG. 27B), ATP linked respiration (FIG. 27C), maximal respiration (FIG. 27D), and spare respiratory capacity (FIG. 27E), as compared to WT fibroblast cells. Units in FIGS. 27B-27E are pmol/min/cells, data normalized to wild-type (WT). Histograms in FIGS. 27B-27E show mean±SEM of >18 individual measurements from 2 independent experiments; one-way ANOVA vs. WT ( P<0.01; ** P<0.0001).

Figure 28B:
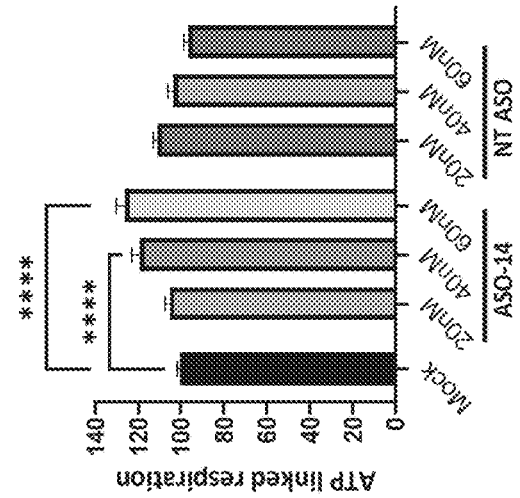
Figure 28D:
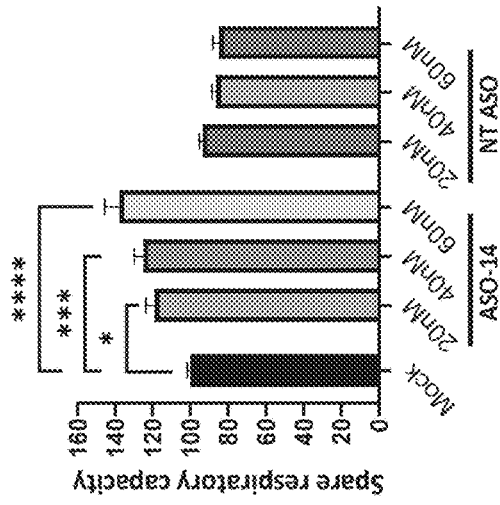
Figure 28A:
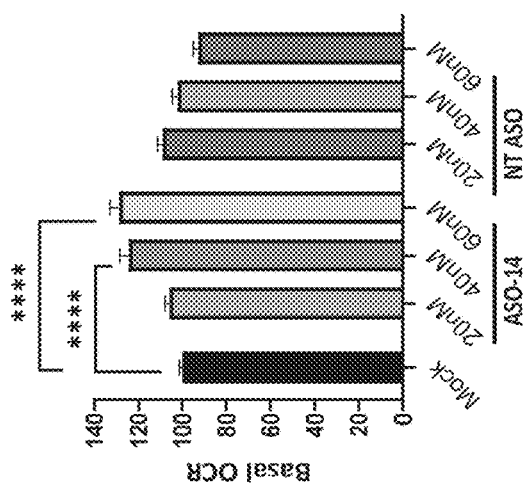
Figure 28C:
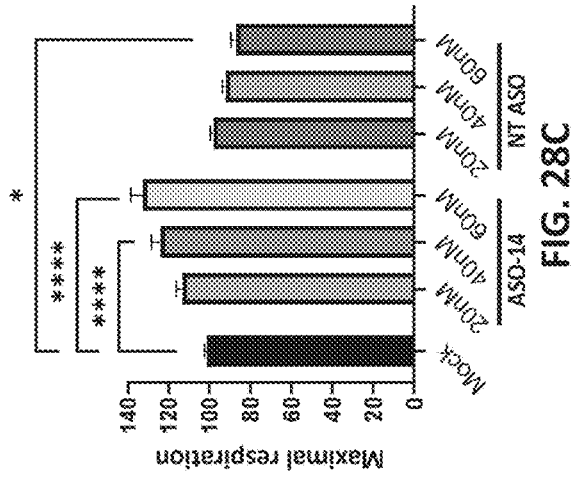
Figure 29A:
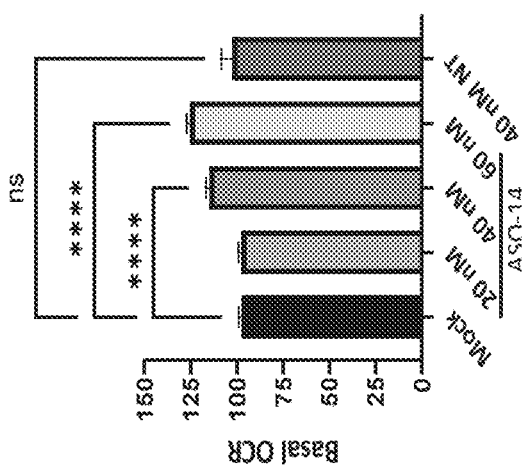
Figure 29B:
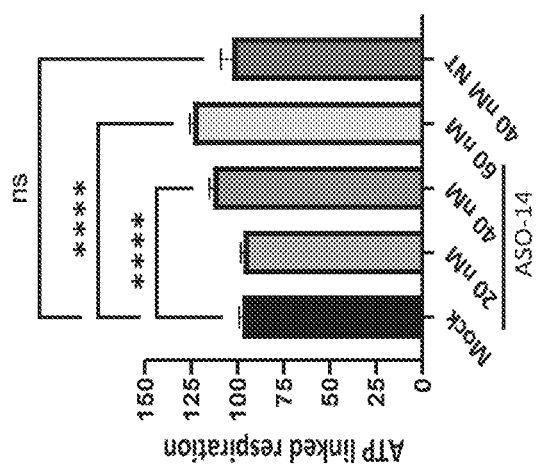
Figure 29C:
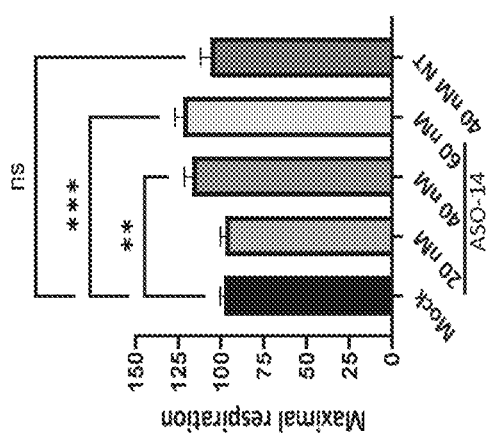
Figure 29D:
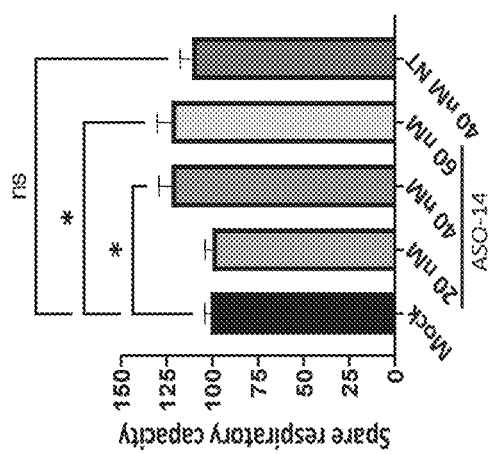

FIGS. 28A-28D demonstrate that ASO-14 increased mitochondrial energetics in F35 patient cell line. As shown in the figures, treatment with 40 nM or 60 nM ASO-14 increased basal oxygen consumption rate (FIG. 28A), ATP linked respiration (FIG. 28B), maximal respiration (FIG. 28C), and spare respiratory capacity (FIG. 28D) of F35 patient cells in a dose-dependent manner. Treatment with 20 nM ASO-14 also significantly increased spare respiratory capacity (FIG. 28D). In contrast, non-targeting ASO (NT ASO, targeting an unrelated gene) did not significantly alter the parameters at any of the tested concentrations. Units in the figures are pmol/min/cells; the Oxygen Consumption Rates (OCR) are normalized to total cell count and plotted to Mock (No ASO). The histograms show mean±SEM of >20 individual measurements from at least 3 independent experiments; one-way ANOVA vs. Mock (*P<0.05; *P<0.001; **P<0.0001).

FIGS. 29A-29D demonstrate that ASO-14 increased mitochondrial energetics in F36 patient cell line. As shown in the figures, ASO-14 also increased basal oxygen consumption rate (FIG. 29A), ATP linked respiration (FIG. 29B), maximal respiration (FIG. 29C), and spare respiratory capacity (FIG. 29D) of F36 patient cells in a dose-dependent manner from 20 nM, 40 nM, to 60 nM. In contrast, non-targeting ASO did not significantly alter the parameters at 40 nM. Units in the figures are pmol/min/cells; the Oxygen Consumption Rates (OCR) are normalized to total cell count and plotted to Mock (No ASO). The histograms show mean±SEM of >20 individual measurements from 2-5 independent experiments; one-way ANOVA vs. Mock (*P<0.05;  P<0.01; *P<0.001 **** P<0.0001).

The experiments in F35 and F36 cells suggest that the dose-dependent improvement in mitochondrial bioenergetics by ASO-14 is mutation-independent.

The foregoing preclinical data support the TANGO disease modifying approach in ADOA. As demonstrated by the data, the exemplary antisense oligomer, ASO-14, reduced non-productive exon inclusion, increased total OPA1 mRNA and protein expression in all three patient fibroblast cell lines; increased ASO-14 dose increased mitochondrial respiration in two fibroblast cell lines. The data further suggest that the ASO mediated increase in OPA1 protein expression is disease modifying in ADOA in a mutation-independent manner.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the present disclosure may be employed in practicing the present disclosure. It is intended that the following claims define the scope of the present disclosure and that methods and structures within the scope of these claims and their equivalents be covered thereby.

The invention claimed is:

1. A pharmaceutical composition comprising:
(a) a pharmaceutically acceptable excipient; and
(b) a therapeutic agent, wherein the therapeutic agent comprises an antisense oligomer that comprises the sequence set forth in any one of SEQ ID NO: 36, 92-96, or 166-168, and wherein the antisense oligomer comprises a 2'-O-methoxyethyl moiety.

2. The pharmaceutical composition of claim 1, wherein the antisense oligomer comprises a backbone modification.

3. The pharmaceutical composition of claim 2, wherein the backbone modification comprises a phosphorothioate linkage or a phosphorodiamidate linkage.

4. The pharmaceutical composition of claim 2, wherein the antisense oligomer comprises a phosphorothioate linkage.

5. The pharmaceutical composition of claim 1, wherein each nucleotide of the antisense oligomer comprises a 2'-O-methoxyethyl moiety.

6. The pharmaceutical composition of claim 1, wherein the antisense oligomer consists of from 18 to 50 nucleotides.

7. The pharmaceutical composition of claim 1, wherein the antisense oligomer consists of from 18 to 20 nucleotides.

8. The pharmaceutical composition of claim 1, wherein the antisense oligomer consists of 18 nucleotides.

9. The pharmaceutical composition of claim 1, wherein the therapeutic agent promotes exclusion of a non-sense mediated RNA decay-inducing exon (NMD exon), thereby increasing a level of a processed mRNA that is processed from the pre-mRNA, wherein the pre-mRNA is transcribed from an OPA1 gene and comprises the NMD.

10. The pharmaceutical composition of claim 1, wherein the antisense oligomer comprises the sequence of SEQ ID NO: 36.

11. The pharmaceutical composition of claim 1, further comprising a gene editing molecule or a polynucleotide encoding the gene editing molecule.

12. The pharmaceutical composition of claim 11, wherein the gene editing molecule comprises CRISPR-Cas9.

13. The pharmaceutical composition of claim 1, wherein the pharmaceutical composition is formulated for intravitreal injection.

14. The pharmaceutical composition of claim 1, wherein the antisense oligomer comprises the sequence of SEQ ID NO: 92.

15. The pharmaceutical composition of claim 1, wherein the antisense oligomer comprises the sequence of SEQ ID NO: 93.

16. The pharmaceutical composition of claim 1, wherein the antisense oligomer comprises the sequence of SEQ ID NO: 94.

17. The pharmaceutical composition of claim 1, wherein the antisense oligomer comprises the sequence of SEQ ID NO: 95.

18. The pharmaceutical composition of claim 1, wherein the antisense oligomer comprises the sequence of SEQ ID NO: 96.

19. The pharmaceutical composition of claim 1, wherein the antisense oligomer comprises the sequence of SEQ ID NO: 166.

20. The pharmaceutical composition of claim 1, wherein the antisense oligomer comprises the sequence of SEQ ID NO: 167.

21. The pharmaceutical composition of claim 1, wherein the antisense oligomer comprises the sequence of SEQ ID NO: 168.

* * * * *

SEQUENCE LISTING

```
Sequence total quantity: 607
SEQ ID NO: 1            moltype = DNA  length = 111668
FEATURE                 Location/Qualifiers
source                  1..111668
                        mol_type = genomic DNA
                        organism = Homo sapiens
SEQUENCE: 1
ataaacaaac attataaaat aatgtggatt taatcattaa caaacaattt caagttcttg    60
cacagtttca caaaggttaa tgtgacccaa agcttcacct ttataaagac aactctcgaa   120
tctgtattgc aagccccatc tccctgtgga actccaaagc ttgatttcta actgccacct   180
gaataaccca ttcacacttc agcaccaatc atcattccaa agccagcatt atcatccct   240
tgtaatcagc ttttctatat ttgtgactgt tactaataat gtcaattgac tttggcttca   300
accccattat cttttgattc ctcttcctag tttcttcatt tagcttttca ttgttttaaa   360
tactccgaag tatcctttca aagaatctct cacttcttcc cattaccagg ctttggttaa   420
gggccctcac acttgacttt ctcaacagcc ccctatccag tcttcctgac cctcagtttc   480
cctctttaca aattcatcct tttctgtttc tccaggatta tctttttga gcccacttta   540
tgacactata gtctgcctct gtgggtagta actgttgcta cccattactt ggtcctcagc   600
ttgtactacc tcacattaat gtttacctt tatgtatgtc tgtcttccta accaaaccat   660
ggttagttga gggtgggaac tgtggtttac tctttttaaa aaaatatatc ctcaggcctg   720
gcacggtggc tgatgcctgt aatcctagca ctttggaagg ttgaggcagg cagattactt   780
gaggtcagga gtttgaaacc agcctggcca aaatggtgaa accccgtctc tactaaaata   840
caaaaactta gccaggcatg gtggcatgca cctgtaatcc cagctactca ggagactgag   900
gcaggagaat cacttaaacc tgggaggtgg aggttacagt gagccgagat tgtgccactg   960
cgctccagcc tgggcgacaa agtgagactc tgtctcaaaa caaacaaaca aacaaacaaa  1020
aaccaaatat atatatatgt gtgtgtgtgt gtgtatataa tttgtgtgtg tatatatatg  1080
tatttatatc ctcgactagg gttcatagga agtgactgta aatgtttgtt aataaggatt  1140
ataacatgct tttctgaggg ctggggagag tttgataatg atgatggtgc aaacatgtat  1200
gacttcagct aattattggc ttctccagga aaccacaaag agtagtgtta aggaacttgg  1260
agatctccca agaagaactt tgcaaaagct tttatgtata aatttaaata taaaacttat  1320
gaaatcaatt ttaaacattt ccatttccat taacatctct cattaccttc ctttctgaaa  1380
atttctgatt cgttggataa ttctgaaaag ggtcccttt cctgctaagg taaatattta   1440
gagttttacc tggtgaattg ctcaattccc agctgaactg gaaaatttag tttaaagtag  1500
taaaattatt tcatgacttc tggatcagaa aaatattttt aacatgtttt tacaagtaat  1560
taatacacaa gttcagagta taaagggtt tacaataaat gtaagcctcc ctcccactca   1620
tgacccacta acttcaagtc cttccttgac tctgcccttc actagggctt atcaactcaa  1680
atattttcgt gggttaggca tgtaacataa atgagtaatg caagtatgtc tgttgtataa  1740
tgtcatatta aattgtattc atataattta ttcatataat tttacttgcc tacttgcata  1800
cttgtgttct tttgccaaaa aaaaaaaaaa aaaaagctct ttctcattgt tttggaaatg  1860
gctgaccctc tcagtccttc attttctctc acttttcata ttgtaatcat ccagcaggtt  1920
cttcctgctc actgcacaga caaaatcatt tcactgagac cagggcatcg cagtagaaaa  1980
agagtttaac tgattcaaga ccagcctatg caggagaact ggagttgtca ctcaaatcaa  2040
tcttcctgaa ggctctgagg ttagaggttt ttatggacaa tttagtgggc aaggggtagg  2100
gaatggatgc tgctgattgg ttggggatga aataatagga aaacattcct tgtgtgctga  2160
gtccacctct gggcggggcc acaggatcac ttgagtcatg agtcataagt ctcgatgggg  2220
tgagtctgaa atataccgca aaaagcagt cttagattct atagtaatga tgttatctat   2280
aggagcaatt ggggaagtca taagatttgt gagttctggc cacattgatt cctgagcagt  2340
aagggactat agaaaccata cctacgtctt agcacagttc aggcccctct catgatcctg  2400
ttctcttggc ctttcttaca aaggtggttt ttggttcctg agcaacgagg gagttagctt  2460
taggaaggga ctattataat cctttctttc aagttaaact ataaactaca ttcctcccca  2520
aagttcattt ggcttaagtc caggaatgag caaggacagc ttgaggtca gaagcaagat   2580
ggagtcaact atgtcaggtt cctcttgtca taattttgcc aaggcagttt caatataagt  2640
agtggttgtt tttcctctta attttacta agaaaagtag aagcacaagc ttcatgataa   2700
acagtaattg atgtgttcaa tttcagaaag atgaaggagt gtgaactacc ggagaggaca  2760
tgagtgcctg aaggataaaa ctactacttg gctcctggtt ccgagacatt ttttgtatat  2820
aagaattgaa ggttgatgtt gttaggcatc ctgatatttt tatgtgattt tttaaaatgt  2880
gaaatttgtt gatttttatt tggcaacaaa tgtagcattt ttttgcttgt ttgttttga   2940
gacggagtct cgatctgtcg ctcaggctgg agtgcagtgg cacaatctca gctcactgca  3000
acctctgcct cctgggttca agcaatttt ctgcctcagc ctccgagtag ctggctaatt   3060
tttttatttt tagtagagac agggtttcac catattggcc aggctggtct caaactcctg  3120
acctcgtgat ctgccttcct cggcctccca aagtgctggg attacaggca taagccgcca  3180
tgcccagccc aaatgtagtg ttatttttaa aacactgcat aggccaactac tgtctaaacc  3240
aaacaaaaca ggtctgtggg ctgaatttgg tccaatggtt gcagtttatt atacaacagt  3300
ttgcccttt tcatggcaa cactatgtat ctatgggaga tcattcctta tcaggacata   3360
cagacctaaa gcataggttt tcatggctag tacggatgta atttatgtgt ctagttccta  3420
tacatggaca tttatactga ttccaatctt ttcccatttc atacagtgca gaaataaaca  3480
tcatcatgca tacatctttg catacatggg aatgattcca caggataaat gcctagaagt  3540
```

-continued

```
agaactgcaa aacaagggct tcataaaaca tatgataacc atatataaat ggtgatggtg    3600
gttagtttct cctttttta tggttaaagt cttttatccc taattttct tttttgttgt    3660
tgttgttaaa gtctcttggt ttctcttatt ttattttcta aaataacaag gaagtaacga    3720
ttacaaagac acttttgta caaccctaca atcccaggaa gatctacagt ttgcacaggt    3780
tggtacagca aattgctctc tggacctgcc attgaaacag tcaccacaat aaataaagaa    3840
aattctaaga gtcctgcatt tgggaagttt actatcaatg gctaggtcta ctccttggtg    3900
tattgtgagt gcatgggtcc agactatga ttctgacaat taaggaaaa ggaattgtct    3960
ttatgctctg tgtatttgtg tatgtgtgtg gcatgggtgg ggggcgggta gtggggagga    4020
ggtgaaaggt ccctgaagta aagaggatgc acaggaccct tttattttag tccctaaaaa    4080
ttggcttcat aaccgttcac aggccacatc cctttacgg gccctggttt ccttacaaaa    4140
cataaaaggt ttgtgttgga aggggaaagg agtatttaaa gtgatggagg agaggagctc    4200
aagatggctg agatctggc ctgtccaaca ttgagaaatt tgggagggga gccatcaaag    4260
aagcctggga gcagcagttc cagggaaaaa ggagaatgtg atggccagag agccaaaaga    4320
aaaagtagtt gaaggagtgc tcagcactag gcatctgaac tgaatgctgt ggcaggctca    4380
ctggccacaa acaataggga gctggtggag gccttgacga ggaccatttc aacaaactgg    4440
tgggcttaaa atccggaaga aacagttgaa caaatcattt tgacgccttt tataaaccac    4500
acaagcttat tccaaacccg ttactggcct aactgattta agtccctttc ccatctgatc    4560
ctcagagatt ctaagggact tagcctatcc atgactcttc gtcctgcttc tcacctccca    4620
tgattgccct aacgatgtga aagtgctttc aaacaaagat gcccaagaaa gaagtaggc    4680
aaatgtgcaa gcattagttt gtagtacgct attactgtat ttcaccttgc actctctagt    4740
ttccttcgtg ctccctcaat atccaactct taataaattc atggctcccg gtgagcattc    4800
atcaattctc attccacgcc tttagcccctt cccgttcccg cccaactctc gctccctccc    4860
ctggccaaat ctctaacctg caaggctaat tccgaattcc aaatcggaag caagagggcg    4920
gggccccgtg agaggcgatg gattgctcca gtccgttccc gacgcactgt gcgcatgcgc    4980
tggtcctccg cggaccgttc gtgctgcccg cctagaaagg gtgaagtggt tgtttccgtg    5040
acggactgag tacgggtgcc tgtcaggctc ttgcggaagt ccatgcgcca ttgggaggc    5100
ctcggccgcg gctctgtgcc cttgctgctg agggccactt cctggtcat tcctggaccg    5160
ggagccgggc tggggctcac acgggggctc ccgcgtggcc gtctcggcgc ctgcgtgacc    5220
tccccgccgg cgggatgtgg cgactacgtc gggccgctgt ggcctggtaa gtgcaggctc    5280
taatctggcc ccgttaattc tggggcctct tgagagtggg gctgtcttat ctctatctcc    5340
aaaaatgtgc aggtgactct caggccaggc cgacggcagt tggagaattc ccagatgttc    5400
ttgaggaccc agaatgacag gagccctggc tgggcttacg ttcggagccg gcttcaatac    5460
tggcccttt ctctggccct acccaacccg aaaattctgg acgcctctca atcttggccc    5520
gtctctattg tccttttgtc tctgcccttt acacccttgt gtcttcagtg ttctgtctgt    5580
tctctggttgc ctctttttgcc ttttttctgt cctctccctg ccaggtttgg ctctgtccat    5640
gagtcacctc tctccacatt tctcctaact ctcggtgtct tctttttctt ccatttccac    5700
gccatgtgta cattgcatct tcaggtacct gggctcttct atcggggaaa ggggcgtccg    5760
tctctttccc tagcccgctg atagaagtca gaactagagc aatgacgcac acggtgtcag    5820
agacggtgat tcgagatgcc ctttcaatag cagctttttt ctgtgtttcg ggagggagac    5880
ttactttttg atgcaaggtc gtgaacgtgg caccacctt ctaatctcaa tcattgttgc    5940
cctggggtgg tttaattcta aatagaaaat catagaaatc ttttcatttc tgtgcgttac    6000
tatatgcatt gtaatgagat taaattggat tttataggaa attttgttct agtatcatta    6060
gataccttca agcttagctc attgttgcag gcatttgata ggaagtaaga tgcatcaagc    6120
aaaattggaa aaacgtggtt ttcctgaatt aacttctaag cagttgtttt gaatttttc    6180
cagacctttt taagtggtat agataattta tcgtgtttat aaggaatgga atgcattcgt    6240
tagtttgttt ttgttttgtt ttgagacgga gtcttgctct gtcgtccagg ctggagtgca    6300
gtagcgctat ctcggctcac tgcaacctcc gcctcccagg ttcaagcaat tctcctgtct    6360
ccgcctccgg agtagctgga attacaggca cgcgccagca cgcctagcta attttgtat    6420
ttttagtaga gagggggttt caccattttg gccaggctgg tctcgaactc ctgacctcat    6480
gtgatccacc ctcctcgact tcccaaagtg ctgggattac aaccgtgagc caccgcgccc    6540
ggcccaattt gtttttatata ggttaactgg agtccaaaat acagaactag atgagataat    6600
aatagttaac agtgttagtc agttagaatt attgcatagg tatttttaat ctcatggaat    6660
tttagtcttt gagtaagttc acagcccttg gtattaaagt aagttattta caaccccttgc    6720
atttctactt ctcaatattt agtgaggaaa catatctgat tttctttaaa taaaagaga    6780
aaagactgca gaagatagca ttctctgttg gagcaattaa gatgtataag aagaactaca    6840
aagacggagt tttaaaacaa actgatttat aagtggtatt tatttaattg gctgtcattg    6900
ggctaaatta tttctaaagt taccatggat gccattgagt catggcttaa aaatgtctcc    6960
tggtgatggc acagtttagc tacctaaaga agtagagatg tgggaagcca gaagccccaa    7020
gctctgcagt tttctttttg ctatagttcc tttgcatgtt gtgaaagaat acagttaaat    7080
tcctgctccc taacagatga gagcataagc atttcttttgg gcatacatat gtaaatacat    7140
gctcatggac atgtgaaaag atcaatacta acatttgggt gcaataaata attgtgtaaa    7200
attattttta aaagaattac atattaggaa atgatatatt gattaaaagt gatagtcaat    7260
gaacaagaga gtagatttct gggggaaacc tattttgcat catacttgat ttttagtttt    7320
gactgaatat tgaagtctat attcaaaatt cttttccttt agaactgtaa aggcattgct    7380
gcatttcttt ctaatgtaat tgtttattgc tgctgagaat tcttatgaca atctgatttt    7440
ttcatcttca tgattatctt gttttttcct tcatggaatc tgttagggtc ttgactttat    7500
cctttatcct aaatttctca aggcttggac caggtgtggg tttggttttg ttttcttttg    7560
ctactcattt gacttggcac actcagtggg cctttccctt tatctttctt cattctgag    7620
acgttttttct ctcttatttt ttattatctt cctttcattt ttcctgtcct ttttcttttt    7680
agacatctct taggaggata gtggtcctct tagattgata tgttatgtcc gtgatttcca    7740
aagtaagatt tgtactcgtc gtctgttaaa aggaaaagca tacatatacc ctatgtatat    7800
atgcacactt ttttattttt aaattatata tgtatctgta ctaattattt acattgtaag    7860
tcaaccctaa cataatctta aaggataaga tacaaaacat actgcatcta gaagcttcag    7920
tacttttctc ctgaatccca gtagatcctt ttgttcatcc cacgggatgc attccgaccc    7980
catcctccca ctccctttgg ataccacatt accacagctc tgcatcactt aacttttcct    8040
ttatgttttt caccttttt ttttttttt tttttgcattt tatgtcctgg ggaatttcct    8100
taattcattt catggtttta ctgttgatt tttttaatatt ggccatcgca acttttcttt    8160
tctttccctt tcctttcctt tcctttcctt tcctttct ttcttttctt ttcttttctt    8220
aattttcttt tctttctct tctttctgt tctttctt tctttctt tcttttctt    8280
```

```
cacacaggat cttggcgtgt tgtccaggct ggcctcgaac tcctgggctc aggtaatcct    8340
ctcaccttgg cctcccaaaa tgccaggatt acaggcgtgc gccactgcat ttggcggcaa    8400
cttaatttt ttatttttat ttttccttt agaggacacc tagcactgag cattgcaact     8460
tttcatttcc atgaacttt aagaaaactc ttaaagacat gtttaattct gtacactttc    8520
tattgttctt tgattgctgt ttttgaataa caacaaggag tacgccttag cattttgatg    8580
gtatcctctt aatagtcgca ataatagtcc ccttggcgct ctgtatactc tcaagtctta    8640
aatgttttgt atgcagctgt acgttgacag ttgaatggtc tcgctccaag tggatcagca    8700
agaacataaa gaatcattta actggtacag gctgcggctt gtgaattccc tattaacacc    8760
aaagaagacg tgtgagactc cgtactgaaa ctaaagacga cttgtgagtt ccacactgag    8820
atcaaataag tctttatgat ggtgacagag agtggtgtca acgcctaaag ttttggttaa    8880
tctctctaaa ttgaggggct gaccaaaagg gggaacttaa ctgtattaga cataattttg    8940
agaaacatgg gtatgtggat ggtaatgagg gaaatgggtg tagatgagat tgcctaggga    9000
gagtgagaag taggttaggt ctaagccttg atgagttccc aacatttcca agggtagttg    9060
aggatactga aaatgagtgg ccagtgagat agaggtaaag ctagagactg cccaggggag    9120
aggaattttc aacaatgagg aggtgtcaac attgtcaggt attgctgaga ggtcagataa    9180
aaccagaatt gagcaaaatg gccattggaa gcctatggtg ccctccgtaa gagctgtttc    9240
gctgaagtga tagaaacgga aatcaggctg ggcacagtgg ctcactcctg taatcccagc    9300
actttgggag gccgaggtgg gcggatcacc tgaggttagg agttcgagac cagcctggcc    9360
aacatggtga aaccctgtct ctactaaaaa tacaaaaagt agccaggtgt ggtggcaggt    9420
ccctgtaatc ccagctactc aggaggctga ggcaggagaa tcgcttgagc cccagaggcg    9480
gaggttgcag tgagcagaga tcgagccact gcactccaac ctgggtgaca gagcaagact    9540
ccgtttcaaa aaaaaaaaaa aaaaagaaa tggaaatcag gatggtttgg cttttatttt    9600
aataaaatag ctagagcagg gaatggggt acttttttc cccctttaa gatgagacat    9660
agccaggtgc agtggcttac acctgtaatc ccaacacttt gaaagggagg gtcgcttgag    9720
ctcaggagtt tgagaccagc ctaggcaaca tagcaagacc ttgtctctac taaaattcaa    9780
aaaaaattaa ctgggcatgc tggcacacac ctctagtccc agctatttat gaagctgagg    9840
caggaggatc acacttgagc ccagatacgt ggggctgcag tgagccctga taatgccatt    9900
gcactccacg ttgggcaaca gagcaagact tcgtctcaaa aataaataaa tacccctgtct   9960
caaaaataaa aaataaatat gggaggagag atttgactta gattcctcaa agggcaggag  10020
gaaagagaat tccaaacagt gattcacctt taatgggaaa aagatcgctt aattttacat  10080
gaggaagaag aggattggtg gagatacagt aggtgaacag tttttgtatg aggaagttga  10140
acatgtgtca ttctaatagc ttccattctc tgtgaagtag agggcaaggt catctactga  10200
gagttgggga ggtcaagaga gataagggga gattagaaga gctcttctag cagagagtgg  10260
aagaatgaat tgctaagaga gatgaagtag gattgttaga tagttttgag ggccctgttg  10320
agatgtgctt ccagttgggt gtgattttct ccagtagtgc tttatttccc tgggtacagg  10380
cagagagaaa aacaataagg ctcatgtagg gtttgtattt tgttggacaa gtcaaacaga  10440
aaagtcagag gacgagggag tttagaatgt ttgcaaaaga gttattgaaa cgatgaaccg  10500
cataatctaa ggtggtaagt gggtgaatag ataaggagga tgtgaatagg taaggagaag  10560
aaagaaatat cagattattg attattgatg gcgactctct aatacagtta ttatgccatt  10620
ttaaccgatt aagaaactaa ggctttagaa aattcataat ttgccctaac tgcacagcta  10680
gtaagcagtg gaaatgtgat tggaaccaga gttcttctga ctcaatagac taaatggatg  10740
taaggatgta gttgaaagaa gggtgagcta acgttgtgg aaccatgagc tctttctctg   10800
gttgatatcc ctctctgtaa gtgataacat gggtcacgct ggataaaacc ttgtggtgat  10860
tggtgacttt cctttgtcct tcctcctgtg cctagtctgg cgagtatctg cctttccctt  10920
tccttctca ttgctgccac ctaactttag gctcttcccc ttacatctgg gtaactgaaa   10980
taagatcacc ttttttgttcc ccttctgatt tactttgacc taacattatc tttactattt  11040
tctttaaatt aatgtttcat tagtcttatt ctactcagga atctgtagtt tccccattgc  11100
ctacgaaaaa aagttaagcc tcagcctat attcagtgac tcttcaattg gatattcagt   11160
ccagttttac tcctcctatg agccttctat gccagctcct tgggtctctt gcccttcat    11220
tgtctcagct ctgcaccctt cttctcttt ttattcttt ttttttttg tacttttttg      11280
gtttcttt tggttttctt ttttgtttta tttattaaac ctccatcaca cttcatccta     11340
tggagttttg aaccacagca aggtgcagta tcatcctggg gctctggagg aagtggcagg  11400
gagtccaaaa tgtcaccta gcttcttatc tggggccaca tgtatttctg catctgctgc   11460
ttcccacact cttgcccaca agtgtcgctt gtggaaataa tttgagattt actgtctggc  11520
tgacctagt ttcaatctct tttccaccat ttgctaatca ttctaccttg ggcaaaacat   11580
agaattaaaa gaaaacttca gacaagttaa atttgatgga gtttaattga gcaaagaaaa  11640
aaaatgatcc acaaattggg cagtctccag aatcaccgca gattcagaga gactccaggg  11700
gtgcctcgtg gtcagaacaa atttatagac agaaaaggta aagtgaccta caggaatcag  11760
aattgagaca tagaaacagt gagattggtt acagctcggc gtttgcctta tttgaacgca  11820
gtttgaacac tcagcagtct atgagtggtt gaagtatggc cgctgggatt ggcaacact    11880
cagctgttat tacagatgca tactactaag ttaggttttc gattttgtct gcctatttga  11940
gctaggttac agttcgtcca caaggactca aatataaaag tacggagtcc tcttcgggcc  12000
atatttagtt cgctttaaca attcccccctt ttggtcagcc cctcaattta gagagattga  12060
ccaaaacttt aggcgttgac accactctct gtcaccatca taaagactta tttggtctca  12120
gtgtggaact cacaagtcgt ctttagtttc agtatggagt ctcacacatc ttctttggtt  12180
ttaatagggta attcacaagt tgcaactttg taccagctaa atgattcttt atgttcttgc  12240
tgatccagtt ggagtaagac cattcaactg tcaatgtaca gctgcataca aaacatttaa  12300
gacttgagag tatacagtgc accaagggga ctattattat gactgttaag aggacaccgt  12360
caaatgcta aggtgtactc cttaataaaa gttcttatga aatgaactga accaaatcag  12420
ccaagttaag gttcagacaa tataagcagt tcagcagtat tggggtctga ttggtcagag  12480
tcttcagttg gagtatgata gtgattaagg atcatagttc gctgtaaagt agcttgactt  12540
aaagaggtgc tcgttttcat tgttaccttg ttaatacaag tcataataac ttgaaaacct  12600
gctagaagag atataaagat tagaaaccct tggaaaaccc aagcttgcca ttcaccacttt 12660
aggatgcctg caaaccaact gttagttgct cctataaaca tatcgtgggt tcctttctct  12720
tgagagattt ctttattgta cttggtggca gtgtctaagg aaacagcagt atcagccacc  12780
ttttaaatta agcttttgt agtaacagaa tcagggagg gattagtaca aaattcagtt    12840
ttgtttaaca ccaaacatag gcctccagct tgagcaaaaa gaagatctaa gactgcatga  12900
tcttccatta agtgtttttcg ttgaatatgt atgttgtcat gtgcctttct gagagtagct  12960
tctacccatc tgaaaccctg ggaggtctga ttggctacca aatccaagaa ttttcccaat  13020
```

```
atacaaatta gttttaaatt ccgtacaaat ggtacttcac taccaccaag agtgagcccc   13080
caggaacccc agtggaatct ttccccggta gaaactagct tatcctcgtc tatttcgagg   13140
ctagtgctaa tttcagttat tgatcatttt ggcctccaag tataagggct atcatgagaa   13200
ttttcagggg aagcaattcg aaaggcagga gcaggccagg ccagataaca agaaccaaac   13260
caaccaaggg ggcagaacag aatatgcaga ttctccacga acccaataga gaccctcagg   13320
ggttggaaaa gggggccacc tagttgtatt tgagcaggga tcattcaggt ttgttcgacc   13380
atgaatctgt agctcctgaa taacatccag tgggaaattt acttttctat ggcccctttg   13440
tagtgtgttg taagggtgta taaccacatc tagtaaaaag agaccctact ggatatacaa   13500
gcaatcactt gtactaacat aagtaattcc caaatcttga gtatgtgatg cctgcaagca   13560
caatatacgt tttgtaggca tcatttggat ttgttttttta tatttggtgt gatcgacttt   13620
atcagttgaa aaagagtgtt gttttttagtg agtgtaggaa agcaagtact agtgatgttt   13680
agagtatcaa gaatagcttt ccattcttcc cttggggttt cagggtgact cattgggaaa   13740
cgtggagggg cactggcacc cttggaatca tttcctgatt ttttggcatt agcccacaaa   13800
cccaacagtt accctggttt tgtgctagag cataagcttg agctgaagcc atccactgat   13860
tatggtccca tggattttca tgtaaggaaa aggaaaggat tagggaaaaa aataaggaaa   13920
acagaaaaac acataaggct ttcatggtgg tagagaagtc ttgatctgtg atctaggaa    13980
agctgtctgt aaccaggatg ctgtctgctt ctggagaaga atttccctgg tcagctttac   14040
cttaaagtct ccaacgggta tatagtacca ggagtctgag gggccctttt tgaattgtga   14100
gatgtggacc catggttcaa agccctgaag cttctctgca ctgtgggtgg taagaaggac   14160
ttggtatggt cccatccaac gaggttcaag agtgatcttc ttctgatgtc atttccggaa   14220
ggcccagtct ccaaattcca gaccatggag ggtttgattg tcctcagttg gtggatcttg   14280
aaatgcttcc tttacctggt ggaagtatac tttggcgtaa tacattaaag ccttgcagta   14340
tttagtcata tcagagttta agagagcagg agaagcatga gatgctatta ttagggacat   14400
gggcctccca gtgactattt cataaggggt caatttatgt tttccaacag gattgaatct   14460
gattgccatt aaaaccaaaa ggtagtacct ttggccaagg caactcaatt gattcagtta   14520
acttggacag tttcagttttt caaatgccat ttgttctttc aagctttcct gaagactgag   14580
ggtaataagg acaatggtaa tgcaactgtg tcagtaacac cttatttaac tgctttataa   14640
cttgctcagt aaaatgagtt cctctatcac tggagacttt tagagggatc ccccataaag   14700
gaaaaacatt ttctaataat ttcttagcta tggtcacagc atcagctttc ctacatggga   14760
aggcctttat ccaaccagaa aacatgcaaa ctattacaag aacatactga tacccccattg   14820
agggtggtaa ctgaatgaag tccatctgta aatgttcaaa tggtccatca ggtggtgaaa   14880
atatactgcc tctagttttt ctgggattat gagtttgaca agtcaaacat tgattataag   14940
ccattttagt aatgtcagaa tagtcacccc accagtattt tttcataatt tggatcactt   15000
tgtctgttcc atgatgaatg ctgtggagagct ttcaaatggg agcaagttcaa agattcagga   15060
aggaccaggc ggccgtccgg gcccttttgtg agtctttgct tcacgttaaa tttcatcct    15120
tttagatacc agttttgttt ttgcaaatca gatgcgttgc actgtttatt aaataggtca   15180
tcgtaaggaa attggcttgg attaatctta tggagttcat tcagattgcg tatcttgatg   15240
gttccagcac tagctgattg agcataaaaa tctgctaaag catttcactg atatttgggt   15300
tcatttctac aagtatgagc ttcagtctta ataacagtaa tctgcatttg taacaggata   15360
gcagaaagga gctcatctgt ttggagtcca tttttgatgg ggatcccact agaggtgaga   15420
aaccttcgta gtttccatat catgccaaaa tcacgtacta ctccaaaagc atgtctacta   15480
tccgtaaata tttactgact tgtccttagc tgtgtgacat gttcaggtaa gggcagaaag   15540
ttctgcaggt tgggctgact tgacttgaag agttcgcttc tctattaact catttttgggt   15600
ggtaacagca tatcctgact gatatttttt tttctgagtt tttggcatag gacccatcaa   15660
caaaaagtgt taattcagga ttatccagtg gagtatcttg tatagcaaca cgaggggcca   15720
ctatttctga tactacactc acaccgttgt ggtcttcacc atcatcaggc agagataaca   15780
gagtagcagc attaagtaga ttacagcctt ttagatgaag ataagaagga gataggagaa   15840
gtaattcata agatgttagt ctactcactg aaaaatgctg ggtttgattg gaatttaata   15900
gactttccac agcgtgtggg acttgcaaat taagttcatt tcctaaaacc agatctgatg   15960
aagcttctac cagcttggct gctgctactg cttttaaaca attaggatat gccttagaga   16020
ctgggcctaa ttgcaggcta tagtatgcag tggtcctatg tttagcaccg tgttcctgga   16080
tattacattc atgaacaaac aaagtgaaag gtttagtgta atttgaagt cctaaagctg     16140
ggggctgttg taaggccaac ttcatttggc taaaagcctg ctcatgactg tcttcccaag   16200
gtaaaggctc tggtacagca tttttagtga gctcatacag tggtgaagct attaaggaaa   16260
aatttggaac ccaggatctg caatatcctg caagcctaag aaagcctttt gtcttttggt   16320
tgcaggtcga ggaaaacttt aaataggttt tatcctctca ggtaagaggg aaatcccttc   16380
agcagccaag tcatgtccca aatagtggac ttttcttttt gaaaattgaa gttttggcca   16440
ggcatggtgg ctaacgcctg taatcccagc actttgggag gctgaggcag gcggatcacc   16500
tgaggtcggg agttcaagga agcctgacc aacatggaga aaccctgtct ctactaaaaa    16560
tacaaaatta gccaggcgtg gtggtgcatg cctgtaatcc cagctactcg ggaggctgag   16620
gcaggagaat cgcttgaacc caggaggcag aggttgtggt gagccagtat cacaccattg   16680
cactccagcc tggcaacaa gagtgaaact ccatctcaaa aaaaaaaaaa aagaaaaaag     16740
aaagaaaaaa attgaagttt tccattgaa gccctgtgac ctttatatgc aagttgctgt    16800
aaaaggtaaa ctgagtcaat ttccgggcac tccttaatag gagagcataa caataagtta   16860
tctacatact gaatgagagt agaattttga ggaaactgta gtgtcattaa ctcctgatgc   16920
agtgcctggg gaaaatatga aggggcttca gtaaacccctt gtggcattac actccaggtg   16980
tattgctgat ttttccaagt aaaggcaaac aagtattgac tttctttatg gaatgctaga   17040
gaaggctgag ccaagatcta ttactgtgga caacttggaa tcagtgggta cattaggtta   17100
taaagtatta ggattttgga ctacaggaaa tcttggtatt acaattttat taattgcctg   17160
taaatctgga acaaatctcc agtctcatcc atttttgtttt ttaactggta ggattggagt   17220
gttacagggg ctggtgcatg gaattatgag tccttgttta attaaatctt ctacaattgg   17280
tgagagccct taaattgctt caggttttag tggatattgt ggtaattagg caaaggttta   17340
gaatgatctg ttagtacttt tataggttct acactttttaa ttcttcctat atcagttggg   17400
aagaggccca taaacattag gtgtttttcga aagatcaggt gttacagg cttgagtttc     17460
gatcttatca atttctgcct gtagacagca taacaattct agttcaggag aatcaggaaa   17520
actcttaaga ttatttctgt ttctgaggaa aatttttaggt gcccttttag ctttgaaagt   17580
aaatcttgcc ctaccaagtt tactggaaca gtatcacgta gtaaaaaact gtgtttttct    17640
gaaaggggc tcagagttaa ttggatgggt tcagatatgg gaacctctgg aacttgatttt    17700
gaaacccctg tcacagaaat gaccttttta ctctaaggga tttgttggct tattaaggtg   17760
```

```
gggtttatgg tagatagagt agccctggta tccataagga ctatacacaa ctccctattt    17820
attttaacct ctgtttcccc atgttccttt aaaggtatta cggggagcaa tccactggag    17880
aatcccttag agcctccttt aagttgaata ttgtcaggag gactaaggtc tcttgggctc    17940
cctctagtgg tgaaacagtt tggcctagag ggaggtttat cagccgacaa tcccttttcc    18000
agtgccctgg ttgtttgcaa tacaggcaga catcttgggg taaagaaatt cttgttctgg    18060
gacctcttga tttgatttt  ttaatatata attttaaaaa tattttccaa agtgtgactt    18120
aaaaaaattt ttttttatta tactttaagt tttagggtac atgtgcacaa cgtgcaggtt    18180
tgttacatat gtatacatgt gccatgttgg tgtgctgcac ccattaactc atcatttaca    18240
ttaggtatat ctcctaatgc tatccctccc ccctccccca accccacaac aggccccagt    18300
gtgtgatgtt ccccttcctg tgtccaagtg ttctcactgt tcagttccca cctacgagtg    18360
agaacatgcg gtgtttggtt ttttgtcctt gtgatagttt gctgagaatg atggtttcca    18420
gcttcatcca tgtccctaca aaggacatta actcatcatt ttttatggct ccatagtatt    18480
ccatggtgta tatatgccac attttcttaa tccagtctat cattgttgga catttgtgtt    18540
ggttccaagt ctttgctatt gtgaatagtg ctgcaataaa catacgtgtg catgtgtctt    18600
tatagcagca tgatttataa tcctttgggt atataccag taatgggatg ctgggtcaa     18660
acggtatttc tagttctaga tccctgagga attgccacac tgacttccac aatggttgaa    18720
ctagtttaca gtcccaccaa cagtgtaaaa gtgttcctat ttctccacat cctctccagc    18780
acctgttgtt tcctgacttt ttaatgattg ccattctaac tggtgtgagt tggtatctca    18840
ttgtggtttt gatttgcatt tctctgatgg ccagtgatga tgagcatttt ttcatgtgtc    18900
ttttggctgc ataaatgtct tctttgaga agtgtctgtt catatccttc acccacttgt     18960
tgatggggtt gtttgtttt  ctcttgtaag tttgtttgag ttctttgtag attctggata    19020
ttagccctt  gtcagatgag aagtttcaga aatttctcc cattctgtag gttgcctgtc     19080
cactctgatg gtagtttctt ttgctgtgca gaagctcttt actttaatga gatccccattt    19140
gtcaattttg gcttttgttg ccattgcttt tggtgtttta gacatgaagt ccttggccat    19200
gcctatgtcc tgaatggtat tgcctaggtt ttccttctagg attttttatgg ttttaggtct   19260
aaattaagtc ttttaatctat cttgaattaa tttttgtata aggtgtaagg aagggatcca    19320
gtttcagctt tctacatatg gctagccagt tttcccagca ccattatta  aatagggaat    19380
cgtttccccg tttcttgttt ttgtcaggtt tgtcaaagat cagatagttg tagatatgcg    19440
gcgttatttc tgagggctct gttctgttcc attggcctat atctctgttt tggtaccagt    19500
accatgctgt tttggtgact gtagccttgt atagtttgaa gtcaggtagc gtgatgcctc    19560
cagctttgtt ctttggctta ggattgactt ggcaatgcag gctcttttt  ggttccatat    19620
gaactttaaa gtagtttttt ccaattctgt gaagaaagtc tttggtagct tgatggggat    19680
ggcattgaat ctataaatta ccctgggcag tatggccatt tcacgatat  tgattcttcc    19740
tacccatgag catggaatgt tcttttcattt gttttatttt ctcttttattt cctgagcag   19800
tggtttgtag ttctccttga agaggtcttt cacatccctt gtatgttgga ttcctaggta    19860
ttttattctc tttgaagcaa ttgtgaatga gagttcactc atgatttggc tctctgtttg    19920
tctgttattg gtatataaga atgctctctt ttgttctttg ttagtcttgc tagcggtcta    19980
tcaattttgt tgatcttttc gaaaaaccag ttactggatt cattgatttt ttgaagggtt    20040
ttgtctct   ctatctcctt cagttctgct ctggtcttat ttatttcttg ccttctgctg    20100
gcttttgaat gtgtttcctc ttgcttctct agttctttta atttgtgacgt tagggtgtca   20160
attttagatc tttcctactt tctcttgtgg gcatttagtg ctataaattt ccctctacac    20220
actgctttga atgtgtccca gagattctgg tatgttgtgt ctttgttctc attggtttca    20280
aagaacatct ttacttctgc cttcatttcg ttatgtaccc agtagtcatt caggagcagg    20340
ttgttcagtt tccatgtagt tgagcagttt tgagtgagtt tcttaatcct gagttctagt    20400
ttgattccac tgtggtctga gagacagttt gttataattt gtattctttt acattttctg    20460
aggagagctt tatttccaac tatgtggtca atttggaat aagtgcagtg tggtgctaag     20520
aagaacgtat gttctgttga tttggggtgg agagttctgt agatgtgtat taggtccgct    20580
tggtcagag  ctgagttgaa ttcctggata tccttgttaa cttctctgtct cgttggtctg   20640
tctaatgttg acagtggggt gttaaagtct cccattattg ttgtgtggga gtctgagtct    20700
ctttgtaggt cactcagggc ttgctttatg aatctgggtg ctcctgtatt ggttgcatat    20760
atatttagga tagttagctc ttcttgttga attgatccct ttaccattat gtaatgtagt    20820
tctttgtctc ttttgatctt tgttggttta aagtctgttt taccagagac taggattgaa    20880
acccctgcct ttttttgttt tccatttgct tggtagatct tcctccatcc ctttatttg     20940
agcctatgtg tgactctgca cgtgagatgg gtttcctgaa tacagcacac tgatgggtct    21000
tgactcttta tccaattgc cagtccgtgt cttttaaggg gagcatttag cccattttaca    21060
tttaaggtta atattgttat gtgtgaattt gatcctgtca ttctctcaac atttgcttgt    21120
ctgtaaagga ttttatttct ccttcactta tgaagcttag ttttggctgga tatgaaattc    21180
tgggttgaaa attcttttct ttaagaatgt tgaatattgg cctccactct cttctggcgt    21240
gtagagtttc tgccgagaga tcagctgttg gtctgatggg cttcccttg  tgggtaacct    21300
gaccttctc  tctagctgcc attaacattt tttccttcat ttcaactttg gtgaatctga    21360
caattatgtg tcttggagtt gctctttcg aggagtatct ttgtggcatt ctctgtgttt     21420
cctgaatttg aatgttggcc tgccttgcta gattggggaa gttctcctgg ataatatcct    21480
gcagagtgtt ttccaacttg gttccattct tcccgtcact ttcaggtaca ccaatcgac     21540
gtagatttgg tcttttcaca tagtcccata tttcttgtcg gttttgttcg ttctttttta    21600
ttcttttttc tctaaacttc tcttcccgct tcatttcatt gatttgatct tccatcactg    21660
atacccttc  ttccagttga tcgaatcggc tactgaggct tgtgcatccg tcacgtagtt    21720
ctcgtgcctt ggttttcagc tccatcaggt ccttaaggg  cttctctgca ttagttattc   21780
tagttagccg ttcgtcgaat tttttcaag gttttaact tctttgccat gggttcgaac     21840
ttcctcctt  agcttggata gtttgattgt ctgaagtctt cttcctcag tcgtcaaag      21900
tcattctctg tccagctttg ttccgttgct ggtgaggagc tgcattcctt tggaggagga    21960
gaggtgctct gatttttaga attttcagta ttttttgctct gtttcttccc catctttgtg    22020
gttttgtcta cctttggtct tgatgatgg tgatgtacag atggttttt ggtgtggatg       22080
tcctttctgt ttgttagttt tccttctaac agtcaggacc ctcagctgca ggtctattgg    22140
agtttgttgg aggtccactc cagaccatgt ttgcctgggt atcagcaggc gaggctgcag    22200
aacaacgaat attggtgaac agcagatgtt gctgcctgat cgttcctctg gaagtttgt     22260
ctcagagggg taccccggcca tgtgaggtgt cagtctgccc ctactgggg  gtgcctccca   22320
gttaggctat tcggggtca gggacccact tgaggaggca gtctgtctgt tctcagatct     22380
caagctgtgt gctgggagaa ccactgctct cttccaagct gtcagacagg gacatttaag    22440
tctgcagagg tttctgctgc cttttgttcg gctatgccct gcctgcagag gtggagtcta    22500
```

-continued

```
cagaggaagg caggcctcct tgagctgcag tgggctccac ccagttcgag cttcccagct   22560
gcttttttta cctgctcaag cctccgcaat ggcgggcacc cctcccccag cctcgctgcc   22620
accttgcagt ttgatctcag actgctgtgc tagcaatgag cgaggctcca tgggcatagg   22680
acccgctgag ccaggcgcgg gatatagtct cctggtgtgc tgtttgctaa gaccatcgga   22740
aaagcgcagt attagggtgg gagtgaccca attttcaggt tgctgtctgt cacccctttc   22800
cttggctagg aaagggaatt ccctgacccc ttgtgcttcc tgggtgaggc gatgcctcgc   22860
cctgctttgg ctcatgctcg gtgcgctgca cccactgtcc tgcacccact gtctgacaat   22920
ccccagtgag atgaacccag tacctcagtt ggaaatgcag aaatcacccg ttttctgcgt   22980
cgctcaagct gggagctgta gactggagct gttcctattt ggccatcttg gaaccgcccg   23040
attgtgattt aaaatgagaa cgagatggtc cctttggttc ctggtccctg taactgttgc   23100
aattgaaggg gcataagctt attagccttt tgaggttttt tttgctctag agtcttctca   23160
aaatgcttag ctaggttggg cacgatggct cacgcctgta atcccagcac tttgaaggc   23220
caaggtggga ggatcacgag gtcaggagat caagaccatc ctggctaaga tggtgaaatc   23280
ccatctctac taaaaataca cagattagct gggcatggtg gcacacgcct gtagtcgcag   23340
ctactcggga ggctgaggca agagaattgc ttgaacctgg gaggcagagg ttgcagtgag   23400
ccgagattgc gccactacac tctagcctgg gtgacagagc aagactccac ctcaaaaaaa   23460
aaaaaaaaaa aaaaaaaagt tcagctaagg ccaccaattc agtcacatct ctaacttccc   23520
attgcaactt atgttttta gttaaactgc taagttcagg atggagtcca tttataagta   23580
aagcagttaa tgctgtttca gccccctgcag ggaatactcc ttgctgtact ttgagcccag   23640
gatgtttcac aaatatttct aagcgacttc tgtaatctga aactggttca tcttttcttt   23700
tctttttttt ttgcttacaa gattgtatga tggaccaatt ttttgtggaa aaattttagg   23760
aactgaatgt taaaaggttt tcagcgattt ttctagctat ttttggttct tcttgtgagg   23820
agctcttaga gggcccttta aaatgtcctc ctcaggtttg tcccattctg ctgctgccat   23880
ccatttctga gcttcaccag cccccagtat catatgaata aattggtaaa ttcatgaagt   23940
cctggatcgt aagctcctat taggattcta aattcctcag taaattttg agactttcc   24000
cttggaccag ggaagtcctt cacaatgggg ctaagctcag ttttagacca tggagtgaaa   24060
gtagttacag caggcaggcc tggctgatat aaggtctcac tttgtaagac atctgtctaa   24120
cttccttttt tttttttttt ttttttttaaa tcatcttcag ggtgaaagtg taatttaaca   24180
aaaagtttag tggactcaga gtatgtaggt agagatggac aaagaaggaa cagtccgagt   24240
tagatcagtc aaagtacagt cctctttctt catgtccttg gtctgttgct taagctttc   24300
atttggtttt tgcaaagaat cttttaagga ggcacttttt gattcactta gtcttttgga   24360
ggcctttgcg tatccatgag acaatacatc ccactgtatt tgtgggggct ttgatcccct   24420
ttttctaata tgccttgcaa acaattttat ccaaattaaa acttctccat tgtggccatt   24480
ttaattctaa gttttcttta gtgaggttaa cccattttac tgaaaatgca catgtctggg   24540
gcccataatt tttatacgta aaattagctg gagtccctga agatggagtc ccagactcct   24600
tggattgaga tgatcccatt attaaataag gtacttatca gaggtctgag gcctctaact   24660
gaatccaatc cagttaatta tcaaatccaa tttgatcttg gatccagtcc aggctaagta   24720
ttgcttgagt aaactcggag agctcaaaac acaagttagt ggagctcgga atctgagaga   24780
aaactcaccc atgacctcca gttacaatca agagaccagt gagagcaacg gcctcagtgg   24840
gtacctcacc aaggtcacctg gtgttccagg gggttgccag agttttctt caaatcccac   24900
ttctgacacc agatctgtta aagaaaact tcagacaagt taaatttgat ggagtttaat   24960
taagcaagga aaataaacac tttgcaaatc aggcagcctc cagaattgaa tgcagtttga   25020
acacttagca gtctattagt gcttgaagta tggccactgg gattggccaa cactcagcta   25080
ttattacaga tgcatactac tcaggttttc cattttgtct gcctattgtg ctaggttatg   25140
gtttgtccac aagaacacaa atatagaagt atggagtcct tctcaggcca tatttagttt   25200
gctttaacaa tacttaaaaa aaaaaattgt aaaataagga tacttaacct tactcggtgt   25260
ttctgagagt taacatttat atagttatgc tgtagtgaaa acagctaggg taatgtctgg   25320
tatgtatagg aacacaagag ataccgctttt tcccatatcc ccataccatt cttcacagca   25380
ttgctcctgt cttccttgat tcctcctcct cctttctttgt ttttttttg tttgtttgtt   25440
tgttttttt tggaggtgga gtctcactct gttgcccagg ctggagtgca gtggtgtgat   25500
ctcagcttac tgcaacctct gcctcctggg ttcaagtgat tctcctgcct cagcctccg   25560
aatagctggg attacaggca cacaccaaca cactcagcta atttttgtat ttttagtagg   25620
gatgggtttt caccatgttg gccaggctgg tcttgaactc ctgacctcag gtgattcacc   25680
cacctcagcc tcccaaagtg ctgggattac aggtgtgagc caccacaccc tgcctccttc   25740
ttaagaagtt tccagtccct tgtaattaaa ggaattaata ttttttaact acttagaatc   25800
agactggccc tgattattag taagcaacta atagtaagca agcaactatg tatgcaacta   25860
tgagtgtatg ttaagatatg gttgttggta acctttcatt ctcttcagga agaagaagag   25920
ggtggagctc tacagtcaat gtgtacattt aaattctgtt cccttttcgag cttttttgct   25980
actttcattc ttctggggat ccaggtgctt gagttgggat tgattaactt ccttaatttc   26040
cacccctgtg ctgtcaggat cgggagacat agatgaaggt gttctaaact gctagaaatt   26100
ttgtttttga aagcaaaagt ttgcatgcat ttttgtttc aacttttact tacagtgaat   26160
agtagttaat aaaataagtc cctgcctttt ctctctttgg tttcaattcc tgagaccagg   26220
atcatagccc acatattaga gtggagtccc actgctttgg tttgaatcat gcctttgttt   26280
cttatgtcag tgtgactttg gcaagttat ttaagtcttt gcaccacatt ttcctcatct   26340
gtaaaatgag gataatacta gtactttcta catgggattg ttagcaggat taaatgagat   26400
agcacatact gtaaccatgt ctggcacata gtcaatggtt agtaaatgtg aactattgtg   26460
tgacattgtg gttagtcacg tatggggctg tgtttccttt agtatattgc tcttttaatg   26520
tcatttcctt tgtactgtta ccctctctga tcttctttcc atattcattt ttcttttcagt   26580
gaggtctgcc agtctttagt gaaacacagc tctggaataa aaggaagttt accactacaa   26640
aaactacatc tggtttcacg aagcatttat cattcacatc atcctacctt aaagcttcaa   26700
cgaccccaat taaggacatc ctttcagcag ttctcttctc tgacaaacct tccttttacgt   26760
aaactgaaat tctctccaat taaatatggc taccagcctc gcaggaattt ttggccagca   26820
agattagcta cgagactctt aaaacttcgc tatctcatac taggatcggc tgttgggggt   26880
ggctcacacag ccaaaaaggt gaactgaca ttcctcctgg ttttccaatt attatatcat   26940
gattaagttt ctatagcata aatcattttt gtgtagtgga atacaattgg atgtttaaac   27000
atttattttg tgtctctacc atggactaga ttgttttaat gatgctaata ggaagatgcc   27060
tttagaatct tagttataat tacaggaaat taaaatggcc tagtgaaggg agcacagggc   27120
tgggaatagg aacacctagg tttgattttg agcttagaca tttagtagca cagatgtgaa   27180
agtcaggtgg cattctcaca caagcacttc ttggcaggtc tgggaccaga ggcaaggcgt   27240
```

```
cctgtctccc agtctgtctt ccttctaccc cacagtaata tttagggcaa aattatgaaa 27300
cctgtttgaa ataggagtat attctgaatt tttacatttt ccatatttaa cagaggagtg 27360
ttaacttgtt ttatatgctt gtttgctgag accacttaat tttgtttctt aaaagttttg 27420
aacataatac attattctta gtagattaat gtgttttaat taaataattt ttctttacat 27480
gtttatttgg catgcagagc atctgattga cacactttct tgtctttttag acttttgatc 27540
agtggaaaga tatgataccg gaccttagtg aatataaatg gattgtgcct gacattgtgt 27600
gggaaattga tgagtatatc gattttggtt tgtatcatga acattaaaat actttttttg 27660
gtcatctcga ggaaagagaa atagtttatt gagatagttt cttaacttat gaacctaata 27720
tatcacggtt ttattttaat gatataagta atagaatatc aatgaaaaaa tctgtataaa 27780
agaaatacccc agtagcccat aattttacca cagctgccac taactgtttg gagcatttttc 27840
tttttaattat acttactata tgtggttagt atctttttaa cttatcgatt gagacaggat 27900
cttgctctgt cactcaggct gaagtgcggt cttggaatca taactcactg cagccctgaa 27960
ctggctaaag tagtccttcc gactctgcct cccaagtagc cgggactaca tgtgtgtgcc 28020
accatgcccg actgattttt taatttcttg tagagatgca gtctcactat gttgcccagg 28080
ctagtctcaa attccttagc tcaaacctct cacctcagcc tctcaaagca ctgagattac 28140
aagtgtgagc cactatgcct ggcttgagtt ttttttcttt aatttttttc ttttcatgaa 28200
tactaccaca gaatagtatt ttagttccct tttttaaaaat tatgtaatca tggtgaatat 28260
tcactttggt attttgtctt ttgctaccta acatattttg tcagcatttc catgctgcca 28320
agtagccttt ctattaataa tatcattttc tgcattatgt aatgttgccc agagcatatt 28380
tattgtgacc cacctagcta gctccttttg attggatacc ttggttatct ctaccttttg 28440
tagccaagtt cttttaaaagt ctgttagtat ccagggtaat ttcttttctt agttggccac 28500
tgccctccct tttcaatag gtggatgaga aaaagtata ttggatcgct atgattgcca 28560
gtaattcatg gtgatcttta agaaatatat tttcatcaaa ttttttttaaa accttttgtca 28620
gatttcttag tttaggtgta tgtggaggtg gaattaatct atacttgcac ttattcacag 28680
aatttataaa gataaaactg ttctatgttg acgaatccat ttgcaaaaaa agcacactttt 28740
caaattgttc ttctaaatatt aatgaggaga gctttcaaat tgatgtattt gccagtacca 28800
cagcgtagtg gctgagagcc tgtattctga agctggactg cctgggctgg aacccgggct 28860
cctccacttc cttgctgtgt accttagttt ctcatctgta aatggtgttg ataatagtag 28920
ctgttttgta gggttgtcat gaggattaaa caagttaata ctttagccct ttataagaat 28980
agtatctgac atattttctt agtttcatac tctatatgtt ttgatctttt ccagagaaaa 29040
ttagaaaagc ccttcctagt tcagaagacc ttgtaaagtt agcaccagac tttgacaaga 29100
ttgttgaaag ccttagctta ttgaaggact ttttaccttc aggtaaggaa gaagctgttt 29160
gatctaattt aaaaatttaa gaaccatgga ggaaaatac atggattatt tgtttattcc 29220
catttttta aaattaaat atttagtacc aatgaaaaac aggacatttt ttaaaaagat 29280
aaacacaaag ttttgttaca caatgttttt aatctttgtg tagcccagta aaatgacagt 29340
tcctaagcac ttaaacatac ttggctttta gtgaggggaa aaaatgtatc acttgttctt 29400
gacaagtaga tgagacttcc tatgtatttg cttttcataa gtggttggac caatttggtg 29460
gttttaaaac aaatttaagt atgatagacc ataatgagta gcatttatta agtttaatcc 29520
tggcatattt gcccaattat tgccctatcg taatatgaaa tctgagatct cagacatctt 29580
tgtttgctca tttctgttaa attttacatt tctatttccc cttttgctga tttttcacag 29640
gtcacaaatt ggttagtgaa gtcataggag cttctgacct acttctcttg ttaggtgtgt 29700
aaacagacat ttttgctgac cttaacatgc cttttaaatg cttctaataa actagttgca 29760
aataaaattg cagaccaaat ttataatgct gcttatgctg aattttaaaa ccccagaact 29820
atattaggca aactcattat ccttttaggtg gaaataataa aataattatt ttgtgataac 29880
actaaaattc ttaaatatgt atgtgtatta taagattaaa gctattaaaa gaaaatttac 29940
ttagcaaaaa tattttcttg aaatagatct aattgttttt gataattgaa atgaaaagta 30000
attttagtttt gtctcatctg ccctgtcatg gttgacattt aaattttgttt tccggctggg 30060
cgcggtggct catgcctgta atcccagcat tttgggaggc caaggcaggc ggatcatgag 30120
gtcaggagat cgagaccatc ctggctaaca cggtgaaacc ccatctctac taaaaataca 30180
aaaaatttgc cgggcgtggt ggcacacgcc tgtagtccta gctactcggg aggctgaggc 30240
aggagaatta cttgaaccca ggaggcggag gttgcagtga gccaagatcg cgccactgca 30300
ctccagcctg ggcgacagag ggagactctg ccccccaccc ccaaaaaaaa aagaaaaga 30360
aaaaaaaatt gttttcctgc tatacatggt ctgtaatgcc agtggtatgt ggctgaactg 30420
taagtactct catgtaaaat aatccttacc aaagattgtc ttattttttt attgtaatttt 30480
tcagttatat atttttaatt gttaggttaa acatatgcct cgattgctat agttagtttt 30540
tttttttattt tctgcacagg ttatcagtca tgttccttaa aataagaata aaggcgattt 30600
gattcttttga atctgagttg ctctaaaaaat ccattcacct tttcattgac tcgatgtaat 30660
ttgaaattca gcttaggctg ttgacatcac tggagaatgt aaagggttgc atatttatct 30720
ttaaggttct ccggaagaaa cggcgtttag agcaacagat cgtggatctg aaagtgacaa 30780
gcattttaga aaggtaagtg taaaagagaa ttgttcatgt aggtagtctt gaaagattttt 30840
ttaaagtttt tacttctttg gaagatttta aaatgataac atctgagaag caaatacaaa 30900
aacatccaag tagagatatc gttactaatc ttagtgcaaa gtacaaggta ttacgtggca 30960
gttctggaaa tataattgag aagcccatttt cttttcacata tgtccagtga agcattagtt 31020
tcgaggggttg tccccaagaa agagttgtgt tgttaagtgt gtggggggag aaaggctcgt 31080
ttagacaagg caagcggact tcttttcttt ccctaggacc tctcatactg taatatactc 31140
atgcgcattg tgaatttcca aggagtcaaa gcatacagtg ttttcccaaa ttatttatca 31200
acagaacccct tttgctcatg gaacgtcgta tagggactag atttcacttt ggggaaacta 31260
gaaagggaat aggaattggg ttattaggaa ataaatcaat tccctgatat tgatagttaa 31320
caaagttatg tatggggtta tttattttca acacatattc attaacaaaa 31380
tccatatgaa agttataggg gaattgctga ggtagaataa catactttgt tgtatttttat 31440
aatactcata tatttacctg acgtttttctg agtcttcact ttttttcattc ttttggaatt 31500
ggtaaaataa ctgattcctt gaaagttttt ttctaaataa tacctagata atagatttat 31560
agaaaaaata ttgtatgaat gttttaacat tcatgataata tggaacatgt aatttttata 31620
ctggaggtta ttatagtttt aatacatcaa agaaataatg tttatttttgg aagcagaaag 31680
aagaaataat ttctatgaat aggttttcat ctctttcctt gttcttcaac tttgaacttt 31740
ttatattccca aattttaatt atatttcaaa agattttttt cttttgccctt taattttat 31800
cttttggaga aaaatgtatg tcaaaatgta tgtacgtgta tttgtctttt gatttgatct 31860
tttttgaccc tcttttgcat tgacattatt ttaaccaaag gacactctg attgttcatg 31920
ctactggggg aaaaaaaaat aagtagaaat tagcctaata gttgtggctt atttttgagtg 31980
```

```
aaggccttag cccttaaggc aattaaattt actgtggaga gaagagctaa tctaatgggg   32040
agaaggagcc tttgttacag gtgtggtagt gtggttcttt gagtgacaag atttctgttt   32100
gccagattgg ttaggagaag tctgtgtgtc tgctttctct cttatggcct aggatcactg   32160
tggtgaatga aaaacctgtc tcagggcctg actcagataa ttcccttaaa acccggctaa   32220
ggtcatagat gaataatcag taattgaaca gaagctctgc aatagaaaag aagccagata   32280
attatttttg gaaatttaat tatatttaca gatttatttt tatacagtag acatggaatt   32340
aaatttatta cattatgttc taatttactc tttgcttgtt ttgatttgct tgtttgacaa   32400
tacatgtcct tgtaaactat ttccttttaa cttttttctca atttatggtg cttattttcc   32460
ccattaaaga cttaccaatt tttttttaaa ctatttgtta cacatactga atctagagtt   32520
gtaattaagc tactttcatt actggttaag tcaaattata gcaaatgcta ctataaaaat   32580
ttactatcca aaaatgtgtc tcaagcccca actgatggtt tcaaattctg ttattaataa   32640
tatgcagcat tgtgtttgca aagcttggct gttacttgtg atgcttgaga atgatgagtc   32700
actcagctaa actgagtgat tttgagactt gtgtacaaat tgatggttga atgtaagcat   32760
gcaaagagag accttagctt agcagtaccc tttttgaaat cactctgaca tcaagtttga   32820
aaatgtgggc aataatcaga ggtggtaagg tggccaggct ttagctgaat acttttttaa   32880
ctggttcagt ctgagggctg aaagcccag atttaaacag tatttagaat ttgaagcagt    32940
caagtattag tttaatggtt gtcaggtttg taacaaagtt tctggctaga cttctactag   33000
aaatgtaaaa gtgcatgtga atcagctttt taaaaaagta ataataattg aaaaacattt   33060
ctacaactag aactaaagaa aagatttgtc ctttctaata ggaaaacaca tctggagaag   33120
tgctggcaac tagcagaaca gttaggacca ttcagaatca actgaagtga aagtgacggg   33180
gagctgaggg gaacacagat agtttgactt cagtcagaca gaataaacat gatgaaccga   33240
taacctgtga ttcccagcct gggggttacta ctggagtttt aggtgtcctg gaaagttata   33300
ataccggtct tcaaaaagtc tacagaaagc atagatttcc acataatgct gcacaggcta   33360
acgaattaat caagtttctt tggtttggcc tggatttata tccattcagt ttgtggacac   33420
tactgaatta tttatgtcat gttgatcaaa agttctgata tgatttgatt aatgaaacat   33480
tgaaaaaaat agtaaaacca accattttta accttacact actatcttga ggtatgattg   33540
acatacatta aaaccacctc ttaataaatg cttcttgtta atcaaaaatt tgaaaacgta   33600
tgtccactgg aggaaaaaag acatagccct ggatgtgaac tgaatattac tgagactcgg   33660
agaccttcag aactacctga agatgaatcg aagtgctgcc tactttagag aattggacta   33720
atttaatttg ggagtcagca gattgctgta tatcagtcat catatatacc ggtgacaaga   33780
ccacttagtt cattcccttt tttagattcc gtaagattat tgtgttccag tgaaattgat   33840
ttgcaaaatg agacatttta ttttctgtgc ttttgttcta tcatgtttct gattggtcat   33900
aagcatctca cagaagtaag aaatatggcg attcagaagg caacaagcac atttataatt   33960
tatagaaaat atttgaagga cttttttcatg gcccaaatca tgaaaagtag tagtattgtt   34020
ttaagtataa ttattaaatt ataatacatt aatgttcttt cttgcaacat attactctca   34080
ttcttttttt tttttttttt ttttgagacg gagtctcact ctgtcacccg gctgagtac    34140
agtggtacga tcttggccca ctgcaacctc tgcctcccgg gttcaagcga ttctcctgcc   34200
tcagcctccc aagtagctgg gattacaggc tcctgccacc acgcctagct aatttttta    34260
tttttagtag agacagggtt tcaccaggtt ggccaggatg gtcttgatct cttgacctca   34320
tggtccgtcc acctctgcct cccaaagtgt tgggattaca ggcgtgagcc acccagcagt   34380
ctgattctta attttatagt ttatgttgta cctccccagc tgaagtatct ctttttcttt   34440
ttcccgcgtg tttagtgttc actcatcttt atagcatagc tcaattgtca cttcatgaag   34500
ccttccataa cctttgtagc tccattaatt atattctttt gagtgtttaa aacacttgcc   34560
atatgaaaca ctatttactt tggcttacat tcttactatc taatcggcca tttctgttac   34620
taaatctttt tctcagagca cctgggatag tcttgtgtct tagtaaaatc agttgattga   34680
tttaactcgg tagagtagag gctgattaaa gtaaataaat ctggttgatg ccaacaaaat   34740
tttggtcccc tcaatttttt gctctcatta cctgcaaatt ctccctggcc ttcatatttg   34800
gcaaccattg aggagaacaa ggctgtaaaa gtagttcatg tacttgatat tctgaattgg   34860
aattaagcag agttgcttaa gtaggacttg cttttctggg atttcttatg caacaaataa   34920
tgtagtaact ggaaatccaa gttcaagaca ctggcagatt cgatgtcttt tgaggaccct   34980
tggcttcata gatgatgcct tctccctata tccttacata gcaaaagggg ccaggcagct   35040
ctggccttttt tttgtaaggc caataactcc agaaacctca tgacctcatc acctcccaaa   35100
ggccccacct ctcaatacta tcacattgtg aggctaggtt tcaacatatg aattgtggga   35160
gacaaaaatt cagaccatag tataaatttt caagattact taaactcttc tctaccaaac   35220
tcattaactt ttaggttagc acagtatttt cattgatatt ttggtttctg gagttattac   35280
taatttttctt gatctgatgt tataattaaa aaaaaacagg actttgtacg tgaaatgaga   35340
ctgagataag gaagctgatt cagagatgga gatttaaaaa aagagagatg agagattgag   35400
atctgcagtg tcaaactgac aatagccagg agtcaggaga tattaagaga ctatatcatc   35460
tgtgattgtt aaatgattat tattgttatt tataaatact actgtatttt atatattata   35520
tacattgttt taaaaattat ttttgtacca tttcttgaaa gaaaaatgtc taagcttggg   35580
aaaatattta ttgaaaaatg tggtttgtac atctgaggag tgtatcttgc acagtaggtg   35640
catagatttc ttcctcttcc tgttccacat ggccttagct tagaggctgt gtggccatca   35700
cttggtatttt agggtaagac tggtgcacaa aatcaaagac aggtaacctt ggtataagtg   35760
tagtatcatg taaatagctt ttctatgtct aattcttgtt ttcttcctac tttttcagga   35820
ggtcaatttc agttcatttc aactatcttt acataatagt gctttagtaa caggcatgga   35880
aggaaagaga catgtcccta gagtgttttt ttgaaatcta atagatgatt ggagtattta   35940
ccatgcagtt gtgtatatac ataagcagtg aattcgagag gaattttaa gctgtaaaaa    36000
aaagcattgt gtgccttata gacgcgagtg agaaatgtgg aatatggctg atccaaaggg   36060
aatgagttat ctcaattgat taatcacagt cagttagaca ttgaactctt tgttctactc   36120
tttgcccct tctcactatt gctcttgact agtcttaaga aagaaatgtg gaatattttc    36180
tcacggcttt gggatttat aaattagaat actagtggta tgtaaataca gcaggtacac    36240
tactgtataa accaacatag gaagccttct ttaaaggaa ttgtttgaga aatttgaaca    36300
cttggataat ttgaataaag gattgtgata aatgatcaaa tgaaagaaaa taaatcaggt   36360
tactcttctt tctgcttgat aaagcaataa ttttttttaa aggtaaaaat tatgagaatg   36420
atgaggatag tagttagcat tgtctttctt tgataggttt gttaatgatc ataaaactga   36480
tttattaaaa gacatgtctt tttataacta ttttatactg ttgtatctgg aaacaaatat   36540
tgaatttcat ttgtcatgtg gaagaaatca actagtttta acctttgatt tataataaat   36600
caaccacttt catttattgt ctaatactgg caatgaacac agcctaatgt atcaaaacta   36660
acagaataaa aattctccaa gttatatcca gactttaaga cactttctaa ttatataaaa   36720
```

```
taaaatatttt tgggcagtca ttttttaact ctgaaactat ttaaaactcc taatttagaa   36780
tatcttaata aatacccatt ttcctctttt tattttttata acttggtaaa aattgagtcc   36840
attgttttcc cagaacgctg ttcttaaaca aatggttacc tccttcatta gaactttact   36900
tttttttagga tttctaatta agaaaacatt aggcttgtaa cattgtcaaa tcttggtggt   36960
cttctccca cgttttttga ggtcgattat ctaagaggcc atcagttaat aaagctatgc   37020
aggaaatgac atcatgccac atgtgaatat cctgtattaa aaattgtatc aatatactat   37080
tttataatta tgaagtggaa tgaattttag aaatagaaaa ggtgatttt tgtgcatagg    37140
tccaaactgt gttttgtttt catttcagaa tttcataata actatattgt ctccatatct   37200
taattgtgtt tttttatagc acttttgttt agtaatttgt atatgcttgg ctgtattctc   37260
agaggctgtt tctatttaat gttgtcaaaa cagctcataa aaagtgaaaa ttcggtcaga   37320
ctagttattt gatattatat atgaaatcaa aacaacctga aacattatct tttaatttaa   37380
ataaagaacc ccaaatttta atcaaatgta tgcaaaggca catagaatat atgacttaat   37440
gtacaacctt tattaacttg atgatggaaa cctgttccta gggacccttta cttgaataaa   37500
tgaaatatca agaaaaaata ctaacttaag aataataatt taataagtaa gtaagctatt   37560
atgatcttca atcagtcctg agagaatcat ggttgagaat tagaaaattt agaccagtaa   37620
gatcaacact gttaaaaaaa aaaaaaaatc agtattttt ctccatattt tttatatatc    37680
tggatcattt tatttagcac ttattattgc acttttcttt tcactttta aactatgctg    37740
ttttatttt ctgagacatc tgatttactg aggaggaaaa tggaaatgcg gtacagagcc    37800
caagggtatg acggctttaa atgagtttcc atttctgttt taagttaacc atccctccct   37860
agcttacatc tgttcctttg ttgcacccctt ggtttaacat tattctcctc cccaatttcc   37920
tcttctcctc attgtgaact cgtggcaggg tctgcttggt gagctcattc tcttacaaca   37980
acaaattcaa gagcatgaag aggaagcgcg cagagccgct ggcaaatata gcacgagcta   38040
tgcccaacag aagcgcaagg tgatggatgg tttaaggggg ctaccgatac attcacacta   38100
atcagccatt tctgccaaga tcatgtcacc tcaatctgtt catggactcc aaatacaaga   38160
aattaatttg acaaagtgaa aatataaaag atgcatcata taaatatgta acttttctgg   38220
agtgggtagt ataggtaaag ccaaaagaaa caaattcaag cagaggaatt ttggtttctg   38280
aaaattaggt tgtctgtagg gtccctgtat ttatacttag aacaaaatta ggaatttctg   38340
tttatgtggt ccagttattg agtcaccta agtttgtagg catcttacct acctacttgc    38400
tccccaagtt tttatttcta aaatgaaaag cattgctgta gatgaccagt ttacactaaa   38460
gaataacatt tatttatttg ttttagctaa agtatatgga cagggaacat tcatattctt   38520
gtagaagaaa attattttga cttttgggca aaagcatgta gttcttatac actttgacaa   38580
actcattgcg tacattttc acattaatca aagtcagcac aaataaattt tcaccttgga    38640
ccacggaggg tttgaacact ggaaatttga tataattctg gttgctaaag aacaagttct   38700
aataaaagct taagtgtata ccaatatgtg gctgttggtg caatcagcag gtccgtaaaa   38760
atatgatttt aatggttagg taatcccaca acggagatcc caaagttcat gtttggaaga   38820
gacttttggg tcaaagtgaa atcagtgtaa tgaatttaaa attatactct gagatcttga   38880
aatcagctaa ttatgttaca tcttattagc tcagaaaagt tttgaagtta tacaaaatg    38940
ctagtcagga aaaaagattc agtcatgtaa ttcttgtaca ttctactatt taaatcaacc   39000
aatattatag attatgattt agtgcagtaa ttctgctggc taaccttatc tcatttggtg   39060
gtggttagta cttcagagta ctccaccatag tttcatttat gttttcagca tcacttcctg   39120
gtttttctca attccatggc tgtggaatca attcatatgt atatttagct tcggtgagca   39180
aaaacatagc tagaaaaaga aaagaagtga gttttcctacc tggttaaatt aaagtcgatg   39240
tgttaagcca aggaggactt cttttgaatg gtactttaac aatccctgtt ctgtatactg   39300
tgaatatatc atttaaatag cctaataaat tggatgctaa ggctgagcca cctatacttt   39360
agttttgtta tggaaagaag ggagaggagc aagtatgttc ttatatgtta cttagaaata   39420
agaatgtagc tgtagttaca cattgttctt aagttttttt cgtaagacaa cttgaaatga   39480
gtcccatagg cctgctattt aacattctaa gatatgactt aaggttaatg atgagctttt   39540
gaatctgaca attcaagaga tatccataat gaatactgat tcattttcta cattgctgaa   39600
agctaatgtt catttaagc ctactttagt agcctttatt tgggcttaga gatgttattc     39660
ctctttctga tatttattgg gttatctgtt taacccttt atatctcccct ttcccgattt    39720
gtaaattaga gactggcaag acttttttacc ctgagtagag caccaaacat ggcttgttc    39780
tgcccacact gtagttacct tgagggaag taaatgggac tttaaaagca atttatgctc    39840
ttttatagtg aaattatccc tcttactatc ccgaaagact gttaccttac aatatcctcc   39900
actcctttcc ccctgtagtt actatagaga tgactttcg gttcttcact gccataatga    39960
tcaaaatcct aatcatgag attttttatca ttccaggcat gtgaggttta cttgatgcat   40020
aaaaccgcaa gtactttttg ttgtttttta attgttttt ctctcttatc ttcttgaaag    40080
tctaagtaga tcatcattt tgatgtctta ttagtagcaa ctaataaatt ttccctgtat    40140
cttctcagca aaagaactca agcagagaca gaagattaga actaccattg gtagttttgc   40200
ttcctatgga tatgttcaca tacatagaaa tttttacaat gacctttta tatatgtatt    40260
tcagaatttc agaatggcct caatgcctta ataggaagaa atacttgaaa ttttttaatt   40320
agggcttggt tttgtgagga gctagtaaag gtttttctct ttcagcttta gcttgtttct   40380
gcggaggatt ccgctcttc tccatcagtt tcatagccct ggaattgtag aaaagctctg    40440
gtttcaagac cattgatatc catttctgtc agggtgagtt ttaaattat ttcatgatgc    40500
aaacaatata ttgaacaaca ggacatgaac ttgttcttat tgtaagtggc tgaatttttt   40560
cagtaaagca catcaaaata aaatataccc caattgctag ttaagaccat gagtgacaga   40620
ttgaaaatag cttgtgttat tctcttaaga aaatatataa aaattatcat ctcatcaatc   40680
tttaatgttt gttttataaa tctaaatgtt tttatattgt ttcctaggaa atattaggtc   40740
taatttttta ctttaccacc agctgtcttt tattttactc tttttttgag acggagtttc   40800
gctcttgttc cttaggctag agtgcagtgg cactatctcg gctcactgcg acctctgcct   40860
cccgggttca agcgattctc ctgcctcagt ctcccgagta gctgggatta caggcacatg   40920
ccactacacc aggctaattt tgtatttta gtagagacgg ggtttcttca tgttggtcag    40980
gctggtctcg aactcccgac ctcaggtgat ccgcctgcct cggcctccca gagtgctggg   41040
attacaggca tgagccaccg cacctggcca gctgtctttt aatataacat tatgattaat   41100
tgtgatgtc cattaacta agcggagagg aaacatgctg tgaaccatg tgtgagttat      41160
tcattgtacc agaaaggcaa atgatacatt ttatcctaaa attcaaattt ataaacatct   41220
taacacttgt gatcattaaa tactactaat ctagcatata aattatattt gtaggcgggg   41280
cacggtggct cacgcctgta atcccagcac tttgggaggc tgaggtgggc agatcacgag   41340
gtcaggagat cgagaccatc ctggctaaca tggtgaaacc ccatctctac taaaaataca   41400
aaaaaaatta gctgggtgtg ctggcgggca cctgtagtcc cagctacttg ggaggctgag   41460
```

```
gcaggagaat ggcgtgaccc caggaggcag agcttccagc ctgggcgact ccgtctcaaa   41520
aaaaaagaaa aaagaaatta tatttgtaat attctactaa ccttatatca ttttaacttt   41580
ttatataact ttttttatttt accaaattaa gttaacctttt tatagcccttt ggcttatact  41640
aaacatccta acttttttgt ttaattgtat tagttttttaa gttattgccc cagatgtcaa   41700
gtaatgttgg atttttctata taatttagg atatattgca tgaagtcagt tagtatttac   41760
atttaaaact aaaacaattt atactaatac agtttataca tttcatacta atttagctac   41820
agttggataa atatttaatg gaacaaagta aatcaaagta ccttttcaaa tgaattggaa   41880
attaaatcca cataacaatt ttttatgacc acactattac agtgtgatgg catgccaaat   41940
gatcataatg tggaattatg tatttcttca ttggcttttca agattctgtt ctttagtttg   42000
tgggctcctc tccaacttgc ttgtctcctc acagtttagg cgactgtttta taattcttgt   42060
ccatcctgca taaacacaca cagtcaaaat gaaaaaaagc ttctatcagc agatctgtgc   42120
ttgctgtaca gaaatgggaa acaattgaa gtttgcatta tcttttttct aattaccaga   42180
tcgtttttgg agctatttag gcatacgctt ttaaggaaaa aagaaaaaaa gagtgtacct   42240
tttgtttcta acaaaggttg ttatctatat tattgaaata aaaaattggg gatagttagt   42300
acaaagtatt tagaaatagg aattaaaatc ttaaaataac ttttcatagc atggacaaga   42360
cttattaatg tctacctcaa taagcaaatc atttaaaaat ttttcatgta tatttgctgc   42420
catgatgtgt tgtgattgct taaataacca atgaatgaag atcaacaagg atttaaatga   42480
agaagaatat ggatttaact atttttctcct gtgaaataag ttcatattta caagtttttga  42540
ttttcagaaa ttagacaatt attttttaaag gctgggatga caacttctgc ctcttaccaa   42600
gaagtcaaag cacagttatg tgaattcatc ataaatcaca tcattttat tatattttgt    42660
atttataatt gtattgtgac tacttttaaaa cctgttataa aataaaattg tttttttaata  42720
ttttatttta gaattattag cattaataac aatttgaagt agtttacaca ataccctgtga  42780
gttttatttt tgtttatat tgaaattaat tttagttgct ttacttggct tcattgctat    42840
ggatgcattc tctgtgttac gagttagcag atcttttcctt ggaactgaat ttaaaagcaa   42900
gcatttggct ccacttaaat ctctgaaaat gcaacttgtt cttttgcatttt attacataat  42960
tcgctactta tggtacagaa atggatacaa tacaaaaata tttccttata agatacactg   43020
tgaccaatga gctttttaaa tagctgtaat cagtaacatg tatttgactt ttcaaaacac   43080
atttctggag ggatatcagt gctttatttc cccaaatatc tgaatccctta tgctttagta   43140
caaaacaact tctgaagaat ttagtaacca tatgtgttga tctcttgttt ttctaactag   43200
tcttttcataa gaaatgacta gaatagcaac agggaaatga ttgcctttta aggttttttgt  43260
ttctcaatat aaaattttgg tgaaccatt ttattgataa atacaggtat ttttactttc    43320
ttaaatcact tgatttaaaa ttactttgat taaatatgca tataaagtca gttgtttta    43380
actctcaata cttatcaaaa aaattttaact tgctgtacat tctgtataaa cctaattcta   43440
ttcaactaaa attattttaa acatttaggt gtcagacaaa gagaaaattg accaacttca   43500
ggaagaactt ctgcacactc aggtaatcat gatgactaag aaaaactagg gacttttaaa   43560
aattatattc gaatgtaact ttggtgtatt ggacatttat tttttcaaca gagcaaaatt   43620
tggaaggtgt aatgatagaa ccttattatt atcgatagat gcaaaagcta attgagaaat   43680
aaggaataaa gacagaacta gataagtatg gagttaactc atttatatgt aaaaacctat   43740
tttgagtgaa tcttatgccc aaaagggaga aagtggcttg tccttatata aacttatgct   43800
tgcatttttta cattgataag ctaatacagt taaagaaatt cgagttgagt ctaccacatc   43860
gttctagtgg gctctcagga accttttactt tgcttcgcaa gtctgaaagc agtcagacaa   43920
tgcttatcta aagctctttc tggcactact tagaaaagct attttcttat agttggtgat   43980
aaaattatta ctttaaggac ctattttgt caatgtaatg agtgggtaac attctagtac    44040
aaaattaccc tatcacagcc aggcacggtg gctcacgcct gtaatcccaa cactttggga   44100
ggccgaagtg ggcggatcac aaggtcagga gatcgagacc atcctggcta acacagtgaa   44160
acccccttctc tactaaaaat acaaaaaatt agctgggcgt ggtggcaggc gcctgtagtc   44220
ccagctactc aggaggctga ggcaggagaa tggtgtgaac ccaggaggcg gagcttgcag   44280
tgagcccaga tggcgccact gcactccagc ctgggcgaca gagcaagact ccatctcaaa   44340
aagaaaaaaa agttacccta ttactcaatc atcagttttt ctatataggt gacactgaca   44400
tgcattaatt aacttatttt ttaaagttca aagagttact atcagctggg catggtgggt   44460
catgcctgta atcccagcac tttgagaggc tgaggcagga ggatcgcttg agcccaggag   44520
tttgagacca gcttgggcaa cccggagaaa ccccgtatct ataaaaattt ttttaaaaat   44580
tagccaggtg tggtggttgt gcctgtagtc ccagcaactg ggaggctaag gcgggaggat   44640
cacttgagcc ccaggaggtc aaggctactg taagccatga ttgctccctg gccaatagag   44700
caagaccctg tctggaagaa aacaaaaaag aataagaaaa agagttaatc ttggatctct   44760
tttttgtgaa aaagtgaaac gactacaagt tgaatatctc ttatctgagg tgcttggggc   44820
cagcgtgttt tggatttcag attttttgaat tagggataat cagtcagtag tatgttttga   44880
gtcacaggtt tctttggtat ctatttattg agtctcaaac ctcactatac gctagactca   44940
cctgtgctct gagtggcact atatctatgt ttttaagggt tcctagccag gtgattccaa   45000
tctgcaacca ggggtaagag tcattggtca caaagcatag cctctggagc acattagaaa   45060
tgcacattct tgaccccatc ccataccttc tgaagaatca gaaactctgg gatgaaactc   45120
agcaatctgt ttttaaatgc cctcaagata attctgatgc attctaaagt ttgagaatta   45180
ttgttctaga gctttgagag acagctcaat agcacatctc ttcaggatgg ctacaaattg   45240
gcatctgtac caaaatgttt ccatcccag aaatgtgata ccccaaaatt gatttttgt    45300
ttacaaagaa atgagccagt ggaaattcta ccctcttata tgccttgata caaacccttc   45360
aatttgtgca attgtaattg tcagtcacta ggcactgata gactgtatta tggagaattc   45420
actgggttat ctatatcaat gatgtccaat agaaatatac aagccacctg tgtaattttt   45480
aattttttaca ttaaaaaggg gtaaaaagaa acgtggaagt agttttaata atatatttaa   45540
cccagtctat cccagatagt atcattcaa catgtgatca gtataaaaaa tatgaatgag   45600
gtatttttaca cttacagcac aaacctcact caggccagcc acatttcagg tgcttgataa   45660
ctacatgtgg ctagtagctg ccgtgttaaa caacacagat ctaatcctta gatactacca   45720
gaattttgtt aaatatacta ttactagata taaatgagtg agtttatgta aaaatatgtt   45780
tatagtagag tctagccagt agtctgcct gtctcatact atgtaggtgt tcaatatgt    45840
tcttt taattggc ttgagttgga cttgctgtaa ggatagaacc attctgttgt              45900
gttaattact ttgttcttga aagattccaa taagctaaaa aaattgtaag gaatatttt     45960
tattataaaa ggcatattat aagttggaca taaacattct gctggttgta agaatggggtt   46020
atttttaata gttttctctg tgttgttaat gtttagagaa gaaataaaag ctgggaagac    46080
aaattagaaa ggatcaaatt tatttgagac ggaaaatgtg tagacaagca actacttaca    46140
aaaaaaaaac ctgtttagac atattagtct tctttaaaaa tctgtttttta tatgattctt   46200
```

```
tttgattttg gtgttttgtt ttgttttttt gtcaagtagt tgcttggcta cacatttttcc    46260
ttctcaatta aatttggtcc tttctgattt gtcttccag  cttttttttgt cttcgccagg    46320
ctggagtgca gtggtgcaat cttggctcgc tgcaacctcc gcctcccggg ttcaagcgat    46380
tctcctgcct cagcctccct agtagctggg actacaggtg cccgccacga cgcctggcta    46440
attttagta gagacagggt ttcaccatgt tggccagaat gctctcgatc tcttggcatc    46500
gtgatccgtc tgcctcggcc tcccaaagtg ctgggattac aggtgtgagc ctctgcgccc    46560
agcctatatc attttttgaa ataataat   attatctctg gacatggaaa cataacaaaa    46620
catagaagag tttgagcctc tgacagccct ctattcaaaa ccctgctcct ctactaagtg    46680
accttggtca ggctctcaga tattcctcgc tctttattcc tagtctgtgt aattcctgca    46740
ttatggggtt tttgtgaagg ctaagggagt taatgcgttt gcaccactta ctaaggagtc    46800
tgtcacataa tgcatgcttg ggtactgcta gctattattt tatagcatct taattaaaat    46860
ctaaaataat gtgaagaaag ggaagaattt gaattttgt  taagtggccc tgtaatgtga    46920
agacttaaaa ttttgatata ataggaaata ctcccttcta gaatgtattt aagaactact    46980
tctttaaatt cttacgttt  cactatttca aaataatttt ttcaatgtga gtagcaagga    47040
attttccaag tgaaattctt aattatgata gaaaattaca atgatttcca ctgtttgtaa    47100
gagataaatag tcattgttta ttttattcct aatgttttcg tagatgcttt taaaatgtaa    47160
tacatttttaa ataggagata tgacttcaag attttggaag attttaattt agacttaata    47220
ctatttgata acccatcttt tgcttatata gttcacttta ttattttatt gcagttgaag    47280
tatcagagaa tcttggaacg attagaaaag gagaacaaag aattgagaaa attagtattg    47340
cagaaagatg acaaaggcat tcatcataga aagcttaagg tattctaagt ttgtcttgtt    47400
tattctcaaa attttaccgc ttaacgttgt gtgttcatca gtaccagttt ctaaggagct    47460
gtaaagtatt ctgtcatcct tttcttctta acctaatgtg cttggaggat gggaggatctc    47520
ttcctatatt aagacatttt ataagttgta gtctccaaat acttgtttta tactatgccc    47580
ataaaatctt tacacttta  agagttattt cgtgtgaatc agtttatttt tctgaaatat    47640
ctagtttatc tctaggctta acttttacat aaaattttat ataaaatcag aattgttaat    47700
tgatggacat gtaagtgact tatcatcatt gcttttacttg tatgccagtg aatgattaga    47760
ccactttctt cagttttttaa aaaattaaca cttttcttct aaggagagct ttcttaggca    47820
tttcaaagaa cttttcgaaaa agtgtgtgct ggtattgtta ctatcagcac attggtgaac    47880
ttatttacca ataaatcaag tcttactatt ccccacccaa ctaaaccaca tgtgctaaat    47940
tgaattgaaa caattattta acttaaatct catataagta agcagagttt atatgtagca    48000
aaactgcagt aaatcatggc atgtacattc tgtagtcaag gtccaaagat aatacagttc    48060
tagcttaaca aacatgcatt agtagctttg actataaatc atgactgcat aaaacagata    48120
acatgactat ttacaagtgg cacttagaac tgagaaaagt catttccaag tgctaatata    48180
tgtagagttt acctcagaaa cagtattttc tctcataaaa tgcatggca  attaacattt    48240
tttggtttatt tttaggctgg tgggttggca attgcttgcc atttaatttt ttctagggat    48300
taagaaatga aaggaccctt aagccatcat tttgctcctg ccttagcatt aaaacttatc    48360
cataattatt aaatgcttga tggtacccct ttttttcagg cctgtgtatt tttttgttca    48420
ttcattcatc aaatttacat gaagcttgtt acacgcaatg caaggcacca cattcatttc    48480
tgattctaca gcaagaaacg atacaggata tttgcccttg ctacactcat atttcagcct    48540
gcccagttgt cagtggatac ttaaccaccc ttactggttt aacagtcttc ctggtttatc    48600
ctttattcag atgcttgctt gcacgtgctc tctgtcctct ctctttctct ctcatgcatg    48660
cctcaaactt agcaaagaat aatttcattg tcagttggtt acctgaccac cttttttttg    48720
ccttttggt  gttaatggtc ttttcttgca ttcagtatta gctcatcagt attaagtaat    48780
aattccatc  ttatttaatt agaatgttag gaaatcctga attaatttac tttattaaat    48840
cattgtatct aaaataaactg aatgagaaat ggactttaa  tctgtaccgt tttagttttt    48900
acgatgaaga tgtatttatg taatttgaga aaacagtaca atgattatgg aaaaacaatt    48960
tgaatttatc acttttttct cttgacacat ctgttatatt tttttcttta cttttactgt    49020
tttatattat aacttttaa  aattttaca  gaaatctttg attgacatgt attctgaagt    49080
tcttgatgtt ctctctgatt atgatgccag ttataatacg caagatcatc tgccacgggt    49140
atgtgaaaaa ttgatagtga acttgccaat tagcaaaaaa agaagcagct tagcttccta    49200
aaaattatgt gtatatatgt acacatacac atatatacat actagatgta ggcatttata    49260
ttttttatgt aatcttacat gttccaagta atgtcttaag caatattatt tgactatttt    49320
agttcattat aaatattaat aaatataagt acattatatt tatgagttac tgtatgtgtt    49380
ataaaggaag atatttggct ttatatgtct taatattagt aatatttaaa tactgaacag    49440
tggattaaat tagccatatg cgtgaaattt aagctaatag aattgaaaat gtgtttgtaa    49500
acagtaaact agctatggaa aagatttatg gaaagttaat aacctggttt tagaaatact    49560
ggtttaaatt agcacaagtt tttaaaataa aaattaggct ataaacagtg gatccagtta    49620
tagttttgct gttcctattt tcaatgtgca cacatgcatc aatcaccatt tttttacgga    49680
ttttaaaaata ttttttcacc tgtagaaatt ttaaaagact aaaaaactca gagcagcatt    49740
acaaataggt tttaattttta atttggtatc agaaaaatat gaataagtat tctttgtttt    49800
gtgggaaggt tgttgtggtt ggagatcaga gtgctggaaa gactagtgtg ttggaaatga    49860
ttgcccaagc tcgaatattc ccaagaggat ctggggagat gatgacacgt tctccagtta    49920
aggtaagaac ataggccgtc tcagtgaggt tccttaggag agtaactgct tcagtgagac    49980
ctgttcattg tgttgaaatg aggacttta  accaaagaaa gctttgatac agtgatttg     50040
gaatgatccc tagtgtggaa atcagtagaa ggcacagcca ggaggccagt gtggcaggag    50100
ctgagtgagg ggagagtggt aggagaggat gacagagacc cagttgggag gcctttggat    50160
tttattctga ataagataag agagaagtta agagaatgag aatattggaa gtggagtcaa    50220
tgaatataga taattttcta gttttattgt gacaaaagag cagagaaatg aagcagtagc    50280
aattgaatat tgttgaatta agggaaggtt ttaacccctt ttcctgttta gaaaaaaagt    50340
gcagctcaac accagtgctc atttaatttt acgtaaacac actctctgaa gctgaagcaa    50400
atctgactaa ttttcaatgt gaaaataaaa tataaaaact gttcttagag ttatttctaa    50460
acagtactaa catcagaatc gtcccaatca tcagaatgtc tgttttttaa aagtcagatt    50520
tatcaaatca atcttcggcc aacaacttttt tgagaatgat gtaacatca  cacataggaa    50580
tccgcatttt tctaggattt gacattttca gctattgaaa attactatat tttgtaaatg    50640
gacgtaccgc tactaaaaac agaatgcttg aaatagaatg tcttttgttt ccaaagtcag    50700
tacactagag ctatgtgaaa ataatcataa aagtgaagat attttatggc agagttatgt    50760
tggggcaaat gctgcagctg caagcggtgc tggcaaatat tgtcggagca agtgggaaaa    50820
ggattaaaga tgtttatatg ctgattataa tgatctaata aaggggggaa atgatgcaag    50880
agagagggaa aattgcaaga gcaaagttac tgaggtgaag gagattgtga cttggtgtac    50940
```

```
tagtccatat ctgggagcac tgacaatttc tccagggtca caggaagaag gtatgggget    51000
gcagagtctt tcattgaaca gatatttacg gaatgcttaa tatgtaccag tagcattcta    51060
ggcaatatgt tggtaaacag caacaacaaa gaagaacctt gccttaatgg agggtatgtt    51120
ctagtagagg gagacagata atagataata aatataatac ataattgtat agtaggttag    51180
aaggcaatag tgttgtacaa caagaaaaag cagaaccagg cagaaccagt gagggtgcca    51240
gagtattcat agattgcatt gataaggtgg catttgaacc aagatttgca gaaagtgagg    51300
gagtagtcct gaggatatcc tgtgttcagc aaggagaata gctgatgcaa agcctctgag    51360
gtggttgtgt ggctgtcatg ttcaaggaac aacaaagagg cctgtgtggt caggtcgggg    51420
tgaagagcta gccatggtcg gggcaaatga tgacattaga ggaataatga agagcgggga    51480
ggaacagatc aataaggcct tataggccat tgtacagact tccgttttaa gtaaaatgaa    51540
aagccagtgc aggatttcga gcaaagtaac aaaagtgcct tttaaaaggc tgctcttttg    51600
aaaatagttg tagccaagat gtagaaccag ggagtctagg ctactggagt atccaggtga    51660
tacttgggct agggaagtag cagtgaaact ggtaagaaat ggatagatta taaatgtgtt    51720
ttgaaagtag aattaacagg atttcttgac aggtttgata ttgagagggg agagaagaaa    51780
agcaatgggg agagagagag agagtgtcaa tcatcaatga tgcctccagg gtctttagcc    51840
tgaacaaatt gaaggatgta gtttgcatgg aagtctgtca gtggatcagg tttgggggaa    51900
gaagatcagg agttcagttt tggacttgct gagtggtgat aacaagcagt tgggtataca    51960
agtttagaca gaggtgtggg ccagagacat acatttagga gtcatgatca actatcctaaa   52020
agtagtatt aaagtcatga tcttactgga gaagatcttc aagggagtga gtagagatag    52080
agaaaacaca gaagcaagca gtatattctg ggcactctga acattaagat gttgagggaa    52140
gagaaaataa caaaggaatg tgtgaaggcc caaccagtat agtaagaggg aaagcagagc    52200
aggacagtgt gcgcaaagtc aggtaaacaa aaagaaaaca tggaggagga gggagtgctc    52260
agtgaggtca catgctgctg atccatcaag gaaggtgaac atagaaacca gtcgttgagt    52320
tcaccagtgg aggcaagaaa ggggaacgtg tggaagtttc cttctgattg cttccgctta    52380
ctcagtgaaa tactaagcca gatgatcagc tgttaattag aaaggagaag agattaaaga    52440
ctgaggcagg aagaaaaagt gaagtctgtt aacagatcgt ggtgactcta ggagtgaatc    52500
agtggagaaa gtcaagtgat attaggatta ctgaggtgga ctgaagtccc tttaagttct    52560
gtggacataa atttaaaatg aatcattatg attgtgtttt gttttttta tgtttagctg    52620
gtggggggta ggtgtagaat aattggaaga ttgaaattac caagaattat ggcaagaata    52680
gtgggagaaa gacagtgagg ctgatgctga aatcttcaag aaatgaaatc tgtttacaag    52740
tgcaacaggg tatgggcagc ctagtgtgat tcatctagat tgcacttttg tgggtctagc    52800
tatggattga atcgtgttat gtgttactag ttctgtgtgt ggtactgtgt gactgtacca    52860
gactttacat atccatttta ctaccgatgg gaatttgggg tacatctaac ctagagaaaa    52920
aaacaaaatg aacctcagac tacacctcat atcctgttca ataatcagtt gtaaaaacat    52980
gggagagaaa cctacctttt acattgttac tagcatccta attgtagaag ctgtggatga    53040
tacttcaaga agaaattaat tttgttttgg caggcagggt gtggacaggt ttccttgaaa    53100
cagatgaggc tggtctcttt ccggtttgtc attagtccct tagtgtttac tagagcttct    53160
ccttgaccaa ccctgaattc cagtttttg tttcctaga gcagtgaaag tgccaaaacc    53220
ccagcttagc attttaacct cctagcagc ttcttctgc ttggtttcct aaaatgtgaa    53280
tgccgtgaaa ggaaattgtg cgcaggatgt aggggttttgt tttgttttgg aggtttattt    53340
ctgcagttca ttttttcttg ggattgtggc accttaagac gtgactactt aataactcgg    53400
aattccaatc ttgtctactc aacccagtga aactgctaca cattttaagt ttttctcttg    53460
ggcctttgcc ctgtgctaca aatcagcaaa tcctctgatg gaaaatagct aacagctttt    53520
ccaacagctg tttattgttt taaatttag cctgtttagc taatctcagt agaaggaatt    53580
gtatttttaa agtaaaataa ctatagagaa gctagaaagg tgtcaattag gcatttagaa    53640
gttcttgtga aaccactgac tgttaatata cattgctata acatttcttg gctgggtgca    53700
gtggctcatg cctgtaatcc cagcacttg gaggctgag gaggcggat cactcgaggt    53760
caagagttca agaccagcct ggccaacatg gcgaaaccct gtctctacta aaagtacaaa    53820
aaacttgcca ggtgtggtgg cgggcatctg taatcccagc tactcgggag gctgaggcag    53880
gagaatcacc tgaaaccgcg aagtggaggt tgcagtgagc cgagatcatg ccactgcact    53940
tcagcctggg cgacagaatg agactcggtc tcaaaacaaa caaaaaaca aacaaaacaa    54000
aatttcttac ccaaatatca ctccttgagt gaagcctgtc gtagctccct tatcatcagt    54060
tccattctct tctgtggcac cctaggtttt gtcactctct tctattatgt ctgtgtatat    54120
ttctcccagc atgtgatgag gtctaaaact gggacagtca gctctgtgtt tccccaccta    54180
caacacctga cacatagttc actctctata gaggttgaat gaatgaattg tccttttacct   54240
aaattcatct ttgaggttaa atgcaaggtt tccttttagt gtttcaagtt ttagagagat    54300
gattttggge ttagtgctgt gtatagcatt gactggggaa agaaagaggc agcagcattt    54360
taggtcataa gcgatataaa ggaaccagca ttcttgttgg gaaatcacaa catatatgac    54420
atatatacaa acaatacaaa tacaaaatta ttgtcttgtc agaactacca tgttgacagc    54480
ttcagggggt gccccagcag tagtgtgaag ggactcttgg atttgtgcaa tgcagtagcc    54540
ctgtctagac cacatacggg ctgtgggaat taatattact tataaataca tcattaccct   54600
tcagtttct gttactatca ggtgactctg agtgaaggtc ctcaccatgt ggccctattt    54660
aaagatagtt ctcgggagtt tgatcttacc aagaagaag atgtaagtaa aattcatcta    54720
aggttgatat gtgtaatttt ataacctgga tgagcttata aagacagtt aaagaatatt    54780
tgtgaattaa gattttctta gattttctta ggatttgtg ttttccatta gcttgcagca    54840
ttaagacatg aaatagaact tcgaatgagg aaaaatgtga agaaggctg taccgttagc    54900
cctgaggtaa gggttgcaat tcatttcagt gacgttttat ggaaattaaa tgtttatgat    54960
ttcaaataaa tcaaaatcta ggtattatg tttagattgc tgctatctag atatgatagag   55020
ctttaaaaa aaaatccaaa taatatatca ttttgtgggt aatttccag aataattact    55080
tttaggatca gagaaagaat accattttg tgagcgtctt atctgaatgg atgagatata    55140
gaattttag aatacatttc accaaaaaaa attcttgaca aattccccc aaactttagc    55200
attgttttat ttttattttt cctgagtaga ccatatcctt aaatgtaaaa ggccctggac    55260
tacagaggat ggtgcttgtt gacttaccag gtgtgattaa tgtaagtata tacaaaacat    55320
gtatttatt ttattcttat tgtgtgaagc attataatg acattaaaa cctttttctt    55380
taagactgtg acatcaggca tggctcctga cacaaaggaa actattttca gtatcagcaa    55440
agcttacatg cagaatccta atgccatcat actgtgtatt caaggtaaat catatcaaaa    55500
gatttaatg tactgatatg ttttcttctt tagcaatcca agcttgcat taaatagttt    55560
gtgttatgta aacatacaag ataaatgcat ttttgccttc tcttcgtatt catttattta   55620
gtaaattaaa ttgaagttga aattatttg ataagttta cataagcatc attgaaattt    55680
```

```
ttatcggcta ggatttcttt ttagtaaata acgtaaatgt attaaaatct ttccttgctat    55740
aatgtagaca caggggtata atttgtactg agttttaaaa gtctactttta catcttaaaa    55800
ttccacagtg tcattttttt attttttttca gatggatctg tggatgctga acgcagtatt    55860
gttacagact tggtcagtca aatggaccct catggaagga gaaccatatt cgttttgacc    55920
aaagtagacc tggcagagaa aaatgtagcc agtccaagca gggtgaggtc aaattcttttg   55980
ttgcgagaat agattcttttg taaaagctcc agctgtgata gggatttgtt atttaaaaaa    56040
acaacaacaa caacaaaaaa acaccttaca actaagatttt attacaatga aaggataaag    56100
caaaatcaca aaaggaaatg gtacatggta tgaagtctga aggaaaccag gctcacgttt    56160
ttccactagt tcattcccag tagactctac tgggcacatt taattcctcc agcaacaagc    56220
tgcttgttag agactcagct cctaaggttt tcatcggagg ttagtcattt cggcaccctc    56280
atgtaccaaa attatttcat actcccaaaa ggaaagcata tgttataatt aaaccacatt    56340
acttcagtag tgagccactg ttatataagg aaaggtttat atcagtgtag ggaactgttt    56400
accagttaag ttttcagata ccagccaaag acaggcaggc cttttttaagg acagtagtct    56460
caggcctgct gtgttaaccc ttttctaggt agccaccata acctctgttc tgctttcttt    56520
ttaagggtaa ggcctgccgt ggcattaatg gttctgatat ggagaagggg agaagtgagg    56580
tagaaacaaa tttctgtggc ctcctcccca tctttcttca ttcctttcat ttctttcaac    56640
tctaggatag tgagtttata tttcttctga gatgcaactg aagcttattt cagtcctttt    56700
tgtataaaag attcagcatt agcttaggtg taacttgtct taaaggaggg attctcatcc    56760
cattattaat ctgaatgggc ttcagggggt agaaactcta acatatgtga aaggtctcta    56820
tgcaaatatg cattttttctg ggtacatagt ctttttttttt ttttagtcac atttagaaat    56880
ggattttttga tcctaaaaga gttgagaagc agtggatcca aatattaaag aagaaggtgg    56940
gaggggagga aggagtaaaa gaagacaatc cagcttggtt agaatttaga tattgaaga    57000
aagtatggaa aaataataat agctaccatt tattgagtgc ttcatgcctg gcactgtatc    57060
atattgtccc ataatctcac caaccttttt gaaaaaatta agttgtttac ttaaggtcgc    57120
ataactacta ggcagcagag caggaattca aactaaggtc tgtctgactt taaagaacta    57180
cacatcattc cgggtttttcg atacgtgtgt tttaataata catttttcaat gtagtaaaat   57240
taaatgtatt ttttttcaaat agcaatggaa aaacattttta aatgcttttg tgcagattta    57300
tttaactata tacatgtata gcattatttt gctttctaaa ttgtatatta cgcttttaaa    57360
acttatgtaa actatatctc acattaattt ttcccacttt taaaaataga ttcagcagat    57420
aattgaagga aagctcttcc caatgaaagc tttaggttat tttgctgttg taacaggaaa    57480
aggtatgcaa agatggatta taataactta ttttttagttt ctgttgttttt caaataataa    57540
agagtaattt tcttgatgaa aatttgacca tcattcttcc ccaggggaaca gctctgaaag    57600
cattgaagct ataagagaat atgaagaaga gtttttttcag aattcaaagc tcctaaagta    57660
ggtatcttgt taaaacattt aaacatttta cagtaagaga gtagcttaaa ttgaactgtt    57720
ttcacttaaa acatcaggtt ttataactat tagtttaaca tcggatttct agaatttttc    57780
ccaaatagtg aactgtatct aataaacaag tccttagcta ctttttggca gaattgagag    57840
cagtttatca catggtacaa tacatactgg catgcttcct tggacgtggg cactgaaaga    57900
caacatagat atctgcctct tacttttattt tacttataaa gtggttttag aaaatcgacg    57960
ctttcacttt taaacgtgta catattctc ttacagtatt gggggaagatt ggagtggggt    58020
tgtcgaagaa gtatccctag atatatattg acaggagata agataagcaa aaagagctaa    58080
aggccagttg tattactgta tactaaaact ttatatgttg agtttctgga aatagaaaag    58140
tatgtttgtt cctaggttag tacggtaagt caagatagtt cttgcaaacc ataatcttac    58200
gtgcttttggg gagtgcactg acaacatata gaactgtgct gtctaatatg gtatcactag    58260
ttttgtgtag ttattaaaat ttaaattagt tggaattaaa ttaatttctg gaagatggct    58320
ttcttcatgt tctttttaaa ggcatggtgg ctcacacctg taatcccagt actttgagag    58380
gccaaggcag gcggatcact tgaggccagg agtttgagac cagcctgtcc aacatggtga    58440
aaccccatct ctactaaaag tacaaaaaaa attagctggg catggcgatg ggcagctgta    58500
accccagcta ctcaggaggc tgaggcggga gaatcgcttg aacccgagg gggtgggggg    58560
cggaagttgt agtgacccaa tatcacgcca ctgcactcca gccccgacga cagtgcaaga    58620
ttccaattca aaaaaataat aaaataaaat ataacattaa atttaaatta gttaaaattc    58680
aacaaaattc aaaatacagt tcctcagtta cactagccaa acatttccag ggctcaataa    58740
cccagtgtgc cagtagctac cgtattggaa tgtttttcctc ctcacataaa ttttttattga   58800
acagcactgg tatgaaaggt aagagtggct gttagcaagc acattcgcag acttggtggt    58860
agtattgttg tccttttttgt catttttaata tactttagct cttgttattt ttttttaata    58920
ggacaagcat gctaaaggca caccaagtga ctacaagaaa tttaagcctt gcagtatcag    58980
actgcttttg gaaaatggta cgagagtctg ttgaacaaca ggctgatagt ttcaaaggta    59040
agttggattt tttaaagaag caagcaaatt aagacatttt attagctggc aatctttggc    59100
atccatcga ttctgtactt cttttccttta acagttgctt ggtagttcat ttacaattag    59160
acagtatctg gaaaatagaa gaatacaaac cttcagtttgt tatacaagaa caagattttt    59220
cctttcagag gaaacatctc tagaaacaca tttgcagagt tcaaacagat gagaacattt    59280
gctagtgctt ggaagtacac aataaactat agagaattct agattcaccc tgttgaggat    59340
gaaggagcag atgtgtttggg aagcagagcc ctctgaactt cctttacttg gcaccatttc    59400
ctgaatccca cactttcctg ctcagtgtct tttatcggaa gagaatatat ttgcttttctc   59460
ttttcccata tgtaaatcct acctgatcct acctatttat gccagttagt ccctcgtgcaa    59520
tcttgtatta ctttcatttc cattttacag aagaggaaac agaagacagt tacttaccca    59580
aataacttat cctattaccc agtgtcacac aacatgggta ataggccag gatttggctg    59640
ttggtggtac aactgcagag tccattctct cagcagctct atggtactaa actacttcag    59700
ctgtgtgcta atggatttaa catggagaaa ctagaatcag ggagaatagt tttgaaagct    59760
attgcaaaaa tgaaattctg agacgttgag atcccagagt actaagggt cataggcgca    59820
ctctcagaaa ttcagttaat acagaggata tgtattttaa ccactttaac cactacatct    59880
ggaaagaagg agggtcatca aacttgaact tttccttctt cctcagcaac acgttttaac    59940
cttgaaactg aatggaagaa taactatcct cgcctgcggg aacttgaccg ggtaaatttt    60000
ggatactcgt gtatttgta tatatcttaa tttaatgttg tttgctaact aaatttatgt    60060
tgagaaaaa atcctgataag ctaaagtact ttggttttga ctataactac taatttgtaa    60120
gaatacatct ctaggagcag ttatctcttt cagtaattta aattatttat tatataacat    60180
taaaaatgga ttataagatg tcaaacaag tgttgaaagt gttttctgag aaggtaatga    60240
atgtgcttta aaggtttttgt agaattcgtg tattcctgta atttagtggg aattaaacat    60300
tgttttttcct tgatttttaaa atccccatta gttaataaaa cacagcatta atatatagtt    60360
actgatgtac taaattaata tgtattgatg ctttcacata acgtgaacaa gtgttatgtg    60420
```

-continued

```
aaaaactgca ttcaaacttg agaaggtaga tatttatgtc agtttcttg tccttatctg    60480
cataatggca ttcctaaaaa aaacactag aagtgcattt ttgctagtca tgtataatta    60540
aacccaaatt cagcctagtc aaaaacctcc ctttggttat ctctgaaaat catgacaggg   60600
taaatttact gtcttatgga aatcttactt acttgtattt atattgccta gaatgaacta    60660
tttgaaaaag ctaaaaatga aatccttgat gaagttatca gtctgagcca ggttacacca    60720
aaacattggt aagtatttga tattaatctc ttttctgaaa gactttactg tacaggttat   60780
aatgaaatgc taaaacttag attgataaag cagtgattta ttgttgcctt ggctcatagg    60840
caaaaacgta atagtatatt tttttggcaa tatctaacta cttttgtagt ctaaccagtt    60900
gaatttcttc atgttctttt taaatcttga ttctctttgc ctttttcttta tcttatacct   60960
aataaatacg taatcatgat ttctgtaaaa tcctttgggc agaagtttg tcaaattata    61020
ctttaggtaa atatcaacct gtcaaaattg atttataaag ggagttggta tatattttca   61080
ggttctccat tctgagtaag aacagttagt gctttctgta acatgtggtt aatatgttgt   61140
atacaaatca cattttgaac ttaatgctat taatacttga aattttaaa aatagcaagt    61200
aaatgcacct ttttgaaaaa tatgttaatc ttttctaagg caaactgtta cctcagttt    61260
atattttatg taagtttggc cattcctaaa ttcagtggaa tgagcacgg taaaacaagc    61320
tatgtataaa tagccttgac atttttgtag tcacatgtta attaacaaat tcctcatgca   61380
gaaattatct ttctaatgaa gactgtggta tttttaagaa tttattttg gagcagagct    61440
atcctcactg ccattcattg taaatatttt ctgtacctag tctattcact cagttaaagg   61500
ttatcaaaag tgagcctaga tagtagtatc tggtctgttt gaattcagca tcactagttt    61560
cctcatttca gtgcccttc ttcctcagtg gtgaaacctc ttctatcttc aagtagtcca    61620
catttgcctg ttttaatct ccgttcctta tccaaaaaaa gagatctaat tgtatctatt    61680
cttgttgatt aactcaaacat tgttatgaca caacttagtc ttgttttatt gtatcttagc   61740
ccagttccat ggcttttgtgt cagtcagctt tcaagttaca aagagatata taggttaca    61800
gattgagtat aatactagtt gccttgctag attgtatgag ggcattaat gtatataaaa    61860
gtgatatgta aactgtaaca actaataatg ctgtttatgg ggagaaaatg tggtccttct   61920
ataaattaat ttttggtatc atcaaatgga aaggttagtt ttgtttggac agagcaaccc    61980
tgaaatcaaa gtatttcttc actaaagtga gccttgaaga taaatgtaat ttatttaata    62040
caaaggtaac tgaagagaat tgtgagggga cagtgaacgc ataccaccag attgcccatt   62100
gaaaaggcaa cggtcagatc tgggacatct ggctgctaga gatttacttg tgtaagctgc    62160
cggatcatat atgattctct gtgttttcag actgtagagg ctgaaaaaat gttatgttaa   62220
cgcaaatata aatcagagta gcaggtccaa gccttagctg ttcataccac attgaattca   62280
agtacattac accccaaata ttttccacat attttattat tttgacatag ttgatgttgt    62340
cttgaagttt ttattggtat cttttttgctg aataatccta tgtgatattt taggacactg   62400
cctaaaatgt ttacaattat ttaagtcata agactgtttg atctatattt ggttatctgg   62460
aaagtgttaa aagcatttta tgtcataaca tgacagtttg ttatttcctt tagacattcc   62520
actgtccttc agttaagttt taggaaggtt attaggggta tagatttgac atataataca    62580
ttatagtagg aaatactcac tcagcatttt tacgctgtgc ctggtttca agagtgaatc    62640
actgacattc agaaggagat attgatatat cattaacatc atgtgaccag caatgtagac    62700
atatctttc tagaaggata gctggctagc ttcacagaaa tacatttttt ctaaaaatgc    62760
tactatggta cattttaga aattctcgga cttcagaaat caaagatttg caatatcata   62820
atttgaaatt taaaacatga ataagtgtta aggcagaggc aggaatatgg taagggccac    62880
gagatgaaa caagaaaggc gacacaggta gctgtgtcct gtggctttaa cataaatggg   62940
ggcaagaggc aggagataaa acagtaagatg taagcaaaat attgggttta ttaaccatat    63000
tcagaagctt agtgtgtatt ccataagcag taggggagg gtggtcactg aagaggatta    63060
ggtcaggttt gcatttttaga aaggtctttg tagtaggcaa aatggaatac aggcggagaa    63120
aactgtaagc aaggaggcag ttggcttttg caataattta ggcaagatgt gatcatggct   63180
taaacttgga tagtgagtgg tagtacaggt agagaagaga cacttgtgag atacttgaga    63240
ggttacctaa aagatagaat tgacaggatt tagtgattgt gtagataatg aagagtctat   63300
taaataatga gtatgtttat attcagtaat tacattgcta ggaatatatg caaatgatat   63360
atttgacaaa gatgaacaca caagaccttt caccttgatt tttaaataa atgtgaagaa    63420
atggaaagca atttatgtgt cccatttga attatatagt atttggttta tatagagcag    63480
attactgctc tatggataga agtagccttt gaaaagtata ggatgttgac atggaaaact    63540
aaatacaata tacttttaga tttaaaaaag ggatttataa aacagtatgt ataattatga    63600
accacttgtg taaatacaca caaatagtta cgtagacata atttttttaa taataaaacc    63660
ataaatagtg gttatcttat aaaagaggaa ctatgggtta cttcttacat ttcctgtatt    63720
ggttgaaatt attatatgga gtataatagt cctctacttt aaaataaaaa aaatccatt    63780
ttaaaagaa tttaattaaa gtggaatgta ggtaaagttt ctgtagataa agaaggcaat     63840
aaaactatta ccttattat attttgctaa ttatattttg tgtattagta gaagttatcc    63900
ctggttgatg gcaaaacctg gaatagaaa gtcacctata ataacacaga atatagtcca    63960
ggcacggtgg ctcatgcctg taatcccagc actttgggag gccctatgg tcggatcact    64020
taagctcagg aattcaagac caacctgggc aacatggtga aaaccctgtc tctaataaat    64080
atacaaaaat tagccaggca tggtggtgca cgcttgtaat cccatctact tgggtggctg    64140
aagtgggaga atcgcttgaa cccaggaagc ggaggttgct gtgagccgag actgtgccac    64200
tgcacttcag cctgggtgac agagtgagac cctgtctgaa aacaaacaaa caaaaaaaaa    64260
aaaccataga atataggctg ggaaaattgt tagatgatag cagcaagcaa taaggtagca    64320
gatgacataa ctagatgaag tggcttcaca gtgtaatggt ttttatgta acattgagaa    64380
ctgatggttc agaagagaga ctgggtgag gaggacttaa cttctacttt ctaactctga    64440
aggccattta actgctgaat agcttcatct cagcagaatt tgaggacaga ggacaatcac    64500
tttccttaag gaaaggtttg gaggtaagaa tagggaaaga gaatgagagt gtaaaatgat    64560
ttgtcatgga accgggtatt acaggagcac aacagaaatt gttggatgg aggggagcag     64620
tgggagtctg agacagagga cagcagcttg gcgatgaaag gcaggagagg ctgggcaagg    64680
agaagtgata acagctgcat ctgtggatgt caaagcagca acctcccttg agaaagttgc    64740
cttttagcttc tcgggatttg gtaatcagga ttttaaaaag ggtgtcaggg atatggattc   64800
ctggcccaca gactccaggg aaaataaca gactatgtct cttctgaagc aggatgagaa    64860
aaaagccctg gaggtcagag gctggatcct ggtcttcagt tcaactttca gtaatcttct    64920
tgagattgtg tataaagtgg tatctgaaga ggaggccctg acaggctgct ttcttcatc    64980
ttgctcctta aattctccca ctctctgtca ttaactcagt gactaaattg tctttgtcct   65040
tttgggcccc agtcatatat cctcctcaga ctctgatttc tttactggtt gtaactgaa     65100
agtgacctga aagttagcag tgggaaacca ggatctgtgt tgattgattc agtagactta    65160
```

```
attttacaca aaatgtttag taaatagtct tggagggtag gagatgttga ctctcctcac   65220
cagagaagtt cagctgggct tttggacagc aggatatttc tgctaccctg agatttgtgg   65280
ctatatccta aagggttgag attattctta agaaggatcc cctgataagc agagtttttt   65340
ttttatattg tagtattcta agtttattac ccaaataaat atttccttga gatttcaaat   65400
tgaaatagtt gtatttttt attagtgacc catgttcttt taagatgtct ttcaaggcag    65460
aattttcaac atgattatgc atcttttaca ttgttaccctt aatcatgaat tattgaaaaa  65520
ttttatctac agcattctat aacatctctg tgctgtgatc tgataagttg tcatatttat   65580
accaagaaat tttcagtctc agactctccc gtaagcacat gaagtatatg ttaatactag   65640
gcagataagt gtgcatgaaa agatgctcag aattattagt cattagagaa atacaacgta   65700
aaaccacaat gaccactata aacttactaa aatggctaca attttaaatg acagactata   65760
ccaagtgttg gcaaggatgt agaggatcta gaactctcat tctctgctag tggaaatgta   65820
aactgaggca aacatttcaa aaaaaaatta aacatgtaat taccatatga tccaaacatt   65880
ccactcttag gtatttacct aagaggaatg aaagcatgtg ttcataagaa agacttgtac   65940
gtgaattctc atagcagctt tatttgtagt agccaaaagc tggaaacagc ctaagggtct   66000
atcaacacaa gaatggataa acacattcat gcaacataat actacacaga aataaaaaga   66060
agtgaaatat tgctagatgc ggtgtctcac acttgtaatc ccaacacttt gggaggccaa   66120
ggcaagagga ttgcttgagc ccaggagttc aagaccagcc tcagcaacat agtgagaccc   66180
catctctaca aaattttaaa aaattagcca ggcataatgg cgtccacctg tagtcccacc   66240
tactcgggag gataaggtgg gaggatggct tgagcccagg aggttgaggc tccagtgagc   66300
catgaatgtg ccactgtact ccatccagcc tgggcaacta agcaagaccc tgtctcaaaa   66360
aaaaaaaaag tgaaatatta atacatacaa cagcatgatg aacctcaaaa taattatgct   66420
gggagtggaag aacaaagaca aaaaaagagt atatgccaca tgattgcatt tatataaatt   66480
tctagaaaat acaaagtaat cacagtgaca gaaagcagtt ccagtggtta caacttttga   66540
ggatgatgga tgcgttcatt atcttgactg gtgcgattta caggtatata cacatgtgaa   66600
aacttatcaa aattttaaat atgtacagtt tattataagt taatgatact tcagtcaagc   66660
tgtttttaaa aacaatatta tatttagatt tggtgctttt gatacttttt tatttcaggg   66720
aggaaatcct tcaacaatct ttgtgggaaa gagtatcaac tcatgtgatt gaaaacatct   66780
accttccagc tgcgcagacc atgaattcag gaacttttaa caccacagtg gatatcaagc   66840
ttaaacagtg gactgataaa caacttccta ataaagcagt agaggttagg atataattta   66900
attaaatggg taagaagcat tatctgaagg gagtaggagc tgtgaatttt agattttatt   66960
cccatcacag cctctatctt tcttttaggt ctttatatct catttattct ttattcctca   67020
tctctgtttt gggactaacc ttaatgttgc taccagttac tacggttata aaaatttact   67080
aattggtatg atgttggcct gagggtattg gtacttcttc caaagacaat atttaacaag   67140
caaattttgc ttgaatatga aatatttgct tgagtatttg cttgaatgtg aaatattttg   67200
aacattttct gtggattctg tggattatag agattccata aagaaaaatac ttaatagatg   67260
aagcatttca tctgagctca gttatactta aattatcatt ttcttaggat cctgacagaa   67320
gattaaacta ggaattatta aaaacaaaa caaacaaaa caaaaaacta ccttaaagaa     67380
tctatttctg ctaccatgta tcttggcttt atcacttaat agctgtgtga tccttttgcct  67440
agttgcttaa ctttcctatg tgttttttca tctataaaat ggtgacaata atgttgccta   67500
cctcacagca ttgttataag gattaagtaa gtaattatat gtaaaatact tagacaatgc   67560
ccagcccatg gtaactgctc agggaatgga cctgctgtta ttatggtcct catcatctga   67620
attgatccat catgtacatc accccataaa cagcgattgt tcaagctaag agtcagtgtg   67680
tcctgtgctt gtgtgtgagg ttgctcacaa aattgaagtc aatgttaaaa gtaattttgt   67740
ttttcatacc tatcttaaag gcagtgtcag tttctaatta ttcggatgtg atttcacccc   67800
tttcctatct tgctccagtg ttaacttcct tatctctgtt ctcaatttct tcaagcccct   67860
ttctaagaac tccagcagcc tccctgccta agttgcacgt tgctgagccc tggcagttct   67920
tgacacattt accccctgaag aagttagaga gctgctgcta cccccttcagt agctctcatt   67980
actggcacta acatttttttc tgcgcccctgt cccatgatag gatattttca catcctaagg  68040
ttcaagcagt ggaagtggtt atgaaagcat caattttttct ttccactgct gcttttctgtc  68100
cctcagcact aggtgtcatg gaaagaatgt agatctggtg agaaggtcag gaaacatgga   68160
tcttaatact caccccacca ctcactccgt attttttggac agtcacttttc ttttttaaaa  68220
tgagagaggg ctaaaatcca gcattaaaaa gcccacatag ttataagtag attttgttct   68280
tcattatttt tgacactgtg ctcttccttt caccgttcag atcattagga gttagctata   68340
atacaaagct gaatactctt cggctatgtt ttaaagtgtt ggtgcattgc ttcatatctt   68400
tgcttaaaga caaagctatg aagatgactg aatcattaag acatttaaaa ccttttgcag   68460
tgtgaaagaa gcagtcagac tcatgtcttta gaggttgaaa taaataaatg aactaacttg   68520
ggtgcaggc ttagaataca taccttatct tgaagagaca gccctgttca gctacagtag    68580
gtggtgtcat gtaggaatat gggtatatcc ttctcagtta gtccaagaga agccgtaaat   68640
gcagacttttt atatgaaatc tctcaatttt taaatattag catgcaattt taaaaatgag   68700
aaccgctata catgtctagg aaaacatacc aggaagccat atctgtcccc agcaacccgt   68760
gtgagacctc tacatcatgg tttatatttg ccttttttgtt aatgtagttt cacatatatt   68820
ttctgataag ctgatttatt tatcacatct gtttggcttg agctcgtgtt attttttcatg  68880
ttaaccattg aagtatgtag taataaatatg gctttttttc tttcaaataa ttataggttg   68940
cttgggagac cctacaagaa gaatttttccc gcttttatgac agaaccgaaa gggaaagagc  69000
atgatgacat atttgataaa cttaaagagg ctgttaagga agaaagtatt aaacgacaca   69060
agtggaatga ctttgcggag gacagcttgg tatgttgttt gtatactggg gtatcagcct   69120
catattttta tataacttct caaattgata cttttttcata ggagacttta tatgactaaa   69180
ttacattctg aattaaaaat aatgaagtaa agaaacagat ttatgatctg taatctgccc   69240
tttaatattt ccctgcccctt ctaaaatcac ctgttgctgt ttctttcttg gctatcattt   69300
cagaaaaaag taaaactttg cagtaaacag actctgataa acttctacaa attgtcatct   69360
gttagccatt ttatgggcct gtctgtagat aggtgcttct aatttttaccc tctgtgataa   69420
tgaaaggaac tacatgcgtt ggttttcagt ggattataaa atgttagacg cctaaaatca   69480
taacaccagc taccatgtat tgaatgctta ctatgtgcca ggaactctgc taggtatttt   69540
gcaagcatta tttgatttaa ttcttaacca tcctgttatt tgtcattgac agagctggga   69600
ttcaagcccc tctctaatgg caaagcctgg ttcctgacac cacctgataa atctttttgtt  69660
atgtagactg ctctcactac caaaatcaaa tctgttaagt gcctgctgtg ctcagagagt   69720
tactagaggt gttgttgaat tacaggattg agcgattttc tgggaaaatg cagagctggt   69780
tgtaattata attttgttttt aaagaagtgt ttgtcttat ggccgggcgt ggtggctcac     69840
acctgtaatc ccagcacttt gggaggccga ggtgggtgga tcacctgagg tcggagtttt   69900
```

```
gagaccagcc tgaccaacgt ggataaaccc cgtctctact aaaaatacaa aattaaccag  69960
gcatggtggt gcatgcctgt aatcccagct actcgggagg ctgaggcagg agaattgctt  70020
gaacccagga aggggaggtt gcggttagcc gagatcgtgc cattgcactc cagccaaggc  70080
aacaagagca aaactccgtt ttcaaaaaaa aaaaaaaaaa agaaagaaaa ccatatttat  70140
tcttgttaaa tgccttatta agactggctt actgagaaaa cagcttcatt tttattcatc  70200
caaaaattat aaaatttgga agccaatttt caactgtaat aaataacttt tatgattttta  70260
tagacctttt aaatgtctac cttattactt ttttcgttgc tgttaacact gggaataatg  70320
gttaataatt tttttctcct cattttttgaa aaggctaaca tgtaggtcac atggcaaaaa  70380
gcgatgaaca tgatctgaat tattaaaccc tgaattttga gtttctagat gttgcatttc  70440
atgtagttaa atttgtaata ttttgtataa tgtaaatgtg taatattacc cacgcacccc  70500
atatggttag cttgtttaat ttgggccagg agagaatctc cactctttat tttttagata  70560
gcaagctaac aaataagcag gcaagtaaaa gaagcttatg catttttata ggaaggatat  70620
attttttatgc tggtttatat acatggttat ttttccatat ttactaagct gtcaatttga  70680
ataaaactac taaaatgatg agatgtaaaa caagttggct tttctcttc ttgttatttt  70740
cagagggtta ttcaacacaa tgctttgaa gaccgatcca tatctgataa acagcaatgg  70800
gatgcagcta tttatttttat ggaagaggct ctgcaggctc gtctcaagga tagtaagtgg  70860
agacacggct tattgagttc tgagttcaca gtggtgaagg agtcatccaa ctttagtgaa  70920
catttgtaga aatagattga acatttcaaa gtctttgtca ttaatactat agtcgaatat  70980
tatttgtgga attttttttag tcaactgctt tgtaactact aaaaccaatg aataaaatgg  71040
acacatgatg cttatatgca tttatattct ataaagctat aatgcagaat attttagtgt  71100
gttcgctact gtacttatag gaattttata agcaattata cttttaggta tcttaaacac  71160
atatataatt aaactcttac acatgtgcca tatcagtcat gtgggttttt tccttttattt  71220
caactgcctt catattgata tagcactttg aaatagttaa gaaagcaaga ccattattag  71280
ttataatttg tgtgtgtgta agtgataaaa ttcttgatta attaattttt ttttctagct  71340
gaaaatgcaa ttgaaaacat ggtgggtcca gactggaaaa agaggtggtt atactggaag  71400
aatcggaccc aagaacaggt agaaataaac aagtctctag tcttatgatg atataattt  71460
gttcatttta attcaggcat taaaatataa ccttttgtg gctctagacc agtctcagga  71520
atattaaatg ttttatatca tacttttcaa aatataatga atctttagaa taaagaataa  71580
actacataag aaagttttt ttaagtgaag tagccatgtt gttaaaagac aagagatgaa  71640
acatgcccct tttgtggttg attacattgt tcatttcaat tccctgtttg aggtaaaaag  71700
gaagattaaa gttatgaaca ggccaggcac ggtgtctcat tcctgtaatc acaacccttt  71760
gggaggccaa gtcagaggaa tcgcttgagt taaggagttc gagaccagcc tggcaacat  71820
agcaagacct cctctttact aaaagtcaaa aaaaattagc caggtgtggt ggcgcatacc  71880
tgttatccca gctactagtg aggctgaggt ggggaaggatt gcttgagcct gggagatcga  71940
agctgcaggg aaaataactt gtgaatagaa aaaatagta aggttttcag aggatgtcga  72000
atgaatatga ttggcgggaa aagatacaat ttttcttgcc ttattttatt atcttatcta  72060
tatctaccat taaagtccct acccctcacc tccaccctg ttcattcctt tccgattctt  72120
atagcttctt ttcctatcta gcattcagtc ttataccact gtctcattcc ttgttcattc  72180
cttaaatgaa agaatctaaa tagaaatatag aatctaacta cataaattaa tgaaataatg  72240
aagatgaaaa agatttagca tccaatccat tttcttttct tgtttgcttt gttccttgaa  72300
ttcatttaga gaaaggagat caagtaatgg aaaaatagag gagacaaagg gaataaaaat  72360
tgaccaaatg agatgtccct atttcttttat ttttatttt cattttcatt ttaaatacag  72420
ttaattgtat aatctatatc ctatttttttt cctagtttcc cacatttctt gtttcataag  72480
ttctctatca gatgtgagtc tcaacttttcc tcaaaataat gaagagacag tcttctttt  72540
ctctgtgttt ctttactatt tttttttttg gtaatgactt ttgtgaaaaa tgagccatta  72600
agagactgaa gcaaagctga ggaagcagac agttagtgat tgggtcatgc atgtgttcag  72660
ggtgcgttgg ttatctctgc tctacagatg ggccgagaga aggaggtctg tcagaagaga  72720
atttctagag atccatccaa ggtttctgac tttgatagag gaagatgcat tgattagaaa  72780
gagctgctgt aagggagata aactgcaaaa gaaaaatggt atctggcctt caagacttag  72840
tgatattagg cctaaagtct ctagaacagt tggtggcaga acttgcctca gcaactgact  72900
ggtggtaaat gtgcttttggc caaacactct ctgaaagaag tgattcctgc tcgtaagtta  72960
ttttttgtcag gaacttaaac ccatagggga atcccttcaa gagaaagaaa ggaatttgct  73020
ttaaagtcag tgcaaagggg ctgtaagcct agaagaggaa tctggaaacc ctttacagaa  73080
gagccttctc cccacaggat ttcagggcag catgtgtgag acccaggctg actgtagaac  73140
agaggccata atttggaata tagaagggag gggcatctga atcacccggg gaggtgttta  73200
tatatagtgt tttgtttttt cttcaaaagc tagcctcatg tcagactcat tgagtcaagc  73260
tctccttctc tatcctttct atccctccca ctcccagttg aagacaagtg ttttcaacct  73320
catacctgga ggttacagtg agacatggat tctagaagag gttgagaata tccctaggtc  73380
tcacatcgta agttcactta gctgaatgac aggatttggc aggaaaagaa acttaaagat  73440
gagaaatcca ttctctgaaa agtatttttgt gcttttgtgt ttctttttgtt ttctaggaaa  73500
attcatccct ttgaaacatt ctcgccttgt ttaagccaaa ctaatggaaa tttttggtcag  73560
gatagatcca agagtagttc tctccttctaa tggccaagtg tggtgacagt caaatgatgg  73620
gtagaaaggg ggaagtaaaa catgaggcag gatgagcttg gaacaccat taccagcgat  73680
ttccttttcca tctcagactg aatagtacat gtttaagcaa acagtgaact ttctctttat  73740
caaatgctct tttttctgaa gtattagttt tcagagagta ttaattagta gttccattta  73800
caagttaatt gtttgcattt atgtgttaat cttgtctact cagatttcat agctgtgata  73860
gagtttgggg caaaaaaaaa cactcagttt cgtagctgtg gtagatttc tattctagta  73920
atttatttag ggtaatgatt gaatttaaag ctagttttct ctatcatata caattttgag  73980
tggaggttttg aaaaatgaca agattaattt aacacagtat aagaatcttg ttatcaaaca  74040
taactagtgt aggtaagttt tcctccttttg gtaaagagat tatgaataat tacagataag  74100
agactggaag tgaatttaag aaggacagat acctcacagg agcagtctga agtaccattt  74160
tttatgaaaa agcttttttaa aaatcaagct atgcatttta tatttattgg aaaagaaaca  74220
tgtcaacaag tttaagtcct tacagtaatc tcgttcttaa gtagttct tagatatgaa  74280
gcatttttaga acatcagctc tttcctatgca ttcaggggtgc ttttcctag attcaaatta  74340
taccctacgg tcaagaaaga aagaaaatac atggtaagat tcctggtgct gtaacttcca  74400
caggaaaaaa catttcagca aaagtaaaata cataacaagt agggctaatc cctgggttttt  74460
ctaccctctc ataggcaaa ttcttctgtg ttcataggcc atttaccata ttcataagcc  74520
gggtgctgt gttcttttctt gtgtttcttt cttgtttgtt gtgattaagc ttgtgttatc  74580
ttttatgcaa tagtaatgta tttattaaaa ttgagactgt ttttcaagca ccaaattatg  74640
```

```
aaccatctaa acacagtcct tttttaaaca ttttaaagtg tgttcacaat gaaaccaaga   74700
atgaattgga gaagatgttg aaatgtaatg aggagcaccc agcttatctt gcaagtgatg   74760
aaataaccac agtccggaag aaccttgaat cccgaggagt agaagtagat ccaagcttgg   74820
taataaaatac tgctgagaag caggaatctg cttccttaat atttgtttct tgcagtaaat   74880
gttactacat gtgttagtta gatatttaag tgcttaattt gacttttgtc acgtgtacat   74940
ttgctgacag taaaagctta gtcattttga ttgcgtgaag agaaggaatt ttattctcag   75000
tattgctttt ttaagagtaa tgctttaatt tgtaaatgga gaaatttact ttggcaagtt   75060
caatggtcaa cagtcagttc atgcaaaatg ggatgaaacc gacctagacc tttgccccac   75120
gtcacgctgt ttcagattgc aaaatagaat ttctgtttaa aaatggcata tatatgtgtt   75180
tttgtgtgtg gtttacagtc aaatgtaact caattagatg tgagtggatt cagaaaaaat   75240
aaaaatgttg tttttattaa attggatatg accattgagt tctttctcca ttgtcctctt   75300
ttgttaatgt gagaataaaa atagtctaca ctttaggcta cttttttgctt accttcatga   75360
tgctttttt gaggatgaat tttaaaaaat actttcgggc ccacgttttt taaaaactac   75420
attctctact gcttagttaa gatgtaagga attcaaaagc tccttataat attagcttaa   75480
gtgaacacaa ttagaaaaat aagtctagtg gggaaagcaa tcattaacaa atttcaaagc   75540
cacacaaact cttttaaaga ttatgtgcta tttatgtttc tgtacttgag ggatgagtat   75600
acttattta aattccacca caggtcagaa caagtaaaaa aataaaaata aaattggtaa   75660
aactcaaagc agttatatac atctagcatt attatatat tgaaaatgag atgaaagcta   75720
atgattacat gagctgtttg agttgaatgt ggatttaggt tttattcctg ttggtcccag   75780
ctctcgttaa caataagtta tattcagttt gacacttttta aacgttatgt ggcacgttgg   75840
tgaatacagt aggaggggatt ttctcttcag agtggtatag aagagatgtt acgtgatttt   75900
tttttaaac tttttgctca tgtcttaggc aatgaattga ctgtatgtct taattagttt   75960
ctaagaccaa gaaaacctca ggttttttaa gtgacagttt gttcagtgca ctttgcaaag   76020
ctataaaata gtagcaaag taccacgaga agaatattgc atggactaga tcaggaca    76080
tgtgaattct agtgtatttc cattatatta gctaataata tgtcctttaa taattgatac   76140
cactttctg acctcactta cctcatctgt caaaaggggt tgatgttttt ctagttaaca   76200
ttattattgt tttgctcaaa aaaggacaga gggtattaaa gaatattgga cactcagagt   76260
atctagtaat aaagtggtag ggatcatatt ggtatggtag cagtaaaatt ttataaacag   76320
aaaggaaatg ttgagttgct agacatgatc tgagaccatc ttaagttcta actctgtttt   76380
tagataaggc tttcaacctc ttttctgcatt ggtttcctca cctctaacta gggaaggta   76440
atacctaccc tgtctactcc acaagatgat tatttgatta tagtaacagc atttgtttaa   76500
atcattgcta atttttaagt acataaaactg gtaatgggtc agagtagtag taaatctaat   76560
ctttgcctta aaaaaagtaa gtgaataaaa aaatttgaat aactatgtaa agaataacct   76620
tgcttttgct tttaattaac tttttttggta aatataattt ttgtacaact tctcagtgtg   76680
gttgatcaac atgaagaata tacagtaact ctgggctttc tttttctca tttttagatta   76740
aggatacttg gcatcaagtt tatagaagac atttttttaaa aacagctcta aaccattgta   76800
accttttgtcg aagaggtttt tattactacc aaaggcattt tgtagattct gaggtaaggt   76860
ttccaaaaac aaagagaagt attttaagc aacagttgtc aaaatatgct taaaagtaaa   76920
ctttagctta agcattaatt ttaagtcctt tgatcatctg gggaaaaaaa gtatgtgtaa   76980
tttataaaga ataatctaac tcttatattt tcaaagatat ttgccacttt gttcgtgata   77040
cgtgcatatt atccccaatg cttataagaa tatgtgaata taaatagtaa aaaaaagtgt   77100
gaatataaat agtaaaaaaa ataaaaaat aacaggaaat agtcccttat tcctgacct    77160
gtaagaattt tagttaacat tttatgtat ttcttttcgt acataggggag               77220
agagacagag agggaaagag aaagtgtgtg tgtatctgtg tgtgtaacat aaccatccat   77280
ttgcataatg gaaatcatcc tgcaaaacag ttttttatcat gcttttttca ggtgtcataa   77340
ttatttcttc atatcactaa atcttgtttt aaataatcat aaagttcttg tattaaaatg   77400
attcataatt taaagtaacc cctaggtggc agcagtctga tatattttca gcatttttctt   77460
acaagcaaaa atgctttttaa atatcctttt gataaagctc agttaatcaa caatcttatt   77520
taattgagac ttctaacatg ctgttctttt gttttcagta gatgaacata aatttatatt   77580
taaatgcacc taattaaaag tggcaagttt tttttgcata attttaattg tagagtgaac   77640
ttctttctat agaaacttct gtagaaagaa gaaacttctg tagaaactgc cttctgtaga   77700
ataagcttct ttttaaatac atcacttat tttcacacag ctgaatttta aaaatgacctt   77760
gagtacagac tcaaagaaaa gaggttaacc taaggacgta tttaagataa acatggttag   77820
ctgaaactaa atataaatgg aggggtatatg ctgtgaattt caacttacat acaatgtaat   77880
gtaattttgct actactcaag cttattttact ttgtcattag aattgaaaca aagctatcta   77940
ggtgtcagac agatataagc caaattatgc agaatttcat ggctccgtac agaaaggatt   78000
ctgtagctta tatctacagt atatgcatta ggtaaatctg agtactttt aagcttagga   78060
catatctact ggttctagta gttgtatgtg tttacgatga tagttttcat ttttaactttg   78120
catctggtaa tcttagttac ttaatatttc agttggaatg caatgatgtg gtcttgtttt   78180
ggcgtataca gcgcatgctt gctatcaccg caaatacttt aaggcaacaa cttacaaata   78240
ctgaaggtaa gccacatagg gactgcagtc ttattttgac attaaaaaat aatagtggta   78300
atatccatat ttaatagaag gatgccaaaa tacttcccaa aagtagattt attagaaaaa   78360
ctggccaggt gtggtagctc atgcctgtaa tctcagcatg ttgagaggcc gaggcaggaa   78420
aaccgcttga ggcctgtagt ttgagccag cctgggcaac tgttgagac tctatctcta   78480
caaacaataa aataaaattag ccgggcatgg tggcacacat ctgtagttct agctacttgg   78540
gaggctgaga tgggaggatc acttgagccc taggattttg aggctacaat gagctatgat   78600
catactactg cactctagcc taggtgacag agtaagacct tgtctcttta aaaaaaaaag   78660
acaaaaatta ttatttgctt ttaaaataaa tcataattgg aaaagatggg tgataaaaca   78720
taccaggagt ttattttcat tgcatgaaac tctgttggga atggactcct aggtatcact   78780
tagttttttg ggaaatctgc acttccatta aagtgtatag cttaagaata tgacattctc   78840
tgagactata taggtttcat gctgataaaa ctactgtata acagagatttt tctatgacta   78900
tgaaagtat tagcaatagt tctaacatga taaaaaattt actctccata tatataggtt   78960
aattttatca tctcttattca ttttataaaaa cgatgctcct caggtttttt aactttcttt   79020
aaacagttag gcgattagag aaaaatgtta aagaggtatt ggaagatttt gctgaagatg   79080
gtgagaagaa gattaaattg cttactggta aacgcgttca actggcggaa gacctcagtg   79140
agtagtcttt actgccctct accttactac ctttccacct ttccatttc catttgtttg   79200
ttgatccatt taatctcaaa cttacagaaa agttacaagg aactgggctg agcacggtgg   79260
ctcacgcttg taatcccagc actttgggag gccaagatgg gtggaaaaca aggtcagaag   79320
atcaagacca tcctggctaa cacagtgaaa ccccgtctct actaaaaata caaaaaactt   79380
```

```
agccaggtgt ggtggtgggt gcctatagtc ccagctactt gggaggctga ggcaggagaa    79440
tggtgtgaac ccgggaggcg gagcttgcgg tgagccaaga tcctgccact gcactccagc    79500
ctgagcgaca gggcgagatt ctgtctcaaa aaaaaaaaaa aaaaaaaagt tacaaggaat    79560
ttttttcttc tctgaagtat ttgagagtaa gttgctgacc ttaagtccta tcacttccaa    79620
gtaggttcat gtatagttct tagaaacaga ttttctcata gcaaccgaac attgataaat    79680
tacaatatct aattctcaga cccctttcaa gtttcacccg ttgtcccagt attatccctc    79740
catataacaa gatgttccag gctcaatacc tgcccagct tccttttttt gaagaatggt    79800
gtttagaaat ggagacctag aaattatata tgctgttatt ggaatatcac tgttccctgg    79860
tttctcagtg gaaagagcta ggaactaagt gttgtgaatg tttgtgtgtg tgcaggtgaa    79920
tatacacaca ctgacatctg tattcctaaa tcatgtgtat atttatttat taaaaactgt    79980
gagttgatgc tgatacttcc catttttaatc cagcattaca aggtttgttc tagtgttctc    80040
cctttcgata tttgtcactt gctttcctga tagaaaacgg gcttctagta tccttaatat    80100
attttcatat tttggtcagt cctccctatac gtaacccaac ttgaatgaag atatgtccttt   80160
ttccattgca gaaatgttct tttttcccag ctcggactca acactacaca ccaggccacc    80220
acatggcgcc gcacccagca ttgacacttc ttttaccttg tctgggctct gacatccgtg    80280
ccaggttgct cttcgtcatg gagtccctt tactgagctc tgctctgacg ctttgtgcca    80340
ggtgcctctc catctcatcc ttcccacccg ctagcctctg cccgacccca gacagattcc    80400
ttcctcacct gaagccagac catgcctttg tggagataac ctctttaccc tgcctgtgct    80460
tcgccagcct gcaccaggcc accctcctgc acagatactc tcctcagtac tggaccaggc    80520
taccaacagc cccatgtgaa cccattgtaa cccaggtcag gcattaacac ctgcagtagg    80580
ctaccatggc ttcccccttcc caccccccta gcttggccct actaataatc actttgtcac    80640
tgtttggggt tgatatttgg ttgttttcttg tagttccta gcttaagt aggattgcat     80700
actaaaattt acttagatct ttgagaactc aaggaaatca gtgaaacatt attgttatta    80760
aataaaata aaatacctgt agttggtacc tctgtttgag cctgccttgt tacaagtttc     80820
actgacttca gcttcgtgta acaaagtatc ttttctttc aacgtgtact taaatttcct     80880
gtcttattag ttttcgata tctaaaagga aaaaagcag atatcgttaa taaattagaa      80940
agaagttctg caaatttaaa agtgccttct aagctgagtt gtaggattac agtacaatcc    81000
atagggttat cctgaagaag ccaggcaggg ctcttctgtg ttacaccctg tgcctgcgca    81060
gcatgctcac cccttgccat cagcgcttgc ggccccattc tctccctcta gtaataatct    81120
aagttctgca ttgcttctc ctttcctttt ctttcttcct ttaaatattc ttctttcgag    81180
acatatctca ttttaactttt tattttcatt ttctgtcact tttggttttt ctcatgccac    81240
cttggcaatg tagttaagtt tgtgctaacg tagaagatta gtgctcaaat ctgaattgcc    81300
atttactact agctgtgtca tcttcggcag ggaatctccc agagccttag cttctttatt   81360
tgtaaaatga ctattatagt ggttatttct caggattgtt agaattactt ccgcaaacat    81420
ttgcaagtcc ctggttcata atttcatgct aaattagtac cgttacagga agtggtatat    81480
cattgtcaca gtgtatacaa atatatttct ttatatccc tcgtgatata attatcaaga    81540
cagtgaaaca attcaatgaa ttttaccagc ataacacatt ttaagtgat tggaaaatca    81600
taagtatctt ttcttatgtt tttagtagag gcttcaac cccattactc tccgctccca    81660
atttgattat ttaaaggaag tggattacta actcagatat gtacactgtc aagccaagtt    81720
ctatgttcta ctgctggttt tcctgagaaa gcagtcatat aactcccttg aaatgattta    81780
ctactttgt acatataaaa ttataatggt gttaatgtac caaataatgt ccttggaagc    81840
aagggttttg ccagtaactc agctgcatca gtcaccctca aggagatgag ccatgacttt    81900
gttcattagt tggaaaagag tctggaagt gccttttcgt tctgtttat ctttggtcttg    81960
acacttggga atagggtcat ggatacttca gccagaaaac tttccaaatt taagttatta    82020
atgtattata aggatcaaag tttctagtat agcctgttca attagaacat agtgtgttgg    82080
ttgattggat ttggagaaag ggaggcaatc aaattttac tacagtttca gcctgttaca    82140
gaatattgta tagagtgtta aaatgttgat gcattcatat ttttgccagt tttaagcttg    82200
tacgatttta aatcatttcc ttaccttgga gacttccccc ccaccttttt tttttttttt   82260
gagatggagt ctcgctgtgt cgcccaggct agagtgcagt ggcacgatct cggctcactg    82320
caaggtggtt ctcccacctc tgcctcccga gtagctgggg ctacaggcgc ccgccaccat    82380
gcctgctta tttttgtat ttttagtaga gacggggttt cccatgtta gccaggatgg     82440
tctcgatctc ctgacctcat gatccgcccg cctcggcctc ccaaagtgct ggaattatag    82500
gcatgagcca ccatgcccag ccctgactgc cctttaagat gagtacataa gtagtagtag    82560
tacatttttc tttcacatcc tggagaagat atactgtgtt cactattgaa atgaaaccat    82620
aaagctagag ttaggaagat tgaagaaatg aaaaaggagc tcacatgatt ttgtctcagg    82680
agaggctctt ccaggattct ttggagatat ggtagattcc atagctggag caggggaaaagg   82740
acaggatgag cctgtgggtg tagaaaggaa gggagtgctt gaaagatgat gaggagatgt    82800
cagcaggtca cagaaaccct ctgaaggagg ctccaactgg ccaggctggg gacaatttgg    82860
gccccaaaat aatgacagta acaaattgta actcattgaa tgaaatagga atccatacat    82920
tggtaatttat ataaataagg gaataaaacc atgatgcaaa agggatgtt tatgtcatca     82980
cgcaaaatat gttcacagaa aatatgtact aattaaaaga gggaaaagag taactttaca    83040
gtggatgaag cctggcaatc atcactttaa gcaagtggtc agagttaata ttatcagtaa    83100
tggtcaaatc aaaaccatat gcaagaagac tctaaaatgc aagaagactc ctgaagtact    83160
tcttaccaaa gatgtagaac ttaaattcag tcataacaat acatgagaca aacccaagtt    83220
agagcacagt ctgcaaaata actggcctgt aatcttcaaa tgcatcaaga tcatgaaaga    83280
caaggaaaga gtgaagagct gctccagttg gaagagactt aaaactaaat gcaatgtatg    83340
atcctagatt ggatcttttt gctctaagga cattaatggg ccagttagtg atatttgaag    83400
gggatccgag ggttccattg tagtaatata tcagtgttaa ttttaaatt tttattaggt    83460
tgggattatt ttggaaaata ccattattca tagcgaatac aaagtagaat atttggggat    83520
gataatgcat gattacaaca aatgtttcag gagaaatatg atctttgtag tggtcttgca    83580
acttttctgt aagtctgaaa ttgttttatgc ataaaaggtt aaaaaaaggt taaattttgt    83640
ttttataact aataatggat tagggtcatg tgaaagtact ttagaggaaa tgagactttt    83700
gagaacatca tccctgaaga cgttgaaaca ctgagttacc tcatggataa tttaatagga    83760
tatgcagctg atttttctac cttaattct tgtttgcagt catacccat acttagaatt     83820
gtctggtgtt aaaatatgcc cactgggact tcatgaaat tcttttgatt ttctagaaaa    83880
ttcagtttca aaggatttt taaatagata ttttaagttt ggtgtcaact tagataaaat    83940
ctgtttggag tccagtgta agtttagta atgtgtccaa tctgttattt gaaatagtat    84000
aactttgaaa tactttcttt ggagagatga agattggtat gttatagttc aattcaaagt    84060
tgttctttct attatgatct attttataat tcataaaatc tatcttatga ttgtcatcat    84120
```

```
aagtgcaatt tgttttttgc cccattctac ctcagaaact aagtatctgg gcatcaataa    84180
caattggtag tagtgtttgc tgctaagcca agtttcacca gtacagtgtg gaattatttt    84240
attgttttt  ctgtgaacat tgtatctgct gttactaggt tattgtgagg tattgggcct    84300
tcatagaaat tgcctggaac ccttgttcac taaagcctgt tacactttt  attctctgtg    84360
cgtgtaatca gagacttatt gatactgaca cattcaaggg gcattattga tcatttagat    84420
tgctctaaga cctaaggagt cttggccgga tgcggtgcct cacgcctgta atcccagcac    84480
tatgggaggc cgaggcgggt ggatcacctg aggtcaggag ttcgagatca gcctggccaa    84540
catggtgaaa ccccgtctct actaaaaatg cgaaaattag ctgggcatgg tggcaggcgc    84600
ctgtaattcc agctactcgg gaggctgaga caggagaatc gcctgaaccc gggaggcaga    84660
ggttgcagtg agccaagact gtgccattgc attccagcct gggtaacaga gcgagactcc    84720
atctcaaaaa aaaaaaaaaa acgaaaaaca aaaacctaag gagtcttttc tccttatttt    84780
acaataaatt cctttgatt  ttgtgtaaaa acttgaaact gtttatgaat gtaaaataac    84840
atttgaatac ttttcttgtg ccagatatta ggttaaatgc tttatgtgaa ttttcatttg    84900
attctcacaa cttttgagtt aggtagttat ttttctcatt ttacagatga aatggagggt    84960
taggaactcg taggtagtag atgctgaagc tgagatttgg gcctgggtct tttcactact    85020
gtgccagaat catttgggag ggagtaaaaa ctcaagcctt tggaaaatat gatgacataa    85080
aattgtcctt tatattgaga agcttccata gttaccagtg tccttcacag ggttgatcgg    85140
aaagacatac atgttagtga tgatgataat gatgaagata atcattatta ccacaggtac    85200
ttcctataat ataagcatct ttcaaattgt atgagaactt tcatagaaca tctgagtaaa    85260
tgaacagtac agtgtgcatg aaaccactaa gcaaaccaag ggaagttaat tttctttata    85320
tgaattgtaa acatgtctct agatatcctt tatcagattc caccatgcgt aagtagtgtc    85380
taagttgccc catatttaga gttttttcaat gaggttgtgt tcctacttag aatcctaaag    85440
ttcagctata acagatatat taataaaatc tgtggaatct ttaattgagc ataatggtag    85500
ctgttatttt aacttgaggc tttttgttga gctggattgg aagtgcaact tattagaaat    85560
tacagtgtat ttattcctat ttcttgttct ttatgtgaga aagatatac  tttagtagac    85620
tgaatacttc agagctgtat ctcatttacc aataaaatgt gaaaacagtg gtaaattcct    85680
tcacttgggc taccattgta caggcctatt ttaatggtat agtttgatat ccttaatgtt    85740
aaaagcaata tagcttaaag aggctggtaa attagaattt tccaatatcc tcagcttttt    85800
ttcctctcac agttaatttg ctctgctgac tccctacgcg aggtggcaac agctggccct    85860
tttactggag cttgtgggga ttagagagtc gggctcgcag cagcgtgctc ggcctcttgc    85920
ctctgttgac tgttctttat tgtttgatgc ctgagcatct cccagacagc gagcaattgt    85980
ttctggaaac ttaaagtttg tttctcttgg gagtagacaa tgcttttggg gcttgtcttt    86040
gtgtttcttc actttcccag tctcctctta tccttcatcc tgtgctttct cttgataatt    86100
agaaaggagc aaagatacca cctttttatt taggtctgca tgagattcta aaacttagaa    86160
gtataggcta tagatgaaag tttctttttt cagtaagcca cctcagtaac aaatcatgtt    86220
ttaaatgaaa actttgttct tcataatatc atttagtgag agaaaacaaa tgcatgagtg    86280
cattttgaa  attatggtac taaaagggag cagcagcaag gtgacctaat actgccattt    86340
taaaagctag gattagaaat gtatcataac tgcttaaatc taaaaagatt ctttcactga    86400
atccaaaata tagttctaat ttataggata gttataaaa  atctctatgc catgtggaaa    86460
catgaataaa aagtagtcag aacatagcta aatagaaccc tgaggtaggc agaatgattt    86520
tattcttcac atttagaaaa gaaaacatca aggtaccctg gaacttaatt tctacagtga    86580
cttcacattc cgacacttct cccatacctg ccatacccct gagtgttgtt acggatgaga    86640
atatcgtctg tgaagtagta tgagatgaaa atttcctag aaagattatt gtactcggaa     86700
tttggaactg aaaagtgtag aaaggggaag tgatgtgttt aaaactgttt gcggaggtgg    86760
ggctctgcca tgtgtatttt gacaaagcta cacaggtgat tcttgccatc cccgattacc    86820
gtgtacccgc ctgcccctga gctggcactc caaagagttc tttcagtgca tagcaagaca    86880
attttcatg  ctattaattg ggataaaatt gacatacatt catttgtaga gtctgagaca    86940
caacgtcact ttggaaaatt tggtgagcaa tttgaactgc atctgcactg gtgtgttctt    87000
tttgtttctg tagacttaac caaagaaaat gaactttaaa gggactttaa aggcatctgc    87060
actggtgtgt tctttttgtt tctgtagact taaccaaaga aaatgaattt taaggaaga    87120
gagggtgata ccaagttgta gaattctagg tatgtaggtt cagaggagat tttttttttt    87180
taagaaaaaa aaaaaaaaaa aaaaaaacac ccaatcaaga agaatagagc agggtgtccc    87240
gaagagaacg tgtgagctcg aagcatcccg gcagcatctt tcatatctca gtactgttgc    87300
tctgtttctt gggctcacaa caccatttcc tctctcctgg cttttaacac atctcgaggc    87360
aaccttttcc cttttctttt atgcacttct ctcactgctg ctcttctata tcatcatcac    87420
ttcaacctaa cccagtattt ttatcccacc tgcttattta ccttccttca gtgactaaaa    87480
accttactca gatactgcca gtgttgttta attgagcaga atagaggctt ctcactatag    87540
gcaactgtaa atcaatgaaa ataaccattt aaagaagaaa aacatttca  tgtctatcac    87600
ggtcgatccc ttctgccaaa gtgatttggt tcattcataa attccccata cctcgtgtgt    87660
tacatattgt actgtacaca tttactgtga gttcgattgt gatcttgtaa tacagactgt    87720
tcattagccc ccttctcttg acttaaaaag ttgggggggaa ctaactcttt tcatcccaag    87780
gaaactttct tctactctgt cttgccagaa agttactgct catttctctt gtagagcagc    87840
ttgcctgtgt ggcattcact cctgttctgc ccactccctt cctaatatcg tgcagtctgg    87900
ctttcatcta tatcaaaacc actttattgat agatcaccaa tgttttccta atgccgattt    87960
acccagttca ccaggaaact ttaataactt tttatgttta ttaggaattt ttaagttcat    88020
tggaatacat tcaagtactt tttggaatga ttatatgatg tagaaatgtg tatgtttgag    88080
agacagaaaa attgattttt ttttcctctt cactacagaa taaataatgt atttgtttta    88140
tggtagcaat acttgaactc tttaaggcat cttttcatgg taaatctggc aattttaaaa    88200
atctgggctt tgtaaaataa tttttttttat agtaaggcag ttaacacatt aaagcaacta    88260
ggaaagatag tgaagaatta ttttttacctt gagtctgtat agatgaagta ggctctgctt    88320
tgtgttggaa cagaacaaac aaacaaaaaa acctgagttg atacaaagat aaagtaatcc    88380
tcaaggaaag tcctctctgt tagagaagtg gttatttaca cacagaattc cacatgacaa    88440
cgcctgagtg gtgtggtttc caggttattg atgagaaaat cgagactcaa aatgggtctt    88500
ttagaatgaa actttcttt  catggcctaa gtctgtctt  aaaagtcacc gttgtgggcg    88560
ggtgtggtgg ctcacgcctg taatcccagc acttaggag  gccaaggtgg gcggatcaca    88620
aggtcaggag atcagacca  tcctggctaa cacagtgaaa ccccgtctct actaaaaata    88680
caaaaaattt agccaggcgt ggtggcgggc gcctgtagtc ccagctgctg ggaggctga     88740
gcaggagaa  tggcgtgaac ctgggaggcg gagcttgcgg tgagccgaga tcgcgccact    88800
gcactccagc ctgggtgaca gagcaagact cgtctcaaaa aaaaaaaaaa aaaaaaaaaa    88860
```

```
agtcactgtt gaagaatatc aataaattag tacaagcgta aaagaacatt ttcttttcta    88920
taatattata catgctgctg gtaatcaaca cttactagc aagtatattc ttttgcttta     88980
aactcaagtt ttaactgatt aagaataaag acaagaatgt tctctacaat aatgtatgga    89040
ttgaatttgc catttatcat tttaatgtag gttttactta tatactattg tgaaaatact    89100
cttaatgtat tcaaaaggcc agtgcacaat ttttttttctt tttactttctt ttttttttt   89160
ttttttcttt agaaagagtg tcacttgctg cccaggctag agtgcagtgg tgtgatcatg    89220
gctcactgca gccttgaact cctgggctca agtgatctaa tacctttaaa gttgggaata    89280
aactttatct taagcgtttt tatttttaaa ttatgttttt gcatatttga tagaaaaagt    89340
agaatgtagt aattgaaaac ctaatcacaa aacaattcat tggactctgc aacagtatat    89400
aaaaaataaa attaaacgag ataggaaatc ttaagggatt ggtggattga tgcacatgaa    89460
actggtaacc tctgttaagt acagttctcc aggtagttgg agaaattagt taaatgtgaa    89520
gagaatttta attttgcact attttgtaca tttctaaact gtgtctccca cagcccttct    89580
cccccagtga gcacgattca gaattacttt gaaatgttgt agtcttaatt atcctattca    89640
tggaaatgac gaagctaata cacgatgtgc tctatcttaa aagtaacaga tattttccca    89700
agtaacctac tgctggttgt gatgctgagg gacatttcat gggactgcat ggtcgttgct    89760
catcgtgata ccatcctcag tggttggggg attcacagtg aattctcata tcctgtaact    89820
atgcatcatg gatctatcat ctgaaaataa atcaaaatct ttgttgaact cacagttcc     89880
acacttgtat cacccattta agattgttc attgttacct cctgtgtaca gaatatttca    89940
tttcaatttc tcttagaaca gctcattcat ctattctcta gtttcaatat tctgagcagt    90000
agaagtttgc tgttttgatt aacttcagtt agatctcttt tctgggccaa gaattaaagc    90060
cattttatct ttagtctctc cttttgttgg cactgcttca tagactgtgt catatataca    90120
gatctgtctt tagactgatc tttaccaaag tacactactg gaatttgagg gttttttttt   90180
ttaacatcct tttcattatg agagagctag tgtatatgca ttgtgggaaa ttagaaaacta  90240
tagatggcaa aatttaaaa aataattgcc accaccagc gattgcactg tagtttaaga     90300
cactttgaa tgtggtccta gggacataat ttctggaaca cattttcgt gaagaggtct     90360
caggttggct tcttataccc acagctcgtt gtcattgcc ctagttttaa tttcccatcg    90420
ctcagtgggc tagattttttt ttcatttct tcatataaac ttatttcaga aatgttcatt   90480
aagaggaata agcagcatta gtaaaaatga aacctatggt acccattact ttatatagtt    90540
caagtattct ggaagccata ttgtagcata gcatgtactg aaatcactc tccttttgaac    90600
agtaatcca tacctgtatt tgggacctgg ccttcctttg tgtgcttgtg tattcattat     90660
atccccttc tctcttcaaa gatgctcaag tcattctcat cttaaaacta atggggttgaa   90720
ccttccatgc agtctagtag ctactgtgaa ctctaatctc tattacaaag gttagctctt     90780
tgagtctcac ttctactgaa gttgttttt tttcccaaga ttactgaaaa tttaagagaa     90840
aataatggcc caggcatgca ttcaggacta gaaaatactt ccatgtacag aaaaccaaac    90900
accacatgtt ctcactcata agtgggaatt gaaccattgag aacacatgga cacagggagg   90960
ggaacagcat acgccagggc ctgttgggc gtgggggcg aggggaggga acttagagga      91020
cttaagtgca gcagaccacc atggcacacg tatacctgtg tagcctgcac attctgcaca    91080
tagagcccgc ttttgttttt gttttgtt ttaagaagaa ataacgggga aaaaaaggt       91140
ttcaaaactc ataaagaaag agaaagagag ggaggaggga agggaagaaa atgcttccat    91200
gtaactgcat catttggtac tttggagtcc atatcctact tgaaactcta ggatctggcc    91260
ctcacattta tgtagtgctt tattttacag tttacaaaac ttctgcttgt ccatgtgtgt    91320
ctgtaaagtc atatgaggca ttatgcccat tgttcagata gagaaattaa cgttcattga    91380
cataaatggt taagcccatt atgtaaatat ttatggcaaa gctggggcta atcatatgtg    91440
ttacagatag gactttttt aaagaattgt ttaggtattc tgttcatcat tagtctctgg    91500
gtttgtgttt gtggtaacca tagacaacca agttcatata atttggcttc ttttttatgt   91560
gattttgat acgtgttaag gatctataac aatgaatttg cctcctaaag aggtacataa    91620
tgttttcatt cctccaaaaa gataattcta ggtttataaa tctatgtatg ctcagtgcca    91680
gttgaatttt gtgattgttc aatagaaaag aaattgtgac ttaaaggtga ttttccagtt   91740
taatggaata aatgaaatta gtttagaagt tattttatt tttctgagcc tgattctcac    91800
tcagttgtga taaacagcac ctctgtaaga taaactcggt gataaaccga gaacttctga   91860
aatcagccta acatgaatac ctgttcttct tgtgctaagt ttcataatgc tttatcctaa   91920
tacaccattt tttaagaaa tggaacttgt atttcatttt tgctttcatc tcacctaatt    91980
cataatttta ttaaaaccta cgatttttaa tttcttttt tatgaatttt tagtttggtg    92040
tataaatcag aattacattc tctgatcttt tactttaa attacagtga tgaactgact     92100
gtttaagaat cattctcatg attcattcgt ctgttatgcc tccttttaa agcttcagca    92160
ctgaaggtct tttgacaaac caatatttat aacagtttga cagcaggatg aggaacagcg   92220
tttgtcttg taacagcttg aagaaagacc ctttccagga cccagtcatg cagttacaat    92280
cttgacctct ttcttatgct gggaacatgc atacagcagc acctccatg tgttttcttg    92340
tcccattgac tgtccattca cttcccatct gttttgcagt cttaaaggaa cagaagggc    92400
cttcttataa atctgtcttt gcaggtgata aatgatgcct acctctttaa gagctgcctg    92460
ggtggttttc ctttcttag aacatttctg cttttcctcct aactaaatca gggaaaaata   92520
caattttagg aataagagaa aaagaagaaa agatgaattt taaagcatt taattgacta    92580
agaatatttt actgatcttt tttaatcttc ccaattaatt gcctaaatca tatttttaa    92640
aatgtattat cgatatttag attttgtca gggagtaaaa tgatgtatt catttgaaa      92700
taatgtaact ctttttgag aaaacaagc catgtatcat taatgagtta acatataaaa     92760
taactttta agtttttgt gataatttaa gtgtggagca tcttatgtat tggatacaaa     92820
agtaaaatat ttcagagtaa atcattgtaa tcttatggta aaatctattc attttttaca   92880
tttaaaaaga tgatcataaa tcccataaac attatgctt ttacttctgt tgctgaaaat    92940
aagtattgta ggaatagata ttgatatcat tgggtttct aagaattcag cagaaataaa   93000
aataatttac ttttctccc atgcagaaat tatttatgca aggtttatg taacaaatat     93060
tgtccctcta tggccctgca gaatattctt aaattactga tttaaaaact attaccagta   93120
taaaatgacc acttttagaa tattgtggtg tattatgtga atcagctggc taataatata   93180
tcttctgtgg actagcttgt tagtttgttt attaattccc tggcatattc caaaggaat    93240
tgaggcagc ttacatatat cctacgcaaa agataaaact acttaagtga aaaatttggg    93300
ttgaaagaaa aggaaaatcc aggcaagtga aataaagtaa actttcagat aaaattggtg   93360
ccctcaaag tgcatgctca agggttctac gtacaggcag acctcattgt attgcatgtc    93420
actttattgc acttcacagt tattgcattt ttaacaatag aagttttgtg gcaaccctgc    93480
attgaacaag cctgttggca ctatttccc aacagccatg tgctcaccc atgtcactgt    93540
cacatttgg taattcttgc aatattcaa attttttcat tattattctg tctgtcatgg    93600
```

-continued

```
tgatctttga tgtttgtatt gtagctattt tgggtaccac taactgtgcc catatagtc  93660
agtgaccta atcagtaaac gtgtgtattc tggctgttcc accaactaga cattccctgt  93720
ctctctcctc ctcttcaggc ctccctattc cataggacac aacaatattg aaatttggcc  93780
agctaataac cctacaatgg cctctacatg ttcaagtgaa agaaagagtg ccatatttca  93840
ctttaaatca acaactagaa atgattaagc ttagtaaagg aggtttgttg aaagccaaaa  93900
tgggctatta gccaaattgt gaatgcaaaa gaaaagttct tgaaggaaat taaaagtgtt  93960
attccagtga acacacgaat gataaagcag aacagcctta ttgcctgaga cgcaggaagt  94020
ttcactggtc tggatagaag atcaaaccag ccataacatt cccttaagct aaaacctaat  94080
ccagagcaag ttcctaactc tattcaattc tccgaaagct gagaggtgag gaagctgcag  94140
aataaaattt gaagctagca aagtttggtt cataaggttt aagaggaaaa aagccattct  94200
gcaacatgaa agtgcaaggt gctgatgtag cagctcagc aagttatcaa gaatatctaa  94260
ctaagataat tgatgaaggt gattatacta acaacagat tcttgatgca gatgaagtag  94320
ctgtctattg gaagacgatg ccatctagta atttaatagc tagagagag tcaatgccca  94380
gcttcgaggc ttcgaaagag aggctatccc tcattttgg gtgccaatgc agcaggtgcc  94440
tttaagttga agccaaccta aagaattac cattctgaaa atcctaggc ccttaaggat  94500
tatgctaagt ctatcctgct tgttttctaa aagtggaaca aaaagcctgg atgacagcac  94560
atctgtttac agcatggttt actgaatatt ataactctcg agacctgctc agaaaagttt  94620
tctttcaaaa tattactgct cattgacaat gcatctgaca aagcaagagt tctgagggag  94680
atgtacaagg agatttatgt tgttttgtg cctgctagca caacatccat tctgcagcc  94740
atggatcaag gaatactttc aaccttgaag tcttattatt ttaaaaatac gtgtcttaag  94800
gccctagctg ccatagatag tgattcctct gatggatta ggagaaaaaa aaggaaaag  94860
cttctggaaa ggactcacca ttttagatgc tgttaagacc attcaggatt cagggagga  94920
ggtcagaatg tcaccattaa cagttgaa gaagttgatt ccaaccctca tggatgactt  94980
tgaagagttt gggacttaag aggaggaagt aactgcagat atggtagaga cagcaataga  95040
actagaatta gttctgttgt aatatgataa aacttgaaca gatgaaacat tgcttttat  95100
ggacaagcaa agaaagtggt ttcttttttc ttttttttt tttggcagt ctcagtttga  95160
agaagtggt ttcttgagat ggaatctgtt cctggtgaag atgctgtgaa cattgttgaa  95220
atggcagtaa aggaattaga atattacata aacttagtag ataaagcagc tgcaggttt  95280
gagaagatag tgtcccaatt tttaaagaag aaaaatttga gtaaattgg gtaaattta  95340
cccaaaatta cctattgtgg gtaaaatgct atcagacagc atcacatcct actgtgaaat  95400
ctttcatgaa aggaagaatc aatcagtgca gcaaactaca attgttgtct tattttaaga  95460
aatttgccata gccaccgtaa cctgcaacag ccaccacct gatcagtcag cagccatcaa  95520
cgtcagggcc agaccctcca ccagcaaaaa gattatgact tgctgaaggc tcaggtgatc  95580
cttagcattt gttagcaata aagtacttt aaataagtta tgtacattgt ctttttagc  95640
ataatgctat tacacactta atatattaca gtatactgta aacgtaactt aaacgcaccg  95700
gaaaaccaaa aaaccttatg tgactcactt tattgtgata tacgctttat tgtggcagtc  95760
tagaaccaaa cttgcatatc tcccaagtat gctgggactt tgctagaggt aagctgcaaa  95820
tttagcccctc agtttcctgg tggctggcag ttacaaaatg gaaagcagag gtcattccat  95880
cattcatggt ggccatcaga caacaacaca gcagttgctt aggagaagca tgggtcttct  95940
tcgtacgcac aactgagaga aatttccctt aaagtggaca ctgagttaga tgatacaatg  96000
aatctaatgg ctacacataa tcatgaaat catgggccc tttattgtaa tgtttctcat  96060
gcgggctaac atgcgtagtt ctaggaaaa tatgatgctg tccaaacata cagctatttg  96120
gtttggctta tctaaagata aaatacatag tatccagaga aatagatgaa ctgtatgtcc  96180
tccatacagt ctcccataaa tattattct tttcagct gatccttta gtaatatca  96240
ggtagcagaa agttcaagat tttacactca ttgacattga caagcacctg gaatggtact  96300
acctttttt tttttttttt tttgagac agagctttgc tctgtcaccc aggctgggagt  96360
gcagtggcat gatcttggct cactacaacc tccgcctcct ggattcaagt gattctcctg  96420
cctcagcctc caggtagct gggattacag gcgcccgcca ctacgcccgg ctaatttttg  96480
tatttttagt agagatgggt tttgccatg ttggccaggg tgatcttgaa ctcctgacct  96540
catgtgatcc acccgcctcg gcctcccaaa gtgctgggat tacaggcgtg agccactgcg  96600
cccagccaag tactatttt attagttaag tcagagccat aatcattata actgagctga  96660
aattagaatt gccatccact taagaaagtt gagtggtcta acaagtataa aagcctaaat  96720
ataaggctaa ttcatgttca tactgaagcc tttgggaa taggcctaa aatatgtaga  96780
aagtattga agcggttta attgtactag ccaaaggag cctagtagaa atgcttgtgt  96840
tataagagtt tattttaa aaagctgaat ttatctgacc aggcgcggtg gttcacgcct  96900
gtaatccag cactttggga ggccaaggca ggtggatcac gaggtcagga gtttgagacc  96960
agcctagcca atatggtgaa accccatcac tactaaaaat acaaaaaat tggccaggca  97020
tggtgatgcc tgcctgtagt cccagctact ccggaggctg aggcagaaga atcatttgaa  97080
accgggaggc ggaggttgca gtgagccgag attgcgccac tgcactccag cctggacgac  97140
agagcgagac tccatctcaa aaaaaaaaaa agctgaattt atcaacaaat tgctgtggag  97200
tttttatat attcagcagg catcagtgt aattacctc acagactttc ttaaggtgc  97260
tttctttcta aattatactt tatgggggtc acaaaatagc aattttttaa taatcacctt  97320
taatgattaa gtattgttta agtcagatca ctcaactatg aatgcatgaa tattcatgga  97380
catctattac atagcaagca gtgctatgct gggccgagtg atttaaatg acagactttt  97440
tggtaagtag agaatttacc caagcagtcc ttgctgttct ccacattaat gctcagaaaa  97500
aatacattat aaaaatgatc tttccaaaat gaattatgaa gccccatgag aatgatatgg  97560
caattgtgtg ttacatattt tactagagga ttaatatcca ataaataaa agatactaag  97620
gaataaacaa aaaaaattta aaagatgaag tatataatga attagaacaa tacatttaa  97680
tcataagttt taaattagtg tggactttga attctcctgg acagattcct tcatttata  97740
gataaagcta ggactgtgac ttatccagtt atgaggttaa cggcgaatac aacattgtca  97800
tatatttaa atgacacaca ttcaacatg ttctctgctt tataaaaatc atatcaaata  97860
attgccccat agattattaa aggtgttaga ctagggattc ttaaaaaaaa ttttcatcaa  97920
atgtttcttt cattattaat cccatgaagt ccatgttaca gaagatttg tctacaacag  97980
tagcttaca ttcttctcgt tagaaataca accaccagtt agagttccta atcagtataa  98040
ggaagtagtt gttaggagag gggatggggtt tcttgtccaa atgaagtttt ccatttgagt  98100
ttttgaagta gtgaaactaa cccagcgttt acaggcccca gaaatctggg aacctcagct  98160
ttcaaagtac tgtaccagtc tttaacagtt ttcctggacg tgtgaattga tgcctccttc  98220
tgtaacatgc aggagtgttc tgtctgtctt cattgagtgt taaaaataa tcatgcctat  98280
ttcaaggaaa aaatctacag aactaagatg cagaagataa gtgctagatt taatcatatt  98340
```

```
ccttcatcta tctgttttggt tcaacctttc atcaactaaa agatgcacct ttttcttgt    98400
gctaactcta agattttagc tacagtttttg agaatcttga gtgtagtctc ttgtttacct   98460
tttttccttt ttttgtttcc cccacaccct agattcattt aaatactgaa cttctaaagg   98520
gcaagtatat agtgtagttt aataaaaagc aaaccttttc atgaacaata tatattcat    98580
aataagaagc gttcctttac ttttcagtac tctagtgaat agctttctac agtagaatct   98640
cacttagagg gtgtcttaaa gcttaacacc aagtgctcag gcagcatgtt atacaacagt   98700
tccattaagg tacatttgga tctttggatg tgtggtttgc ttaaagtaca ctgcattagt   98760
aagttggcag cttgctttct ttaaaaacat caaaagtttt aaaaggttta tttcagggca   98820
tgtgttagtg ttttgtgtgt ggttcttttgt tcctgttcta aactgttatt aaccactgaa  98880
gtgaaccttc tcccgggttt ggccttttgg tattcacagt gtattcaaaa cctaattaca   98940
gattagtcta tatttgagac ttttagagca agtatcagaa gacccaaaaa gaaaatgaga   99000
gtagcagtat catttcatgt agagataaag agacccaaaa catgaatggg tgtcaagtca   99060
gctgaagaaa agaaaaaaga gaaggaactt cattcactga gacggtttat gagttgggga   99120
ttatgggaat attcatgact caatcaagaa gcacagtgaa ttgatgtttg aaatagctca   99180
tcttttaagt aaacattgga taaatgaaa gtagactcag tattcactac acgtagaaat    99240
agctatttct gtatagcaga aatagcagtt tgttaatccc ttcctgagtt ggtttaatttt  99300
accaagtaaa tcacaaattt tattctttat ttgtgaatat ttaattcaaa tatttaatgg   99360
aaatatgagt ttgctttata attagtcatg ctgatccata cacgtatttc tgagagaaag   99420
caatttctaa tggtgaaata gttacaataa tattttgaa atttgaaagc accgtgatac    99480
tgaagcatta atctgaagga tcggaaagta gggagttttt gttgccaaca tttaacttca   99540
ttgtttatgg ataacttggt tttctgggca gccagatggc acagttagta tacagacatt   99600
cttggaaact tgtatcaaaa tttaaaatga atgaatttat gagaaataat tctgcttatt   99660
atttgtaatg tagctttcttt gaaaagcaag aaatcggaat gtagtttcta aagctgcaag  99720
tgaatatgta tacatagcca gctctttcag ccttgataat aaggtgcaac cattaagatg   99780
aagggatttt ttttttcccac ttgtgttttt gggcccgagt atcctgatct gtgttgcttg  99840
tctggttcag gtgtgagcca ccagcttttct ttgacttttca ttatctatgt gtatcttgcc 99900
tcctgttccc aggcttgctc tagctcttct gatcctgtct tcctccctct tgatcactag   99960
tgtagtattc atgaagccag ctaagttagt ttttcccttt gaaaaccaca gcccttatct   100020
tctgtgccat attttgggca acttcgttta tcattgattg accgtacgca gtgatcaggc   100080
cttgttctag acactgaaga ctctgagcat ttttggggcc attttgtact cctgtattgt   100140
tctccagggg cttctccaag tgtgcgtcaa tttagtcttc tcaagagggc atcattttca   100200
tcagaatatg atagcatatt atggagtgtc cggtcatcct taggcataga ctacttagga   100260
ggtgtaactg ttttttgttccc tgattttttac tgaaatgggt ctttttctttt tttttttttt 100320
tttttttttt tttttttttt tttttttttt tttgagacag agtctcgcta tgtcaccagg   100380
ctggagtgca gtggcatgat ctcagctcac tgcaacctcc gcctcccgat tctccctagg   100440
atgcgtctta ttttaagtca aaggtaatac ttaaaaaaga ccaaagagac ttaaaataac   100500
agcatttgct tcgtcactat gagctttgtt attatgagtt aacatacagt agcagactgg   100560
gtgtagtagc tcacgccctg taattccagc agtttgtgaa gccgagtggg gaggattgct   100620
tgaggccaag acttcggaga cagcctgggc aacatagtga gaccccccatc ttgacaaaaa  100680
aaattgtttt aaattagcca ggtgtggtgc tgcatgcctg tggtcccagc tacttggaag   100740
gctaaggtag gagaatcgct tgagcctggg aggtcgaggc tgtagtgagc cgtgtttgca   100800
tcactgcact cctgggtgac agtgcaagac tctgcgtcag acaaacaaac atcgtagcag   100860
tgtgttttct taatcagaga agtgtagaca aggctaactc caggctttaa tgtcctcata   100920
tttagcaatg atacctgcaa ggttgtatga gaaccaaatg aaacgccaaa tttgaaaata   100980
catagtagat acatcatagc agagtaagcc aggaatgctc tcaaaggta ggatatcatc    101040
tgtgtcctca tatcacttta tgaagtacat tgtgaaagtg aaagaacaaa gaaatataaatg 101100
tttttagtt aatgttttaaa ggatacatttt atcataattg ctctttttaac actcacctcc  101160
agtctcccct ccgttcacac ctcctacccc cattacttcc tggtaactta gttaagtgtc   101220
ctttgtcatt cctgaggttt caaggcatgg tagtactgtg tcctgatatt ctaatcgtaa   101280
atatttaagg gaaattcggc atttttttcat tttgtggttt tcatattaaa gtacattaaa   101340
tagtctttttt gcttttattt aggaaaaaaa ctgcttacct gttaatttta gaaaaatctg   101400
atttttcattt agaccttaca gggtgagaca cctgcatcag ggtggctctt ggtatctttc   101460
aattcaattg gatcttctct gaatagtctc ttgtagggag tgaggctgct gtaccacctc   101520
cctgcagtag tccatccagc ttaagatggg ggtcaccagt aggccaaaag aatgggtaga   101580
cctgccatg cactgccctca ttgtactcaa atcgtgtatc aaatggagtt ggatttcttc   101640
tcttcataca gtacagcatt tccaagtaga aatatttctc aatgaaatgt ggagagaagc   101700
acccgtttga gattcccgtg tgttgtgtga tttaagttag atggttttt aagaccacat    101760
tcatttccag cattctaggt aacaatttag aaaatgtctt tctcctaacc tccccacttt   101820
ttaaaaatcc tccaactgat gaactgatgt gaaactttct tacattccat gaaaaaaaaa   101880
aaaaataggt taagctgttt ctaagcaact agatgaatta atttttaaac taagaatgtg   101940
gccttatttt gggaaaacaa gaatatttac ttgtttgtct gctgtttaaa aaatggaagt   102000
cagcctacca aaaattgag actcaacttc taggagatgg gttaggattt ttttttttaa    102060
gtttctctag tttaattttta tatataaggg gttaatgcta ccttcataat aactattatc   102120
atattttctc aatacatagc ttgattaaaa caactggact cccccccac cccaccccac    102180
acacacacag atttatatc agtctgaatc taatgcctag aataagaagt gcttcagcca    102240
ggcatagtgg cactcacctg tagtctcagc tactcaggag gctgaggcag caggatcaat   102300
tgagcccagg agtctgagtc tagcctgggc aacatagtga gacctagaag ttttaaatta   102360
ctggaaaaat aaatatgaaaa gaataaatta ctggaaaaag aaatatgaaa tgttacgtgt   102420
tttatatcca accgtggtag gcttttttga gttcctgcaa tgctaataag aattcataaa   102480
aaggacaatt cttcatttttc ttgggtactc atcactaata gctgcctcgc tggtaaaaag   102540
gaatacatgt atcttcaatt gcagattatt tactttttaaa tataaaagat ataaatgtca  102600
aatattaaat gcatcttaca tggttttcct acatagtgaa agtagaatgc ttgccagttt   102660
tgcctctagg tcactcactt tgaaccagcc aacccacctt aattgatcat ttccactaat   102720
atgttaaatt accttaaaag aacaaaaata tttatcatgc ttactataac ctgtgtttta   102780
aaataggagg ccaggcacag tggctcacac ctgtaatccc aggactttgg gaggccaagg   102840
caggaggatc acttgagccc aggtgttcag gaccagcctg gcaacaaag tgagatccta    102900
tctccacaaa aaaattaaaa ataaaaactt agccaggcgt ggtggcacgt gcctgtggtc   102960
ttagctacgt gggaggccaa ggcgggagga tcacctgagc tcaggaggtt gaggctgcag   103020
taagccctgc caacaccact gcacgccaac ctgggcgaca gagtaggacc cccatctcag   103080
```

```
aatataaaat aaagtaggag gtgcatgtga agtagtatag atcatgactt ttccaatttt   103140
aagaggggat tggcatgtac tatgagcagt tcacatttgt ggaggaaatc tacatttcag   103200
agagtatata tttcatttgg aagtctataa acatgaaaac ctaaaataaa taatgtaaat   103260
ctacctctag tggctctggt atttttaaac ttatttatag ctggcaaagt acttttttgt   103320
atgtattttt atagcaccat tgcacttctc atgtttgttg caagcatctc ccacagcttc   103380
ctttgtcttt taattttatg acatataaat aaaagtatac atttcaatat ggccatattg   103440
attgatcttt tcctttgtaa ctcttactac tttatattta aaaagtcatt tcccagtcta   103500
aggccacctc tattttcttt tagttttttta aaatggtttc attgttttat atttgcctat   103560
gatccagaca ttagtaactg tgggttctta attgggcttc agagaattgg agaattcctt   103620
aaaattctct acataattgt acatgtactt aatacatgct tttttccatg ttaagagtcc   103680
agagtttttg ttagatcctc aaaggggtca gtcagtctct cctcccactt ccaaaaaatg   103740
tctgagacct actactataa tccatctgga ctttatttgg gtaaaaggtg gtatggtgag   103800
actcatatttt ttcttttttcc cgcaaatagt taagtatacc aaccatttag taaataatta   103860
cctcctgatt tgtgatacct ttgaaaaata aatgttttttc ttttattttta tctccacaga   103920
gaaagttaga gaaattcaag aaaaacttga tgctttcatt gaagctcttc atcaggagaa   103980
ataaattaag tgagtaaaaa ttctctaact gtattggtgc tgactaaata caaaattaca   104040
cttttcttaa tagtttatca ttctgcttca tttacatcct gcttgtcact tatgctgtaa   104100
tttcaatggc atgaatctct gaaactagct tccgaatttc atttgtataa cgttgctttg   104160
aataacttga ttgccttctg gctgaattaa gaatatcctc tagaactcat tttgaataga   104220
acaaaggtga acacagagct aagatattgt ataatatgca ggtgactcat tttctaggtg   104280
taaagaattg agctgtagtt gacattactt tattcttctt gcctatagtc tatcaataat   104340
gatgtgtatg ttaaatattt aacttagaaa gttttctgtt tgacttaatt aaaattttaa   104400
taattgttct taatccttat ctcttttgtt taaaaacatt tagataagtg ttttttcctac   104460
ttaatttata tagccttaga atttagtact ccttgaattt actttcttgt ctgattctgc   104520
tttctggcat tagaggcatg ttcctaataa aatacatatt taaggacttt tccttagtag   104580
cataatcaat taattgttgc tgaagaattt taatcagtaa gtcacttgct tgagaggaga   104640
cctcgctctg ccaccaggc tggagtgcag tagtgcaatc actgttcact gcagcctcaa   104700
cctcctgggc tcaagcagtc ctcccacatc agcctctcaa ggaactgggg ccacaggctc   104760
atgccaccat gcccagctaa tttctttaat ttttttgtaga gatgggtttt caccccgttg   104820
tccaggctgg catttgcttt tataaaagaa gttgaggaaa gaaaaatact gtagttaagt   104880
cattatcact tcaaatattt tgtcactttt gtctgtgacc cttaccctac agacagcctg   104940
cagcaggctc agaactagaa ggagtagaaa tgtaaaaggt tccctccctg gctacgctcg   105000
gttcaggtca gttcagaaaa ggctcttaaa ccaaactacc tactttcctg tcaggaaaat   105060
gtatttgaga aagcagggtg gaaagggaag tacaacttcc atggtacatc attcggaaca   105120
gtgtgccagc aaggaggag agaaacaaga cctagaaaac ttgaaaataa agctttgtaa   105180
cttttatttca tttgttgctt tagtaagtta agacaggcca gtgcggtggc tcactcctgt   105240
aatcccagca cttagggaga ccaaggcggg cggatcactt gaggtcagga gttggagacc   105300
agcctgacca acatggtgaa accccgtctc taataaaaat acaaaaattg cccaggtgtg   105360
ctggcacatg cctgtaatcc cagctactcg ggagcctgag tcaggagaat cacttgaacc   105420
tggaaggtag tggttgcagt aagcagaaat cgtgccactg cactccagcc tgggcgacag   105480
agcgagactc ttgtctcaaa aaaaaagtga agacagatat atggaaatat acaaaaatac   105540
ataatcatct ttaacacaag ctaaacataa ttttttgtgtt ttataagtgt ccgtgttcat   105600
aaatgtcttt tatgtcttttt gtgtatgaat attttatttt aaaaccatta agtgttacaa   105660
tatcacccta atcatggtgg ttaccgtgaa tacttactag tagaaataaa catctgtagc   105720
gcctcctcga tctcccctttt agcaccagag cttacatcat agttctatttt actgacctgt   105780
gtgtgctttg cggggaaaaa ttgatgaaag ccccggaagc cccgttaaaa agacaagctg   105840
tattctgtt ttttaaacaa aatgaggaag ctgaaagcca gccagtgttt tacataatgg   105900
tgtctctccc ctcagctgat cagtgtgaca tccagagttg ctgttgctgc tacctgtcta   105960
gtctctaaga cccttttcaa cccttgtgac ttaagactct gtgaacttttt acaaagtatc   106020
ttgtgatctg gacagatgat ctgttttgta ccctgcagat gcatttaaaa gaataaatct   106080
ggcagaatgg taaccttgct tcattctgac cattttatca aagttaccaa ggaccccaag   106140
gaatactttc tcaagtatag ttttaacaca taggattcct aattaattgt tattctaata   106200
tttgctgaag gtgtttatat gctatacagt catacacaga ttcttcttca attaatttta   106260
gtatatgctt ttaacttatg tttgataaaa aaattatgcc aatattgtta ggtcggtgat   106320
agactatata agtttagtaa aactagcaaa ggtaagcagt taggcttcaa cattgttgttg   106380
atcatgcagt catcaacttt gtttagaaat tttgcattta tctccccctga cctcagtttg   106440
ttaaatgggt ttatttttac agaatcgtac tcataatcag ctctgcatac atctgaagaa   106500
caaaacatc aacgtctttt gtccagcctc ttttttcttct gctgttccac ctttctaaac   106560
atacaataaa gtcatgggat aaaaataatc gatgatgtt acgggcgctt taaccatcag   106620
ctgcctctcg aatggaagaa cagtggtaat ggattaacat cctattttgt tgtactaaag   106680
tgacaaatcg gaataatata attggtatgg ccattaggtt cagtccttga agataagaaa   106740
cttgttctct gtttgttgtc ttatttgtgg tggcactcgt ttaatggatt aactgaggtt   106800
gctcaatgtt cagtttcttt tccagaaata caatgctagg tgttttgaaa taaaacttat   106860
atagcaattg tttaaagtta tcaattgtat ataaaatcac agtagcctgc taaatcattg   106920
tatgtgtctg tagtattcta ttcccagaaa ctatttgacc atgataattc agtttatatt   106980
caccacatga aagaaaaatg ggtaacagaa gaacccttaa aacaggttaa tttggattgt   107040
aacgttcagt gaaagaaatt tcaacccttc atagccagcg aagaaatttg ccttggaagc   107100
caagtcagta ccagcttacc tatttgattc agttgctgtt ttctcactct ctatatccat   107160
ttgaaattga ttttatttttag atgttgtata cttacgttag gctttctgtt aatagtggtt   107220
tttctcctgt tgacagagcc accgattat gacacaggat gaggaagatt aaggataatc   107280
aattgactaa tttcatttag aatattatca aacatttcaa ctaggtatca gaaaaaggct   107340
ttctttcata agactatttt aaatagaaat tatttcaaca attaaagtaa tgttgaccat   107400
cccctctca gctgaataaa gaaaaattta gttcaattta ttgcaattta attcaaatac   107460
taccttcaca acattttcat gtgttttaaa taatatttt ttaattggct aaaggacatt   107520
caagcaaaga aatgctttct ttacttaaaa tgtctatctc atttgctgcc ttttcactaa   107580
gcctttactt tgttaataaa agtgtccatt gtgtgatgtt tttgatttta cagtttgcta   107640
aatcttattt tcttggagtt gcttttggt aacagcccca ttgctactcc ccatttatt   107700
gttttacatc aatgcatgct tcgttgtgat ccctcaagat gtaacacttg gtatgctcgg   107760
ttgaggatat gaaaaaatac ttccgaaacc aggaattcaa tgtatgtttg ttttatactg   107820
```

```
tttgataaga aaagtaggtc cagccttaag cagcacagat gcgctggtag atgcatagtc    107880
aggaactttt tttatttctt ttaggtctag ggacaggagt gaatagaaag ggaggagagc    107940
tctattatgt tctatacaca gattaggaga tgaccttact gggtacaccc ctctaaccag    108000
tgcttacagg ttaatgcatg ttaatgaata tttttgcagt tgtaaagcat aacaattaca    108060
actacacatc tatttctaaa gaataaaaca ggaccatatt tatttacttc tgtcaactat    108120
agaaagaaag accttcagct gtatttccac agatttctcc caaggaaaag gctaatatta    108180
gtcactactg ttatcacatc cctttgtata agttttaaaa agagatggag ggagatcttc    108240
atttctttga ggagatcagt attgtaacgt atgtgaatag atgataacaa ttaatattac    108300
taaaagtccc acatgagagt cctgacgccc tctccatgcc ccacagtaat gtggcttctt    108360
tcatgggttt ttttttcttc ttttagctg atctcatcct aagcatgctt tattttcct    108420
tgaaagctag gtatttatca actgcagatg ttattgaaag aaaataaaat tcagtctcaa    108480
gagtaaaccc tgtgtcttgt gtctgtagtt caaaagtcag aaatgattct aatttaaaca    108540
aaaagatact aaatatacag aagttaaatt cgaactagcc acagaatcat ttgttttat    108600
gtcagaattt gcaaagagtg gagtggacaa agctctgtat ggaagactga acaactgtaa    108660
atagatgata tccaaactta atttggctag gacttcaatt ttaaaaatca gtgtacctag    108720
gcagtgcaca gcacgaaata agtggcccct gcagcttccc cgtttaaccc actgtgctat    108780
agttgcgggt ggaacagtca acctttctag tagtttatga tattgccctc tttgtattcc    108840
catttctac agttttttcc gcagacttct ttctgcaaat tattcagcct ccaaatgcaa    108900
atgaatgata taaaaataag tagggaacat ggcagagagt ggtgcttccc agcctcacaa    108960
tgtgggaatt tgacatagga tgagagtcag agtataggtt taaaagataa aatctttagt    109020
taataatttt gtatttattt attctagatg tatgtatctg aggaaagaaa tctggtattt    109080
ttgctttcca ataaagggga tcaaagtaat ggttttttcc tcagttctct aagctggtct    109140
atgttatagc tctagcagta tggaaatgtg ctttaaaata tgcttacctt ttgaatgatc    109200
atggctatat gttgttgaga tatttgaaac ttaccttgtt ttcacttgtg cactgtgaat    109260
gaactttgta ttatttttt aaaaccttca cattacgtgt agatattatt gcaacttata    109320
ttttgcctga gcttgatcaa aggtcatttg tgtagatgag taattaaaaa atatttaaat    109380
cacattataa ttctattatt ggagagcatc ttttaaattt ttttctgttt taacagggga    109440
aagagaaacc tgtataccta gggtcattat ttgaccccat agtataacca gattcatggt    109500
ctaacaagct ctcagtgtgg cttttctctg aatgcttgaa tttcacatgc cttgcatttc    109560
acagttgtac tccatggtca accggtgctt ttttccacat cgtggtactt gtcaaaacat    109620
tttgttattt tccttggtaa aatatataaa aaaggttttc taatttcact ttgctgccaa    109680
ggctgtcatt ttcattaatg ctgccaacat gttcatatga ggcttactaa gaagttataa    109740
ctaagcttta gaactggaag agactttaat ttcatctacc atctgattat aaactcctgt    109800
tactcacttt gttattcctc cagaactttg ctcataaatg ataccttacta attgtcgatc    109860
attggatatg tcaagttagg tagcgtatag gtgtgccttc ttaattcctt cagaagatgc    109920
agaggcaaga acatgtttca atcgtgttag cattggtttt ctttatcagt gctaacagac    109980
tcagtgtgag gccccatact ttatttaaa ctaggttttc atccttgtgt aattcaagtt    110040
cagaatcttc gtgtatcaaa acgtttgaag aatttagtta ctgaagattt aatagagcaa    110100
ttaatttttt tagcatgtct gattgaagaa ttaatatatt tatcaaattg aaatagctac    110160
catgtgccta tagataatac agatgtattt aattatgaag tacgtcttaa ataaccaca    110220
tacccgattt gtgataacta aaacaatcat gtcctgcaca tattagaccc agttaataag    110280
tgtagaaaac ttaagtgttc aaacaaatac tacaaaaatt gttaaaggtt caaaaccagg    110340
agacagtatc aggaaaggctt aaatatgggt gatctctgac tggaagaaga cagcttctaa    110400
aactaagggt aggaaaaacc tatatcataa ggcatttgtt taaatttata tcctaaaatg    110460
acagaattga gcttgaaaat tgagagtatg tatgtgattc ctctccaaga cttctcgtga    110520
gttacgtaca tattctgcag aagccgcgtt aaggtgcatt tgtggccaag tcactgacaa    110580
ggaggtaaat actacttata aatgctgtta aatgaaaatc tttttttttt tttttttt    110640
tttttgagtt ggagtcttgc tctgtcgccc aggctggagt gcagtggcgc gatctcagct    110700
cactgcaagc tccacctccc gggttcaggc cattctcctg cctcagcctc ccgagtagct    110760
gggactacag gcacctgcca ccatgcctgg ctaattttt gtattttag tagagatggg    110820
gtttcccat gttagccagg atggtctcaa tctcctgacc tcgtgatcca cccgcctcgg    110880
cctcccaaag tgctgggatc acaggcgtga ttgttactct ttgtgataaa aaattcttgt    110940
tcctgctgtt agtacttta attcattaac ccaggtgtaa actgttcctt tccaagtatt    111000
tgggaaattc agagatctgt ttttgaaaaa actaggccag aggcacccct gaagatctag    111060
tcacagtgca gtgatactgc cagcagcccc ccacagagat atgtcttacg gctgtattaa    111120
gaatataagt tacactcttt aatgttcaga acagaatact cattctgctg cttactcttg    111180
tagttattaa atcacagagc aacaatacgg aagttagaat tttatccatt tgtcagaaaa    111240
tatgctcatg gtttatgtga cctaatactt tccaaaagct cttgagacct ctgatatttg    111300
tgagagaata tgtagggaat aggttaacct ccttttttg ctttggtaaa cttcatctga    111360
gattaggcca aatcatcaga aagcaatact gcctgggctg ctacttacct acctctttga    111420
tattacgtcc ttggcttcac aggcaagacc ttatgacaca tctatttgaa gaaaatacac    111480
agtctctttt gcagaagtct aacctaatga catgtcttga ttatcactga aattcattaa    111540
ggattactag atagtaccag cggttccccc tccagacaca tgtatgtact gctctccttg    111600
tgacaatgag aactcaagac tttaccattt tctttgcttc agctgccagg aaatgctgaa    111660
attaattt                                                             111668

SEQ ID NO: 2           moltype = DNA  length = 5409
FEATURE                Location/Qualifiers
source                 1..5409
                       mol_type = other DNA
                       organism = Homo sapiens
SEQUENCE: 2
gtgatggatg gtttaagggg gctaccgata cattcacact aatcagccat ttctgccaag     60
atcatgtcac ctcaatctgt tcatggactc caaatacaag aaattaattt gacaaagtga    120
aaatataaaa gatgcatcat ataaatatgt aacttttctg gagtgggtag tataggtaaa    180
gccaaaagaa acaaattcaa gcagaggaat tttggtttct gaaaattagg ttgtctgtag    240
ggtccctgta tttatactta gaacaaaatt aggaatttct gtttatgtgg tccagttatt    300
gagtcaccct aagtttgtag gcatcttacc tacctacttg ctcccccaagt ttttatttct    360
aaaatgaaaa gcattgctgt agatgaccag tttcactaa agaataacat ttatttattt    420
```

```
gttttagcta aagtatatgg acagggaaca ttcatattct tgtagaagaa aattattttg    480
acttttgggc aaaagcatgt agttcttata cactttgaca aactcattgc gtacattttt    540
cacattaatc aaagtcagca caaataaatt ttcaccttgg accacggagg gtttgaacac    600
tggaaatttg ataattct ggttgctaaa gaacaagttc taataaaagc ttaagtgtat    660
accaaatgt ggctgttggt gcaatcagca ggtccgtaaa aatatgattt taatggttag    720
gtaatcccac aacggagatc ccaaagttca tgtttggaag agacttttgg gtcaaagtga    780
aatcagtgta atgaatttaa aattatactc tgagatcttg aaatcagcta attatgttac    840
atcttattag ctcagaaaag ttttgaagtt atatacaaat gctagtcagg aaaaaagatt    900
cagtcatgta attcttgtac attctactat ttaaatcaac caatattata gattatgatt    960
tagtgcagta attctgctgg ctaacccttat ctcatttggt ggtggttagt acttcagagt   1020
actcaccata gtttcattta tgttttcagc atcacttcct ggttttttctc aattccatgg   1080
ctgtggaatc aattcatatg tatatttagc ttcggtgagc aaaaacatag ctagaaaaag   1140
aaaagaagtg agtttcctac ctggttaaat taaagtcgat gtgttaagcc aaggaggact   1200
tcttttgaat ggtacttttaa caatccctgt tctgtatact gtgaatatat cattaaata   1260
gcctaataaa ttggatgctt aggctgagcc acctatactt tagttttgtt atggaaagaa   1320
gggagaggag caagtatgtt cttatatgtt acttagaaat aagaatgtag ctgtagttac   1380
acattgttct taagttttt tcgtaagaca acttgaaatg agtcccatag gcctgctatt   1440
taacattcta agatatgact taaggttaat gatgagcttt tgaatctgac aattcaagag   1500
atatccataa tgaatactga ttcatttttct acattgctga aagctaatgt tcattttaag   1560
cctactttag tagcctttat ttgggcttag agatgttatt cctctttctg atatttattg   1620
ggttatctgt ttaacccttt tatatctccc tttcccgatt tgtaaattag agactggcaa   1680
gactttttac cctgagtaga gcaccaaaca tggcttgttt ctgcccacac tgtagttacc   1740
ttgaggggaa gtaatgggaa ctttaaaagc aatttatgct cttttatagt gaaattatcc   1800
ctcttactat cccgaaagac tgttaccttaa caatatcctc cactcctttc ccctgtagt   1860
tactatagag atgactttttc ggttcttcac tgccataatg atcaaaatcc taattcatga   1920
gattttttatc attccaggca tgtgaggttt acttgatgca taaaaccgca agtacttttt   1980
gttgttttttt aattgttttt tctctcttat cttcttgaaa gtctaagtag atcatcatttt   2040
ttgatgtctt attagtagca actaataaat tttccctgta tcttctcagc aaaagaactc   2100
aagcagagac agaagattag aactaccatt ggtagttttg cttcctatgg atatgttcac   2160
atacatagaa attttttacaa tgacctttt atatatgtat ttcagaattt cagaatggcc   2220
tcaatgcctt aataggaaga aatacttgaa attttttaaat tagggcttgg ttttgtgagg   2280
agctagtaaa ggttttttctc tttcagctttt agcttgtttc tgcggaggat tccgctcttt   2340
ctccatcagt ttcatagccc tggaattgta gaaaagctct ggtttcaaga ccattgatat   2400
ccatttctgt cagggtgagt tttaaattta ttcatgatg caaacaatat attgaacaac   2460
aggacatgaa cttgttcttg ttgtaagtgg ctgaattttta tcagtaaagc acatcaaaat   2520
aaaatatacc ccaattgcta gttaagacct agagtgacag attgaaaata gcttgtgtta   2580
ttctcttaag aaaatatata aaaattatca tctcatcaat ctttaatgtt tgttttataa   2640
atctaaatgt ttttatattg tttcctagga aatattaggt ctaattttttt acttaccac   2700
cagctgtctt ttattttact cttttttttga gacggagttt cgctcttgtt gcttaggcta   2760
gagtgcagtg gcactatctc agctcactgc gacctctgcc tcccgggttc aagcgattct   2820
cctgcctcag tctcccgagt agctgggatt acaggcacat gccactacac caggctaatt   2880
ttgtatttttt agtagagacg gggtttcttc atgttggtca ggctggtctc gaactcccga   2940
cctcaggtga tccgcctgcc tcggcctccc agagtgctgg gattacaggc gtgagccacc   3000
gcacctggcc agctgtctttt taatataaca ttatgattaa ttgtgatgtt ccattaaact   3060
aagcggagag gaaacatgct ggtaaaccat gtgtgagtta ttcattgtac cagaaaggca   3120
aatgatacat tttatcctaa aattcaaatt tataaacatc ttaacacttg tgatcattaa   3180
atactactaa tctagcatat aaattatatt tgtaggcggg gcacggtggc tcacgcctgt   3240
aatcccagca ctttgggagg ctgaggtggg cagatcacga ggtcaggaga tcgagaccat   3300
cctggctaac atggtgaaac cccatctcta ctaaaaatac aaaaaaaatt agctgggtgt   3360
gctggcgggc acctgtagtc ccagctactt gggaggctga ggcaggagaa tggcgtgacc   3420
ccaggaggca gagcttccag cctgggcgac tccgtctcca aaaaaagaa aaagaaatt   3480
atatttgtaa tattctacta acctatatc attttaactt tttatataac tttttattt   3540
taccaaatta agttaaccttt ttatagcccc tggcttatac taaacatcct aacttttttg   3600
tttaattgta ttagttttta agttattgcc ccagatgtca agtaatgttg gattttctat   3660
aataatttag gatatattgc atgaagtcag ttagtatta catttaaaac taaaacaatt   3720
tatactaata cagtttatac atttcatact aatttagcta cagttggata aatatttaat   3780
ggaacaaagt aaatcaaagt accttttcaa atgaattgga aattaaatcc acataacaat   3840
tttttatgac cacactatta cagtgtgatg gcatgccaaa tgatcataat gtggaattat   3900
gtatttcttc attggctttc aagattctgt tctttagttt gtgggctcct ctccaacttg   3960
cttgtctcct cacagtttag gcgactgttt ataattcttg tccatcctgc ataaacacac   4020
acagtcaaaa tgaaaaaaag cttctcatcag cagatctgtg cttgctgtac agaaatggga   4080
aaacaattga agtttgcatt atcttttttc taattaccag atcgttttg gagctattta   4140
ggcatacgct tttaaggaaa aagaaaaaa agagtgtacc ttttgtttct aacaaaggtt   4200
gttatctata ttattgaaat aaaaaaaattgg ggatagttat gacaaagtat ttagaaatag   4260
gaattaaaat cttaaaataa ctttttcatag catggacaag acttattaat gtctacctca   4320
ataagcaaat catttaaaaa ttttttcatgt atatttgctg ccatgatgtg ttgtgattgc   4380
ttaaataacc aatgaatgaa gatcaacaag gatttaaatg aagaagaata tggatttaac   4440
tattttctcc tgtgaaataa cagttcattt acaagtttttg attttcagaa attagacaat   4500
tatttttaaa ggctgggatg acaacttctg cctcttacca agaagtcaaa gcacagttat   4560
gtgaattcat cataaatcac atcattttta ttatattttg tatttataat tgtattgtga   4620
ctactttaaa acctgttata aaataaaatt gttttttaat attttattttt agaattatta   4680
gcattaataa caatttgaag tagttacac aatacctgtg agttttattt ttgttttata   4740
ttgaaattaa tttttagttgc tttacttggc ttcattgcta tggatgcatt ctctgtgtta   4800
cgagttagca gatctttcct tggaactgaa ttaaaaagca agcatttggc tccacttaaa   4860
tctctgaaaa tgcaacttgt tctttgcatt tattacataa ttcgctactt atggtacaga   4920
aatggataca atacaaaaat atttccttat aagatacact gtgaccaatg agcttttttaa   4980
atagctgtaa tcagtaacat gtatttgact tttcaaaaca catttctgga gggatatcag   5040
tgctttattt ccccaaatat ctgaatccct atgctttagt acaaaacaac ttctgaagaa   5100
tttagtaacc atatgtgttg atctcttgtt tttctaacta gtctttcata agaaatgact   5160
```

```
agaatagcaa cagggaaatg attgcctttt aaggttttg tttctcaata taaaattttg    5220
gtgaaccatt tttattgata aatacaggta ttttactttt cttaaatcac ttgatttaaa    5280
attactttga ttaaatatgc atataaagtc agttgttttt aactctcaat acttatcaaa    5340
aaaatttaac ttgctgtaca ttctgtataa acctaattct attcaactaa aattatttta    5400
aacatttag                                                            5409

SEQ ID NO: 3           moltype = DNA   length = 24782
FEATURE                Location/Qualifiers
source                 1..24782
                       mol_type = other DNA
                       organism = Homo sapiens
SEQUENCE: 3
gtgagtagtt cttactgccc tctaccttac tacctttcca cctttcccat ttccatttgt    60
ttgttgatcc atttaatctc aaacttacag aaaagttaca aggaactggg ctgagcacgg    120
tggctcacgc ttgtaatccc agcactttgg gaggccaaga tgggtggaaa acaaggtcag    180
aagatcaaga ccatcctggc taacacagtg aaaccccgtc tctactaaaa atacaaaaaa    240
cttagccagg tgtggtggtg ggtgcctata gtcccagcta cttgggaggc tgaggcagga    300
gaatggtgtg aacccgggag gcggagcttg cggtgagcca agatcctgcc actgcactcc    360
agcctgagcg acagggcgag attctgtctc aaaaaaaaaa aaaaaaaaaa agttacaagg    420
aattttttc ttctctgaag tatttgagag taagttgctg accttaagtc ctatcacttc    480
caagtaggtt catgtatagt tcttagaaac agattttctc atagcaaccg aacattgata    540
aattacaata tctaattctc agaccccttt caagtttcgc ccgttgtccc agtattatcc    600
ctccatataa caagatgttc caggctcaat acctgaccca gcttcctttt tttgaagaat    660
ggtgtttaga aatggagacc tagaaattat atatgctgtt attggaatat cactgttccc    720
tggtttctca gtgaaagag ctaggaacta agtgttgtga atgtttgtgt gtgtgcaggt    780
gaatatacac acactgacat ctgtattcct aaatcatgtg tatatttatt tattaaaaac    840
tgtgagttga tgctgatact tcccatttta atccagcatt acaaggtttg ttctagtgtt    900
ctcccttttcg atatttgtca cttgcttcc tgatagaaaa cgggcttcta gtatccttaa    960
tatattttca tatttggtc agtcctccta tacgtaaccc aacttgaatg aagatatgtc    1020
cttttccatt gcagaaatgt tcttttttccc cagctcggac tcaacactac acaccaggcc    1080
accacatggc gccgcaccca gcattgacac ttcctttacc ttgtctgggc tctgacatcc    1140
gtgccaggtt gctcttcgtc atggagtccc tttactgag ctctgctctg acgctttgtg    1200
ccaggtgcct ctccatctca tccttcccac ccgctagcct ctgcccgacc ccagacagat    1260
tccttcctca cctgaagcca gaccatgcct ttgtggagat accctctta ccctgcctgt    1320
gcttcgccag cctgcaccag gccaccctcc tgcacagata ctctcctcag tactggacca    1380
ggctaccaac agcccccatgt gaacccattg taacccaggt caggcattaa cacctgcagt    1440
aggctaccat ggcttcccct tcccaccccc ctagcttggc cctactaata atcactttgt    1500
cactgttttgg ggttgatatt tggttgtttc ttgtaggttc ctagctttaa gataggattg    1560
catactaaaa tttacttaga tctttgagaa ctcaaggaaa tcagtgaaac attattgtta    1620
ttaaataaaa ataaaatacc tgtagttggt acctctgttt gagcctgcct tgttacaagt    1680
ttcactgact tcagcttcgt gtaacaaagt atctttttct ttcaacgtgt acttaaattt    1740
cctgtcttat tagttttctg atatctaaaa ggaaaaaaag cagatatcgt taataaatta    1800
gaaagaagtt ctgcaaattt aaaagtgcct tctaagctga gttgtaggat tacagtacaa    1860
tccatagggt tatcctgaag aagccaggca gggctcttct gtgttacacc ctgtgcctgc    1920
gcagcatgct caccccttgc catcagcgct tgcggcccca ttctctccct ctagtaataa    1980
tctaagttct gcattgcttt ctcctttcct tttcttctt cctttaaata ttcttctttc    2040
gagacatatc tcatttaac tttatttttc attttctgtc tttctcatgc    2100
caccttggca atgtagttaa gtttgtgcta acgtagaaga ttagtgctca aatctgaatt    2160
gccatttact actagctgtg tcatcttcgg cagggaatct cccagagcct tagcttcttt    2220
atttgtaaaa tgactattat agtggttatt tctcaggatt gttagaatta cttccgcaaa    2280
catttgcaag tccctggttc ataatttcat gctaaattag taccgttaca ggaagtgta    2340
tatcattgtc acagtgtata caaatatatt tcttttatat ccctcgtgat ataattcata    2400
agacagtgaa acaattcaat gaatttttacc agcataacac atttttaagt gattggaaaa    2460
tcataagtat cttttcttat gttttagta gaggcttgc aaccccatta ctctccgctc    2520
ccaatttgat tattaaagg aagtggatta ctaactcaga tatgtacact gtcaagccaa    2580
gttctatgtt ctactgctgg ttttcctgag aaagcagtca tataactccc ttgaaatgat    2640
ttactacttt tgtacatata aaattataat ggtgttaatg taccaaataa tgtccttgga    2700
agcaaggggt ttgccagtaa ctcagctgca tcagtcaccc tcaaggagat gagccatgac    2760
tttgttcatt agttggaaaa gagtcggag agtgccttgc cgttactgtt tatctttggt    2820
ctgacacttg gggataggt catggatact tcagccagaa aactttccaa attaagtta    2880
ttaatgtatt ataaggatca aagtttctag tatagcctgt tcaattagaa catagtgtgt    2940
tggttgattg gatttggaga aagggaggca atcaaatttt tactacagtt tcagcctgtt    3000
acagaatatt gtatagagtg ttaaaatgtt gatgcattca tatttttgcc agttttaagc    3060
ttgtacattt ttaaatcatt tccttacctt ggagacttcc cccccacctt tttttttttt    3120
tttgagatgg agtctcgctg tgtcgcccag gctagagtgc agtggcacga tctcggctca    3180
ctgcaaggtg gttctcccac ctctgcctcc cgagtagctg ggctacagg cgcccgccac    3240
catgcctggc ttattttttg tatttttagt agagacgggg tttccccatg ttagccagga    3300
tggtctcgat ctcctgacct catgatccgc ccgcctcggc ctcccaaagt gctggaatta    3360
caggcatgag ccaccatgcc cagccctgac tgccctttaa gatgagtaca taagtagtaa    3420
tagtacattt ttcttttcaca tcctggagaa gatatactgt gttcactatt gaatgaaac    3480
cataaagcta gagttaggaa gattgaagaa atgaaaagg agctcacatg attttgtctc    3540
aggagaggct cttccaggat tctttggaga tatggtagat tccatagctg gagcaggaa    3600
aggacaggat gagcctgtgg gtgtagaaag gaagggagtg cttgaaagat gatgaggaga    3660
tgtcagcagg tcacagaaac cctccgaagg aggctccaac tggccaggct ggggacaatt    3720
tgggccccaa aataatgaca gtaacaaatt gtaactcatt gaatgaaata ggaatccata    3780
cattggtaat tatataaata agggaataaa accatgatgc aaaaagggat gtttatgtca    3840
tcacgcaaaa tatgttcaca gaaaatatgt actaattaaa agagggaaaa gagtaacttt    3900
acagtggatg aagcctggca atcatcactt taagcaagtg gtcagagtta atattatcag    3960
taatggtcaa atcaaaaacca tatgcaagaa gactctaaaa tgcaagaaga ctcctgaagt    4020
```

```
acttcttacc aaagatgtag aacttaaatt cagtcataac aatacatgag acaaacccaa   4080
gttagagcac agtctgcaaa ataactggcc tgtaatcttc aaatgcatca agatcatgaa   4140
agacaaggaa agagtgaaga gctgctccag ttggaagaga cttaaaacta aatgcaatgt   4200
atgatcctag attggatctt tttgctctaa ggacattaat gggccagtta gtgatatttg   4260
aaggggatcc gagggttcca ttgtagtaat atatcagtgt taattttttaa attttatta   4320
ggttgggatt attttggaaa ataccattat tcatagcgaa tacaaagtag aatatttggg   4380
gatgataatg catgattaca acaaatgttt caggagaaat atgatctttg tagtggtctt   4440
gcaacttttc tgtaagtctg aaattgttta tgcataaaag gttaaaaaaa ggttaaattt   4500
tgtttttata actaataatg gattagggtc atgtgaaagt acttttagagg aaatgagact   4560
tttgagaaca tcatccctga agacgttgaa acactgagtt acctcatgag taatttaata   4620
ggatatgcag ctgattttttc taccttaatt tcttgtttgc agtatctacc catacttaga   4680
attgtctggt gttaaaatat gcccactggg actttcatga aattcttttg attttctaga   4740
aaattcagtt tcaaaggatt ttttaaatag atattttaag tttggtgtca acttagataa   4800
aatctgtttg gagtcccagt gtaagttta gtaatgtgtc caatctgttt attgaaatag   4860
tataacttta gaatactttc tttggagaga tgaagattgg tatgttatag ttcaattcaa   4920
agttgttctt tctattatga tctattttat aattcataaa atctatctta tgattgtcat   4980
cataagtgca atttgttttt tgccccattc tacctcagaa actaagtatc tgggcatcaa   5040
taacaattgg tagtagtgtt tgctgctaag ccaagtttca ccagtacagt gtggaattat   5100
tttattgttt tttctgtgaa cattgtatct gctgttacta ggttattgtg aggtattggg   5160
ccttcataga aattgcctgg aaccccttgtt cactaaagcc tgttacactt tttattctct   5220
gtgcgtgtaa tcagagactt attgatactg acacattcaa ggggcattat tgatcattta   5280
gattgctcta agacctaagg agtcttggcc ggatgcggtg cctcacgcct gtaatcccag   5340
cactatggga ggccgaggcg ggtggatcac ctgaggtcag gagttcgaga tcagcctggc   5400
caacatggtg aaaccccgtc tctactaaaa atgcgaaaat tagctgggca tggtggcagg   5460
cgcctgtaat tccagctact cgggaggctg agacaggaga tcgcctgaa cccgggaggc   5520
agaggttgca gtgagccaag actgtgccat tgcattccag cctgggtaac agagcgagac   5580
tccatctcaa aaaaaaaaaa aaacgaaaa acaaaaacct aaggagtctt ttctcctat   5640
tttacaataa attccttttg attttgtgta aaaacttgaa actgtttatg aatgtaaaat   5700
aacatttgaa tacttttctt gtgccagata ttaggttaaa tgctttatgt gaattttcat   5760
ttgattctca aacttttga gttaggtagt tatttttctc attttacaga tgaaatggag   5820
ggttaggaac tcgtaggtag tagatgctga agctgagatt tgggcctggg tcttttcact   5880
actgtgccag aatcatttgg gagggagtaa aaactcaagc ctttggaaaa tatgatgaca   5940
taaaattgtc ctttatattg agaagcttcc atagttacca gtgtccttca cagggttgat   6000
cggaaagaca tacatgttag tgatgatgat aatgatgaag ataatcatta ttaccacagg   6060
tacttcctat aatataagca tctttcaaat tgtatgagaa cттттcataga acatctgagt   6120
aaatgaacag tacagtgtgc atgaaaccac taagcaaacc aagggaagtt aattttcttt   6180
atatgaattg taaacatgtc tctagatatc ctttatcaga ttccaccatg cgtaagtagt   6240
gtctaagttg ccccatattt agagtttttc aatgaggttg tgttcctact tagaatccta   6300
aagttcagct ataacagata tattaataaa atctgtgaa tctttaattg agcataatgg   6360
tggctgttat tttaacttga ggctttttgt tgagctggat tggaagtgca acttattaga   6420
aattacagtg tatttattcc tatttcttgt tctttatgtg agagaagata tacттттagta   6480
gactgaatac ttcagagctg tatctcattt accaataaaa tgtgaaaaca gtggtaaatt   6540
ccttcacttg ggctaccatt gtacaggcct atttttaatg tatagtttga tatccttaat   6600
gttaaaagca atatagctta aagaggctgg taaattagaa ttttccaata tcctcagctt   6660
tttttcctct cacagttaat ttgctctgct gactccctac gcgaggtggc aacagctggc   6720
ccttttactg gagcttgtgg ggattagaga gtcgggctcg cagcagcgtg ctcggcctct   6780
tgcctctgtt gactgttctt tattgtttga tgcctgatcc tctcccagac agcgagcaat   6840
tgtttctgga aacttaaagt ttgtttctct tgggagtaga caatgctttt ggggcttgtc   6900
tttgtgtttc ttcactttcc cagtctcctc ttatccttca tcctgtgctt tctcttgata   6960
attagaaagg agcaaagata ccaccttttt atttaggtct gcatgagatt ctaaaactta   7020
gaagtatagg ctatagatga aagtttctt tttcagtaag ccacctcagt aacaaatcat   7080
gttttaaatg aaaactttgt тcтткataat atcatttagt gagagaaaac aaatgcatga   7140
gtgcattttt gaaattatgg tactaaaagg gagcagcagc aagtgacctг aatactgcca   7200
тттттaaaagc taggattaga aatgtatcat aactgcttaa atctaaaaag atttcttcac   7260
tgaatccaaa atatagttct aatttatagg atagttataa gaaatctcta tgccatgtgg   7320
aaacatgaat aaaaagtagt cagaacatag ctaaatagaa ccctgaggta ggcagaatga   7380
tttttatctt cacatttaga aaagaaaaca tcaaggtacc ctggaactta atttctacag   7440
tgacтткaca ttccgacact tctcccatac ctgccatacc cttgagtgtt gttacggatg   7500
agaatatcgt ctgtgaagta gtatgagatg gaaattttcc tagaaagatt атттgтactcg   7560
gaatttggaa ctgaaaagtg tagaaagggg aagtgatgtg tttaaaactg tttgcggagg   7620
tggggctctg ccatgtgtat tttgacaaag ctacacaggt gатстcттгcc atccccgatt   7680
accgtgtacc cgcctgcccc tgagctggca ctccaaagag ttctttcagt gcatagcaag   7740
acaatttttc atgctattaa ttgggataaa attgacatac atccatttgt agagtctgag   7800
acacaacgtc actttggaaa atttggtgag caatttgaag tgcatctgca ctggtgttgt   7860
cttttttgtt ctgtagactt aaccaaagaa aatgaacttt aaagggactt taaaggcatc   7920
тgcактggтg tgtttctttt gtttctgtag acttaaccaa agaaaatgaa тттттaaagga   7980
agagagggtg ataccaagtt gtagaattct aggtatgtag gttcagagga gatttttttt   8040
ttttaagaaa aaaaaaaaaa aaaaaaaaaa cacccaatca agagaaatag agcagggtgt   8100
cccgaagaga acgtgtgagc tcgaagcatc ccggcagcat ctttcatatc тcагтacтgт   8160
tgctctgttt cttgggctca caacaccatt tcctctctcc тggcтттттaa cacatctcga   8220
ggcaaccttt tccttttctt ттттатgcacт tctctcactg cgtctcttct atatcatcat   8280
cacttcaacc taacccagta tttttatccc acctgcttat taccttcct tcagtgacta   8340
aaaaccttac tcagatactg ccagтgтттgт ttaattgagc agaatagagg cttctcacta   8400
таggсaактg taaatcaatg aaaaатаасса tttaaagag aaaacatt tcatgtctat   8460
cacggtcgat cccttctgcc aaagtgatt ggttcatca taaattccc atacctcgtg   8520
tgttacatat tgtactgtac catттттacтg aatgttcgat tgtgatcttg taatacagac   8580
тgттcатттag cccccttctc тtgacтттaaa aagttggggg gaactaactc тттттcатссс   8640
aaggaaactt tcttctactc tgtcttgcca gaaagttact gctcatttct cttgtagagc   8700
agcttgcctg тgтggcатты actcctgttc tgcccactcc cttcctaata tcgtgcagtc   8760
```

```
tggctttcat ctatatcaaa accacttatt gatagatcac caatgatttc ctaatgccag   8820
tctacccagt tcaccaggaa actttaataa cttttatgt ttattaggaa ttttaagtt   8880
cattggaata cattcaagta cttttggaa tgattatatg atgtagaaat gtgtatgttt   8940
gagagacaga aaaattgatt ttttttcct cttcactaca gaataaataa tgtatttgtt   9000
ttatggtagc aatacttgaa ctcttaagg catcttttca tggtaaatct ggcaattta   9060
aaaatctggg ctttgtaaaa taatttttt tatagtaagg cagttaacac attaaagcaa   9120
ctaggaaaga tagtgaagaa ttattttac cttgagtctg tatagatgaa gtaggctctg   9180
ctttgtgttg gaacagaaca aacaaacaaa aaaacctgag ttgatacaaa gataaagtaa   9240
tcctcaagga aagtcctctc tgttagagaa gtggttattt acacacagaa ttccacatga   9300
caacgcctga gtggtgtggt tccaggtta ttgatgagaa aatcgagact caaaatgggt   9360
cttttagaat gaagtacatt tttcatggcc taagtctgtc tttaaaagtc accgttgtgg   9420
ccgggtgtgg tggctcacgc ctgtaatccc agcactttag gaggccaagg tgggcggatc   9480
acaaggtcag gagatccaga ccatcctggc taacacagtg aaaccccgtc tctactaaaa   9540
atacaaaaaa tttagccagg cgtggtggcg ggcgcctgta gtcccagctg ctggggaggc   9600
tgaggcagga gaatgcgtg aacctgggag gcggagcttg cggtgagccg agatcgcgcc   9660
actgcactcc agcctgggtg acagagcaag actcgtctca aaaaaaaaaa aaaaaaaaa   9720
aaaagtcact gttgaagaat atcaataaat tagtacaagc gtaaagaac attttctttt   9780
ctataatatt atacatgctg ctggtaatca acacttact agcaagtata ttctttgct   9840
ttaaactcaa gttttaactg attaagaata aagacaagaa tgttctctac aataatgtat   9900
ggattgaatt tgccatttat cattttaatg taggttttac ttatatacta ttgtgaaaat   9960
actcttaatg tattcaaaag gccagtgcac aattttttt tcttttactt cttttttttt  10020
tttttttc tttagaaaga gtgtcacttg ctgcccagc tagagtgcag tggtgtgatc  10080
atggctcact gcagccttga actcctgggc tcaagtgatc taataccttt aaagttggga  10140
ataaacttta tcttaagcgt tttatttttt aaattatgtt tttgcatatt tgatagaaaa  10200
agtagaatgt agtaattgaa aacctaatca caaaacaatt cattggactc tgcaacagta  10260
tataaaaaat aaaattaaac gagataggaa atcttaaggg attggtggat tgatgcacat  10320
gaaactggta acctctgtta agtacagttc tccaggtagt tggagaaatt agttaaatgt  10380
gaagagaatt ttaattttgc actatttgt acatttctaa actgtgtctc ccacagccct  10440
tctccccag tgagcacgat tcagaattac tttgaaatgt tgtagtctta attatccctat  10500
tcatggaaat gacgaagcta atacacgatg tgctctatct taaaagtaac agatatttc  10560
ccaagtaacc tactgctggt tgtgatgctg agggacattt catgggactg catggtcgtt  10620
gctcatcgtg ataccatcct cagtggttgg gggattcaca gtgaattctc atatcctgta  10680
actatgcatc atggatctat catctgaaaa taaatcaaaa tctttgttga actcacagtt  10740
tccacacttg tatcacccat ttaagattgt ttcattgtta cctcctgtgt acagaatatt  10800
tcatttcaat ttctcttaga acagctcatt catctattct ctagtttcaa tattctgagc  10860
agtagaagtt tgctgttttg attaacttca gttagatctc ttttctgggc caagaattaa  10920
agccatttta tctttagtct ctcctttgt tggcactgct tcatagactg tgtcatatat  10980
acagatctgt ctttagactg atctttacca aagtacacta ctggaatttg agggtttttt  11040
ttttaacat ccttttcatt atgagagagc tagtgtatat gcattgtggg aaattagaaa  11100
ctatagatgg caaaatttta aaaaataatt gccaccaccc agagattgca ctgtagttta  11160
agacactttt gaatgtggtc ctagggacat aatttctgga acacattttt cgtgaagagg  11220
tctcaggttg gcttcttata cccacagctc gttgtcattg cccctagttt taatttccca  11280
tcgctcagtg ggctagattt ttttcattt tcttcatata aacttattc agaaaatgttc  11340
attaagagga ataagcagca ttagtaaaaa tgaaacctat ggtacccatt actttatata  11400
gttcaagtat tctggaagcc atattgtagc atagcatgta ctgaaaatca ctctcctttg  11460
aacagtaatc ccatacctgt atttgggacc tggccttcct ttgtgtgctt gtgtattcat  11520
tatatcccct ttctctcttc aaagatgctc aagtcattct catcttaaaa ctaatgggtt  11580
gaaccttcca tgcagtctag tagctactgt gaactctaat ctctattaca aaggttagct  11640
ctttgagtct cacttctact gaagttgttt ttttttccca agattactga aaatttaaga  11700
gaaaataatg gcccaggcat gcattcagga ctagaaaata cttccatgta cagaaaacca  11760
aacaccacat gttctcactc ataagtggga attgaacatt gagaacacat ggacacaggg  11820
aggggaacag catacgccag ggcctgttgg ggcgtggggg gcgaggggag ggaacttaga  11880
ggacttaagt gcagcagacc accatggcac acgtatacct gtgtagcctg cacattctgc  11940
acatagagcc cgcttttgtt tttgtttttg ttttaagaa gaaataacgg ggaaaaaaa  12000
ggtttcaaaa ctcataaaga aagagaaaga gagggaggga gggagggaag aaaatgcttc  12060
catgtaactg catcatttgg tactttggag tccatatcct acttgaaact ctaggatctg  12120
gccctcacat ttatgtagtg ctttatttta cagtttacaa aacttctgct tgtccatgtg  12180
tgtctgtaaa gtcatatgag gcattatgcc cattgttcag atagagaaat taacgttcat  12240
tgacataaat ggttaagccc attatgtaaa tatttatggc aaagctgggg ctaatcatat  12300
gtgttacaga taggactttt tttaaagaat tgtttaggta ttctgttcat cattagtctc  12360
tgggtttgtg tttgtggtaa ccatagacaa ccaagttcat ataatttggc ttcttttta  12420
tgtgatttt gatacgtgtt aaggatctat aacaatgaat ttgcctccta agaggtaca  12480
taatgttttc attcctccaa aaagataatt ctaggtttat aaatctatgt atgctcagtg  12540
ccagttgaat tttgtgattg ttcaatagaa aagaaatttgt gacttaaagg tgattttcca  12600
gtttaatgga ataaatgaaa ttagtttaga agttattttt attttctga gcctgattct  12660
cactcagttg tgataaacag cacctctgta agataaactc ggtgataaac cgagaacttc  12720
tgaaatcagc ctaacatgaa tacctgttct tcttgtgcta agtttcataa tgctttatcc  12780
taatacacca tttttaag aaatggaact tgtatttcat ttttgctttc atctcaccta  12840
attcataatt ttattaaaac ctacgattt taatttcttt tttatgaat ttttagtttg  12900
gtgtataaat cagaattaca ttctctgatc ttttactttt aaaattacag tgatgaactg  12960
actgtttaag aatcattctc atgattcatt cgtctgttat gcctccttt taaagcttca  13020
gcactgaagg tcttttgaca aaccaatatt tataacagtt tgacagcagg atgaggaaca  13080
gcgtttgtct ttgtaacagc ttgaagaaag accctttcca ggacccagtc atgcagttac  13140
aatcttgacc tcttttcttat gctgggaaca tgcatacagc agacctccc atgtgttttc  13200
ttgtcccatt gactgtccat tcacttccca tctgtttgc agtcttaaag gaacagaagg  13260
ggccttctta taaatctgtc tttgcaggtg ataaatgatg cctacctctt taagagctgc  13320
ctgggtggtt ttccttttct tagaacattt ctgcttcct cctaactaaa tcagggaaaa  13380
atacaatttt aggaataaga gaaaagaag aaaagatgaa ttttaaagc atttaattga  13440
ctaagaatat tttactgatc ttttttaatc ttcccaatta attgcctaaa tcatattttt  13500
```

```
taaaatgtat tatcgatatt tagattttty tcagggagta aaatgaatgt attcattttg  13560
aaataatgta actctttttt gagaaaacaa agccatgtat cattaatgag ttaacatata  13620
aaataacttt ttaagttttt tgtgataatt taagtgtgga gcatcttatg tattggatac  13680
aaaagtaaaa tatttcagag taaatcattg taatcttatg gtaaaatcta ttcatttttt  13740
acatttaaaa agatgatcat aaatcccata aacattttgta cttttacttc tgttgctgaa  13800
aataagtatt gtaggaatag atattgatat cattgggttt tctaagaatt cagcagaaat  13860
aaaaataatt tactttttct cccatgcaga aattatttat gcaaggtttt atgtaacaaa  13920
tattgtccct ctatggccct gcagaatatt cttaaattac tgatttaaaa actattacca  13980
gtataaaatg accactttta gaatattgtg gtgtattatg tgaatcagct ggctaataat  14040
atatcttctg tggactagct tgttagtttg tttattaatt ccctggcata ttccaaaagg  14100
aatttgaggc agcttacata tatcctacgc aaaagataaa actacttaag tgaaaaattt  14160
gggttgaaag aaaaggaaaa tccaggcaag tgaaataaag taaactttca gataaaattg  14220
gtgcccctca aagtgcatgc tcaagggttc tacgtacagg cagacctcat tgtattgcat  14280
gtcactttat tgcacttcac agttattgca ttttaacaa tagaagtttt gtggcaaccc  14340
tgcattgaac aagcctgttg gcactatttt cccaacagcc atgtgctcac ctcatgtcac  14400
tgtcacattt tggtaattct tgcaatattt caaattttt cattattatt ctgtctgtca  14460
tggtgatctt tgatgtttgt attgtagcta ttttgggtac cactaactgt gcccatatta  14520
gtcagtgacc ttaatcagta aacgtgtgta ttctggctgt tccaccaact agacattccc  14580
tgtctctctc ctcctcttca ggcctcccta ttccatagga cacaacaata ttgaaatttg  14640
gccagctaat aacccctacaa tggcctctac atgttcaagt gaaagaaaga gtgccatatt  14700
tcactttaaa tcaacaacta gaaatgatta agcttagtaa aggaggtttg ttgaaagcca  14760
aaatggcta ttagccaaat tgtgaatgca aagaaaagt tcttgaagga aattaaaagt  14820
gttattccag tgaacacacg aatgataaag cagaacagcc ttattgcctg agacgcagga  14880
agtttcactg gtctggatag aagatcaaac cagccataac attcccttaa gctaaaacct  14940
aatccagagc aagttcctaa ctctattcaa ttctccgaaa gctgagaggt gaggaagctg  15000
cagaataaaa tttgaagcta gcaaagtttg gttcataagg tttaagagga aaaaagccat  15060
tctgcaacat gaaagtgcaa ggtgctgatg tagcagctgc agcaagttat caagaatatc  15120
taactaagat aattgatgaa ggtgattata ctaaacaaca gattcttgat gcagatgaag  15180
tagctgtcta ttggaagacg atgccatcta gtaatttaat agctagagag aagtcaatgc  15240
ccagcttcga ggcttcgaaa gagaggctat cccctcattt tgggtgccaa tgcagcaggt  15300
gcctttaagt tgaagccaac ctaaagaatt taccattctg aaatcctag ggcccttaag  15360
gattatgcta agtctatcct gcttgttttc taaaagtgga acaaaaagcc tggatgacag  15420
cacatctgtt tacagcatgg tttactgaat attataactc tcgagacctg ctcagaaaag  15480
tttcttca aaatattact gctcattgac aatgcatctg gtcaagcaag agttctgagg  15540
gagatgtaca aggagattta tgttgttttt gtgcctgcta gcacaacatc cattctgcag  15600
cccatggatc aaggaatact ttcaaccttg aagtcttatt attttaaaaa tacgtgtctt  15660
aaggccctag ctgccataga tagtgattcc tctgatggat ttaggagaaa aaaaaaggaa  15720
aagcttctgg aaaggactca ccattttaga tgctgttaag accattcagg attcatggga  15780
ggaggtcaga atgtcaccat taacagtttg gaagaagttg attccaaccc tcatggatga  15840
ctttgaagag tttgggactt aagaggagga agtaactgca gatatggtag agacagcaat  15900
agaactagaa ttagttctgt tgtaaatga taaaacttga acagatgaaa cattgctttt  15960
tatgacaag caaagaaagt ggtttctttt ttcttttttt ttttttttggc agtctccagtt  16020
tgaagaaagt ggtttcttga gatggaatct gttcctggtg gaacattgtt  16080
gaaatggcag taaaggattt agaatattac ataaacttag tagataaagc agctgcaggg  16140
tttgagaaga tagtgtccca attttaaag aagaaaaatt tgagtaaatt tgggtaaaat  16200
ttacccaaaa ttacctattg tgggtaaaat gctatcagac agcatcacat cctactgtga  16260
aatctttcat gaaaggaaga atcaatcagt gcagcaaact acaattgttg tcttatttta  16320
agaaattgcc atagccaccg taacctgcaa cagccaccac cctgatcagt cagcagccat  16380
caacgtcagg gccagaccct ccaccagcaa aaagattatg acttgctgaa ggctcaggtg  16440
atccttagca tttgttagca ataaagtact tttaaataag ttatgtacat tgtcttttta  16500
gacataatgc tattacacac ttaatatatt acagtatact gtaaacgtaa cttaaacgca  16560
ccggaaaacc aaaaaccttt atgtgactca ctttattgtg atatacgctt tattgtggca  16620
gtctagaacc aaacttgcat atctcccaag tatgctggga ctttgctaga ggtaagctgc  16680
aaatttagcc ctcagtttcc tggtggctgg cagttacaaa atggaaagca gaggtcattc  16740
catcattcat ggtggccatc agacaacaac acagcagttg cttaggagaa gcatgggtct  16800
tcttcgtacg cacaactgag agaaaattcc cttaaagtgg acactgagtt agatgataca  16860
atgaatctaa tggctacaca taatcatgaa aatcatgggg cccttttattg taatgtttct  16920
catgcgggct aacatgcgta gttctaggga aaatatgatg ctgtccaaac atacagctat  16980
ttggttgc ttatctaaag ataaaataca tagtatccag agaaaatagat gaactgtatg  17040
tcctccatac agtctcccat aaatattatt tcttttgca gctgatcctt ttagtaaata  17100
tcaggtagcc agaagttcaa gattttacac tcattgacat tgacaagcac ctggaatggt  17160
actacctttt tttttttttt ttttttttga gacagagtct tgctctgtca cccaggctgg  17220
agtgcagtgg catgatcttg gctcactaca acctccgcct cctggattca agtgattctc  17280
ctgcctcagc ctcccaggta gctgggatta caggcgcccg ccactacgcc cggctaattt  17340
ttgtattttt agtagagatg ggtttttgcgc atgttggcca gggtgatctt gaactcctga  17400
cctcatgtga tccacccgcc tcggcctccc aaagtgctgg gattacaggc gtgagccact  17460
gcgcccagcc aagtactatt tttattagtt aagtcagagc cataatcatt ataactgagc  17520
tgaattaga attgccatcc acttaagaaa gttgagtggt ctaacaagta taaaagccta  17580
aatataaggc taattcatgt tcatactgaa gcctttggg gaataggcct taaaatatgt  17640
agaaagtatt tgaagcggtt ttaattgtac tagccaaaag gagcctagta gaaatgcttg  17700
tgttataaga gttattttt taaaaagctg aatttatctg accaggcgcg gtggttcacg  17760
cctgtaatcc cagcactttg ggaggccaag gcaggtggat cacgaggtca ggagtttgag  17820
accagcctag ccaatatggt gaaaccccat cactactaaa aatacaaaaa aattggccag  17880
gcatggtgat gcctgcctgt agtccgagct actccggagg ctgaggcaga agaatcattt  17940
gaaaccggga ggcggaggtt gcagtgagcc gagattgcgc cactgcactc cagcctggac  18000
gacagagcga gactccatct caaaaaaaaa aaagctgaa tttatcaaca aattgctgtg  18060
gagttttta tatattcagc aggcatcagt tgtaattac ctcacagact ttcttaaggt  18120
tgctttcttt ctaaattata ctttatgggg gtcacaaaat agcaattttt aaataatcac  18180
ctttaatgat taagtattgt ttaagtcaga tcactcaact atgaatgcat gaatattcat  18240
```

```
ggacatctat tacatagcaa gcagtgctat gctgggccga gtgattttaa atgacagact   18300
ttttggtaag tagagaattt acccaagcag tccttgctgt tctccacatt aatgctcaga   18360
aaaaatacat tataaaaatg atctttccaa aatgaattat gaagccccat gagaatgata   18420
tggcaatttg tggttacata ttttactaga ggattaatat ccaataaata aaagatact    18480
aaggaataaa caaaaaaaat ttaaaagatg aagtatataa tgaattagaa caatacattt   18540
taatcataag ttttaaatta gtgtggactt tgaattctcc tggacagatt ccttcatttt   18600
atagataaag ctaggactgt gacttatcca gttatgaggt taacggcgaa tacaacattg   18660
tcatatattt taaatgacac acattacaac atgttctctg ctttataaaa atcatatcaa   18720
ataattgccc catagattat taaaggtgtt agactaggga ttcttaaaaa aaattttcat   18780
caaatgtttc tttcattatt aatcccatga agtccatgtt acagaagatt ttgtctacaa   18840
cagtgcagtt acattcttct cgttagaaat acaaccacca gttagagttc ctaatcagta   18900
taaggaagta gttgttagga gaggggatgg gtttcttgtc caaatgaagt tttccatttg   18960
agttttttgaa gtagtgaaac taacccagcg tttacaggcc ccagaaatct gggaacctca   19020
gcttttcaaag tactgtacca gtcttttaaca gttttcctgg acgtgtgaat tgatgcctcc   19080
ttctgtaaca tgcaggagtg ttctgtctgt cttcattgag tgttaaaaaa taatcatgcc   19140
tatttcaagg aaaaaaatcta cagaactaag atgcagaaga taagtgctag atttaatcat   19200
attccttcat ctatctgttt ggttcaacct ttcatcaact aaaagatgca ccttttttct    19260
tgtgctaact ctaagatttt agctacagtt ttgagaatct gtagtgtagt ctcttgttta   19320
cctttttttcc tttttttgtt tcccccacac cctagattca tttaaatact gaacttctaa   19380
agggcaagta tatagtgtag tttaataaaa agcaaacctt ttcatgaaca atatatatta   19440
cataataaga agcgttcctt tacttttcag tactctagtg aatagctttc tacagtagaa   19500
tctcacttag agggtgtctt aaagcttaac accaagtgct caggcagcat gttataacaac   19560
agttccatta aggtacattt ggatcttttgg atgtgtggtt tgcttaaagt acactgcatt   19620
agtaagttgg cagcttgctt tctttaaaaa catcaaaagt tttaaaaggt ttatttcagg    19680
gcatgtgtta gtgttttgtg tgtggttctt tgttcctgtt ctaaactgtt attaaccact   19740
gaagtgaacc ttctcccggg tttggccttt tggtattcac agtgtattca aaacctaatt   19800
acagattagt ctatatttga gactttttaga gcaagtatca gaagacccaa aaagaaaaatg  19860
agagtagcag tatcatttca tgtagagata aagagaccca aaacatgaat gggtgtcaag   19920
tcagctgaag aaaagaaaaa agagaaggaa cttcattcac tgagacggtt tatgagttgg   19980
ggattatggg atattcatg actcaatcaa gaagcacagt gaattgatgt ttgaaatagc   20040
tcatctttta agtaaacatt ggataaatg aaagtagact cagtattcac tacacgtaga   20100
aatagctatt tctgtatagc agaaaatagca gtttgttaat cccttcctga gttggtttaa   20160
tttaccaagt aaatcacaaa ttttattctt tatttgtgaa tatttaattc aaatatttaa   20220
tggaaatatg agtttgcttt ataattagtc atgctgatcc atacacgtat ttctgagaga   20280
aagcaaatttc taatggtgaa atagttacaa taatatttt gaaatttgaa agcaccgtga   20340
tactgaagca ttaatctgaa ggatcggaaa gtagggagtt tttgttgcca acatttaact   20400
tcattgttta tggataactt ggttttctgg gcagccagat ggcacagtta gtatacagac   20460
attcttggaa acttgtatca aaatttaaaa tgaatgaatt tatgagaaat aattctgctt   20520
attatttgta atgtagcttt cttgaaaagc aagaaatcgg tagtagttt ctaaagctgc    20580
aagtgaatat gtatacatag ccagctcttt cagcccttgat aataaggtgc aaccattaag   20640
atgaagggat ttttttttttcc cacttgtgtt tttgggcccg agtatcctga tctgtgttgc   20700
ttgtctggtt caggtgtgag ccaccagctt tctttgactt tcattatcta tgtgtatctt    20760
gcctcctgtt cccaggcttg ctctagctct tctgatcctg ttcttcctcc tcttgatcac   20820
tagtgtagta ttcatgaagc cagctaagtt agttttttccc tttgaaaacc acagcccta    20880
tcttctgtgc catatttttgg gcaacttcgt ttatcattga ttgaccgtac gcagtgatca   20940
ggccttgttc tagacactga agactctgag catttttggg cccatttttgt actcctgtat   21000
tgttctccag gggcttctcc aagtgtgcgt caatttagtc ttctcaagag ggcatcattt   21060
tcatcagaat atgatagcat attatgagt gtccggtcat ccttaggcat agactactta   21120
ggaggtgtaa ctgttttgtt ccctgattt tactgaaatg ggtctttttct ttttttttttt   21180
ttttttttttt tttttttttt tttttttttt tttttgaga cagagtctcg ctatgtcacc   21240
aggctggagt gcagtggcat gatctcagct cactgcaaac tccgcctccc gattctccct   21300
gaaatgcgtc ttattttaag tcaaaggtaa tacttaaaaa agaccaaaga gacttaaaat   21360
aacagcattt gcttcgtcac tatgagcttt gttattatga gttaacatac agtagcagac   21420
tgggtgtagt agctcacgcc ctgtaattcc agcagtttgt gaagccgagt ggggaggatt   21480
gcttgaggcc aagacttcga gaccagcctg ggcaacatag tgagacccc atcttgacaa    21540
aaaaaattgt tttaaattag ccaggtgtgg tgctgcatgc ctgtggtccc agctacttgg   21600
aaggctaagg taggagaatc gcttgagcct gggaggtcga ggctagtg agccgtgttt     21660
gcatcactgc actcctgggt gacagtgcaa gactctgcgt cagacaaaca aacatcgtag    21720
cagatgtgtt tcttaatcag agaagtgtag acaaggctaa ctccaggctt taatgtcctc   21780
atatttagca atgataccctg caaggttgta tgagaaccaa atgaaacgcc aaatttggaa   21840
atacatagta gatacatcat agcagagtaa gccaggaatg cttctcaaag gtaggatatc   21900
atctgtgtcc tcatatcact ttatgaagta cattgtgaaa gtgaaagaac aaagaaataa   21960
atgtttttta gttaatgttt aaaggataca tttatcataa ttgctctttt aacactcacc   22020
tccagtctcc cctccgttca cacctcctac ccccattact tcctggtaac ttagttaagt   22080
gtcctttgtc attcctgagg tttcaaggca tggtagtact gtgtcctgat attctaatcg   22140
taaatattta agggaaattc ggcatttttt cattttgtgg ttttcatatt aaagtacatt   22200
aaatagtctt tttgctttta tttaggaaaa aaactgctta cctgttaatt ttagaaaaat   22260
ctgatttttca tttagacctt acagggtgag acacctgcat cagggtggct cttgttatct   22320
ttcaattcaa ttggatcttc tctgaatagt tccttgtagg gagtgaggct gctgtaccac   22380
ctccctgcag tagtccatcc agcttaagat gggggtcacc agtaggccaa aagaatgggt   22440
agacctggcc atgcactgcc ctattgtact caaatcgtgt atcaaatgga gttggatttc   22500
ttctcttcat acagtacagc atttccaagt agaaatattt ctcaatgaaa tgtggagaga    22560
agcacccgtt tgagattccc gtgtgttgtg tgatttaagt tagatggttt tttaagacca   22620
cattcatttc cagcaattcta ggtaacaatt aagaaagtgt cttctcccta acctcccccac   22680
ttttaaaaa tcctccaact gatgaactga tgtgaaactt tcttacattc actgaaaaaa    22740
aaaaaaaata ggttaagctg tttctaagca actagatgaa ttaattttta aactaagaat   22800
gtggccttat tttgggaaaa caagaatatt tacttgtttg tctgctgttt aaaaaatgga   22860
agtcagccta ccaaaaaatt gagactcaac ttctaggaga tgggttagga ttttttttttt   22920
taagtttctc tagtttaatt ttatatataa ggggttaatg ctaccttcat aataactatt   22980
```

-continued

```
atcatatttt ctcaatacat agcttgatta aaacaactgg actccccccc caccccaccc  23040
cacacacaca cagattttat atcagtctga atcaatgcc  tagaataaga agtgcttcag  23100
ccaggcatag tggcactcac ctgtagtctc agctactcag gaggctgagg cagcaggatc  23160
aattgagccc aggagtctga gtctagcctg ggcaacatag tgagacctag aagttttaaa  23220
ttactggaaa aataaatatga aaagaataaa ttactggaaa aagaatatga aaatgttacg  23280
ttctttatat ccaaccgtgg taggcttttt tgagttcctg caatgctaat aagaattcat  23340
aaaaaggaca attcttcatt ttcttgggta ctcatcacta atagctgcct cgctggtaaa  23400
aaggaataca tgtatcttca attgcagatt atttactttt aaatataaaa gatataaatg  23460
tcaaatatta aatgcatctt acatggtttt cctacatagt gaaagtagaa tgcttgccag  23520
ttttgcctct aggtcactca cttttgaacca gccaacccac cttaattgat catttccact  23580
aatatgttaa attccttaa aagaacaaaa atatttatca tgcttactat aacctgtgtt  23640
ttaaaatagg aggccaggca cagtggctca cacctgtaat cccaggactt tgggaggcca  23700
aggcaggagg atcacttgag cccaggtgtt caggaccagc ctgggcaaca aagtgagatc  23760
ctatctccac aaaaaaatta aaaataaaaa cttagccagg cgtggtggca cgtgcctgtg  23820
gtcttagcta cgtgggaggc caaggcggga ggatcacctg agctcaggag gttgaggctg  23880
cagtaagccc tgccaacacc actgcacgcc aacctgggcg acagagtagg accccatct   23940
cagaatataa aataaagtag gaggtgcatg tgaagtagta tagatcatga cttttccaat  24000
tttaagaggg gattggcatg tactatgagc agttcacatt tgtggaggaa atctacattt  24060
cagagagtat atatttcatt tggaagtcta taaacatgaa aacctaaaat aaataatgta  24120
aatctacctc tagtggctct ggtatttta  aacttattta tagctggcaa agtacttttt  24180
tgtatgtatt tttatagcac cattgcactt ctcatgtttt ttgcaagcat ctcccacagc  24240
ttcctttgtc ttttaattt  atgacatata acattttcaa tacattttcaa tatggccata  24300
ttgattgatc ttttccttg  taactcttac tactttatat ttaaaaagtc atttcccagt  24360
ctaaggccac ctctattttc ttttagtttt taaaatggt  ttcattgttt tatatttgcc  24420
tatgatccag acattagtaa ctgtgggttc ttaattgggc ttcagagaat ctgagaattc  24480
cttaaaattc tctacataat tgtacatgta cttaatacat gcttttttcc atgttaagag  24540
tccagagttt ttgttagatc ctcaaagggg tcagtcagtc tctcctccca cttccaaaaa  24600
atgtctgaga cctactacta taatccatct ggacttttatt tgggtaaaag gtggtatggt  24660
gagactcata ttttcttt   tcccgcaaat agttaagtat accaaccatt tagtaaataa  24720
ttacctcctg atttgtgata cctttgaaaa ataaatgttt ttctttattt ttatctccac  24780
ag                                                                 24782
```

SEQ ID NO: 4           moltype = DNA length = 5409
FEATURE                Location/Qualifiers
source                 1..5409
                       mol_type = other DNA
                       organism = Homo sapiens
SEQUENCE: 4

```
gtgatggatg gtttaagggg gctaccgata cattcacact aatcagccat ttctgccaag  60
atcatgtcac ctcaatctgt tcatggactc caaatacaag aaattaattt gacaaagtga  120
aaatataaaa gatgcatcat ataaatatgt aacttttctg gagtgggtag tataggtaaa  180
gccaaaagaa acaaattcaa gcagaggaat tttggttttct gaaaattagg ttgtctgtag  240
ggtccctgta tttatactta gaacaaaatt aggaatttct gtttatgtgg tccagttatt  300
gagtcaccct aagtttgtag gcatcttacc tacctacttg ctcccaagt  ttttatttct  360
aaaatgaaaa gcattgctgt agatgaccag tttacactaa agaataacat ttatttattt  420
gttttagcta aagtatatgg acagggaaca ttcatattct tgtagaagaa aatttatttg  480
actttttgggc aaaagcatgt agttcttata cactttgaca aactcattgc gtacattttt  540
cacattaatc aaagtcagca caaataaatt ttcaccttgg accacggagg gtttgaacac  600
tggaaatttg atataattct ggttgctaaa gaacaagttc taataaaagc ttaagtgtat  660
accaatatgt ggctgttggt gcaatcagca ggtccgtaaa aatatgattt taatggttag  720
gtaatcccac aacggagatc ccaaagttca tgtttggaag agacttttgg gtcaaagtga  780
aatcagtgta atgaatttaa aattatactc tgagatcttg aaatcagcta attatgttac  840
atcttattag ctcagaaaag ttttgaagtt atatacaaat gctagtcagg aaaaaagatt  900
cagtcatgta attcttgtac attctactat ttaaatcaac caatattata gattatgatt  960
tagtcagta  attctgctgg ctaacccttat ctcatttgt ggtggttagt acttcagagt  1020
actcaccata gtttcattta tgttttcagc atcacttcct ggttttttctc aattccatgg  1080
ctgtggaatc aattcatatg tatatttagc ttcggtgagc aaaaacatag ctagaaaaag  1140
aaaagaagtg agtttcctac ctggttaaat taaagtcgat gtgttaagcc aaggaggact  1200
tcttttgaat ggtactttaa caatcccttgt tctgtatact gtgaatatat catttaaata  1260
gcctaataaa ttggatgctt aggctgagcc acctacttt  tagttttgtt atggaaagaa  1320
gggagaggag caagtatgtt cttatatgtt acttagaaat aagaatgtag ctgtagttac  1380
acattgttct taagtttttt tcgtaagaca acttgaaatg agtcccatag gctgctatt   1440
taacattcta agatatgact taaggttaat gatgagcttt tgaatctgac aattcaagag  1500
atatccataa tgaatactga ttcattttct acattgctga aagctaatgt tcattttaag  1560
cctactttag tagcctttat ttgggcttag agatgttatt cctctttctg atatttattg  1620
ggttatctgt ttaacccttt tatatctccc tttcccgatt tgtaaattag agactggcaa  1680
gacttttac  cctgagtaga gcaccaaaca tggcttgttt ctgcccacac tgtagttacc  1740
ttgaggggaa gtaaatggga ctttaaaagc aattatgct cttttatagt gaaattatcc  1800
ctcttactat cccgaaagac tgttaccta  caatatcct  cactcctttc ccctgtagt   1860
tactatagag atgactttc  ggttcttcac tgccataatg atcaaaatcc taattcatga  1920
gatttttatc attccaggca tgtgaggttt acttgatgca taaaaccgca agtactttt   1980
gttgttttt  aattgttttt tctctcttat cttcttgaaa gtctaagtag atcatcattt  2040
ttgatgtctt attagtagca actaataaat tttccctgta tcttctcagc aaaagaactc  2100
aagcagagac agaagattag aactaccatt ggtagttttg cttcctatgg atatgttcac  2160
atacatagaa attttttacaa tgaccttttt atatatgtat ttcagaattt cagaatggcc  2220
tcaatgcctt aataggaaga aatacttgaa attttttaaat tagggcttgg ttttgtgagg  2280
agctagtaaa ggttttctc tttcagcttt agcttgtttc tgcggaggat ccgctcttt   2340
ctccatcagt ttcatagccc tggaattgta gaaaagctct ggtttcaaga ccattgatat  2400
ccatttctgt cagggtgagt tttaaatta  tttcatgatg caaacaatat attgaacaac  2460
```

```
aggacatgaa cttgttcttg ttgtaagtgg ctgaatttta tcagtaaagc acatcaaaat 2520
aaaatatacc ccaattgcta gttaagacct agagtgacag attgaaaata gcttgtgtta 2580
ttctcttaag aaaatatata aaaattatca tctcatcaat ctttaatgtt tgtttttataa 2640
atctaaatgt ttttatattg tttcctagga aatattaggt ctaattttt actttaccac 2700
cagctgtctt ttattttact ctttttttga gacggagttt cgctcttgtt gcttaggcta 2760
gagtgcagtg gcactatctc agctcactgc gacctctgcc tcccgggttc aagcgattct 2820
cctgcctcag tctcccgagt agctgggatt acaggcacat gccactacac caggctaatt 2880
ttgtattttt agtagagacg gggtttcttc atgttggtca ggctggtctc gaactcccga 2940
cctcaggtga tccgcctgcc tcggcctccc agagtgctgg gattacaggc atgagccacc 3000
gcacctggcc agctgtcttt taatataaca ttatgattaa ttgtgatgtt ccattaaact 3060
aagcggagag gaaacatgct ggtaaaccat gtgtgagtta ttcattgtac cagaaaggca 3120
aatgatacat tttatcctaa aattcaaatt tataaacatc ttaacacttg tgatcattaa 3180
atactactaa tctagcatat aaattatatt tgtaggcggg gcacggtggc tcacgcctgt 3240
aatcccagca ctttgggagg ctgaggtggg cagatcacga ggtcaggaga tcgagaccat 3300
cctggctaac atggtgaaac cccatctcta ctaaaaatac aaaaaaaatt agctgggtgt 3360
gctggcgggc acctgtagtc ccagctactt gggaggctga ggcaggagaa tggcgtgacc 3420
ccaggaggca gagcttccag cctgggcgac tccgtctcaa aaaaaaagaa aaagaaatt 3480
atatttgtaa tattctacta accttatatc attttaactt tttatataac tttttttattt 3540
taccaaatta agttaacctt ttatagccct tggcttatac taaacatcct aacttttttg 3600
tttaattgta ttagttttta agttattgcc ccagatgtca agtaatgttg gattttctat 3660
aataaatttag gatatattgc atgaagtcag ttagtattta catttaaaac taaaacaatt 3720
tatactaata cagtttatac atttcatact aatttagcta cagttggata aatatttaat 3780
ggaacaaagt aaatcaaagt acctttttcaa atgaattgga aattaaatcc acataacaat 3840
tttttatgac cacactatta cagtgtgatg gcatgccaaa tgatcataat gtggaattat 3900
gtatttcttc attggctttc aagattctgt tctttagttt gtgggctcct ctccaacttg 3960
cttgtctcct cacagtttag gcgactgttt ataattcttg tccatcctgc ataaacacac 4020
acagtcaaaa tgaaaaaaag cttctatcag cagatctgtg cttctgtac agaaatggga 4080
aaacaattga agtttgcatt atctttttc taattaccag atcgttttttg gagctattta 4140
ggcatacgct tttaaggaaa aaagaaaaaa agagtgtacc ttttgtttct aacaaaggtt 4200
gttatctata ttattgaaat aaaaaaattgg ggatagttat gacaaagtat ttagaaatag 4260
gaattaaaat cttaaaataa cttttcatag catggacaag acttattaat gtctacctca 4320
ataagcaaat catttaaaaaa ttttcatgt atatttgctg ccatgatgtg ttgtgattgc 4380
ttaaataacc aatgaatgaa gatcaacaag gatttaaatg aagaagaata tggatttaac 4440
tattttctcc tgtgaaataa gttcatattt acaagttttg attttcagaa attagacaat 4500
tattttaaa ggctgggatg acaacttctg cctcttacca agaagtcaaa gcacagttat 4560
gtgaattcat cataaatcac atcatttta ttatattttg tatttataat tgtattgtga 4620
ctactttaaa acctgttata aaataaaatt gtttttaat attttatttt agaattatta 4680
gcattaataa caatttgaag tagtttacac aatacctgtg agtttattt tgttttata 4740
ttgaaattaa ttttagttgc tttacttggc ttcattgcta tggatgcatt ctctgtgtta 4800
cgagttagca gatcttcct tggaactgaa tttaaaagca agcattggc tccacttaaa 4860
tctctgaaaa tgcaacttgt tctttgcatt tattacataa ttcgctactt atggtacaga 4920
aatggataca atacaaaaat atttcctat aagatacact gtgaccaatg agcttttta 4980
atagctgtaa tcagtaacat gtatttgact tttcaaaaca catttctgga gggatatcga 5040
tgctttattt ccccaaatat ctgaatccct atgctttagt acaaaacaac ttctgaagaa 5100
tttagtaacc atatgtgttg atctcttgtt tttctaacta gtctttcata agaaatgact 5160
agaatagcaa cagggaaatg attgccttt aaggttttg tttctcaata taaaatttg 5220
gtgaaccatt ttttattgata aatacaggta ttttttacttt ttgatttaaa 5280
attactttga ttaaatatgc atataaagtc agttgttttt aactctcaat acttatcaaa 5340
aaaatttaac ttgctgtaca ttctgtataa acctaattct attcaactaa aattatttta 5400
aacatttag                                                          5409

SEQ ID NO: 5          moltype = DNA   length = 21301
FEATURE               Location/Qualifiers
source                1..21301
                      mol_type = other DNA
                      organism = Homo sapiens
SEQUENCE: 5
gtaagtgcag gctctaatct ggccccgtta attctgggc ctcttgagag tggggctgtc 60
ttatctctat ctccaaaaat gtgcaggtga ctctccaggcc aggccgacgg cagttggaga 120
attcccagat gttcttgagg acccagaatg acaggagccc tggctgggct tacgttcgga 180
gccggcttca atactggccc ttttctctgg ccctacccaa cccgaaaatt ctggacgcct 240
ctcaatcttg gcccgtctct attgtccttt tgtctctgcc ctttacaccc ttgtgtcttc 300
agtgttctgt ctgtctctgg ttgcctcttt tgccttttt ctgtcctctc cctgccaggt 360
ttggctctgt ccatgagtca cctctctcca cattctcct aactctcggt gtcttcttt 420
tcttccattt ccacgccatg tgtacattgc atcttcaggt acctgggctc ttctatcggg 480
gaaaggggcg tccgtctctt tccctagccc gctgatagaa gtcagaacta gagcaatgac 540
gcacacggtg tcagagacgg tgattcgaga tgccctttca atagcagctt ttttctgtgt 600
ttcgggaggg agacttactt tttgatgcaa ggtcgtgaac gtggcaccac cttttctaatc 660
tcaatcattg ttgccctggg gtggtttaat tctaaataga aaatcataga aatctttca 720
tttctgtgcg ttactatatg cattgtaatg agattaaatt ggattttata ggaaattttg 780
ttctagtatc attagatacc ttcaagctta gtcattgtt gcaggcattt gataggaagt 840
aagatgcatc aagcaaaatt ggaaaaacgt ggttttcctg aattaacttc taagcagttg 900
ttttgaattt tttccagacc ttttttaagtg gtatagataa tttatcgtgt ttataaggaa 960
tggaatgcat tcgttagttt gttttttgttt tgtttttgga cggatcttg tctgtcgtt 1020
caggctggag tgcagtagcg ctatctcggc tcactgcaac ctccgcctcc caggttcaag 1080
caattctcct gtctccgcct ccggagtagc tggaattaca ggcacgcgcc agcacgccta 1140
gctaatttt gtattttag tagagagggg gtttcaccat tttggccagg ctggtctcga 1200
actcctgacc tcatgtgatc caccctcctc gacttcccaa agtgctggga ttacaaccgt 1260
gagccaccgc gcccggccca attttgttta tataggttaa ctggagtcca aaatacagaa 1320
```

```
ctagatgaga taacaatagt taacagtgtt agtcagttag aattattgca taggtatttt  1380
taatctcatg gaattttagt ctttgagtaa gttcacagcc cttggtatta aagtaagtta  1440
tttacaaccc ttgcatttct acttctcaat atttagtgag gaaacatatc tgattttctt  1500
taaataaaaa gagaaaagac tgcagaagat agcattctct gttggagcaa ttaagatgta  1560
taagaagaac tacaaagacg gagttttaaa acaaactgat ttataagtgg tatttattta  1620
attggctgtc attgggctaa attatttcta aagttaccat ggatgccatt gagtcatggc  1680
ttaaaaatgt ctcctggtga tggcacagtt tagctaccta aagaagtaga gatgtgggaa  1740
gccagaagcc ccaagctctg cagtttttct tttgctatag ttcctttgca tgttgtgaaa  1800
gaatacagtt aaattcctgc tccctaacag atgagagcat aagcatttct ttgggcatac  1860
atatgtaaat acatgctcat ggacatgtga aagatcaat actaacattt ggtgcaata  1920
aataattgtg taaaattatt tttaaagaa ttacatatta ggaaatgata tattgattaa  1980
aagtgatagt caatgaacaa gagagtagat ttctggggga aacctatttt gcatcatact  2040
tgattttag ttttgactga atattgaagt ctatattcaa aattcttttc ctttagaact  2100
gtaaaggcat tgctgcattt tcttctaatg taattgttta ttgctgctga gaattcttat  2160
gacaatctga tttttttcatc ttcatgatta tcttgttttt cccttcatgg aatctgttag  2220
ggtcttgact ttatccttta tcctaaattt ctcaaggctt ggaccaggtg tgggtttggt  2280
tttgttttct tttgctactc atttgacttg gcacactcag tgggcctttc cctttatctt  2340
tcttcatttc tgagacgttt ttctctctta tttttatta tcttccttt attttcctg  2400
tccttttct ttctagacat ctcttaggag gatagtggtc ctcttagatt gatatgttat  2460
gtccgtgatt tccaaagtaa gatttgtact cgtcgtctgt taaaaggaaa agcatacata  2520
tacctatgt atatatgcac acttttttat ttttaaatta tatatgtatc tgtactaatt  2580
atttacattg taagtcaacc ctaacataat cttaaaggat aagatacaaa acatactgca  2640
tctagaagct tcagtacttt cttcctgaat cccagtagat cctttttgttc atcccacggg  2700
atgcattccg ccccccatcct cccactccct ttggatacca cattaccaca gctctgcatc  2760
acttaactttt cctcttatgt ttttcacctt ttttttttttt ttttttttgc atttttatgtc  2820
ctgggggaatt tccttaattc atttcatggt tttactgttg attttttttaa tattggccat  2880
cgcaactttt cttttcttt cctttcctt cctttctttt cctttcctttt tcttttcttt  2940
tcttttctttt tcttaatttt cttttcttt ctttctttt ctgttcttt cttttcttt  3000
ctttctttt ctttcacaca ggatcttggc gtgttgtcca ggctggcctc gaactcctgg  3060
gctcaggtaa tcctctcacc ttggcctccc aaaatgccag gattacaggc gtgcgccact  3120
gcatttggcg gcaacttaat tttttttattt ttatttttcc ttttagagga cacctagcac  3180
tgagcattgc aacttttcat ttccatgaac ttttaagaaa actcttaaag acatgtttaa  3240
ttctgtacac tttctattgt tctttgattg ctgttttttga ataacaacaa ggagtacgcc  3300
ttagcatttt gatggtatcc tcttaatagt cgcaataata gtccccttgg cgctctgtat  3360
actctcaagt cttaaatgtt ttgtatgcag ctgtacgttg acagttgaat ggtctcgctc  3420
caagtggatc agcaagaaca taagaatca tttaactggt acaggctgcg cgttgtgaat  3480
tccctattaa caccaaagaa gacgtgtgag actccgtact gaaactaaag acgacttgtg  3540
agttccacac tgagatcaaa taagtcttta tgatggtgac agagagtggt gtcaacgcct  3600
aaagttttgg ttaatctctc taaattgagg ggctgaccaa aaggggggaac ttaactgtat  3660
tagacataat tttgagaaac atgggtatgt ggatggtaat ggaggaaatg ggtgtagatg  3720
agattgccta gggagagtga gaagtaggtt aggtctaagc cttgatgagt tcccaacatt  3780
tccaagggta gttgaggata ctgaaaatga gtggccagtg agatagaggt aaagctagag  3840
actgcccagg gggagaggaat tttcaacaat gaggaggtgt caacattgtc aggtattgct  3900
gagaggtcag ataaaaccag aattgagcaa aatggccatt ggaagcctat ggtgccctcc  3960
gtaagagctg tttcgctgaa gtgatagaaa cggaaatcag gctgggcaca gtggctcact  4020
cctgtaatcc cagcactttg ggaggccgag gtgggcggat cacctgaggt taggagttcg  4080
agaccagcct ggccaacatg gtgaaaccct gtctctacta aaaatacaaa aagtagccag  4140
gtgtggtggc aggtccctgt aatcccagct actcaggagg ctgaggcagg agaatcgctt  4200
gagcccagca ggcggaggtt gcagtgagca gagatcgagc cactgcactc caacctgggt  4260
gacagagcaa gactccgttt caaaaaaaaa aaaaaaaaa gaaatggaaa tcaggatggt  4320
ttggctttta ttttaataaa atagctagaa cagggaaatg gggtactttt tttcccccctt  4380
ttaagatgag acatagccag gtgcagtggc ttacacctgt aatcccaaca ctttgaaaggt  4440
gagggtcgct tgagctcagg agtttgagac cagcctaggc aacatagcaa gaccttgtct  4500
ctactaaaat tcaaaaaaa ttaactgggc atgctggcac acacctctag tcccagctat  4560
ttatgaagct gaggcaggag gatcacactt gagcccagat acgtggggct gcagtgagcc  4620
ctgataatgc cattgcactc cacgttgggc aacagagcaa gacttcgtct caaaaataaa  4680
taaataccct gtctcaaaaa taaaaaataa atatgggagg agagatttga cttagattcc  4740
tcaaagggca ggaggaaaga gaattccaaa cagtgattca cctttaatgg gagaaagatc  4800
gcttaattt acatgaggaa gaagaggatt ggtgagata cagtaggtga acagtttttg  4860
tatgaggaag ttgaacatgt gtcattctaa tagcttccat tctctgtgaa gtagagggca  4920
aggtcatcta ctgagagttg gggaggtcaa gagagataag gggagattag aagagctctt  4980
ctagcagaga gtgaagaat gaattgctaa gagagatgaa gtaggattgt taagtagttt  5040
tgagggcct gttgagatgt gcttccagtt gggtgtgatt ttctccagta gtgctttatt  5100
tccctgggta caggcagaga gaaaaacaat aaggctcatg tagggtttgt atttttgttgg  5160
acaagtcaaa cagaaaagtc agaggacgag ggagttagaa atgtttgcaa aagagttatt  5220
gaaacgatga accgcataat ctaaggtggt aagtgggtga atagataagg aggatgtgaa  5280
taggtaagga gaagaaagaa atatcagatt attgattatt gatggcgact ctctaataca  5340
gctattatgc catttttaacc gattaagaaa ctaaggcttt agaaaattca taatttgccc  5400
taactgcaca gctagtaagc agtggaaatg tgattggaac cagagttctt ctgactcaat  5460
agactaaatg gatgtaagga tgtagttgaa agaagggtga gctaaacgtt gtggaaccat  5520
gagctctttc tctggttgat atccctctct gtaagtgata acatgggtca cgctggataa  5580
aaccttgtgg tgattggtga ctttccttg tccttcctcc tgtgcctagt ctggcgagta  5640
tctgcctttc cctttccttt ctcattgctg ccacctaact ttaggctctt ccccttacat  5700
ctgggtaact gaaataagat cacctttttg ttcccctttct gatttacttt gacctaacat  5760
tatcttact attttctta aattaatgtt tcattagtct tattctactc aggaactctg  5820
tagttcccca ttgcctacga aaaaaagtta agcctcagcc ttatattcag tgactcttca  5880
attggatatt cagtccagtt ttactcctcc tatgagcctt ctatgccagc tccttgggtc  5940
tcttgccctt tcattgtctc agctctgcac ccttcttct ctttttttatt cttttttttt  6000
tttgtacttt ttggttttc ttttggtttt cttttttgt tttatttatt aaacctccat  6060
```

```
cacacttcat cctatggagt tttgaaccac agcaaggtgc agtatcatcc tggggctctg   6120
gaggaagtgg cagggagtcc aaaatgtcac cttagcttct tatctggggc acatgtatt    6180
tctgcatctg ctgcttccca cactcttgcc cacaagtgtc gcttgtggaa ataatttgag   6240
atttactgtc tggctgaccc tagtttcaat ctcttttcca ccatttgcta atcattctac   6300
cttgcgcaaa acatagaatt aaaagaaaac ttcagacaag ttaaatttga tggagtttaa   6360
ttgagcaaag aaaaaaaatg atccacaaat tgggcagtct ccagaatcac cgcagattca   6420
gagagactcc aggggtgcct cgtggtcaga acaaatttat agacagaaaa ggtaaagtga   6480
cctacaggaa tcagaattga gacatagaaa cagtgagatt ggttacagct cggcgtttgc   6540
cttatttgaa cgcagtttga acactcagca gtctatgagt ggttgaagta tggccgctgg   6600
gattggccaa cactcagctg ttattacaga tgcatactac taagttaggt tttcgatttt   6660
gtctgcctat ttgagctagg ttacagttcg tccacaagga ctcaaatata aaagtacgga   6720
gtcctcttcg ggccatattt agttcgcttt aacaattccc ccttttggtc agcccctcaa   6780
tttagagaga ttgaccaaaa ctttaggcgt tgacaccact ctctgtcacc atcataaaga   6840
cttatttggt ctcagtgtgg aactcacaag tcgtccttag tttcagtatg gagtctcaca   6900
catcttcttt ggtgttaata gggaattcac aagttgcaac tttgtaccag ctaaatgatt   6960
cttatatgttc ttgctgatcc agttggagta agaccattca actgtcaatg tacagctgca   7020
tacaaaacat ttaagacttg agagtataca gtgcaccaag gggactatta ttatgactgt   7080
taagaggaca ccgtcaaaat gctaaggtgt actccttaat aaaagttctt atgaaatgaa   7140
ctgaaccaaa tcagccaagt taaggttcag acaatataag cagttcagca gtattggggt   7200
ctgattggtc agagtcttca gttggagtat gatagtgatt aaggatcata gttcgctgta   7260
aagtagcttg acttaaagag gtgctcgttt tcattgttac cttgttaata caagtcataa   7320
taacttgaaa acctgctaga agagatataa agattagaaa cccttggaaa acccaagctt   7380
gccattcacc acttaggatg cctgcaaacc aactgttagt tgctcctata aacatatcgt   7440
gggttccttt ctcttgagag atttctttat tgtacttggt ggcagtgtct aaggaaacag   7500
cagtatcagc cacctttttaa attaagcttt ttgtagtaac agaatcaggg gagggattag   7560
tacaaaattc agtttttgttt aacaccaaac ataggcctcc agcttgagca aaaagaaagat   7620
ctaagactgc atgatcttcc attaagtgtt ttcgttgaat atgtatgttg tcatgtgcct   7680
ttctgagagt agcttctacc catctgaaac cctgggaggt ctgattggct accaaatcca   7740
agaattttcc caatatacaa attagttttaa aattccgtac aaatggtact tcactaccac   7800
caagagtgag ccccccaggaa cccccagtgga atctttcccc ggtagaaact agcttatcct   7860
cgtctatttc gaggctagtg ctaatttcag ttattgatca ttttggcctc caagtataag   7920
ggctatcatg agaattttca ggggaagcaa ttcgaaaggc aggagcaggc caggccagat   7980
aacaagaacc aaaccaacca aggaggcaga acagaatatg cagattctcc acagacccaa   8040
tagagaccct caggggttgg aaaaggggggc cacctagttg tatttgagca gggatcattc   8100
aggtttgttc gaccatgaat ctgtagctcc tgaataacat ccagtgggaa atttactttt   8160
ctatggcccc tttgtagtgt gttgtaaggg tgtataacca catctagtaa aaagagaccc   8220
tactggatat acaagcaatc acttgtacta acataagtaa ttcccaaatc ttgagtatgt   8280
gatgcctgca agcacaatat acgttttgta ggcatcattt ggatttgttt tttatatttg   8340
gtgtgatcga ctttatcagt tgaaaaagag tgttgttttt agtgagtgta ggaaagcaag   8400
tactagtgat gtttagagta tcaagaatag cttttccattc ttcccttggg gtttcaggggt   8460
gactcattgg gaaacgtgga ggggcactgg caccccttgga atcatttcct gatttttggg   8520
cattagccca caaacccaac agttaccctg gttttgtgct agagcataag cttgagctga   8580
agccatccac tgattatggt cccatggatt ttcatgtaag gaaaaggaaa ggattaggga   8640
aaaaaataag gaaaacagaa aaacacataa ggctttcatg gtggtagaga agtcttgatc   8700
tgtgatctag ggaaagctgt ctgtaaccag gatgctgtct gcttctggga agagatttcc   8760
ctggtcagct ttaccttaaa gtctccaacg ggtatatagt accaggagtc tgaggggggcc   8820
cttttgaatt gtgagatgtg gacccatggt tcaaagccct gaagcttctc tgcactgtgg   8880
gtggtaagaa ggacttggta tggtcccatc caacgaggtt caagagtgat cttcttctga   8940
tgtcatttcc ggaaggccca gtctccaaat tccagaccat ggagggttttg attgtcctca   9000
gttggtggat cttgaaatgc ttcctttacc tggtggaagt atactttggc gtaatacatt   9060
aaagccttgc agtatttagt catatcagag tttaagagag caggagagac atgagatgct   9120
attattaggg acatgggcct cccagtgact atttcataag gggtcaattt atgttttcca   9180
acaggattga atctgattgc cattaaaacc aaaaggtagt acctttggcc aaggcaactc   9240
aattgattca gttaacttgg acagtttcag ttttcaaatg ccatttgttc tttcaagctt   9300
tcctgaagac tgagggtaat aaggacaatg gtaatgcaac tgtgtcagta acaccttatt   9360
taactgcttt ataacttgct cagtaaaatg agttcctcta tcactgagga cttttagggg   9420
gatccccat aaaaggaaaaa catttttcaa taattttctta gctatggtca cagcatcagc   9480
tttcctacat gggaaggcct ttatccaacc agaaaacatg caaactatta caagaacata   9540
ctgataccccc attgagggtg gtaactgaat gaagtccatc tgtaaatgtt caaatggtca   9600
atcaggtggt ggaaatatac tgcctctagt ttttctggga ttatgagttt gacaagtcaa   9660
acattgatta taagccattt tagtaatgtc agaatagtca ccccaccagt attttttcat   9720
aatttggatc actttgtctg ttccatgatg agctgtggag agctttcaat aatgggaagct   9780
tcaaagattc aggaaggacc aggcggccgt ccgggccctt tgtgagtctt tgcttcacgt   9840
taaatttaca tccttttaga taccagttttt gttttttgcaa acatgacgt ttgcacctaa   9900
tattaaatag gtcatcgtaa ggaaattggc ttggattaat cttatggagt tcattcagat   9960
tgcgtatctt gatggttcca gcactagctg attgagcata aaaatctgct aaagcatttc  10020
actgatattt gggttcattt ctacaagtat gagcttcagt cttaataaca gcaatctgca  10080
tttgtaacag gatagcagaa aggagctcat ctgtttggag tccatttttg atgggggatcc  10140
cactagaggt gagaaaccttt cgtagtttcc atatcatgcc aaaatcacgt actactccaa  10200
aagcatgtct actatccgta aatatttact gactcgtcct tagctgtgtg acatgttcag  10260
gtaagggcag aaagttctgc aggttgggct gacttgactt gaagagttcg cttctctatt  10320
aactcattttt gggtggtaac agcatatcct gactgatatt ttttttttctg agttttggc  10380
ataggaccca tcaacaaaaa gtgttaattc aggattatcc agtggagtat cttgtatagc  10440
aacacgaggg gccactattt ctgatactac actcacaccg ttgtggtctt caccatcatc  10500
aggcagagat aacagagtag cagcattaag tagattacag cctttagat gaagataaga  10560
aggagatagg agaagtaatt cataagatgt tagtctactc actgaaaaat gctgggtttg  10620
attggaattt aatagacttt ccacagcgtg tgggacttgc aaattaagtt catttcctaa  10680
aaccagatct gatgaagctt ctaccagctt ggctgctgct actgcttttta aacaattagg  10740
atatgccttta gagactgggc ctaattgcag gctatagtat gcagtggtcc tatgtttagc  10800
```

```
accgtgttcc tgattattac attcatgaac aaacaaagtg aaaggtttag tgtaatttgg   10860
aagtcctaaa gctgggggct gttgtaaggc caacttcatt tggctaaaag cctgctcatg   10920
actgtcttcc caaggtaaag gctctggtac agcatttta gtgagctcat acagtggtga    10980
agctattaag gaaaaatttg gaacccagga tctgcaatat cctgcaagcc taagaaagcc   11040
ttttgtcttt tggttgcagg tcgaggaaaa cttaaatag gtttatcct ctcaggtaag     11100
agggaaatcc cttcagcagc caagtcatgt cccaaatagt ggacttttc ttttgaaaat    11160
tgaagttttg gccaggcatg gtggctaacg cctgtaatcc cagcactttg ggaggctgag   11220
gcaggcggat cacctgaggt cgggagttca aggacagcct gaccaacatg gagaaaccct   11280
gtctctacta aaaatacaaa attagccagg cgtggtggtg catgcctgta atcccagcta   11340
ctcgggaggc tgaggcagga gaatcgcttg aacccaggag gcagaggttg tggtgagcca   11400
gtatcacacc attgcactcc agcctgggca acaagagtga aactccatct caaaaaaaaa   11460
aaaaaagaaa aagaaaaaga aaaaattgaa gtttttccat tgaagccctg tgacctttat   11520
atgcaagttg ctgtaaaagg taaactgagt caatttccgg gcactcctta ataggagagc   11580
ataacaataa gttatctaca tactgaatga gagtagaatt ttgaggaaac tgtagtgtca   11640
ttaactcctg atgcagtgcc tggggaaaat atgaaggggc ttcagtaaac ccttgtggca   11700
ttacactcca ggtgtattgc tgatttttcc aagtaaaggc aaacaagtat tgactttctt   11760
tatggaatgc tagagaaggc tgagccaaga tctattactg tggacaactt ggaatcagtg   11820
ggtacattag gttataaagt attaggattt gggactacag gaaatcttgg tattacaatt   11880
ttattaattg cctgtaaatc tggaacaaat ctccagtctc atccattttg ttttttaact   11940
ggtaggattg gagtgttaca ggggctggtg catggaatta tgagtcctg tttaattaaa     12000
tcttctacaa ttggtgagag cccttaaatt gcttcaggtt ttagtggata ttgtggtaat   12060
taggcaaagg tttagaatga tctgttagta ctttatagg ttctacactt ttaattcttc    12120
ctatatcagt tgggaagagg cccataaaca ttaggtgttt tcgaaagatc aggggtatta   12180
caggcttgag tttcgatctt atcaattct gcctgtagac agcataacaa ttctagttca    12240
ggagaatcag gaaaactctt aagattattt ctgtttctga ggaaaatttt aggtgccctt   12300
ttagctttga aagtaaatct tgccctacca agttactgg aacagtatca cgtagtaaaa    12360
aactgtgttt ttctgaaagg gggctcagag ttaattggat gggttcagat atgggaacct   12420
ctggaacttg atttgaaacc cctgtcacag aaatgacctt tttactctaa gggatttgtt   12480
ggcttattaa ggtgggggttt atggtagata gagtagccct ggtatccata aggactatac   12540
acaactccct atttatttta acctctgttt ccccatgttc ctttaaaagt attacgggga   12600
gcaatccact ggagaatccc ttagagcctc ctttaagttg aatattgtca ggaggactaa   12660
ggtctcttgg gctccctcta gtggtgaaac agtttggcct agaggggaggt ttatcagccg   12720
acaatccctt ttccagtgcc ctggttgttt gcaatacagg cagacatctt ggggtaaaga   12780
aattcttgtt ctgggacctc ttgatttgat tttttaata tataattta aaaatatttt     12840
ccaaagtgtg acttaaaaaa atttttttt attatacttt aagttttagg gtacatgtgc    12900
acaacgtgca ggtttgttac atatgtatac atgtgccatg ttggtgtgct gcacccatta   12960
actcatcatt tacattaggt atatctccta atgctatccc tcccccctcc cccaacccca   13020
caacaggccc cagtgtgtga tgttcccctt cctgtgtcca agtgttctca ctgttcagtt   13080
cccaccctacg agtgagaaca tgcggtgttt ggtttttgt cctgtgata gtttgctgag    13140
aatgatggtt tccagcttca tccatgtccc tacaaaggac attaactcat catttttat    13200
ggctccatag tattccatgg tgtatatatg ccacattttc ttaatccagt ctatcattgt   13260
tggacatttg tgttggttcc aagtctttgc tattgtgaat agtgctgcaa taaacatacg   13320
tgtgcatgtg tcttatagc agcatgattt ataatccttt gggtatatac ccagtaatgg    13380
gatggctggg tcaaacggta tttctagttc tagatccctg aggaattgcc acactgactt   13440
ccacaatggt tgaactagtt tacagtccca ccaacagtgt aaaagtgttc ctatttctcc   13500
acatcctctc cagcacctgt tgtttcctga cttttttaatg attgccattc taactggtgt   13560
gagttggtat ctcattgtgg ttttgatttg catttctctg atggccagtg atgatgagca   13620
tttttttcatg tgtctttgg ctgcataaat gtcttctttt gagaagtgtc tgttcatatc    13680
cttcacccac ttgttgatgg ggttgttgt ttttctcttg taagtttgtt tgagttctt     13740
gtagattctg gatattagcc ctttgtcaga tgagaagttt cagaaattt ctcccattct    13800
gtaggttgcc tgttcactct gatggtagtt tcttttgctg tgcagaagct cttttactta   13860
atgagatccc atttgtcaat tttggctttt gttgccattg cttttggtgt tttagacatg   13920
aagtccttgg ccatgcctat gtcctgaatg gtattgccta ggttttcttc taggattttt   13980
atggttttag gtctaaatta agtctttaat ctatcttgaa ttaattttg tataaggtgt    14040
aaggaaggga tccagtttca gcttttctaca tatggctagc cagttttccc agcaccattt   14100
attaaatagg gaatcgtttc cccgtttctt gttttttgtca ggtttgtcaa agatcagata   14160
gttgtagata tgcggcgtta tttctgaggg ctctgttctg ttccattggc ctatatctct   14220
gttttggtac cagtaccatg ctgttttggt gactgtagcc ttgtatagtt tgaagtcagg   14280
tagcgtgatg cctccagctt tgttctttgg cttaggattg acttggcaat gcaggctctt   14340
ttttggttcc atatgaactt taaagtagtt ttttccaatt ctgtgaagaa agtctttgt    14400
agcttgatgg ggatggcatt gaatctataa attaccctgg gcagtatggc cattttcacg   14460
atattgattc ttcctaccca tgagcatgga atgttcttcc atttgtttgt atcctctttt   14520
atttccttga gcagtggttt gtagttctcc ttgaagaggt ctttcacatc cctgtatgt    14580
tggattccta ggtattttat tctctttgaa gcaattgtga atgagagttc actcatgatt   14640
tggctctctg tttgtctgtt attggtatat aagaatgctc tctttgttc tttgttagtc    14700
ttgctagcgg tctatcaatt ttgttgatct tttgaaaa ccagtactg gattcattga      14760
tttttgaag ggttttttgt gtctctatct ccttcagttc tgctctggtc ttatttattt    14820
cttgccttct gctgcttttt gaatgtgtt gctcttgctt ctctagttct tttaattgtg    14880
acgttagggt gtcaattta gatctttcct actttctcct gtgggcatt agtgctataa     14940
atttccctct acacactgct ttgaatgtgt cccagagatt ctggtatgtt gtgtctttgt   15000
tctcattggt ttcaaagaac atctttactt ctgccttcat ttcgttatgt acccagtagt   15060
cattcaggag caggttgttc agtttccatg tagttgagca gttttgagtg agtttcttaa   15120
tcctgagttc tagtttgatt ccactgtggt ctgagagaca gtttgttata atttgtattc   15180
ttttacattt tctgaggaga gcttttttc caactatgtg gtcaatttg gaataagtgc     15240
agtgtggtgc taagaagaac gtatgttctg ttgatttggg gtggagagtt ctgtagatgt   15300
gtattaggtc cgcttggtgc agagctgagt tgaattcctg gatatccttg ttaactttct   15360
gtctcgttgg tctgtctaat gttgacagtg gggtgttaaa gtctcccatt attgttgtgt   15420
gggagtctga gtctctttgt aggtcactca gggcttgctt tatgaatctg ggtgctcctg   15480
tattggttgc atatatattt aggatagtta gctcttcttg ttgaattgat ccctttacca   15540
```

```
ttatgtaatg gccttctttg tctcttttga tctttgttgg tttaaagtct gttttaccag   15600
agactaggat tgaaacccct gccttttttt gttttccatt tgcttggtag atcttcctcc   15660
atccctttat tttgagccta tgtgtgactc tgcacgtgag atgggtttcc tgaatacagc   15720
acactgatgg gtcttgactc tttatccaat ttgccagtcc gtgtctttta attggagcat   15780
ttagcccatt tacatttaag gttaatattg ttatgtgtga atttgatcct gtcattctct   15840
caacatttgc ttgtctgtaa aggatttat ttctccttca cttatgaagc ttagtttggc   15900
tggatatgaa attctgggtt gaaaattctt ttctttaaga atgttgaata ttggcctcca   15960
ctctcttctg gcgtgtagag tttctgccga gagatcagct gttggtctga tgggcttccc   16020
tttgtgggta acctgacctt tctctctagc tgccattaac attttttcct tcatttcaac   16080
tttggtgaat ctgacaatta tgtgtcttgg agttgctctt ttcgaggagt atctttgtgg   16140
cattctctgt gtttcctgaa tttgaatgtt ggcctgcctt gctagattgg ggaagttctc   16200
ctggataata tcctgcagag tgttttccaa cttggttcca ttcttcccgt cactttcagg   16260
tacaccaatc agacgtagat ttggtctttt cacatagtcc catattctt ggaggctttg   16320
ttcgttctt tttattcttt ttctctaaa cttctcttcc cgcttcattt cattgatttg   16380
atcttccatc actgatacccc ttttcttcag ttgatcgaat cggctactga ggcttgtgca   16440
tccgtcacgt agttctcgtg ccttggtttt cagctccatc aggtcccttta aggacttctc   16500
tgcattagtt attctagtta gccgttcgtc gaattttttt caaggttttt aacttctttg   16560
ccatgggttc gaacttcctc ctttagcttg gatagtttga ttgtctgaag tcttcttctc   16620
tcagctcgtc aaagtcattc tctgtccagc tttgttccgt tgctggtgag gagctgcatt   16680
cctttggagg aggagaggtg ctctgatttt tagaattttc agtattttg ctctgtttct   16740
tccccatctt tgtggttttg tctacctttg gtctttgatg atggtgatgt acagatgggt   16800
ttttggtgtg gatgtccttt ctgtttgtta gtttccttc taacagtcag gaccctcagc   16860
tgcaggtcta ttggagtttg ctggaggtcc actccagacc atgtttgcct gggtatcagc   16920
agcggaggct gcagaacaac gaatattggt gaacagcaga tgttgctgcc tgatcgttcc   16980
tctgaagtt ttgtctcaga ggggtacccg gccatgtgag gtgtcagtct gcccctactg   17040
gggggtgcct cccagttagg cattcgggg gtcagggacc cacttgagga ggcagtctgt   17100
ctgttctcag atctcaagct gtgtgctggg agaaccactg ctctcttcca agctgtcaga   17160
cagggacatt taagtctgca gaggtttctg ctgccttttg ttcggctatg ccctgcctgc   17220
agaggtggag tctacagagg aaggcaggcc tccttgagct gcagtgggct ccacccagtt   17280
cgagcttccc agctgctttt tttacctgct caagcctccg caatgcgggg caccctccc   17340
ccagcctcgc tgccaccttg cagtttgatc tcagactgct gtgctagcaa tgagcgaggc   17400
tccatgggca taggacccgc tgagccaggc gcgggatata gtcctggt gtgctgtttg   17460
ctaagaccat cggaaaagcg cagtattagg gtgggagtga cccaattttc caggtgctgt   17520
ctgtcccccc tttccttggc taggaaaggg aattccctgc cccttgtgc ttcctgggtg   17580
aggcgatgcc tcgccctgct ttggctcatg ctccggtcgcg tgcacccact gtcctgcacc   17640
cactgtctga caatccccag tgagatgaac ccagtacctc agttggaaat gcagaaatca   17700
cccgttttct gcgtcgctca agctgggagc tgtagactgg agctgttcct atttggccat   17760
cttggaaccg ccccgattgtg atttaaaatg agaacgagat ggtcccttg gttcctggtc   17820
cctgtaactg ttgcaattga aggggcataa gcttattagc cttttgaggt tttttttgct   17880
ctagagtctt ctcaaaatgc ttagctaggt tgggcacgat ggctcacgcc tgtaatccca   17940
gcactttgga aggccaaggt gggaggatca cgaggtcagg agatcaagac catcctggct   18000
aagatggtga atcccatct ctactaaaaa tacacagatt agctgggcat ggtggcacac   18060
gcctgtagtc gcagctactc gggaggctga ggcaagagaa ttgcttgaac ctgggaggca   18120
gaggttgcag tgagccgaga ttgcgccact acactctagc ctgggtgaca gagcaagact   18180
ccacctcaaa aaaaaaaaa aaaaaaaaa aagttcagct aaggccacca attcagtcac   18240
atctctaact tcccattgca acttatgttt tttagttaaa ctgctaagtt caggatggag   18300
tccatttata agtaaagcag ttaatgctgt ttcagccct gcagggaata ctccttgctg   18360
tactttgagc ccaggatgtt tcacaaatat ttctaagcga cttctgtaat ctgaaactgg   18420
ttcatcttt ctttctttt tttttgctt acaagattgt atgatggacc aattttttgt   18480
ggaaaaattt taggaactga atgttaaaag gttttcagcg atttttctag ctattttgg   18540
tccttcttgt gaggagctct tagagggccc tttaaaatgt cctcctcagg tttgtccatt   18600
tctgctgctg ccatccattt ctgagcttca ccagccccca gtatcatatg aataaaattgc   18660
taaattcatg aagtcctgga tcgtaagctc ctattaggat tctaaattcc tcagtaaatt   18720
tttgagactt ttcccttgga ccaggaagt ccttcacaat ggggctaagc tcagttttag   18780
accatggagt gaaagtagtt acagcaggca ggcctggctg atataaggtc tcactttgta   18840
agacatctgt ctaacttcct tttttttt ttttttttt taaatcatct tcagggtgaa   18900
agtgtaattt aacaaaaagt ttagtggact cagagtatgt aggtagagat ggacaaagaa   18960
ggaacagtcc gagttagatc agtcaaagta cagtcctctt tcttcatgtc cttggtctgt   19020
tgcttaagct tttcatttgg tttttgcaaa gaatctttta aggaggcact ttttgattca   19080
cttagtcttt tggaggcctt tgcgtatcca tgagacaata catcccactg tatttgtggg   19140
ggctttgatc cccttttttct aatatgcctt gcaaacaatt ttatccaaat taaaacttct   19200
ccattgtggc catttaatt ctaagttttc tttagtgagg ttaacccatt ttactgaaaa   19260
tgcacatgtt ctgggcccat aattttata cgtaaaatta gctggagtcc ctgaagatgg   19320
agtcccagac tccttggatt gagatgatcc cattattaaa taaggtactt atcagaggtc   19380
tgaggcctct aactgaatcc aatccagtta attatcaaat ccaatttgat cttggatcca   19440
gtccaggcta agtattgctt gagtaaactc ggagagctca aaacacaagt tagtgagct   19500
cggaatctga gagaaactc acccatgacc tccagttaca atcaagagac cagtgagagc   19560
aacggcctca gtgggtaccc caccaggtca cctggtgttc caggggggttg ccagagtttg   19620
tcttcaaatc ccacttctga caccagatc gttaaagaa aacttcagac aagttaaatt   19680
tgatggagtt taattaagca aggaaaataa acactttgca aatcaggcag cctccagaat   19740
tgaatgcagt tgaacactt agcagtctat tagtgcttga agtatggcca ctgggattgg   19800
ccaacactca gctattatta cagatgcata ctactcaggt tttccatttt gtctgcctat   19860
tgtgctaggt tatggtttgt ccacaagaac acaaatatag aagtatggag tccttctcag   19920
gccatattta gtttgcttta acaatactta aaaaaaaat aggatactta   19980
accttactcg gtgtttctga gagttaacat ttatatagtt atgctgtagt gaaaacagct   20040
agcgtaatgt ctggtatgta taggaacaca agagataccg cttttcccat atccccatac   20100
cattcttcac agcattgctc ctgtcttcct tgattcctcc tcctccttct tgttttttt   20160
tttgtttgtt tgtttgtttt tttttggagg tggagtctca ctctgttgcc caggctggag   20220
tgcagtggtg tgatctcagc ttactgcaac ctctgcctcc tgggttcaag tgattctcct   20280
```

-continued

```
gcctcagcct cctgaatagc tgggattaca ggcacacacc aacacactca gctaattttt    20340
gtattttag tagggatggg gtttcaccat gttggccagg ctggtcttga actcctgacc    20400
tcaggtgatt cacccacctc agcctcccaa agtgctggga ttacaggtgt gagccaccac    20460
accctgcctc cttcttaaga agtttccagt cccttgtaat taaaggaatt aatattttt    20520
aactacttag aatcagactg gccctgatta ttagtaagca actaatagta agcaagcaac    20580
tatgtatgca actatgagtg tatgttaaga tatggttgtt ggtaaccttt cattctcttc    20640
aggaagaaga agagggtgga gctctacagt caatgtgtac atttaaattc tgttcccttt    20700
cgagcttttt tgctactttc attcttctgg ggatccaggt gcttgagttg ggattgatta    20760
acttccttaa tttccacccc tgtgctgtca ggatcgggag acatagatga aggtgttcta    20820
aactgctaga aattttgttt ttgaaagcaa agtttgcat gcattttgt tttcaacttt    20880
tacttacagt gaatagtagt taataaaata agtccctgcc ttttctctct ttggtttcaa    20940
ttcctgagac caggatcata gcccacatat tagagtggag tcccactgct ttggtttgaa    21000
tcatgccttt gtttcttatg tcagtgtgac tttgggcaag ttatttaagt ctttgcacca    21060
cattttcctc atctgtaaaa tgaggataat actagtactt tctacatggg attgttagca    21120
ggattaaatg agatagcaca tactgtaacc atgtctggca catagtcaat ggttagtaaa    21180
tgtgaactat tgtgtgacat tgtggttagt cacgtatggg gctgtgtttc ctttagtata    21240
ttgctctttt aatgtcattt cctttgtact gttaccctcc ctgatcttc ttccatattc    21300
a                                                                   21301
```

| | |
|---|---|
| SEQ ID NO: 6 | moltype = DNA  length = 18 |
| FEATURE | Location/Qualifiers |
| misc_feature | 1..18 |
| | note = Description of Artificial Sequence: Synthetic oligonucleotide |
| source | 1..18 |
| | mol_type = other DNA |
| | organism = synthetic construct |

SEQUENCE: 6
aggccattct gaaattct                                               18

| | |
|---|---|
| SEQ ID NO: 7 | moltype = DNA  length = 18 |
| FEATURE | Location/Qualifiers |
| misc_feature | 1..18 |
| | note = Description of Artificial Sequence: Synthetic oligonucleotide |
| source | 1..18 |
| | mol_type = other DNA |
| | organism = synthetic construct |

SEQUENCE: 7
cattgaggcc attctgaa                                               18

| | |
|---|---|
| SEQ ID NO: 8 | moltype = DNA  length = 18 |
| FEATURE | Location/Qualifiers |
| misc_feature | 1..18 |
| | note = Description of Artificial Sequence: Synthetic oligonucleotide |
| source | 1..18 |
| | mol_type = other DNA |
| | organism = synthetic construct |

SEQUENCE: 8
taaggcattg aggccatt                                               18

| | |
|---|---|
| SEQ ID NO: 9 | moltype = DNA  length = 18 |
| FEATURE | Location/Qualifiers |
| misc_feature | 1..18 |
| | note = Description of Artificial Sequence: Synthetic oligonucleotide |
| source | 1..18 |
| | mol_type = other DNA |
| | organism = synthetic construct |

SEQUENCE: 9
cctattaagg cattgagg                                               18

| | |
|---|---|
| SEQ ID NO: 10 | moltype = DNA  length = 18 |
| FEATURE | Location/Qualifiers |
| misc_feature | 1..18 |
| | note = Description of Artificial Sequence: Synthetic oligonucleotide |
| source | 1..18 |
| | mol_type = other DNA |
| | organism = synthetic construct |

SEQUENCE: 10
ttcttcctat taaggcat                                               18

```
SEQ ID NO: 11               moltype = DNA  length = 18
FEATURE                     Location/Qualifiers
misc_feature                1..18
                            note = Description of Artificial Sequence: Synthetic
                             oligonucleotide
source                      1..18
                            mol_type = other DNA
                            organism = synthetic construct
SEQUENCE: 11
agtatttctt cctattaa                                                       18

SEQ ID NO: 12               moltype = DNA  length = 18
FEATURE                     Location/Qualifiers
misc_feature                1..18
                            note = Description of Artificial Sequence: Synthetic
                             oligonucleotide
source                      1..18
                            mol_type = other DNA
                            organism = synthetic construct
SEQUENCE: 12
tttcaagtat ttcttcct                                                       18

SEQ ID NO: 13               moltype = DNA  length = 18
FEATURE                     Location/Qualifiers
misc_feature                1..18
                            note = Description of Artificial Sequence: Synthetic
                             oligonucleotide
source                      1..18
                            mol_type = other DNA
                            organism = synthetic construct
SEQUENCE: 13
aaaaatttca agtatttc                                                       18

SEQ ID NO: 14               moltype = DNA  length = 18
FEATURE                     Location/Qualifiers
misc_feature                1..18
                            note = Description of Artificial Sequence: Synthetic
                             oligonucleotide
source                      1..18
                            mol_type = other DNA
                            organism = synthetic construct
SEQUENCE: 14
aatttaaaaa tttcaagt                                                       18

SEQ ID NO: 15               moltype = DNA  length = 18
FEATURE                     Location/Qualifiers
misc_feature                1..18
                            note = Description of Artificial Sequence: Synthetic
                             oligonucleotide
source                      1..18
                            mol_type = other DNA
                            organism = synthetic construct
SEQUENCE: 15
gccctaattt aaaaattt                                                       18

SEQ ID NO: 16               moltype = DNA  length = 18
FEATURE                     Location/Qualifiers
misc_feature                1..18
                            note = Description of Artificial Sequence: Synthetic
                             oligonucleotide
source                      1..18
                            mol_type = other DNA
                            organism = synthetic construct
SEQUENCE: 16
accaagccct aatttaaa                                                       18

SEQ ID NO: 17               moltype = DNA  length = 18
FEATURE                     Location/Qualifiers
misc_feature                1..18
                            note = Description of Artificial Sequence: Synthetic
                             oligonucleotide
source                      1..18
                            mol_type = other DNA
                            organism = synthetic construct
SEQUENCE: 17
acaaaaccaa gccctaat                                                       18
```

```
SEQ ID NO: 18               moltype = DNA  length = 18
FEATURE                     Location/Qualifiers
misc_feature                1..18
                            note = Description of Artificial Sequence: Synthetic
                            oligonucleotide
source                      1..18
                            mol_type = other DNA
                            organism = synthetic construct
SEQUENCE: 18
tcctcacaaa accaagcc                                                         18

SEQ ID NO: 19               moltype = DNA  length = 18
FEATURE                     Location/Qualifiers
misc_feature                1..18
                            note = Description of Artificial Sequence: Synthetic
                            oligonucleotide
source                      1..18
                            mol_type = other DNA
                            organism = synthetic construct
SEQUENCE: 19
ctagctcctc acaaaacc                                                         18

SEQ ID NO: 20               moltype = DNA  length = 18
FEATURE                     Location/Qualifiers
misc_feature                1..18
                            note = Description of Artificial Sequence: Synthetic
                            oligonucleotide
source                      1..18
                            mol_type = other DNA
                            organism = synthetic construct
SEQUENCE: 20
ctttactagc tcctcaca                                                         18

SEQ ID NO: 21               moltype = DNA  length = 18
FEATURE                     Location/Qualifiers
misc_feature                1..18
                            note = Description of Artificial Sequence: Synthetic
                            oligonucleotide
source                      1..18
                            mol_type = other DNA
                            organism = synthetic construct
SEQUENCE: 21
aaaaccttta ctagctcc                                                         18

SEQ ID NO: 22               moltype = DNA  length = 18
FEATURE                     Location/Qualifiers
misc_feature                1..18
                            note = Description of Artificial Sequence: Synthetic
                            oligonucleotide
source                      1..18
                            mol_type = other DNA
                            organism = synthetic construct
SEQUENCE: 22
agagaaaaac ctttacta                                                         18

SEQ ID NO: 23               moltype = DNA  length = 18
FEATURE                     Location/Qualifiers
misc_feature                1..18
                            note = Description of Artificial Sequence: Synthetic
                            oligonucleotide
source                      1..18
                            mol_type = other DNA
                            organism = synthetic construct
SEQUENCE: 23
ctgaaagaga aaaacctt                                                         18

SEQ ID NO: 24               moltype = DNA  length = 18
FEATURE                     Location/Qualifiers
misc_feature                1..18
                            note = Description of Artificial Sequence: Synthetic
                            oligonucleotide
source                      1..18
                            mol_type = other DNA
                            organism = synthetic construct
SEQUENCE: 24
aagctgaaag agaaaaac                                                         18
```

```
SEQ ID NO: 25          moltype = DNA  length = 18
FEATURE                Location/Qualifiers
misc_feature           1..18
                       note = Description of Artificial Sequence: Synthetic
                       oligonucleotide
source                 1..18
                       mol_type = other DNA
                       organism = synthetic construct
SEQUENCE: 25
ctaaagctga agagaaa                                                         18

SEQ ID NO: 26          moltype = DNA  length = 18
FEATURE                Location/Qualifiers
misc_feature           1..18
                       note = Description of Artificial Sequence: Synthetic
                       oligonucleotide
source                 1..18
                       mol_type = other DNA
                       organism = synthetic construct
SEQUENCE: 26
aagctaaagc tgaaagag                                                        18

SEQ ID NO: 27          moltype = DNA  length = 18
FEATURE                Location/Qualifiers
misc_feature           1..18
                       note = Description of Artificial Sequence: Synthetic
                       oligonucleotide
source                 1..18
                       mol_type = other DNA
                       organism = synthetic construct
SEQUENCE: 27
aacaagctaa agctgaaa                                                        18

SEQ ID NO: 28          moltype = DNA  length = 18
FEATURE                Location/Qualifiers
misc_feature           1..18
                       note = Description of Artificial Sequence: Synthetic
                       oligonucleotide
source                 1..18
                       mol_type = other DNA
                       organism = synthetic construct
SEQUENCE: 28
agaaacaagc taaagctg                                                        18

SEQ ID NO: 29          moltype = DNA  length = 18
FEATURE                Location/Qualifiers
misc_feature           1..18
                       note = Description of Artificial Sequence: Synthetic
                       oligonucleotide
source                 1..18
                       mol_type = other DNA
                       organism = synthetic construct
SEQUENCE: 29
cgcagaaaca agctaaag                                                        18

SEQ ID NO: 30          moltype = DNA  length = 18
FEATURE                Location/Qualifiers
misc_feature           1..18
                       note = Description of Artificial Sequence: Synthetic
                       oligonucleotide
source                 1..18
                       mol_type = other DNA
                       organism = synthetic construct
SEQUENCE: 30
tcctccgcag aaacaagc                                                        18

SEQ ID NO: 31          moltype = DNA  length = 18
FEATURE                Location/Qualifiers
misc_feature           1..18
                       note = Description of Artificial Sequence: Synthetic
                       oligonucleotide
source                 1..18
                       mol_type = other DNA
                       organism = synthetic construct
SEQUENCE: 31
cggaatcctc cgcagaaa                                                        18
```

```
SEQ ID NO: 32          moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 32
aagagcggaa tcctccgc                                                    18

SEQ ID NO: 33          moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 33
ggagaaagag cggaatcc                                                    18

SEQ ID NO: 34          moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 34
ctgatggaga aagagcgg                                                    18

SEQ ID NO: 35          moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 35
tgaaactgat ggagaaag                                                    18

SEQ ID NO: 36          moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 36
ggctatgaaa ctgatgga                                                    18

SEQ ID NO: 37          moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 37
tccagggcta tgaaactg                                                    18

SEQ ID NO: 38          moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 38
acaattccag ggctatga                                                    18
```

```
SEQ ID NO: 39            moltype = DNA   length = 18
FEATURE                  Location/Qualifiers
misc_feature             1..18
                         note = Description of Artificial Sequence: Synthetic
                           oligonucleotide
source                   1..18
                         mol_type = other DNA
                         organism = synthetic construct
SEQUENCE: 39
tttctacaat tccagggc                                                       18

SEQ ID NO: 40            moltype = DNA   length = 18
FEATURE                  Location/Qualifiers
misc_feature             1..18
                         note = Description of Artificial Sequence: Synthetic
                           oligonucleotide
source                   1..18
                         mol_type = other DNA
                         organism = synthetic construct
SEQUENCE: 40
gagcttttct acaattcc                                                       18

SEQ ID NO: 41            moltype = DNA   length = 18
FEATURE                  Location/Qualifiers
misc_feature             1..18
                         note = Description of Artificial Sequence: Synthetic
                           oligonucleotide
source                   1..18
                         mol_type = other DNA
                         organism = synthetic construct
SEQUENCE: 41
aaccagagct tttctaca                                                       18

SEQ ID NO: 42            moltype = DNA   length = 18
FEATURE                  Location/Qualifiers
misc_feature             1..18
                         note = Description of Artificial Sequence: Synthetic
                           oligonucleotide
source                   1..18
                         mol_type = other DNA
                         organism = synthetic construct
SEQUENCE: 42
cttgaaacca gagctttt                                                       18

SEQ ID NO: 43            moltype = DNA   length = 18
FEATURE                  Location/Qualifiers
misc_feature             1..18
                         note = Description of Artificial Sequence: Synthetic
                           oligonucleotide
source                   1..18
                         mol_type = other DNA
                         organism = synthetic construct
SEQUENCE: 43
atggtcttga aaccagag                                                       18

SEQ ID NO: 44            moltype = DNA   length = 18
FEATURE                  Location/Qualifiers
misc_feature             1..18
                         note = Description of Artificial Sequence: Synthetic
                           oligonucleotide
source                   1..18
                         mol_type = other DNA
                         organism = synthetic construct
SEQUENCE: 44
tatcaatggt cttgaaac                                                       18

SEQ ID NO: 45            moltype = DNA   length = 18
FEATURE                  Location/Qualifiers
misc_feature             1..18
                         note = Description of Artificial Sequence: Synthetic
                           oligonucleotide
source                   1..18
                         mol_type = other DNA
                         organism = synthetic construct
```

```
SEQUENCE: 45
atggatatca atggtctt                                                    18

SEQ ID NO: 46            moltype = DNA  length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 46
cagaaatgga tatcaatg                                                    18

SEQ ID NO: 47            moltype = DNA  length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 47
cctgacagaa atggatat                                                    18

SEQ ID NO: 48            moltype = DNA  length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 48
caccctgaca gaaatgga                                                    18

SEQ ID NO: 49            moltype = DNA  length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 49
actcaccctg acagaaat                                                    18

SEQ ID NO: 50            moltype = DNA  length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 50
aaaactcacc ctgacaga                                                    18

SEQ ID NO: 51            moltype = DNA  length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 51
tttaaaactc accctgac                                                    18

SEQ ID NO: 52            moltype = DNA  length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
```

```
SEQUENCE: 52
aaatttaaaa ctcaccct                                                   18

SEQ ID NO: 53           moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 53
aataaattta aaactcac                                                   18

SEQ ID NO: 54           moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 54
catgaaataa atttaaaa                                                   18

SEQ ID NO: 55           moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 55
tgcatcatga aataaatt                                                   18

SEQ ID NO: 56           moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 56
ttgtttgcat catgaaat                                                   18

SEQ ID NO: 57           moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 57
atatattgtt tgcatcat                                                   18

SEQ ID NO: 58           moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 58
gttcaatata ttgtttgc                                                   18

SEQ ID NO: 59           moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
```

```
SEQUENCE: 59
ctgttgttca atatattg                                                    18

SEQ ID NO: 60           moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 60
atgtcctgtt gttcaata                                                    18

SEQ ID NO: 61           moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 61
agttcatgtc ctgttgtt                                                    18

SEQ ID NO: 62           moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 62
gaacaagttc atgtcctg                                                    18

SEQ ID NO: 63           moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 63
aacaagaaca agttcatg                                                    18

SEQ ID NO: 64           moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 64
cttacaacaa gaacaagt                                                    18

SEQ ID NO: 65           moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 65
agccacttac aacaagaa                                                    18

SEQ ID NO: 66           moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 66
aattcagcca cttacaac                                                    18
```

```
SEQ ID NO: 67           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 67
gataaaattc agccactt                                                        18

SEQ ID NO: 68           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 68
ttactgataa aattcagc                                                        18

SEQ ID NO: 69           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 69
gtgctttact gataaaat                                                        18

SEQ ID NO: 70           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 70
ttgatgtgct ttactgat                                                        18

SEQ ID NO: 71           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 71
tggagaaaga gcggaatc                                                        18

SEQ ID NO: 72           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 72
atggagaaag agcggaat                                                        18

SEQ ID NO: 73           moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 73
gatggagaaa gagcggaa                                                        18
```

```
SEQ ID NO: 74              moltype = DNA  length = 18
FEATURE                    Location/Qualifiers
misc_feature               1..18
                           note = Description of Artificial Sequence: Synthetic
                             oligonucleotide
source                     1..18
                           mol_type = other DNA
                           organism = synthetic construct
SEQUENCE: 74
tgatggagaa agagcgga                                                       18

SEQ ID NO: 75              moltype = DNA  length = 18
FEATURE                    Location/Qualifiers
misc_feature               1..18
                           note = Description of Artificial Sequence: Synthetic
                             oligonucleotide
source                     1..18
                           mol_type = other DNA
                           organism = synthetic construct
SEQUENCE: 75
actgatggag aaagagcg                                                       18

SEQ ID NO: 76              moltype = DNA  length = 18
FEATURE                    Location/Qualifiers
misc_feature               1..18
                           note = Description of Artificial Sequence: Synthetic
                             oligonucleotide
source                     1..18
                           mol_type = other DNA
                           organism = synthetic construct
SEQUENCE: 76
aactgatgga gaaagagc                                                       18

SEQ ID NO: 77              moltype = DNA  length = 18
FEATURE                    Location/Qualifiers
misc_feature               1..18
                           note = Description of Artificial Sequence: Synthetic
                             oligonucleotide
source                     1..18
                           mol_type = other DNA
                           organism = synthetic construct
SEQUENCE: 77
aaactgatgg agaaagag                                                       18

SEQ ID NO: 78              moltype = DNA  length = 18
FEATURE                    Location/Qualifiers
misc_feature               1..18
                           note = Description of Artificial Sequence: Synthetic
                             oligonucleotide
source                     1..18
                           mol_type = other DNA
                           organism = synthetic construct
SEQUENCE: 78
gaaactgatg gagaaaga                                                       18

SEQ ID NO: 79              moltype = DNA  length = 18
FEATURE                    Location/Qualifiers
misc_feature               1..18
                           note = Description of Artificial Sequence: Synthetic
                             oligonucleotide
source                     1..18
                           mol_type = other DNA
                           organism = synthetic construct
SEQUENCE: 79
atgaaactga tggagaaa                                                       18

SEQ ID NO: 80              moltype = DNA  length = 18
FEATURE                    Location/Qualifiers
misc_feature               1..18
                           note = Description of Artificial Sequence: Synthetic
                             oligonucleotide
source                     1..18
                           mol_type = other DNA
                           organism = synthetic construct
```

```
SEQUENCE: 80
tatgaaactg atggagaa                                                 18

SEQ ID NO: 81           moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 81
ctatgaaact gatggaga                                                 18

SEQ ID NO: 82           moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 82
gctatgaaac tgatggag                                                 18

SEQ ID NO: 83           moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 83
gggctatgaa actgatgg                                                 18

SEQ ID NO: 84           moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 84
agggctatga aactgatg                                                 18

SEQ ID NO: 85           moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 85
cagggctatg aaactgat                                                 18

SEQ ID NO: 86           moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 86
ccagggctat gaaactga                                                 18

SEQ ID NO: 87           moltype = DNA  length = 22
FEATURE                 Location/Qualifiers
misc_feature            1..22
                        note = Description of Artificial Sequence: Synthetic
                        oligonucleotide
source                  1..22
                        mol_type = other DNA
                        organism = synthetic construct
SEQUENCE: 87
ctgatggaga aagagcggaa tc                                            22
```

```
SEQ ID NO: 88            moltype = DNA  length = 20
FEATURE                  Location/Qualifiers
misc_feature             1..20
                         note = Description of Artificial Sequence: Synthetic
                          oligonucleotide
source                   1..20
                         mol_type = other DNA
                         organism = synthetic construct
SEQUENCE: 88
ctgatggaga aagagcggaa                                                    20

SEQ ID NO: 89            moltype = DNA  length = 22
FEATURE                  Location/Qualifiers
misc_feature             1..22
                         note = Description of Artificial Sequence: Synthetic
                          oligonucleotide
source                   1..22
                         mol_type = other DNA
                         organism = synthetic construct
SEQUENCE: 89
aactgatgga gaaagagcgg aa                                                 22

SEQ ID NO: 90            moltype = DNA  length = 20
FEATURE                  Location/Qualifiers
misc_feature             1..20
                         note = Description of Artificial Sequence: Synthetic
                          oligonucleotide
source                   1..20
                         mol_type = other DNA
                         organism = synthetic construct
SEQUENCE: 90
aactgatgga gaaagagcgg                                                    20

SEQ ID NO: 91            moltype = DNA  length = 22
FEATURE                  Location/Qualifiers
misc_feature             1..22
                         note = Description of Artificial Sequence: Synthetic
                          oligonucleotide
source                   1..22
                         mol_type = other DNA
                         organism = synthetic construct
SEQUENCE: 91
gaaactgatg gagaaagagc gg                                                 22

SEQ ID NO: 92            moltype = DNA  length = 22
FEATURE                  Location/Qualifiers
misc_feature             1..22
                         note = Description of Artificial Sequence: Synthetic
                          oligonucleotide
source                   1..22
                         mol_type = other DNA
                         organism = synthetic construct
SEQUENCE: 92
ggctatgaaa ctgatggaga aa                                                 22

SEQ ID NO: 93            moltype = DNA  length = 20
FEATURE                  Location/Qualifiers
misc_feature             1..20
                         note = Description of Artificial Sequence: Synthetic
                          oligonucleotide
source                   1..20
                         mol_type = other DNA
                         organism = synthetic construct
SEQUENCE: 93
ggctatgaaa ctgatggaga                                                    20

SEQ ID NO: 94            moltype = DNA  length = 22
FEATURE                  Location/Qualifiers
misc_feature             1..22
                         note = Description of Artificial Sequence: Synthetic
                          oligonucleotide
source                   1..22
                         mol_type = other DNA
                         organism = synthetic construct
SEQUENCE: 94
agggctatga aactgatgga ga                                                 22
```

-continued

```
SEQ ID NO: 95          moltype = DNA   length = 20
FEATURE                Location/Qualifiers
misc_feature           1..20
                       note = Description of Artificial Sequence: Synthetic
                        oligonucleotide
source                 1..20
                       mol_type = other DNA
                       organism = synthetic construct
SEQUENCE: 95
agggctatga aactgatgga                                                  20

SEQ ID NO: 96          moltype = DNA   length = 22
FEATURE                Location/Qualifiers
misc_feature           1..22
                       note = Description of Artificial Sequence: Synthetic
                        oligonucleotide
source                 1..22
                       mol_type = other DNA
                       organism = synthetic construct
SEQUENCE: 96
ccagggctat gaaactgatg ga                                               22

SEQ ID NO: 97          moltype = DNA   length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 97
ttcttacccca tttaatta                                                   18

SEQ ID NO: 98          moltype = DNA   length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 98
tgcttcttac ccatttaa                                                    18

SEQ ID NO: 99          moltype = DNA   length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 99
taatgcttct tacccatt                                                    18

SEQ ID NO: 100         moltype = DNA   length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 100
agataatgct tcttaccc                                                    18

SEQ ID NO: 101         moltype = DNA   length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 101
cagataatgc ttcttacc                                                    18
```

```
SEQ ID NO: 102           moltype = DNA  length = 18
FEATURE                  Location/Qualifiers
misc_feature             1..18
                         note = Description of Artificial Sequence: Synthetic
                          oligonucleotide
source                   1..18
                         mol_type = other DNA
                         organism = synthetic construct
SEQUENCE: 102
cccttcagat aatgcttc                                                    18

SEQ ID NO: 103           moltype = DNA  length = 18
FEATURE                  Location/Qualifiers
misc_feature             1..18
                         note = Description of Artificial Sequence: Synthetic
                          oligonucleotide
source                   1..18
                         mol_type = other DNA
                         organism = synthetic construct
SEQUENCE: 103
ctactccctt cagataat                                                    18

SEQ ID NO: 104           moltype = DNA  length = 18
FEATURE                  Location/Qualifiers
misc_feature             1..18
                         note = Description of Artificial Sequence: Synthetic
                          oligonucleotide
source                   1..18
                         mol_type = other DNA
                         organism = synthetic construct
SEQUENCE: 104
agctcctact cccttcag                                                    18

SEQ ID NO: 105           moltype = DNA  length = 18
FEATURE                  Location/Qualifiers
misc_feature             1..18
                         note = Description of Artificial Sequence: Synthetic
                          oligonucleotide
source                   1..18
                         mol_type = other DNA
                         organism = synthetic construct
SEQUENCE: 105
ttcacagctc ctactccc                                                    18

SEQ ID NO: 106           moltype = DNA  length = 18
FEATURE                  Location/Qualifiers
misc_feature             1..18
                         note = Description of Artificial Sequence: Synthetic
                          oligonucleotide
source                   1..18
                         mol_type = other DNA
                         organism = synthetic construct
SEQUENCE: 106
taaaattcac agctccta                                                    18

SEQ ID NO: 107           moltype = DNA  length = 18
FEATURE                  Location/Qualifiers
misc_feature             1..18
                         note = Description of Artificial Sequence: Synthetic
                          oligonucleotide
source                   1..18
                         mol_type = other DNA
                         organism = synthetic construct
SEQUENCE: 107
aaatctaaaa ttcacagc                                                    18

SEQ ID NO: 108           moltype = DNA  length = 18
FEATURE                  Location/Qualifiers
misc_feature             1..18
                         note = Description of Artificial Sequence: Synthetic
                          oligonucleotide
source                   1..18
                         mol_type = other DNA
                         organism = synthetic construct
SEQUENCE: 108
gaataaaatc taaaattc                                                    18
```

```
SEQ ID NO: 109           moltype = DNA   length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 109
gatgggaata aaatctaa                                                         18

SEQ ID NO: 110           moltype = DNA   length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 110
gctgtgatgg gaataaaa                                                         18

SEQ ID NO: 111           moltype = DNA   length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 111
tagaggctgt gatgggaa                                                         18

SEQ ID NO: 112           moltype = DNA   length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 112
aaagatagag gctgtgat                                                         18

SEQ ID NO: 113           moltype = DNA   length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 113
aaaagaaaga tagaggct                                                         18

SEQ ID NO: 114           moltype = DNA   length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 114
gacctaaaag aaagatag                                                         18

SEQ ID NO: 115           moltype = DNA   length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
```

```
SEQUENCE: 115
ataaagacct aaaagaaa                                                  18

SEQ ID NO: 116          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 116
gagatataaa gacctaaa                                                  18

SEQ ID NO: 117          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 117
ggctgtgatg ggaataaa                                                  18

SEQ ID NO: 118          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 118
aggctgtgat gggaataa                                                  18

SEQ ID NO: 119          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 119
gaggctgtga tgggaata                                                  18

SEQ ID NO: 120          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 120
agaggctgtg atgggaat                                                  18

SEQ ID NO: 121          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 121
atagaggctg tgatggga                                                  18

SEQ ID NO: 122          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 122
gatagaggct gtgatggg                                                  18
```

```
SEQ ID NO: 123          moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 123
agatagaggc tgtgatgg                                                  18

SEQ ID NO: 124          moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 124
aagatagagg ctgtgatg                                                  18

SEQ ID NO: 125          moltype = DNA   length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 125
tagaggctgt gatgggaata aa                                             22

SEQ ID NO: 126          moltype = DNA   length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 126
atagaggctg tgatgggaat aa                                             22

SEQ ID NO: 127          moltype = DNA   length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 127
gatagaggct gtgatgggaa ta                                             22

SEQ ID NO: 128          moltype = DNA   length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 128
agatagaggc tgtgatggga at                                             22

SEQ ID NO: 129          moltype = DNA   length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 129
aagatagagg ctgtgatggg aa                                             22
```

```
SEQ ID NO: 130          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 130
gaggctgtga tgggaataaa                                                  20

SEQ ID NO: 131          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 131
agaggctgtg atgggaataa                                                  20

SEQ ID NO: 132          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 132
tagaggctgt gatgggaata                                                  20

SEQ ID NO: 133          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 133
atagaggctg tgatgggaat                                                  20

SEQ ID NO: 134          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 134
gatagaggct gtgatgggaa                                                  20

SEQ ID NO: 135          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 135
agatagaggc tgtgatggga                                                  20

SEQ ID NO: 136          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 136
aagatagagg ctgtgatggg                                                  20
```

```
SEQ ID NO: 137          moltype = DNA   length = 16
FEATURE                 Location/Qualifiers
misc_feature            1..16
                        note = Description of Artificial Sequence: Synthetic
                        oligonucleotide
source                  1..16
                        mol_type = other DNA
                        organism = synthetic construct
SEQUENCE: 137
ctgtgatggg aataaa                                                          16

SEQ ID NO: 138          moltype = DNA   length = 16
FEATURE                 Location/Qualifiers
misc_feature            1..16
                        note = Description of Artificial Sequence: Synthetic
                        oligonucleotide
source                  1..16
                        mol_type = other DNA
                        organism = synthetic construct
SEQUENCE: 138
gctgtgatgg gaataa                                                          16

SEQ ID NO: 139          moltype = DNA   length = 16
FEATURE                 Location/Qualifiers
misc_feature            1..16
                        note = Description of Artificial Sequence: Synthetic
                        oligonucleotide
source                  1..16
                        mol_type = other DNA
                        organism = synthetic construct
SEQUENCE: 139
ggctgtgatg ggaata                                                          16

SEQ ID NO: 140          moltype = DNA   length = 16
FEATURE                 Location/Qualifiers
misc_feature            1..16
                        note = Description of Artificial Sequence: Synthetic
                        oligonucleotide
source                  1..16
                        mol_type = other DNA
                        organism = synthetic construct
SEQUENCE: 140
aggctgtgat gggaat                                                          16

SEQ ID NO: 141          moltype = DNA   length = 16
FEATURE                 Location/Qualifiers
misc_feature            1..16
                        note = Description of Artificial Sequence: Synthetic
                        oligonucleotide
source                  1..16
                        mol_type = other DNA
                        organism = synthetic construct
SEQUENCE: 141
gaggctgtga tgggaa                                                          16

SEQ ID NO: 142          moltype = DNA   length = 16
FEATURE                 Location/Qualifiers
misc_feature            1..16
                        note = Description of Artificial Sequence: Synthetic
                        oligonucleotide
source                  1..16
                        mol_type = other DNA
                        organism = synthetic construct
SEQUENCE: 142
agaggctgtg atggga                                                          16

SEQ ID NO: 143          moltype = DNA   length = 16
FEATURE                 Location/Qualifiers
misc_feature            1..16
                        note = Description of Artificial Sequence: Synthetic
                        oligonucleotide
source                  1..16
                        mol_type = other DNA
                        organism = synthetic construct
```

-continued

```
SEQUENCE: 143
tagaggctgt gatggg                                                    16

SEQ ID NO: 144           moltype = DNA  length = 16
FEATURE                  Location/Qualifiers
misc_feature             1..16
                         note = Description of Artificial Sequence: Synthetic
                         oligonucleotide
source                   1..16
                         mol_type = other DNA
                         organism = synthetic construct
SEQUENCE: 144
atagaggctg tgatgg                                                    16

SEQ ID NO: 145           moltype = DNA  length = 16
FEATURE                  Location/Qualifiers
misc_feature             1..16
                         note = Description of Artificial Sequence: Synthetic
                         oligonucleotide
source                   1..16
                         mol_type = other DNA
                         organism = synthetic construct
SEQUENCE: 145
gatagaggct gtgatg                                                    16

SEQ ID NO: 146           moltype = DNA  length = 16
FEATURE                  Location/Qualifiers
misc_feature             1..16
                         note = Description of Artificial Sequence: Synthetic
                         oligonucleotide
source                   1..16
                         mol_type = other DNA
                         organism = synthetic construct
SEQUENCE: 146
agatagaggc tgtgat                                                    16

SEQ ID NO: 147           moltype = DNA  length = 16
FEATURE                  Location/Qualifiers
misc_feature             1..16
                         note = Description of Artificial Sequence: Synthetic
                         oligonucleotide
source                   1..16
                         mol_type = other DNA
                         organism = synthetic construct
SEQUENCE: 147
aagatagagg ctgtga                                                    16

SEQ ID NO: 148           moltype = DNA  length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 148
aggctgtgat gtgaataa                                                  18

SEQ ID NO: 149           moltype = DNA  length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 149
agaggctgtg atgtgaat                                                  18

SEQ ID NO: 150           moltype = DNA  length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 150
tagaggctgt gatgtgaa                                                  18
```

```
SEQ ID NO: 151           moltype = DNA  length = 18
FEATURE                  Location/Qualifiers
misc_feature             1..18
                         note = Description of Artificial Sequence: Synthetic
                           oligonucleotide
source                   1..18
                         mol_type = other DNA
                         organism = synthetic construct
SEQUENCE: 151
gatagaggct gtgattgg                                                    18

SEQ ID NO: 152           moltype = DNA  length = 16
FEATURE                  Location/Qualifiers
misc_feature             1..16
                         note = Description of Artificial Sequence: Synthetic
                           oligonucleotide
source                   1..16
                         mol_type = other DNA
                         organism = synthetic construct
SEQUENCE: 152
ggctgtgatg tgaata                                                      16

SEQ ID NO: 153           moltype = DNA  length = 16
FEATURE                  Location/Qualifiers
misc_feature             1..16
                         note = Description of Artificial Sequence: Synthetic
                           oligonucleotide
source                   1..16
                         mol_type = other DNA
                         organism = synthetic construct
SEQUENCE: 153
gaggctgtga tgtgaa                                                      16

SEQ ID NO: 154           moltype = DNA  length = 16
FEATURE                  Location/Qualifiers
misc_feature             1..16
                         note = Description of Artificial Sequence: Synthetic
                           oligonucleotide
source                   1..16
                         mol_type = other DNA
                         organism = synthetic construct
SEQUENCE: 154
tagaggctgt gattgg                                                      16

SEQ ID NO: 155           moltype = DNA  length = 16
FEATURE                  Location/Qualifiers
misc_feature             1..16
                         note = Description of Artificial Sequence: Synthetic
                           oligonucleotide
source                   1..16
                         mol_type = other DNA
                         organism = synthetic construct
SEQUENCE: 155
atgaaactga tggaga                                                      16

SEQ ID NO: 156           moltype = DNA  length = 16
FEATURE                  Location/Qualifiers
misc_feature             1..16
                         note = Description of Artificial Sequence: Synthetic
                           oligonucleotide
source                   1..16
                         mol_type = other DNA
                         organism = synthetic construct
SEQUENCE: 156
ctatgaaact gatgga                                                      16

SEQ ID NO: 157           moltype = DNA  length = 16
FEATURE                  Location/Qualifiers
misc_feature             1..16
                         note = Description of Artificial Sequence: Synthetic
                           oligonucleotide
source                   1..16
                         mol_type = other DNA
                         organism = synthetic construct
SEQUENCE: 157
ggctatgaaa ctgatg                                                      16
```

```
SEQ ID NO: 158            moltype = DNA  length = 14
FEATURE                   Location/Qualifiers
misc_feature              1..14
                          note = Description of Artificial Sequence: Synthetic
                           oligonucleotide
source                    1..14
                          mol_type = other DNA
                          organism = synthetic construct
SEQUENCE: 158
gaaactgatg gaga                                                            14

SEQ ID NO: 159            moltype = DNA  length = 14
FEATURE                   Location/Qualifiers
misc_feature              1..14
                          note = Description of Artificial Sequence: Synthetic
                           oligonucleotide
source                    1..14
                          mol_type = other DNA
                          organism = synthetic construct
SEQUENCE: 159
atgaaactga tgga                                                            14

SEQ ID NO: 160            moltype = DNA  length = 14
FEATURE                   Location/Qualifiers
misc_feature              1..14
                          note = Description of Artificial Sequence: Synthetic
                           oligonucleotide
source                    1..14
                          mol_type = other DNA
                          organism = synthetic construct
SEQUENCE: 160
ctatgaaact gatg                                                            14

SEQ ID NO: 161            moltype = DNA  length = 14
FEATURE                   Location/Qualifiers
misc_feature              1..14
                          note = Description of Artificial Sequence: Synthetic
                           oligonucleotide
source                    1..14
                          mol_type = other DNA
                          organism = synthetic construct
SEQUENCE: 161
ggctatgaaa ctga                                                            14

SEQ ID NO: 162            moltype = DNA  length = 24
FEATURE                   Location/Qualifiers
misc_feature              1..24
                          note = Description of Artificial Sequence: Synthetic
                           oligonucleotide
source                    1..24
                          mol_type = other DNA
                          organism = synthetic construct
SEQUENCE: 162
tagaggctgt gatgggaata aaat                                                 24

SEQ ID NO: 163            moltype = DNA  length = 24
FEATURE                   Location/Qualifiers
misc_feature              1..24
                          note = Description of Artificial Sequence: Synthetic
                           oligonucleotide
source                    1..24
                          mol_type = other DNA
                          organism = synthetic construct
SEQUENCE: 163
atagaggctg tgatgggaat aaaa                                                 24

SEQ ID NO: 164            moltype = DNA  length = 25
FEATURE                   Location/Qualifiers
misc_feature              1..25
                          note = Description of Artificial Sequence: Synthetic
                           oligonucleotide
source                    1..25
                          mol_type = other DNA
                          organism = synthetic construct
SEQUENCE: 164
atagaggctg tgatgggaat aaaat                                                25
```

```
SEQ ID NO: 165         moltype = DNA   length = 25
FEATURE                Location/Qualifiers
misc_feature           1..25
                       note = Description of Artificial Sequence: Synthetic
                       oligonucleotide
source                 1..25
                       mol_type = other DNA
                       organism = synthetic construct
SEQUENCE: 165
aaagatagag gctgtgatgg gaata                                              25

SEQ ID NO: 166         moltype = DNA   length = 21
FEATURE                Location/Qualifiers
misc_feature           1..21
                       note = Description of Artificial Sequence: Synthetic
                       oligonucleotide
source                 1..21
                       mol_type = other DNA
                       organism = synthetic construct
SEQUENCE: 166
ggctatgaaa ctgatggaga a                                                  21

SEQ ID NO: 167         moltype = DNA   length = 24
FEATURE                Location/Qualifiers
misc_feature           1..24
                       note = Description of Artificial Sequence: Synthetic
                       oligonucleotide
source                 1..24
                       mol_type = other DNA
                       organism = synthetic construct
SEQUENCE: 167
ggctatgaaa ctgatggaga aaga                                               24

SEQ ID NO: 168         moltype = DNA   length = 25
FEATURE                Location/Qualifiers
misc_feature           1..25
                       note = Description of Artificial Sequence: Synthetic
                       oligonuceotide
source                 1..25
                       mol_type = other DNA
                       organism = synthetic construct
SEQUENCE: 168
agggctatga aactgatgga gaaag                                              25

SEQ ID NO: 169         moltype = DNA   length = 18
FEATURE                Location/Qualifiers
misc_feature           1..18
                       note = Description of Artificial Sequence: Synthetic
                       oligonucleotide
source                 1..18
                       mol_type = other DNA
                       organism = synthetic construct
SEQUENCE: 169
catttaatta aattatat                                                      18

SEQ ID NO: 170         moltype = DNA   length = 18
FEATURE                Location/Qualifiers
misc_feature           1..18
                       note = Description of Artificial Sequence: Synthetic
                       oligonucleotide
source                 1..18
                       mol_type = other DNA
                       organism = synthetic construct
SEQUENCE: 170
ccatttaatt aaattata                                                      18

SEQ ID NO: 171         moltype = DNA   length = 18
FEATURE                Location/Qualifiers
misc_feature           1..18
                       note = Description of Artificial Sequence: Synthetic
                       oligonucleotide
source                 1..18
                       mol_type = other DNA
                       organism = synthetic construct
SEQUENCE: 171
cccatttaat taaattat                                                      18
```

```
SEQ ID NO: 172          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 172
acccatttaa ttaaatta                                                        18

SEQ ID NO: 173          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 173
tacccattta attaaatt                                                        18

SEQ ID NO: 174          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 174
ttacccattt aattaaat                                                        18

SEQ ID NO: 175          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 175
cttacccatt taattaaa                                                        18

SEQ ID NO: 176          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 176
tcttacccat ttaattaa                                                        18

SEQ ID NO: 177          moltype = DNA  length = 17
FEATURE                 Location/Qualifiers
misc_feature            1..17
                        note = Description of Artificial Sequence: Synthetic
                         oligonucleotide
source                  1..17
                        mol_type = other DNA
                        organism = synthetic construct
SEQUENCE: 177
gatagaggct gtgatgg                                                         17

SEQ ID NO: 178          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 178
ggctgtgaaa ctgatgga                                                        18
```

```
SEQ ID NO: 179           moltype = DNA  length = 20
FEATURE                  Location/Qualifiers
misc_feature             1..20
                         note = Description of Artificial Sequence: Synthetic
                          oligonucleotide
source                   1..20
                         mol_type = other DNA
                         organism = synthetic construct
SEQUENCE: 179
ggctgtgaaa ctgatggaga                                                 20

SEQ ID NO: 180           moltype = DNA  length = 16
FEATURE                  Location/Qualifiers
misc_feature             1..16
                         note = Description of Artificial Sequence: Synthetic
                          oligonucleotide
source                   1..16
                         mol_type = other DNA
                         organism = synthetic construct
SEQUENCE: 180
gctatgaaac tgatgg                                                     16

SEQ ID NO: 181           moltype = DNA  length = 14
FEATURE                  Location/Qualifiers
misc_feature             1..14
                         note = Description of Artificial Sequence: Synthetic
                          oligonucleotide
source                   1..14
                         mol_type = other DNA
                         organism = synthetic construct
SEQUENCE: 181
tatgaaactg atgg                                                       14

SEQ ID NO: 182           moltype = DNA  length = 14
FEATURE                  Location/Qualifiers
misc_feature             1..14
                         note = Description of Artificial Sequence: Synthetic
                          oligonucleotide
source                   1..14
                         mol_type = other DNA
                         organism = synthetic construct
SEQUENCE: 182
gctatgaaac tgat                                                       14

SEQ ID NO: 183           moltype = DNA  length = 20
FEATURE                  Location/Qualifiers
misc_feature             1..20
                         note = Description of Artificial Sequence: Synthetic
                          oligonucleotide
source                   1..20
                         mol_type = other DNA
                         organism = synthetic construct
SEQUENCE: 183
gctgtgaaac tgatggagaa                                                 20

SEQ ID NO: 184           moltype = DNA  length = 20
FEATURE                  Location/Qualifiers
misc_feature             1..20
                         note = Description of Artificial Sequence: Synthetic
                          oligonucleotide
source                   1..20
                         mol_type = other DNA
                         organism = synthetic construct
SEQUENCE: 184
gggctgtgaa actgatggag                                                 20

SEQ ID NO: 185           moltype = DNA  length = 18
FEATURE                  Location/Qualifiers
misc_feature             1..18
                         note = Description of Artificial Sequence: Synthetic
                          oligonucleotide
source                   1..18
                         mol_type = other DNA
                         organism = synthetic construct
SEQUENCE: 185
tgtgaaactg atggagaa                                                   18
```

```
SEQ ID NO: 186          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 186
ctgtgaaact gatggaga                                                       18

SEQ ID NO: 187          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 187
gctgtgaaac tgatggag                                                       18

SEQ ID NO: 188          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 188
gggctgtgaa actgatgg                                                       18

SEQ ID NO: 189          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 189
tgaaactgat ggagaa                                                         16

SEQ ID NO: 190          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 190
gtgaaactga tggaga                                                         16

SEQ ID NO: 191          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 191
tgtgaaactg atggag                                                         16

SEQ ID NO: 192          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 192
ctgtgaaact gatgga                                                         16
```

```
SEQ ID NO: 193            moltype = DNA  length = 16
FEATURE                   Location/Qualifiers
misc_feature              1..16
                          note = Description of Artificial Sequence: Synthetic
                            oligonucleotide
source                    1..16
                          mol_type = other DNA
                          organism = synthetic construct
SEQUENCE: 193
gctgtgaaac tgatgg                                                            16

SEQ ID NO: 194            moltype = DNA  length = 16
FEATURE                   Location/Qualifiers
misc_feature              1..16
                          note = Description of Artificial Sequence: Synthetic
                            oligonucleotide
source                    1..16
                          mol_type = other DNA
                          organism = synthetic construct
SEQUENCE: 194
ggctgtgaaa ctgatg                                                            16

SEQ ID NO: 195            moltype = DNA  length = 16
FEATURE                   Location/Qualifiers
misc_feature              1..16
                          note = Description of Artificial Sequence: Synthetic
                            oligonucleotide
source                    1..16
                          mol_type = other DNA
                          organism = synthetic construct
SEQUENCE: 195
gggctgtgaa actgat                                                            16

SEQ ID NO: 196            moltype = DNA  length = 15
FEATURE                   Location/Qualifiers
misc_feature              1..15
                          note = Description of Artificial Sequence: Synthetic
                            oligonucleotide
source                    1..15
                          mol_type = other DNA
                          organism = synthetic construct
SEQUENCE: 196
cggtccagga atgac                                                             15

SEQ ID NO: 197            moltype = DNA  length = 15
FEATURE                   Location/Qualifiers
misc_feature              1..15
                          note = Description of Artificial Sequence: Synthetic
                            oligonucleotide
source                    1..15
                          mol_type = other DNA
                          organism = synthetic construct
SEQUENCE: 197
ccggtccagg aatga                                                             15

SEQ ID NO: 198            moltype = DNA  length = 15
FEATURE                   Location/Qualifiers
misc_feature              1..15
                          note = Description of Artificial Sequence: Synthetic
                            oligonucleotide
source                    1..15
                          mol_type = other DNA
                          organism = synthetic construct
SEQUENCE: 198
cccggtccag gaatg                                                             15

SEQ ID NO: 199            moltype = DNA  length = 15
FEATURE                   Location/Qualifiers
misc_feature              1..15
                          note = Description of Artificial Sequence: Synthetic
                            oligonucleotide
source                    1..15
                          mol_type = other DNA
                          organism = synthetic construct
SEQUENCE: 199
tcccggtcca ggaat                                                             15
```

```
SEQ ID NO: 200           moltype = DNA  length = 15
FEATURE                  Location/Qualifiers
misc_feature             1..15
                         note = Description of Artificial Sequence: Synthetic
                          oligonucleotide
source                   1..15
                         mol_type = other DNA
                         organism = synthetic construct
SEQUENCE: 200
ctcccggtcc aggaa                                                          15

SEQ ID NO: 201           moltype = DNA  length = 15
FEATURE                  Location/Qualifiers
misc_feature             1..15
                         note = Description of Artificial Sequence: Synthetic
                          oligonucleotide
source                   1..15
                         mol_type = other DNA
                         organism = synthetic construct
SEQUENCE: 201
gctcccggtc cagga                                                          15

SEQ ID NO: 202           moltype = DNA  length = 15
FEATURE                  Location/Qualifiers
misc_feature             1..15
                         note = Description of Artificial Sequence: Synthetic
                          oligonucleotide
source                   1..15
                         mol_type = other DNA
                         organism = synthetic construct
SEQUENCE: 202
ggctcccggt ccagg                                                          15

SEQ ID NO: 203           moltype = DNA  length = 15
FEATURE                  Location/Qualifiers
misc_feature             1..15
                         note = Description of Artificial Sequence: Synthetic
                          oligonucleotide
source                   1..15
                         mol_type = other DNA
                         organism = synthetic construct
SEQUENCE: 203
cgggagcccc cgtgt                                                          15

SEQ ID NO: 204           moltype = DNA  length = 15
FEATURE                  Location/Qualifiers
misc_feature             1..15
                         note = Description of Artificial Sequence: Synthetic
                          oligonucleotide
source                   1..15
                         mol_type = other DNA
                         organism = synthetic construct
SEQUENCE: 204
gcgggagccc ccgtg                                                          15

SEQ ID NO: 205           moltype = DNA  length = 15
FEATURE                  Location/Qualifiers
misc_feature             1..15
                         note = Description of Artificial Sequence: Synthetic
                          oligonucleotide
source                   1..15
                         mol_type = other DNA
                         organism = synthetic construct
SEQUENCE: 205
cgcgggagcc cccgt                                                          15

SEQ ID NO: 206           moltype = DNA  length = 15
FEATURE                  Location/Qualifiers
misc_feature             1..15
                         note = Description of Artificial Sequence: Synthetic
                          oligonucleotide
source                   1..15
                         mol_type = other DNA
                         organism = synthetic construct
SEQUENCE: 206
acgcgggagc ccccg                                                          15
```

```
SEQ ID NO: 207           moltype = DNA  length = 15
FEATURE                  Location/Qualifiers
misc_feature             1..15
                         note = Description of Artificial Sequence: Synthetic
                         oligonucleotide
source                   1..15
                         mol_type = other DNA
                         organism = synthetic construct
SEQUENCE: 207
cacgcgggag ccccc                                                          15

SEQ ID NO: 208           moltype = DNA  length = 15
FEATURE                  Location/Qualifiers
misc_feature             1..15
                         note = Description of Artificial Sequence: Synthetic
                         oligonucleotide
source                   1..15
                         mol_type = other DNA
                         organism = synthetic construct
SEQUENCE: 208
ccacgcggga gcccc                                                          15

SEQ ID NO: 209           moltype = DNA  length = 15
FEATURE                  Location/Qualifiers
misc_feature             1..15
                         note = Description of Artificial Sequence: Synthetic
                         oligonucleotide
source                   1..15
                         mol_type = other DNA
                         organism = synthetic construct
SEQUENCE: 209
gccacgcggg agccc                                                          15

SEQ ID NO: 210           moltype = DNA  length = 15
FEATURE                  Location/Qualifiers
misc_feature             1..15
                         note = Description of Artificial Sequence: Synthetic
                         oligonucleotide
source                   1..15
                         mol_type = other DNA
                         organism = synthetic construct
SEQUENCE: 210
ggccacgcgg gagcc                                                          15

SEQ ID NO: 211           moltype = DNA  length = 15
FEATURE                  Location/Qualifiers
misc_feature             1..15
                         note = Description of Artificial Sequence: Synthetic
                         oligonucleotide
source                   1..15
                         mol_type = other DNA
                         organism = synthetic construct
SEQUENCE: 211
cggccacgcg ggagc                                                          15

SEQ ID NO: 212           moltype = DNA  length = 15
FEATURE                  Location/Qualifiers
misc_feature             1..15
                         note = Description of Artificial Sequence: Synthetic
                         oligonucleotide
source                   1..15
                         mol_type = other DNA
                         organism = synthetic construct
SEQUENCE: 212
acggccacgc gggag                                                          15

SEQ ID NO: 213           moltype = DNA  length = 15
FEATURE                  Location/Qualifiers
misc_feature             1..15
                         note = Description of Artificial Sequence: Synthetic
                         oligonucleotide
source                   1..15
                         mol_type = other DNA
                         organism = synthetic construct
SEQUENCE: 213
gacggccacg cggga                                                          15
```

```
SEQ ID NO: 214            moltype = DNA  length = 15
FEATURE                   Location/Qualifiers
misc_feature              1..15
                          note = Description of Artificial Sequence: Synthetic
                           oligonucleotide
source                    1..15
                          mol_type = other DNA
                          organism = synthetic construct
SEQUENCE: 214
agacggccac gcggg                                                          15

SEQ ID NO: 215            moltype = DNA  length = 18
FEATURE                   Location/Qualifiers
misc_feature              1..18
                          note = Description of Artificial Sequence: Synthetic
                           oligonucleotide
source                    1..18
                          mol_type = other DNA
                          organism = synthetic construct
SEQUENCE: 215
gctagggagg gatggtta                                                       18

SEQ ID NO: 216            moltype = DNA  length = 18
FEATURE                   Location/Qualifiers
misc_feature              1..18
                          note = Description of Artificial Sequence: Synthetic
                           oligonucleotide
source                    1..18
                          mol_type = other DNA
                          organism = synthetic construct
SEQUENCE: 216
tgtaagctag ggagggat                                                       18

SEQ ID NO: 217            moltype = DNA  length = 18
FEATURE                   Location/Qualifiers
misc_feature              1..18
                          note = Description of Artificial Sequence: Synthetic
                           oligonucleotide
source                    1..18
                          mol_type = other DNA
                          organism = synthetic construct
SEQUENCE: 217
acagatgtaa gctaggga                                                       18

SEQ ID NO: 218            moltype = DNA  length = 18
FEATURE                   Location/Qualifiers
misc_feature              1..18
                          note = Description of Artificial Sequence: Synthetic
                           oligonucleotide
source                    1..18
                          mol_type = other DNA
                          organism = synthetic construct
SEQUENCE: 218
aaggaacaga tgtaagct                                                       18

SEQ ID NO: 219            moltype = DNA  length = 18
FEATURE                   Location/Qualifiers
misc_feature              1..18
                          note = Description of Artificial Sequence: Synthetic
                           oligonucleotide
source                    1..18
                          mol_type = other DNA
                          organism = synthetic construct
SEQUENCE: 219
caacaaagga acagatgt                                                       18

SEQ ID NO: 220            moltype = DNA  length = 18
FEATURE                   Location/Qualifiers
misc_feature              1..18
                          note = Description of Artificial Sequence: Synthetic
                           oligonucleotide
source                    1..18
                          mol_type = other DNA
                          organism = synthetic construct
SEQUENCE: 220
gggtgcaaca aaggaaca                                                       18
```

| | | |
|---|---|---|
| SEQ ID NO: 221<br>FEATURE<br>misc_feature | moltype = DNA   length = 18<br>Location/Qualifiers<br>1..18<br>note = Description of Artificial Sequence: Synthetic<br>oligonucleotide | |
| source | 1..18<br>mol_type = other DNA<br>organism = synthetic construct | |
| SEQUENCE: 221<br>accaagggtg caacaaag | | 18 |
| SEQ ID NO: 222<br>FEATURE<br>misc_feature | moltype = DNA   length = 18<br>Location/Qualifiers<br>1..18<br>note = Description of Artificial Sequence: Synthetic<br>oligonucleotide | |
| source | 1..18<br>mol_type = other DNA<br>organism = synthetic construct | |
| SEQUENCE: 222<br>gttaaaccaa gggtgcaa | | 18 |
| SEQ ID NO: 223<br>FEATURE<br>misc_feature | moltype = DNA   length = 18<br>Location/Qualifiers<br>1..18<br>note = Description of Artificial Sequence: Synthetic<br>oligonucleotide | |
| source | 1..18<br>mol_type = other DNA<br>organism = synthetic construct | |
| SEQUENCE: 223<br>ataatgttaa accaaggg | | 18 |
| SEQ ID NO: 224<br>FEATURE<br>misc_feature | moltype = DNA   length = 18<br>Location/Qualifiers<br>1..18<br>note = Description of Artificial Sequence: Synthetic<br>oligonucleotide | |
| source | 1..18<br>mol_type = other DNA<br>organism = synthetic construct | |
| SEQUENCE: 224<br>ggagaataat gttaaacc | | 18 |
| SEQ ID NO: 225<br>FEATURE<br>misc_feature | moltype = DNA   length = 18<br>Location/Qualifiers<br>1..18<br>note = Description of Artificial Sequence: Synthetic<br>oligonucleotide | |
| source | 1..18<br>mol_type = other DNA<br>organism = synthetic construct | |
| SEQUENCE: 225<br>ggggaggaga ataatgtt | | 18 |
| SEQ ID NO: 226<br>FEATURE<br>misc_feature | moltype = DNA   length = 18<br>Location/Qualifiers<br>1..18<br>note = Description of Artificial Sequence: Synthetic<br>oligonucleotide | |
| source | 1..18<br>mol_type = other DNA<br>organism = synthetic construct | |
| SEQUENCE: 226<br>aaattgggga ggagaata | | 18 |
| SEQ ID NO: 227<br>FEATURE<br>misc_feature | moltype = DNA   length = 18<br>Location/Qualifiers<br>1..18<br>note = Description of Artificial Sequence: Synthetic<br>oligonucleotide | |
| source | 1..18<br>mol_type = other DNA<br>organism = synthetic construct | |

```
SEQUENCE: 227
agaggaaatt ggggagga                                                    18

SEQ ID NO: 228          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 228
ggagaagagg aaattggg                                                    18

SEQ ID NO: 229          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 229
aatgaggaga agaggaaa                                                    18

SEQ ID NO: 230          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 230
ttcacaatga ggagaaga                                                    18

SEQ ID NO: 231          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 231
acgagttcac aatgagga                                                    18

SEQ ID NO: 232          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 232
ctgccacgag ttcacaat                                                    18

SEQ ID NO: 233          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 233
agaccctgcc acgagttc                                                    18

SEQ ID NO: 234          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 234
caagcagacc ctgccacg                                                    18
```

```
SEQ ID NO: 235          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 235
ctcaccaagc agaccctg                                                   18

SEQ ID NO: 236          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 236
gagctcacca agcagacc                                                   18

SEQ ID NO: 237          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 237
agaatgagct caccaagc                                                   18

SEQ ID NO: 238          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 238
gtaagagaat gagctcac                                                   18

SEQ ID NO: 239          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 239
ttgttgtaag agaatgag                                                   18

SEQ ID NO: 240          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 240
atttgttgtt gtaagaga                                                   18

SEQ ID NO: 241          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 241
cttgaatttg ttgttgta                                                   18
```

```
SEQ ID NO: 242              moltype = DNA  length = 18
FEATURE                     Location/Qualifiers
misc_feature                1..18
                            note = Description of Artificial Sequence: Synthetic
                              oligonucleotide
source                      1..18
                            mol_type = other DNA
                            organism = synthetic construct
SEQUENCE: 242
atgctcttga atttgttg                                                         18

SEQ ID NO: 243              moltype = DNA  length = 18
FEATURE                     Location/Qualifiers
misc_feature                1..18
                            note = Description of Artificial Sequence: Synthetic
                              oligonucleotide
source                      1..18
                            mol_type = other DNA
                            organism = synthetic construct
SEQUENCE: 243
tcttcatgct cttgaatt                                                         18

SEQ ID NO: 244              moltype = DNA  length = 18
FEATURE                     Location/Qualifiers
misc_feature                1..18
                            note = Description of Artificial Sequence: Synthetic
                              oligonucleotide
source                      1..18
                            mol_type = other DNA
                            organism = synthetic construct
SEQUENCE: 244
cttcctcttc atgctctt                                                         18

SEQ ID NO: 245              moltype = DNA  length = 18
FEATURE                     Location/Qualifiers
misc_feature                1..18
                            note = Description of Artificial Sequence: Synthetic
                              oligonucleotide
source                      1..18
                            mol_type = other DNA
                            organism = synthetic construct
SEQUENCE: 245
gcgcgcttcc tcttcatg                                                         18

SEQ ID NO: 246              moltype = DNA  length = 18
FEATURE                     Location/Qualifiers
misc_feature                1..18
                            note = Description of Artificial Sequence: Synthetic
                              oligonucleotide
source                      1..18
                            mol_type = other DNA
                            organism = synthetic construct
SEQUENCE: 246
gctctgcgcg cttcctct                                                         18

SEQ ID NO: 247              moltype = DNA  length = 18
FEATURE                     Location/Qualifiers
misc_feature                1..18
                            note = Description of Artificial Sequence: Synthetic
                              oligonucleotide
source                      1..18
                            mol_type = other DNA
                            organism = synthetic construct
SEQUENCE: 247
ggccagcggc tctgcgcg                                                         18

SEQ ID NO: 248              moltype = DNA  length = 18
FEATURE                     Location/Qualifiers
misc_feature                1..18
                            note = Description of Artificial Sequence: Synthetic
                              oligonucleotide
source                      1..18
                            mol_type = other DNA
                            organism = synthetic construct
```

```
SEQUENCE: 248
atattggcca gcggctct                                                        18

SEQ ID NO: 249           moltype = DNA  length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 249
gtgctatatt ggccagcg                                                        18

SEQ ID NO: 250           moltype = DNA  length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 250
agctcgtgct atattggc                                                        18

SEQ ID NO: 251           moltype = DNA  length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 251
ggcatagctc gtgctata                                                        18

SEQ ID NO: 252           moltype = DNA  length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 252
tgttgggcat agctcgtg                                                        18

SEQ ID NO: 253           moltype = DNA  length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 253
gcttctgttg ggcatagc                                                        18

SEQ ID NO: 254           moltype = DNA  length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 254
cttgcgcttc tgttgggc                                                        18

SEQ ID NO: 255           moltype = DNA  length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 255
caccttgcgc ttctgttg                                                        18
```

```
SEQ ID NO: 256           moltype = DNA  length = 18
FEATURE                  Location/Qualifiers
misc_feature             1..18
                         note = Description of Artificial Sequence: Synthetic
                          oligonucleotide
source                   1..18
                         mol_type = other DNA
                         organism = synthetic construct
SEQUENCE: 256
tccatcacct tgcgcttc                                                    18

SEQ ID NO: 257           moltype = DNA  length = 18
FEATURE                  Location/Qualifiers
misc_feature             1..18
                         note = Description of Artificial Sequence: Synthetic
                          oligonucleotide
source                   1..18
                         mol_type = other DNA
                         organism = synthetic construct
SEQUENCE: 257
aaccatccat caccttgc                                                    18

SEQ ID NO: 258           moltype = DNA  length = 18
FEATURE                  Location/Qualifiers
misc_feature             1..18
                         note = Description of Artificial Sequence: Synthetic
                          oligonucleotide
source                   1..18
                         mol_type = other DNA
                         organism = synthetic construct
SEQUENCE: 258
ccttaaacca tccatcac                                                    18

SEQ ID NO: 259           moltype = DNA  length = 18
FEATURE                  Location/Qualifiers
misc_feature             1..18
                         note = Description of Artificial Sequence: Synthetic
                          oligonucleotide
source                   1..18
                         mol_type = other DNA
                         organism = synthetic construct
SEQUENCE: 259
agcccccta aaccatcc                                                     18

SEQ ID NO: 260           moltype = DNA  length = 18
FEATURE                  Location/Qualifiers
misc_feature             1..18
                         note = Description of Artificial Sequence: Synthetic
                          oligonucleotide
source                   1..18
                         mol_type = other DNA
                         organism = synthetic construct
SEQUENCE: 260
tcggtagccc ccttaaac                                                    18

SEQ ID NO: 261           moltype = DNA  length = 18
FEATURE                  Location/Qualifiers
misc_feature             1..18
                         note = Description of Artificial Sequence: Synthetic
                          oligonucleotide
source                   1..18
                         mol_type = other DNA
                         organism = synthetic construct
SEQUENCE: 261
atgtatcggt agcccct                                                     18

SEQ ID NO: 262           moltype = DNA  length = 18
FEATURE                  Location/Qualifiers
misc_feature             1..18
                         note = Description of Artificial Sequence: Synthetic
                          oligonucleotide
source                   1..18
                         mol_type = other DNA
                         organism = synthetic construct
SEQUENCE: 262
tgtgaatgta tcggtagc                                                    18
```

```
SEQ ID NO: 263          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 263
attagtgtga atgtatcg                                                       18

SEQ ID NO: 264          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 264
ggctgattag tgtgaatg                                                       18

SEQ ID NO: 265          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 265
gaaatggctg attagtgt                                                       18

SEQ ID NO: 266          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 266
tggcagaaat ggctgatt                                                       18

SEQ ID NO: 267          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 267
gatcttggca gaaatggc                                                       18

SEQ ID NO: 268          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 268
gacatgatct tggcagaa                                                       18

SEQ ID NO: 269          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 269
gaggtgacat gatcttgg                                                       18
```

```
SEQ ID NO: 270           moltype = DNA  length = 18
FEATURE                  Location/Qualifiers
misc_feature             1..18
                         note = Description of Artificial Sequence: Synthetic
                          oligonucleotide
source                   1..18
                         mol_type = other DNA
                         organism = synthetic construct
SEQUENCE: 270
agattgaggt gacatgat                                                    18

SEQ ID NO: 271           moltype = DNA  length = 18
FEATURE                  Location/Qualifiers
misc_feature             1..18
                         note = Description of Artificial Sequence: Synthetic
                          oligonucleotide
source                   1..18
                         mol_type = other DNA
                         organism = synthetic construct
SEQUENCE: 271
tgaacagatt gaggtgac                                                    18

SEQ ID NO: 272           moltype = DNA  length = 18
FEATURE                  Location/Qualifiers
misc_feature             1..18
                         note = Description of Artificial Sequence: Synthetic
                          oligonucleotide
source                   1..18
                         mol_type = other DNA
                         organism = synthetic construct
SEQUENCE: 272
gtccatgaac agattgag                                                    18

SEQ ID NO: 273           moltype = DNA  length = 18
FEATURE                  Location/Qualifiers
misc_feature             1..18
                         note = Description of Artificial Sequence: Synthetic
                          oligonucleotide
source                   1..18
                         mol_type = other DNA
                         organism = synthetic construct
SEQUENCE: 273
ttggagtcca tgaacaga                                                    18

SEQ ID NO: 274           moltype = DNA  length = 18
FEATURE                  Location/Qualifiers
misc_feature             1..18
                         note = Description of Artificial Sequence: Synthetic
                          oligonucleotide
source                   1..18
                         mol_type = other DNA
                         organism = synthetic construct
SEQUENCE: 274
tgtatttgga gtccatga                                                    18

SEQ ID NO: 275           moltype = DNA  length = 18
FEATURE                  Location/Qualifiers
misc_feature             1..18
                         note = Description of Artificial Sequence: Synthetic
                          oligonucleotide
source                   1..18
                         mol_type = other DNA
                         organism = synthetic construct
SEQUENCE: 275
tttcttgtat ttggagtc                                                    18

SEQ ID NO: 276           moltype = DNA  length = 7155
FEATURE                  Location/Qualifiers
source                   1..7155
                         mol_type = other DNA
                         organism = Homo sapiens
SEQUENCE: 276
gtaagtgtaa aagagaattg ttcatgtagg tagtcttgaa agattttta aagtttttac        60
ttctttggaa gattttaaaa tgataacatc tgagaagcaa atacaaaaac atccaagtag      120
agatatcgtt actaatctta gtgcaaagta caaggtatta cgtggcagtt ctggaaatat      180
aattgagaag cccatttctt tcacatatgt ccagtgaagc attagtttcg agggttgtcc      240
ccaagaaaga gttgtgttgt taagtgtgtg gggggagaaa ggctcgttta gacaaggcaa      300
gcggacttct tttctttccc taggacctct catactgtaa tatactcatg cgcattgtga      360
```

```
atttccaagg agtcaaagca tacagtgttt tcccaaatta tttatcaaca gaaccctttt   420
gctcatggaa cgtcgtatag ggactagatt tcactttggg gaaactagaa agggaatagg   480
aattgggtta ttaggaaata aatcaattcc ctgatattga tagttaacaa agttatgtat   540
ggggttattt atggtatgtt attttcaaca catattcatt aacaaaatcc atatgaaagt   600
tataggagaa ttgctgaggt agaataacat actttgtttg tatttataat actcatatat   660
ttacctgacg ttttctgagt cttcactttt ttcattcttt tggaattggt aaaataactg   720
attccttgaa agttttttc taaataatac ctagataata gatttataga aaaaatattg   780
tatgaatgtt ttaacattca tgtaatatgg aacatgtaat ttttatactg gaggttatta   840
tagtttttaat acatcaaaga aataatgttt attttggaag cagaaagaag aaataaattc   900
tatgaatagg ttttcatctc tttccttgtt cttcaacttt gaactttta tattccaaat   960
tttaattata tttcaaaaga ttttttttct tgcctttta attttatctt ttggagaaaa  1020
atgtatgtca aaatgtatgt acgtgtattt gtctttgat ttgatctttt ttgaccctct  1080
tttgcattga cattatttta accaaaggac actcttgatt gttcatgcta ctgggggaaa  1140
aaaaaataag tagaaaattag cctaatagtt gtggcttatt ttgagtgaag gcctagccc  1200
ttaaggcaat taaatttact gtggagagaa gagctaatct aatggggaga aggagccttc  1260
gttacaggtg tggtagtgtg gttctttgag tgacaagatt tctgtttgcc agattggtta  1320
ggagaagtct gtgtgtctgc tttctctctt atggcctagg atcactgtgg tgaatgaaaa  1380
acctgtctca gggcctgact cagataaatc ccttaaaacc cggctaaggt catagatgaa  1440
taatcagtaa ttgaacagaa gctctgcaat agaaaagaag ccagataatt attttttggaa  1500
atttaattat atttacagat tttatttat acagtagaca tggaattaaa tttattacat  1560
tatgttctaa tttactcttt gcttgttttg atttgcttgt ttgacaatac atgtccttgt  1620
aaactatttc cttttaactt ttctcaatt tatggtgctt attttcccca ttaaagactt  1680
accaattttt tttttaacta tttgttacac atactgaatc tagagttgta attaagctac  1740
tttcattact ggttaagtca aattatagca aatgctacta taaaaattta ctatccaaaa  1800
atgtgtctca agccccaact gatggtttca aattctgtta ttaataatat gcagcattgt  1860
gtttgcaaag cttggctgtt acttgtgatg cttgagaatg atgatgcact cagctaaact  1920
gagtgatttt gagacttgtg tacaaattga tggttgaatg taagcatgca aagagagacc  1980
ttagcttagc agtacccttt ttgaaatcac tctgacatca agtttgaaaa tgtgggcaat  2040
aatcagaggt ggtaaggtgg ccaggcttta gctgaatact tttttaactg gttcagtctg  2100
agggctgaaa gccccagatt taaacagtat ttagaatttg aagcagtcaa gtattagttt  2160
aatggttgtc aggtttgtaa caaagtttct ggctagactt ctactagaaa tgtaaaagtg  2220
catgtgaatc agctttttaa aaagtaata ataattgaaa aacatttcta caactagaac  2280
taaagaaaag atttgtcctt tctaatagga aaacacatct ggagaagtgc tggcaactag  2340
cagaacagtt aggaccattc agaatcaact gaagtgaaag tgacggggag ctgaggggaa  2400
cacagatagt ttgacttcag tcagacagaa taaacatgat gaaccgataa cctgtgattc  2460
ccagcctggg gttactactg gagttttagg tgtcctggaa agttataata ccggtcttca  2520
aaaagtctac agaaagcata gatttccaca taatgctgca caggctaacg aattaatcaa  2580
gtttcttttgg tttggcctgg atttatatcc attcagtttg tggacactac tgaattattt  2640
atgtcatgtt gatcaaaagt tctgatatga tttgattaat gaaacattga aaaaaaatagt  2700
aaaaccaacc atttttaacc ttacactact atcttgaggt atgattgaca tacattaaaa  2760
ccacctctta ataaatgctt cttgttaatc aaaaatttga aaacgtatgt ccactggagg  2820
aaaaaagaca tagccctgga tgtgaactga atattactga gactcggaga ccttcagaac  2880
tacctgaaga tgaatcgaag tgctgcctac tttagagaat tggactaatt taattttggga  2940
gtcagcagat tgctgtatat cagtcatcat atataccggt gacaagacca cttagttcat  3000
tccctttttt agattctgta agattattgt gttccagtga aattgatttg caaaatgaga  3060
cattttattt tctgtgctt tgttctatca tgttctgat tggtcataag catctcacag  3120
aagtaagaaa tatggcgatt cagaaggcaa caagcacatt taaatttat agaaaatatt  3180
tgaaggactt tttcatggcc caaatcatga aaagtagtag tattgtttta agtataatta  3240
ttaaattata atacattaat gttctttctt gcaacatatt actctcattc ttttttttt  3300
tttttttttt tgagacggag tctcactctg tcacccggct ggagtacagt ggtacgatct  3360
tggcccactg caacctctgc ctcccgggtt caagcgattc tcctgcctca gcctcccaag  3420
tagctgggat tacaggctcc tgccaccacg cctagctaat ttttgtattt ttagtagaga  3480
cagggtttca ccaggttggc caggatggtc ttgatctctt gacctcatgg tccgtccacc  3540
tctgcctccc aaagtgttgg gattacaggc gtgagccacc cagcagtctg attcttaatt  3600
ttatagttta tgttgtacct ccccagctga agtatctctt ttcttttttc ccgcgtgttt  3660
agtgttcact catctttata gcatagctca attgtcactt catgaagcct tccataacct  3720
ttgtagctcc attaattata ttcttctgag tgtttaaaac acttgccata tgaaacacta  3780
tttactttgg cttacattct tactatctaa tcggccattt ctgttactaa atcttttttct  3840
cagagcacct gggatagtct tgtgtcttag taaaatcagt tgattgattt aactcggtag  3900
agtagaggct gattaaagta aataaatctg gttgatgcca acaaaatttt ggtcccctca  3960
attttttgct ctcattacct gcaaattctc cctggccttc atatttggca accattgagg  4020
agaacaaggc tgtaaaagta gttcatgtac ttgatattct gaattggaat taagcagagt  4080
tgcttaagta ggacttgctt ttctgggatt tcttatgcaa caaataatgt agtaactgga  4140
aatccaagtt caagacactg gcagattcga tgtcttttga ggacccttgg cttcatagat  4200
gatgccttct ccctatatcc ttacatagca aaaggggcca ggcagctctg gccttttttt  4260
gtaaggccaa taactccaga aacctcatga cctcatcacc tcccaaaggc cccacctctc  4320
aatactatca cattgtgagg ctaggtttca acatatgaat tgtgggagac aaaaattcag  4380
accatagtat aatatttcaa gattacttaa actcttctct accaaactca ttaactttta  4440
ggttagcaca gtattttcat tgatattttg gtttctggag ttattactaa ttttcttgat  4500
ctgatgttat aattaaaaaa aaacaggact ttgtacgtga aatgagactg agataaggaa  4560
gctgattcag agatggagat ttaaaaaaag agagatgaga gattgagatc tgcagtgtca  4620
aactgacaat agccaggagt caggagatat taagagacta tcatctgt gattgttaat  4680
gattatttat tgttattat aaatactact gtattttata tattatatac attgttttaa  4740
aaattattt tgtaccattt cttgaaagaa aatgtctaa gcttgggaaa atatttattg  4800
aaaatgtgg tttgtacatc tgaggagtgt atcttgcaca gtaggtgcat agatttcttc  4860
ctcttcctgt tccacatggc cttagcttag aggctgtgtg gccatcactt ggtatttagg  4920
gtaagactga tgcacaaaat caaagacagg taaccttggt ataagtgtag tatcatgtaa  4980
atagcttttc tatgtctaat tcttgttttc ttcctacttt ttcaggaggt caatttcagt  5040
tcatttcaac tatctttaca taatagtgct ttagtaacag gcatgaagg aaagagacat  5100
```

```
gtccctagag tgttttcttg aaatctaata gatgattgga gtatttacca tgcagttgtg   5160
tatatacata agcagtgaat tcgagaggaa ttttttaagct gtaaaaaaaa gcattgtgtg   5220
ccttatagac gcgagtgaga aatgtggaat atggctgatc caaagggaat gagttatctc   5280
aattgattaa tcacagtcag ttacagattg aactctttgt tctactcttt gccccttcat   5340
cactattgct cttgactagt cttaagaaag aaatgtggaa tattttctca cggctttggg   5400
attttataaa ttagaatact agtggtatgt aaatacagca ggtacactac tgtataaacc   5460
aacataggaa gccttcttta aagggaattg tttgagaaat ttgaacactt ggataaatttg   5520
aataaaggat tgtgataaat gatcaaatga aagaaaataa atcaggttac tcttcttcct   5580
gcttgataaa gcaataattt ttttttaaagg taaaaattat gagaatgatg aggatagtag   5640
ttagcattgt ctttctttga taggtttgtt aatgatcata aaactgattt atttaaagac   5700
atgtcttttt ataactattt tatactgttg tatctggaaa caaatattga atttcatttg   5760
tcatgtggaa gaaatcaact agttttaacc tttgatttat aataaatcaa ccactttcat   5820
ttattgtcta atactggcaa tgaacacagc ctaatgtatc aaaactaaca gaataaaat   5880
tctccaagtt atatccagac tttaagacac tttctaatta tataaaataa aatattttgg   5940
gcagtcattt tttaactctg aaactattta aaactcctaa tttagaatat cttaataaat   6000
acccatttc ctctttttat ttttataact tggtaaaaat tgagtccatt gttttcccag   6060
aacgctgttc ttaaacaaat ggttacctcc ttcattagaa ctttacttt tttaggattt   6120
ctaattaaga aaacattagg cttgtaacat tgtcaaatct tggtggtctt tcttccacgt   6180
tttttgaggt cgattatcta agaggccatc agttaataaa gctatgcagg aaatgacatc   6240
atgccacatg tgaatatcct gtattaaaaa ttgtatcaat atactatttt ataattatga   6300
agtggaatga attttagaaa tagaaaaggt gattttttgt gcataggtcc aaactgtgtt   6360
ttgttttcat ttcagaattt cataataact atattgctc catatcttaa ttgtgttttt   6420
ttatagcact tttgtttagt aatttgtata tgcttggctg tattctcaga ggctgttttct   6480
atttaatgtt gtcaaaacag ctcataaaaa gtgaaaattc ggtcagacta gttatttgat   6540
attatatatg aaatcaaaac aacctgaaac attatcttt aatttaaata aagaacccca   6600
aattttaatc aaatgtatgc aaaggcacat agaataatta acttaagtgta caaccttat   6660
taacttgatg atggaaacct gttcctaggg acctttactt gaataaatga aatatcaaga   6720
aaaaatacta acttaagaat aataatttaa taagtaagta agctattatg atcttcaatc   6780
agtcctgaga gaatcatggt tgagaattag aaaatttaga ccagtaagat caacactgtt   6840
aaaaaaaaaa aaaaatcagt attttttctc catatttttt atatatctgg atcattttat   6900
ttagcactta ttattgcact ttcctttca cttttttaaac tatgctgttt tatttttctg   6960
agacatctga tttactgagg aggaaaatgg aaatgcggta cagagcccaa gggtatgacg   7020
gctttaaatg agtttccatt tctgttttaa gttaaccatc cctccctagc ttacatctgt   7080
tcctttgttg caccccttggt ttaacattat tctcctcccc aatttcctct tctcctcatt   7140
gtgaactcgt ggcag                                                   7155

SEQ ID NO: 277           moltype = DNA   length = 111
FEATURE                  Location/Qualifiers
source                   1..111
                         mol_type = other DNA
                         organism = Homo sapiens
SEQUENCE: 277
ggtctgcttg gtgagctcat tctcttacaa caacaaattc aagagcatga agaggaagcg    60
cgcagagccg ctggccaata tagcacgagc tatgcccaac agaagcgcaa g            111

SEQ ID NO: 278           moltype = DNA   length = 5409
FEATURE                  Location/Qualifiers
source                   1..5409
                         mol_type = other DNA
                         organism = Homo sapiens
SEQUENCE: 278
gtgatggatg gtttaagggg gctaccgata cattcacact aatcagccat ttctgccaag    60
atcatgtcac ctcaatctgt tcatggactc caaatacaag aaattaattt gacaaagtga   120
aaatataaaa gatgcatcat ataaatatgt aacttttctg gagtgggtag tataggtaaa   180
gccaaaagaa acaaattcaa gcagagaat tttggttttc gaaaattgaa ttgtctgtag   240
ggtccctgta tttatactta gaacaaaatt aggaatttct gtttatgtgg tccagttatt   300
gagtcacct aagtttgtag gcatcttacc tacctacttg ctcccaagt ttttatttct   360
aaaatgaaaa gcattgctgt agatgaccag tttacactaa agaataacat ttatttattt   420
gttttagcta aagtatatgg acagggaaca ttcatattct tgtagaagaa aattattttg   480
acttttgggc aaaagcatgt agttcttata cactttgaca aactcattgc gtacattttt   540
cacattaatc aaagtcagca caaataaatt ttcaccttgg accacggagg tttgaacac    600
tggaaatttg atataattct ggttgctaaa gaacaagttc taataaaagc ttaagtgtat   660
accaatatgt ggctgttggt gcaatcagca ggtccgtaaa aatatgattt taatggttag   720
gtaatcccac aacggagatc ccaaagttca tgtttggaag gactttttgg gtcaaagtga   780
aatcagtgta atgaatttaa aattatactc tgagatcttg aaatcagcta attatgttac   840
atcttattag ctcagaaaag ttttgaagtt atatacaaat gctagtcagg aaaaaagatt   900
cagtcatgta attcttgtac attctactat ttaaatcaac caatattata gattatgatt   960
tagtcagta attctgctgg ctaacccttat ctcattttggt ggtggttagt acttcagagt  1020
actccaccata gtttcattta tgttttcagc atcacttcct tgttttttctc aattccatgg  1080
ctgtggaatc aattcatatg tatatttagc ttccggtgagc aaaaacatag ctagaaaaag  1140
aaaagaagtg agtttcctac ctggttaaat taaagtcgat gtgttaagcc aaggaggact  1200
tcttttgaat ggtactttaa caatcccgtg tctgtatact gtgaatatat catttaaata  1260
gcctaataaa ttgatgcttt aggctgagcc acctatactt tagttttgtt atggaaagaa  1320
gggagaggag caagtatgtt cttatatgtt acttagaaat aagaatgtag ctgtagttac  1380
acattgttct taagtttttt tcgtaagaca acttgaaatg agtcccatag gcctgctatt  1440
taacattcta agatatgact taaggttaat gatgagcttt tgaatctgac aattcaagag  1500
atatccataa tgaatactga ttcatttct acattgctga aagctaatgt tcatttaag  1560
cctactttag tagcctttat ttgggcttag agatgttatt cctctttctg atattttattg  1620
ggttatctgt ttaacccttt tatatctccc tttcccgatt tgtaaattag agactggcaa  1680
```

```
gacttttttac cctgagtaga gcaccaaaca tggcttgttt ctgcccacac tgtagttacc    1740
ttgaggggaa gtaaatggga cttttaaaagc aatttatgct ctttttatagt gaaattatcc   1800
ctcttactat cccgaaagac tgttaccttta caatatcctc cactcctttc ccctgtagt    1860
tactatagag atgacttttc ggttcttcac tgccataatg atcaaaatcc taattcatga    1920
gattttttatc attccaggca tgtgaggttt acttgatgca taaaaccgca agtacttttt   1980
gttgttttttt aattgttttt tctctctttat ctttcttgaaa gtctaagtag atcatcattt 2040
ttgatgtctt attagtagca actaataaat tttccctgta tcttctcagc aaaagaactc    2100
aagcagagac agaagattag aactaccatt ggtagttttg cttcctatgg atatgttcac    2160
atacatagaa attttttacaa tgaccttttt atatatgtat ttcagaattt cagaatggcc   2220
tcaatgcctt aataggaaga aatacttgaa attttttaaat tagggcttgg ttttgtgagg   2280
agctagtaaa ggttttttctc tttcagctttt agcttgtttc tgcggaggat tccgctctttt 2340
ctccatcagt ttcatagccc tggaattgta gaaaagctct ggtttcaaga ccattgatat    2400
ccatttctgt cagggtgagt tttaaattta tttcatgatg caaacaatat attgaacaac    2460
aggacatgaa cttgttcttg ttgtaagtgg ctgaattttta tcagtaaagc acatcaaaat   2520
aaaatatacc ccaattgcta gttaagacct agagtgacag attgaaaata gcttgtgtta    2580
ttctcttaag aaaatatata aaattatca tctcatcaat ctttaatgtt tgttttataa     2640
atctaaatgt ttttatattg tttcctagga aatattaggt ctaatttttt actttaccac   2700
cagctgtctt ttatttttact ctttttttga gacggagttt cgctcttgtt gcttaggcta   2760
gagtgcagtg gcactatctc agctcactgc gacctctgcc tcccgggttc aagcgattct    2820
cctgcctcag tctcccgagt agctgggatt acaggcacat gccactacac caggctaatt   2880
ttgtatttttt agtagagacg gggttctctc atgttggtca ggctggtctc gaactcccga   2940
cctcaggtga tccgcctgcc tcggcctccc agagtgctgg gattacaggc atgagccacc    3000
gcacctggcc agctgtctttt taatataaca ttatgattaa ttgtgatgtt ccattaaact   3060
aagcggagag gaaacatgct ggtaaccat gtgtgagtta ttcattgtac cagaaaggca    3120
aatgatacat tttatcctaa aattcaaatt tataaacatc ttaacacttg tgatcattaa    3180
atactactaa tctagcatat aaattatatt tgtaggcggg gcacggtggc tcacgcctgt    3240
aatcccagca ctttgggagg ctgaggtggg cagatcacga ggtcaggaga tcgagaccat    3300
cctggctaac atggtgaaac cccatctcta ctaaaaatac aaaaaaaatt agctgggtgt    3360
gctggcgggc acctgtagtc ccagctactt gggaggctga ggcaggagaa tggcgtgacc    3420
ccaggaggca gagcttccag cctgggcgac tccgtctcaa aaaaaagaa aaaagaaatt    3480
atatttgtaa tattctacta accttatatc atttttaactt tttatataac ttttttattt  3540
taccaaatta agttaacctt ttatagcccct tggcttatac taaacatcct aacttttttg   3600
tttaattgta ttagttttta agttattgcc ccagatgtca agtaatgttg gattttctat    3660
aataatttag gatatattgc atgaagtcag ttagtattta catttaaaac taaaacaatt    3720
tatactaata cagtttatac atttcatact aatttagcta cagttggata aatatttaat    3780
ggaacaaagt aaatcaaagt accttttcaa atgaattgga aattaaatcc acataacaat    3840
ttttatgac cacactatta cagtgtgatg gcatgccaaa tgatcataat gtggaattat     3900
gtatttcttc attggctttc aagattctgt tctttagttt gtgggctcct ctccaacttg    3960
cttgtctcct cacagtttag gcgactgttt ataattcttg tccatcctgc ataaacacac    4020
acagtcaaaa tgaaaaaaag cttctatcag cagatctgtg cttgctgtac agaaatggga    4080
aaacaattga agtttgcatt atctttttttc taattaccag atcgttttttg gagctattta  4140
ggcatacgct tttaaggaaa aagaaaaaa agagtgtacc ttttgtttct aacaaaggtt    4200
gttatctata ttattgaaat aaaaaaattgg ggatagttat gacaaagtat ttagaaatag  4260
gaattaaaat cttaaaataa cttttcatag catggacaag acttattaat gtctacctca    4320
ataagcaaat cattttaaaaa ttttttcatgt atatttgctg ccatgatgtg ttgtgattgc    4380
ttaaataacc aatgaatgaa gatcaacaag gatttaaatg aagaagaata tggatttaac    4440
tattttctcc tgtgaaataa gttcatattt acaagttttg atttttcagaa attagacaat   4500
tattttttaaa ggctgggatg acaacttctg cctcttacca agaagtcaaa gcacagttat   4560
gtgaattcat cataaatcac atcattttta ttatattttg tatttataat tgtattgtga    4620
ctactttaaa acctgttata aaataaaatt gttttttaat attttattttt agaattatta   4680
gcattaataa caatttgaag tagttacac aatacctgtg agttttattt ttgtttttaa    4740
ttgaaattaa ttttagttgc tttacttggc ttcattgcta tggatgcatt ctctgtgtta    4800
cgagttagca gatctttcct tggaactgaa tttaaaagca agcatttggc tcccacttaaa   4860
tctctgaaaa tgcaacttgt tctttgcatt tattacataa ttcgctactt atggtacaga    4920
aatggataca atacaaaaat atttccttat aagatacact gtgaccaatg agcttttttaa  4980
atagctgtaa tcagtaacat gtatttgact tttcaaaaca catttctgga gggatatcag    5040
tgctttattt ccccaaatat ctgaatccct atgctttagt acaaaacaac ttctgaagaa    5100
tttagtaacc atatgtgttg atctctttgtt tttctaacta gtctttcata agaaatgact    5160
agaatagcaa cagggaaatg attgcctttt aaggttttttg tttctcaata taaaatttttg  5220
gtgaaccatt tttattgata aatacaggta ttttttacttt cttaaatcac ttgatttaaa   5280
attactttga ttaaatatgc atataaagtc agttgttttt aactctcaat acttatcaaa    5340
aaaatttaac ttgctgtaca ttctgtataa acctaattct attcaactaa aattattttta  5400
aacatttag                                                            5409
```

SEQ ID NO: 279         moltype = DNA   length = 108
FEATURE                Location/Qualifiers
source                 1..108
                       mol_type = other DNA
                       organism = Homo sapiens
SEQUENCE: 279
ctttagcttg tttctgcgga ggattccgct ctttctccat cagtttcata gccctggaat    60
tgtagaaaag ctctggtttc aagaccattg atatccattt ctgtcagg              108

```
SEQ ID NO: 280          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 280
tcttgaattt gttgttgt                                                 18

SEQ ID NO: 281          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 281
ctcttgaatt tgttgttg                                                 18

SEQ ID NO: 282          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 282
gctcttgaat tgttgtt                                                  18

SEQ ID NO: 283          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 283
tgctcttgaa tttgttgt                                                 18

SEQ ID NO: 284          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 284
catgctcttg aatttgtt                                                 18

SEQ ID NO: 285          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 285
tcatgctctt gaatttgt                                                 18

SEQ ID NO: 286          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 286
ttcatgctct tgaatttg                                                 18
```

```
SEQ ID NO: 287          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 287
cttcatgctc ttgaattt                                                       18

SEQ ID NO: 288          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 288
tgaatttgtt gttgta                                                         16

SEQ ID NO: 289          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 289
ttgaatttgt tgttgt                                                         16

SEQ ID NO: 290          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 290
cttgaatttg ttgttg                                                         16

SEQ ID NO: 291          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 291
tcttgaattt gttgtt                                                         16

SEQ ID NO: 292          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 292
ctcttgaatt tgttgt                                                         16

SEQ ID NO: 293          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 293
gctcttgaat ttgttg                                                         16
```

-continued

```
SEQ ID NO: 294          moltype = DNA   length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 294
tgctcttgaa tttgtt                                                            16

SEQ ID NO: 295          moltype = DNA   length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 295
atgctcttga atttgt                                                            16

SEQ ID NO: 296          moltype = DNA   length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 296
catgctcttg aatttg                                                            16

SEQ ID NO: 297          moltype = DNA   length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 297
tcatgctctt gaattt                                                            16

SEQ ID NO: 298          moltype = DNA   length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 298
ttcatgctct tgaatt                                                            16

SEQ ID NO: 299          moltype = DNA   length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 299
cttcatgctc ttgaat                                                            16

SEQ ID NO: 300          moltype = DNA   length = 308
FEATURE                 Location/Qualifiers
misc_feature            1..308
                        note = Description of Artificial Sequence: Synthetic
                         polynucleotide
source                  1..308
                        mol_type = other DNA
                        organism = synthetic construct
SEQUENCE: 300
atttcagaat ggcctcaatg ccttaatagg aagaaatact tgaaattttt aaattagggc            60
ttggttttgt gaggagctag taaaggtttt tctctttcag ctttagcttg tttctgcgga           120
ggattccgct ctttctccat cagtttcata gccctggaat tgtagaaaag ctctggtttc           180
```

```
aagaccattg atatccattt ctgtcagggt gagttttaaa tttatttcat gatgcaaaca    240
atatattgaa caacaggaca tgaacttgtt cttgttgtaa gtggctgaat tttatcagta    300
aagcacat                                                             308

SEQ ID NO: 301           moltype = DNA  length = 258
FEATURE                  Location/Qualifiers
misc_feature             1..258
                         note = Description of Artificial Sequence: Synthetic
                         polynucleotide
source                   1..258
                         mol_type = other DNA
                         organism = synthetic construct
SEQUENCE: 301
attgagcata aaaatctgct aaagcatttc actgatattt gggttcattt ctacaagtat     60
gagcttcagt cttaataaca gcaatctgca tttgtaacag gatagcagaa aggagctcat    120
ctgtttggag tccattttg atggggatcc cactagaggt gagaaacctt cgtagtttcc     180
atatcatgcc aaaatcacgt actactccaa aagcatgtct actatccgta aatatttact    240
gacttgtcct tagctgtg                                                   258

SEQ ID NO: 302           moltype = DNA  length = 110
FEATURE                  Location/Qualifiers
misc_feature             1..110
                         note = Description of Artificial Sequence: Synthetic
                         polynucleotide
source                   1..110
                         mol_type = other DNA
                         organism = synthetic construct
SEQUENCE: 302
gtatttcaga atttcagaat ggcctcaatg ccttaatagg aagaaatact tgaaattttt     60
aaattagggc ttggttttgt gaggagctag taaaggtttt tctctttcag                110

SEQ ID NO: 303           moltype = DNA  length = 151
FEATURE                  Location/Qualifiers
misc_feature             1..151
                         note = Description of Artificial Sequence: Synthetic
                         polynucleotide
source                   1..151
                         mol_type = other DNA
                         organism = synthetic construct
SEQUENCE: 303
gagctagtaa aggtttttct ctttcagctt tagcttgttt ctgcggagga ttccgctctt     60
tctccatcag tttcatagcc ctggaattgt agaaaagctc tggtttcaag accattgata    120
tccattctg tcagggtgag ttttaaattt a                                    151

SEQ ID NO: 304           moltype = DNA  length = 104
FEATURE                  Location/Qualifiers
misc_feature             1..104
                         note = Description of Artificial Sequence: Synthetic
                         polynucleotide
source                   1..104
                         mol_type = other DNA
                         organism = synthetic construct
SEQUENCE: 304
gtgagtttta aatttatttc atgatgcaaa caatatattg aacaacagga catgaacttg     60
ttcttgttgt aagtggctga attttatcag taaagcacat caaa                     104

SEQ ID NO: 305           moltype = DNA  length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 305
aggccattct gaaattct                                                   18

SEQ ID NO: 306           moltype = DNA  length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 306
cattgaggcc attctgaa                                                   18
```

```
SEQ ID NO: 307              moltype = DNA  length = 18
FEATURE                     Location/Qualifiers
misc_feature                1..18
                            note = Description of Artificial Sequence: Synthetic
                            oligonucleotide
source                      1..18
                            mol_type = other DNA
                            organism = synthetic construct
SEQUENCE: 307
taaggcattg aggccatt                                                         18

SEQ ID NO: 308              moltype = DNA  length = 18
FEATURE                     Location/Qualifiers
misc_feature                1..18
                            note = Description of Artificial Sequence: Synthetic
                            oligonucleotide
source                      1..18
                            mol_type = other DNA
                            organism = synthetic construct
SEQUENCE: 308
cctattaagg cattgagg                                                         18

SEQ ID NO: 309              moltype = DNA  length = 18
FEATURE                     Location/Qualifiers
misc_feature                1..18
                            note = Description of Artificial Sequence: Synthetic
                            oligonucleotide
source                      1..18
                            mol_type = other DNA
                            organism = synthetic construct
SEQUENCE: 309
ttcttcctat taaggcat                                                         18

SEQ ID NO: 310              moltype = DNA  length = 18
FEATURE                     Location/Qualifiers
misc_feature                1..18
                            note = Description of Artificial Sequence: Synthetic
                            oligonucleotide
source                      1..18
                            mol_type = other DNA
                            organism = synthetic construct
SEQUENCE: 310
agtatttctt cctattaa                                                         18

SEQ ID NO: 311              moltype = DNA  length = 18
FEATURE                     Location/Qualifiers
misc_feature                1..18
                            note = Description of Artificial Sequence: Synthetic
                            oligonucleotide
source                      1..18
                            mol_type = other DNA
                            organism = synthetic construct
SEQUENCE: 311
tttcaagtat ttcttcct                                                         18

SEQ ID NO: 312              moltype = DNA  length = 18
FEATURE                     Location/Qualifiers
misc_feature                1..18
                            note = Description of Artificial Sequence: Synthetic
                            oligonucleotide
source                      1..18
                            mol_type = other DNA
                            organism = synthetic construct
SEQUENCE: 312
aaaaatttca agtatttc                                                         18

SEQ ID NO: 313              moltype = DNA  length = 18
FEATURE                     Location/Qualifiers
misc_feature                1..18
                            note = Description of Artificial Sequence: Synthetic
                            oligonucleotide
source                      1..18
                            mol_type = other DNA
                            organism = synthetic construct
```

```
SEQUENCE: 313
aatttaaaaa tttcaagt                                                        18

SEQ ID NO: 314            moltype = DNA  length = 18
FEATURE                   Location/Qualifiers
misc_feature              1..18
                          note = Description of Artificial Sequence: Synthetic
                          oligonucleotide
source                    1..18
                          mol_type = other DNA
                          organism = synthetic construct
SEQUENCE: 314
gccctaattt aaaaattt                                                        18

SEQ ID NO: 315            moltype = DNA  length = 18
FEATURE                   Location/Qualifiers
misc_feature              1..18
                          note = Description of Artificial Sequence: Synthetic
                          oligonucleotide
source                    1..18
                          mol_type = other DNA
                          organism = synthetic construct
SEQUENCE: 315
accaagccct aatttaaa                                                        18

SEQ ID NO: 316            moltype = DNA  length = 18
FEATURE                   Location/Qualifiers
misc_feature              1..18
                          note = Description of Artificial Sequence: Synthetic
                          oligonucleotide
source                    1..18
                          mol_type = other DNA
                          organism = synthetic construct
SEQUENCE: 316
acaaaaccaa gccctaat                                                        18

SEQ ID NO: 317            moltype = DNA  length = 18
FEATURE                   Location/Qualifiers
misc_feature              1..18
                          note = Description of Artificial Sequence: Synthetic
                          oligonucleotide
source                    1..18
                          mol_type = other DNA
                          organism = synthetic construct
SEQUENCE: 317
tcctcacaaa accaagcc                                                        18

SEQ ID NO: 318            moltype = DNA  length = 18
FEATURE                   Location/Qualifiers
misc_feature              1..18
                          note = Description of Artificial Sequence: Synthetic
                          oligonucleotide
source                    1..18
                          mol_type = other DNA
                          organism = synthetic construct
SEQUENCE: 318
ctagctcctc acaaaacc                                                        18

SEQ ID NO: 319            moltype = DNA  length = 18
FEATURE                   Location/Qualifiers
misc_feature              1..18
                          note = Description of Artificial Sequence: Synthetic
                          oligonucleotide
source                    1..18
                          mol_type = other DNA
                          organism = synthetic construct
SEQUENCE: 319
ctttactagc tcctcaca                                                        18

SEQ ID NO: 320            moltype = DNA  length = 18
FEATURE                   Location/Qualifiers
misc_feature              1..18
                          note = Description of Artificial Sequence: Synthetic
                          oligonucleotide
source                    1..18
                          mol_type = other DNA
                          organism = synthetic construct
```

```
SEQUENCE: 320
aaaaccttta ctagctcc                                                  18

SEQ ID NO: 321          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 321
agagaaaaac ctttacta                                                  18

SEQ ID NO: 322          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 322
ctgaaagaga aaacctt                                                   18

SEQ ID NO: 323          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 323
aagctgaaag agaaaaac                                                  18

SEQ ID NO: 324          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 324
ctaaagctga aagagaaa                                                  18

SEQ ID NO: 325          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 325
aagctaaagc tgaaagag                                                  18

SEQ ID NO: 326          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 326
aacaagctaa agctgaaa                                                  18

SEQ ID NO: 327          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
```

-continued

```
SEQUENCE: 327
agaaacaagc taaagctg                                                 18

SEQ ID NO: 328          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 328
cgcagaaaca agctaaag                                                 18

SEQ ID NO: 329          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 329
tcctccgcag aaacaagc                                                 18

SEQ ID NO: 330          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 330
cggaatcctc cgcagaaa                                                 18

SEQ ID NO: 331          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 331
aagagcggaa tcctccgc                                                 18

SEQ ID NO: 332          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 332
ggagaaagag cggaatcc                                                 18

SEQ ID NO: 333          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 333
ctgatggaga aagagcgg                                                 18

SEQ ID NO: 334          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
```

```
SEQUENCE: 334
tgaaactgat ggagaaag                                                 18

SEQ ID NO: 335           moltype = DNA  length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 335
ggctatgaaa ctgatgga                                                 18

SEQ ID NO: 336           moltype = DNA  length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 336
tccagggcta tgaaactg                                                 18

SEQ ID NO: 337           moltype = DNA  length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 337
acaattccag ggctatga                                                 18

SEQ ID NO: 338           moltype = DNA  length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 338
tttctacaat tccagggc                                                 18

SEQ ID NO: 339           moltype = DNA  length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 339
gagcttttct acaattcc                                                 18

SEQ ID NO: 340           moltype = DNA  length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 340
aaccagagct tttctaca                                                 18

SEQ ID NO: 341           moltype = DNA  length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
```

```
SEQUENCE: 341
cttgaaacca gagctttt                                                    18

SEQ ID NO: 342          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 342
atggtcttga aaccagag                                                    18

SEQ ID NO: 343          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 343
tatcaatggt cttgaaac                                                    18

SEQ ID NO: 344          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 344
atggatatca atggtctt                                                    18

SEQ ID NO: 345          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 345
cagaaatgga tatcaatg                                                    18

SEQ ID NO: 346          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 346
cctgacagaa atggatat                                                    18

SEQ ID NO: 347          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 347
caccctgaca gaaatgga                                                    18

SEQ ID NO: 348          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
```

-continued

```
SEQUENCE: 348
actcaccctg acagaaat                                                 18

SEQ ID NO: 349          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 349
aaaactcacc ctgacaga                                                 18

SEQ ID NO: 350          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 350
tttaaaactc accctgac                                                 18

SEQ ID NO: 351          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 351
aaatttaaaa ctcaccct                                                 18

SEQ ID NO: 352          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 352
aataaattta aaactcac                                                 18

SEQ ID NO: 353          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 353
catgaaataa atttaaaa                                                 18

SEQ ID NO: 354          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 354
tgcatcatga aataaatt                                                 18

SEQ ID NO: 355          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
```

```
SEQUENCE: 355
ttgtttgcat catgaaat                                                        18

SEQ ID NO: 356          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 356
atatattgtt tgcatcat                                                        18

SEQ ID NO: 357          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 357
gttcaatata ttgtttgc                                                        18

SEQ ID NO: 358          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 358
ctgttgttca atatattg                                                        18

SEQ ID NO: 359          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 359
atgtcctgtt gttcaata                                                        18

SEQ ID NO: 360          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 360
agttcatgtc ctgttgtt                                                        18

SEQ ID NO: 361          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 361
gaacaagttc atgtcctg                                                        18

SEQ ID NO: 362          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 362
aacaagaaca agttcatg                                                        18
```

```
SEQ ID NO: 363          moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 363
cttacaacaa gaacaagt                                                    18

SEQ ID NO: 364          moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 364
agccacttac aacaagaa                                                    18

SEQ ID NO: 365          moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 365
aattcagcca cttacaac                                                    18

SEQ ID NO: 366          moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 366
gataaaattc agccactt                                                    18

SEQ ID NO: 367          moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 367
ttactgataa aattcagc                                                    18

SEQ ID NO: 368          moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 368
gtgctttact gataaaat                                                    18

SEQ ID NO: 369          moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 369
ttgatgtgct ttactgat                                                    18
```

```
SEQ ID NO: 370           moltype = DNA  length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 370
tggagaaaga gcggaatc                                                       18

SEQ ID NO: 371           moltype = DNA  length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 371
atggagaaag agcggaat                                                       18

SEQ ID NO: 372           moltype = DNA  length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 372
gatggagaaa gagcggaa                                                       18

SEQ ID NO: 373           moltype = DNA  length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 373
tgatggagaa agagcgga                                                       18

SEQ ID NO: 374           moltype = DNA  length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 374
actgatggag aaagagcg                                                       18

SEQ ID NO: 375           moltype = DNA  length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 375
aactgatgga gaaagagc                                                       18

SEQ ID NO: 376           moltype = DNA  length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 376
aaactgatgg agaaagag                                                       18
```

```
SEQ ID NO: 377          moltype = DNA   length = 18
FEATURE                 Location/Qualifiers
misc_feature            1..18
                        note = Description of Artificial Sequence: Synthetic
                          oligonucleotide
source                  1..18
                        mol_type = other DNA
                        organism = synthetic construct
SEQUENCE: 377
gaaactgatg gagaaaga                                                       18

SEQ ID NO: 378          moltype = DNA   length = 18
FEATURE                 Location/Qualifiers
misc_feature            1..18
                        note = Description of Artificial Sequence: Synthetic
                          oligonucleotide
source                  1..18
                        mol_type = other DNA
                        organism = synthetic construct
SEQUENCE: 378
atgaaactga tggagaaa                                                       18

SEQ ID NO: 379          moltype = DNA   length = 18
FEATURE                 Location/Qualifiers
misc_feature            1..18
                        note = Description of Artificial Sequence: Synthetic
                          oligonucleotide
source                  1..18
                        mol_type = other DNA
                        organism = synthetic construct
SEQUENCE: 379
tatgaaactg atggagaa                                                       18

SEQ ID NO: 380          moltype = DNA   length = 18
FEATURE                 Location/Qualifiers
misc_feature            1..18
                        note = Description of Artificial Sequence: Synthetic
                          oligonucleotide
source                  1..18
                        mol_type = other DNA
                        organism = synthetic construct
SEQUENCE: 380
ctatgaaact gatggaga                                                       18

SEQ ID NO: 381          moltype = DNA   length = 18
FEATURE                 Location/Qualifiers
misc_feature            1..18
                        note = Description of Artificial Sequence: Synthetic
                          oligonucleotide
source                  1..18
                        mol_type = other DNA
                        organism = synthetic construct
SEQUENCE: 381
gctatgaaac tgatggag                                                       18

SEQ ID NO: 382          moltype = DNA   length = 18
FEATURE                 Location/Qualifiers
misc_feature            1..18
                        note = Description of Artificial Sequence: Synthetic
                          oligonucleotide
source                  1..18
                        mol_type = other DNA
                        organism = synthetic construct
SEQUENCE: 382
gggctatgaa actgatgg                                                       18

SEQ ID NO: 383          moltype = DNA   length = 18
FEATURE                 Location/Qualifiers
misc_feature            1..18
                        note = Description of Artificial Sequence: Synthetic
                          oligonucleotide
source                  1..18
                        mol_type = other DNA
                        organism = synthetic construct
```

-continued

```
SEQUENCE: 383
agggctatga aactgatg                                                      18

SEQ ID NO: 384         moltype = DNA  length = 18
FEATURE                Location/Qualifiers
misc_feature           1..18
                       note = Description of Artificial Sequence: Synthetic
                       oligonucleotide
source                 1..18
                       mol_type = other DNA
                       organism = synthetic construct
SEQUENCE: 384
cagggctatg aaactgat                                                      18

SEQ ID NO: 385         moltype = DNA  length = 18
FEATURE                Location/Qualifiers
misc_feature           1..18
                       note = Description of Artificial Sequence: Synthetic
                       oligonucleotide
source                 1..18
                       mol_type = other DNA
                       organism = synthetic construct
SEQUENCE: 385
ccagggctat gaaactga                                                      18

SEQ ID NO: 386         moltype = DNA  length = 22
FEATURE                Location/Qualifiers
misc_feature           1..22
                       note = Description of Artificial Sequence: Synthetic
                       oligonucleotide
source                 1..22
                       mol_type = other DNA
                       organism = synthetic construct
SEQUENCE: 386
ctgatggaga aagagcggaa tc                                                 22

SEQ ID NO: 387         moltype = DNA  length = 20
FEATURE                Location/Qualifiers
misc_feature           1..20
                       note = Description of Artificial Sequence: Synthetic
                       oligonucleotide
source                 1..20
                       mol_type = other DNA
                       organism = synthetic construct
SEQUENCE: 387
ctgatggaga aagagcggaa                                                    20

SEQ ID NO: 388         moltype = DNA  length = 22
FEATURE                Location/Qualifiers
misc_feature           1..22
                       note = Description of Artificial Sequence: Synthetic
                       oligonucleotide
source                 1..22
                       mol_type = other DNA
                       organism = synthetic construct
SEQUENCE: 388
aactgatgga gaaagagcgg aa                                                 22

SEQ ID NO: 389         moltype = DNA  length = 20
FEATURE                Location/Qualifiers
misc_feature           1..20
                       note = Description of Artificial Sequence: Synthetic
                       oligonucleotide
source                 1..20
                       mol_type = other DNA
                       organism = synthetic construct
SEQUENCE: 389
aactgatgga gaaagagcgg                                                    20

SEQ ID NO: 390         moltype = DNA  length = 22
FEATURE                Location/Qualifiers
misc_feature           1..22
                       note = Description of Artificial Sequence: Synthetic
                       oligonucleotide
source                 1..22
                       mol_type = other DNA
                       organism = synthetic construct
SEQUENCE: 390
gaaactgatg gagaaagagc gg                                                 22
```

```
SEQ ID NO: 391        moltype = DNA   length = 22
FEATURE               Location/Qualifiers
misc_feature          1..22
                      note = Description of Artificial Sequence: Synthetic
                        oligonucleotide
source                1..22
                      mol_type = other DNA
                      organism = synthetic construct
SEQUENCE: 391
ggctatgaaa ctgatggaga aa                                                  22

SEQ ID NO: 392        moltype = DNA   length = 20
FEATURE               Location/Qualifiers
misc_feature          1..20
                      note = Description of Artificial Sequence: Synthetic
                        oligonucleotide
source                1..20
                      mol_type = other DNA
                      organism = synthetic construct
SEQUENCE: 392
ggctatgaaa ctgatggaga                                                     20

SEQ ID NO: 393        moltype = DNA   length = 22
FEATURE               Location/Qualifiers
misc_feature          1..22
                      note = Description of Artificial Sequence: Synthetic
                        oligonucleotide
source                1..22
                      mol_type = other DNA
                      organism = synthetic construct
SEQUENCE: 393
agggctatga aactgatgga ga                                                  22

SEQ ID NO: 394        moltype = DNA   length = 20
FEATURE               Location/Qualifiers
misc_feature          1..20
                      note = Description of Artificial Sequence: Synthetic
                        oligonucleotide
source                1..20
                      mol_type = other DNA
                      organism = synthetic construct
SEQUENCE: 394
agggctatga aactgatgga                                                     20

SEQ ID NO: 395        moltype = DNA   length = 22
FEATURE               Location/Qualifiers
misc_feature          1..22
                      note = Description of Artificial Sequence: Synthetic
                        oligonucleotide
source                1..22
                      mol_type = other DNA
                      organism = synthetic construct
SEQUENCE: 395
ccagggctat gaaactgatg ga                                                  22

SEQ ID NO: 396        moltype = DNA   length = 18
FEATURE               Location/Qualifiers
misc_feature          1..18
                      note = Description of Artificial Sequence: Synthetic
                        oligonucleotide
source                1..18
                      mol_type = other DNA
                      organism = synthetic construct
SEQUENCE: 396
ttcttaccca tttaatta                                                       18

SEQ ID NO: 397        moltype = DNA   length = 18
FEATURE               Location/Qualifiers
misc_feature          1..18
                      note = Description of Artificial Sequence: Synthetic
                        oligonucleotide
source                1..18
                      mol_type = other DNA
                      organism = synthetic construct
```

```
SEQUENCE: 397
tgcttcttac ccatttaa                                                       18

SEQ ID NO: 398           moltype = DNA   length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 398
taatgcttct tacccatt                                                       18

SEQ ID NO: 399           moltype = DNA   length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 399
agataatgct tcttaccc                                                       18

SEQ ID NO: 400           moltype = DNA   length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 400
cagataatgc ttcttacc                                                       18

SEQ ID NO: 401           moltype = DNA   length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 401
cccttcagat aatgcttc                                                       18

SEQ ID NO: 402           moltype = DNA   length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 402
ctactcccttt cagataat                                                      18

SEQ ID NO: 403           moltype = DNA   length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 403
agctcctact cccttcag                                                       18

SEQ ID NO: 404           moltype = DNA   length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 404
ttcacagctc ctactccc                                                       18
```

```
SEQ ID NO: 405          moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 405
taaaattcac agctccta                                                       18

SEQ ID NO: 406          moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 406
aaatctaaaa ttcacagc                                                       18

SEQ ID NO: 407          moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 407
gaataaaatc taaaattc                                                       18

SEQ ID NO: 408          moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 408
gatgggaata aaatctaa                                                       18

SEQ ID NO: 409          moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 409
gctgtgatgg gaataaaa                                                       18

SEQ ID NO: 410          moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 410
tagaggctgt gatgggaa                                                       18

SEQ ID NO: 411          moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 411
aaagatagag gctgtgat                                                       18
```

```
SEQ ID NO: 412          moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 412
aaaagaaaga tagaggct                                                       18

SEQ ID NO: 413          moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 413
gacctaaaag aaagatag                                                       18

SEQ ID NO: 414          moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 414
ataaagacct aaagaaa                                                        18

SEQ ID NO: 415          moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 415
gagatataaa gacctaaa                                                       18

SEQ ID NO: 416          moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 416
ggctgtgatg ggaataaa                                                       18

SEQ ID NO: 417          moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 417
aggctgtgat gggaataa                                                       18

SEQ ID NO: 418          moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
```

```
                               -continued

SEQUENCE: 418
gaggctgtga tgggaata                                              18

SEQ ID NO: 419          moltype = DNA   length = 18
FEATURE                 Location/Qualifiers
misc_feature            1..18
                        note = Description of Artificial Sequence: Synthetic
                          oligonucleotide
source                  1..18
                        mol_type = other DNA
                        organism = synthetic construct
SEQUENCE: 419
agaggctgtg atgggaat                                              18

SEQ ID NO: 420          moltype = DNA   length = 18
FEATURE                 Location/Qualifiers
misc_feature            1..18
                        note = Description of Artificial Sequence: Synthetic
                          oligonucleotide
source                  1..18
                        mol_type = other DNA
                        organism = synthetic construct
SEQUENCE: 420
atagaggctg tgatggga                                              18

SEQ ID NO: 421          moltype = DNA   length = 18
FEATURE                 Location/Qualifiers
misc_feature            1..18
                        note = Description of Artificial Sequence: Synthetic
                          oligonucleotide
source                  1..18
                        mol_type = other DNA
                        organism = synthetic construct
SEQUENCE: 421
gatagaggct gtgatggg                                              18

SEQ ID NO: 422          moltype = DNA   length = 18
FEATURE                 Location/Qualifiers
misc_feature            1..18
                        note = Description of Artificial Sequence: Synthetic
                          oligonucleotide
source                  1..18
                        mol_type = other DNA
                        organism = synthetic construct
SEQUENCE: 422
agatagaggc tgtgatgg                                              18

SEQ ID NO: 423          moltype = DNA   length = 18
FEATURE                 Location/Qualifiers
misc_feature            1..18
                        note = Description of Artificial Sequence: Synthetic
                          oligonucleotide
source                  1..18
                        mol_type = other DNA
                        organism = synthetic construct
SEQUENCE: 423
aagatagagg ctgtgatg                                              18

SEQ ID NO: 424          moltype = DNA   length = 22
FEATURE                 Location/Qualifiers
misc_feature            1..22
                        note = Description of Artificial Sequence: Synthetic
                          oligonucleotide
source                  1..22
                        mol_type = other DNA
                        organism = synthetic construct
SEQUENCE: 424
tagaggctgt gatgggaata aa                                         22

SEQ ID NO: 425          moltype = DNA   length = 22
FEATURE                 Location/Qualifiers
misc_feature            1..22
                        note = Description of Artificial Sequence: Synthetic
                          oligonucleotide
source                  1..22
                        mol_type = other DNA
                        organism = synthetic construct
SEQUENCE: 425
atagaggctg tgatgggaat aa                                         22
```

```
SEQ ID NO: 426          moltype = DNA  length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 426
gatagaggct gtgatgggaa ta                                              22

SEQ ID NO: 427          moltype = DNA  length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 427
agatagaggc tgtgatggga at                                              22

SEQ ID NO: 428          moltype = DNA  length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 428
aagatagagg ctgtgatggg aa                                              22

SEQ ID NO: 429          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 429
gaggctgtga tgggaataaa                                                 20

SEQ ID NO: 430          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 430
agaggctgtg atgggaataa                                                 20

SEQ ID NO: 431          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 431
tagaggctgt gatgggaata                                                 20

SEQ ID NO: 432          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 432
atagaggctg tgatgggaat                                                 20
```

```
SEQ ID NO: 433        moltype = DNA  length = 20
FEATURE               Location/Qualifiers
misc_feature          1..20
                      note = Description of Artificial Sequence: Synthetic
                       oligonucleotide
source                1..20
                      mol_type = other DNA
                      organism = synthetic construct
SEQUENCE: 433
gatagaggct gtgatgggaa                                                  20

SEQ ID NO: 434        moltype = DNA  length = 20
FEATURE               Location/Qualifiers
misc_feature          1..20
                      note = Description of Artificial Sequence: Synthetic
                       oligonucleotide
source                1..20
                      mol_type = other DNA
                      organism = synthetic construct
SEQUENCE: 434
agatagaggc tgtgatggga                                                  20

SEQ ID NO: 435        moltype = DNA  length = 20
FEATURE               Location/Qualifiers
misc_feature          1..20
                      note = Description of Artificial Sequence: Synthetic
                       oligonucleotide
source                1..20
                      mol_type = other DNA
                      organism = synthetic construct
SEQUENCE: 435
aagatagagg ctgtgatggg                                                  20

SEQ ID NO: 436        moltype = DNA  length = 16
FEATURE               Location/Qualifiers
misc_feature          1..16
                      note = Description of Artificial Sequence: Synthetic
                       oligonucleotide
source                1..16
                      mol_type = other DNA
                      organism = synthetic construct
SEQUENCE: 436
ctgtgatggg aataaa                                                      16

SEQ ID NO: 437        moltype = DNA  length = 16
FEATURE               Location/Qualifiers
misc_feature          1..16
                      note = Description of Artificial Sequence: Synthetic
                       oligonucleotide
source                1..16
                      mol_type = other DNA
                      organism = synthetic construct
SEQUENCE: 437
gctgtgatgg gaataa                                                      16

SEQ ID NO: 438        moltype = DNA  length = 16
FEATURE               Location/Qualifiers
misc_feature          1..16
                      note = Description of Artificial Sequence: Synthetic
                       oligonucleotide
source                1..16
                      mol_type = other DNA
                      organism = synthetic construct
SEQUENCE: 438
ggctgtgatg ggaata                                                      16

SEQ ID NO: 439        moltype = DNA  length = 16
FEATURE               Location/Qualifiers
misc_feature          1..16
                      note = Description of Artificial Sequence: Synthetic
                       oligonucleotide
source                1..16
                      mol_type = other DNA
                      organism = synthetic construct
SEQUENCE: 439
aggctgtgat gggaat                                                      16
```

```
SEQ ID NO: 440             moltype = DNA  length = 16
FEATURE                    Location/Qualifiers
misc_feature               1..16
                           note = Description of Artificial Sequence: Synthetic
                            oligonucleotide
source                     1..16
                           mol_type = other DNA
                           organism = synthetic construct
SEQUENCE: 440
gaggctgtga tgggaa                                                             16

SEQ ID NO: 441             moltype = DNA  length = 16
FEATURE                    Location/Qualifiers
misc_feature               1..16
                           note = Description of Artificial Sequence: Synthetic
                            oligonucleotide
source                     1..16
                           mol_type = other DNA
                           organism = synthetic construct
SEQUENCE: 441
agaggctgtg atggga                                                             16

SEQ ID NO: 442             moltype = DNA  length = 16
FEATURE                    Location/Qualifiers
misc_feature               1..16
                           note = Description of Artificial Sequence: Synthetic
                            oligonucleotide
source                     1..16
                           mol_type = other DNA
                           organism = synthetic construct
SEQUENCE: 442
tagaggctgt gatggg                                                             16

SEQ ID NO: 443             moltype = DNA  length = 16
FEATURE                    Location/Qualifiers
misc_feature               1..16
                           note = Description of Artificial Sequence: Synthetic
                            oligonucleotide
source                     1..16
                           mol_type = other DNA
                           organism = synthetic construct
SEQUENCE: 443
atagaggctg tgatgg                                                             16

SEQ ID NO: 444             moltype = DNA  length = 16
FEATURE                    Location/Qualifiers
misc_feature               1..16
                           note = Description of Artificial Sequence: Synthetic
                            oligonucleotide
source                     1..16
                           mol_type = other DNA
                           organism = synthetic construct
SEQUENCE: 444
gatagaggct gtgatg                                                             16

SEQ ID NO: 445             moltype = DNA  length = 16
FEATURE                    Location/Qualifiers
misc_feature               1..16
                           note = Description of Artificial Sequence: Synthetic
                            oligonucleotide
source                     1..16
                           mol_type = other DNA
                           organism = synthetic construct
SEQUENCE: 445
agatagaggc tgtgat                                                             16

SEQ ID NO: 446             moltype = DNA  length = 16
FEATURE                    Location/Qualifiers
misc_feature               1..16
                           note = Description of Artificial Sequence: Synthetic
                            oligonucleotide
source                     1..16
                           mol_type = other DNA
                           organism = synthetic construct
SEQUENCE: 446
aagatagagg ctgtga                                                             16
```

```
SEQ ID NO: 447          moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 447
aggctgtgat gtgaataa                                                         18

SEQ ID NO: 448          moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 448
aggctgtgat gtgaataa                                                         18

SEQ ID NO: 449          moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 449
aggctgtgat gtgaataa                                                         18

SEQ ID NO: 450          moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 450
agaggctgtg atgtgaat                                                         18

SEQ ID NO: 451          moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 451
agaggctgtg atgtgaat                                                         18

SEQ ID NO: 452          moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 452
agaggctgtg atgtgaat                                                         18

SEQ ID NO: 453          moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
```

```
SEQUENCE: 453
tagaggctgt gatgtgaa                                                      18

SEQ ID NO: 454          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 454
tagaggctgt gatgtgaa                                                      18

SEQ ID NO: 455          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 455
tagaggctgt gatgtgaa                                                      18

SEQ ID NO: 456          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 456
gatagaggct gtgattgg                                                      18

SEQ ID NO: 457          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 457
gatagaggct gtgattgg                                                      18

SEQ ID NO: 458          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 458
gatagaggct gtgattgg                                                      18

SEQ ID NO: 459          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 459
agatagaggc tgtgatgg                                                      18

SEQ ID NO: 460          moltype = DNA  length = 16
FEATURE                 Location/Qualifiers
misc_feature            1..16
                        note = Description of Artificial Sequence: Synthetic
                        oligonucleotide
source                  1..16
                        mol_type = other DNA
                        organism = synthetic construct
SEQUENCE: 460
ggctgtgatg tgaata                                                        16
```

```
SEQ ID NO: 461         moltype = DNA   length = 16
FEATURE                Location/Qualifiers
misc_feature           1..16
                       note = Description of Artificial Sequence: Synthetic
                         oligonucleotide
source                 1..16
                       mol_type = other DNA
                       organism = synthetic construct
SEQUENCE: 461
ggctgtgatg tgaata                                                          16

SEQ ID NO: 462         moltype = DNA   length = 16
FEATURE                Location/Qualifiers
misc_feature           1..16
                       note = Description of Artificial Sequence: Synthetic
                         oligonucleotide
source                 1..16
                       mol_type = other DNA
                       organism = synthetic construct
SEQUENCE: 462
ggctgtgatg tgaata                                                          16

SEQ ID NO: 463         moltype = DNA   length = 16
FEATURE                Location/Qualifiers
misc_feature           1..16
                       note = Description of Artificial Sequence: Synthetic
                         oligonucleotide
source                 1..16
                       mol_type = other DNA
                       organism = synthetic construct
SEQUENCE: 463
gaggctgtga tgtgaa                                                          16

SEQ ID NO: 464         moltype = DNA   length = 16
FEATURE                Location/Qualifiers
misc_feature           1..16
                       note = Description of Artificial Sequence: Synthetic
                         oligonucleotide
source                 1..16
                       mol_type = other DNA
                       organism = synthetic construct
SEQUENCE: 464
gaggctgtga tgtgaa                                                          16

SEQ ID NO: 465         moltype = DNA   length = 16
FEATURE                Location/Qualifiers
misc_feature           1..16
                       note = Description of Artificial Sequence: Synthetic
                         oligonucleotide
source                 1..16
                       mol_type = other DNA
                       organism = synthetic construct
SEQUENCE: 465
gaggctgtga tgtgaa                                                          16

SEQ ID NO: 466         moltype = DNA   length = 16
FEATURE                Location/Qualifiers
misc_feature           1..16
                       note = Description of Artificial Sequence: Synthetic
                         oligonucleotide
source                 1..16
                       mol_type = other DNA
                       organism = synthetic construct
SEQUENCE: 466
tagaggctgt gattgg                                                          16

SEQ ID NO: 467         moltype = DNA   length = 16
FEATURE                Location/Qualifiers
misc_feature           1..16
                       note = Description of Artificial Sequence: Synthetic
                         oligonucleotide
source                 1..16
                       mol_type = other DNA
                       organism = synthetic construct
SEQUENCE: 467
tagaggctgt gattgg                                                          16
```

```
SEQ ID NO: 468          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 468
tagaggctgt gattgg                                                           16

SEQ ID NO: 469          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 469
atagaggctg tgatgg                                                           16

SEQ ID NO: 470          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 470
gatagaggct gtgatg                                                           16

SEQ ID NO: 471          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 471
agatagaggc tgtgat                                                           16

SEQ ID NO: 472          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 472
ggctatgaaa ctgatggaga                                                       20

SEQ ID NO: 473          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 473
ctatgaaact gatggaga                                                         18

SEQ ID NO: 474          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 474
gctatgaaac tgatggag                                                         18
```

```
SEQ ID NO: 475          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 475
ggctatgaaa ctgatgga                                                    18

SEQ ID NO: 476          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 476
atgaaactga tggaga                                                      16

SEQ ID NO: 477          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 477
atgaaactga tggaga                                                      16

SEQ ID NO: 478          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 478
ctatgaaact gatgga                                                      16

SEQ ID NO: 479          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 479
ctatgaaact gatgga                                                      16

SEQ ID NO: 480          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 480
ggctatgaaa ctgatg                                                      16

SEQ ID NO: 481          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 481
ggctatgaaa ctgatg                                                      16
```

```
SEQ ID NO: 482          moltype = DNA   length = 14
FEATURE                 Location/Qualifiers
misc_feature            1..14
                        note = Description of Artificial Sequence: Synthetic
                         oligonucleotide
source                  1..14
                        mol_type = other DNA
                        organism = synthetic construct
SEQUENCE: 482
gaaactgatg gaga                                                           14

SEQ ID NO: 483          moltype = DNA   length = 14
FEATURE                 Location/Qualifiers
misc_feature            1..14
                        note = Description of Artificial Sequence: Synthetic
                         oligonucleotide
source                  1..14
                        mol_type = other DNA
                        organism = synthetic construct
SEQUENCE: 483
atgaaactga tgga                                                           14

SEQ ID NO: 484          moltype = DNA   length = 14
FEATURE                 Location/Qualifiers
misc_feature            1..14
                        note = Description of Artificial Sequence: Synthetic
                         oligonucleotide
source                  1..14
                        mol_type = other DNA
                        organism = synthetic construct
SEQUENCE: 484
ctatgaaact gatg                                                           14

SEQ ID NO: 485          moltype = DNA   length = 14
FEATURE                 Location/Qualifiers
misc_feature            1..14
                        note = Description of Artificial Sequence: Synthetic
                         oligonucleotide
source                  1..14
                        mol_type = other DNA
                        organism = synthetic construct
SEQUENCE: 485
ggctatgaaa ctga                                                           14

SEQ ID NO: 486          moltype = DNA   length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 486
tagaggctgt gatgggaata aa                                                  22

SEQ ID NO: 487          moltype = DNA   length = 24
FEATURE                 Location/Qualifiers
misc_feature            1..24
                        note = Description of Artificial Sequence: Synthetic
                         oligonucleotide
source                  1..24
                        mol_type = other DNA
                        organism = synthetic construct
SEQUENCE: 487
tagaggctgt gatgggaata aaat                                                24

SEQ ID NO: 488          moltype = DNA   length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 488
atagaggctg tgatgggaat aa                                                  22
```

```
SEQ ID NO: 489         moltype = DNA  length = 24
FEATURE                Location/Qualifiers
misc_feature           1..24
                       note = Description of Artificial Sequence: Synthetic
                       oligonucleotide
source                 1..24
                       mol_type = other DNA
                       organism = synthetic construct
SEQUENCE: 489
atagaggctg tgatgggaat aaaa                                                24

SEQ ID NO: 490         moltype = DNA  length = 25
FEATURE                Location/Qualifiers
misc_feature           1..25
                       note = Description of Artificial Sequence: Synthetic
                       oligonucleotide
source                 1..25
                       mol_type = other DNA
                       organism = synthetic construct
SEQUENCE: 490
atagaggctg tgatgggaat aaaat                                               25

SEQ ID NO: 491         moltype = DNA  length = 25
FEATURE                Location/Qualifiers
misc_feature           1..25
                       note = Description of Artificial Sequence: Synthetic
                       oligonucleotide
source                 1..25
                       mol_type = other DNA
                       organism = synthetic construct
SEQUENCE: 491
aaagatagag gctgtgatgg gaata                                               25

SEQ ID NO: 492         moltype = DNA  length = 21
FEATURE                Location/Qualifiers
misc_feature           1..21
                       note = Description of Artificial Sequence: Synthetic
                       oligonucleotide
source                 1..21
                       mol_type = other DNA
                       organism = synthetic construct
SEQUENCE: 492
ggctatgaaa ctgatggaga a                                                   21

SEQ ID NO: 493         moltype = DNA  length = 22
FEATURE                Location/Qualifiers
misc_feature           1..22
                       note = Description of Artificial Sequence: Synthetic
                       oligonucleotide
source                 1..22
                       mol_type = other DNA
                       organism = synthetic construct
SEQUENCE: 493
ggctatgaaa ctgatggaga aa                                                  22

SEQ ID NO: 494         moltype = DNA  length = 24
FEATURE                Location/Qualifiers
misc_feature           1..24
                       note = Description of Artificial Sequence: Synthetic
                       oligonucleotide
source                 1..24
                       mol_type = other DNA
                       organism = synthetic construct
SEQUENCE: 494
ggctatgaaa ctgatggaga aaga                                                24

SEQ ID NO: 495         moltype = DNA  length = 25
FEATURE                Location/Qualifiers
misc_feature           1..25
                       note = Description of Artificial Sequence: Synthetic
                       oligonucleotide
source                 1..25
                       mol_type = other DNA
                       organism = synthetic construct
SEQUENCE: 495
agggctatga aactgatgga gaaag                                               25
```

```
SEQ ID NO: 496          moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 496
catttaatta aattatat                                                       18

SEQ ID NO: 497          moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 497
ccatttaatt aaattata                                                       18

SEQ ID NO: 498          moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 498
cccatttaat taaattat                                                       18

SEQ ID NO: 499          moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 499
acccatttaa ttaaatta                                                       18

SEQ ID NO: 500          moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 500
tacccattta attaaatt                                                       18

SEQ ID NO: 501          moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 501
ttacccattt aattaaat                                                       18

SEQ ID NO: 502          moltype = DNA   length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 502
cttacccatt taattaaa                                                       18
```

```
SEQ ID NO: 503            moltype = DNA  length = 18
FEATURE                   Location/Qualifiers
misc_feature              1..18
                          note = Description of Artificial Sequence: Synthetic
                          oligonucleotide
source                    1..18
                          mol_type = other DNA
                          organism = synthetic construct
SEQUENCE: 503
tcttacccat ttaattaa                                                       18

SEQ ID NO: 504            moltype = DNA  length = 17
FEATURE                   Location/Qualifiers
misc_feature              1..17
                          note = Description of Artificial Sequence: Synthetic
                          oligonucleotide
source                    1..17
                          mol_type = other DNA
                          organism = synthetic construct
SEQUENCE: 504
gatagaggct gtgatgg                                                        17

SEQ ID NO: 505            moltype = DNA  length = 18
FEATURE                   Location/Qualifiers
misc_feature              1..18
                          note = Description of Artificial Sequence: Synthetic
                          oligonucleotide
source                    1..18
                          mol_type = other DNA
                          organism = synthetic construct
SEQUENCE: 505
ggctgtgaaa ctgatgga                                                       18

SEQ ID NO: 506            moltype = DNA  length = 20
FEATURE                   Location/Qualifiers
misc_feature              1..20
                          note = Description of Artificial Sequence: Synthetic
                          oligonucleotide
source                    1..20
                          mol_type = other DNA
                          organism = synthetic construct
SEQUENCE: 506
ggctgtgaaa ctgatggaga                                                     20

SEQ ID NO: 507            moltype = DNA  length = 16
FEATURE                   Location/Qualifiers
misc_feature              1..16
                          note = Description of Artificial Sequence: Synthetic
                          oligonucleotide
source                    1..16
                          mol_type = other DNA
                          organism = synthetic construct
SEQUENCE: 507
ctatgaaact gatgga                                                         16

SEQ ID NO: 508            moltype = DNA  length = 16
FEATURE                   Location/Qualifiers
misc_feature              1..16
                          note = Description of Artificial Sequence: Synthetic
                          oligonucleotide
source                    1..16
                          mol_type = other DNA
                          organism = synthetic construct
SEQUENCE: 508
gctatgaaac tgatgg                                                         16

SEQ ID NO: 509            moltype = DNA  length = 16
FEATURE                   Location/Qualifiers
misc_feature              1..16
                          note = Description of Artificial Sequence: Synthetic
                          oligonucleotide
source                    1..16
                          mol_type = other DNA
                          organism = synthetic construct
SEQUENCE: 509
ggctatgaaa ctgatg                                                         16
```

```
SEQ ID NO: 510            moltype = DNA  length = 14
FEATURE                   Location/Qualifiers
misc_feature              1..14
                          note = Description of Artificial Sequence: Synthetic
                           oligonucleotide
source                    1..14
                          mol_type = other DNA
                          organism = synthetic construct
SEQUENCE: 510
atgaaactga tgga                                                           14

SEQ ID NO: 511            moltype = DNA  length = 14
FEATURE                   Location/Qualifiers
misc_feature              1..14
                          note = Description of Artificial Sequence: Synthetic
                           oligonucleotide
source                    1..14
                          mol_type = other DNA
                          organism = synthetic construct
SEQUENCE: 511
tatgaaactg atgg                                                           14

SEQ ID NO: 512            moltype = DNA  length = 14
FEATURE                   Location/Qualifiers
misc_feature              1..14
                          note = Description of Artificial Sequence: Synthetic
                           oligonucleotide
source                    1..14
                          mol_type = other DNA
                          organism = synthetic construct
SEQUENCE: 512
ctatgaaact gatg                                                           14

SEQ ID NO: 513            moltype = DNA  length = 14
FEATURE                   Location/Qualifiers
misc_feature              1..14
                          note = Description of Artificial Sequence: Synthetic
                           oligonucleotide
source                    1..14
                          mol_type = other DNA
                          organism = synthetic construct
SEQUENCE: 513
gctatgaaac tgat                                                           14

SEQ ID NO: 514            moltype = DNA  length = 14
FEATURE                   Location/Qualifiers
misc_feature              1..14
                          note = Description of Artificial Sequence: Synthetic
                           oligonucleotide
source                    1..14
                          mol_type = other DNA
                          organism = synthetic construct
SEQUENCE: 514
ggctatgaaa ctga                                                           14

SEQ ID NO: 515            moltype = DNA  length = 20
FEATURE                   Location/Qualifiers
misc_feature              1..20
                          note = Description of Artificial Sequence: Synthetic
                           oligonucleotide
source                    1..20
                          mol_type = other DNA
                          organism = synthetic construct
SEQUENCE: 515
gctgtgaaac tgatggagaa                                                     20

SEQ ID NO: 516            moltype = DNA  length = 20
FEATURE                   Location/Qualifiers
misc_feature              1..20
                          note = Description of Artificial Sequence: Synthetic
                           oligonucleotide
source                    1..20
                          mol_type = other DNA
                          organism = synthetic construct
SEQUENCE: 516
gggctgtgaa actgatggag                                                     20
```

```
SEQ ID NO: 517          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 517
tgtgaaactg atggagaa                                                       18

SEQ ID NO: 518          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 518
ctgtgaaact gatggaga                                                       18

SEQ ID NO: 519          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 519
gctgtgaaac tgatggag                                                       18

SEQ ID NO: 520          moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 520
gggctgtgaa actgatgg                                                       18

SEQ ID NO: 521          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 521
tgaaactgat ggagaa                                                         16

SEQ ID NO: 522          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 522
gtgaaactga tggaga                                                         16

SEQ ID NO: 523          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 523
tgtgaaactg atggag                                                         16
```

```
SEQ ID NO: 524          moltype = DNA  length = 16
FEATURE                 Location/Qualifiers
misc_feature            1..16
                        note = Description of Artificial Sequence: Synthetic
                        oligonucleotide
source                  1..16
                        mol_type = other DNA
                        organism = synthetic construct
SEQUENCE: 524
ctgtgaaact gatgga                                                        16

SEQ ID NO: 525          moltype = DNA  length = 16
FEATURE                 Location/Qualifiers
misc_feature            1..16
                        note = Description of Artificial Sequence: Synthetic
                        oligonucleotide
source                  1..16
                        mol_type = other DNA
                        organism = synthetic construct
SEQUENCE: 525
gctgtgaaac tgatgg                                                        16

SEQ ID NO: 526          moltype = DNA  length = 16
FEATURE                 Location/Qualifiers
misc_feature            1..16
                        note = Description of Artificial Sequence: Synthetic
                        oligonucleotide
source                  1..16
                        mol_type = other DNA
                        organism = synthetic construct
SEQUENCE: 526
ggctgtgaaa ctgatg                                                        16

SEQ ID NO: 527          moltype = DNA  length = 16
FEATURE                 Location/Qualifiers
misc_feature            1..16
                        note = Description of Artificial Sequence: Synthetic
                        oligonucleotide
source                  1..16
                        mol_type = other DNA
                        organism = synthetic construct
SEQUENCE: 527
gggctgtgaa actgat                                                        16

SEQ ID NO: 528          moltype = DNA  length = 15
FEATURE                 Location/Qualifiers
misc_feature            1..15
                        note = Description of Artificial Sequence: Synthetic
                        oligonucleotide
source                  1..15
                        mol_type = other DNA
                        organism = synthetic construct
SEQUENCE: 528
cggtccagga atgac                                                         15

SEQ ID NO: 529          moltype = DNA  length = 15
FEATURE                 Location/Qualifiers
misc_feature            1..15
                        note = Description of Artificial Sequence: Synthetic
                        oligonucleotide
source                  1..15
                        mol_type = other DNA
                        organism = synthetic construct
SEQUENCE: 529
ccggtccagg aatga                                                         15

SEQ ID NO: 530          moltype = DNA  length = 15
FEATURE                 Location/Qualifiers
misc_feature            1..15
                        note = Description of Artificial Sequence: Synthetic
                        oligonucleotide
source                  1..15
                        mol_type = other DNA
                        organism = synthetic construct
```

```
SEQUENCE: 530
cccggtccag gaatg                                                       15

SEQ ID NO: 531          moltype = DNA   length = 15
FEATURE                 Location/Qualifiers
misc_feature            1..15
                        note = Description of Artificial Sequence: Synthetic
                        oligonucleotide
source                  1..15
                        mol_type = other DNA
                        organism = synthetic construct
SEQUENCE: 531
tcccggtcca ggaat                                                       15

SEQ ID NO: 532          moltype = DNA   length = 15
FEATURE                 Location/Qualifiers
misc_feature            1..15
                        note = Description of Artificial Sequence: Synthetic
                        oligonucleotide
source                  1..15
                        mol_type = other DNA
                        organism = synthetic construct
SEQUENCE: 532
ctcccggtcc aggaa                                                       15

SEQ ID NO: 533          moltype = DNA   length = 15
FEATURE                 Location/Qualifiers
misc_feature            1..15
                        note = Description of Artificial Sequence: Synthetic
                        oligonucleotide
source                  1..15
                        mol_type = other DNA
                        organism = synthetic construct
SEQUENCE: 533
gctcccggtc cagga                                                       15

SEQ ID NO: 534          moltype = DNA   length = 15
FEATURE                 Location/Qualifiers
misc_feature            1..15
                        note = Description of Artificial Sequence: Synthetic
                        oligonucleotide
source                  1..15
                        mol_type = other DNA
                        organism = synthetic construct
SEQUENCE: 534
ggctcccggt ccagg                                                       15

SEQ ID NO: 535          moltype = DNA   length = 15
FEATURE                 Location/Qualifiers
misc_feature            1..15
                        note = Description of Artificial Sequence: Synthetic
                        oligonucleotide
source                  1..15
                        mol_type = other DNA
                        organism = synthetic construct
SEQUENCE: 535
cgggagcccc cgtgt                                                       15

SEQ ID NO: 536          moltype = DNA   length = 15
FEATURE                 Location/Qualifiers
misc_feature            1..15
                        note = Description of Artificial Sequence: Synthetic
                        oligonucleotide
source                  1..15
                        mol_type = other DNA
                        organism = synthetic construct
SEQUENCE: 536
gcgggagccc ccgtg                                                       15

SEQ ID NO: 537          moltype = DNA   length = 15
FEATURE                 Location/Qualifiers
misc_feature            1..15
                        note = Description of Artificial Sequence: Synthetic
                        oligonucleotide
source                  1..15
                        mol_type = other DNA
                        organism = synthetic construct
```

```
SEQUENCE: 537
cgcgggagcc cccgt                                                          15

SEQ ID NO: 538           moltype = DNA  length = 15
FEATURE                  Location/Qualifiers
misc_feature             1..15
                         note = Description of Artificial Sequence: Synthetic
                         oligonucleotide
source                   1..15
                         mol_type = other DNA
                         organism = synthetic construct
SEQUENCE: 538
acgcgggagc ccccg                                                          15

SEQ ID NO: 539           moltype = DNA  length = 15
FEATURE                  Location/Qualifiers
misc_feature             1..15
                         note = Description of Artificial Sequence: Synthetic
                         oligonucleotide
source                   1..15
                         mol_type = other DNA
                         organism = synthetic construct
SEQUENCE: 539
cacgcgggag ccccc                                                          15

SEQ ID NO: 540           moltype = DNA  length = 15
FEATURE                  Location/Qualifiers
misc_feature             1..15
                         note = Description of Artificial Sequence: Synthetic
                         oligonucleotide
source                   1..15
                         mol_type = other DNA
                         organism = synthetic construct
SEQUENCE: 540
ccacgcggga gcccc                                                          15

SEQ ID NO: 541           moltype = DNA  length = 15
FEATURE                  Location/Qualifiers
misc_feature             1..15
                         note = Description of Artificial Sequence: Synthetic
                         oligonucleotide
source                   1..15
                         mol_type = other DNA
                         organism = synthetic construct
SEQUENCE: 541
gccacgcggg agccc                                                          15

SEQ ID NO: 542           moltype = DNA  length = 15
FEATURE                  Location/Qualifiers
misc_feature             1..15
                         note = Description of Artificial Sequence: Synthetic
                         oligonucleotide
source                   1..15
                         mol_type = other DNA
                         organism = synthetic construct
SEQUENCE: 542
ggccacgcgg gagcc                                                          15

SEQ ID NO: 543           moltype = DNA  length = 15
FEATURE                  Location/Qualifiers
misc_feature             1..15
                         note = Description of Artificial Sequence: Synthetic
                         oligonucleotide
source                   1..15
                         mol_type = other DNA
                         organism = synthetic construct
SEQUENCE: 543
cggccacgcg ggagc                                                          15

SEQ ID NO: 544           moltype = DNA  length = 15
FEATURE                  Location/Qualifiers
misc_feature             1..15
                         note = Description of Artificial Sequence: Synthetic
                         oligonucleotide
source                   1..15
                         mol_type = other DNA
                         organism = synthetic construct
```

```
SEQUENCE: 544
acggccacgc gggag                                                       15

SEQ ID NO: 545          moltype = DNA   length = 15
FEATURE                 Location/Qualifiers
misc_feature            1..15
                        note = Description of Artificial Sequence: Synthetic
                        oligonucleotide
source                  1..15
                        mol_type = other DNA
                        organism = synthetic construct
SEQUENCE: 545
gacggccacg cggga                                                       15

SEQ ID NO: 546          moltype = DNA   length = 15
FEATURE                 Location/Qualifiers
misc_feature            1..15
                        note = Description of Artificial Sequence: Synthetic
                        oligonucleotide
source                  1..15
                        mol_type = other DNA
                        organism = synthetic construct
SEQUENCE: 546
agacggccac gcggg                                                       15

SEQ ID NO: 547          moltype = DNA   length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 547
gctagggagg gatggtta                                                    18

SEQ ID NO: 548          moltype = DNA   length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 548
tgtaagctag ggagggat                                                    18

SEQ ID NO: 549          moltype = DNA   length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 549
acagatgtaa gctaggga                                                    18

SEQ ID NO: 550          moltype = DNA   length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 550
aaggaacaga tgtaagct                                                    18

SEQ ID NO: 551          moltype = DNA   length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 551
caacaaagga acagatgt                                                    18
```

```
SEQ ID NO: 552         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 552
gggtgcaaca aaggaaca                                                        18

SEQ ID NO: 553         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 553
accaagggtg caacaaag                                                        18

SEQ ID NO: 554         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 554
gttaaaccaa gggtgcaa                                                        18

SEQ ID NO: 555         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 555
ataatgttaa accaaggg                                                        18

SEQ ID NO: 556         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 556
ggagaataat gttaaacc                                                        18

SEQ ID NO: 557         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 557
ggggaggaga ataatgtt                                                        18

SEQ ID NO: 558         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 558
aaattgggga ggagaata                                                        18
```

```
SEQ ID NO: 559            moltype = DNA   length = 18
FEATURE                   Location/Qualifiers
misc_feature              1..18
                          note = Description of Artificial Sequence: Synthetic
                            oligonucleotide
source                    1..18
                          mol_type = other DNA
                          organism = synthetic construct
SEQUENCE: 559
agaggaaatt ggggagga                                                      18

SEQ ID NO: 560            moltype = DNA   length = 18
FEATURE                   Location/Qualifiers
misc_feature              1..18
                          note = Description of Artificial Sequence: Synthetic
                            oligonucleotide
source                    1..18
                          mol_type = other DNA
                          organism = synthetic construct
SEQUENCE: 560
ggagaagagg aaattggg                                                      18

SEQ ID NO: 561            moltype = DNA   length = 18
FEATURE                   Location/Qualifiers
misc_feature              1..18
                          note = Description of Artificial Sequence: Synthetic
                            oligonucleotide
source                    1..18
                          mol_type = other DNA
                          organism = synthetic construct
SEQUENCE: 561
aatgaggaga agaggaaa                                                      18

SEQ ID NO: 562            moltype = DNA   length = 18
FEATURE                   Location/Qualifiers
misc_feature              1..18
                          note = Description of Artificial Sequence: Synthetic
                            oligonucleotide
source                    1..18
                          mol_type = other DNA
                          organism = synthetic construct
SEQUENCE: 562
ttcacaatga ggagaaga                                                      18

SEQ ID NO: 563            moltype = DNA   length = 18
FEATURE                   Location/Qualifiers
misc_feature              1..18
                          note = Description of Artificial Sequence: Synthetic
                            oligonucleotide
source                    1..18
                          mol_type = other DNA
                          organism = synthetic construct
SEQUENCE: 563
acgagttcac aatgagga                                                      18

SEQ ID NO: 564            moltype = DNA   length = 18
FEATURE                   Location/Qualifiers
misc_feature              1..18
                          note = Description of Artificial Sequence: Synthetic
                            oligonucleotide
source                    1..18
                          mol_type = other DNA
                          organism = synthetic construct
SEQUENCE: 564
ctgccacgag ttcacaat                                                      18

SEQ ID NO: 565            moltype = DNA   length = 18
FEATURE                   Location/Qualifiers
misc_feature              1..18
                          note = Description of Artificial Sequence: Synthetic
                            oligonucleotide
source                    1..18
                          mol_type = other DNA
                          organism = synthetic construct
```

```
SEQUENCE: 565
agaccctgcc acgagttc                                                 18

SEQ ID NO: 566          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 566
caagcagacc ctgccacg                                                 18

SEQ ID NO: 567          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 567
ctcaccaagc agaccctg                                                 18

SEQ ID NO: 568          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 568
gagctcacca agcagacc                                                 18

SEQ ID NO: 569          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 569
agaatgagct caccaagc                                                 18

SEQ ID NO: 570          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 570
gtaagagaat gagctcac                                                 18

SEQ ID NO: 571          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 571
ttgttgtaag agaatgag                                                 18

SEQ ID NO: 572          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 572
atttgttgtt gtaagaga                                                 18
```

```
SEQ ID NO: 573         moltype = DNA  length = 18
FEATURE                Location/Qualifiers
misc_feature           1..18
                       note = Description of Artificial Sequence: Synthetic
                         oligonucleotide
source                 1..18
                       mol_type = other DNA
                       organism = synthetic construct
SEQUENCE: 573
cttgaatttg ttgttgta                                                       18

SEQ ID NO: 574         moltype = DNA  length = 18
FEATURE                Location/Qualifiers
misc_feature           1..18
                       note = Description of Artificial Sequence: Synthetic
                         oligonucleotide
source                 1..18
                       mol_type = other DNA
                       organism = synthetic construct
SEQUENCE: 574
atgctcttga atttgttg                                                       18

SEQ ID NO: 575         moltype = DNA  length = 18
FEATURE                Location/Qualifiers
misc_feature           1..18
                       note = Description of Artificial Sequence: Synthetic
                         oligonucleotide
source                 1..18
                       mol_type = other DNA
                       organism = synthetic construct
SEQUENCE: 575
tcttcatgct cttgaatt                                                       18

SEQ ID NO: 576         moltype = DNA  length = 18
FEATURE                Location/Qualifiers
misc_feature           1..18
                       note = Description of Artificial Sequence: Synthetic
                         oligonucleotide
source                 1..18
                       mol_type = other DNA
                       organism = synthetic construct
SEQUENCE: 576
cttcctcttc atgctctt                                                       18

SEQ ID NO: 577         moltype = DNA  length = 18
FEATURE                Location/Qualifiers
misc_feature           1..18
                       note = Description of Artificial Sequence: Synthetic
                         oligonucleotide
source                 1..18
                       mol_type = other DNA
                       organism = synthetic construct
SEQUENCE: 577
gcgcgcttcc tcttcatg                                                       18

SEQ ID NO: 578         moltype = DNA  length = 18
FEATURE                Location/Qualifiers
misc_feature           1..18
                       note = Description of Artificial Sequence: Synthetic
                         oligonucleotide
source                 1..18
                       mol_type = other DNA
                       organism = synthetic construct
SEQUENCE: 578
gctctgcgcg cttcctct                                                       18

SEQ ID NO: 579         moltype = DNA  length = 18
FEATURE                Location/Qualifiers
misc_feature           1..18
                       note = Description of Artificial Sequence: Synthetic
                         oligonucleotide
source                 1..18
                       mol_type = other DNA
                       organism = synthetic construct
SEQUENCE: 579
ggccagcggc tctgcgcg                                                       18
```

```
SEQ ID NO: 580           moltype = DNA  length = 18
FEATURE                  Location/Qualifiers
misc_feature             1..18
                         note = Description of Artificial Sequence: Synthetic
                          oligonucleotide
source                   1..18
                         mol_type = other DNA
                         organism = synthetic construct
SEQUENCE: 580
atattggcca gcggctct                                                       18

SEQ ID NO: 581           moltype = DNA  length = 18
FEATURE                  Location/Qualifiers
misc_feature             1..18
                         note = Description of Artificial Sequence: Synthetic
                          oligonucleotide
source                   1..18
                         mol_type = other DNA
                         organism = synthetic construct
SEQUENCE: 581
gtgctatatt ggccagcg                                                       18

SEQ ID NO: 582           moltype = DNA  length = 18
FEATURE                  Location/Qualifiers
misc_feature             1..18
                         note = Description of Artificial Sequence: Synthetic
                          oligonucleotide
source                   1..18
                         mol_type = other DNA
                         organism = synthetic construct
SEQUENCE: 582
agctcgtgct atattggc                                                       18

SEQ ID NO: 583           moltype = DNA  length = 18
FEATURE                  Location/Qualifiers
misc_feature             1..18
                         note = Description of Artificial Sequence: Synthetic
                          oligonucleotide
source                   1..18
                         mol_type = other DNA
                         organism = synthetic construct
SEQUENCE: 583
ggcatagctc gtgctata                                                       18

SEQ ID NO: 584           moltype = DNA  length = 18
FEATURE                  Location/Qualifiers
misc_feature             1..18
                         note = Description of Artificial Sequence: Synthetic
                          oligonucleotide
source                   1..18
                         mol_type = other DNA
                         organism = synthetic construct
SEQUENCE: 584
tgttgggcat agctcgtg                                                       18

SEQ ID NO: 585           moltype = DNA  length = 18
FEATURE                  Location/Qualifiers
misc_feature             1..18
                         note = Description of Artificial Sequence: Synthetic
                          oligonucleotide
source                   1..18
                         mol_type = other DNA
                         organism = synthetic construct
SEQUENCE: 585
gcttctgttg ggcatagc                                                       18

SEQ ID NO: 586           moltype = DNA  length = 18
FEATURE                  Location/Qualifiers
misc_feature             1..18
                         note = Description of Artificial Sequence: Synthetic
                          oligonucleotide
source                   1..18
                         mol_type = other DNA
                         organism = synthetic construct
SEQUENCE: 586
cttgcgcttc tgttgggc                                                       18
```

```
SEQ ID NO: 587          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 587
caccttgcgc ttctgttg                                                      18

SEQ ID NO: 588          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 588
tccatcacct tgcgcttc                                                      18

SEQ ID NO: 589          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 589
aaccatccat caccttgc                                                      18

SEQ ID NO: 590          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 590
ccttaaacca tccatcac                                                      18

SEQ ID NO: 591          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 591
agcccccttt aaccatcc                                                      18

SEQ ID NO: 592          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 592
tcggtagccc ccttaaac                                                      18

SEQ ID NO: 593          moltype = DNA  length = 18
FEATURE                 Location/Qualifiers
misc_feature            1..18
                        note = Description of Artificial Sequence: Synthetic
                        oligonucleotide
source                  1..18
                        mol_type = other DNA
                        organism = synthetic construct
SEQUENCE: 593
atgtatcggt agcccct                                                       18
```

```
SEQ ID NO: 594           moltype = DNA  length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 594
tgtgaatgta tcggtagc                                                       18

SEQ ID NO: 595           moltype = DNA  length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 595
attagtgtga atgtatcg                                                       18

SEQ ID NO: 596           moltype = DNA  length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 596
ggctgattag tgtgaatg                                                       18

SEQ ID NO: 597           moltype = DNA  length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 597
gaaatggctg attagtgt                                                       18

SEQ ID NO: 598           moltype = DNA  length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 598
tggcagaaat ggctgatt                                                       18

SEQ ID NO: 599           moltype = DNA  length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
SEQUENCE: 599
gatcttggca gaaatggc                                                       18

SEQ ID NO: 600           moltype = DNA  length = 18
FEATURE                  Location/Qualifiers
misc_feature             1..18
                         note = Description of Artificial Sequence: Synthetic
                         oligonucleotide
source                   1..18
                         mol_type = other DNA
                         organism = synthetic construct
```

```
SEQUENCE: 600
gacatgatct tggcagaa                                                 18

SEQ ID NO: 601           moltype = DNA  length = 18
FEATURE                  Location/Qualifiers
misc_feature             1..18
                         note = Description of Artificial Sequence: Synthetic
                          oligonucleotide
source                   1..18
                         mol_type = other DNA
                         organism = synthetic construct
SEQUENCE: 601
gaggtgacat gatcttgg                                                 18

SEQ ID NO: 602           moltype = DNA  length = 18
FEATURE                  Location/Qualifiers
misc_feature             1..18
                         note = Description of Artificial Sequence: Synthetic
                          oligonucleotide
source                   1..18
                         mol_type = other DNA
                         organism = synthetic construct
SEQUENCE: 602
agattgaggt gacatgat                                                 18

SEQ ID NO: 603           moltype = DNA  length = 18
FEATURE                  Location/Qualifiers
misc_feature             1..18
                         note = Description of Artificial Sequence: Synthetic
                          oligonucleotide
source                   1..18
                         mol_type = other DNA
                         organism = synthetic construct
SEQUENCE: 603
tgaacagatt gaggtgac                                                 18

SEQ ID NO: 604           moltype = DNA  length = 18
FEATURE                  Location/Qualifiers
misc_feature             1..18
                         note = Description of Artificial Sequence: Synthetic
                          oligonucleotide
source                   1..18
                         mol_type = other DNA
                         organism = synthetic construct
SEQUENCE: 604
gtccatgaac agattgag                                                 18

SEQ ID NO: 605           moltype = DNA  length = 18
FEATURE                  Location/Qualifiers
misc_feature             1..18
                         note = Description of Artificial Sequence: Synthetic
                          oligonucleotide
source                   1..18
                         mol_type = other DNA
                         organism = synthetic construct
SEQUENCE: 605
ttggagtcca tgaacaga                                                 18

SEQ ID NO: 606           moltype = DNA  length = 18
FEATURE                  Location/Qualifiers
misc_feature             1..18
                         note = Description of Artificial Sequence: Synthetic
                          oligonucleotide
source                   1..18
                         mol_type = other DNA
                         organism = synthetic construct
SEQUENCE: 606
tgtatttgga gtccatga                                                 18
```

```
SEQ ID NO: 607        moltype = DNA  length = 18
FEATURE               Location/Qualifiers
misc_feature          1..18
                      note = Description of Artificial Sequence: Synthetic
                      oligonucleotide
source                1..18
                      mol_type = other DNA
                      organism = synthetic construct
SEQUENCE: 607
tttcttgtat ttggagtc                                                      18
```